US012398187B2

(12) United States Patent
Trager et al.

(10) Patent No.: US 12,398,187 B2
(45) **Date of Patent: *Aug. 26, 2025**

(54) CD19-DIRECTED CHIMERIC ANTIGEN RECEPTORS AND USES THEREOF IN IMMUNOTHERAPY

(71) Applicant: Nkarta, Inc., South San Francisco, CA (US)

(72) Inventors: James Barnaby Trager, Albany, CA (US); Luxuan Guo Buren, San Francisco, CA (US); Chao Guo, San Francisco, CA (US); Mira Tohmé, San Francisco, CA (US); Ivan Chan, Millbrae, CA (US); Alexandra Leida Liana Lazetic, San Jose, CA (US)

(73) Assignee: Nkarta, Inc., South San Francisco, CA (US)

( * ) Notice: Subject to any disclaimer, the term of this patent is extended or adjusted under 35 U.S.C. 154(b) by 444 days.

This patent is subject to a terminal disclaimer.

(21) Appl. No.: 17/571,325

(22) Filed: Jan. 7, 2022

(65) Prior Publication Data

US 2022/0233590 A1 Jul. 28, 2022

Related U.S. Application Data

(63) Continuation of application No. 17/089,449, filed on Nov. 4, 2020, now Pat. No. 11,253,547, which is a continuation of application No. PCT/US2020/020824, filed on Mar. 3, 2020.

(60) Provisional application No. 62/932,165, filed on Nov. 7, 2019, provisional application No. 62/895,910, filed on Sep. 4, 2019, provisional application No. 62/814,180, filed on Mar. 5, 2019.

(51) Int. Cl.

| | |
|---|---|
| ***A61K 35/17*** | (2025.01) |
| ***A61K 40/15*** | (2025.01) |
| ***A61K 40/31*** | (2025.01) |
| ***A61K 40/42*** | (2025.01) |
| ***A61P 35/00*** | (2006.01) |
| ***C07K 14/54*** | (2006.01) |
| ***C07K 14/55*** | (2006.01) |
| ***C07K 14/705*** | (2006.01) |
| ***C07K 14/725*** | (2006.01) |
| ***C07K 16/28*** | (2006.01) |
| ***C12N 5/0783*** | (2010.01) |

(52) U.S. Cl.

CPC .............. *C07K 14/55* (2013.01); *A61K 40/15* (2025.01); *A61K 40/31* (2025.01); *A61K 40/4211* (2025.01); *A61P 35/00* (2018.01); *C07K 14/5443* (2013.01); *C07K 14/7051* (2013.01); *C07K 14/70517* (2013.01); *C07K 14/70578* (2013.01); *C07K 16/2803* (2013.01); *C07K 16/2878* (2013.01); *C12N 5/0646* (2013.01); *A61K 2239/38* (2023.05); *A61K 2239/48* (2023.05); *C07K 2317/56* (2013.01); *C07K 2317/622* (2013.01); *C07K 2319/02* (2013.01); *C07K 2319/03* (2013.01)

(58) Field of Classification Search

None

See application file for complete search history.

(56) References Cited

U.S. PATENT DOCUMENTS

| | | | |
|---|---|---|---|
| 4,596,227 | A | 6/1986 | Hashizume |
| 4,650,764 | A | 3/1987 | Temin et al. |
| 4,690,915 | A | 9/1987 | Rosenberg et al. |
| 4,729,684 | A | 3/1988 | Sakaoka |
| 4,844,893 | A | 7/1989 | Honsik et al. |
| 4,980,289 | A | 12/1990 | Temin et al. |
| 5,124,263 | A | 6/1992 | Temin et al. |
| 5,359,046 | A | 10/1994 | Capon |
| 5,399,346 | A | 3/1995 | Anderson |
| 5,415,874 | A | 5/1995 | Bender et al. |
| 5,595,756 | A | 1/1997 | Bally et al. |
| 5,653,977 | A | 8/1997 | Saleh |
| 5,674,704 | A | 10/1997 | Goodwin et al. |
| 5,686,281 | A | 11/1997 | Roberts |
| 5,712,149 | A | 1/1998 | Roberts |
| 5,902,733 | A | 5/1999 | Hirt et al. |
| 6,103,521 | A | 8/2000 | Capon et al. |
| 6,261,839 | B1 | 7/2001 | Multhoff et al. |

(Continued)

FOREIGN PATENT DOCUMENTS

| | | |
|---|---|---|
| CN | 101684456 | 3/2010 |
| CN | 102268405 A | 12/2011 |

(Continued)

OTHER PUBLICATIONS

U.S. Appl. No. 14/764,070 (U.S. Pat. No. 9,511,092), filed Jul. 28, 2015 (Dec. 6, 2016), Chimeric Receptor With NKG2D Specificity for Use in Cell Therapy Against Cancer and Infectious Disease.

(Continued)

*Primary Examiner* — Michael D Burkhart

(74) *Attorney, Agent, or Firm* — Knobbe, Martens, Olson & Bear, LLP

(57) ABSTRACT

Provided for herein in several embodiments are immune cell-based (e.g., natural killer (NK) cell) compositions comprising CD19-directed chimeric antigen receptors. In some, embodiments the anti-CD19 binder portion of the CAR is humanized. In several embodiments, the humanized anti-CD19 CAR expressing cells exhibit enhanced expression of the CAR as well as enhanced cytotoxicity and/or persistence. Several embodiments include methods of using of the anti-CD19 CAR expressing immune cells in immunotherapy.

24 Claims, 124 Drawing Sheets

Specification includes a Sequence Listing.

(56) References Cited

U.S. PATENT DOCUMENTS 6,303,121 B1 10/2001 Kwon
6,319,494 B1 11/2001 Capon et al.
6,355,476 B1 3/2002 Kwon et al.
6,361,998 B1 3/2002 Bell et al.
6,410,319 B1 6/2002 Raubitschek et al.
6,464,973 B1 10/2002 Levitsky et al.
6,797,514 B2 9/2004 Berenson et al.
7,052,906 B1 5/2006 Lawson et al.
7,070,995 B2 7/2006 Jensen
7,390,483 B2 6/2008 Levitsky et al.
7,435,596 B2 10/2008 Campana et al.
7,446,179 B2 11/2008 Jensen et al.
7,446,190 B2 11/2008 Sadelain et al.
7,735,596 B2 6/2010 Sasaki et al.
7,740,871 B2 6/2010 Ambinder et al.
7,763,243 B2 7/2010 Lum et al.
7,932,055 B2 4/2011 Spee et al.
7,994,298 B2 8/2011 Zhang et al.
8,012,469 B2 9/2011 Levitsky et al.
8,026,097 B2 9/2011 Campana et al.
8,252,914 B2 8/2012 Zhang et al.
8,383,096 B2 2/2013 Ambinder et al.
8,389,282 B2 3/2013 Sadelain et al.
8,399,645 B2 3/2013 Campana et al.
8,802,374 B2 8/2014 Jensen
8,877,182 B2 11/2014 Alici
8,906,682 B2 12/2014 June et al.
8,911,993 B2 12/2014 June et al.
8,916,381 B1 12/2014 June et al.
8,926,964 B2 1/2015 Hariri et al.
8,975,071 B1 3/2015 June et al.
9,101,584 B2 8/2015 June et al.
9,102,760 B2 8/2015 June et al.
9,102,761 B2 8/2015 June et al.
9,212,229 B2 12/2015 Schönfeld et al.
9,328,156 B2 5/2016 June et al.
9,365,641 B2 6/2016 June et al.
9,447,194 B2 9/2016 Jensen
9,464,140 B2 10/2016 June et al.
9,464,274 B2 10/2016 Hariri et al.
9,481,728 B2 11/2016 June et al.
9,487,800 B2 11/2016 Schönfeld et al.
9,499,629 B2 11/2016 June et al.
9,511,092 B2 12/2016 Campana et al.
9,518,523 B2 12/2016 June et al.
9,540,445 B2 1/2017 June et al.
9,580,685 B2 2/2017 Jensen
9,605,049 B2 3/2017 Campana et al.
9,623,082 B2 4/2017 Copik et al.
9,629,877 B2 4/2017 Cooper et al.
9,701,758 B2 7/2017 Cooper et al.
9,765,342 B2 9/2017 Kochenderfer
9,834,590 B2 12/2017 Campana et al.
9,856,322 B2 1/2018 Campana et al.
10,100,281 B2 10/2018 Jensen
10,125,193 B2 11/2018 Cooper et al.
10,174,095 B2 1/2019 Brogdon et al.
10,221,245 B2 3/2019 Brogdon et al.
10,253,086 B2 4/2019 Bitter et al.
10,322,146 B2 6/2019 Bot et al.
10,391,126 B2 8/2019 Cooper et al.
10,428,305 B2 10/2019 Campana et al.
10,471,098 B2 11/2019 Katz et al.
10,533,055 B2 1/2020 Chen et al.
10,538,739 B2 1/2020 Campana et al.
10,736,920 B2 8/2020 Yu et al.
10,774,309 B2 9/2020 Campana et al.
10,774,311 B2 9/2020 Campana et al.
10,801,012 B2 10/2020 Campana et al.
10,829,735 B2 11/2020 Bedoya et al.
10,829,737 B2 11/2020 Campana et al.
10,836,999 B2 11/2020 Campana et al.
10,844,120 B2 11/2020 Wiltzius et al.
10,918,665 B2 2/2021 Brentjens et al.
10,927,184 B2 2/2021 Brogdon et al.
11,141,436 B2 10/2021 Trager et al.
11,154,575 B2 10/2021 Trager et al.
11,166,985 B2 11/2021 Terrett et al.
11,253,547 B2 2/2022 Trager et al.
11,254,912 B2 2/2022 Terrett et al.
11,365,236 B2 6/2022 Leong et al.
11,413,310 B2 8/2022 Albertson et al.
11,491,187 B2 11/2022 Bot et al.
11,497,773 B2 11/2022 Dequeant et al.
11,555,076 B2 1/2023 Lombana et al.
11,560,548 B2 1/2023 Campana et al.
11,649,438 B2 5/2023 Terrett et al.
11,673,937 B2 6/2023 Campana et al.
11,679,130 B2 6/2023 Dequeant et al.
11,688,564 B1 6/2023 Ashraf et al.
11,690,874 B2 7/2023 Xiao et al.
11,873,512 B2 1/2024 Campana et al.
11,896,616 B2 2/2024 Kamiya et al.
12,012,458 B2 6/2024 Trager et al.
2002/0018783 A1 2/2002 Sadelain et al.
2002/0037282 A1 3/2002 Levitsky et al.
2002/0147307 A1 10/2002 Hilton et al.
2003/0022311 A1 1/2003 Dunnington et al.
2003/0129649 A1 7/2003 Kobilka et al.
2003/0147869 A1 8/2003 Riley
2003/0157713 A1 8/2003 Ohno et al.
2003/0215427 A1 11/2003 Jensen
2004/0038886 A1 2/2004 Finney et al.
2004/0043401 A1 3/2004 Sadelain et al.
2004/0115216 A1 6/2004 Schneck et al.
2004/0126363 A1 7/2004 Jensen et al.
2004/0161433 A1 8/2004 Teshigawara et al.
2005/0042208 A1 2/2005 Sagawa et al.
2005/0048549 A1 3/2005 Cao et al.
2005/0069542 A1 3/2005 Baker et al.
2005/0113564 A1 5/2005 Campana et al.
2005/0127473 A1 6/2005 Sakagami
2005/0255118 A1 11/2005 Wehner
2006/0057680 A1 3/2006 Zheng et al.
2006/0079442 A1 4/2006 Ilan et al.
2006/0093605 A1 5/2006 Campana et al.
2006/0140922 A1 6/2006 Levitsky et al.
2006/0233770 A1 10/2006 Ambinder et al.
2006/0247191 A1 11/2006 Finney et al.
2006/0257407 A1 11/2006 Chen et al.
2006/0292119 A1 12/2006 Chen et al.
2007/0077241 A1 4/2007 Spies et al.
2007/0160578 A1 7/2007 Waldmann et al.
2007/0166327 A1 7/2007 Cooper et al.
2008/0026413 A1 1/2008 Savage
2008/0177047 A1 7/2008 Fujita-Yamaguchi
2008/0247990 A1 10/2008 Campbell
2008/0248043 A1 10/2008 Babcook et al.
2008/0260758 A1 10/2008 Levitsky et al.
2008/0299137 A1 12/2008 Svendsen et al.
2009/0011498 A1 1/2009 Campana et al.
2009/0175846 A1 7/2009 Mi et al.
2009/0202501 A1 8/2009 Zhang et al.
2009/0281035 A1 11/2009 Spee et al.
2010/0029749 A1 2/2010 Zhang et al.
2010/0178276 A1 7/2010 Sadelain et al.
2010/0272760 A1 10/2010 Ambinder et al.
2011/0059137 A1 3/2011 Antonia et al.
2011/0287058 A1 11/2011 Levitsky et al.
2011/0318339 A1 12/2011 Smider et al.
2012/0015434 A1 1/2012 Campana et al.
2012/0029063 A1 2/2012 Zhang et al.
2012/0058906 A1 3/2012 Smider et al.
2012/0148552 A1 6/2012 Jensen
2012/0148553 A1 6/2012 Hariri et al.
2012/0192298 A1 7/2012 Weinstein et al.
2012/0258085 A1 10/2012 Alici
2012/0282256 A1 11/2012 Campana et al.
2012/0321666 A1 12/2012 Cooper et al.
2013/0052158 A1 2/2013 Van Rhee
2013/0058921 A1 3/2013 Van Rhee
2013/0071414 A1 3/2013 Dotti et al.
2013/0072401 A1 3/2013 Ye et al.
2013/0121960 A1 5/2013 Sadelain et al.

(56) References Cited

U.S. PATENT DOCUMENTS

| | | | |
|---|---|---|---|
| 2013/0216509 | A1 | 8/2013 | Campana et al. |
| 2013/0251752 | A1 | 9/2013 | Antonia et al. |
| 2013/0266551 | A1 | 10/2013 | Campana et al. |
| 2013/0280221 | A1 | 10/2013 | Schönfeld et al. |
| 2013/0280285 | A1 | 10/2013 | Schönfeld et al. |
| 2013/0288368 | A1 | 10/2013 | June et al. |
| 2013/0296273 | A1 | 11/2013 | Curd et al. |
| 2013/0309258 | A1 | 11/2013 | June et al. |
| 2013/0323214 | A1 | 12/2013 | Gottschalk et al. |
| 2014/0023626 | A1 | 1/2014 | Peled |
| 2014/0099309 | A1 | 4/2014 | Powell, Jr. et al. |
| 2014/0099340 | A1 | 4/2014 | June et al. |
| 2014/0115198 | A1 | 4/2014 | White |
| 2014/0227237 | A1 | 8/2014 | June et al. |
| 2014/0271635 | A1 | 9/2014 | Brogdon et al. |
| 2014/0286934 | A1 | 9/2014 | Blein et al. |
| 2014/0286973 | A1 | 9/2014 | Powell, Jr. |
| 2014/0302608 | A1 | 10/2014 | Dominici et al. |
| 2014/0322183 | A1 | 10/2014 | Milone et al. |
| 2014/0328812 | A1 | 11/2014 | Campana et al. |
| 2014/0341869 | A1 | 11/2014 | Campana et al. |
| 2014/0349402 | A1 | 11/2014 | Cooper et al. |
| 2015/0072425 | A1 | 3/2015 | Hariri et al. |
| 2015/0139943 | A1 | 5/2015 | Campana et al. |
| 2015/0157603 | A1 | 6/2015 | Higgins et al. |
| 2015/0190471 | A1 | 7/2015 | Copik et al. |
| 2015/0218649 | A1 | 8/2015 | Saenger et al. |
| 2015/0224143 | A1 | 8/2015 | Malmberg et al. |
| 2015/0225470 | A1 | 8/2015 | Zhang et al. |
| 2015/0273089 | A1 | 10/2015 | Gray |
| 2015/0275209 | A1 | 10/2015 | Ji et al. |
| 2015/0306141 | A1 | 10/2015 | Jensen et al. |
| 2015/0329640 | A1 | 11/2015 | Finer |
| 2015/0344844 | A1 | 12/2015 | Better et al. |
| 2015/0368342 | A1 | 12/2015 | Wu et al. |
| 2016/0000828 | A1 | 1/2016 | Campana et al. |
| 2016/0008398 | A1 | 1/2016 | Sadelain et al. |
| 2016/0009784 | A1 | 1/2016 | Campana et al. |
| 2016/0030659 | A1 | 2/2016 | Cheney |
| 2016/0045551 | A1 | 2/2016 | Brentjens et al. |
| 2016/0046724 | A1 | 2/2016 | Brogdon et al. |
| 2016/0046729 | A1 | 2/2016 | Schönfeld et al. |
| 2016/0122766 | A1 | 5/2016 | Wucherpfenning et al. |
| 2016/0122782 | A1 | 5/2016 | Crisman et al. |
| 2016/0152723 | A1 | 6/2016 | Chen et al. |
| 2016/0158285 | A1 | 6/2016 | Cooper et al. |
| 2016/0158359 | A1 | 6/2016 | Gilbert |
| 2016/0185862 | A1 | 6/2016 | Wu et al. |
| 2016/0207989 | A1 | 7/2016 | Short |
| 2016/0228547 | A1 | 8/2016 | Wagner et al. |
| 2016/0235787 | A1 | 8/2016 | June et al. |
| 2016/0250258 | A1 | 9/2016 | Delaney et al. |
| 2016/0272718 | A1 | 9/2016 | Wang et al. |
| 2016/0289293 | A1 | 10/2016 | Pulé et al. |
| 2016/0289294 | A1 | 10/2016 | Pulé et al. |
| 2016/0296562 | A1 | 10/2016 | Pulé et al. |
| 2016/0326265 | A1 | 11/2016 | June et al. |
| 2016/0333108 | A1 | 11/2016 | Forman et al. |
| 2016/0362472 | A1 | 12/2016 | Bitter et al. |
| 2016/0377035 | A1 | 12/2016 | Osawa et al. |
| 2017/0002322 | A1 | 1/2017 | Hariri et al. |
| 2017/0014508 | A1 | 1/2017 | Pulé et al. |
| 2017/0015975 | A1 | 1/2017 | Fu et al. |
| 2017/0016025 | A1 | 1/2017 | Poirot et al. |
| 2017/0044227 | A1 | 2/2017 | Schönfeld et al. |
| 2017/0049819 | A1 | 2/2017 | Friedman et al. |
| 2017/0051071 | A1 | 2/2017 | Rueger et al. |
| 2017/0073423 | A1 | 3/2017 | Juillerat et al. |
| 2017/0073638 | A1 | 3/2017 | Campana et al. |
| 2017/0081411 | A1 | 3/2017 | Engels et al. |
| 2017/0088620 | A1 | 3/2017 | Nioi et al. |
| 2017/0101466 | A1 | 4/2017 | Handa et al. |
| 2017/0107178 | A1 | 4/2017 | Cowley et al. |
| 2017/0107286 | A1 | 4/2017 | Kochenderfer |
| 2017/0107491 | A1 | 4/2017 | Campana et al. |
| 2017/0129967 | A1 | 5/2017 | Wels et al. |
| 2017/0137515 | A1 | 5/2017 | Chang et al. |
| 2017/0137783 | A1 | 5/2017 | Bedoya et al. |
| 2017/0158749 | A1 | 6/2017 | Cooper et al. |
| 2017/0183415 | A1 | 6/2017 | Brogdon et al. |
| 2017/0226223 | A1 | 8/2017 | Williams et al. |
| 2017/0232070 | A1 | 8/2017 | Junghans |
| 2017/0239294 | A1 | 8/2017 | Thomas-Tikhonenko et al. |
| 2017/0260594 | A1 | 9/2017 | Molinero et al. |
| 2017/0281766 | A1 | 10/2017 | Wiltzius |
| 2017/0283482 | A1 | 10/2017 | Campana et al. |
| 2017/0283775 | A1 | 10/2017 | June et al. |
| 2017/0291949 | A1 | 10/2017 | Zhou |
| 2017/0296678 | A1 | 10/2017 | Sezc et al. |
| 2017/0333481 | A1 | 11/2017 | Jantz et al. |
| 2017/0334968 | A1 | 11/2017 | Cooper et al. |
| 2017/0355957 | A1 | 12/2017 | Biondi et al. |
| 2017/0368098 | A1 | 12/2017 | Chen et al. |
| 2017/0368101 | A1 | 12/2017 | Bot et al. |
| 2018/0002397 | A1 | 1/2018 | Shah et al. |
| 2018/0002435 | A1 | 1/2018 | Sasu et al. |
| 2018/0008638 | A1 | 1/2018 | Campana et al. |
| 2018/0028633 | A1 | 2/2018 | Chen |
| 2018/0044391 | A1 | 2/2018 | Gundram et al. |
| 2018/0044417 | A1 | 2/2018 | Pulé et al. |
| 2018/0046571 | A1 | 2/2018 | Magill et al. |
| 2018/0051292 | A1 | 2/2018 | Kochenderfer |
| 2018/0057563 | A1 | 3/2018 | Campana et al. |
| 2018/0057609 | A1 | 3/2018 | June et al. |
| 2018/0057795 | A1 | 3/2018 | Childs et al. |
| 2018/0086831 | A1 | 3/2018 | Pule et al. |
| 2018/0086846 | A1 | 3/2018 | Wiltzius et al. |
| 2018/0092338 | A1 | 4/2018 | Hering et al. |
| 2018/0100016 | A1 | 4/2018 | Song |
| 2018/0104278 | A1 | 4/2018 | Zhang et al. |
| 2018/0112007 | A1 | 4/2018 | Bamdad et al. |
| 2018/0117146 | A1 | 5/2018 | Yu et al. |
| 2018/0118842 | A1 | 5/2018 | Brentjens et al. |
| 2018/0118845 | A1 | 5/2018 | Campana et al. |
| 2018/0125889 | A1 | 5/2018 | Leek et al. |
| 2018/0133296 | A1 | 5/2018 | Barrett et al. |
| 2018/0134765 | A1 | 5/2018 | Landgraf et al. |
| 2018/0134787 | A1 | 5/2018 | Liu et al. |
| 2018/0135013 | A1 | 5/2018 | Campana et al. |
| 2018/0135014 | A1 | 5/2018 | Campana et al. |
| 2018/0135015 | A1 | 5/2018 | Campana et al. |
| 2018/0135016 | A1 | 5/2018 | Campana et al. |
| 2018/0153977 | A1 | 6/2018 | Wu et al. |
| 2018/0162939 | A1 | 6/2018 | Ma et al. |
| 2018/0186878 | A1 | 7/2018 | Rosenthal |
| 2018/0187149 | A1 | 7/2018 | Ma et al. |
| 2018/0200298 | A1 | 7/2018 | Jensen et al. |
| 2018/0201901 | A1 | 7/2018 | Duchateau et al. |
| 2018/0244748 | A1 | 8/2018 | Gill et al. |
| 2018/0258391 | A1 | 9/2018 | June et al. |
| 2018/0273903 | A1 | 9/2018 | Zhang et al. |
| 2018/0312580 | A1 | 11/2018 | Chen et al. |
| 2018/0312588 | A1 | 11/2018 | Wiltzius et al. |
| 2018/0319862 | A1 | 11/2018 | Thompson et al. |
| 2018/0325955 | A1 | 11/2018 | Terrett et al. |
| 2018/0353544 | A1 | 12/2018 | Rezvani et al. |
| 2018/0369283 | A1 | 12/2018 | Bot et al. |
| 2018/0371052 | A1 | 12/2018 | Ma et al. |
| 2019/0010514 | A1 | 1/2019 | Poirot et al. |
| 2019/0038733 | A1 | 2/2019 | Campana et al. |
| 2019/0046571 | A1 | 2/2019 | Campana et al. |
| 2019/0046602 | A1 | 2/2019 | Pereg et al. |
| 2019/0062430 | A1 | 2/2019 | Wu et al. |
| 2019/0062735 | A1 | 2/2019 | Welstead et al. |
| 2019/0144558 | A1 | 5/2019 | Pearse et al. |
| 2019/0153061 | A1 | 5/2019 | Brogdon et al. |
| 2019/0202913 | A1 | 7/2019 | Kochenderfer |
| 2019/0290693 | A1 | 9/2019 | Qi et al. |
| 2019/0336504 | A1 | 11/2019 | Gill et al. |
| 2019/0338011 | A1 | 11/2019 | Zhang et al. |
| 2019/0376037 | A1 | 12/2019 | Campana et al. |
| 2019/0388526 | A1 | 12/2019 | Morgan et al. |
| 2020/0016208 | A1 | 1/2020 | Kamiya et al. |
| 2020/0062843 | A1 | 2/2020 | Wang et al. |

(56) References Cited

U.S. PATENT DOCUMENTS

2020/0063100 A1 2/2020 Terrett et al.
2020/0101142 A1 4/2020 Suri et al.
2020/0102379 A1 4/2020 Wang
2020/0116208 A1 4/2020 Riedisser et al.
2020/0123217 A1 4/2020 Zhang et al.
2020/0131244 A1 4/2020 Leong et al.
2020/0223918 A1 7/2020 Ma et al.
2020/0246382 A1 8/2020 Perez et al.
2020/0255803 A1 8/2020 Zhang et al.
2020/0276237 A1 9/2020 Shiku et al.
2020/0318173 A1 10/2020 Zhang et al.
2020/0340995 A1 10/2020 Campana et al.
2020/0390816 A1 12/2020 Kerbauy et al.
2020/0407686 A1 12/2020 Campana et al.
2021/0009951 A1 1/2021 Hu
2021/0017248 A1 1/2021 Bluestone et al.
2021/0017271 A1 1/2021 Tan et al.
2021/0022187 A1 1/2021 Xu et al.
2021/0046115 A1 2/2021 Seow et al.
2021/0054409 A1 2/2021 Zhu et al.
2021/0060072 A1 3/2021 Terrett et al.
2021/0060073 A1 3/2021 Trager et al.
2021/0070856 A1 3/2021 Trager et al.
2021/0070857 A1 3/2021 Trager et al.
2021/0077527 A1 3/2021 Lee
2021/0079347 A1 3/2021 Terrett et al.
2021/0115404 A1 4/2021 Campana et al.
2021/0130454 A1 5/2021 Jefferies et al.
2021/0139935 A1 5/2021 Carson et al.
2021/0221871 A1 7/2021 Ewert et al.
2021/0230548 A1 7/2021 Daher et al.
2021/0252056 A1 8/2021 Metelitsa et al.
2021/0254000 A1 8/2021 Brahmandam et al.
2021/0254005 A1 8/2021 Kang et al.
2021/0254097 A1 8/2021 O'Dea et al.
2021/0261675 A1 8/2021 Fan et al.
2021/0268027 A1 9/2021 Maus
2021/0269502 A1 9/2021 Jensen et al.
2021/0269518 A1 9/2021 Durrant et al.
2021/0284714 A1 9/2021 Durrant et al.
2021/0284752 A1 9/2021 Brogdon et al.
2021/0290673 A1 9/2021 Yao et al.
2021/0290677 A1 9/2021 Durrant et al.
2021/0292389 A1 9/2021 Abel et al.
2021/0293787 A1 9/2021 Schomer et al.
2021/0301286 A1 9/2021 Bradner et al.
2021/0322547 A1 10/2021 Durrant et al.
2021/0324071 A1 10/2021 Cooper et al.
2021/0324340 A1 10/2021 Valamehr et al.
2021/0324388 A1 10/2021 Vinanica et al.
2021/0332133 A1 10/2021 Force et al.
2021/0338723 A1 11/2021 Fehniger et al.
2021/0338727 A1 11/2021 Trager et al.
2021/0338729 A1 11/2021 Ma et al.
2021/0338833 A1 11/2021 Irvine et al.
2021/0347851 A1 11/2021 Isaacs et al.
2021/0353543 A1 11/2021 Trudeau et al.
2021/0355190 A1 11/2021 Kenderian et al.
2021/0363218 A1 11/2021 Fan et al.
2021/0363245 A1 11/2021 Kochenderfer et al.
2021/0386788 A1 12/2021 Suri et al.
2021/0388100 A1 12/2021 Satpayev et al.
2021/0388389 A1 12/2021 Chen et al.
2021/0395362 A1 12/2021 Wu et al.
2021/0395364 A1 12/2021 Wu et al.
2021/0401886 A1 12/2021 Kenderian et al.
2022/0002424 A1 1/2022 Trager et al.
2022/0008465 A1 1/2022 Trede et al.
2022/0008473 A1 1/2022 Terrett et al.
2022/0016165 A1 1/2022 Bot et al.
2022/0016167 A1 1/2022 Medin et al.
2022/0023344 A1 1/2022 Terrett et al.
2022/0025048 A1 1/2022 Huntington et al.
2022/0031746 A1 2/2022 Gillenwater et al.
2022/0033505 A1 2/2022 Obermajer et al.
2022/0033509 A1 2/2022 Pul et al.
2022/0040229 A1 2/2022 Durrant et al.
2022/0040234 A1 2/2022 Wang et al.
2022/0047633 A1 2/2022 Grupp
2022/0047635 A1 2/2022 Liu et al.
2022/0047636 A1 2/2022 Maus
2022/0047714 A1 2/2022 Mulligan et al.
2022/0056092 A1 2/2022 Ols et al.
2022/0073585 A1 3/2022 Fehniger et al.
2022/0073597 A1 3/2022 Young et al.
2022/0088070 A1 3/2022 Albertson et al.
2022/0089589 A1 3/2022 Gray et al.
2022/0098251 A1 3/2022 Fischer et al.
2022/0118019 A1 4/2022 Benton et al.
2022/0119544 A1 4/2022 Elliott et al.
2022/0125840 A1 4/2022 Qin et al.
2022/0127329 A1 4/2022 Gershovich et al.
2022/0135699 A1 5/2022 Chang
2022/0152110 A1 5/2022 Kaufman et al.
2022/0153838 A1 5/2022 Kochenderfer
2022/0154191 A1 5/2022 Rehm et al.
2022/0162555 A1 5/2022 Meissner et al.
2022/0169694 A1 6/2022 Bot et al.
2022/0169984 A1 6/2022 Ding et al.
2022/0170044 A1 6/2022 Cobbold et al.
2022/0177573 A1 6/2022 Kvalheim et al.
2022/0185858 A1 6/2022 Li et al.
2022/0185880 A1 6/2022 Wang et al.
2022/0185882 A1 6/2022 Staunton et al.
2022/0193136 A1 6/2022 Chen et al.
2022/0195010 A1 6/2022 Bitter et al.
2022/0204619 A1 6/2022 Kochenderfer
2022/0211761 A1 7/2022 Sadelain et al.
2022/0218748 A1 7/2022 Scheinberg et al.
2022/0220200 A1 7/2022 Tan et al.
2022/0227865 A1 7/2022 Schrepfer et al.
2022/0233593 A1 7/2022 Trager et al.
2022/0241327 A1 8/2022 Ma et al.
2022/0249558 A1 8/2022 Benton et al.
2022/0249568 A1 8/2022 Yao et al.
2022/0249631 A1 8/2022 Susarchick et al.
2022/0249638 A1 8/2022 Wu et al.
2022/0257659 A1 8/2022 Pul et al.
2022/0265708 A1 8/2022 Xiao et al.
2022/0265717 A1 8/2022 Shiku et al.
2022/0265722 A1 8/2022 Li et al.
2022/0273710 A1 9/2022 Pul et al.
2022/0275334 A1 9/2022 Delaney et al.
2022/0280642 A1 9/2022 Gilbert
2022/0281971 A1 9/2022 Shimasaki et al.
2022/0289814 A1 9/2022 Fan et al.
2022/0290103 A1 9/2022 Patterson et al.
2022/0298223 A1 9/2022 Maher et al.
2022/0298240 A1 9/2022 Jiao et al.
2022/0306698 A1 9/2022 Frost et al.
2022/0306988 A1 9/2022 Slukvin et al.
2022/0313720 A1 10/2022 Lobb et al.
2022/0313738 A1 10/2022 Fan et al.
2022/0323004 A1 10/2022 Balagurunathan et al.
2022/0331358 A1 10/2022 Schrepfer et al.
2022/0332780 A1 10/2022 Elpek et al.
2022/0348633 A1 11/2022 Ma et al.
2022/0348649 A1 11/2022 Aftab
2022/0348871 A1 11/2022 Kim et al.
2022/0356260 A1 11/2022 Pul et al.
2022/0364055 A1 11/2022 Treanor et al.
2022/0378829 A1 12/2022 Terrett et al.
2022/0378830 A1 12/2022 Garcia et al.
2022/0387488 A1 12/2022 Terrett et al.
2022/0387571 A1 12/2022 Terrett et al.
2022/0387572 A1 12/2022 Terrett et al.
2022/0411754 A1 12/2022 Trager et al.
2023/0002471 A1 1/2023 Leong et al.
2023/0004622 A1 1/2023 Ekron
2023/0028399 A1 1/2023 Rajangam et al.
2023/0046228 A1 2/2023 Yu et al.
2023/0159892 A1 5/2023 Penaflor et al.
2023/0172980 A1 6/2023 Li et al.
2023/0183313 A1 6/2023 Zhang et al.

(56) References Cited

U.S. PATENT DOCUMENTS

| | | | |
|---|---|---|---|
| 2023/0190814 | A1 | 6/2023 | Ramsborg et al. |
| 2023/0212319 | A1 | 7/2023 | Chaudhary |
| 2023/0220343 | A1 | 7/2023 | Campana et al. |
| 2023/0265390 | A1 | 8/2023 | Trager et al. |
| 2023/0296273 | A1 | 9/2023 | Han et al. |
| 2023/0346838 | A1 | 11/2023 | Pule et al. |
| 2023/0390392 | A1 | 12/2023 | Trager et al. |
| 2024/0025962 | A1 | 1/2024 | Orentas et al. |
| 2024/0092862 | A1 | 3/2024 | Campana et al. |
| 2024/0191196 | A1 | 6/2024 | Campana et al. |
| 2024/0335536 | A1 | 10/2024 | Trager et al. |
| 2024/0358758 | A1 | 10/2024 | Shook et al. |
| 2024/0360234 | A1 | 10/2024 | Trager et al. |

FOREIGN PATENT DOCUMENTS

| | | | |
|---|---|---|---|
| CN | 102924596 | A | 2/2013 |
| CN | 103113470 | A | 5/2013 |
| CN | 105838677 | | 8/2016 |
| CN | 105985931 | | 10/2016 |
| CN | 106085958 | A | 11/2016 |
| CN | 106459914 | A | 2/2017 |
| CN | 107109363 | A | 8/2017 |
| CN | 107567461 | | 1/2018 |
| CN | 107636015 | A | 1/2018 |
| CN | 107709548 | A | 2/2018 |
| CN | 107827990 | | 3/2018 |
| CN | 108840930 | A | 11/2018 |
| CN | 109320615 | A | 2/2019 |
| CN | 110623979 | A | 12/2019 |
| CN | 112143707 | | 12/2020 |
| EP | 0129191 | A1 | 12/1984 |
| EP | 0138494 | A2 | 4/1985 |
| EP | 0210350 | A1 | 2/1987 |
| EP | 0952213 | A1 | 10/1999 |
| EP | 830599 | B1 | 4/2000 |
| EP | 1231262 | A1 | 8/2002 |
| EP | 1306427 | A1 | 5/2003 |
| EP | 1053301 | B1 | 4/2004 |
| EP | 1645291 | A1 | 4/2006 |
| EP | 1233058 | B1 | 12/2006 |
| EP | 1820017 | A2 | 8/2007 |
| EP | 1036327 | B1 | 7/2009 |
| EP | 2411507 | A1 | 2/2012 |
| EP | 2493485 | A1 | 9/2012 |
| EP | 2493486 | A1 | 9/2012 |
| EP | 2141997 | B1 | 10/2012 |
| EP | 2593542 | A1 | 5/2013 |
| EP | 2614151 | A1 | 7/2013 |
| EP | 2756521 | A2 | 7/2014 |
| EP | 2537416 | B1 | 11/2014 |
| EP | 2856876 | A1 | 4/2015 |
| EP | 2866834 | A1 | 5/2015 |
| EP | 2893003 | A1 | 7/2015 |
| EP | 2903637 | A1 | 8/2015 |
| EP | 2904106 | A2 | 8/2015 |
| EP | 2948544 | A1 | 12/2015 |
| EP | 2956175 | A1 | 12/2015 |
| EP | 2961831 | A1 | 1/2016 |
| EP | 2964753 | A1 | 1/2016 |
| EP | 2968492 | A1 | 1/2016 |
| EP | 2968601 | A1 | 1/2016 |
| EP | 2970426 | A2 | 1/2016 |
| EP | 2970482 | A1 | 1/2016 |
| EP | 2986636 | A1 | 2/2016 |
| EP | 2593540 | A1 | 3/2016 |
| EP | 3008173 | A2 | 4/2016 |
| EP | 3012268 | A1 | 4/2016 |
| EP | 2614077 | B1 | 8/2016 |
| EP | 3057986 | A1 | 8/2016 |
| EP | 3063175 | A2 | 9/2016 |
| EP | 3071221 | A1 | 9/2016 |
| EP | 3071222 | A1 | 9/2016 |
| EP | 3071223 | A1 | 9/2016 |
| EP | 3083671 | A1 | 10/2016 |
| EP | 3083691 | A2 | 10/2016 |
| EP | 3094653 | A1 | 11/2016 |
| EP | 3105318 | A1 | 12/2016 |
| EP | 3105335 | A1 | 12/2016 |
| EP | 3115373 | A1 | 1/2017 |
| EP | 3115573 | A1 | 1/2017 |
| EP | 3126380 | A1 | 2/2017 |
| EP | 3134432 | A2 | 3/2017 |
| EP | 3180359 | A1 | 6/2017 |
| EP | 2649086 | B1 | 7/2017 |
| EP | 3189132 | A1 | 7/2017 |
| EP | 3230321 | A2 | 10/2017 |
| EP | 3240805 | A1 | 11/2017 |
| EP | 3313872 | A1 | 5/2018 |
| EP | 3214091 | B1 | 10/2018 |
| EP | 3474867 | A1 | 5/2019 |
| EP | 3483182 | A1 | 5/2019 |
| EP | 3539986 | A1 | 9/2019 |
| EP | 3556772 | A1 | 10/2019 |
| EP | 3567049 | | 11/2019 |
| EP | 3630132 | A1 | 4/2020 |
| EP | 3641768 | A1 | 4/2020 |
| EP | 3684820 | A1 | 7/2020 |
| EP | 3690033 | A1 | 8/2020 |
| EP | 3119425 | B1 | 9/2020 |
| EP | 3766895 | A1 | 1/2021 |
| EP | 3798233 | A1 | 3/2021 |
| EP | 3851110 | A1 | 7/2021 |
| EP | 3864142 | A1 | 8/2021 |
| EP | 3914619 | A1 | 12/2021 |
| EP | 3962535 | A1 | 3/2022 |
| EP | 3989986 | A1 | 5/2022 |
| EP | 4004193 | A1 | 6/2022 |
| EP | 4032092 | A1 | 7/2022 |
| EP | 4067382 | A1 | 10/2022 |
| EP | 4103204 | A1 | 12/2022 |
| JP | 2016-514462 | | 5/2016 |
| JP | 2017-112982 | A | 6/2017 |
| JP | 2017-515506 | | 6/2017 |
| JP | 2019-505498 | A | 2/2019 |
| KR | 10-2660336 | B1 | 4/2024 |
| WO | 92/17198 | A1 | 10/1992 |
| WO | WO 1995/007358 | | 3/1995 |
| WO | WO 1996/023814 | | 8/1996 |
| WO | WO 1996/024671 | | 8/1996 |
| WO | WO 1996/041163 | A1 | 12/1996 |
| WO | WO 1997/023613 | | 7/1997 |
| WO | WO 1998/026061 | | 6/1998 |
| WO | WO 1999/000494 | | 1/1999 |
| WO | WO 1999/038954 | A1 | 8/1999 |
| WO | WO 1999/06557 | | 11/1999 |
| WO | WO 1999/057268 | | 11/1999 |
| WO | WO 2000/014257 | | 3/2000 |
| WO | WO/0023573 | | 4/2000 |
| WO | WO 2001/029191 | A1 | 4/2001 |
| WO | WO 2001/038494 | A1 | 5/2001 |
| WO | WO 2002/010350 | A1 | 2/2002 |
| WO | WO 2002/033101 | | 4/2002 |
| WO | WO 2002/077029 | | 10/2002 |
| WO | 03/26693 | A2 | 4/2003 |
| WO | WO 2003/089616 | | 10/2003 |
| WO | WO 2004/027036 | A3 | 1/2004 |
| WO | WO 2004/027036 | A2 | 4/2004 |
| WO | WO 2004/039840 | | 5/2004 |
| WO | WO 2004/091657 | | 10/2004 |
| WO | 2005/000890 | A1 | 1/2005 |
| WO | WO 2005/044996 | A2 | 5/2005 |
| WO | WO 2005/118788 | A2 | 12/2005 |
| WO | WO 2006/036445 | | 4/2006 |
| WO | WO 2006/052534 | | 5/2006 |
| WO | WO 2006//061626 | A3 | 7/2006 |
| WO | WO 2006/089133 | | 8/2006 |
| WO | 2006/093605 | A1 | 9/2006 |
| WO | 2006/112869 | A2 | 10/2006 |
| WO | 2006/119115 | A2 | 11/2006 |
| WO | WO 2006/121852 | | 11/2006 |
| WO | WO 2007/046006 | | 4/2007 |
| WO | WO 2008/121420 | A1 | 10/2008 |
| WO | 2009/073905 | A2 | 6/2009 |

(56) References Cited

FOREIGN PATENT DOCUMENTS

| | | | |
|---|---|---|---|
| WO | WO 2009/091826 | | 7/2009 |
| WO | WO 2009/117566 | A1 | 9/2009 |
| WO | 2009/126789 | A2 | 10/2009 |
| WO | WO 2010/071836 | | 6/2010 |
| WO | 2010/095031 | A2 | 8/2010 |
| WO | WO 2010/110734 | A1 | 9/2010 |
| WO | WO 2011/020047 | | 2/2011 |
| WO | WO 2011/053321 | | 5/2011 |
| WO | WO 2011/053322 | A1 | 5/2011 |
| WO | 2011/069019 | A2 | 6/2011 |
| WO | WO 2011/080740 | | 7/2011 |
| WO | WO 2011/150976 | | 12/2011 |
| WO | 2012/007646 | A1 | 1/2012 |
| WO | WO 2012/009422 | A1 | 1/2012 |
| WO | 2012/040323 | A2 | 3/2012 |
| WO | WO 2012/031744 | A1 | 3/2012 |
| WO | WO 2012/071411 | | 5/2012 |
| WO | 2012/078540 | A1 | 6/2012 |
| WO | WO 2012/079000 | | 6/2012 |
| WO | WO 2012/136231 | | 10/2012 |
| WO | 2013/043196 | A1 | 3/2013 |
| WO | WO 2013/040371 | | 3/2013 |
| WO | WO 2013/040557 | A2 | 3/2013 |
| WO | WO 2013/040557 | A3 | 3/2013 |
| WO | 2013/123720 | A1 | 8/2013 |
| WO | 2013/123726 | A1 | 8/2013 |
| WO | WO 2013/126720 | A2 | 8/2013 |
| WO | WO 2013/126726 | A1 | 8/2013 |
| WO | WO 2013/138244 | A2 | 9/2013 |
| WO | WO 2014/005072 | | 1/2014 |
| WO | WO 2014/011993 | A2 | 1/2014 |
| WO | WO 2014/055413 | A2 | 4/2014 |
| WO | WO 2014/055442 | A2 | 4/2014 |
| WO | WO 2014/055657 | A1 | 4/2014 |
| WO | WO 2014/055668 | A1 | 4/2014 |
| WO | WO 2014/099671 | A1 | 6/2014 |
| WO | WO 2014/117121 | | 7/2014 |
| WO | WO 2014/127261 | A1 | 8/2014 |
| WO | WO 2014/134165 | A1 | 9/2014 |
| WO | WO 2014/138704 | A1 | 9/2014 |
| WO | WO 2014/145252 | A2 | 9/2014 |
| WO | WO 2014/153270 | A1 | 9/2014 |
| WO | WO 2014/164554 | A1 | 10/2014 |
| WO | WO 2014/172584 | A1 | 10/2014 |
| WO | WO 2014/186469 | | 11/2014 |
| WO | WO 2014/201021 | A2 | 12/2014 |
| WO | 2015/042661 | A2 | 4/2015 |
| WO | WO 2015/058018 | A1 | 4/2015 |
| WO | WO 2015/066551 | A2 | 5/2015 |
| WO | WO 2015/075468 | A1 | 5/2015 |
| WO | WO 2015/075469 | A1 | 5/2015 |
| WO | WO 2015/075470 | A1 | 5/2015 |
| WO | WO 2015/092024 | A2 | 6/2015 |
| WO | WO 2015/095895 | A1 | 6/2015 |
| WO | WO 2015/105522 | A1 | 7/2015 |
| WO | WO 2015/120421 | A1 | 7/2015 |
| WO | WO 2015/123642 | A1 | 8/2015 |
| WO | WO 2015/142314 | A1 | 9/2015 |
| WO | WO 2015/142661 | A1 | 9/2015 |
| WO | WO 2015/150771 | A1 | 10/2015 |
| WO | WO 2015/154012 | A1 | 10/2015 |
| WO | WO 2015/164759 | A2 | 10/2015 |
| WO | WO 2015/174928 | | 11/2015 |
| WO | 2015/188119 | A1 | 12/2015 |
| WO | 2015/193411 | A1 | 12/2015 |
| WO | WO 2015/187528 | A1 | 12/2015 |
| WO | 2016/014565 | A2 | 1/2016 |
| WO | 2016/014576 | A1 | 1/2016 |
| WO | WO 2016/011210 | A2 | 1/2016 |
| WO | WO 2016/025880 | A1 | 2/2016 |
| WO | 2016/044605 | A1 | 3/2016 |
| WO | WO 2016/030691 | A1 | 3/2016 |
| WO | WO 2016/033331 | A1 | 3/2016 |
| WO | WO 2016/033690 | A1 | 3/2016 |
| WO | WO 2016/040441 | A1 | 3/2016 |
| WO | WO 2016/042041 | A1 | 3/2016 |
| WO | WO 2016/042461 | A1 | 3/2016 |
| WO | WO 2016/061574 | A1 | 4/2016 |
| WO | WO 2016/069607 | | 5/2016 |
| WO | WO 2016/073602 | A2 | 5/2016 |
| WO | WO 2016/073629 | A1 | 5/2016 |
| WO | WO 2016/073755 | A2 | 5/2016 |
| WO | WO 2016/075612 | A1 | 5/2016 |
| WO | 2016/100232 | A1 | 6/2016 |
| WO | WO 2016/090034 | A2 | 6/2016 |
| WO | WO 2016/100985 | A2 | 6/2016 |
| WO | 2016/118857 | A1 | 7/2016 |
| WO | WO 2016/109410 | A2 | 7/2016 |
| WO | WO 2016/109661 | A1 | 7/2016 |
| WO | WO 2016/109668 | A1 | 7/2016 |
| WO | WO 2016/115482 | A1 | 7/2016 |
| WO | 2016/126213 | A1 | 8/2016 |
| WO | 2016/134284 | A1 | 8/2016 |
| WO | WO 2016/123122 | A1 | 8/2016 |
| WO | WO 2016/123333 | A1 | 8/2016 |
| WO | WO 2016/124765 | A1 | 8/2016 |
| WO | WO 2016/124930 | A1 | 8/2016 |
| WO | WO 2016/126608 | A1 | 8/2016 |
| WO | 2016/138491 | A1 | 9/2016 |
| WO | 2016/139487 | A1 | 9/2016 |
| WO | 2016/149264 | A1 | 9/2016 |
| WO | WO 2016/13849 | A1 | 9/2016 |
| WO | WO 2016/141357 | A1 | 9/2016 |
| WO | WO 2016/142314 | | 9/2016 |
| WO | WO 2016/149254 | A1 | 9/2016 |
| WO | WO 2016/151315 | A1 | 9/2016 |
| WO | WO 2016/154055 | A1 | 9/2016 |
| WO | WO 2016/154585 | A1 | 9/2016 |
| WO | 2016/160721 | A1 | 10/2016 |
| WO | 2016/164731 | A2 | 10/2016 |
| WO | 2016/168773 | A2 | 10/2016 |
| WO | WO 2016/172537 | A1 | 10/2016 |
| WO | WO 2016/172583 | A1 | 10/2016 |
| WO | WO 2016/174405 | A1 | 11/2016 |
| WO | WO 2016/174406 | A1 | 11/2016 |
| WO | WO 2016/174407 | A1 | 11/2016 |
| WO | WO 2016/174408 | A1 | 11/2016 |
| WO | WO 2016/174409 | A1 | 11/2016 |
| WO | WO 2016/174461 | A1 | 11/2016 |
| WO | WO 2016/174652 | A1 | 11/2016 |
| WO | WO 2016/179684 | A1 | 11/2016 |
| WO | 2016/191567 | A1 | 12/2016 |
| WO | 2016/191756 | A1 | 12/2016 |
| WO | WO 2016/191587 | A1 | 12/2016 |
| WO | WO 2016/191755 | A1 | 12/2016 |
| WO | WO 2016/196388 | A1 | 12/2016 |
| WO | WO 2016/197108 | A1 | 12/2016 |
| WO | WO 2016/201304 | A1 | 12/2016 |
| WO | WO 2016/210293 | A1 | 12/2016 |
| WO | WO 2017/004150 | A1 | 1/2017 |
| WO | WO 2017/011804 | A1 | 1/2017 |
| WO | 2017/015783 | A1 | 2/2017 |
| WO | 2017/024318 | A1 | 2/2017 |
| WO | 2017/027325 | A1 | 2/2017 |
| WO | 2017/029512 | A1 | 2/2017 |
| WO | WO 2017/021701 | A1 | 2/2017 |
| WO | WO 2017/023859 | A1 | 2/2017 |
| WO | WO 2017/024131 | | 2/2017 |
| WO | WO 2017/025038 | A1 | 2/2017 |
| WO | WO 2017/028374 | | 2/2017 |
| WO | WO 2017/029511 | A1 | 2/2017 |
| WO | 2017/040324 | A1 | 3/2017 |
| WO | WO 2017/032777 | A1 | 3/2017 |
| WO | WO 2017/034615 | A1 | 3/2017 |
| WO | WO 2017/037083 | A1 | 3/2017 |
| WO | WO 2017/041749 | A1 | 3/2017 |
| WO | WO 2017/049166 | A1 | 3/2017 |
| WO | WO 2017/058752 | A1 | 4/2017 |
| WO | WO 2017/058753 | A1 | 4/2017 |
| WO | WO 2017/058850 | A1 | 4/2017 |
| WO | WO 2017/062820 | A1 | 4/2017 |
| WO | WO 2017/062952 | A1 | 4/2017 |
| WO | WO 2017/069958 | A2 | 4/2017 |
| WO | 2017/075440 | A1 | 5/2017 |

(56) References Cited

FOREIGN PATENT DOCUMENTS

WO 2017/079694 A2 5/2017
WO WO 2017/079673 A1 5/2017
WO WO 2017/079705 A1 5/2017
WO WO 2017/079881 A1 5/2017
WO WO 2017/093969 6/2017
WO WO 2017/096329 A1 6/2017
WO WO 2017/100176 A1 6/2017
WO 2017/123548 A1 7/2017
WO WO 2017/127729 A1 7/2017
WO WO 2017/127755 A1 7/2017
WO 2017/172981 A2 10/2017
WO WO 2017/172952 10/2017
WO WO 2017/182643 10/2017
WO 2017/186928 A1 11/2017
WO WO 2017/192440 11/2017
WO WO 2017/214207 12/2017
WO WO 2017/222593 12/2017
WO 2018/006882 A1 1/2018
WO WO 2018/013918 1/2018
WO WO 2018/022646 2/2018
WO WO 2018/023025 2/2018
WO WO 2018/026819 2/2018
WO 2018/057915 A1 3/2018
WO WO 2018/049248 A1 3/2018
WO 2018/064602 A1 4/2018
WO WO 2018/075807 4/2018
WO 2018/081476 A2 5/2018
WO 2018/098363 A2 5/2018
WO WO 2018/089476 5/2018
WO 2018/106732 A1 6/2018
WO WO 2018/103503 6/2018
WO 2018/126074 A1 7/2018
WO WO 2018/124766 7/2018
WO WO 2018/136762 A1 7/2018
WO 2018/160993 A1 9/2018
WO WO 2018/161017 9/2018
WO WO 2018/170458 A1 9/2018
WO WO 2018/170506 A1 9/2018
WO 2018/195339 A1 10/2018
WO WO2018/182511 10/2018
WO WO 2018/183385 10/2018
WO 2018/223101 A1 12/2018
WO 2018/237022 A1 12/2018
WO 2019/006418 A2 1/2019
WO 2019/028051 A1 2/2019
WO 2019/055896 A1 3/2019
WO 2019/057100 A1 3/2019
WO 2019/077037 A1 4/2019
WO WO 2019/062817 4/2019
WO WO 2019/075395 A1 4/2019
WO 2019/089884 A2 5/2019
WO 2019/090004 A1 5/2019
WO 2019/091478 A1 5/2019
WO 2019/112899 A2 6/2019
WO WO 2019/112347 A2 6/2019
WO WO 2019/118885 6/2019
WO WO 2019/126574 6/2019
WO 2019/129220 A1 7/2019
WO 2019/138354 A1 7/2019
WO 2019/140100 A1 7/2019
WO WO 2019/129002 7/2019
WO WO 2019/133793 7/2019
WO 2019/149269 A1 8/2019
WO 2019/154313 A1 8/2019
WO 2019/155286 A2 8/2019
WO 2019/155288 A1 8/2019
WO 2019/165121 A1 8/2019
WO 2019/169290 A1 9/2019
WO 2019/173324 A1 9/2019
WO 2019/193476 A1 10/2019
WO 2019/199689 A1 10/2019
WO 2019/209991 A1 10/2019
WO 2019/213610 A1 11/2019
WO 2019/220109 A1 11/2019
WO WO 2019/217253 11/2019
WO 2019/241426 A1 12/2019
WO 2019/246546 A1 12/2019
WO 2020/011706 A1 1/2020
WO 2020/014271 A1 1/2020
WO 2020/018922 A1 1/2020
WO 2020/028654 A1 2/2020
WO 2020/030979 A2 2/2020
WO 2020/044239 A1 3/2020
WO 2020/047452 A2 3/2020
WO 2020/055932 A2 3/2020
WO 2020/056045 A1 3/2020
WO WO 2020/055862 A1 3/2020
WO 2020/065330 A2 4/2020
WO 2020/069405 A1 4/2020
WO 2020/069409 A1 4/2020
WO 2020/072536 A1 4/2020
WO 2020/086742 A1 4/2020
WO WO 2020/077356 4/2020
WO WO 2020/083282 4/2020
WO 2020/092057 A1 5/2020
WO 2020/092850 A1 5/2020
WO 2020/108090 A1 6/2020
WO 2020/112563 A1 6/2020
WO 2020/112975 A1 6/2020
WO 2020/113029 A2 6/2020
WO 2020/113188 A2 6/2020
WO 2020/113194 A2 6/2020
WO 2020/123716 A1 6/2020
WO 2020/124021 A1 6/2020
WO 2020/132039 A2 6/2020
WO 2020/146250 A1 7/2020
WO 2020/150534 A2 7/2020
WO 2020/172440 A1 8/2020
WO 2020/176740 A1 9/2020
WO 2020/180551 A1 9/2020
WO 2020/180882 A1 9/2020
WO 2020/185121 A2 9/2020
WO WO 2020/181221 9/2020
WO WO 2020/190737 9/2020
WO 2020/163755 A9 10/2020
WO 2020/193628 A1 10/2020
WO 2020/198128 A1 10/2020
WO 2020/200325 A1 10/2020
WO WO 2020/210232 10/2020
WO 2020/172643 A3 11/2020
WO 2020/222176 A1 11/2020
WO 2020/231819 A1 11/2020
WO WO 2020/223327 11/2020
WO WO 2020/224606 11/2020
WO WO 2020233589 11/2020
WO 2020/247392 A1 12/2020
WO 2020/253879 A1 12/2020
WO WO 2021/009694 1/2021
WO 2021/020559 A1 2/2021
WO 2021/021907 A1 2/2021
WO 2021/021989 A1 2/2021
WO 2021/035054 A1 2/2021
WO 2021/037221 A1 3/2021
WO 2021/038036 A1 3/2021
WO 2021/041617 A1 3/2021
WO 2021/044373 A2 3/2021
WO 2021/050789 A1 3/2021
WO 2021/055616 A1 3/2021
WO 2021/061832 A1 4/2021
WO 2021/108455 A1 6/2021
WO 2021/108671 A1 6/2021
WO 2021/121193 A1 6/2021
WO 2021/150078 A1 7/2021
WO 2021/150760 A2 7/2021
WO 2021/157601 A1 8/2021
WO 2021/163391 A1 8/2021
WO 2021/168375 A1 8/2021
WO 2021/188681 A1 9/2021
WO WO 2021/173471 9/2021
WO 2021/202604 A1 10/2021
WO 2021/207290 A1 10/2021
WO WO 2021/205173 10/2021
WO 2021/221782 A1 11/2021
WO 2021/252804 A1 12/2021

(56) References Cited

FOREIGN PATENT DOCUMENTS

| | | | |
|---|---|---|---|
| WO | WO 2022/012683 | | 1/2022 |
| WO | WO 2022/036224 | | 2/2022 |
| WO | 2022/120370 | A2 | 6/2022 |
| WO | 2022/125837 | A1 | 6/2022 |
| WO | WO 2022/120107 | | 6/2022 |
| WO | WO 2022/133057 | | 6/2022 |
| WO | 2022/146891 | A2 | 7/2022 |
| WO | 2022/147444 | A2 | 7/2022 |
| WO | 2022/161355 | A1 | 8/2022 |
| WO | 2022/179563 | A1 | 9/2022 |
| WO | 2022/197762 | A1 | 9/2022 |
| WO | 2022/204282 | A1 | 9/2022 |
| WO | 2022/212384 | A1 | 10/2022 |
| WO | WO 2022/216811 | | 10/2022 |
| WO | WO 2022/216963 | | 10/2022 |
| WO | 2022/241036 | A1 | 11/2022 |
| WO | 2022/251120 | A2 | 12/2022 |
| WO | 2023/004425 | A2 | 1/2023 |
| WO | 2023/280307 | A1 | 1/2023 |
| WO | WO 2023/003809 | | 1/2023 |
| WO | 2023/069936 | A1 | 4/2023 |
| WO | 2023/108150 | A1 | 6/2023 |
| WO | WO 2023/122337 | | 6/2023 |
| WO | WO 2023/164256 | | 8/2023 |
| WO | 2023/172879 | A2 | 9/2023 |
| WO | WO 2023/228093 | | 11/2023 |
| WO | WO 2023/240042 | | 12/2023 |
| WO | WO 2023/240064 | | 12/2023 |
| WO | 2024/006925 | A2 | 1/2024 |
| WO | 2024/056809 | A1 | 3/2024 |

OTHER PUBLICATIONS

U.S. Appl. No. 15/337,854 (U.S. Pat. No. 10,538,739), filed Oct. 28, 2016 (Jan. 21, 2020), Chimeric Receptor With NKG2D Specificity for Use in Cell Therapy Against Cancer and Infectious Disease.

U.S. Appl. No. 15/857,147 (U.S. Pat. No. 10,801,012), filed Dec. 28, 2017 (Oct. 13, 2020), Chimeric Receptor With NKG2D Specificity for Use in Cell Therapy Against Cancer and Infectious Disease.

U.S. Appl. No. 15/857,166 (U.S. Pat. No. 10,774,309), filed Dec. 28, 2017 (Sep. 15, 2020), Natural Killer Cell Immunotherapy for Treating Cancer.

U.S. Appl. No. 15/857,268 (U.S. Pat. No. 10,829,737), filed Dec. 28, 2017 (Nov. 11, 2020), Chimeric Receptor With NKG2D Specificity for Use in Cell Therapy Against Cancer and Infectious Disease.

U.S. Appl. No. 15/857,315 (U.S. Pat. No. 10,836,999), filed Dec. 28, 2017 (Nov. 17, 2020), Chimeric Receptor With NKG2D Specificity for Use in Cell Therapy Against Cancer and Infectious Disease.

U.S. Appl. No. 17/067,016, filed Oct. 9, 2020, Chimeric Receptor With NKG2D Specificity for Use in Cell Therapy Against Cancer and Infectious Disease.

U.S. Appl. No. 16/550,548 (U.S. Pat. No. 10,774,311), filed Aug. 26, 2019 (Sep. 15, 2020), Natural Killer Cells Modified to Express Membrane-Bound Interleukin 15 and Uses Thererof.

U.S. Appl. No. 16/986,742, filed Aug. 6, 2020, Natural Killer Cells Modified to Express Membrane-Bound Interleukin 15 and Uses Thererof.

U.S. Appl. No. 15/309,362 (U.S. Pat. No. 10,428,305), filed Nov. 7, 2016 (Oct. 1, 2019), Modified Natural Killer Cells and Uses Thereof.

U.S. Appl. No. 16/497,678, filed Sep. 25, 2019, Truncated NKG2D Chimeric Receptors and Uses Thereof in Natual Killer Cell Immunotherapy.

U.S. Appl. No. 16/497,682, filed Sep. 25, 2019, Stimulatory Cell Lines for Ex Vivo Expansion and Activation of Natural Killer Cells.

U.S. Appl. No. 16/967,888, filed Aug. 6, 2020, Adhesion Receptor Constructs and Uses Thereof in Natural Killer Cell Immunotherapy.

U.S. Appl. No. 16/967,881, filed Aug. 6, 2020, Activating Chimeric Receptors and Uses Thereof in Natural Killer Cell Immunotherapy.

U.S. Appl. No. 11/074,525 (U.S. Pat. No. 7,435,596), filed Mar. 8, 2005 (Oct. 14, 2008), Modified Cell Line and Method for Expansion of NK Cell.

U.S. Appl. No. 12/206,204 (U.S. Pat. No. 8,026,097), filed Sep. 8, 2008 (Sep. 27, 2011), Expansion of NK Cells and Therapeutic Uses Thereof.

U.S. Appl. No. 15/802,968, filed Nov. 3, 2017, Methods for Expanding Immune Cells.

U.S. Appl. No. 17/274,022, filed Mar. 5, 2021, Natural Killer Cell Compositions and Immunotherapy Methods for Treating Tumors.

U.S. Appl. No. 17/309,209, filed May 6, 2021, Methods for the Simultaneous Expansion of Multiple Immune Cell Types, Related Compositions and Uses of Same in Cancer Immunotherapy.

U.S. Appl. No. 17/089,449 (U.S. Pat. No. 11,253,547), filed Nov. 4, 2020 (Feb. 22, 2022), CD19-Directed Chimeric Antigen Receptors and Uses Thereof in Immunotherapy.

U.S. Appl. No. 17/089,578 (U.S. Pat. No. 11,141,436), filed Nov. 4, 2020 (Oct. 12, 2021), Immune Cells Engineered to Express CD19-Directed Chimeric Antigen Receptors and Uses Thereof in Immunotherapy.

U.S. Appl. No. 17/089,474 (U.S. Pat. No. 11,154,575), filed Nov. 4, 2020 (Oct. 26, 2021), Cancer Immunotherapy Using CD19-Directed Chimeric Antigen Receptors.

U.S. Appl. No. 17/571,325, filed Jan. 7, 2022, CD19-Directed Chimeric Antigen Receptors and Uses Thereof in Immunotherapy.

U.S. Appl. No. 17/628,105, filed Jan. 18, 2022, Methods and Compositions for Enhanced Expansion and Cytotoxicity of Natural Killer Cells.

U.S. Appl. No. 17/596,166, filed Dec. 3, 2021, Combinations of Engineered Natural Killer Cells and Engineered T Cells for Immunotherapy.

U.S. Appl. No. 17/303,952, filed Jun. 10, 2021, Genetically Modified Natural Killer Cells for CD70-Directed Cancer Immunotherapy.

Abken et al., "Chimeric T-cell receptors: highly specific tools to target cytotoxic T-lymphocytes to tumour cells," Cancer Treat Rev., 23(2):97-112, Mar. 1997.

Abken, H., et al., "Tuning tumor-specific T-cell activation: a matter of costimulation?" Trends in Immunol. 23: 240-245 (2002).

Aguera-Gonzales et al. 2011, Eur. J. Immunol. 41:3667-3676.

Alderson et al., "Molecular and Biological Characterization of Human 4-1BB and its Ligand," Eur. J. Immunol., 1994, 24: 2219-2227.

Allison and Lanier, "Structure, function, and serology of the T-cell antigen receptor complex," Annu Rev Immunol, 1987, 5:503-40.

Alvarez-Vallina, L. and Hawkins, R.E., "Antigen-specific targeting of CD28-mediated T cell co-stimulation using chimeric single-chain antibody variable fragment—CD28 receptors," Eur. J. Immunol. 26: 2304-2309 (1996).

Ang S.O. et al, "Avoiding the need for clinical-grade OKT3: ex vivo expansion of T cells using artificial antigen presenting cells genetically modified to crosslink CD3." Biology of Blood and Marrow Transplantation, Jan. 9, 2012, vol. 18, No. 2, pp. S258.

Annenkov, A., and Chernajovsky, Y., "Engineering mouse T lymphocytes specific to type II collagen bytransduction with a chimeric receptor consisting of a single chain Fv and TCR zeta," Gene Therapy 7: 714-722 (2000).

Antony, G.K., et al., "Interleukin 2 in cancer therapy," Curr Med Chem., 17(29): 3297-3302 (2010).

Aoudjit and Vuori., "Integrin Signaling in Cancer Cell Survival and Chemoresistance," Chemotherapy Research and Practice., 2012(Article ID 283181), 16 pages, 2012.

Appelbaum, "Haematopoietic cell transplantation as immunotherapy," Nature, 2001, 411(6835): 385-9.

ATCC No. CCL-243, 1975.

Baek, H.J. et al., "Ex vivo expansion of natural killer cells using cryopreserved irradiated feeder cells," Anticancer Research, 33: Feb. 20, 2011 (2013).

Barber et al. 2008, Exp. Hematol., 36:1318:1328.

Barber et al. 2009, J. Immunol. 183:6939-6947.

Barber, et al. 2007, Cancer Res 67(10):5003-5008.

Barber, et al. 2011, Gene Therapy 18:509-516.

Barber, et al. 2008, J. Immunol 180:72-78.

(56) References Cited

OTHER PUBLICATIONS

Barber et al. 2009, J. Immunol 183: 2365-2372.
Barrett, D.M., et al., "Chimeric Antigen Receptor Therapy for Cancer," Annu Rev. Med. 65: 333-347 (2014).
Bartholomew et al., "Mesenchymal stem cells suppress lymphocyte proliferation in vitro and prolong skin graft survival in vivo," Exp Hematol, Jan. 2002, 30(1): 42-8.
Batlevi, C.L., et al. "Novel immunotherapies in lymphoid malignancies," Nature Rev. Clin. Oncol. 13:25-40 (2016).
Bedouelle, et al. "Diversity and junction residues as hotspots of binding energy in an antibody neutralizing the dengue virus" the FEBS Journal, (Jan. 2006) 273, 34-46.
Bejcek et al., "Development and Characterization of Three Recombinant Single Chain Antibody Fragments (scFvs) Directed against the CD19 Antigen," Cancer Res., 1995, 55:2346-2351.
Berger, C. et al., "Safety and immunologic effects of IL-15 administration in nonhuman primates," Blood, 114(12): 2417-2426 (2009).
Besser, M.J., et al., "Adoptive Transfer of Tumor-Infiltrating Lymphocytes in Patients with Metastatic Melanoma: Intent-to-Treat Analysis and Efficacy after Failure to Prior Immunotherapies," Clin. Cancer Res. 19: 4792-4800 (2013).
Better et al., "Manufacturing and Characterization of KTE-C19 in a Multicenter Trial of Subjects with Refractory Aggressive Non-Hodgkin Lymphoma (NHL) (ZUMA-1)," Poster session presented at the American Association for Cancer Research Annual Meeting, New Orleans, Louisiana.
Billadeau et al. "NKG2D-DAP10 triggers human NK cell-mediated killing via a Syk-independent regulatory pathway" Nature Immunology (2003), vol. 4, No. 6, pp. 557-564.
Bischof et al., "Autonomous induction of proliferation, JNK and NF-alphaB activation in primary resting T cells by mobilized CD28," Eur J Immunol., 30(3):876-882, Mar. 2000.
Boyman, O. et al., "The role of interleukin-2 during homeostasis and activation of the immune system," Nat Rev Immunol., 12(3): 180-190 (2012).
Brentjens et al., "Eradication of Systemic B-Cell Tumors by Genetically Targeted Human T Lymphocytes Co-Stimulated B Cd80 and Interleukin-15," Nature Medicine, 2003, 9: 279-286.
Brentjens, R.J., et al., "CD19-Targeted T Cells Rapidly Induce Molecular Remissions in Adults with Chemotherapy-Refractory Acute Lymphoblastic Leukemia," Sci. Trans. Med. 5: 1-9 (2013).
Brentjens, R.J., et al., "Safety and persistence of adoptively transferred autologous CD19-targeted T cells in patients with relapsed or chemotherapy refractory B-cell leukemias," Blood 119(18): 4817-4828 (2011).
Bridgeman, J.S., et al., "Building Better Chimeric Antigen Receptors for Adoptive T Cell Therapy," Current Gene Therapy 10: 77-90 (2010).
Brocker et al., "New simplified molecular design for functional T cell receptor," Eur J Immunol., 23(7):1435-1439, Jul. 1993.
Bronte, V., and Mocellin, S., "Suppressive Influences in the Immune Response to Cancer," J. Immunother . 32: 1-11 (2009).
Brown et al. "Tolerance to Single, but Not Multiple, Amino Acid Replacements in Antibody VH CDR2" The Journal of Immunology (May 1, 1996) 156, 3285-3291.
Budagian, V. et al., "IL-15/IL-15 receptor biology: A guided tour through an expanding universe," Cytokine & Growth Factor Reviews, 17(4): 259-280 (2006).
Bukczynski et al., "Costimulation of Human CD28-T Cells by 4-1BB Ligand," Eur. J. Immunol., 2003, 33: 446-454.
Burkett, P.R. et al., "Coordinate expression and trans presentation of interleukin (IL)-15Ralpha and IL-15 supports natural killer cell and memory CD8+ T cell homeostasis," J Exp Med., 200(7): 825-834 (2004).
Caligiuri et al., "Immunotherapeutic approaches for hematologic malignancies," Hematology Am Soc Hematol Educ Program, 2004, 37-53.
Campana et al., "Immunophenotyping of Leukemia," Jour of Immunol Methods, 2000, 243: 59-75.
Caratelli et al., "Fcy Chimeric Receptor—Engineered T Cells: Methodology, Advantages, Limitations, and Clinical Relevance," Front Immunol., vol. 8, Article 457, 8 pages (Apr. 27, 2017).
Cardoso AA, et al. Pre-B acute lymphoblastic leukemia cells may induce T-cell anergy to alloantigen. Blood 88:41-48 (1996).
Carlsten et al., "Genetic manipulation of NK cells for cancer immunotherapy: techniques and clinical implications," Frontiers in Immunology, vol. 6, Article 266, Jun. 2015.
Carson, W.E. et al., "A potential role for interleukin-15 in the regulation of human natural killer cell survival," J Clin Invest., 99(5): 937-943 (1997).
Carter, P., et al., "Identification and validation of cell surface antigens for antibody targeting in oncology," Endocrine-Related Cnacer 11: 659-687 (2004).
Cesano, A., et al. "Reversal of Acute Myelogenous Leukemia in Humanized SCID Mice Using a Novel Adoptive Transfer Approach," J. Clin. Invest. 94: 1076-1084 (1994).
Chambers, C.A., "The expanding world of co-stimulation: the two-signal model revisited," Trends in Immunol., 2001, 22(4):217-223.
Champlin R. "T-cell depletion to prevent graft-versus-host disease after bone marrow transplantation," Hematol Oncol Clin North Am. Jun. 1990;4(3):687-98.
Chang, Y.H. et al., "A chimeric receptor with NKG2D specificity enhances natural killer cell activation and killing of tumor cells," Cancer Res., 73(6): 1777-1786 (2013).
Chertova, E. et al., "Characterization and favorable in vivo properties of heterodimeric soluble IL-15.IL-15Ralpha cytokine compared to IL-15 monomer," J Biol Chem., 288(25): 18093-18103 (2013).
Cheung et al., "Anti-Idiotypic Antibody Facilitates scFv Chimeric Immune Receptor-Gene Transduction and Clonal expansion of Human Lymphocytes for Tumor Therapy," Hybridoma and Hybridomics, 2003, 24(4): 209-218.
Chiorean and Miller, "The biology of natural killer cells and implications for therapy of human disease," J Hematother Stem Cell Res, Aug. 2001, 10(4): 451-63.
Cho, D. et al., "Expansion and activation of natural killer cells for cancer immunotherapy," The Korean Journal of Laboratory Medicine, 29(2): 89-96 (2009).
ClinicalTrials.gov, "A Multi-Center Study Evaluating KTE-C19 in Pediatric and Adolescent Subjects With Relapsed/Refractory B-precursor Acute Lymphoblastic Leukemia (ZUMA-4)," available at https://clinicaltrials.gov/show/NCT02625480, NCT02625480.
ClinicalTrials.gov, "A Phase 1-2 Multi-Center Study Evaluating KTE-C19 in Subjects With Refractory Aggressive Non-Hodgkin Lymphoma (ZUMA-1) (ZUMA-1)," available at https://clinicaltrials.gov/show/NCT02348216, NCT02348216.
ClinicalTrials.gov, "A Phase 2 Multicenter Study Evaluating Subjects With Relapsed/Refractory Mantle Cell Lymphoma (ZUMA-2)," available at https://clinicaltrials.gov/show/NCT02601313, NCT02601313.
ClinicalTrials.gov, "A Study Evaluating KTE-C19 in Adult Subjects With Relapsed/Refractory Bprecursor Acute Lymphoblastic Leukemia (r/r All) (ZUMA-3) (ZUMA-3)," available at https://clinicaltrials.gov/show/NCT02614066, NCT02614066.
ClinicalTrials.gov, "Administration of Anti-CD19-chimeric-antigen-receptor-transduced T Cells From the Original Transplant Donor to Patients With Recurrent or Persistent B-cell Malignancies After Allogeneic Stem Cell Transplantation," available at https://clinicaltrials.gov/show/NCT01087294, NCT01087294.
ClinicalTrials.gov, "Anti-CD19 White Blood Cells for Children and Young Adults With B Cell Leukemia or Lymphoma," available at https://clinicaltrials.gov/show/NCT01593696, NCT01593696.
ClinicalTrials.gov, "CAR T Cell Receptor Immunotherapy for Patients With B-cell Lymphoma," available at https://clinicaltrials.gov/show/NCT00924326, NCT00924326.
ClinicalTrials.gov, "CD19 CAR T Cells for B Cell Malignancies After Allogeneic Transplant," available at https://clinicaltrials.gov/show/NCT01475058, NCT01475058.

(56) References Cited

OTHER PUBLICATIONS

ClinicalTrials.gov, "CD19 Chimeric Receptor Expressing T Lymphocytes in B-Cell Non Hodgkin's Lymphoma, ALL & CLL (CRETI-NH)," available at https://clinicaltrials.gov/show/NCT00586391, NCT00586391.
ClinicalTrials.gov, "CD19+ CAR T Cells for Lymphoid Malignancies," available at https://clinicaltrials.gov/show/NCT02529813, NCT02529813.
ClinicalTrials.gov, "Consolidation Therapy With Autologous T Cells Genetically Targeted to the B Cell Specific Antigen CD19 in Patients With Chronic Lymphocytic Leukemia Following Upfront Chemotherapy With Pentostatin, Cyclophosphamide and Rituximab," available at https://clinicaltrials.gov/show/NCT01416974, NCT01416974.
ClinicalTrials.gov, "Genetically Engineered Lymphocyte Therapy in Treating Patients With B-Cell Leukemia or Lymphoma That is Resistant or Refractory to Chemotherapy," available at https://clinicaltrials.gov/show/NCT01029366, NCT01029366.
ClinicalTrials.gov, "High Dose Therapy and Autologous Stem Cell Transplantation Followed by Infusion of Chimeric Antigen Receptor (CAR) Modified T-Cells Directed Against CD19+ B-Cells for Relapsed and Refractory Aggressive B Cell Non-Hodgkin Lymphoma," available at https://clinicaltrials.gov/show/NCT01840566, NCT01840566.
ClinicalTrials.gov, "In Vitro Expanded Allogeneic Epstein-Barr Virus Specific Cytotoxic Tlymphocytes (EBV-CTLs) Genetically Targeted to the CD19 Antigen in B-cell Malignancies," available at https://clinicaltrials.gov/show/NCT01430390, NCT01430390.
ClinicalTrials.gov, "Precursor B Cell Acute Lymphoblastic Leukemia (B-ALL) Treated With Autologous T Cells Genetically Targeted to the B Cell Specific Antigen CD19," available at https://clinicaltrials.gov/show/NCT01044069, NCT01044069.
ClinicalTrials.gov, "Study Evaluating the Efficacy and Safety of JCAR015 in Adult B-cell Acute Lymphoblastic Leukemia (B-ALL) (Rocket)," available at https://clinicaltrials.gov/show/NCT02535364, NCT02535364.
ClinicalTrials.gov, "T Cells Expressing a Fully-human AntiCD19 Chimeric Antigen Receptor for Treating B-cell Malignancies," available at https://clinicaltrials.gov/show/NCT02659943, NCT02659943.
ClinicalTrials.gov, "T-Lymphocytes Genetically Targeted to the B-Cell Specific Antigen CD19 in Pediatric and Young Adult Patients With Relapsed B-Cell Acute Lymphoblastic Leukemia," available at https://clinicaltrials.gov/show/NCT01860937, NCT01860937.
ClinicalTrials.gov, "Treatment of Relapsed or Chemotherapy Refractory Chronic Lymphocytic Leukemia or Indolent B Cell Lymphoma Using Autologous T Cells Genetically Targeted to the B Cell Specific Antigen CD19", Available at: https://clinicaltrials.gov/show/NCT00466531, NCT00466531.
Colman, P.M., "Effects of amino acid sequence changes on antibody-antigen interactions" Biomolecular Research Institute, (1994) 145, 33-36.
Cooper, M.A. et al., "In vivo evidence for a dependence on interleukin 15 for survival of natural killer cells," Blood, 100(10): 3633-3638 (2002).
Cooper et al., "T-Cell Clones can be Rendered Specific for CD I 9: Toward the Selective Augmentation of the Graft-Versus-B Lineage Leukemia Effect," Blood, 2003, pp. 1637-1644, vol. 101.
Cruz et al., "Infusion of donor-derived CD19-redirected virus-specific T cells for B-cell malignancies relapsed after allogeneic stem cell transplant: a phase 1 study," Blood 122(17):2965-2973 (2013).
Damle et al., "Differential regulatory signals delivered by antibody binding to the CD28 (Tp44) molecule during the activation of human T lymphocytes," J Immunol., 140(6):1753-1761, Mar. 15, 1988.
Darcy, P.K., et al., "Expression in cytotoxic T lymphocytes of a single-chain anti-carcinoembryonic antigen antibody. Redirected Fas ligand-mediated lysis of colon carcinoma," Eur. J. Immunol. 28: 1663-1672 (1998).
Davila, M.L., et al., "Efficacy and Toxicity Management of 19-28z CAR T Cell Therapy in B Cell Acute Lymphoblastic Leukemia," Science Translat. Med. 6(24) (2014).
DeBenedette et al., "Role of 4-1BB ligand in costimulation of T lymphocyte growth and its upregulation on M12 B lymphomas by cAMP," J Exp Med, Mar. 1995, 181(3): 985-92.
DeBenedette, MA, et al.. "Costimulatin ofCD28—T Lymphocytes by 4-1 BB Ligand," J. Jmmzmol., 1997, pp. 551-559, vol. 158.
Diefenbach et al. "Selective associations with signaling proteins determine stimulatory versus costimulatory activity of NKG2D", 2002, Nat. Immunol. 3:1142-1149.
Dotti et al., "Design and Development of Therapies using Chimeric Antigen Receptor-Expressing T cells," Immunol Rev., 257(1), 35 pages Jan. 2014.
Dubois, S. et al., "IL-15Ra recycles and presents IL-15 In trans to neighboring cells," Immunity, 17(5): 537-547 (2002).
Dubois, S., et al., "Preassociation of IL-15 with IL-15R alpha-lgG1-Fc enhances its activity on proliferation of NK and CD8+/CD44high T cells and its antitumor action," Journal of Immunology, 180(4):2099-2106 (2008).
Ellis et al., "Interactions of CD80 and CD86 with CD28 and CTLA4," J Immunol., 156(8):2700-2709, Apr. 15, 1996.
Eshhar et al., "Specific activation and targeting of cytotoxic lymphocytes through chimeric single chains consisting of antibody-binding domains and the y or C subunits of the immunoglobulin and T-cell receptors," Proc. Natl. Acad. Sci. USA, 1993, 90(2):720-724.
Eshhar, Z, et al .. "Functional Expression of Chimeric Receptor Genes in Human T Cells," J. Immunol. Methods, 2001, 248(1-2):67-76.
Eshhar, Z., "Tumor-specific T-bodies: towards clinical application," Cancer Immunol. Immunother. 45: 131-136 (1997).
Fagan, E.A., and Eddleston, A.L.W.F., "Immunotherapy for cancer: the use of lymphokine activated killer (LAK) cells," Gut 28: 113-116 (1987).
Farag et al., "Natural killer cell receptors: new biology and insights into the Graft-versus-leukemia effect," Blood, 2002, 100(6):1935-1947.
Fehniger, T.A. et al., "Interleukin 15: biology and relevance to human disease," Blood, 97(1): 14-32 (2001).
Fehniger TA, et al.; "Ontogeny and expansion of human natural killer cells: clinical implications", Int Rev Immunol. Jun. 2001; 20(3-4):503-534.
Ferlazzo, G. et al., "Distinct roles of IL-12 and IL-15 in human natural killer cell activation by dendritic cells from secondary lymphoid organs," PNAS, 101(47): 16606-16611 (2004).
Fernández-Messina, L. et al., "Human NKG2D-ligands: cell biology strategies to ensure immune recognition," Frontiers in Immunology, Sep. 2012, vol. 3, Article 299.
Finney et al., "Chimeric receptors providing both primary and costimulatory signaling in T cells from a single gene product," J Immunol. Sep. 15, 1998;161(6):2791-2797.
Finney et al., "Activation of resting human primary T cells with chimeric receptors: costimulation from CD28, inducible costimulator, CD134, and CD137 in series with signals from the TCR zeta chain", J Immunol. Jan. 1, 2004; 172(1):104-113.
Fujisaki, H. et al., "Expansion of highly cytotoxic human natural killer cells for cancer cell therapy," Cancer Res., 69(9): 4010-4017 (2009).
Fujisaki, H. et al., "Replicative potential of human natural killer cells," Br J Haematol,145(5): 606-613 (2009).
Gardner, R., et al., "Acquisition of a CD19 negative myeloid phenotype allows immune escape of MLL-rearranged B-ALL from CD19 CAR-T cell therapy," Blood (forthcoming 2016).
Garrity et al. "The activating NKG2D receptor assembles in the membrane with two signaling dimers into a hexameric structure", 2005, Proc. Natl. Acad. Sci. USA. 102:7641-7646.
Geiger and Jyothi, "Development and application for receptor-modified T lymphocytes for adoptive immunotherapy," Transfus Med Rev, Jan. 2001, 15(1): 21-34.
Geiger et al., "Integrated src kinase and costimulatory activity enhances signal transduction through single-chain chimeric receptors in T lymphocytes", Blood. Oct. 15, 2001; 98(8):2364-2371.

(56) References Cited

OTHER PUBLICATIONS

GenBank Accession No. AF072844.1, "*Homo sapiens* membrane protein DAP10 (DAP10) mRNA, complete cds", Aug. 4, 1999, 2 pages total.
GenBank Accession No. NM_011612 GI: 6755830, Mus musculus tumor necrosis factor receptor superfamily, member 9 (Tnfrsf9), mRNA, dated Oct. 26, 2004, 8 pages.
GenBank Accession No. NM_000734 GI: 37595563, *Homo sapiens* CD3Z antigen, zeta polypeptide (TiT3 complex) (CD3Z), transcript variant 2, mRNA, dated Oct. 27, 2004, 8 pages.
GenBank Accession No. NM_001768 GI: 27886640, *Homo sapiens* CD8 antigen, alpha polypeptide (p32) (CD8A), transcript variant 1, mRNA, dated Oct. 27, 2004, 5 pages.
GenBank Accession No. NM_007360.3, "*Homo sapiens* killer cell lectin like receptor K1 (KLRK1), mRNA", Sequence ID 315221123, Jan. 12, 2013.
Germain et al., "T-cell signaling: the importance of receptor clustering," Curr Biol., 7(10): R640-R644, Oct. 1, 1997.
Ghobadi, et al., "Updated Phase 1 Results from ZUMA-1: A Phase 1-2 Multicenter Study Evaluating the Safety and Efficacy of KTE-C19 (Anti-CD19 CAR T Cells) in Subjects With Refractory Aggressive Non-Hodgkin Lymphoma," Slides accompanying oral presentation at the American Association for Cancer Research Annual Meeting, New Orleans, Louisiana.
Ghorashian, S., et al., "CD19 chimeric antigen receptor T cell therapy for haematological malignancies," Br. J. Haematol. 169:463-478 (2015).
Gilfillan et al. "NKG2D recruits two distinct adapters to trigger NK cell activation and costimulation" Nature Immunnology (2002), vol. 3, No. 12, pp. 1150-1155.
Gill, S., et al., "Chimeric antigen receptor T cell therapy: 25 years in the making," Blood Rev. (2015).
Gillet et al., Selectable markers for gene therapy, Chapter 26 of Gene and Cell Therapy: Therapeutic Mechanisms and Strategies, 3rd Ed. N.S. Templeton Ed, (CRC Press: Bpca Ratpm. FL), pp. 555 and 558, 2009.
Ginaldi, L., et al., "Levels of expression of CD19 and CD20 in chronic B cell leukaemias," J. Clin. Pathol. 51: 364-369 (1998).
Giuliani, M. et al., "Generation of a novel regulatory NK cell subset from peripheral blood CD34+ progenitors promoted by membrane-bound IL-15," PLos One, 3(5): e2241 (2008).
Gong et al., "Cancer Patient T Cells Genetically Targeted to Prostate-Specific Membrane Antigen Specifically Lyse Prostate Cancer Cells and Release Cytokines in Response to Prostate-Specific Membrane Antigen," Neoplasia, 1999, 1(2): 123-127.
Goodier and Londei, "CD28 is not directly involved in the response of human CD3-CD56+ natural killer cells to lipopolysaccharide: a role for T cells," Immunology, Apr. 2004, 111(4): 384-90.
Goodwin et al., "Molecular cloning of a ligand for the inducible T cell gene 4-1 BB: a member of an emerging family of cytokines with homology to tumor necrosis factor", Eur J Immunol. Oct. 1993. 23(10):2631-2641.
Gross and Eshhar, "Endowing T cells with antibody specificity using chimeric T cell receptors," FASEB J. Dec. 1992;6(15):3370-3378.
Grupp et al., "Chimeric antigen receptor-modified T cells for acute lymphoid leukemia," N Engl J Med. Apr. 18, 2013; 368(16):1509-1518.
Harada H, et al., "Selective expansion of human natural killer cells from peripheral blood mononuclear cells by the cell line, HFWT", Jpn J Cancer Res. Mar. 2002; 93(3):313-319.
Harada H, et al.; "A Wilms tumor cell line, HFWT, can greatly stimulate proliferation of CD56+human natural killer cells and their novel precursors in blood mononuclear cells", Exp Hematol. Jul. 2004; 32(7):614-621.
Harding et al., "CD28-mediated signalling co-stimulates murine T cells and prevents induction of anergy in T-cell clones," Nature, 356(6370):607-609, Apr. 16, 1992.
Hayashi. T et a!, "Identification of the NKG2D Haplotypes Associated with Natural Cytotoxic Activity of Peripheral Blood Lymphocytes and Cancer Immunosurveillance", Cancer Research (2006}, vol. 66 No. 01. pp. 563-570.
Haynes NM, et al., "Rejection of syngeneic colon carcinoma by CTLs expressing single-chain antibody receptors codelivering CD28 costimulation", J Immunol. Nov. 15, 2002; 169(10):5780-5786.
Haynes NM, et al., "Single-chain antigen recognition receptors that costimulate potent rejection of established experimental tumors", Blood. Nov. 1, 2002; 100(9):3155-3163.
Heuser, C., et al., "T-cell activation by recombinant immunoreceptors: Impact of the intracellular signalling domain on the stability of receptor expression and antigen-specific activation of grafted T cells," Gene Therapy 10: 1408-1419 (2003).
Ho E.L. et al., "Murine Nkg2d and Cd94 are clustered within the natural killer complex and are expressed independently in natural killer cells," Proc. Natl. Acad. Sci. USA, vol. 95, pp. 6320-6325, May 1998.
Hollyman, D., et al., "Manufacturing Validation of Biologically Functional T Cells Targeted to CD19 Antigen for Autologous Adoptive T cell Therapy," J. Immunother. 32: 169-180 (2009).
Hombach , et al., Tumor-specific T cell activation by recombinant immunoreceptors: CD3 zeta signaling and CD28 costimulation are simultaneously required for efficient IL-2 secretion and can be integrated into one combined CD28/CD3 zeta signaling receptor molecule, J Immunol. Dec. 1, 2001; 167(11 ):6123-6131.
Hombach et al., "T-Cell Activation by Recombinant Receptors: CD28 Costimulation Is Required for Interleukin 2 Secretion and Receptor-mediated T-Cell Proliferation but Does Not Affect Receptor-mediated Target Cell Lysis," Cancer Res., 2001, 61:1976-1982.
Hombach et al., "The recombinant T cell receptor strategy: insights into structure and function of recombinant immunoreceptors on the way towards an optimal receptor design for cellular irnrnunotherapy," Curr Gene Ther. May 2002;2(2):211-226.
Hombach, A., et al., "Adoptive immunotherapy with genetically engineered T cells: modification of the lgG1 Fc 'spacer' domain in the extracellular moiety of chimeric antigen receptors avoids 'offtarget' activation and unintended initiation of an innate immune response," Gene Therapy 17: 1206-1213 (2010).
Hombach, A., et al., "T cell activation by recombinant FcεRI γ-chain immune receptors: an extracellular spacer domain impairs antigendependent T cell activation but not antigen recognition," Gene Therapy 7: 1067-1075 (2000).
Horng et al. 2007, Nat. Immunol. 8:1345-1352.
Hsu, C. et al., "Cytokine-independent growth and clonal expansion of a primary human CD8+ T-cell clone following retroviral transduction with the IL-15 gene," Blood, 109(12): 5168-5177 (2007).
Hsu, K.C. et al., "Improved outcome in HLA-identical sibling hematopoietic stem-cell transplantation for acute myelogenous leukemia predicted by KIR and HLA genotypes," Blood, 105(12): 4878-4884 (2005).
Huang Q.S. et al, Expansion of human natural killer cells ex vivo. Chine J Cell Mol Immunol, Dec. 31, 2008, vol. 24, No. 12, pp. 1167-1170.
Huang, et al. "Abstract A207: Utilizing human OX40 knock-in mice (HuGEMM™) to assess antitumor efficacy of OX40-agonistic antibodies" Molecular Cancer Therapeutics, (Jan. 1, 2018) vol. 17, Issue 1 Supplement in 4 pages.
Hurtado et al., "Potential role of 4-1BB in T cell activation. Comparison with the costimulatory molecule CD28," J Immunol, Oct. 1995, 155(7): 3360-7.
Ignacio et al., "Monoclonal antibodies against the 4-1BB T-cell activation molecule eradicate established tumors," Nature Med., 1997, 3:682-685.
Imai, C. et al., "Genetic modification of primary natural killer cells overcomes inhibitory signals and induces specific killing of leukemic cells," Blood, 106: 376-383 (2005).
Imai C, et al., "T-cell immunotherapy for B-lineage acute lymphoblastic leukemia using chimeric antigen receptors that deliver 4-1 BB-mediated costimulatory signals", Blood. Nov. 16, 2003; 102(11):66a-67a.

(56) References Cited

OTHER PUBLICATIONS

Imai et al. "Genetic modification of T cells for cancer therapy", Journal of Biological Regulators and Homeostatic Agents, 18 (1): p. 62-71; Jan. 2004; (abstract only).
Imai, C., et al; "A novel method for propagating primary natural killer (NK) cells allows highly Efficient expression of anti-CD19 chimeric receptors and generation of powerful cytotoxicity Against NK-resistent acute lymphoblastic leukemia cells." Abstract# 306 Blood 104 (Nov. 16, 2004).
Imamura, M. et al., "Autonomous growth and increased cytotoxicity of natural killer cells expressing membrane-bound interleukin-15," Blood, 124(7): 1081-1088 (Jul. 8, 2014).
Ishii, H. et al., "Monocytes enhance cell proliferation and LMP1 expression of nasal natural killer/T-cell lymphoma cells by cell contact-dependent interaction through membrane-bound IL-15," International Journal of Cancer, 130(1): 48-58 (2012).
Ishiwata I, et al., "Carcinoembryonic proteins produced by Wilms' tumor cells in vitro and in vivo", Exp Pathol. 1991; 41(1):1-9.
Jena et al., "Redirecting T-cell specificity by introducing a tumor-specific chimeric antigen receptor," Blood, 2010, 116(7):1035-1044.
Jenkins et al., "Inhibition of antigen-specific proliferation of type 1 murine T cell clones after stimulation with immobilized anti-CD3 monoclonal antibody," J Immunol., 144(1):16-22, Jan. 1, 1990.
Jensen, M.C., et al., "Anti-transgene Rejection Responses Contribute to Attenuated Persistence of Adoptively Transferred CD20/CD19-Specific Chimeric Antigen Receptor Redirected T Cells in Humans," Biol. Blood Marrow Transplant 16: 1245-1256 (2010).
Jiang, W. et al., "hIL-15 gene-modified human natural killer cells (NKL-IL15) augments the anti-human hepatocellular carcinoma effect in vivo," Immunobiology, 219: 547-553 (Mar. 12, 2014).
Kabalak, G. et al., "Assocaition of an NKG2D gene variant with systematic lupus erythematosus in two populations," Human Immunology 71 (2010) 74-78.
Kalos et al, "T Cells with Chimeric Antigen Receptors Have Potent Antitumor Effects and Can Establish Memory in Patients with Advanced Leukemia," Sci Transl Med. Aug. 10, 2011;3(95):95ra73.
Kershaw, M.H., et al., "A Phase I Study on Adoptive Immunotherapy Using Gene-Modified T Cells for Ovarian Cancer," Clin. Cancer Res. 12:6106-6115 (2006).
Khammari, A., et al., "Long-term follow-up of patients treated by adoptive transfer of melanoma tumor-infiltrating lymphocytes as adjuvant therapy for stage III melanoma," Cancer Immunol. Immunother. 56: 1853-1860 (2007).
Kim Y J, et al., "Human 4-1 BB regulates CD28 co-stimulation to promote Th1 cell responses. Eur J Immunol", Mar. 1998; 28(3):881-890.
Kim Y J, et al., "Novel T cell antigen 4-1 BB associates with the protein tyrosine kinase p561ck1", J Immunol. Aug. 1, 1993; 151(3):1255-1262.
Kitaya, K. et al., "IL-15 expression at human endometrium and decidua," Biology of Reproduction, 63(3): 683-687 (2000).
Kitaya, K. et al., "Regulatory role of membrane-bound form interleukin-15 on human uterine microvascular endothelial cells in circulating CD16(−) natural killer cell extravasation into human endometrium," Biology of Reproduction, 89(3): 70 (2013).
Klein E, et al., "Properties of the K562 cell line, derived from a patient with chronic myeloid leukemia", Int J Cancer. Oct. 15, 1976; 18(4 ):421-431.
Klingemann HG, et al., "Ex vivo expansion of natural killer cells for clinical applications", Cytotherapy. 2004; 6(1 ):15-22.
Kobayashi, H. et al., "Role of trans-cellular IL-15 presentation in the activation of NK cell-mediated killing, which leads to enhanced tumor immunosurveillance," Blood, 105(2): 721-727 (Jan. 2005).
Kober, J., et al. "The capacity of the TNF family members 4-1BBL, OX40L, CD70, GITRL, CD30L, and Light to costimulate human T cells", Eur J Immuno, vol. 38, No. 10, pp. 2678-2688 (Oct. 28, 2008).
Kochenderfer, J.N. et al. "Construction and Preclinical Evaluation of an Anti-CD19 Chimeric Antigen Receptor," J. Immunother. 32(7):689-702 (2009).
Kochenderfer, J.N., et al. "Chemotherapy-Refractory Diffuse Large B-Cell Lymphoma and Indolent B-Cell Malignancies Can be Effectively Treated With Autologous T Cells Expressing an Anti-CD19 Chimeric Antigen Receptor," J. Clin. Oncol. (2014).
Kochenderfer, J.N., et al. "Donor-derived CD19-targeted T cells cause regression of malignancy persisting after allogeneic hematopoietic stem cell transplantation," Blood 122(25): 4129-4139 (2013).
Kochenderfer, J.N., et al., "B-cell depletion and remissions of malignancy along with cytokineassociated toxicity in a clinical trial of anti-CD19 chimeric-antigen-receptor-transduced T cells," Blood 119(12):2709-2720 (2012).
Kochenderfer, J.N., et al., "Eradication of B-lineage cells and regression of lymphoma in a patient treated with autologous T cells genetically engineered to recognize CD19," Blood 116(20):4099-4102 (2010).
Koehler et al. "Engineered T Cells for the Adoptive Therapy of B-Cell Chronic Lymphocytic Leukaemia," Advances in Hematology, vol. 2012, Article ID 595060, 13 pages; doi:10.1155/2012/595060.
Kohn et al. "CARs on track in the clinic," Mar. 2011, Molecular Therapy:The Journal of the American Society of Gene Therapy, 19:432-438.
Koka, R. et al., "Cutting edge: murine dendritic cells require IL-15R alpha to prime NK cells," J Immunol., 173(6): 3594-3598 (Sep. 2004).
Kolb HJ, et al., "Graft-versus-leukemia effect of donor lymphocyte transfusions in marrow grafted patients," Blood, 1995, 6:2041-2050.
Kowolik, C.M., "CD28 Costimulation Provided through a CD19-Specific Chimeric Antigen Receptor Enhances In vivo Persistence and Antitumor Efficacy of Adoptively Transferred T Cells," Cancer Research 66: 10995-11004 (2006).
Lafreniere, R. and Rosenberg, S.A., "Successful Immunotherapy of Murine Experimental Hepatic Metastases with Lymphokine-activated Killer Cells and Recombinant Interleukin 2," Cancer Res. 45: 3735-3741 (1985).
Langer et al., "Comparative Evaluation of Peripheral Blood T Cells and Resultant Engineered Anti-CD19 CAR T-Cell Products From Patients With Relapsed/Refractory Non-Hodgkin Lymphoma (NHL)," Poster session presented at the American Association for Cancer Research Annual Meeting, New Orleans, Louisiana, 2016.
Lapteva, N. et al., "Large-scale ex vivo expansion and characterization of natural killer cells for clinical applications," Cytotherapy, 14(9): 1131-1143 (2012).
Le Blanc et al., "Mesenchymal stem cells inhibit and stimulate mixed lymphocyte cultures and mitogenic responses independently of the major histocompatability complex," Scand J Immunol, Jan. 2003, 57(1): 11-20.
Lee, D.W., et al., "T cells expressing CD19 chimeric antigen receptors for acute lymphoblastic leukaemia in children and young adults: a phase 1 dose-escalation trial," Lancet 385:517-528 (2015).
Lehner at al. "Redirecting T Cells to Ewing's Sarcoma family of Tumors by a Chimeric NKG2D Receptor Expressed by Lentiviral Transduction or Mrna Transfection", 2012, PloS. One 7:e31210.
Leung, W. et al., "Determinants of antileukemia effects of allogeneic NK cells," J Immunol., 172(1): 644-650 (Jan. 2004).
Li et al., "Human iPSC-Derived Natural Killer Cells Engineered with Chimeric Antigen Receptors Enhance Anti-tumor Activity," Cell Stem Cell 23, 1-12, Aug. 2, 2018.
Liao, W. et al., "Interleukin-2 at the crossroads of effector responses, tolerance, and immunotherapy," Immunity, 38(1): 13-25 (2013).
Liebowitz et al., "Costimulatory approaches to adoptive immunotherapy," Curr Opin Oncol, Nov. 1998, 10(6): 533-41.
Lozzio et al., "Properties and Usefulness of the Originl K-562 Human Myelogenous Leukemia Cell Line," Leukemia Research, vol. 3, No. 6, pp. 363-370, 1979.
Lode et al., "Targeted cytokines for cancer immunotherapy," Immunol Res., 21(2-3):279-288, 2000.

(56) References Cited

OTHER PUBLICATIONS

Lozzio CB, et al., "Human chronic myelogenous leukemia cell-line with positive Philadelphia chromosome", Blood. Mar. 1975; 45(3):321-334.
Lugli, E. et al., "Transient and persistent effects of IL-15 on lymphocyte homeostasis in nonhuman primates," Blood, 116(17): 3238-3248 (2010).
Martinez et al. "Cutting Edge: NKG2D-Dependent Cytotoxicity Is Controlled by Ligand Distribution in the Target Cell Membrane", 2011, J. Immunol. 186:5538-5542.
Maude et al., "Chimeric antigen receptor T cells for sustained remissions in leukemia," N Engl J Med., 371(16):1507-1517, Oct. 16, 2014.
McLaughlin et al., "Adoptive T-cell therapies for refractory/relapsed leukemia and lymphoma: current strategies and recent advances," Ther Adv Hematol., 6(6):295-307, Dec. 2015.
Melero I, et al., "Amplification of tumor immunity by gene transfer of the co-stimulatory 4-1 BB ligand: synergy with the CD2S co-stimulatory pathway," Eur J Immunol., 1998, 28(3):1116-1121.
Melero I, et al., "NK1 .1 cells express 4-1BB(CDw137) costimulatory molecule and are required for tumor immunity elicited by anti-4-1 BB monoclonal antibodies," Cell Immunol., 1998, 190(2): 167-172.
Miller et al., "Role of monocytes in the expansion of human activated natural killer cells," Blood, Nov. 1992, 80(9): 2221-9.
Miller, J.S., "Therapeutic applications: natural killer cells in the clinic," Hematology Am Soc Hematol Educ Program 2013: 247-253 (2013).
Miller, J.S. et al., "Successful adoptive transfer and in vivo expansion of human haploidentical NK cells in cancer patients," Blood, 105: 3051-3057 (Apr. 2005).
Milone MC, et al., "Chimeric receptors containing CD137 signal transduction domains mediate enhanced survival of T cells and increased anti leukemic efficacy in vivo", Mol Ther. Apr. 21, 2009; 17(8):1453-1464.
Mishra, A. et al., "Aberrant overexpression of IL-15 initiates large granular lymphocyte leukemia through chromosomal instability and DNA hypermethylation," Cancer Cell, 22(5): 645-655 (2012).
Morandi, B. et al., "NK cells provide helper signal for CD8+ T cells by inducing the expression of membrane-bound IL-15 on DCs," International Immunology, 21(5): 599-606 (2009).
Moretta L, et al., "Unravelling natural killer cell function: triggering and inhibitory human NK receptors," EMBO J., 2004, 23(2):255-259.
Moritz and Groner, "A spacer region between the single chain antibody- and the CD3 Cchain domain of chimeric T cell receptor components is required for efficient ligand binding and signaling activity," Gene Ther. Oct. 1995;2(8):539-546.
Mortier, E., et al., "IL-15Ralpha chaperones IL-15 to stable dendritic cell membrane complexes that activate NK cells via trans presentation," The Journal of Experimental Medicine, 205(5): 1213-1225 (2008).
Murad, et al. "Manufacturing development and clinical production of NKG2D Chimeric Antigen Receptor-expressing T cells for autologous adoptive cell therapy" Cytotherapy, Jul. 2018; 20(7): 952-963.
Musso, T. et al., "Human monocytes constitutively express membrane-bound, biologically active, and interferon-gamma-upregulated interleukin-15," Blood, 93(10): 3531-3539 (1999).
Nagashima et al., "Stable transduction of the interleukin-2 gene into human natural killer cell lines and their phenotypic and functional characterization in vitro and in vivo," Blood, May 1998, 91(10): 3850-61.
Naume et al., "A comparative study of IL-12 (cytotoxic lymphocyte maturation factor)-, IL-2-, and IL-7-induced effects on immunomagnetically purified CD56+ NK cells," J Immunol, Apr. 1992, 148(8): 2429-36.
NCBI Reference Sequence NM_ 198053, "*Homo sapiens* CD247 molecule (CD247), transcript variant 1, mRNA", Jan. 20, 2008, 11 pages total.
NCBI Reference Sequence NM_007360.2, "*Homo sapiens* killer cell lectin-like receptor subfamily K, member 1 (KLRK1 ), mRNA", Dec. 5, 2010, 10 pages total.
Neepalu et al., "Phase 1 Biomarker Analysis of the ZUMA-1 Study: A Phase 1-2 Multi-Center Study Evaluating the Safety and Efficacy of Anti-CD19 CAR T Cells (KTE-C19) in Subjects with Refractory Aggressive Non-Hodgkin Lymphoma," Poster session presented at the American Scoiety of Hematology Annual Meeting, Orlando, Florida.
Negrini, S. et al., "Membrane-bound IL-15 stimulation of peripheral blood natural killer progenitors leads to the generation of an adherent subset co-expressing dendritic cells and natural killer functional markers," Haematologica, 96(5): 762-766 (2011).
Nicholson et al., "Construction and characterisation of a functional CD19 specific single chain Fv fragment for immunotherapy of B lineage leukaemia and lymphoma," Mol Immunol., 34(16-17):1157-1165, Nov.-Dec. 1997.
Wu et al., 1999, An Activating Immunoreceptor Complex Formed by NKG2D and DAP10, Science 285:730-732.
Olsen, S.K. et al., "Crystal structure of the interleukin-15 interleukin-15 receptor α complex Insights into trans and cis presentation," The Journal of Biological Chemistry, 282(51): 37191-37204.
Pan et al., "Regulation of dendritic cell function by NK cells: mechanisms underlying the synergism in the combination therapy of IL-12 and 4-1BB activation," J Immunol, Apr. 2004, 172(8): 4779-89.
Park et al. "Complex regulation of human NKG2D-DAP10 cell surface expression: opposing roles of the Yc cytokines and TGF-B1", 2011, Blood 118:3019-3027.
Park, J.H., and Brentjens, R.J., "Are All Chimeric Antigen Receptors Created Equal?" J. Clin. Oncol. 33: 651-653 (2015).
Park, J.H., et al., "CD19-Targeted 19-28z CAR Modified Autologous T Cells Induce High Rates of Complete Remission and Durable Responses in Adult Patients with Relapsed, Refractory B-Cell ALL," Abstract presented at the American Society of Hematology Annual Meeting, San Francisco, California, available at https://ash.confex.com/ash/2014/webprogram/Paper76573.html.
Park, J.H., et al., Abstract, "682 Implications of Minimal Residual Disease Negative Complete Remission (MRD-CR) and Allogeneic Stem Cell Transplant on Safety and Clinical Outcome of CD19-Targeted 19-28z CAR Modified T cells in Adult Patients with Relapsed, Refractory B-Cell ALL," Am. Soc'y Hematol., available at https://ash.confex.com/ash/2015/webprogram/Paper86688.html.
Parkhurst, M.R. et al., "Adoptive transfer of autologous natural killer cells leads to high levels of circulating natural killer cells but does not mediate tumor regression," Clin Cancer Res., 17(19): 6287-97 (2011).
Patel, S.D., et al., "Impact of chimeric immune receptor extracellular protein domains on T cell function," Gene Therapy 6: 412-419 (1999).
Perussia et al., "Preferential proliferation of natural killer cells among peripheral blood mononuclear cells cocultured with B lymphoblastoid cell lines," Nat Immun Cell Growth Regul, 1987, 6(4): 171-88.
Porter and Antin, "The graft-versus-leukemia of allogeneic cell therapy," Annu Rev Med, 1999, 50:369-86.
Porter DL et al., "Chimeric Antigen Receptor-Modified T Cells in Chronic Lymphoid Leukemia", N. Eng. J. Med. Aug. 25, 2011; 365(8):725-733.
Porter et al., "Induction of graft-versus-host disease as immunotherapy for relapsed chronic myeloid leukemia," N Engl J Med, Jan. 1994, 330(2): 100-6.
Qi L. et al, "Multiple effects of IL-21 on the ex vivo expansion of human primary NK cells." Immunology, Nov. 28, 2014, vol. 143, No. S2, p. 62-176.
Qian, L. et al., "Construction of a plasmid for co-expression of mouse membrane-bound form of IL-15 and RAE-1ε and its biological activity," Plasmid, 65(3): 239-245 (2011).
Ramos and Dotti, "Chimeric antigen receptor (CAR)-engineered lymphocytes for cancer therapy," Expert Opin Biol Ther., 2011, 11(7):855-873.
Ramos, C.A., et al., "CD19-CAR Trials," The Cancer J. 20: 112-118 (2014).

(56) References Cited

OTHER PUBLICATIONS

Riddell, S.R., et al., "T-Cell Therapy of Leukemia," Cancer Control 9: 114-122 (2002).
Roberts et al., "Antigen-specific cytolysis by neutrophils and NK cells expressing chimeric immune receptors bearing zeta or gamma signaling domains," J Immunol, Jul. 1998, 161(1): 375-84.
Robertson MJ, et al.; "Costimulation of human natural killer cell proliferation: role of accessory cytokines and cell contact-dependent signals", Nat Immun. 1996-1997; 15(5):213-226.
Rossi, J.M., et al., "Phase 1 Biomarker Analysis of ZUMA-1 (KTEC19-101) Study: A Phase 1-2 Multi-Center Study Evaluating the Safety and Efficacy of Anti-CD19 CAR T cells (KTE-C19) in Subjects with Refractory Aggressive Non-Hodgkin Lymphoma (NHL)," Abstract presented at the American Society of Hematology Annual Meeting, Orlando, Florida, available at https://ash.confex.com/ash/2015/webprogramscheduler/Paper80339.html.
Roszak, A. et al., "Prevalence of the NKG2D Thr72Ala Polymorphism in Patients with Cervical Carcinoma", Genetic Testing and Molecular Biornarkers {2012), vo!. 16, No. 08, pp. 841-845.
Rowley, J. et al., "Expression of IL-15RA or an IL-15/IL-15RA fusion on CD8+ T cells modifies adoptively transferred T-cell function in cis," European Journal of Immunology, 39: 491-506 (2009).
Rubnitz, J.E. et al., "NKAML: a pilot study to determine the safety and feasibility of haploidentical natural killer cell transplantation in childhood acute myeloid leukemia," J Clin Oncol, 28(6): 955-959 (2010).
Rudikoff, et al. "Single amino acid substitution altering antigen-binding specificity", Nov. 23, 1981, 79, 1979-1983.
Ruggeri, L. et al., "Effectiveness of donor natural killer cell alloreactivity in mismatched hematopoietic transplants," Science, 295(5562): 2097-2100 (2002), https://pubmed.ncbi.nlm.nih.gov/11896281/.
Sadelain et al., "The promise and potential pitfalls of chimeric antigen receptors," Curr Opin Immunol., 2009, 21(2):215-223.
Sadelain, M., "CAR Therapy: the CD19 Paradigm," J. Clin. Investigation 125: 3392-3400 (2015).
Sahm et al., Expression of IL-15 in NK cells results in rapid enruchment and selective cytotoxicity of gene-modified effectors that carry a tumor-specific antigen receptor. Cancer Immunol. Immunother. 61(9):1451-1461, Feb. 2012.
Salih et al., Cutting Edge: Down-Regulation of MICA on Human Tumors by Proteolytic Shedding, 2002, J. Immunol. 169:4098-4102.
Sambrook et al, "Molecular Cloning: A Laboratory Manual," (1989) [Table of Contents and Preface Only].
Sankhla, S.K., et al., "Adoptive immunotherapy using lymphokineactivated killer (LAK) cells and interleukin-2 for recurrent malignant primary brain tumors," J Neurooncol. 27: 133-140 (1995).
Santegoets S.J. et al, "IL-21 promotes the expansion of CD27+ CD28+ tumor infiltrating lymphocytes with high cytotoxic potential and low collateral expansion of regulatory T cells." Journal of Translational Medicine, Feb. 12, 2013, vol. 11, No. 37, pp. e1-e10.
Sattler, S. et al., "Evolution of the C-Type Lectin-Like Receptor Genes od the Dectin-1 Cluster in the NK Gene Complex," The Scientific World Journal, vol. 2012, 2011.
Sentman, et al., "NK Cell Receptors as Tools in Cancer Immunotherapy," Department of Microbiology and Immunology, Dartmouth Medical School, Lebanon, New Hampshire 03756, 2006.
Sentman, et al., "NKG2D CARs as Cell Therapy for Cancer," 2014, The Cancer Journal 20(2):156-159.
Shook D. R. et al., Natural killer cell engineering for cellular therapy of cancer. Tissue Antigens, Nov. 13, 2011, vol. 78, No. 6, pp. 409-415 p. 410 right column 2nd para and p. 411 left column.
Shimasaki, N. et al., "A clinically adaptable method to enhance the cytotoxicity of natural killer cells against B-cell malignancies," Cytotherapy, 14(7): 830-840 (2012).
Sica G, Chen L. Modulation of the immune response through 4-1BB. In: Habib N, ed. Cancer gene therapy: past achievements and future challenges. New York: Kluwer Academic/Plenum Publishers; 355-362 (2000) [Book].
Slavin et al., "Allogeneic cell therapy with donor peripheral blood cells and recombinant human interleukin-2 to treat leukemia relapse after allogeneic bone marrow transplantation," Blood, Mar. 1996, 87(6): 2195-204.
Sneller, M.C. et al., "IL-15 administered by continuous infusion to rhesus macaques induces massive expansion of CD8+ T effector memory population in peripheral blood," Blood, 118(26): 6845-6848 (2011).
Sokolic et al., A selectable bicistronic retroviral vector corrects the molecular defect in a cell line derived from a patient with leukocyte adhesion deficiency, Biol. Blood Marrow Transp. 12(2) Suppl 1:20-21, Feb. 2006.
Somanchi, S.S. et al., "Expansion, purification, and functional assessment of human peripheral blood NK cells," Journal of Visualized Experiments, 48A: 2540 (2011).
Song, De-Gang et al., "In vivo persistence, tumor localization and anti-tumor activity of CAR engineered T cells is enhanced by costimulatory signaling through CD137 (4-1BB)," Cancer Res. Jul. 1, 2011; 71(13): 4617-4627.
Song, De-Gang et al., "Chimeric NKG2D CAR-Expressing T Cell-Meditated Attack of Human Ovarian Cancer Is Enhanced by Histone Deacetylase Inhibition," Human Gene Therapy, 24:295-305 (Mar. 2013).
Spear, et al. 2012, J. Immunol 188: 6389-6398.
Spear, et al. 2013, Immunology and Cell Biology 91: 435-440.
Spear, et al. 2013, OncoImmunology 2(4): e23564-1-e23564-12.
Sun, J., et al., "Early transduction produces highly functional chimeric antigen receptor-modified virus-specific T-cells with central memory markers: a Production Assistant for Cell Therapy (PACT) translational application," J. Immunother. Cancer (2015).
Sureth et al. Efficient generation of gene-modified human natural killer cells via alpharetroviral vectors, J. Mol. Med. 94:83-93, 2016., published online Aug. 25, 2015.
Tagaya, Y. et al., "IL-15: a pleiotropic cytokine with diverse receptor/signaling pathways whose expression is controlled at multiple levels," Immunity, 4(4): 329-336 (1996).
Takahashi C, et al., "Cutting edge: 4-1 BB is a bona fide CDS T cell survival signal", J Immunol. May 1, 1999; 162(9):5037-5040.
Topp, M.S., et al., "Universal chimeric immunoreceptors for targeting B-cell malignancies with engineered CTL: combining CD19-specific TCR zeta signaling with engineered CD28-mediated costimulation," Mol. Ther. 3(5)(part 2 of 2): S21 (2001).
Trinchieri et al., "Response of resting human peripheral blood natural killer cells to interleukin 2," J Exp Med, Oct. 1984, 160(4): 1147-69.
Tsukamoto, K. et al., "Juxtacrine function of interleukin-15/interleukin-15 receptor system in tumour derived human B-cell lines," Clinical and Experimental Immunology, 146(3): 559-566 (2006).
Turaj, et al. "Augmentation of CD134 (OX40)-dependent NK anti-tumour activity is dependent on antibody cross-linking" Scientific Reports, (2018) 8, 2278.
Turtle, "Therapy of B Cell Malignancies with CD19-Specific Chimeric Antigen Receptor Modified T Cells of Defined Subset Composition," Blood 124(21): 384-384, 2014.
Turtle, C.J., et al., Abstract, "A Phase I/II Clinical Trial of Immunotherapy for CD19+ B Cell Malignancies With Defined Composition of CD4+ and CD8+ Central Memory T Cells Lentivirally Engineered to Express a CD19-Specific Chimeric Antigen Receptor" Mol. Ther., 2014, 22(Supp.1):296.
Vajdos, et al. "Comprehensive Functional Maps of the Antigen-binding Site of an Anti-ErbB2 Antibody Obtained with Shotgun Scanning Mutagenesis" J. Mol. Biol. (Jul. 5, 2002) 320, 415-428.
Verdonck et al., "Donor leukocyte infusions for recurrent hematologic malignancies after allogeneic bone marrow transplantation: impact of infused and residual donor T cells," Bone Marrow Transplant, Dec. 1998, 22(11): 1057-63.
Vujanovic, L. et al., "Virally infected and matured human dendritic cells activate natural killer cells via cooperative activity of plasma membrane-bound TNF and IL-15," Blood, 116(4): 575-583 (2010).

(56) References Cited

OTHER PUBLICATIONS

Waldmann, T.A. et al., "Safety (toxicity), pharmacokinetics, immunogenicity, and impact on elements of the normal immune system of recombinant human IL-15 in rhesus macaques," Blood, 117(18): 4787-4795 (2011).
Wang, et al., "Phase I Studies of central-memory-derived CD19 CAR T cell therapy following autologous HSCT in patients with B-Cell NHL," Blood (forthcoming 2016).
Watzl, C. et al., "Signal Transduction During Activation and Inhibition of Natural Killer Cells," Curr Protoc Immunol. Author Manuscript; available in PMC Dec. 9, 2013.
Weissman et al., "Molecular cloning and chromosomal localization of the human T-cell receptor ~ chain: Distinction from the molecular CD3 complex," PNAS USA, 1988, 85:9709-9713.
Westwood, J.A., et al., "Adoptive transfer of T cells modified with a humanized chimeric receptor gene inhibits growth of Lewis-Y expressing tumors in mice," PNAS 102(52): 19051-19056 (2005).
Willimsky, G. and Blankenstein, T., "Sporadic immunogenic tumours avoid destruction by inducing T-cell tolerance," Nature 437: 141-146 (2005).
Wittnebel, S. et al., "Membrane-bound interleukin (IL)-15 on renal tumor cells rescues natural killer cells from IL-2 starvation-induced apoptosis," Cancer Research, 67(12): 5594-5599 (2007).
Wu and Lanier, "Natural killer cells and cancer," Adv Cancer Res, 2003, 90: 127-56.
Xu, Y., et al., "Closely related T-memory stem cells correlate with in vivo expansion of CAR.CD19-T cells and are preserved by IL-7 and IL-15," Blood 123(24):3750-3759 (2014).
Ye L. et al, "Effects of target cell overexpression of IL-15, 4-1BBL and IL-18 combine with IL-2 on NK cell activation and cytotoxicity during ex vivo expansion." Chin J Cancer Biother, Oct. 31, 2014, vol. 21, No. 5, pp. 537-542.
Yim et al., "Molecular cloning and characterization of pig immunoreceptor DAP10 and NKG2D," Immunogenetics—Jan. 2001.
Zanoni, I. et al., "IL-15 cis presentation is required for optimal NK cell activation in lipopolysaccharide-mediated inflammatory conditions," Cell Reports, 4: 1235-1249 (2013).
Zeis, M. et al., "Allogeneic MHC-Mismatched Activated Natural Killer Cells Administered After Bone Marrow Transplantation Provide a Strong Graft-Versus-Leukemia Effect in Mice," BrJ Haematol, 1997, pp. 757-761, vol. 96.
Zhang, J. et al., "Characterization of interleukin-15-gene-modified human natural killer cells: implications for adoptive cellular immunotherapy," Haematologica, 89(3): 338-347 (2004).
Zhang et al., "Chimeric NKG2D-Modified T Cells Inhibit Systematic T-Cell Lymphoma Growth in a Manner Involving Multiple Cytokines and Cytotoxic Pathways," 2007, Cancer Res. 67:11029-11036.
Zhang et al. Chimeric NK-receptor-bearing T cells mediate antitumor immunotherapy, Sep. 1, 2005, Blood Journal 106(5): 1544-1551.
Zhang et al., "Generation of Antitumor Response by Genetic Modification of Primary Human T Cells with a Chimeric NKG2D Receptor," 2006, Cancer Res 66(11):5927-5933.
Zhang, et al. Mouse Tumor vasculature Expresses NKG2D Ligands and can be Targeted by Chimeric NKG2D-Modified T Cells, 2013, J. Immunol 190:2455-2463.
Steel et al., Interleukin-15 biology and its therapeutic implications in cancer, Trends Pharmacol, Sci. 33(1):35-41, Jan. 2012.
Cecele J. Denman, et al., "Membrane-Bound IL-21 Promotes Sustained Ex Vivo Proliferation of Human Natural Killer Cells" PLOS ONE, www.plosone.org, Jan. 18, 2012, vol. 7, in 13 pages.
Wang, et al., "Human NK cells maintain licensing status and are subject to killer immunoglobulin-like receptor (KIR) and KIR-ligand inhibition following ex vivo expansion", Cancer Immunology, Immunotherapy, vol. 65, No. 9, Jul. 8, 2016, pp. 1047-1059.
Bridgeman, J.S., et al., "The Optimal Antigen Response of Chimeric Antigen Receptors Harboring the CD3 ζ Transmembrane Domain Is Dependent upon Incorporation of the Receptor into the Endogenous TCR/CD3 Complex" The Journal of Immunology, Oct. 15, 2019, in 13 pages.
Zah, et al., "T Cells Expressing CD19/CD20 Bispecific Chimeric Antigen Receptors Prevent Antigen Escape by Malignant B Cells", Cancer Immunology Research, Apr. 8, 2016, in 15 pages.
Parihar, et al., "NK cells expressing a chimeric activating receptor eliminate MDSCs and rescue impaired CAR-T cell activity against solid tumors", cancerimmunolres.aacrjournals.org, Jan. 19, 2019, in 47 pages.
Jiang, W. et al., "Functional characterization of interleukin-15 gene transduction into the human natural killer cell line NKL" International Society for Cellular Therapy, (2008), vol. 10, No. 3, 265-274.
International Search Report and Written Opinion for International Application No. PCT/US20/20824, mailed Jul. 30, 2020, in 23 pages.
Schirrmann, et al. "Human natural killer cell line modified with a chimeric immunoglobulin T-cell receptor gene leads to tumor growth inhibition in vivo" Cancer Gene Therapy (2002) 9, 390-398.
Arch et al., "4-1BB and Ox40 Are Members of a Tumor Necrosis Factor (TNF)-Nerve Growth Factor Receptor Subfamily That Bind TNF Receptor-Associated Factors and Activate Nuclear Factor Kb" Molecular and Cellular Biology, Jan. 1998, p. 558-565.
International Search Report and Written Opinion for International Application No. PCT/US 23/69403, mailed Jan. 4, 2024, in 21 pages.
Kawamata, et al, "Activation of OX40 Signal Transduction Pathways Leads to Tumor Necrosis Factor Receptor-associated Factor (TRAF) 2- and TRAF5-mediated NF-kB Activation" The Journal of Biological Chemistry, 1998, vol. 273, No. 10, 5808-5814.
Kussie P.H., et al., "A single engineered amino acid substitution changes antibody fine specificity", J Immunol, Jan. 1994, 152(1), pp. 146-152.
Nkarta Therapeutics, "Press Release: Nkarta announces updated Clinical Data on Anti-CD19 Allogeneic CAR-NK Cell Therapy NKX019 for patients with relapsed or Refractory Non-Hodgkin Lymphoma" (2022) available at https://ir.nkartatx.com/news-releases/news-release-details/nkarta-announces-updated-clinical-data-anti-cd19-allogeneic-car.
Nkarta Power Point Presentation "Next Generation Natural Killer Cells Engineered to Beat Cancer", Dec. 5, 2022, available at https://ir.nkartatx.com/static-files/9cb11d46-a4aa-49a3-baca-dc1a36e5aa60.
Park Jae H., et al. "CD19-targeted CAR T-cell therapeutics for hematologic malignancies: interpreting clinical outcomes to date", Blood, Jun. 30, 2016, 157(26): 3312-3320 (See Abstract).
Pavlova, et al., "Adoptitive immunotherapy with genetically engineered T lymphocytes modified to express chimeric antigen receptors" Onkogematologiia, 2017, vol. 12, No. 1, pp. 17-32 (see annotation).
Romanski, Annette et al., CD-19-CAR engineered NK-92 cells are sufficient to overcome NK cell resistance in B-cell malignancies, J Cell Mol Med, 2016; 20(7): 1287-1294 (see abstract).
Zhao, et al., "A Herceptin-Based Chimeric Antigen Receptor with Modified Signaling Domains Leads to Enhanced Survival of Transduced T Lymphocytes and Antitumor Activity", The Journal of Immunology, 2009; 183:5563-5574.
Shanghai Hospital, "Shanghai Changhai Hospital is the first to realize the treatment of systemic lupus erythematosus with CAR-NK", Cell & Gene Therapy, Jan. 5, 2024, in 9 pages.
Shook et al., "Refinitiv Streetevents Edited Transcript NKTX.OQ-Nkarta Inc NKX101 Clinical Update Conference Call" Jun. 27, 2023, in 16 pages.
Aggarwal, et al., "Trial of Intravenous Immune Globulin in Dermatomyositis" The New England Journal of Medicine, 387; 14, 1264-1278, Oct. 6, 2022.
Almaani, et al., "Glomerular Disease, Update on Lupus Nephritis" The Clinical Journal of the American Society of Nephrology, vol. 12, pp. 825-835, May 2017.
Appel, et al., "Mycophenolate Mofetil versus Cyclophosphamide for Induction Treatment of Lupus Nephritis" Journal of the American Society of Nephrology, vol. 20, 1103.1112 (2009).

(56) References Cited

OTHER PUBLICATIONS

Arbuckle, et al., "Development of Autoantibodies before the Clinical Onset of Systemic Lupus Erythematosus" The New England Journal of Medicine, 349; 16, 1526-1533, Oct. 16, 2003.
Arora, et al., "Expert Perspective: An Approach to Refractory Lupus Nephritis" Arthritis Rheumatol. 74(6): 915-926, Jun. 2022.
Bachier, et al., A Phase 1 Study of NKX101, an Allogeneic CAR Natural Killer (NK) Cell Therapy, in Subjects with Relapsed-Refractory (R/R) Acute Myeloid Leukemia (AML) or Higher-Risk Myelodysplastic Syndrome (MDS), bood journal, vol. 136, Issue Supplement 1, in 7 pages, Nov. 5, 2020.
Bajema, et al., "Revision of the International Society of Nephrology/Renal Pathology Society classification for lupus nephritis: clarification of definitions, and modified National Institutes of Health activity and chronicity indices" Kidney International, 93, 789-796, Feb. 16, 2018.
Bakr, et al., "Induction Immunosuppressive Therapy in Kidney Transplantation" Experimental and Clinical Transplantation, Suppl 1: 60-69, (2014).
Barber, et al., "Global epidemiology of systemic lupus erythematosus" Nature Reviews, Rheumatology, vol. 17, 515-532, Sep. 2021.
Benlysta product insert, Revised Jul. 2017, in 48 pages.
Bergmann, et al., "Treatment of a patient with severe systemic sclerosis (SSc) using CD19-targeted CAR T cells" Ann Rheum Dis., vol. 82, No. 8, pp. 1117-1120, Aug. 2023.
Bernatsky, et al., "Mortality in Systemic Lupus Erythematosus", Arthritis & Rheumatism, vol. 54, No. 8, pp. 2550-2557, Aug. 2006.
Bertsias, et al., "Eular recommendations for the management of systemic lups erythematosus. Report of a Task Force of the Eular standing commiettee for International Clinical Studies Including Therapeutics", Ann Rheum Dis, 67:195-205, May 15, 2007.
Bertsias, et al., "Joint european league Against Rheumatism and European Renal Association_European Dialysis and Transplant Association (EULAR/ERA-EDTA_ recommendations for the management of adult and paediatric lupus nephritis", Ann Rheum Dis., 71:1771-1782, Jul. 31, 2012.
Borchers, et al., "The geoepidemiology of systemic lupus erythematosus", Elsevier Autoimmunity Reviews, 9, A277-A287, (2010).
Breyanzi, Highlights of Prescribing Information, in 11 pages (2021).
Buttler, et al., "Effect of minimal lymphodepletion prior to ACT with TBI-1301, NY-ESO-1 specific gene-engineered TCR-T cells, on clinical responses and CRS", Journal of Clinical Oncology, in 4 pages (2019).
Cabaletta, "Corporate Presentation", Mar. 2023, in 23 pages.
Cabaletta, "IND application cleared within 6 months of in-licensing CABA-201 Binder" Mar. 31, 2023, in 7 pages.
Chen, et al., "Value of a complete or Partial Remission in severe Lupus Nephritis", Clin J Am Soc Nephrol 3:46-53, 2008.
Chen, et al., "Regulatory effects of dexamethasone on NK and T cell immunity" Inflammopharmacology, 26:1331-1338 (2018).
Chen, et al., "B cell targeting in CAR T cell therapy: Side effect or driver of CAR T cell function?" Sci Transl Med. Author manuscript: Jul. 15, 2022, in 12 pages.
Choi, et al., "Donor-Derived natural Killer Cells Infused after Human Leukocyte Antigen-Haploidentical Hematopoietic Cell Transplantation" A Dose-Escalation Study Biol Blood Marrow Transplant 20, 696-704 (2014).
Ciurea, et al., "Phase 1 clinical trial using mbIL21 ex vivo-expanded donor-derived NK cells after haploidentical transplantation" Blood, vol. 130, No. 16, Oct. 19, 2017.
Comi, et al., "The role of B cells in Multiple Sclerosis and related disorders" Ann Neurol. 89(1), 13-23, Jan. 2021.
Contreras, et al., "Sequential Therapies for Proliferative Lupus Nephritis" The New England Journal of Medicine vol. 350, No. 10, 971-980, Mar. 4, 2004.
Cooper, et al., "The epidemiology of autoimune diseases" Elsevier Autoimmunity Reviews 2 119-125 (2003).
Crow, et al., "Type I Interferon in the Pathogenesis of Lupus" J. Immunol. 192(12), 5459-5468, Jun. 15, 2014.
Daikeler, et al., "Allogeneic Hematopoietics SCT for patients with autoimmune diseases", Bone Marrow Transplantation, 44, 27-33 (2009).
Davidson, et al., "Autoimmune Diseases" The new England Journal of Medicine, vol. 345, No. 5 pp. 340-350, Aug. 2, 2001.
Davidson, et al., "Renal remission status and long-term renal survival in patients with lupus nephritis: a retrospective cohort analysis" J Rheumatol, 45(5): 671-677, May 2018.
De Silva, et al., "Haemopoietic stem cell transplantation in Systemic lupus erythematosus: a systematic review", Allergy Asthma Clin Immunol, 15:59 (2019).
Dickinson, et al., "First in Human Data of NKX019, an Allogeneic CAR NK for the treatment of Relapsed/Refractory (R/R) B-cell Malignancies", Wiley Supplement Abstracts, in 2 pages, Dec. 9, 2023.
Doglio, et al., "New insights in systemic lupus erythematosus: From regulatory T cells to CAR-T cell strategies", Review article J Allergy Clin Immunol, vol. 150, No. 6, pp. 1289-1301 Dec. 2022.
Ellebrecht, et al., "Reengineering chimeric antigen receptor T cells for targeted therapy of autoimmune disease" Immunotherapy, vol. 353, Issue 6295, pp. 179-184, Jul. 8, 2016.
Fanouriakis, et al., "2019 Update of the Joint European League Against Rheumatism and European Renal Association-European Dialysis and Transplant Association (EULAR/ERA-EDTA) recommendations for the management of lupus nephritis", Ann Rheum Dis, 79:713-723, 2020.
Fanouriakis, et al., "Update on the diagnosis and management of systemic lupus erythematosus", Ann Rheum Dis. 80:14-25, 2021.
Fasano, et al., "Hydroxychloroquine daily dose, hydroxychloroquine blood levels and the risk of flares in patients with systemic lupus erythematosus" Immunology and Inflammation, Lupus Science & Medicine in 6 pages, (2023).
Fava, et al., "Systemic Lupus Erythematosus Diagnosis and Clinical management" J Autoimmun. 96: 1-13, Jan. 2019.
Furie, et al., "Two-Year, Randomized, Controlled Trial of Belimumab in Lupus Nephritis" The New England Journal of Medicine, 383:12, pp. 1117-1128, Sep. 17, 2020.
Furie, et al., "B-cell depletion with obinutuzumab for the treatment of proliferative lupus nephritis: a randomised, double-blind placebo-controlled trial" Ann Rheum Dis 81:100-107 (2022).
Gauthier, et al., "High IL-15 Serum Concentrations are Associated with Response to CD19 CAR T-Cell Therapy and Robust In Vivo CAR T-Cell Kinetics", Blood, 136:supp 1:37, in 4 pages, Nov. 5, 2020.
Goklemez, et al., "Long-term follow-up after lymphodepleting autologous haematopoietic cell transplantation for treatment-resistant systemic lupus erythematosus" Rheumatology, 61:3317-3328 (2022).
Granit, et al., "Safety and clinical activity of autologous RNA chimeric antigen receptor T-cell therapy in myasthenia gravis (MG-001): a prospective, multicentre, open-label, non-randomised phase 1b/2a study", Lancet Neurol. 22:578-90 (2023).
Grootscholten, et al., Discontinuation of immunosuppression in proliferative lupus nephritis: is it possible? Nephrol Dial Transplant 21:1465-1469 (2006).
Hahn, et al., "American College of Rheumatology guidelines for Screening, Case Definition, Treatment and Management of Lupus Nephritis", Arthritis Care Res. (Hoboken) author manuscript, 64(6): 797-808, Jun. 2012.
Harris, et al., "International, multi-center standardization of acute graft-versus-host disease clinical data collection: a report from the Magic consortium", Biol blood Marrow Transplant, author manuscript, 22(1):4-10, Jan. 2016.
Hay, et al., "Kinetics and biomarkers of severe cytokine release syndrome after CD19 chimeric antigen receptor-modified T-cell therapy", Immunobiology and Immunotherapy, blood, vol. 130, No. 21, Nov. 23, 2017.
He, et al., "Dilemma of immunosuppression and infection risk in systemic lupus erythematosus", Rheumatology, 62, i22-i29, supplement paper, Aug. 3, 2022.
Hill, et al., Durable preservation of antiviral antibodies after CD19-directed chimeric antigen receptor T-cell immunotherapy, blood advances, vol. 3, No. 22, pp. 3590-3601, Nov. 26, 2019.

(56) References Cited

OTHER PUBLICATIONS

Hirayama, et al., "Toxicities of CD19 CAR-T cell immunotherapy", Wiley, Am J Hematol., 94:S42-S49, 2019.
Hirayama, et al., "The response to lymphodepletion impacts PFS in patients with aggressive non-Hodgkin lymphoma treated with CD19 CAR T cells", Immunobiology and Immunotherapy, blood, vol. 133, No. 17, Apr. 25, 2019.
Holbrook, et al., "Direct Suppression of Natural Killer Activity in Human Peripheral Blood Leukocyte Cultures by Glucocorticoids and its Modulation by Interferon", cancer Research, 43, 4019-4025, Sep. 1983.
Illei et al., "Combination therapy with pulses of Cyc and methylprednisolone improves long-term renal outcome without increasing toxicity in patients with lupus nephritis", Evidence-Based Rheumatology, pp. 287-288, (2001).
Isenberg, David et al., "Influence of race/ethnicity on response to lupus nephritis treatment: the ALMS study" Rheumatology, 49:128-140 (2010).
Jacobson, et al., "Epidemiology and Estimated Population Burden of Selected Autoimmune Diseases in the United States" Clinical Immunology and Immunopathology, vol. 84, No. 3, pp. 223-243, Sep. 1997.
Jagasia, et at., "National Institutes of Health Consensus Development Project on Criteria for Clinical Trials in Chronic Graft-versus-Host Disease: I. The 2014 Diagnosis and Staging Working Group Report" Biol Blood marrow Transp author manuscript 21(3): 389-401, Mar. 2015.
Jayne, et al., "Phase II randomised trial of type I interferon inhibitor anifrolumab in patients with active lupus nephritis" Ann Rheum Dis.:496-506 (2022).
Jennette, et al., "B-Cell Mediated Pathogenesis of ANCA-Mediated Vasculitis" Semin Immunopathol., 36(3): 327-338, May 2014.
Jin, et al., "Therapeutic efficacy of anti-CD19 CAR-T cells in a mouse model of systemic lupus erythematosus" Cellular & Molecular Immunology, 18:1896-1903 (2021).
Jin, et al., "CAR-T cell therapy: new hope for systemic lupus erythematosus patients", Cellular & Molecular Immunology 18:2581-2582 (2021).
June, et al., "CAR T cell immunotherapy for human cancer" Cancer Immunotherapy, Science 359, 1361-1365, Mar. 23, 2018.
Kansal, et al., "Sustained B cell depletion by CD19-targeted CAR T cells is a highly effective treatment for murine lupus" Science Translational Medicine, Research article, in 13 pages, Mar. 6, 2019.
Kdigo 2021 Clinical Practice Guideline for the Management of Glomerular Diseases, Kidney International, 100:S1-S276, (2021).
Kilgour, et al., "Advancements in CAR-NK therapy: lessons to be learned from CAR-T therapy", frontiers in Immunology, in 10 pages, May 2, 2023.
King et al., "CAR NK Cell Therapy for T Follicular Helper Cells" Cell Press Open Access, Cell Reports Medicine, in two pages, Apr. 21, 2020.
Kitching, et al., "ANCA-associated vasculitis", Nature Reviews Disease primers, 6, 71, (2020).
Kretschmann, et al., "Successful Generation of CD19 Chimeric Antigen Receptor T Cells from Patients with Advanced Systemic Lupus Erythematosus" Transplantation and Cellular Therapy 29:27-33 (2023).
Kymriah, Highlights of Prescribing Information, in 31 pages (2017).
Lanjewar, et al., "Long-term immunosuppression and multiple transplants predispose systemic lupus erythematosus patients with cytopenias to hematologic malignancies" Medicine, in 9 pages, Feb. 16, 2021.
Leandro, "Rituximab—The First Twenty Years", Centre for Rheumatology, Division of Medicine, University College London, in 15 pages, (2021).
Lee, et al., "ASTCT Consensus Grading for Cytokine Release Syndrome and Neurologic Toxicity Associated with Immune Effector Cells" Biol Blood Marrow Transplant 25: 625-638 (2019).
Liu, et al., "Use of CAR-Transduced Natural Killer Cells in CD19-Positive Lymphoid Tumors" N Engl J Med. 382(6): 545-553, Feb. 6, 2020.
Lundberg, et al., "Classification of myositis" Nature Reviews, Rheumatology, vol. 14, pp. 269-278, May 2018.
Lupkynis, "Highlights of Prescribing Information" in 24 pages, (2021).
Mackensen, et al., "Anti-CD19 CAR T cell therapy for refractory systemic lupus erythematosus" nature medicine, in 20 pages (2022).
Marcus, et al., "Recognition of tumors by the innate immune system and natural killer cells", Adv. Immunol. 122:91-128 (2014).
Marrack, et al., "Autoimmune disease: why and where it occurs" Nature Medicine vol. 7, No. 8, pp. 899-905, Aug. 2001.
Marston, et al., "B cells in the pathogenesis and treatment of rheumatoid arthritis" Curr Opin Rheumatol. 22(3): 307-315, May 2010.
McHugh, et al., "CAR T cells drive out B cells in SLE" Systemic Lupus Erythematosus, Research Highlights, Nature Reviews, Rheumatology, vol. 15, pp. 249, May 2019.
Merino-Vico, et al., "B Lineage Cells in ANCA-Associated Vasculitis" International Journal of Molecular Sciences, 23, 387, in 18 pages (2022).
Merkel, et al., "Overview of and approach to the vasculitides in adults" UpToDate, Oct. 2, 2023 in 17 pages.
Merrill, et al., "Anifrolumab effects on rash and arthritis: impact of the type I interferon gene signature in the phase lib MUSE study in patients with systemic lupus erythematosus", Lupus Science & Medicine, in 7 pages (2018).
Miller, et al., "Successful adoptive transfer and in vivo expansion of human haploidentical NK cells in patients with cancer" Clinical Observations, Interventions, and Therapeutic Trials, Blood, vol. 105, No. 8, pp. 3051-3057, Apr. 15, 2005.
Mok, et al., "Con: Cyclophosphamide for the treatment of lupus nephritis" Nephrol Dial Transplant, 31: 1053-1057 (2016).
"Union Hospital Achieved Breakthrough in Systemic Lupus Erythematosus Treatment with CAR-T Therapy", Union Hospita, Tongji Medical College, Huazhong University of Science and Technology, https://www.whuh.com/en/info/1007/1823.htm, in 4 pages, May 31, 2023.
Morgan, et al., "Distinct Effects of Dexamethasone on Human Natural Killer Cell Responses Dependent on Cytokines", frontiers in immunology, vol. 8, Article 432, in 15 pages, Apr. 13, 2017.
Morvan, et al., "NK cells and cancer: you can teach innate cells new tricks", Nature Reviews Cancer, vol. 16, in 13 pages, Jan. 2016.
ClinicalTrials.gov, "Treatment of Relapsed or Chemotherapy Refractory Chronic Lymphocytic Leukemia or Indolent B Cell Lymphoma Using Autologous T Cells Genetically Targeted to the B Cell Specific Antigen CD 19", Available at: https://clinicaltrials.gov/show/NCT00466531, NCT00466531(Retrieved from the Internet on Jun. 21, 2016).
Imai C, et al., "Chimeric receptors with 4-1BB signaling capacity provoke potent cytotoxicity against acute lymphoblastic leukemia", Leukemia. Feb. 12, 2004; 18(4):676-684.
Neepalu et al., "Phase 1 Biomarker Analysis of the ZUMA-1 Study: A Phase 1-2 Multi-Center Study Evaluating the Safety and Efficacy of Anti-CD19 CAR T Cells (KTE-C19) in Subjects with Refractory Aggressive Non-Hodgkin Lymphoma," Poster session presented at the American Society of Hematology Annual Meeting, Orlando, Florida (Dec. 5-8, 2015).
Song et al., "Chimeric NKG2D CAR-Expressing T Cell-Mediated Attack of Human Ovarian Cancer is Enhanced by Histone Deacetylase Inhibition," Human Gene Therapy, vol. 24, pages.
Hogan, S. L., Falk, R. J., Chin, H., et al. (2005). Predictors of relapse and treatment resistance in antineutrophil cytoplasmic antibody-associated small-vessel vasculitis. Ann Intern Med, 143(9), 621-631. https://doi.ora/10.7326/0003-4819-143-9-200511010-00005.
Hombach et al., "Costimulation by chimeric antigen receptors revisited the T cell antitumor response benefits from combined CD28-OX40 signalling," Int. J. Cane. 129:2935-2944 (2011).
Hong, et al., "Interleukin-6 expands homeostatic space for peripheral T cells" Cytokine 64 (2013) pp. 532-540.
Hooper, et al., "Knockout of CBLB Greatly Enhances Anti-Tumor Activity of CAR T Cells", Lymphoma: Pre-clinical-Chemotherapy

(56) References Cited

OTHER PUBLICATIONS and Biologic Agents: Immunologic Approaches, Blood, 132 (Supplemental 1): 338, Nov. 29, 2018, in 2 pages, Abstract.
Hopp et al., "A Short Polypeptide Marker Sequence Useful for Recombinant Protein Identification and Purification" Bio/Technology, vol. 6, pp. 1204-1210 (Oct. 1988).
Horikawa et al. (2005). Abnormal natural killer cell function in systemic sclerosis: altered cytokine production and defective killing activity. J Invest Dermatol, 125(4), 731-737. https://doi.org/10.1111/i.0022-202X.2005.23767.x.
https ://www.proteinatlas.org/ENSG00000177455-CD19/pathology, accessed Jun. 27, 2019.
Hughes, M., Pauling, J. D., Armstrong-James, L., et al. (2020). Gender-related differences in systemic sclerosis. Autoimmunity Reviews, 19(4), 102494. https://doi.org/https://doi.org/10.1016/j.autrev.2020.102494.
Hunter et al. (2020). ANCA associated vasculitis. Bmj, 369, m1070. https://doi.org/10.1136/bmj.m1070.
Huntington et al. "Interleukin 15-mediated survival of natural killer cells is determined by interactions among Bim, Noxa and Mcl-1," Nat. Immunol. Aug. 2007; 8(8): 856-863.
Huntington, "The unconventional expression of IL-15 and its role in NK cell homeostasis," Immunology and Cell Biology (2014) 92, 210-213.
Huntington, (@Dr_Nick_Bikes) Twiter Feed, May 27, 2021, 1 page.
Hurtado et al., "Signals through 4-1 BB are costimulatory to previously activated splenic T cells and inhibit activation-induced cell death", J Immunol., Mar. 1997, 158(6):2600-2609.
Hurton et al., "Tethered IL-15 augments antitumor activity and promotes a stem-cell memory subset in tumor-specific T cells," Proc. Natl. Acad. Sci, USA, 113(48):E7788-E7797 (Nov. 2016).
Hurton, L.V. et al., "Improved Costimulation of CD19-Speci?c T Cells Transpresenting a Membrane-Bound IL-15," Molecular Therapy vol. 19, Supplement 1, May 2011, S138.
Iacobucci et al., Truncating Erythropoietin Receptor Rearrangements in Acute Lymphoblastic Leukemia, Cancer Cell, vol. 29, No. 2, pp. 186-200, published on Feb. 8, 2016.
Imada et al. "Stat5b Is Essential for Natural Killer Cell-mediated Proliferation and Cytolytic Activity," The Journal of Experimental Medicine, vol. 188, No. 11, Dec. 7, 1998, pp. 2067-2074.
Inaguma et al., "Expression of neural cell adhesion molecule L1 (CD171) in neuroectodermal and other tumors. An immunohistochemical study of 5155 tumors and critical evaluation of CD171 prognostic value in gastrointestinal stromal tumors," Oncotarge., 7(34):55276-55289, Jul. 11, 2016.
International PCT Specification for PCT Application PCT/US2024/023051, filed Apr. 4, 2024.
International PCT Specification for PCT Application PCT/US2024/035555, filed Jun. 26, 2024.
International PCT Specification for PCT Application PCT/US2024/035654, filed Jun. 26, 2024.
International Preliminary Report on Patentability for Int'l Application No. PCT/SG2015/050111, titled "Modified Natural Killer Cells and Uses Thereof," dated Nov. 15, 2016.
International Preliminary Report on Patentability for Int'l Application No. PCT/IB2019/000181, titled: Activating Chimeric Receptors and Uses Thereof in Natural Killer Cell Immunotherapy, Dated: Aug. 11, 2020.
International Preliminary Report on Patentability having a mail date of Jul. 28, 2015, issued in corresponding PCT application No. PCT/US2014/013292.
International Preliminary Report on Patentability, re PCT Application No. PCT/IB2019/000141, dated Aug. 20, 2020.
International Preliminary Report on Patentability, re PCT Application No. PCT/SG2018/050138, dated Oct. 10, 2019.
International Preliminary Report on Patentability, re PCT Application No. PCT/US2018/024650, dated Oct. 10, 2019.
International Preliminary Report on Patentability, re PCT Application No. PCT/US2019/050679, dated Mar. 25, 2021.
International Preliminary Report on Patentability, re PCT Application No. PCT/US2020/020824, dated Sep. 16, 2021.
International Preliminary Report on Patentability, re PCT Application No. PCT/US2020/035752, dated Dec. 16, 2021.
International Preliminary Report on Patentability, re PCT Application No. PCT/US2020/044033, dated Feb. 10, 2022.
International Preliminary Report on Patentability, re PCT Application No. PCT/US2021/012977, dated Jul. 28, 2022.
International Preliminary Report on Patentability, re PCT Application No. PCT/US2021/036879, dated Dec. 22, 2022.
International Preliminary Report on Patentability, re PCT Application No. PCT/US2021/071330, dated Mar. 16, 2023.
International Preliminary Report on Patentability, re PCT Application No. PCT/US2021/072715, dated Jun. 15, 2023.
International Preliminary Report on Patentability, re PCT Application No. PCT/US2022/028839, dated Nov. 23, 2023.
International Preliminary Report on Patentability, re PCT Application No. PCT/US2022/073567, dated Jan. 25, 2024.
International Preliminary Report on Patentability, re PCT Application No. PCT/US2022/074164, dated Feb. 8, 2024.
International Preliminary Report on Patentability, re PCT Application No. PCT/US2023/063795, dated Sep. 19, 2024.
International Search Report and Written Opinion for Int'l Application No. PCT/IB2019/000181, titled: Activating Chimeric Receptors and Uses Thereof in Natural Killer Cell Immunotherapy, Date Mailed: Jun. 28, 2019.
International Search Report and Written Opinion for International Application No. PCT/US2019/050679, mailed Dec. 30, 2019, in 21 pages.
International Search Report and Written Opinion for International Application No. PCT/US2019/062851, mailed Apr. 1, 2020 in 25 pages.
International Search Report and Written Opinion for International Application No. PCT/US21/71330, mailed Feb. 15, 2022, in 20 pages.
International Search Report and Written Opinion issued in International Application No. PCT/US2014/013292, dated Apr. 28, 2014, 15 pages total.
International Search Report and Written Opinion, re PCT Application No. PCT/IB2019/000141, dated Aug. 5, 2019.
International Search Report and Written Opinion, re PCT Application No. PCT/SG2015/050111, dated Aug. 17, 2015.
International Search Report and Written Opinion, re PCT Application No. PCT/SG2018/050138, dated Jul. 4, 2018.
International Search Report and Written Opinion, re PCT Application No. PCT/US2018/024650, dated Jul. 26, 2018.
International Search Report and Written Opinion, re PCT Application No. PCT/US2020/035752, dated Sep. 14, 2020.
International Search Report and Written Opinion, re PCT Application No. PCT/US2020/044033, dated Dec. 18, 2020.
Fujiwara, et al; Hinge and Transmembrane Domains of Chimeric Antigen Receptor Regulate Receptor Expression and Signaling Threshold; Cells; (2020) 9, 1182; doi: 10.3390/cells9051182.
Fundamental Immunology, Third Edition, Chs. 1, 13 and 32, Paul, W.E., ed., pp. 1-20, 467-504, 1143-1178, Raven Press, New York (1993).
Furst, D. E., Fernandes, A. W., Iorga, S. R., Greth, W., & Bancroft, T. (2012). Annual medical costs and healthcare resource use in patients with systemic sclerosis in an insured population. J Rheumatol, 39(12), 2303-2309. https://doi.orq/10.3899/jrheum.120600.
Furuta, S., & Jayne, D. R. W. (2013). Antineutrophil cytoplasm antibody–associated vasculitis: recent developments. Kidney International, 84(2), 244-249. https://doi.org/10.1038/ki.2013.24.
Furuta, S., Nakagomi, D., Kobayashi, Y., et al. (2021). Effect of Reduced-Dose vs High-Dose Glucocorticoids Added to Rituximab on Remission Induction in ANCA-Associated Vasculitis: A Randomized Clinical Trial. JAMA, 325(21), 2178-2187. https://doi.ora/10.1001/iama.2021.6615.
Gacerez, A et al., "How Chimeric Antigen Receptor Design Affects Adoptive T Cell Therapy," Journal of Cellular Physiology, vol. 231, No. 12, pp. 2590-2598 (Jun. 2, 2016).

(56) References Cited

OTHER PUBLICATIONS

Galustian C. et al., MP84-07A tale of tails—A novel approach to immunotherapy of prostate cancer. J Ural., May 10, 2016, vol. 195, No. 4S, pp. e1092.
Gbolahan et al., Locoregional and systemic therapy for hepatocellular carcinoma(, Gastrointest. Oncol. 8(2):215-228, Apr. 2017.
Geetha, D., & Jefferson, J. A. (2020). ANCA-Associated Vasculitis: Core Curriculum 2020. American Journal of Kidney Diseases, 75(1), 124-137. https://doi.org/10.1053/j.ajkd.2019.04.031.
GenBank Accession No. NM 007360 GI: 15221123, *Homo sapiens* killer cell lectin like receptor K1 (KLRK1), mRNA, dated May 29, 2017, 4 pages.
GenBank Accession No. NM_000734 GI: 27886640, *Homo sapiens* CD8 antigen, alpha polypeptide (TiT3 complex) (CD3Z), transcript variant 2, mRNA, dated Oct. 27, 2004, 6 pages.
GenBank Accession No. NM_172175.2, *Homo sapiens* interleukin 15 (IL15), transcript variant 2, mRNA, dated Feb. 12, 2011, 4 pages.
GenBank: Accession No. AF461811.1; *Homo sapiens* NKG2D mRNA, complete cds, dated Jan. 17, 2002.
GenBank: Accession No. NM000734.3; *Homo sapiens* CD247 molecule (CD247), transcript variant 2, mRNA, dated Apr. 16, 2019.
GenBank: Accession No. NM001561.5; *Homo sapiens* TNF receptor superfamily member 9 (TNFRSF9), mRNA, dated Jul. 23, 2019.
GenBank: Accession No. NM001768.6: *Homo sapiens* CD8a molecule (CD8A), transcript variant 1, mRNA, dated Feb. 26, 2020.
Giebel, S. et al., "Survival advantage with KIR ligand incompatibility in hematopoietic stem cell transplantation from unrelated donors" Blood (2003) vol. 102, No. 3, pp. 814-819.
Gilhus NE. Myasthenia Gravis, Respiratory Function, and Respiratory Tract Disease. J Neural. 2023;270(7):3329-3340. doi:10.1007/s00415-023-11733-y.
Gordon, P.A., Winer, J. B., Hoogendijk, J. E., & Choy, E. H. (2012). Immunosuppressant and immunomodulatory treatment for dermatomyositis and polymyositis. Cochrane Database Syst Rev, 2012(8), Cd003643. https://doi.ora/10.1002/14651858.CD003643.oub4.
Grabstein et al., "Cloning of a T cell growth factor that interacts with the ß chain of the interleukin-2 receptor," Comparitive Study, Science, May 13, 1994;264(5161):965-8.
Grauer et al., "Identification, Purification, and Subcellular Localization of Prostate-specific Membrane Antigen PSM Protein in the LNCaP Prostatic Carcinoma Cell Line," Cancer Res., 58: 4787-4789 (1998).
Gravanis et al., "The changing world of cancer drug development: the regulatory bodies' perspective," Chin Clin Oneal, 2014, 3, pp. 1-5 (Year: 2014).
Greene et al., "Covalent dimerization of CD28/CTLA-4 and oligomerization of CD80/CD86 regulate T cell costimulatory interactions," J Biol Chem., 271(43):26762-26771, Oct. 25, 1996.
Greenfield, E.A., et al., "CD28/B7 Costimulation: A Review," Crit. Rev. Immunol. 18: 389-418 (1998).
Greenspan et al. 1999 Defining epitopes: It's not as easy as it seems; Nature Biotechnology, 17:936-937 (Year: 1999).
Greenwald et al., "The B7 Family Revisited," Annu. Rev. ImmunoL, 2005, 23: 515-548.
Gregorini, M., Maccario, R., Avanzini, M.A., et al. (2013). Antineutrophil Cytoplasmic Antibody-Associated Renal Vasculitis Treated With Autologous Mesenchymal Stromal Cells: Evaluation of the Contribution of Immune-Mediated Mechanisms. Mayo Clinic Proceedings, 88(10), 1174-1179. https://doi.ora/10.1016/i.mavocp.2013.06.021.
Grier J. T. et al., "Human immunodeficiency-causing mutation defines CD16 in spontaneous NK cell cytotoxicity", The Journal of Clinical Investigation, vol. 122, No. 10, Oct. 1, 2012, pp. 3769-3780.
Grillo-Lopez, "Rituximab: An Insider's Historical Perspective," Seminars in Oncology 27(6 Suppl 12): 9-16 (2012).
Gronseth GS, Barohn R, Narayanaswami P. Practice advisory: Thymectomy for Myasthenia Gravis (practice parameter update): Report of the Guideline Development, Dissemination, and Implementation Subcommittee of the American Academy of Neurology. Neurology. 2020;94(16):705-709. doi: 10.1212/WNL.0000000000009294.
Gruber et al. "Cbl-b mediates TGF? sensitivity by downregulating inhibitory SMAD7 in primary T cells", Journal of Molecular Cell Biology, May 24, 2013, vol. 5, pp. 358-368.
Guedan et al., Time 2EVOLVE: predicting efficacy of engineered T-cells—how far is the bench from the bedside?: Journal for Immunotherapy Cancer. May 16, 2022; in 16 pages.
Guo et al. "CBLB, CISH and CD70 multiplexed gene knockout with CRISPR/Cas9 enhances cytotoxicity of CD70-CAR NK cells and provides greater resistance to TGF-f,I, for cancer immunotherapy," Nkarta Therapeutics, Inc., Apr. 8, 2022, in 1 page.
Guo et al. "CISH gene-knockout anti-CD70-CAR NK cells demonstrate potent anti-tumor activity against solid tumor cell lines and provide partial resistance to tumor microenvironment inhibition," Nkarta Therapeutics, Inc., Nov. 12, 2021, in 1 paae.
Guo et al. "CRISPR/Cas9-gRNA RNP mediated gene knockout of TGFBR2 and CISH enhances CD19-CAR NK cell function and provides resistance to TGFβ," Nkarta Therapeutics, Inc., presented in a conference on Jun. 22, 2020, in 1 page.
Guo, et al. "ADAM17 knockout NK or CAR NK cells augment Antibody Dependent Cellular Cytotoxicity (ADCC) and antitumor activity", UB Research Poster Template, AACR, 2023, 1 page.
Guo, Xuan, et al., "CBLB ablation with CRISPR/Cas9 enhances cytotoxicity of human placental stem cell-derived NK cells for cancer immunotherapy", Journal for Immuno Therapy of Cancer, Mar. 19, 2021, in 11 pages.
Gura T, "Systems for Identifying New Drugs are Often Faulty," Science 1997, 278(5340): 1041-1042 (Year: 1997).
Hait., "Anticancer drug development: the grand challenges," Nature Reviews/Drug Discovery, 2010, 9, pp. 253-254 (Year: 2010).
Halilu, Fatima, and Lisa Christopher-Stine. (2022). Myositis-specific antibodies: Overview and clinical utilization. Rheumatology and Immunology Research 3, No. 1: 1-10.
Handgretinger, R., et al., "A phase I study of neuroblastoma with the anti-ganglioside GD2 antibody 14.G2a," Cancer Immunol. Immunother. 35: 199-204 (1992).
Hara et al., "NKG2D gene polymorphisms are associated with disease control of chronic myeloid leukemia by dasatinib," Int. J. Hematol., 9 pages, Aug. 9, 2017.
Harigai et al. (2019). 2017 Clinical practice guidelines of the Japan Research Committee of the Ministry of Health, Labour, and Welfare for Intractable Vasculitis for the management of ANCA-associated vasculitis. Modern Rheumatoloav, 29(1), 20-30. https://doi.ora/10.1080/14397595.2018.1500437.
Harmon et al., "Dexamethasone induces irreversible G1 arrest and death of a human lymphoid cell line," J Cell Physiol, Feb. 1979, 98(2): 267-278.
Hasan, A.N., "Soluble and membrane-bound interleukin (IL)-15 Ra/IL-15 complexesmediate proliferation of high-avidity central memory CD81T cells foradoptive immunotherapy of cancer and infections," Clinical and Experimental Immunology, 186: 249-265, 2016.
Haynes, N.M., et al., "Redirecting Mouse CTL Against Colon Carcinoma: Superior Signaling Efficacy of Single-Chain Variable Domain Chimeras Containing TCR-vs Fc£RI-y," J. Immunol. 166: 182-187 (2001).
Hendel, et al., "Chemically modified guide RNAs enhance CRISPR-Cas genome editing in human primary cells", Nat Biotechnol. Sep. 2015, 33(9): 985-989.
Heppner et al., "Tumor heterogeneity: biological implications and therapeutic consequences," 1983, Cancer Metastasis Reviews 2:5-23 (Year: 1983).
Hiemstra et al. (2010). Mycophenolate mofetil vs azathioprine for remission maintenance in antineutrophil cytoplasmic antibody-associated vasculitis: a randomized controlled trial. Jama. Dec. 1;304(21):2381-8.
Hoffmann, S.C. et al. "2B4 Engagement Mediates Rapid LFA-1 and Actin-Dependent NK Cell Adhesion to Tumor Cells as Measured by Single Cell Force Spectroscopy," J. Immunol, 186(5): 2757-2764 (Jan. 2011).

(56) References Cited

OTHER PUBLICATIONS

Walsh SJ, Rau LM. (2000). Autoimmune diseases: a leading cause of death among young and middle-aged women in the United States. Am J Public Health.; 90(9): 1463-1466. doi: 10.2105/ajph.90.9.1463.
Walter et al., "Reconstitution of cellular immunity against cytomegalovirus in recipients of allogeneic bone marrow by transfer of T-cell clones from the donor," N Engl J Med, Oct. 1995, 333(16): 1038-1044.
Wang K, Wei G, Liu D. CD19: a biomarker for B cell development, lymphoma diagnosis and therapy. Exp Hematol Oneal. 2012;1(1):36. Published Nov. 29, 2012. doi: 10.1186/2162-3619-1-36.
Wang, W., "NK cell-mediated antibody-dependent cellular cytotoxicity in cancer immunotherapy," Frontiers in Immunology, 2015, 6, 368.
Warrens AN, et al., "Splicing by overlap extension by PCR using asymmetric amplification: an improved technique for the generation of hybrid proteins of immunological interest," Gene 20;186: 29-35 (1997).
Warzocha et al., "Antisense Strategy: Biological Utility and Prospects in the Treatment of Hematological Malignancies," Leukemia and Lymphoma (1997) vol. 24. pp. 267-281 (Year: 1997).
Watowich et al., "The Erythropoietin Receptor: Molecular Structure and Hematopoietic Signaling Pathways," J. Investig Med. 2011, 59(7): 1067-1072.
Weijtens, M.E.M., et al., "Functional balance between T cell chimeric receptor density and tumor associated antigen density: CTL mediated cytolysis and lymphokine production," Gene Ther. 7: 35-42 (2000).
WHO, "WHO Classification of Tumours of Haematopoietic and Lymphoid Tissues," International Agency for Research on Cancer (IARC), 4th Edition, 40 pages, 2008.
Wilcox et al., "Signaling through NK cell-associated CD137 promotes both helper function for CD8+ cytolytic T cells and responsiveness to IL-2 but not cytolytic activity," J. Immunol., Oct. 2002, 169(8):4230-6.
Wilkie, S. et al., "Selective Expansion of Chimeric Antigen Receptor-targeted T-cells with Potent Effector Function Using Interleukin-4," J Biol Chem., vol. 285, No. 33, pp. 25538-25544 (2010).
Written Opinion issued in International Application No. PCT/US2014/013292, dated Apr. 8, 2014, 11 pages total.
Wudhikarn K, Palomba ML, Pennisi M, et al. Infection during the first year in patients treated with CD19 CART-cells for diffuse large B-cell lymphoma. Blood Cancer J. Aug. 5, 2020;10(8):79. doi:10.1038/s41408-020-00346-7.
Wyss-Coray, T., et al., "The B7 adhesion molecule is expressed on activated human T cells: functional involvement in T-T cell interactions," Eur. J. ImmunoL., 23: 2175-2180 (1993).
Yan et al., "HER2 expression status in diverse cancers: review of results from 37,992 patients," Cancer Metastasis Rev (2015) 34:157-164 (Year: 2015).
Yan et al., "Murine CD8 lymphocyte expansion in vitro by artificial antigen-presenting cells expressing CD137L (4-1 BBL) is superior to CD28, and CD137L expressed on neuroblastoma expands CD8 tumour-reactive effector cells in vivo," Immunology, 2004, 112(1):105-116.
Yang et al. "The signaling suppressor CIS controls proallergic T cell development and allergic airway inflammation," Nature Immunology, vol. 14, No. 7, Jul. 2013, pp. 732-742.
Yang et al., "TGF-β upregulates CD70 expression and induces exhaustion of effector memory T cells in B-cell non-Hodgkin's lymphoma" Leukemia. Sep. 2014;28(9): 1872-84. Epub Feb. 26, 2014.
Yang, et al., "Natural killer cells in inflammatory autoimmune diseases" Clinical & Translational Immunology, vol. 10, e1250, in 17 pages (2021).
Ye et al., "Gene therapy for cancer using single-chain Fv fragments specific for 4-IBB," Nat Med, Apr. 2002, 8(4): 343-348.
Yeoh et al., "Classification, subtype discovery, and prediction of outcome in pediatric acute lymphoblastic leukemia by gene expression profiling," Cancer Cell, Mar. 2002, 1(2): 133-143.
Yescarta, "Highlights of prescribing information" in 31 pages, (2022).
Yescarta™ (axicabtagene ciloleucel) suspension for intravenous infusion. Santa Monica, CA. Kite Pharma Inc. (a Gilead Company). Revised Apr. 2024.
Yi JS, et al. B Cells in the Pathophysiology of Myasthenia Gravis. Muscle Nerve. 2018;57(2):172-184. doi: 10.1002/mus.25973.
Yoshida et al., "A novel adenovims expressing human 4-1BB ligand enhances antitumor immunity," Cancer Immunol Immunother, Feb. 2003, 52(2): 97-106.
Yoshimura et al. "Negative regulation of cytokine signaling and immune responses by SOCS proteins," Arthritis Research & Therapy, Jun. 2005, vol. 7, No. 3, pp. 100-110.
Yoshimura et al. "Negative regulation of cytokine signaling influences inflammation," Current Opinion in Immunology 2003, 15:704-708.
Young, et al., "The pharmacokinetics of low-dose dexamethasone in congenital adrenal hyperplasia" Eur J Clinical Pharmacology, 37: 75-77 (1989).
Zhang et al., "CAR-T Cells in the Treatment of Urologic Neoplasms: Present and Future" Frontiers in Oncology, Jul. 4, 2022, in 11 pages.
Zhang et al., "Improving Adoptive T Cell Therapy by Targeting and Controlling IL-12 Expression to the Tumor Environment," The American Society of Gene & Cell Therapy Molecular Therapy, vol. 19, No. 4, 751-759, 2011.
Zhang, et al., "Regulation of Experimental Autoimmune Encephalomyelitis by Natural Killer (NK) Cells", J. Exp. Med. vol. 186, No. 10, pp. 1677-1687, Nov. 17, 1997.
Zhang, et al., "Treatment of Systemic Lupus Erythematosus using BCMA-CD19 Compound CAR" Stem Cell Reviews and Reports, 17:2120-2123 (2021).
Zhang, W-P., et al., "Preconditioning with fludarabine, busulfan and cytarabine versus standard BuCy2 for patients with acute myeloid leukemia: a prospective, randomized phase II study", Bone Marrow Transplantation, vol. 54, 2019, pp. 894-902.
Zhou et al., "Effects of RNA Interference on CD70 in dendritic cells of patients with immune thrombocytooenia" Blood. Dec. 2, 2016;128(22): 1373. (Abstract Onlv) in two pages.
Zhu, Huang, et al., "Metabolic Reprograming via Deletion of CISH in Human Ipsc-Derived NK Cells Promotes In Vivo Persistence and Enhances Anti-tumor Activity" Cell Stem Cell, Aug. 6, 2020, 27, pp. 224-237.
Zuther, "Generation of the Plasmid pMT/BiP SCA431scFv-Fc-IL 15 (#1118)," Chapter 4.1.8 of an Anti-CD30 Immunocytokine with Combined IL-2 and IL-12 Domains Enhances Anti-Tumor Immunity, p. 70 (Oct. 1, 2009).
Manabe et al., "Interleukin-4 induces programmed cell death (*Apoptosis*) in cases of high-risk acute lymphoblastic leukemia," Blood, Apr. 1994, 83(7): 1731-1737.
Mandal, et al. "Efficient Ablation of Genes in Human Hematopoietic Stem and Effector Cells using CRISPR/Cas9" Cell Stem Cell, vol. 15, p. 643-652, Nov. 6, 2014, including supplement information totalina 27 oaaes.
Mandel, D. E., Malemud, C. J., & Askari, A. D. (2017). Idiopathic Inflammatory Myopathies: A Review of the Classification and Impact of Pathogenesis. Int J Mol Sci, 18(5). httos://doi.ora/10.3390/iims18051084.
Mann et al., "Construction of a retrovirus packaging mutant and its use to produce helper-free defective retrovirus," Cell, May 1983, 33(1): 153-159.
Mantegazza R, et al., When Myasthenia Gravis is Deemed Refractory: Clinical Signposts and Treatment Strategies [published correction appears in Ther Adv Neural Disord. Mar. 21, 2018;11:1756286418765591. doi: 10.1177/1756286418765591]. Ther Adv Neural Disord. 2018; 11:17562856177 49134. Published Jan. 18, 2018. doi: 10.1177/1756285617749134.
Manzke et al., "Immunotherapeutic strategies in neuroblastoma: antitumoral activity of deglycosylated Ricin A conjugated anti-GD2

(56) References Cited

OTHER PUBLICATIONS antibodies and anti-CD3xanti-GD2 bispecific antibodies," Med Pediatr Oncol., 36(1):185-189, Jan. 2001.
Manzke et al., "Locoregional treatment of low-grade B-cell lymphoma with CD3×CD19 bispecific antibodies and CD28 costimulation. I. Clinical phase I evaluation," Int J Cancer., 91(4):508-515, Feb. 15, 2001.
Marcais et al. "The metabolic checkpoint kinase mTOR is essential for interleukin-15 signaling during NK cell development and activation," Nat Immunol., Aug. 2014; 15(8); 749-757, 24 pages.
Marco, Joanna L., and Bridget F. Collins. (2020). Clinical manifestations and treatment of antisynthetase syndrome. Best Practice & Research Clinical Rheumatology 34, No. 4: 101503.
Marincola, F.M., et al., "Escape of Human Solid Tumors from T-Cell Recognition: Molecular Mechanisms and Functional Significance," Adv. Immunol. 74: 181-273 (2000).
Markowitz et al., "A safe packaging line for gene transfer: separating viral genes on two different plasmids," J Virol, Apr. 1988, 62(4): 1120-1124.
Marktel et al., "Immunologic potential of donor lymphocytes expressing a suicide gene for early immune reconstitution after hematopoietic T-cell-depleted stem cell transplantation," Blood, Feb. 2003, 101(4): 1290-1298.
Martinet O., et al., "T cell activation with systemic agonistic antibody versus local 4-1 BB ligand gene delivery combined with interleukin-12 eradicate liver metastases of breast cancer," Gene Ther. Jun. 2002; 9(12):786-792.
Matsumoto et al. "Suppression of STAT5 Functions in Liver, Mammary Glands, and T Cells in Cytokine-Inducible SH2-Containing Protein 1 Transgenic Mice," Molecular and Cellular Biology, Sep. 1999, p. 6396-6407.
Maus MV, et al., "Ex vivo expansion of polyclonal and antigen-specific cytotoxic T lymphocytes by artificial APCs expressing ligands for the T-cell receptor, CD28 and 4-1BB", Nat BiotechnoL Feb. 2002; 20(2): 143-148.
May KF, JR et al., "Anti-4-1 BB monoclonal antibody enhances rejection oflarge tumor burden by promoting survival but not clonal expansion of tumor-specific CDS+ T cells," Cancer Res. 2002, 62(12):3459-3465.
McCune et al., Clinical and immunologic effects of monthly administration of intravenous cyclophosphamide in severe systemic lupus erythematosus. N Engl J Med. 1988;318(22):1423-1431. doi: 10.1056/NEJM198806023182203.
McGrogan A, et al., The Incidence of Myasthenia Gravis: A Systematic Literature Review. Neuroepidemiology. 2010;34(3):171-183. doi:10.1159/000279334.
McKeague, et al., "Challenges and Opportunities for Small Molecule Aptamer Development," Review Article, Journal of Nucleic Acids, vol. 2012, Article ID 748913.
Mei HE, Schmidt S, Dorner T. (2012). Rationale of anti-CD19 immunotherapy: an option to target autoreactive plasma cells in autoimmunity. Arthritis Res Ther. 14 Suppl 5(Suppl 5):S1. doi:10.1186/ar3909.
Melero et al., "Monoclonal antibodies against the 4-IBB T-cell activation molecule eradicate established tumors," Nat. Med., 1997, 3(6): 682-685.
Memorandum Consolidating the Actions in *Trustees of the University of Pennsylvania* v. *St. Jude Children's Research Hospital in the US District Court for the Eastern District of Pennsylvania*, dated Nov. 13, 2013. (Lit. Doc. 20).
Meyer et al., (2015). Incidence and prevalence of inflammatory myopathies: a systematic review. Rheumatology (Oxford), 54(1), 50-63. https://doi.org/10.1093/rheumatology/keu289.
Miah et al. "CISH is induced during DC development and regulate DC-mediated CTL activation," European Journal of Immunology, 2012. 42: 58-68.
Mihara et al., "Development and functional characterization of human bone marrow mesenchymal cells immortalized by enforced expression of telomerase," Br J Haematol, Mar. 2003, 120(5): 846-849.
Miller, Frederick W. (2023) The increasing prevalence of autoimmunity and autoimmune diseases: an urgent call to action for improved understanding, diagnosis, treatment, and prevention. Current opinion in immunology 80:102266.
Minamoto, S. et al., "Acquired Erythopoietin Responsiveness of Interleukin-2-dependent T lymphocytes Retrovirally Transduced with Genes Encoding Chimeric Erythropoietin/Interleukin-2 Receptors," Blood, vol. 86, No. 6, pp. 2281-2287 (1995).
Miosge, "Comparison of predicted and actual consequences of missense mutations," Proc Natl Acad Sci USA Sep. 15, 2015;112(37):E5189-98 (Year: 2015).
Mirzaei, et al. "Chimeric Antigen Receptors T Cell Therapy in Solid Tumor: Challenges and Clinical Applications" Frontiers in Immunology, Dec. 22, 2017, vol. 8, 1-13.
Mirzaei, H.R., et al., "Construction and functional characterization of a fully human anti-CD19 chimeric antigen receptor (huCAR)-expressing primary human T cells," J Cell Physiol. Jun. 2019; 234(6):9207-9215. doi: 10.1002/jcp.27599. Epub Oct. 26, 2018. PMID: 30362586 (Abstract).
Mistry, A.R. et al., "Regulation of Ligands for the Activating Receptor NKG2D" Immunology (2007) vol. 121, pp. 439-447.
Mogi et al., "Tumour rejection by gene transfer of 4-IBB ligand and into a CD80(+) murine squamous cell carcinoma and the requirements of co-stimulatory molecules on tumour and host cells," Immunology, Dec. 2000, 101(4):541-7.
Mohammed, S. et al., "Improving Chimeric Antigen Receptor-Modified T Cell Function by Reversing the Immunosuppressive Tumor Microenvironment of Pancreatic Cancer," Mol. Ther. 4, vol. 25, No. 1, pp. 249-258 (2017).
Mollanoori, et al., "CRISPR/Cas9 and CAR-T cell, collaboration of two revolutionary technologies in cancer immunotherapy, an instruction for successful cancer treatment" Elsevier, Human Immunology, Sep. 23, 2018, 7 pages.
Mondino and Jenkins, "Surface proteins involved in T cell costimulation," J Leukoc Biol, Jun. 1994, 55(6): 805-15.
Monti et al. 2020. Use and reporting of outcome measures in randomized trials for anti-neutrophil cytoplasmic antibody-associated vasculitis: a systematic literature review. In Seminars in arthritis and rheumatism, vol. 50, No. 6, pp. 1314-1325. WB Saunders.
Mora, "Dinutuximab for the treatment of pediatric patients with high-risk neuroblastoma," Expert Rev Clin Pharmacol., 9(5):647-653, Epub Mar. 21, 2016.
Moradzadeh, M., Aghaei M., Mehrbakhsh Z., et al. (2021) Efficacy and safety of rituximab therapy in patients with systemic sclerosis disease (SSc): systematic review and meta-analysis. Clinical rheumatoloav: 1-22.
Morgan, et al., "Case Report of a Serious Adverse Event Following the Administration of T Cells Transduced With a Chimeric Antigen Receptor Recognizing ERBB2" Molecular Therapy, vol. 18, No. 4, 843-851, Apr. 2010.
Morgan, R.A. et al., Recognition of Glioma Stem Cells by Genetically Modified T Cells Targeting EGFRvIII and Development of Adoptive Cell Therapy for Glioma, Human Gene Therapy, 23(10), 1043-1053 (2012).
Morisot, N., Wadsworth S., Davis T., et al. (2020). Preclinical evaluation of NKX019, a CD19-targeting CAR NK cell. J Immunother Cancer 8:A140.
Moritz, D., et al., "Cytotoxic T lymphocytes with a grafted recognition specificity for ERBB2-expressing tumor cells," Proc. Natl. Acad. Sci. USA 91:4318-4322 (1994).
Mosakowska, Magdalena, et al. "Assessment of the correlation of commonly used laboratory tests with clinical activity, renal involvement and treatment of systemic small-vessel vasculitis with the presence of ANCA antibodies." BMC nephrology 22.1 (2021): 290.
Motion to Intervene filed by *Juno Therapeutics, Inc. in Trustees of the University of Pennsylvania* v. *St. Jude Children's Research Hospital in the U.S. District Court for the Eastern District of Pennsylvania*, dated Dec. 13, 2013. (Doc. 24).
Mougiakakos D, Krenke G, Volkl S, et al. CD19-Targeted CART Cells in Refractory Systemic Lupus Erythematosus. N Engl J Med. 2021;385(6):567-569. doi: 10. 1056/NEJMc2107725.

(56) References Cited

OTHER PUBLICATIONS

Muangchan, C., Group, C. S. R., Baron, M., & Pope, J. (2013). The 15% Rule in Scleroderma: The Frequency of Severe Organ Complications in Systemic Sclerosis. A Systematic Review. The Journal of Rheumatology, 40(9), 1545-1556. https://doi.org/10.3899/jrheum.121380.

Mueller, et al., "CD19-Targeted CAR-T Cells in Refractory Systemic Autoimmune Diseases: A Monocentric Experience from the First Fifteen Patients" Blood 142 (2023) 220-221.

Muller et al. 2024. CD19 CART-Cell Therapy in Autoimmune Disease—A Case Series with Follow-up. New England Journal of Medicine. Feb. 22;390(8):687-700.

Muller et al. Definition of critical T cell threshold for prevention of GVHD after HLA non-identical PBPC transplantation in children. Bone Marrow Transplant. 1999; 24(6):575-581. doi: 10.1038/si.bmt.1701970.

Muller T. et al., "Expression of a CD20-specific Chimeric Antigen Receptor Enhances Cytotoxic Activity of NK Cells anc Overcomes NK-Resistance of Lymphoma and Leukemia Cells" Cancer Immunol Immunother (2008) vol. 57, pp. 411-423.

International Search Report and Written Opinion, re PCT Application No. PCT/US2021/012977, dated May 19, 2021.

International Search Report and Written Opinion, re PCT Application No. PCT/US2021/036879, dated Nov. 10, 2021.

International Search Report and Written Opinion, re PCT Application No. PCT/US2021/072715, dated Jun. 10, 2022.

International Search Report and Written Opinion, re PCT Application No. PCT/US2022/028839, dated Jul. 28, 2022.

International Search Report and Written Opinion, re PCT Application No. PCT/US2022/073567, dated Dec. 15, 2022.

International Search Report and Written Opinion, re PCT Application No. PCT/US2022/074164, dated Oct. 18, 2022.

International Search Report and Written Opinion, re PCT Application No. PCT/US2023/063795, dated Oct. 18, 2023.

International Search Report and Written Opinion, re PCT Application No. PCT/US2023/079895, dated Apr. 19, 2024.

International Search Report and Written Opinion, re PCT Application No. PCT/US2024/023051, dated Jul. 26, 2024.

International Search Report and Written Opinion, re PCT Application No. PCT/US2024/035654, dated Sep. 3, 2024.

Israeli, R.S., et al., "Expression of the Prostate-specific Membrane Antigen," Cancer Res., 1994, 54:1807-1811.

Ito et al., "Hyperdiploid acute lymphoblastic leukemia with 51 to 65 chromosomes: a distinct biological entity with a marked propensity to undergo apoptosis," Blood, Jan. 1999, 93(1): 315-20.

Izawa, et al. "Inherited CD70 deficiency in humans reveals a critical role for the CD70-CD27 pathway in immunity to Epstein-Barr virus infection" The Journal of Experimental Medicine, 2017, vol. 214, No. 1, 73-89.

Jaafar et al. (2021). Clinical characteristics, visceral involvement, and mortality in at-risk or early diffuse systemic sclerosis: a longitudinal analysis of an observational prospective multicenter US cohort. Arthritis Res Ther, 23(1), 170. https://doi.ora/10.1186/s13075-021-02548-1.

Jain RK, "Barriers to Drug Delivery in Solid Tumors," 1994, Scientific American, pp. 58-645 (Year: 1994).

Jaspers, et al. "Development of CART cells designed to improve antitumor efficacy and safety", Pharmacol Ther. Author manuscript, Oct. 2017, 178: 83-91.

Jayne et al. (2021). Avacopan for the Treatment of ANCA-Associated Vasculitis. New England Journal of Medicine, 384(7), 599-609. https://doi.org/10.1056/NEJMoa2023386.

Jayne et al. Autologous stem cell transplantation for systemic lupus erythematosus. Lupus. 2004; 13(3):168-176. doi:10.1191/09612033041u525oa.

Jennette, J. C. (2011). Nomenclature and classification of vasculitis: lessons learned from granulomatosis with polyangiitis (Wegener's granulomatosis). Clinical & Experimental Immunology. 164:7-10.

Jensen, M., et al., "CD20 is a molecular target for scFvFc: receptor redirected T cells: implications for cellular immunotherapy of CD20+ malignancy," Biol. Blood and Marrow Transplantation 4: 75-83 (1998).

Jerjen, R., Nikpour, M., Krieg, T., Denton, C. P., & Saracino, A. M. (2022). Systemic sclerosis in adults. Part I: Clinical features and pathogenesis. Journal of the American Academy of Dermatology, 87(5), 937-954.

Jiang et al., "Role of IL-2 in cancer immunotherapy," (2016, Oncoimmunology, vol. 5(6), pp. 1-10). (Year: 2016).

Jiang, Z., et al., "IL-6 trans-signaling promotes the expansion and anti-tumor activity of CAR T cells" Leukemia (2021)35; pp. 1380-1391.

Johnson and Jenkins, "The role of anergy in peripheral T cell unresponsiveness," Life Sci, 1994, 55(23): 1767-1780.

June et al., "The B7 and CD28 receptor families," Immunol Today, Jul. 1994, 15(7): 321-331.

Juno Therapeutics, Inc.'s Answer to Amended Complaint in *Trustees of the University of Pennsylvania v. St. Jude Children's Research Hospital in the U.S. District Court for the Eastern District of Pennsylvania*, dated Dec. 20, 2013. (Lit Doc. 50).

Kaiser, B.K. et al., "Structural basis for NKG2A/CD94 Recognition of HLA-E," Proc Nat'l Acad Sci USA, 105(18): 6696-6701 (Apr. 2008).

Kalinova, D., A. Kopchev, Z. Kolarov, and R. Rashkov. (2020). Immune-mediated necrotizing myopathy with anti-SRP autoantibodies and typical clinical presentation. Clin Med Rev Case Rep 7: 314.

Karaoudi, Meisam, et al. "Generation of Knock-out Primary and Expanded Human NK Cells Using Cas9 Ribonucleoproteins", Journal of Visualized Experiments, Jun. 2018, 136, pp. 1-8.

Kariv, I., et al., "Analysis of the Site of Interaction of CD28 with Its Counter-Receptors CD80 and CD86 and Correlation with Function," J. of Immunol. 157: 29-38 (1996).

Kenderian et al., Identification of PD 1 and TIM3 as checkpoints that limit chimeric antigen receptor T cell efficacy in leukemia. Blood. Dec. 3, 2015;126(23):852, in 4 pages.

Khan, Muhammad, et al. "NK Cell-based Immune Checkpoint Inhibition", frontiers in Immunology, Feb. 13, 2020, vol. 11, Article 167, in 31 pages.

Khanna D, Huang S, Lin CJ, Spino C. (2021). New composite endpoint in early diffuse cutaneous systemic sclerosis: revisiting the provisional American College of Rheumatology Composite Response Index in Systemic Sclerosis. Annals of the rheumatic diseases. May 1;80(5):641-50.

Khanna, D., Furst, D. E., Clements, et al. (2017). Standardization of the modified Rodnan skin score for use in clinical trials of systemic sclerosis. J Scleroderma Relat Disord, 2(1), 11-18. https://doi.org/10.5301/isrd.5000231.

Khanna, D., Lin, C. J. F., Furst, D. E., et al. (2020). Tocilizumab in systemic sclerosis: a randomised, double-blind, placebo-controlled, phase 3 trial. Lancet Respir Med, 8(10), 963-974. https://doi.orq/10.1016/s2213-2600(20)30318-0.

Khor et al. "CISH and Susceptibility to Infectious Diseases," N. Engl J. Med., Jun. 3, 2010; 362(22): 2092-2101, in 15 pages.

Kile et al. "The suppressors of cytokine signalling (SOCS)," CMLS, Cell. Mol. Life Sci. 58 (2001), pp. 1627-1635.

Kite Pharma Inc.'s Reply to Patent Owner'S Response to the Petition re: 1PR2015-01719, 35 pages, Aug. 4, 2016.

Koeffler and Golde, "Acute myelogenous leukemia: a human cell line responsive to colony-stimulating activity," Science, Jun. 1978, 200(4337): 1153-1154.

Kohrt, H.E., "Immunomodulation of NK Cells through 4-1BB (CD137) to Improve the Anti-Lymphoma Activity of Rituximab: Antibody-Based Anti-Lymphoma Snergy," Blood, 2010, 116(21), 422 (Abstract).

Kontermann, et al., "Bispecific antibodies," Drug Discovery Today, 2015, v. 7, n. 20, p. 838-847, Fig. 1.

Kowal-Bielecka, 0., Fransen, J., Avouac, J., et al. (2017). Update of Eular recommendations for the treatment of systemic sclerosis. Annals of the rheumatic diseases, 76(8), 1327-1339.

Krampera et al., "Bone marrow mesenchymal stem cells inhibit the respnose of nai:Ve and memory antigen-specific T cells to their cognate peptide," Blood, May 2003, 101(9): 3722-9.

(56) References Cited

OTHER PUBLICATIONS

Krause et al., "Antigen-dependent CD28 Signaling Selectively Enhances Survival and Proliferation in Genetically Modified Activated Human Primary T Lymphocytes," J. Exp. Med., 1998, 188(4): 619-626.
Krug, C., et al., "Stability and activity of MCSP-specific chimeric antigen receptors (CARs) depend on the scFv antigen-binding domain and the protein backbone," Cancer Immunol. Immunother. 64:1623-1635 (2015).
Kruschinski A. et al., "Engineering Antigen-Specific Primary Human NK Cells Against HER-2 Positive Carcinomas" Proc Natl Acad Sci USA (2008) vol. 105, No. 45, pp. 17481-17486.
Krystufkova, 0., Hulejova, H., Mann, H. F., et al. (2018). Serum levels of B-cell activating factor of the TNF family (BAFF) correlate with anti-Jo-1 autoantibodies levels and disease activity in patients with anti-Jo-1positive polymyositis and dermatomyositis. Arthritis Res Ther, 20(1), 158. httos://doi.org/10.1186/s13075-018-1650-8.
Kulmanov et al., "DeepGO: predicting protein functions from sequence and interactions using a deep ontology-aware classifier," Bioinformatics, 34(4), 2018, 660-668 (Year: 2018).
Kumar B. B. et al., "Natural Killer Cells Expanded and Preactivated Exhibit Enhanced Antitumor Activity against Different Tumor Cells in Vitro", Asian Pacific Journal of Cancer Prevention, vol. 21, No. 6, Jun. 6, 2020, pp. 1595-1605.
Kumar, et al., "Deletion of Cbl-b inhibits CD8+ T-cell exhaustion and promotes CAR T-cell funtion" Journal for Immuno Therapy of Cancer, Jan. 18, 2021, in 6 pages.
Parikh SV, Almaani S, Brodsky S, Rovin BH. Update on Lupus Nephritis: Core Curriculum 2020. Am J Kidney Dis. 2020;76(2):265-281. doi:10.1053/j.ajkd.2019.10.017.
Park et al. "Are All Chimeric Antigen Receptors Created Equal?" J. Clin. Oneal. 33: 651-653 (2015).
Park et al., Follicular dendritic cells produce IL-15 that enhances germinal center B cell proliferation in membrane-bound form. J. Immunol. 173(11):6676-6683, 2004.
Patel et al., "CAR T cell therapy in solid tumors: A review of current clinical trials" EJHaem. Oct. 7, 2021, 24-31.
Peach, R.J. et al., "Complementarity Determining Region 1 (CDR1)-and CDR3-analogous Regions in CTLA-4 and CD28 Determine the Binding to B7-1," J. Exp. Med. 180: 2049-2058 (1994).
Pearce, F. A., Lanyon, P. C., Grainge, M. J., Shaunak, R., Mahr, A., Hubbard, R. B., & Watts, R. A. (2016). Incidence of ANCA-associated vasculitis in a UK mixed ethnicity population. Rheumatology (Oxford), 55(9), 1656-1663. https://doi.org/10.1093/rheumatology/kew232.
Pelechas et al., "Sirukumab: a promising therapy for rheumatoid arthritis" Expert Opinion on Biological Therapy, 2017, vol. 17, No. 6, 755-763.
Pende, D. et al., "Major Histocompatibility Complex Class I-Related Chain A and UL16-Binding Protein Expression on Tumors Cells Lines of Different Histotypes: Analysis of Tumor Susceptibility to NKG2D-Dependent Natural Killer Cell Cytotoxicity" Cancer Research (2002) vol. 62, pp. 6178-6186.
Petition for Inter Partes Review of U.S. Pat. No. 7,446,190 Under 35 U.S.C.?? 311-319 and 37 C.F.R,?? 42.1-.80,42.100-.123, 64 pages, Aug. 13, 2015.
Phillips WO, et al., Pathogenesis of Myasthenia Gravis: Update on Disease Types, Models, and Mechanisms. F1000Res. 2016;5:F1000 FacultyRev-1513. Published Jun. 27, 2016. doi:10.12688/f1000research.8206.1.
Pittari et al., "Revving up Natural Killer Cells and Cytokine-Induced Killer Cells Against Hematological Malignancies", Frontiers in Immunology, vol. 6, May 13, 2015, XP055911635.
Poirot, et al., Multiplex Genome-Edited T-cell Manufacturing Platform for "Off-the_Shelf" Adoptive T-cell Immunotheraples, Cancer Research, Jul. 16, 2015, 3853-3864.
Pollok et al., "Regulation of 4-1BB expression by cell-cell interactions and the cytokines, interleukin-2 and interleukin-4," Eur J Imnunol, Feb. 1995, 25(2): 488-494.
Pollok KE, et al., "Inducible T cell antigen 4-1 BB Analysis of expression and function," J Immunol., 1993, 150(3):771-781.
Pope, J. E., Denton, C. P., Johnson, S. R., Fernandez-Godina, A., Hudson, M., & Nevskaya, T. (2023). State-of-the-art evidence in the treatment of systemic sclerosis. Nature Reviews Rheumatology, 19(4), 212-226. https://doi.ora/10.1038/s41584-023-00909-5.
Prajapati, et al; Functions of NKG2D in CD8+ T cells: an opportunity for immunotherapy; Cellular and Molecular Immunology (2018) 15, 470-479.
Proposed Order in *Trustees of the University of Pennsylvania* v. *St. Jude Children's Research Hospital in the U.S. District Court for the Eastern District of Pennsylvania*, dated Nov. 15, 2013. (Doc. 25).
ProteinAtlas.org [online], "The Human Protein Atlas," accessed Jun. 27, 2019, retrieved from URL<https://www.proteinatlas.org/ENSG00000177455- CD19/pathology>.
Pui et al., "Childhood acute lymphoblastic leukaemia—current status and future perspectives," Lancet Oncol, Oct. 2001, 2(10): 597-607.
Pule et al. "Virus-specific T cells engineered to coexpress tumor-specific receptors: persistence and antitumor activity in individuals with neuroblastoma," Nature Med., 2008, 14(1 1):1264-1270.
Putz et al. "Targeting cytokine signaling checkpoint CIS activates NK cells to protect from tumor initiation and metastasis," Oncoimmunology, 2017, vol. 6, No. 2, 31267892 (10 pages).
Qin et al., "Incorporation of a hinge domain improves the expansion of chimeric antigen receptor T cells" J. Hematol. Oneal. Mar. 13, 2017; 10(1):68.
Qin, et al., "Anti-BCMA CART-cell therapy CT103A in relapsed or refractory AQP4-IgG seropositive neuromyelitis optica spectrum disorders: phase 1 trial interim results" Springer Nature, in 9 pages, Jan. 4, 2023.
Quan XY, Chen HT, Liang SQ, et al. (2022). Revisited cyclophosphamide in the treatment of lupus nephritis. BioMed Research International 2022.
Queval et al. *Mycobacterium tuberculosis* Controls Phagosomal Acidification by Targeting CISH-Meditated Signaling, 2017, Cell Reports 20, pp. 3188-3198.
Rabinovich, P.M. et al., "Synthetic Messenger RNA as a Tool for Gene Therapy" Human Gene Therapy (2006) vol. 17, pp. 1027-1035.
Raghu G, Remy-Jardin M, Richeldi L, et al. (2022). Idiopathic pulmonary fibrosis (an update) and progressive pulmonary fibrosis in adults: an official ATS/ERS/JRS/ALAT clinical practice guideline. American Journal of Respiratory and Critical Care Medicine. May 1;205(9):e18-47.
Rajagopalan et al., Found: a cellular activating ligand for N Kp44, Blood, 122( 17):2921-2922, Oct. 2013.
Ramsborg et al. "Global transcriptional analysis delineates the differential inflammatory response interleukin-15 elicits from cultured human T cells," Experimental Hematology 35 (2007) 454-464.
Ran et al. "Genome engineering using the CRISPR-Cas9 system", Oct. 24, 2013, vol. 8, No. 11, pp. 2281-2308.
Rautela et al. "Efficient genome editing of human natural killer cells by CRISPR RNP," bioRxiv, Sep. 6, 2018, pp. 1-24.
Reighard, et al., "Therapeutic Targeting of Follicular T cells with Chimeric Antigen Receptor-Expressing Natural Killer Cells", Cell Press, in 23 pages, Apr. 21, 2020.
Ren, et al., "A versatile sytem for rapid multiplex genome-edited CART cell generation" Oncotarget, Feb. 9, 2017, vol. 8, No. 10, pp. 17002-17011.
Ren, et al., "Advancing chimeric antigen receptor T cell therapy with CRISPR/Cas9", Protein & Cell, Mar. 30, 2017, 8(9); 634-643.
Ren, et al., "Multiplex Genome Editing to Generate Universal CART Cells Resistant to PD1 Inhibition", Clinical Cancer Research, Nov. 4, 2016, 2255-2266.
Ren, P.-P. et al., Anti-EGFRvIII Chimeric Antigen Receptor-Modified T Cells for Adoptive Cell Therapy of Glioblastoma, Current Pharmaceutical Design, 23(14), 2113-2116 (2017).
Request for Ex Parte Reexamination of U.S. Pat. No. 9,511,092 which has been assigned U.S. Appl. No. 90/014,175, filed Aug. 1, 2018, 49 pages total.

(56) References Cited

OTHER PUBLICATIONS

Response to Election of Species Requirement of Office Action in U.S. Appl. No. 10/981,352, dated Mar. 27, 2007.
Response to Office Action in U.S. Appl. No. 13/548,148, dated Jan. 11, 2013.
Response to Office Action in U.S. Appl. No. 11/074,525 dated Jun. 25, 2007.
Response to Office Action in U.S. Appl. No. 11/074,525, dated Apr. 1, 2008.
Response to Office Action in U.S. Appl. No. 11/074,525, dated Dec. 7, 2007.
Rider, L.G., Aggarwal, R., Machado, P.M., Hogrel, J.Y., Reed, A.M., Christopher-Stine, L. and Ruperto, N., 2018. Update on outcome assessment in myositis. Nature Reviews Rheumatology, 14(5), pp. 303-318.
Riley et al., "The CD28 family: a T-cell rheostat for therapeutic control of T-cell activation," Blood, 2005, 105:13-21.
Riley K, Schwager Z, Stern M, Vleugels RA, Femia A. Assessment of Antimalarial Therapy in Patients Who Are Hypersensitive to Hydroxychloroquine. JAMA Dermatol. 2019; 155(4):491-493. doi: 10.1001 /iamadermatol.2018.5212.
Rituxan (rituximab) injection for intravenous use. South San Francisco, CA Genentech, Inc; Oct. 2012.
Rituxan Highlights of Prescribing Information. US Food and Drug Administration; 2012. [updated Oct. 2012; cited Sep. 25, 2017]. Available from: http://www.accessdata.fda.gov/drugsatfda_docs/label/2012/103705s5367s53881bl.pdf Last accessed Mar. 21, 2024.
Robak, T., New Anti-CD20 Monoclonal Antibodies for the Treatment of B-Cell Lymphoid Malignancies, BioDrugs 25, 13-25 (2011) (Abstract).
Robinson TM, Prince GT, Thoburn C, et al. (2018). Pilot trial of K562/GM-CSF whole-cell vaccination in MOS patients. Leuk Lymphoma.59(12):2801-2811. doi:10.1080/10428194.2018.1443449.
Robson, Joanna C., Peter C. Grayson, Cristina Ponte, et al. 2022. American College of Rheumatology/European Alliance of Associations for Rheumatology classification criteria for granulomatosis with polyanqiitis. Arthritis & Rheumatology 74, No. 3 (2022): 393-399.
Calabrese, et al., "IL-6 biology: implications for clinical targeting in rheumatic disease," S. Nat. Rev. Rheumatol, 10, 720-727 (2014); published online Aug. 19, 2014 (corrected online Sep. 19, 2014).
Call et al., "The structural basis for intramembrane assembly of an activating immunoreceptor complex" Nat Immunol Nov. 2010; 11(11): 1023-1029.
Callen, J. P. (2010). Cutaneous manifestations of dermatomyositis and their management. Curr Rheumatol Rep, 12(3), 192-197. https://doi.org/10.1007/s11926-010-0100-7.
Cao, et al., "DRB1*15 allele is a risk factor for PR3-ANCA disease in African Americans," J Am Soc Nephrol, 22(6), 1161-1167. (2011). https://doi.org/10.1681/asn.2010101058.
Carr AS, et al. A Systematic Review of Population Based Epidemiological Studies in Myasthenia Gravis. BMC Neural. 2010;10:46. Published Jun. 18, 2010. doi:10.1186/1471-2377-10-46.
Ceribelli, et al., "The Immune Response and the Pathogenesis of Idiopathic Inflammatory Myositis: a Critical Review," Clin Rev Allergy Immunol, 52(1), 58-70. (2017). httos://doi.ora/10.1007/s12016-016-8527-x.
Chahin N, et al. Twelve-Month Follow-Up of Patients with Generalized Myasthenia Gravis Receiving BCMA-Directed mRNA Cell Therapy. medRxiv 2024.01.03.24300770. doi.org/10.1101/2024.01.03.24300770.
Chandra, et al., "Clinical trials and novel therapeutics in dermatomyositis," Expert Opin Emerg Drugs, 25(3), 213-228. (2020). https://doi.org/10.1080/14728214.2020.1787985.
Chang et al., "Five Different Anti-Prostate-specific Membrane Antigen (PSMA) Antibodies Confirm PSIvIA Expression in Tumor-associated Neovasculature," Cancer Res., 59: 3192-3198 (1999).
Chao, D. T. et al., "BCL-2 Family: Regulators of Cell Death", Annu. Rev. Immunol. (1998), vol. 16, pp. 395-419.
Chen J, et al. Incidence, Mortality, and Economic Burden of Myasthenia Gravis in China: A Nationwide Population-Based Study. Lancet Reg Health West Pac. 2020;5:100063. Published Nov. 27, 2020. doi: 10.1016/j.lanwpc.2020.100063.
Chen, F., "Construction of Anti-CD20 Single-Chain Antibody-CD28-CD137-TCR Recombinant Genetic Modified T Cells and its Treatment Effect on B Cell Lymphoma," Med Sci Monit 2015; 21:2110-2115 (Jul. 21, 2015).
Cheresh et al., "Disialogangliosides GD2 and GD3 Arc Involved in the Attachment of Human Melanoma and Neuroblastoma Cells to Extracellular Matrix Proteins," J Cell Biol. 1986, 102(3):688-696.
Childs, et al., "Bringing natural killer cells to the clinic: ex vivo manipulation," Hematology Am Soc Hematol Educ Program. Dec. 6, 2013(1):234-246.
Cho et al., "Cytotoxicity of activated natural killer cells against pediatric solid tumors," 2010, Clin Cancer Res Aug 1;16:3901-09.
Choi, B. D. et al., Chimeric antigen receptor T-cell immunotherapy for glioblastoma: practical insights for neurosurgeons, Neurosurg Focus, 44(6):E1 3, 1-6 (2018).
Choi, et al; Optimising NK cell metabolism to increase the efficacy of cancer immunotherapy; Stem Cell Research & Therapy (2021) 12:320; https://doi.org/10.1186/s13287-021-02377-8.
Chung, et al., "American College of Rheumatology/Vasculitis Foundation guideline for the management of antineutrophil cytoplasmic antibody-associated vasculitis," Arthritis & Rheumatology. Aug. 2021;73(8):1366-83.
Ciurea, S. et al., "Results of a phase I trial with Haploidentical mbIL-21 ex vivo expanded NK cells for patients with muliply relapsed and refractory AML" Am J Hematol., Feb. 18, 2024.
Clarke et al., "Folding studies of immunoglobulin-like beta-sandwich proteins suggest that they share a common folding pathway," Structure, 7(9):1145-1153, Sep. 15, 1999.
Clinical trials.gov "A Study of ASP2215 Versus Salvage Chemotherapy in Patients With Relapsed or Refractory Acute Myeloid Leukemia (AML) With FMS-like Tyrosine Kinase (FL T3) Mutation", Mar. 23, 2021, pp. 1-10.
ClinicalTrials.gov "An Exploratory Clinical Study of Anti-CD19 CAR NK Cells in the Treatment of Systemic Lupus Erythematosus" NCT06010472, in 7 pages, Aug. 23, 2023.
ClinicalTrials.gov, "A Clinical Study of CD19/BCMA CAR-T Cells in the Treatment of Refractory POEMS Syndrome, Amyloidosis, Autoimmune Hemolytic Anemia, and Vasculitis" NCT05263817, in 7 pages, Mar. 3, 2022.
ClinicalTrials.gov, "A Study of Anti-CD19 Chimeric Antigen Receptor T-Cell (CD19 CART) Therapy, in Subjects with refractory Lupus nephritis" NCT05938725, in 12 pages, Jul. 10, 2023.
ClinicalTrials.gov, A Study to Evaluate the Efficacy and Safety of Dapirolizumab Pegol in Study Participants with Moderately to Severly Active S Lupus Erythematosus (Phoenycs Go), NCT04294667, in 22 pages, Feb. 23, 2023.
ClinicalTrials.gov, "An Extension Study of GDC-0853 in Participants With Moderate to Severe Active Systemic Lupus Erythematosus" ClinicalTrials.gov Identifier: NCT03407482, in 7 pages, Dec. 19, 2020.
ClinicalTrials.gov, An Open Label Study to Evaluate Daratumumab in participants with Moderate to Severe Systemic Lupus Erythematosus (Daralup), NCT04810754, in 10 pages, Mar. 23, 2021.
ClinicalTrials.gov, "An Open-label, Study to Assess Safety, Efficacy and Cellular Kinetics of YTB323 in Severe, Refractory Systemic Lupus Erythematosus" NCT05798117, in 15 pages, Aug. 21, 2023.
ClinicalTrials.gov, BCMA-CD19 cCAR T Cell Treatment of Relapsed/Refractory Systemic Lupus Erythematosus (SLE), NCT05474885, in 12 pages, Jul. 26, 2022.
ClinicalTrials.gov, "CD19-CART(Relma-cel) for Moderate to Severe Active Systemic Lupus Erythematosus" NCT05765006, in 7 pages, Mar. 15, 2023.
ClinicalTrials.gov, "Descartes-OS CAR-T Cells in Generalized Myasthenia Gravis (MG)", ClinicalTrials.gov NCT04146051, in 11 pages Feb. 6, 2024.
ClinicalTrials.gov, "Evaluate the Safety and Efficacy of CAR-T Cells in the Treatment of Refractory Myasthenia Gravis" NCT05828225, in 7 pages, Apr. 25, 2023.

(56) References Cited

OTHER PUBLICATIONS

ClinicalTrials.gov, "Phase | Clinical Study of GC012F Injection in Treatment of Refractory Systemic Lupus Erythematosus" NCT05846347, in 11 pages, May 11, 2023.
Collins ct al., "Donor leukocyte infusions in 140 patients with relapsed malignancy after allogeneic bone marrow transplantation," J Clin Oncol, Feb. 1997, 15(2): 433-44.
Collins et aL, "Donor leukocyte infusions in acute lymphocytic leukemia," Bone Marrow Transplantation, 2000, 26: 511-516.
Comfort, "Signaling Pathways Activated by Interleukin-2 and Interluekin-4 Receptors Mediate T Lymphocyte Clonal Expansion" Chemical and Materials Engineering Faculty Publications, Oct. 2007, in 97 pages.
Communication (Ex Parte Quayle) issued by the United State Patent and Trademark Office in U.S. Appl. No. 90/014,175, dated Jan. 29, 2019, 17 pages total.
Communication (Final Office Action) issued by the U.S. Patent and Trademark Office in U.S. Appl. No. 90/014,175, dated Jun. 5, 2019, 20 pages total.
Communication Pursuant to Article 94(3) EPC Issued in European Patent Application No. 14743792.5, dated Jun. 9, 2017, 4 pages.
Complaint in *Trustees of the University of Pennsylvania* v. *St. Jude Children's Research Hospital in the U.S. District Court for the Eastern District of Pennsylvania*, dated Mar. 22, 2013.
Cooley S. et al., "Donor selection for natural killer cell receptor genes leads to superior survival after unrelated transplantation for acute myelogenous leukemia", Blood (2010), vol. 116, No. 14, pp. 2411-2419.
Cooley, S. et al., "Adoptive Therapy with T Cells/NK Cells" Biology of Blood and Marrow Transplantation (2007) vol. 13, pp. 33-42.
Cooper et al. (2009). Recent insights in the epidemiology of autoimmune diseases: improved prevalence estimates and understanding of clustering of diseases. Journal of autoimmunity, 33(3-4), 197-207.
Coquet et al., The CD27 and CD70 costimulatory pathway inhibits effector function of T helper 17 cells and attenuates associated autoimmunity. Immunity. Jan. 24, 2013;38(1):53-65. Epub Nov. 15, 2012.
Cordoba, S. P. et al., "The large ectodomains of CD45 and CD148 regulate their segregation from and inhibition of ligated T-cell receptor," Blood, The Journal of the American Society of Hematology, V. 121, N. 21, p. 4295-4302, c. 4301 (2013).
Cortazar et al. (2023). Renal Recovery for Patients with ANCA-Associated Vasculitis and Low eGFR in the Advocate Trial of Avacopan. Kidney International Reports, 8(4), 860-870. https://doi.org/10.1016/j.ekir.2023.01.039.
Culpepper, D. J. et al., "Systematic mutation and thermodynamic analysis of central tyrosine pairs in polyspecific NKG2D receptor interactions," Molecular Immunology, V. 48, N. 4, p. 516-523, c. 521-522 (2011).
Curti, A. et al., "Successful transfer of alloreactive haploidentical KIR ligand-mismatched natural killer cells after Infusion in elderly high risk acute myeloid leukemia patients" Blood (2011) vol. 118, No. 12, pp. 3273-3279.
Cyclophosphamide Initial U.S. Approval: 1959; Revised May 2013. Cyclophosphamide. Deerfield, IL. Baxter Healthcare Corp; May 2013.
Kumar, Santosh; Natural killer cell cytotoxicity and its regulation by inhibitory receptor; (2018) John Wiley & Sons Ltd, Immunology; 154: 383-393.
Kuo et al., "Efficient gene transfer into primary murine lymphocytes obviating the need for drug selection," Blood, Aug. 1993, 82(3): 845-52.
Kurokawa, M. and S. Kombluth, "Caspascs and kinascs in a death grip," Cell, 138(5): 838-854 (2009).
Kwon B, et al., "cDNA sequences of two inducible T-cell genes", Proc Natl Acad Sci U SA., Mar. 1986; 86(6):1963-1967.
Kymriah(Registered) (tisagenlecleucel) suspension for intravenous infusion. East Hanover, NJ. Novartis Pharmaceuticals Corporation; Jun. 2024.
Kymriah™ (tisagenlecleucel) suspension for intravenous infusion. East Hanover, NJ: Novartis Pharmaceuticals Corporation. 2017; Revised May 2018.
KymriahTM (tisagenlecleucel) Full Prescribing Information. Initial U.S. Approval: 2017; Revised May 2018.
LaBonte, M.L. et al., "Molecular Determinants Regulating the Pairing of NKG2 Molecules with CD94 for Cell Surface Heterodimer Expression," J Immunol, 172(11): 6902-6912 (May 2004).
Lamers, C.H.J., et al., "Treatment of Metastatic Renal Cell Carcinoma With Autologous T-Lymphocytes Genetically Retargeted Against Carbonic Anhydrase IX: First Clinical Experience," J. Clin. Oncol. 24: e20-e22 (2006).
Landon-Cardinal, 0., Allenbach, Y., Soulages, A., Rigolet, A., Hervier, B., Champtiaux, N., Monzani, Q., Sole, G., & Benveniste, 0. (2019). Rituximab in the Treatment of Refractory Anti-HMGCR Immune-mediated NecrotizinQ Myopathy. J Rheumatol, 46(6), 623-627. https://doi.orQ/10.3899/jrheum.171495.
Lang et al., "Absence of B7.1-CD28/CTLA-4-mediated co-stimulation in human NK cells," Eur. J. Immunol, Mar. 1998, 28: 780-786.
Lanier, L.L., "DAP10- and DAP12-Associated Receptors in Innate Immunity" Immunological Reviews (2009) vol. 227, pp. 150-160.
Lanier, Lewis L., "NK Cell Recognition," Annual Review of Immunology, vol. 23, No. 1, pp. 225-274 (2005).
Lanzavecchia et al., "Antigen decoding by T lymphocytes: from synapses to fate determination," Nat Immunol., 2 (6):487-492, Jun. 2001.
Lauwerys, et al., "Synergistic Proliferation and Activation of Natural Killer Cells by Interleukin 12 and Interleukin 18", Cytokine, vol. 11, No. 11, Nov. 1, 1999, pp. 822-830.
Lazar et al. Transforming Growth Factor alpha: Mutation of Aspartic Acid 47 and Leucine 48 Results in Different Biological Activities. Mol. Cell. Biol., 8:1247-1252, 1988 (Year: 1988).
LeBein et al., B lymphocytes: how they develop and function, Blood, 112:1570-1580, 2008.
Lee DW, et al. ASTCT consensus for cytokine release syndrome and neurologic toxicity associated with immune effector cells. Biol Blood Marrow Transplant. Apr. 2019; 25: 625-638. doi: 10.1016/j.bbmt.2018.12.758.
Lee et al., "Current concepts in the diagnosis and management of cytokine release syndrome" Blood, Jul. 10, 2014, vol. 124, No. 2, 188-195.
Lee et al., 323. Efficient Generation of CART Cells by Homology Directed Transgene Integration into the TCR-Alpha Locus. Mol Ther. May 2016;24(Sunnlement 1):S130. 1 page.
Lee et al., Multitarget therapy versus monotherapy as induction treatment for lupus nephritis: A meta-analysis of randomized controlled trials. Lupus. (2022), vol. 31, No. 12, pp. 1468-1476. doi:10.1177/09612033221122148.
Leitner et al., "T cell stimulator cells, an efficient and versatile cellular system to assess the role of costimulatory ligands in the activation of human T cells," Journal of Immunological Methods, 362, 131-141, 2010.
Leonard, "Cytokines and Immunodeficiency Diseases," www.nature.com/reviews/immunol, vol. 1, Dec. 2001, pp. 200-209.
Li et al. A combination of CAR-NK and CAR-T cells results in rapid and persistent anti-tumor efficacy while reducing CAR-T cell mediated cytokine release and T-cell proliferation, Nkarta Therapeutics, Inc., published on Aug. 15, 2020, presented in a conference on Jun. 22, 2020, in 1 page.
Li et al., "Costimulation by CD48 and B7-1 induces immunity against poorly immunogenic tumors," J Exp Med, Feb. 1996, 183(2): 639-644.
Li et al., "Polarization Effects of 4-1BB during CD28 Costimulation in Generating Tumor-reactive T Cells for Cancer Immunotherapy," Cancer Research, vol. 63, pp. 2546-2552, May 15, 2003.
Li Q. et al., Bifacial effects of engineering tumour cell-derived exosomes on human natural killer cells. Experimental Cell Research, Dec. 19, 2017, vol. 363, No. 2, pp. 141-150.

(56) References Cited

OTHER PUBLICATIONS

Li, et al., "IL-6 Promotes T Cell Prolif era ti on and Expansion under Inflammatory Conditions in Association with Low-Level ROR-yt Expression" J. Immunol (2018) 201(10); pp. 2934-2946.
Li, et al., "Therapeutically Targeting Glypican-2 via Single-Domain Antibody-Based Chimeric Antigen Receptors and Immunotoxins in Neuroblasoma," PNAS, pp. E6623-E6631 (Jul. 24, 2017).
Li, Yangxi, et al., "Tumor immunotherapy: New aspects of natural killer cells" Chinese Journal of Cancer Research, 2018, 30 (2): 173-196.
Licursi, M. et al., "In Vitro and In Vivo Comparison of Viral and Cellular Internal Ribosome Entry Sites for Bicistronic Vector Expression" Gene Therapy (2011) vol. 18, pp. 631-636.
Lima, et al., "Interleukin-6 Neutralization by Antibodies Immobilized at the Surface of Polymeric Nanoparticles as a Therapeutic Strategy for Arthritic Diseases," ACS Appl. Mater. Interfaces 2018, 10, 13839-13850.
Linsley and Ledbetter, "The role of CD28 receptor during T cell responses to antigen," Annu Rev Immunol, 1993, 191-212.
Liu, E. et al., "GMP-Compliant Universal Antigen Presenting Cells (Uapc) Promote the Metabolic Fitness and Antitumor Activity of Armored Cord Blood CAR-NK Cells", frontiers in Immunology, Feb. 26, 2021, vol. 12, Article 626098, 14 pages.
Liu, H., et al., "Monoclonal Antibodies to the Extracellular Domain of Prostate-specific Membrane Antigen Also React with Tumor Vascular Endothelium," Cancer Res. 57: 3629-3634 (1997).
Liu, L, et al. "Novel CD4-Based Bispecific Chimeric Antigen Receptor Designed for Enhanced Anti-HIV Potency and Absence of HIV Entry Receptor Activity," J. Viral. 89(13):6685-6694 (2015).
Liu, Xiaojuan et al., "CRISPR-Cas9-mediated multiplex gene editing in CAR-T cells", Cell Research (2017), 27: 154-157; published online Dec. 2, 2016, 154-157.
Long, K., & Danoff, S. K. (2019). Interstitial Lung Disease in Polymyositis and Dermatomyositis. Clin Chest Med, 40(3), 561-572. https://doi.org/10.1016/j.ccm.2019.05.004.
Lopez-Requena et al., "Gangliosides, Ab1 and Ab2 antibodies III. The idiotype of anti-ganglioside mAb P3 is immtmogenic in a T cell-dependent manner," Mol Immunol, 2007, 44(11):2915-2922.
Lopez-Requena et al., "Gangliosides, Ab1 and Ab2 antibodies IV, Dominance of VH domain in the induction of anti-idiotypic antibodies by Jene gun immunization," Mol Immunol. Apr. 2007;44(11):3070-3075. Epub Mar. 2, 2007.
Lu et al. "Cbl-b is upregulated and plays a negative role in activated human NK cells" J Immunol, Feb. 15, 2021, 206(4); 677-685.
Lu, et al., "Genetic engineering of dendritic cells to express immunosuppressive molecules (viral IL-10, TGF -??, and CTLA4lg)," J. Leukocyte Biol., Aug. 1999, 66:293-96.
Lundberg et al. (2017). 2017 European League Against Rheumatism/American College of Rheumatology classification criteria for adult and juvenile idiopathic inflammatory myopathies and their major subgroups. Ann Rheum Dis, 76(12), 1955-1964. https://doi.org/10.1136/annrheumdis-2017- 211468.
Ma et al., "Chapter 15: Genetically engineered T cells as adoptive immunotherapy of cancer," Cancer Chemotherapy and Biological Response Modifiers Annual 20, Ch. 15, 315-341, Giaccone.
Macleod et al., "Generation of a Novel Allogeneic CAR T Cell Platform Utilizing an Engineered Meganuclease and AA V Donor Template to Achieve Efficient Disruption of T Cell Receptor Expression and Simultaneous Homology-Directed Insertion of a CD19 CAR" Mol Ther. May 2016;24(Supplement 1): S156. 1 page.
Macleod et al., "Integration of a CD19 CAR into the TCR Alpha Chain Locus Streamlines Production of Allogeneic Gene-Edited CART Cells" Molecular Therapy, vol. 25, No. 4, Apr. 2017, 949-961.
Maher J, et al., "Human T-lymphocyte cytotoxicity and proliferation directed by a single chimeric TCRzeta/CD28 receptor", Nat Biotechnol. Jan. 2002; 20(1):70-75.
Mahr, A., Guillevin, L., Poissonnet, M., & Ayme, S. (2004). Prevalences of polyarteritis nodosa, microscopic polyangiitis, Wegener's granulomatosis, and Churg-Strauss syndrome in a French urban multiethnic population in 2000: a capture-recapture estimate. Arthritis Rheum, 51(1), 92-99. https://doi.ora/10.1002/art.20077.
Maloney, D.G., "Newer Treatments for Non-Hodgkin's Lymphoma: Monoclonal Antibodies," Oncology 12(10): 63-76 (1998).
Thompson, et al., "The pathogenesis of dermatomyositis," Br J Dermatol, 179(6), 1256-1262 (2018). https://doi.org/10.1111/bjd.15607.
Tian, et al., "B cell lineage reconstitution underlines CAR-T cell therapeutic efficacy in patients with refractory myasthenia gravis" EMBO Molecular Medicine, in 22 pages, Mar. 1, 2024.
Torikai, et al., "A foundation for universal T-cell based immunotherapy: T cells engineered to express a CD19-specific chimeric-antigen-receptor and eliminate expression of endogenous TCR" Gene Therapy, Blood, Jun. 14, 2012, vol. 119, No. 24, 5697-5705.
Torok et al., "Pharmacogenetics of Crohn's disease," Pharmacogenomics (2008) 9(7), 881-893 (Year: 2008).
Triplett, J., Kassardjian, C. D., Liewluck, T., et al. (2020). Cardiac and Respiratory Complications of Necrotizing Autoimmune Myopathy. Mayo Clin Proc, 95(10), 2144-2149. httos://doi.orq/10.1016/i.mavoco.2020.03.032.
Trompeter et al., "Rapid and highly efficient gene transfer into natural killer cells by nucelofection," J Immunol Methods, Mar. 2003, 274(1-2): 245-256.
Trustees of the University of Pennsylvania's Answer to Defendant's Counterclaims in *Trustees of the University of Pennsylvania* v. *St. Jude Children's Research Hospital in the U.S. District Court for the Eastern District of Pennsylvania*, dated Nov. 29, 2013. (Doc. 28).
Trustees of the University of Pennsylvania's Answer to Juno Therapeutics, Inc.'s Counterclaim in *Trustees of the University of Pennsylvania* v. *St. Jude Children's Research Hospital in the U.S. District Court for the Eastern District of Pennsylvania*, dated Jan. 13, 2014. (Doc. 56).
Trustees of the University of Pennsylvania's Brief in Support of Motion for Summary Judgment for Invalidity of Patent in Suit in *Trustees of the University of Pennsylvania* v. *St. Jude Children's Research Hospital in the U.S. District Court for the Eastern District of Pennsylvania*, dated Nov. 15, 2013. (Doc. 23).
Trustees of the University of Pennsylvania's Motion for Summary Judgment for Invalidity of Patent in Suit in *Trustees of the University of Pennsylvania* v. *St. Jude Children's Research Hospital in the U.S. District Court for the Eastern District of Pennsylvania*, dated Nov. 15, 2013.
Trustees of the University of Pennsylvania's Motion to Dismiss in *Trustees of the University of Pennsylvania* v. *St. Jude Children's Research Hospital in the U.S. District Court for the Eastern District of Pennsylvania*, dated Jul. 22, 2013. (Doc. 18).
Tunnicliffe, et al., "Immunosuppressive treatment for proliferative lupus nephritis," Cochrane Database Syst Rev. 2018;6(6):CD002922. Published Jun. 29, 2018. doi:10.1002/14651858.CD002922.pub4.
Turtle, et al., "Durable molecular remissions in chronic lymphocytic leukemia treated with CD19-specific chimeric antigen receptor-modified T cells after failure of ibrutinib," J Clin Oncol. 35(26):3010-3020, (2017). httos://doi: 10.1200/JC0.2017.72.8519.
Twitter Thread by Nicholas Huntington, dated May 27, 2021.
U.S. Appl. No. 11/074,525, filed Mar. 8, 2005, U.S. Pat. No. 7,435,596, Oct. 14, 2008, Campana et al.
U.S. Appl. No. 12/206,204, filed Sep. 8, 2008, U.S. Pat. No. 8,026,097, Sep. 27, 2011, Campana et al.
U.S. Appl. No. 13/548, 148, filed Jul. 12, 2012, U.S. Pat. No. 8,399,645, Mar. 19, 2013, Campana et al.
U.S. Appl. No. 14/301,122, filed Jun. 10, 2014, U.S. Pat. No. 9,605,049, Mar. 28, 2017, Campana et al.
U.S. Appl. No. 14/303,331, filed Jun. 12, 2014, U.S. Pat. No. 9,856,322, Jan. 2, 2018, Campana et al.
U.S. Appl. No. 14/872,947, filed Oct. 1, 2015, U.S. Pat. No. 9,834,590, Dec. 5, 2017, Campana et al.
U.S. Appl. No. 15/470,678, filed Mar. 27, 2017, 2017-0283482, Oct. 5, 2017, Campana et al.
U.S. Appl. No. 15/837,715, filed Dec. 11, 2017, Campana et al.
U.S. Appl. No. 18/179,201, filed Mar. 6, 2023, Trager et al.
U.S. Appl. No. 60/383,872, filed May 28, 2002, Sadelain et al.

(56) References Cited

OTHER PUBLICATIONS

U.S. Final Office Action for U.S. Appl. No. 15/309,362, entitled "Modified Natural Killer Cells and Uses Thereof," dated Dec. 20, 2018.
U.S. Non-Final Office Action for U.S. Appl. No. 16/550,548, entitled"Natural Killer Cells Modified to Express Membrane-Bound Interleukin 15 and Uses Thereof," dated Jan. 23, 2020.
Uday K. O. et al., "Distinct Signaling by Chimeric Antigen Receptors (CARs) Containing CD28 Signaling Domain Versus 4-IBB in Primary Human T Cells", Blood, American Society of Hematology, vol. 122, No. 21, Nov. 15, 2013, 1 page abstract.
UniProt P26717 NKG2C_HUMAN. Integrated into UniProtKB/Swiss-Prot 01-AUG-1992. https://www.uniprot.org/uniprotkb/P26717/ entry. Accessed Jul. 17, 2024 (Year: 1992).
UniProtKB accession No. Q65ZC8 "Single-chain Fv" Oct. 11, 2004 retrieved on Oct. 16, 2021, retrieved from the internet: URL: https://www.uniprot.org/uniprot/Q65ZC8.txt.
Upshaw et al., "NKG2D-Mediated Signaling Requires a DAP10-Bound Grb2-Vav1 Intermediate and Phosphatidylinositol-3-kinase in Human Natural Killer Cells", Nat. Immunol. (2006), vol. 7, pp. 524-532.
Vanoli F, Mantegazza R. Antibody Therapies in Autoimmune Neuromuscular Junction Disorders: Approach to Myasthenic Crisis and Chronic Management. Neurotherapeutics. 2022;19(3):897-910. doi:10.1007/s13311-022-01181-3.
Varga, "Clinical manifestations and diagnosis of systemic sclerosis (scleroderma) in adults" UpToDate, in 49 pages (2023).
Vejiga et al. "Immune Masking Strategies to Extend the Pharmacokinetics of Allogeneic Cell Therapies," Nkarta Therapeutics, Inc., Apr. 8, 2022, in 1 page.
Veluchamy JP et al. The Rise of Allogeneic Natural Killer Cells as a Platform for Cancer Immunotherapy: Recent Innovations and Future Developments. Front Immunol. 2017; 8: 631 (Year: 2017).
Venna and Stock, "Management of adult acute lymphoblastic leukemia: moving tmvard a risk-adapted approach," Curr Opin Oncol, Jan. 2001, 13(1): 14-20.
Viel, et al. "TGF-β inhibits the activation and functions of NK cells by repressing the mTOR pathway", www.sciencesignalling.org, Feb. 16, 2016, vol. 9, Issue 415.
Vinanica, N., et al., "Specific stimulation of T lymphocytes with erythropoietin for adoptive immunotherapy", Blood, 135(9): 668-679 (Feb. 27, 2020).
Vinay OS, et al., "Role of 4-1 BB in immune responses", Semin Immunol. Dec. 1998; 10(6):481-489.
Vincze, M., & Danko, K. (2012). Idiopathic inflammatory myopathies. Best Pract Res Clin Rheumatol, 26(1), 25-45. https://doi.org/10.1016/j.berh.2012.01.013.
Viola, "The amplification of TCR signaling by dynamic membrane microdomains," Trends Immunol., 22(6):322-327, Jun. 2001.
Vivier, E. et al., "Innate or Adaptive Immunity? The Example of Natural Killer Cells" Science (2011) vol. 331, pp. 44-49.
Vivier, et al., "Natural killer cells: from basic research to treatments" Frontiers in Immunology, in 4 pages, Jun. 3, 2011.
Vleugels, et al., "Management of refractory cutaneous dermatomyositis in adults" UpToDate, in 28 pages, Sep. 2023.
Vohra et al., Use of Stimulatory Cells in Conjunction with IL-12 and IL-18 augments NK cell expansion and transduction, drives a memory phenotype, and improve in vitro and in vivo CAR NK Activity, Journal for Immuno Therapy of Cancer, vol. 7, Supplement 1: P194, 2019.
Vohra, et al., Stimulatory cells plus IL-12 and IL-18 augments KN cell expansion, transduction, memory phenotype, and in vitro and in vivo CAR NK cytotoxicity & persistence, SITC, Nov. 2019.
Volkmann, E. R., Andreasson K., and Smith V. (2023). Systemic sclerosis. The Lancet 401.10373: 304-318.
Von Budingen, H., Palanichamy, A., Lehmann-Horn, K., Michel, B. A., & Zamvil, S.S. (2015). Update on the autoimmune pathology of multiple sclerosis: B-cells as disease-drivers and therapeutic targets. European neurology, 73(3-4), 238-246.
Voss et al., "Targeting p53, hdm2, and CD19: vaccination and immunologic strategies," Bone Marrow Transplant., 25 Suppl 2:S43-S45, May 2000.
Walcheck, et al., "Ink-CD64/16A cells: a promising approach for ADCC?" Expert Opinion on Biological Therapy, 2019, vol. 19, No. 12, 1229-1232.
Walsh M, Flossmann 0, Berden A, et al. (2012). Risk factors for relapse of antineutrophil cytoplasmic antibody-associated vasculitis. Arthritis & Rheumatism. Feb.;64(2):542-8.
Muller, et al., "CD19-targeted CART cells in refractory antisynthetase syndrome", www.thelancet.com, vol. 401, pp. 815-818, Mar. 11, 2023.
Munitic, et al. "CD70 Deficiency Impairs Effector CDS T Cell Generation and Viral Clearance but Is Dispensable for the Recall Response to Lymphocytic Choriomeningitis Virus", The Journal of Immunology, 2013, vol. 190, p. 1169-1179.
Muzes, et al., "CAR-Based Therapy for Autoimmune Diseases: A Novel Powerful Option" Cells, in 26 pages (2023).
Nadler et al., "B4, a human B lymphocy1e-associated antigen expressed on normal, mitogen-activated, and malignant B lymphocytes," J Immunol, Jul. 1983, 131(1): 244-250.
Nakamura et al., "Chimeric anti-ganglioside GM2 antibody with antitumor activity," Cancer Res. Mar. 15, 1994; 54(6): 1511-6.
Nayyar G. et al., "Overcoming Resistance to Natural Killer Cell Based Immunotherapies for Solid Tumors", Frontiers in Oncology, vol. 9, Feb. 11, 2019, XP055700879.
NCBI Reference Sequence NM_ 198053, "*Homo sapiens* CD247 molecule (CD247), transcript variant 1, mRNA", Feb. 20, 2021, 9 pages total.
NCI Thesaurus, Bicistronic chimeric antigen receptor vector, Retrieved online from: <URL:https://ncit.nci.nih.gov/ncitbrowser/pages/home.jsf;jsessionid= 12B0F7AF7 I E9A4035C38B5E4F6C055B0>, Retrieved on: Jan. 21, 2021, 2021.
Neelapu SS. Managing the toxicities of CAR-T cell therapy. Hematol Oneal. Jun. 2019;37 Suppl 1:48-52. doi: 10.1002/hon.2595.
Neely, et al., "Monocyte Surface-Bound IL-15 Can Function as an Activating Receptor and Participate in Reverse Signaling," The Journal of Immunology, 2004, 172(7): 4225-4234.
Newick, et al. "Chimeric antigen receptor T-cell therapy for solid tumors", Molecular Therapy, Oncolytics, Official Journal of the American Society of Gene & Cell Therapy, Apr. 13, 2016, 7 pages.
NIH National Cancer Institute, NCI Dictionary of Cancer Terms, Antigen-Presenting Cell, Retrieved online from: <URL: https://www.cancer.gov/publications/dictionaries/cancer-terms/def/antigen-presenting-cell> [retrieved on May 8, 2024], 2024.
Nihtyanova, Svetlana I., and Christopher P. Denton. (2010) Autoantibodies as predictive tools in systemic sclerosis. Nature reviews rheumatology 6, No. 2:112-116.
Nish, et al., "T cell-intrinsic role of IL-6 signaling in primary and memory responses" eLife 2014;3:e01949.
Nishigaki et al., "Prevalence and growth characteristics of malignant stem cells in B-lineage acute lymphoblastic leukemia," Blood, May 1997, 89(10): 3735-3744.
Nkarta "Engineering Natural Killer Cells for next generation treatment of cancer and autoimmune diseases" Nkarta Corporate Presentation, in 24 pages, Jan. 2024.
Nkarta Therapeutics Press Release dated Jun. 11, 2018 (accessible at hllps://www.nkartatx.com/news/061118/).
Nkarta Therapeutics, "Press Release: Nkarta Therapeutics Announces Exclusive License to Natural Killer Cell Technology from National University of Singapore and St. Jude Children's Research Hospital" (2018) (available at https://www.nkartatx.com/news/061118/), 2 pages total.
Nkarta Updates Clinical Progress of CAR-NK Cell Therapy NKX101 for Patients with Relapsed or Refractory Acute Myeloid Leukemia, Nkarta, in 3 pages, Jun. 27, 2023.
Nkarta, "Clinical Program Update: NKX101 for Relapsed or Refractory AML" Nkarta NKX101 data presentation, in 19 pages Jun. 10, 2023.
Notice of Allowance and Fee(s) Due in U.S. Appl. No. 13/548,148, dated Jan. 23, 2013.

(56) References Cited

OTHER PUBLICATIONS

Notice of Allowance for U.S. Appl. No. 16/550,548, entitled"Natural Killer Cells Modified to Express Membrane-Bound Interleukin 15 and Uses Thereof," dated May 13, 2020.
Notice of Allowance n for U.S. Appl. No. 15/309,362, entitled "Modified Natural Killer Cells and Uses Thereof," dated May 16, 2019.
Novartis Pharmaceuticals Corp.'s Motion to Intervene in *Trustees of the University of Pennsylvania* v. *St. Jude Children's Research Hospital in the U.S. District Court for the Eastern District of Pennsylvania*, dated Jan. 22, 2014. (Doc. 57).
Nunes et al., "The role of p21ras in CD28 signal transduction: triggering of CD28 With antibodies, but not the ligand B7-1, activates p21ras," J Exp Med, 180(3): 1067-1076, Sep. 1, 1994.
Oddis CV, Reed AM, Aggarwal R, et al. (2013). Rituximab in the treatment of refractory adult and juvenile dermatomyositis and adult polymyositis: a randomized, placebo-phase trial. Arthritis Rheum. Feb;65(2):314-24.
Oddis, et al., "Treatment in myositis" Nature Reviews, Rheumatology, vol. 14, pp. 279-289, May 2018.
Oelke M, et al., "Ex vivo induction and expansion of antigen-specific cytotoxic T cells by HLA-1g-coated artificial antigen-presenting cells," Nat Med., 2003, 9(5):619-624.
Ofev® (nintedanib) capsules, for oral use. Ridgefield, CT. Boehringer Ingelheim Pharmaceuticals, Inc. Revised Oct. 2014.
Office Action in U.S. Appl. No. 10/981,352, dated Nov. 29, 2006.
Office Action in U.S. Appl. No. 13/548,148, dated Aug. 9, 2012.
Office Action in U.S. Appl. No. 13/548,148, dated Oct. 11, 2012.
Office Action in U.S. Appl. No. 11/074,525, dated Jan. 3, 2008.
Office Action of U.S. Appl. No. 10/981,352, dated Jan. 4, 2007.
Office Action of U.S. Appl. No. 10/981,352, dated Jan. 4, 2008.
Office Action of U.S. Appl. No. 10/981,352, dated Jun. 7, 2007.
Office Action of U.S. Appl. No. 10/981,352, dated Mar. 14, 2007.
Office Action of U.S. Appl. No. 11/074,525, dated Mar. 23, 2007.
Office Action of U.S. Appl. No. 11/074,525, dated Sep. 18, 2007.
Oh, et al., "Engineering Cell Therapies for Autoimmune Diseases: from Preclinical to Clinical Proof of Concept" Immune network, 22(5), in 16 pages, Oct. 2022.
Order in *Trustees of the University of Pennsylvania* v. *St. Jude Children's Research Hospital in the U.S. District Court for the Eastern District of Pennsylvania*, dated Nov. 13, 2013.
Order in *Trustees of the University of Pennsylvania* v. *St. Jude Children's Research Hospital in the U.S. District Court for the Eastern District of Pennsylvania*, dated Nov. 18, 2013. (Doc. 21).
Order in *Trustees of the University of Pennsylvania* v. *St. Jude Children's Research Hospital in the U.S. District Court for the Eastern District of Pennsylvania*, dated Nov. 22, 2013. (Doc. 27).
Orvain, et al., "Is there a place for CAR-T cells in the Treatment of chronic autoimmune rheumatic diseases" accepted article, in 33 pages (2021).
Osborn, et al., "Evaluation of TCR Gene Editing Achieved by TALENs, CRISPR/Cas9, and megaTAL Nucleases", www.moleculartherapy.org, vol. 24, No. 3, 570-581, Mar. 2016.
Oyer et al., "Natural killer cells stimulated with PM21 particles expand and biodistribute in vivo: Clinical implications for cancer treatment," Cytotherapy, 18: 653-663, 2016.
Ozkaynak, M.F. et al., "Phase I Study of Chimeric Human/Murine Anti-Ganglioside GD2 Monoclonal Antibody (chl4.18) With Granulocyte-Macrophage Colony-Stimulating Factor in Children With Nueroblastoma Immediately After Hematopoietic Stem-Cell Transplantation: A Children's Cancer Group Study," J. Clinical Oncol. 18: 4077-4085 (2000).
Pakula, A. A. et al., "Genetic analysis of protein stability and function," Annual Review of Genetics, V. 23, N. 1, p. 289-310, c. 305-306 (1989).
Palmer et al. "Cish actively silences TCR signaling in cos+ T cells to maintain tumor tolerance," J. Exp. Med. 2015 vol. 212, No. 12, pp. 2095-2113.
Palmer SC, Tunnicliffe DJ, Singh-Grewal D, et al. Induction and Maintenance Immunosuppression Treatment of Proliferative Lupus Nephritis: A Network Meta-analysis of Randomized Trials. Am J Kidney Dis. 2017;70(3):324-336. doi:10.1053/i.aikd.2016.12.008.
Dalakas MC. Progress in the Therapy of Myasthenia Gravis: Getting Closer to Effective Targeted Immunotherapies. Curr Opin Neurol. 2020; 33(5):545-552. doi: 10.1097/WCO.0000000000000858.
Dalakas MC. Role of Complement, Anti-Complement Therapeutics, and Other Targeted Immunotherapies in Myasthenia Gravis. Expert Rev Clin Immunol. 2022;18(7):691-701. doi:10.1080/1744666X.2022.2082946.
Dalal, A.-R. et al., Third-Generation Human Epidermal Growth Factor Receptor 2 Chimeric Antigen Receptor Expression on Human T Cells Improves with Two-Signal Activation, Human Gene Therapy, 845-852 (2018) (Abstract).
Database Geneseq [Online] "Anti-PSMA IAB2M gamma 1 EH3 (M2) minibody protein SEQ: 10.", retrieved from EBI accession No. GSP:BD003534, Database accession No. BD003534, Apr. 6, 2017.
Database Geneseq [Online] "Her2scFv-CD8hinge-CD8tm-4-1BB-Zeta-T2A-CD19t fusion protein, SEQ ID 36.", retrieved from EBI accession No. GSP:BDW63031, Database accession No. BDW63031, Jun. 29, 2017. (SEQ ID 1 and 36 saved together).
Database Geneseq [Online] "Human anti-HER2 single chain antibody (scFv), SEQ ID 1.", retrieved from EBI accession No. GSP:BDW62996 Database accession No. BDW62996, Jun. 29, 2017. (SEQ ID 1 and 36 saved together).
De Felipe, P., "Polycistronic Viral Vectors," Current Gene Therapy, V. 2, N. 3, p. 355-378, c. 360 (2002).
De La Chapelle, A. et al., "Truncated erythropoietin receptor causes dominantly inherited benign human erythroc) tosis," Proc Natl Acad Sci USA., vol. 90, No. 10, pp. 4495-4499 (May 1993).
De Sousa Abreu et al., Global signatures of protein and mRNA expression levels, Mol. BioSys. 5:1512-1526, 2009.
Declaration in Support of Trustees of the University of Pennsylvania's Motion for Summary Judgment for Invalidity of Patent in Suit in *Trustees of the University of Pennsylvania* v. *St. Jude Children's Research Hospital in the US District Court for the Eastern District of Pennsylvania*, dated Nov. 15, 2013. (Lit Doc. 24).
Delahaye, N. F. et al., "Alternatively spliced NKp30 isoforms affect the prognosis of gastrointestinal stromal tumors" Nature Medicine (2011) vol. 17, No. 6, pp. 700-708.
Delconte et al. "CIS is a potent checkpoint in NK cell-mediated tumor immunity," Nature Immunology, May 23, 2016, vol. 17, pp. 816-824.
Denman et al. Membrane-Bound IL-21 Promotes Sustained Ex Vivo Proliferation of Human Natural Killer Cells. PLos One. Jan. 2012 | vol. 7 | Issue 1 | e30264 (Year: 2012).
Denton et al. (2009). Renal complications and scleroderma renal crisis. Rheumatology (Oxford), 48 Suppl 3, iii32-35. https://doi.org/10.1093/rheumatology/ken483.
Denton, C. P., & Khanna, D. (2017). Systemic sclerosis. The Lancet, 390(10103), 1685-1699. https://doi.org/10.1016/S0140-6736(17)30933-9.
Distler et al. (2019). Nintedanib for Systemic Sclerosis-Associated Interstitial Lung Disease. New England Journal of Medicine, 380(26), 2518-2528. https://doi.org/10.1056/NEJMoa1903076.
Dou et al. "Abstract: Identification of Trim29 as a Key checkpoint inhibitor of natural killer cell functions," Journal of Immunology, May 1, 2018, vol. 200, Iss. 1, pp. 1 of 1.
Dou et al. "Identification fo the E3 Ligase TRIM29 as a Critical Checkpoint Regulator of NK Cell Functions," The Journal of Immunology, Jul. 3, 2019, vol. 203, Iss. 4, pp. 1-8.
Doubrovian, et al., "Evasion from NK Cell Immunity by MHC Class I Chain-Related Molecules Expressing Colon Adenocarcinoma," Journal ofImmunology, vol. 171, pp. 6891-6899, (2003).
Dowell, A. C. , "Studies of Human T cell Costimulation: Potential for the Immunotherapy of Cancer," A thesis submitted to The University of Birmingham for the degree of Doctor of Philosophy, Cruk Institute for Cancer Studies, 2010.
Dresser L, et al. Myasthenia Gravis: Epidemiology, Pathophysiology and Clinical Manifestations. J Clin Med. 2021; 10(11):2235. Published May 21, 2021. doi:10.3390/jcm10112235.

(56) References Cited

OTHER PUBLICATIONS

Dudley, M.E., et al., "Adoptive Transfer of Cloned Melanoma-Reactive T Lymphocytes for the Treatment of Patients with Metastatic Melanoma," J. Immunother. 24: 363-373 (2001).
Eagle, et al., "ULBP6/RAET1L is an additional human NKG2D ligand," 2009, Eur. J_ Immunol. 39: 3207-16.
Eisuke D. et al., "Synergistic effect of IL-2, IL-12 and IL-18 on the activation of ex vivo-expanded human V[gamma]9V [delta]2 T cells", J Osaka Dent Univ, Apr. 1, 2018, pp. 51-57.
Elinav et al. "Suppression of hepatocellular carcinoma growth in mice via leptin, is associated with inhibition of tumor cell growth and natural killer cell activation," Journal of Hepatology 44 (2006), pp. 529-536.
Elliot, et al; Unifying concepts of MHC-dependent natural killer cell; Trends Immunol, Aug. 2011 ; 32(8): 364-372. doi:10.1016/j.it.2011.06.001.
EP Application No. 14743792.5, International Preliminary Report on Patentability Aug. 11, 2015.
European Communication (Communication Pursuant to Article 94(3) EPC) issued by the European Patent Office in European Patent Application No. 14743792.5, dated Nov. 20, 2018, 4 pages total.
European Communication (Communication Pursuant to Article 94(3) EPC) issued in European Patent Application No. 14743792.5, dated Jan. 15, 2018, 3 pages.
European filed Amendment for European Patent Application No. 14743792.5, dated Mar. 16, 2016, 5 pages total.
European Phase Request in European Patent Application No. 14743792.5, dated Aug. 27, 2015, 10 pages total.
European Response to Search Opinion/Written Opinion/IPER in European Patent Application No. 14743792.5, dated Jan. 26, 2017, 9 pages total.
Extended European Search Report and Written Opinion dated Dec. 10, 2020 for International Application No. PCT/SG2018/050138, entitled "Stimulatory Cell Lines for Ex Vivo Expansion and Activation of Natural Killer Cells".
Extended European Search Report and Written Opinion issued by the European Patent Office in European Patent Application No. 14743792.5; dated Jul. 5, 2016, 6 pages.
Eyguem et al., "Targeting a CAR to the TRAC locus with CRISPR/Cas9 enchances tumour rejction" Nature, 2017, 543(7643): 113-117.
Fehniger, "CD70 turns on NK cells to attack lymphoma", Blood Jul. 20, 2017, vol. 130, No. 3, pp. 238-239.
Fehniger, T.A. "Comment on Al Sayed et al., p. 297, CD70 turns on NK cells to attack lymphoma" Lymphoid Neoplasia, Blood, Jul. 20, 2017, vol. 130, No. 3, 2 pages.
Feng, J., Hu, Y., Zhang, M., et al. (2022). Safety and Efficacy of CD19 CAR-T Cells for Refractory Systemic Sclerosis: A Phase I Clinical Trial. Blood, 140(Supplement 1), 10335-10336. https://doi.org/10.1182/blood-2022-169265.
Ferris, R. L. et al., "Tumor Antigen-Targeted, Monoclonal Antibody-Based Immunotherapy: Clinical Response, Cellular Immunity and Immunoescape" Journal of Clinical Oncology (2010) vol. 28, No. 28, pp. 4390-4399.
Figueiredo et al., "Permanent silencing of NKG2A expression for cell-based therapeutics" J. Mol. Med. (2009) 87:199-210.
Fikri al., "Cloning, sequencing, and cell surface expression pattern of bovine immunoreceptor NKG2D and adaptor molecules DAP10 and DAP12," Immunogenetics 59(8): 653-9. (2017).
Findlay, A. R., Goyal N. A., and Mozaffar T. (2015) An overview of polymyositis and dermatomyositis. Muscle & nerve. 51, No. 5:638-656.
Food and Drug Administration. Guidelines on COVID-19. Available at: https://www.fda.gov/emergency-preparedness-and-response/coronavirus-disease-2019-covid-19/covid-19-vaccines.
Foon et al., "Clinical and immune responses in advanced melanoma patients immunized with an anti-idiotype antibody mimicking disialoganglioside GD2," J Clin Oncol., 18(2):376-384, Jan. 2000.
Forsthuber TG, Cimbora OM, Ratchford JN, Katz E, Stuve 0. (2018). B cell-based therapies in CNS autoimmunity: differentiating CD19 and CD20 as therapeutic targets. Ther Adv Neural Disord. 11:1756286418761697.
Fraietta, et al. "Determinants of response and resistance to CD19 chimeric antigen receptor (CA) T cell therapy of chronic lymphocytic leukemia" Nat. Med. May 2018, 24(5): 563-571.
Frankel et al., "Characterization of diphtheria fusion proteins targeted to the human interleukin-3 receptor" Protein Eng., 2000, v.13, n.8, p. 575-581.
Freshney, Animal Cell Culture, Cancer Research Campaign, Dept. of Oncology, University of Glasgow, 1986, 248 pages [Table of Contents Only].
Fretheim, H., Halse, A. K., Seip, M., et al. (2020). Multidimensional tracking of phenotypes and organ involvement in a complete nationwide systemic sclerosis cohort. Rheumatology (Oxford), 59(10), 2920-2929. https://doi.ora/10.1093/rheumatoloav/keaa026.
Fujiwara M et al. Cbl-b Deficiency Mediates Resistance to Programmed Death-Ligand 1/Programmed Death-1 Regulation. Front. Immunol. 2017 8:42 1-12 (Year: 2017).
Aagaard et al., "RNAi therapeutics: Principles, prospects and challenges," Advanced Drug Delivery Reviews, 59(2007) 75-86 (Year: 2007).
AASEQ1_05172022_135256_pep_vs AASEQ2_05172022_135256_pep_align_4-1BBL (Year: 2022).
Abakushina, E.V., "Immunotherapy With Natural Killer Cells in the Treatment of Cancer," Russian Journal of Immunology, vol. 10, No. 2, pp. 131-142 (2016) (Abstract only).
Abken, H. et al., "Antigen-specific T-cell activation independently of the MHC: chimeric antigen receptor-redirected T cells," Frontiers in Immunology, V. 4, Article 371, c. 4 (2013).
Actemra® (tocilizumab) for injection, for intravenous use only. Genentech, Inc, 1 DNA Way, South San Francisco, CA 94080. Revised Dec. 2022.
Agrawal et al., "RNA interference: Biology, Mechanism, and Applications" Microbiology and Molecular Biology, Rev. Dec. 2003; 67(4):657-685.
Al-Bassam et al. Characteristics, Incidence, and Outcome of Patients Admitted to the Intensive Care Unit with Myasthenia Gravis. J Crit Care. 2018;45:90-94. doi:10.1016/j.jcrc.2018.01.003.
Al Sayed et al. "CD70 reverse signaling enhances NK cell function and immunosurveillance in CD27-expressing B-cell malignancies", blood, Jul. 20, 2017, vol. 130, No. 3, pp. 297-309.
Alignment I L-18 (Year: 2022).
Allison AC. Mechanisms of action of mycophenolate mofetil. Lupus. 2005;14 Suppl 1:s2-s8. doi:10.1191/09612033051u2109oa.
Aman, et al. "CIS Associates with the Interleukin-2 Receptor p Chain and Inhibits Interleukin-2-dependent Signaling" The Journal of Biological Chemistry, vol. 274, No. 42, Issue of Oct. 15, 1999, pp. 30266-30272.
Amended Complaint in *Trustees of the University of Pennsylvania* v. *St. Jude Children's Research Hospital in the U.S. District Court for the Eastern District of Pennsylvania*, dated Jun. 10, 2013. (Doc. 15).
American Cancer Society "Tests for Acute Myeloid Leukemia (AML)", Aug. 21, 2018, pp. 1-3.
Anfosi, N. et al., "Human NK Cell Education by Inhibitory Receptors for MHC Class I" Immunity 25, 331-342, Aug. 2006.
Arnau et al., "Current strategies for the use of affinity tags and tag removal for the purification of recombinant proteins" Protein expression and purification, 2006, v. 48, n. 1, p. 1-13.
Aruffo, A., and Seed, B., "Molecular cloning of a CD28 cDNA by a high-efficiency COS cell expression system," Proc. Natl. Acad. Sci., 1987, 84:8573-8577.
Atreya, et al., "Blockade of interleukin 6 trans signaling suppresses T-cell resistance against apoptosis in chronic intestinal inflammation: Evidence in Crohn disease and experimental colitis in vivo" Nature Medicine, vol. 6, No. 5, May 2000; pp. 583-588.
Auerbach et al, "Angiogenesis assays: Problems and pitfalls," Cancer and Metastasis Reviews, 2000, 19: 167-172 (Year: 2000).
Austin HA 3rd, Klippel JH, Balow JE, et al. Therapy of lupus nephritis. Controlled trial of prednisone and cytotoxic drugs. N Engl J Med. 1986;314(10):614-619. doi:10.1056/NEJM198603063141004.

(56) References Cited

OTHER PUBLICATIONS

Azuma, M, et al., "Functional Expression of B7/BB1 on Activated T Lymphocytes," J. Exp. Med. 177: 845-850 (1993).
Baek, A., Park, H.J., Na, S. J., et al. (2012). The expression of BAFF in the muscles of patients with dermatomyositis. J Neuroimmunol, 249(1-2), 96-100. https://doi.org/10.1016/j.jneuroim.2012.04.006.
Bairkdar et al. (2021). Incidence and prevalence of systemic sclerosis globally: a comprehensive systematic review and meta-analysis. Rheumatology, 60(7), 3121-3133. https://doi.ora/10.1093/rheumatoloay/keab190.
Barber et al., "Chimeric NKG2D T Cells Require Both T Cell- and Host-Derived Cytokine Secretion and Perforin Expression to Increase Tumor Antigen Presentation and Systemic Immunity," J. Immunol, vol. 183, pp. 2365-2372 (2009).
Barnett C, et al. Measuring Clinical Treatment Response in Myasthenia Gravis. Neural Clin. 2018;36(2):339-353. doi:10.1016/j.ncl.2018.01.006.
Barrett, et al., "Interleukin 6 Is Not Made by Chimeric Antigen Receptor T Cells and Does Not Impact Their Function" Blood (2016) 128(22):654.
Barsotti, et al., "Current treatment for myositis. Current Treatment for Myositis," Curr Treat Options in Rheu (2018) 4:299-315.
Basu et al. (2014). The characterization and determinants of quality of life in ANCA associated vasculitis. Ann Rheum Dis, 73(1), 207-211. https://doi.org/10.1136/annrheumdis-2012-202750.
Baum et al., "Side effects of retroviral gene transfer into hematopoietic stem cells," Blood, Mar. 2003, 101(6): 2099-2114.
Beans, "Targeting metastasis to halt cancer's spread," PNAS 2018; 115(50): 12539-12543 (Year: 2018).
Beesley et al. (2023) Dysregulated B cell function and disease pathogenesis in systemic sclerosis. Frontiers in Immunology. Jan. 16; 13:999008.
Benfaremo et al. (2020). Putative functional pathogenic autoantibodies in systemic sclerosis. Eur J Rheumatol,? (Suppl 3), S181-s186. https://doi.org/10.5152/eurjrheum.2020.19131.
Benlystar (belimumab) for injection, for intravenous use only. GlaxoSmithKline, Research Triangle Park, NC 27709. Revised Jan. 2017.
Benyamine et al. (2018). Natural Killer Cells Exhibit a Peculiar Phenotypic Profile in Systemic Sclerosis and Are Potent Inducers of Endothelial Microparticles Release. Front Immunol, 9, 1665. httos://doi.ora/10.3389/fimmu.2018.01665.
Berger, C. et al., "CD28 costimulation and immunoaffinity-based selection efficiently gernate primary gene-modified T cells for adoptive immunotherapy," Blood, 101: 476-484 (2003).
Bernard, et al., "Targeting CISH enhances natural cytotoxicity receptor signaling and reduces NK cell exhaustion to improve solid tumor immunity", Journal for ImmunoTherapy of Cancer, May 19, 2022, in 13 pages.
Beziat, V. et al., "NK cell responses to cytomegalovirus infection lead to stable imprints in the human KIR repertoire and involve activating KIRs", blood, Apr. 4, 2013, 121(14), 2678-2688.
Blumberg et al., "Unraveling the autoimmune translational research process layer by layer," (Nat Med.; 18(1): 35-41) (Year: 2015).
Boissel L. et al., "Transfection with mRNA for CD19 Specific Chimeric Antigen Receptor Restores NK Cell Mediated Killing of CLL Cells" Leuk Res. (2009) vol. 33, No. 9, pp. 1255-1259.
Bork et al., "The immunoglobulin fold. Structural classification, sequence patterns and common core," J Mol Biol., 242(4):309-320, Sep. 30, 1994.
Bork, "Powers and Pitfalls in Sequence Analysis: The 70% Hurdle," Genome Research, 2000, 10:398-400 (Year: 2000).
Bottino et al. "CIS is a negative regulator of IL-15-mediated signals in NK cells," Transl Cancer Res 2016:5(suppl 4): S875-877, accepted for publication on Sep. 23, 2016, in 3 pages.
Brand, L.J. et al., "Abstract LB-185: A PSMA-directed natural killer cell approach for prostate cancer immunotherapy," Cancer Research, 77(13 Supplement): Abstract No. LB-185, 1-4 (Jul. 2017).
Breyanzi(Registered) (lisocabtagene maraleucel) suspension for intravenous infusion. Bothell, WA Juno Therapeutics Inc (a Bristol-Myers Squibb Company); May 2024.
Bridgeman J. S. et al., The Optimal Antigen Response of Chimeric Antigen Receptors Harboring the CD3 Transmembrane Domain Is Dependent upon incorporation of the Receptor into the Endogenous TCR/CD3 Complex. J Immunol., May 17, 2010, vol. 184, No. 12, pp. 6938-3949.
Bromley et al., "The immunological synapse and CD28-CD80 interactions," Nat Immunol., 2(12):1159-1166, Dec. 2001.
Brudno, Jn et al., "Safety and feasibility of anti-CD19 CART cells with fully-human binding domains in patients with B-cell lymphoma" pp. 270-280. Nature Medicine, vol. 26, No. 2, Jan. 2021.
Bukiri, H., & Volkmann, E. R. (2022). Current advances in the treatment of systemic sclerosis. Current Opinion in Pharmacology, 64, 102211. https://doi.org/https://doi.org/10.1016/j.coph.2022.102211.
Buren et al. "A combined strategy of CD70 CAR co-expression with membrane bound IL-15 and CISH knockout results in enhanced NK cytotoxicity and persistence," Nkarta Therapeutics, Inc., Nov. 10, 2021, in 1 page.
Buren, Luxuan, et al. "Abstract B64: Coexpression of a CD19-0X40-CD3 CAR with membrane-bound IL-15 enhances natural killer cell function" Cancer Immunol Res (2020), 8 (3 Supplement), Mar. 2, 2020.
Burgess et al. Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue. J. Cell Biol. 111:2129-2138, 1990 (Year: 1990).
Shum, B. P. et al., "Conservation and Variation in Human and Common Chimpanzee CD94 and NKG2 Genes" The Journal of Immunology (2002) vol. 168, pp. 240-252.
Singapore Examination Report dated Dec. 10, 2018, issued in Singapore Patent Application No. 11201505858V, 7 pages total.
Singapore Examination Report dated Mar. 11, 2020, issued in Singapore Patent Application No. 11201505858V, 8 pages total.
Singapore Second Written Opinion dated Jun. 22, 2017, Issued in Singapore Patent Application No. 11201505858V, 5 pages.
Skolnick et al., "From genes to protein structure and function: novel applications of computational approaches in the genomic era," Trends Biotechnol. Jan. 2000; 18(1 ):34-9 (Year: 2000).
Slavik et al., "CD28/CTLA-4 and CD80/CD86 families: signaling and function," Immunol Res., 19(1):1-24, 1999.
Sloan Kettering Institute for Cancer Research'a Patent Owner Response re: IPR2015-01719, 86 pages, May 5, 2016.
Sloan Kettering Institute for Cancer Research's Patent Owner Preliminary Response re: IPR2015-01719, 68 pages, dated Nov. 25, 2015.
Smith BO, Kasamon YL, Kowalski J, et al. (2010). K562/GM-CSF immunotherapy reduces tumor burden in chronic myeloid leukemia patients with residual disease on imatinib mesylate. Clin Cancer Res. 16(1):338-347. doi:10.1158/1078-0432.CCR-09-2046.
Snowden JA, Saccardi R, Allez M, et al. Haematopoietic SCT in severe autoimmune diseases: updated guidelines of the European Group for Blood and Marrow Transplantation. Bone Marrow Transplant. 2012;47(6):770-790. doi:10.1038/bmt.2011.185.
Sobolewski, P., Maslinska, M., Wieczorek, et al. (2019). Systemic sclerosis—multidisciplinary disease: clinical features and treatment. Reumatologia, 57(4), 221-233. https://doi.org/10.5114/reum.2019.87619.
Spear et al., "Chimeric Antigen Receptor T Cells Shape Myeloid Cell Function within the Tumor Microenvironment through IFN-y and GM-CSF," The Journal of Immunology, pp. 6389-6399, 2014.
Specification for U.S. Appl. No. 63/551,941, filed Feb. 9, 2024.
Sporn et al. Chemoprevention of Cancer, Carcinogenesis, vol. 21 (2000), 525-530 (Year: 2000).
Srinivasan et al., "A retro-inverso peptide mimic of CD28 encompassing the MYPPPY motif adopts a polyproline type II helix and inhibits encephalitogenic T cells in vitro," J Immunol., 167(1):578-585, Jul. 1, 2001.

(56) References Cited

OTHER PUBLICATIONS

Srivannaboon et al., "Interleukin-4 variant (BAY 36-1677) selectively induces apoptosis in acute lymphoblastic leukemia cells," Blood, Feb. 2001, 97(3): 752-758.
St. Jude Children's Research Hospital's Answer and Counterclaims in *Trustees of the University of Pennsylvania* v. *St. Jude Children's Research Hospital in the U.S. District Court for the Eastern District of Pennsylvania*, dated Jun. 27, 2013. (Doc 17).
St. Jude Children's Research Hospital's Motion in *Trustees of the University of Pennsylvania* v. *St. Jude Children's Research Hospital in the U.S. District Court for the Eastern District of Pennsylvania*, dated Dec. 3, 2013. (Doc. 31).
St. Jude Children's Research Hospital's Opposition to Trustees of the University of Pennsylvania's Motion to Dismiss Willful Infringement Allegations of Counterclaim in *Trustees of the University of Pennsylvania* v. *St. Jude Children's Research Hospital in the U.S. District Court for the Eastern District of Pennsylvania*, dated Aug. 8, 2013. (Doc. 19).
Staahl, et al. "Efficient genome editing in the mouse brain by local delivery of engineered Cas9 ribonucleoprotein complexes" Nat Biotechnol. May 2017; 35(5): in 16 pages.
Stamper et al., "Crystal structure of the B7-1/CTLA-4 complex that inhibits human immune responses," Nature, 410(6828):608-611, Mar. 29, 2001.
Steen, V. D., & Medsger, T. A. (2007). Changes in causes of death in systemic sclerosis, 1972-2002. Annals of the Rheumatic Diseases, 66(7), 940-944. https://doi.org/10.1136/ard.2006.066068.
Steenblock, et al., "Application of chimeric antigen receptor-natural killer cells for the treatment of type 1 diabetes", Open Exploration, Exploration of Endocrine and Metabolic Diseases, in 4 pages (2023).
Stein, P.H., et al., "The Cytoplasmic Domain of CD28 is both Necessary and Sufficient for Costimulation of Interleukin-2 Secretion and Association with Phosphatidylinositol 3'-Kinase," Mol. Cell. Biol. 14: 3392-3402 (1994).
Stine, et al., "Overview of and approach to the idiopathic inflammatory myopathies" UoToDate, in 23 pages, Sep. 2023.
Stong RC, et al., "Human acute leukemia cell line with the t(4;11) chromosomal rearrangement exhibits B lineage and monocytic characteristics," Blood, 1985,65:21-31.
Suarez, et al., "Chimeric Antigen Receptor T Cells Secreting Anti-PD-L1 Antibodies More Effectively Regress Renal Cell Carcinoma in a Humanized Mouse Model," Oncotarget, vol. 7, No. 23, Apr. 29, 2016.
Suerth et al., "Efficient Generation of Gene-Modified Human Natural Killer Cells via Alpharetroviral Vectors," J. Mol. Med. 94:83-93, 2016, published online Aug. 25, 2015.
Sullivan, K.M., Shah, A., Sarantopoulos, S. and Furst, D.E., 2016. Hematopoietic stem cell transplantation for scleroderma: effective immunomodulatory therapy for patients with pulmonary involvement. Arthritis & rheumatology, 68(10), oo.2361-2371.
Sullivan, L.C. et al., "The Heterodimenc Assembly of the CD94-NKG2 Receptor Family and Implications for Human Leukocyte Antigen-E Recognition," Immunity, 27(6): 900-911 (Dec. 2007).
Sundstrom and Nilsson, "Establishment and characterization of a human histiocylic lymphoma cell line (U-937)," Int J Cancer, May 1976, 17(5): 565-577.
Suppiah, Ravi, Joanna C. Robson, Peter C. Grayson, et al. 2022. American College of Rheumatology/European Alliance of Associations for Rheumatology classification criteria for microscopic oolvanaiitis. Arthritis & Rheumatoloav 74, No. 3 (2022): 400-406.
Sussman et al., "Protein Data Bank (PDB): database of three-dimensional structural information of biological macromolecules," Acta Crystallogr D Biol Crystallogr., 54(Pt 6 Pt 1):1078-1084, Nov. 1, 1998.
Svensson, J., Holmqvist, M., Tjarnlund, A., et al. (2017). Use of biologic agents in idiopathic inflammatory myopathies in Sweden: a descriptive study of real life treatment. Clin Exp Rheumatol, 35(3), 512-515.
Swami et al. "Clinical Pathology Rounds: Diagnosing Plasma Cell Leukemia," Laboratory Medine, Jun. 2000, vol. 3, pp. 312-315.
Szmania, "Ex vivo-expanded natural killer cells demonstrate robust proliferation in vivo in high-risk relapsed multiple myeloma patients," J Immunother.38(1):24-36. 2015doi:10.1097/CJI.0000000000000059.
Tacke et al., "CD28-mediated induction of proliferation in resting T cells in vitro and in vivo without engagement of the T cell receptor: evidence for functionally distinct forms of CD28," Eur J Immunol., 27(1):239-247, Jan. 1997.
Tang, X. et al., "First-in-man clinical trial of CAR NK-92 cells: safety test of CD33-CAR NK-92 cells in patients with relapsed and refractory acute myeloid leukemia", Am. J. Cancer Res., vol. 8, No. 6, Jun. 1, 2018, pp. 1083-1089.
Tassev, D.V. et al., "Retargeting NK9s Cells Using an HLA-A2-Restricted, EBNA3C-Specific Chimeric Antigen Receptor" Cancer Gene Therapy (2011) vol. 19, pp. 84-100.
Taubmann, et al., "Long Term Safety and Efficacy of CAR-T Cell Treatment in Refractory Systemic Lupus Erythematosus-Data from the First Seven Patients", Scientific Abstracts, in 2 pages, (2023).
Tavneos (avacopan) capsules, for oral use. ChemoCentryx, Inc. Revised Oct. 2021.
Teachey, et al., "Identification of Predictive Biomarkers for Cytokine Release Syndrome after Chimeric Antigen Receptor T-cell Therapy for Acute Lymphoblastic Leukemia" Cancer Discovery, Jun. 2016, pp. 664-679.
Tecartus (brexucabtagene autoleucel) suspension for intravenous infusion. Santa Monica, CA Kite Pharma Inc; Initial approval 2020, revised Jun. 2024.
Tecartus, Highlights of Prescribing Information, in 30 pages, (2021).
The human protein atlas, [retrieved from: https://www.proteinatlas.org/ENSG00000177455-CD19/pathology], accessed Jun. 27, 2019, 3 pages.
The Human Protein Atlas, KLRK1, Immune Cell, Retrieved online from: <URL:https://www.proteinatlas.org/ENSG00000213809-KLRK1/immune+cell> [retrieved on May 8, 2024], 2024.
The Human Protein Atlas, NCR3, Immune Cell, Retrieved online from: <URL:https://www.proteinatlas.org/ENSG00000204475-NCR3/immune+cell> [retrieved on May 8, 2024], 2024.
Themeli et al., "Generation of tumor-targeted human T lympocytes from Induced pluripotent stem cells for cancer therapy", Nat Biotechnol., Oct. 2013; 31(10): 928-933.
Thomas et al., "Monoclonal antibody therapy with rituximab for acute lymphoblastic leukemia," Hematol Oncol Clin North Am., 23(5):949-971, Oct. 2009.
Thomas, et al., "Burden of mortality associated with autoimmune diseases among females in the United Kingdom," Am J Public Health.100(11):2279-2287. (2010) doi:10.2105/AJPH.2009.180273.
Rochman, et al., "IL-6 Increases Primed Cell Expansion and Survival" The Journal of Immunology (2005) 174(8); pp. 4761-4767.
Romee R, Rosario M, Berrien-Elliott MM, et al. Cytokine-induced memory-like natural killer cells exhibit enhanced responses against myeloid leukemia. Sci Transl Med. 2016;8(357):357ra123. doi:10.1126/scitranslmed.aaf2341.
Romee R. et al., "Cytokine activation induces human memory-like NK cells", Blood, Jan. 1, 2012, pp. 4751-4760.
Rooney et al., "Use of gene-modified virus-specific T lymphocytes to control Epstein-Barr-virus-related lymphoproliferation," Lancet, Jan. 1995, 345(8941): 9-13.
Rosenberg et al., "Special Report: Use of tumor-infiltrating lymphocytes and interleukin-2 in the immunotherapy of patients with metastatic melanoma," N. Engl. J. Med., 1988, 319:1676-1680.
Rosenberg, S.A., and Dudley, M.E., "Adoptive cell therapy for the treatment of patients with metastatic melanoma," Curr. Opin. Immunol. 21: 233-240 (2009).
Rosenfeld et al., "Phenotypic characterization of a unique non-T, non-B acute lymphoblastic leukaemia cell line," Nature, Jun. 1977, 267(5614): 841-843.
Rosenstein, M. et al., "Extravasation of Intravascular Fluid Mediated by the Systemic Administration of Recombinant Interleukin 2" The Journal of Immunology (1986) vol. 137, No. 5, pp. 1735-1742.

(56) References Cited

OTHER PUBLICATIONS

Ross et al., "Classification of pediatric acute lymphoblastic leukemia by gene expression profiling," Blood, Oct. 2003, 102(8): 2951-2959.
Rossig C, et al., "Epstein-Barr virus-specific human T lymphocytes expressing antitumor chimeric T-cell receptors: potential for improved immunotherapy," Blood, 2002, 99:2009-2016.
Rossig et al., "Targeting of G(D2)-positive tumor cells by human T lymphocytes engineered to express chimeric T-cell receptor genes," Int J Cancer, Oct. 2001, 94(2): 228-236.
Rovin BH, Caster DJ, Cattran DC, et al. Management and treatment of glomerular diseases (part 2): conclusions from a Kidney Disease: Improving Global Outcomes (KDIGO) Controversies Conference. Kidnev Int. 2019;95(2):281-295. doi:10.1016/i.kint.2018.11.008.
Rovin BH, Teng YKO, Ginzler EM, et al. Efficacy and safety of voclosporin versus placebo for lupus nephritis (Aurora 1): a double-blind, randomised, multicentre, placebo-controlled, phase 3 trial [published correction appears in Lancet. May 29, 2021;397(10289):2048]. Lancet. 2021;397(10289):2070-2080. doi:10.1016/S0140-6736(21)00578.
Rupp, et al., "CRISPR/Cas9-mediated PD-1 disruption enhances anti-tumor efficacy of human chimerica antigen receptor T cells", Scientific Reports, Apr. 7, 2017, 7:737, 10 pages.
Sadelain et al., "Targeting tumours with genetically enhanced T lymphocytes," Nat Rev Cancer. Jan. 2003;3(1):35-45.
Sadelain, M. et al., "The Basic Principles of Chimeric Antigen Receptor Design," Cancer Discovery, vol. 3, No. 4, pp. 388-398 (Apr. 1, 2013).
Saikh, et al., "IL-15 induced conversion of monocytes to mature dendritic cells," Clin Exp Immunol 2001; 126(3):447-455.
Sakkas LI, Bogdanos DP. 2016. Systemic sclerosis: new evidence re-enforces the role of B cells. Autoimmunity reviews. Feb. 1;15(2):155-61.
Salomon and Bluestone, "Complexities of CD28/B7: CTLA-4 costimulatory pathways in autoimmunity and transplantation," Annu Rev Immunol, 2001, 19: 225-252.
Sanders DB, et al. International Consensus Guidance for Management of Myasthenia Gravis: Executive Summary. Neurology. 2016;87(4):419-425. doi: 10.1212/WNL.0000000000002790.
Santomasso B, Bachler C, Westin J, f-1ezvanl K, Shpail EJ. The Other Side of CAFI T-Ceii Therapy: Cytokine Release Syndrome, Neurologic Toxicity, and Financial Burden. Am Soc Ciin Oneal Educ Book. 2019;39:433-444. doi:10.1200/EDBK 238691.
Saphnelo, "Highlights of Prescribing Information", in 17 pages (2021).
Saphnelo™ (anifrolumab-fnia) injection, for intravenous use. Initial U.S. Approval: 2021. Wilmington, DE. AstraZeneca Pharmaceuticals LP. Revised Jul. 2021.
Sarkis, et al., "Long term survival and limited migration of genetically modified monocytes/macrophages grafted into the mouse brain," J. Biomed. Sci. Engineer. (2013) 6(5): 561-71.
Sathe et al. "Innate immunodeficiency following genetic ablation of Mcl1 in natural killer cells," Nature Communications, 5:4539, Published Aug. 14, 2014, 10 pages.
Sauter et al., A Phase 1 Study of NKXIOI, a Chimeric Antigen Receptor Natural Killer (CAR-NK) Cell Therapy, with Fludarabine and Cytarabine in Patients with Acute Myeloid Leukemia, Blood, Nov. 2, 2023, vol. 142, Suppl. 1, pp. 2097-2099.
Savoldo, B., et al., "CD28 costimulation improves expansion and persistence of chimeric antigen receptor modified T cells in lymphoma patients," J. Clin. Invest. 121(5):1822-1826 (2011).
Schett, et al., "CART-cell therapy in autoimmune diseases" Therapeutics, in 11 pages, Sep. 22, 2023.
Schlums, H. et al., "Cytomegalovirus Infection Drives Adaptive Epigenetic Diversification of NK Cells with Altered Signaling and Effector Function", Immunity Author manuscript, Mar. 17, 2015, 42(3), 443-456, in 28 pages.
Schmaltz et al., "T cells require TRAIL for optimal graft-versus-tumor activity," Nat Med, Dec. 2002, 8(12):1433-7.
Schmohl J.U., et al., Tetraspecific scFv construct provides NK cell mediated ADCC and self-sustaining stimuli via insertion of IL-15 as a cross-linker. Oncotarget. 2016; 7: 73830-73844.
Schneider et al., "Characterization of EBV-genome negative "null" and "T" cell lines derived from children with acute lymphoblastic leukemia and leukemic transformed non-Hodgkin lymphoma," Int J Cancer, May 1977, 19(5): 621-626.
Schneider-Gold C, et al., Advances and Challenges in the Treatment of Myasthenia Gravis. Ther Adv Neural Disord. 2021; 14:17562864211065406. Published Dec. 21, 2021. doi:10.1177/17562864211065406.
Schroers et al., "Gene transfer into human T lymphocytes and natural killer cells by Ad5/F35 chimeric adenoviral vectors," Exp Hematol, Jun. 2004, 32(6): 536-46.
Schulz, G., et al., "Detection of Ganglioside GD2 in Tumor Tissues and Sera of Neuroblastoma Patients," Cancer Research 44: 5914-5920 (1984).
Schumacher, "T-cell-receptor gene therapy," Nat Rev Immunol, Jul. 2002, 2(7): 512-519.
Schwartz et al., "Structural basis for co-stimulation by the human CTLA-4/B7-2 complex," Nature, 410(6828):604-608, Mar. 29, 2001.
Schwarz et al., "ILA, the human 4-1BB homologue, is inducible in lymphoid and other cell lineages," Blood, Feb. 1995, 85(4): 1043-1052.
Scott, A. M. et al., "Antibody therapy of cancer" Nature Reviews (2012) vol. 12, pp. 278-287.
Search Report and Written Opinion for Singapore Application No. 11201908337V, titled, "Stimulatory cell lines for ex vivo expansion and activation of natural killer cells," Date Completed: Nov. 25, 2020.
Search Report and Written Opinion Issued from the Intellectual Property Office of Singapore in Singapore Patent Application No. 11201505858V; dated Apr. 27, 2016 and May 11, 2016, 8 pages total.
Search Report dated Apr. 27, 2016 and Written Opinion dated Nov. 5, 2016 of Singapore Application No. 11201505858V (11 pages).
Seif et al., "The role of JAK-STAT signaling pathway and its regulators in the fate of T helper cells" Cell Communication and Signaling (2017) 15:23.
Shah N, Li L, McCarty J, et al. (2017). Phase I study of cord blood-derived natural killer cells combined with autologous stem cell transplantation in multiple myeloma. Br J Haematol.;177(3):457-466. doi:10.1111/bih.14570.
Shappley, C., Paik, J. J., & Saketkoo, L.A. (2019). Myositis-Related Interstitial Lung Diseases: Diagnostic Features, Treatment, and Complications. Curr Treatm Opt Rheumatol, 5(1), 56-83.https://doi.ora/10.1007/s40674-018-0110-6.
Sheard, M. A. et al., "Membrane-bound Trail Supplements Natural Killer Cell Cytotoxicity Against Neuroblastoma Cells" J. Immunother. (2013) vol. 36, No. 5, pp. 319-329.
Shimabukum-Vornhagen A, Godel P, Subklewe M, et al. Cytokine release syndrome. J Immunother Cancer. 2018;6(1):56. doi: 10.1186/s40425-018-0343 -•9.
Shimasaki, et al; NK cells for cancer immunotherapy; Nature reviews | Drug Discovery; published online Jan. 6, 2020; www.nature.com/nrd.
Shouval, R., Furie, N., Raanani, P., Nagler, A., & Gafter-Gvili, A. (2018). Autologous Hematopoietic Stem Cell Transplantation for Systemic Sclerosis: A Systematic Review and Meta-Analysis. Biol Blood Marrow Transplant, 24(5), 937-944. https://doi.ora/10.1016/i.bbmt.2018.01.020.
Shuford WW, et al., "4-1 BB costimulatory signals preferentially induce CDS+ T cell proliferation and lead to the amplification in vivo of cytotoxic T cell responses", J Exp Med. Jul. 7, 1997; 186(1):47-55.

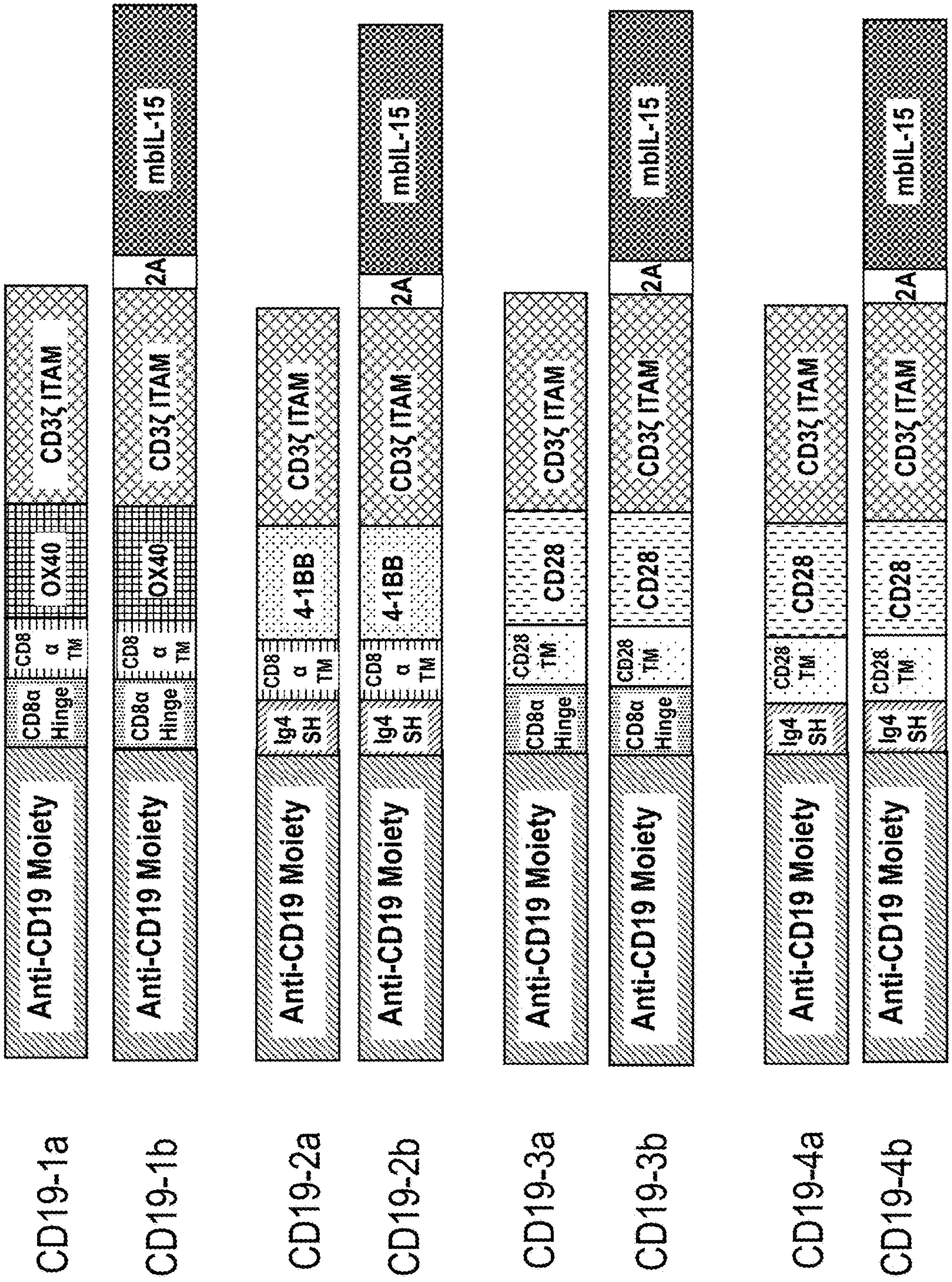

Figure 1A

CD19-1a: Anti-CD19 Moiety | CD8α Hinge | CD8α TM | OX40 | CD3ζ ITAM

CD19-1b: Anti-CD19 Moiety | CD8α Hinge | CD8α TM | OX40 | CD3ζ ITAM | 2A | mbIL-15

CD19-2a: Anti-CD19 Moiety | IgG4 SH | CD8α TM | 4-1BB | CD3ζ ITAM

CD19-2b: Anti-CD19 Moiety | IgG4 SH | CD8α TM | 4-1BB | CD3ζ ITAM | 2A | mbIL-15

CD19-3a: Anti-CD19 Moiety | CD8α Hinge | CD28 TM | CD28 | CD3ζ ITAM

CD19-3b: Anti-CD19 Moiety | CD8α Hinge | CD28 TM | CD28 | CD3ζ ITAM | 2A | mbIL-15

CD19-4a: Anti-CD19 Moiety | IgG4 SH | CD28 TM | CD28 | CD3ζ ITAM

CD19-4b: Anti-CD19 Moiety | IgG4 SH | CD28 TM | CD28 | CD3ζ ITAM | 2A | mbIL-15

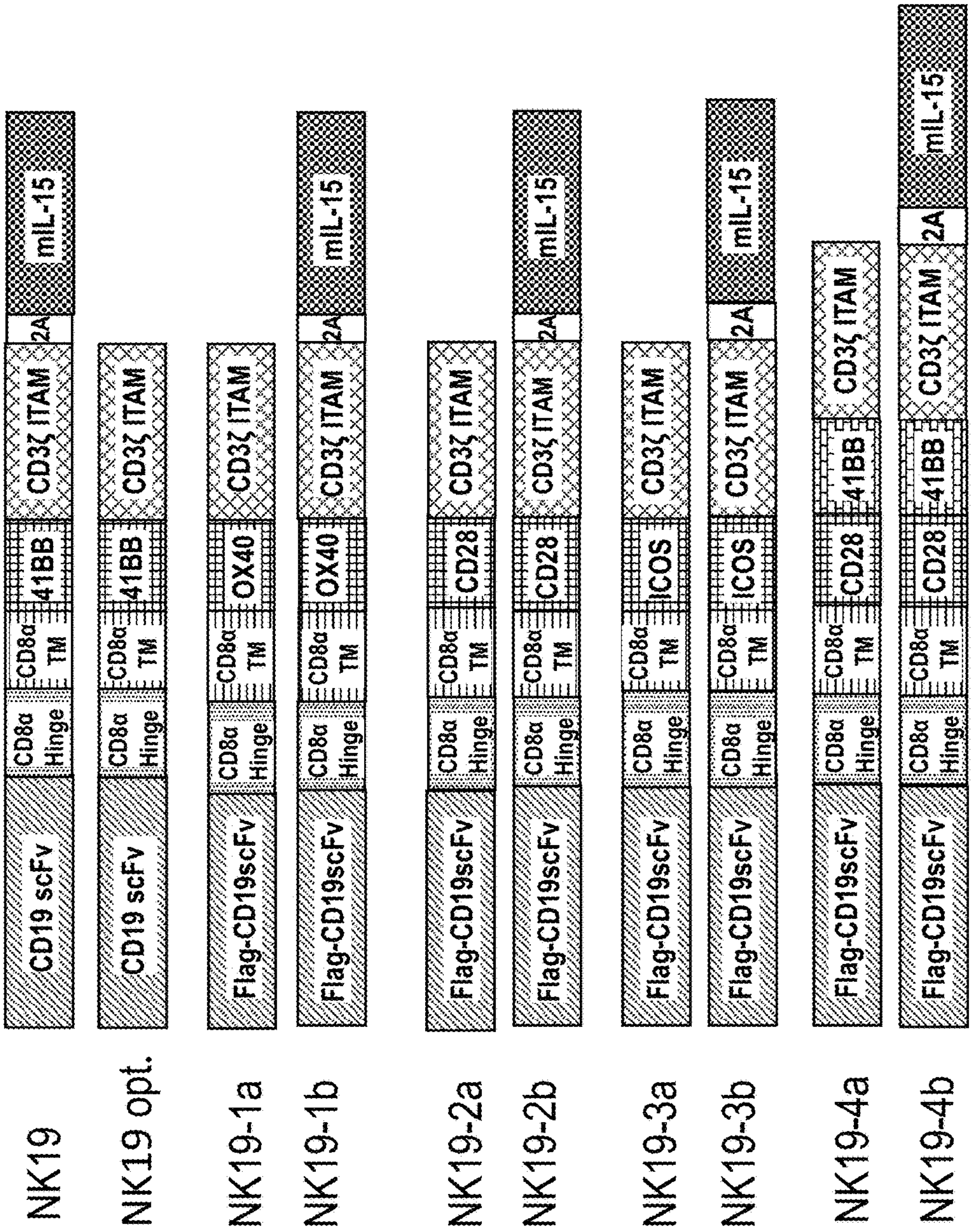

Figure 3A

| Construct | Components |
|---|---|
| NK19 | CD19 scFv – CD8α Hinge – CD8α TM – 41BB – CD3ζ ITAM – 2A – mIL-15 |
| NK19 opt. | CD19 scFv – CD8α Hinge – CD8α TM – 41BB – CD3ζ ITAM |
| NK19-1a | Flag-CD19scFv – CD8α Hinge – CD8α TM – OX40 – CD3ζ ITAM |
| NK19-1b | Flag-CD19scFv – CD8α Hinge – CD8α TM – OX40 – CD3ζ ITAM – 2A – mIL-15 |
| NK19-2a | Flag-CD19scFv – CD8α Hinge – CD8α TM – CD28 – CD3ζ ITAM |
| NK19-2b | Flag-CD19scFv – CD8α Hinge – CD8α TM – CD28 – CD3ζ ITAM – 2A – mIL-15 |
| NK19-3a | Flag-CD19scFv – CD8α Hinge – CD8α TM – ICOS – CD3ζ ITAM |
| NK19-3b | Flag-CD19scFv – CD8α Hinge – CD8α TM – ICOS – CD3ζ ITAM – 2A – mIL-15 |
| NK19-4a | Flag-CD19scFv – CD8α Hinge – CD8α TM – CD28 – 41BB – CD3ζ ITAM |
| NK19-4b | Flag-CD19scFv – CD8α Hinge – CD8α TM – CD28 – 41BB – CD3ζ ITAM – 2A – mIL-15 |

NK19-9a: Flag-CD19 scFv | CD8α Hinge | CD8α TM | CD27 | CD3ζ ITAM

NK19-9b: Flag-CD19 scFv | CD8α Hinge | CD8α TM | CD27 | CD3ζ ITAM | 2A | mIL-15

NK19-10a: Flag-CD19 scFv | CD8α Hinge | CD8α TM | CD70 | CD3ζ ITAM

NK19-10b: Flag-CD19 scFv | CD8α Hinge | CD8α TM | CD70 | CD3ζ ITAM | 2A | mIL-15

NK19-11a: Flag-CD19 scFv | CD8α Hinge | CD8α TM | CD161 | CD3ζ ITAM

NK19-11b: Flag-CD19 scFv | CD8α Hinge | CD8α TM | CD161 | CD3ζ ITAM | 2A | mIL-15

NK19-12a: Flag-CD19 scFv | CD8α Hinge | CD8α TM | CD40L | CD3ζ ITAM

NK19-12b: Flag-CD19 scFv | CD8α Hinge | CD8α TM | CD40L | CD3ζ ITAM | 2A | mIL-15

NK19-13a: Flag-CD19 scFv | CD8α Hinge | CD8α TM | CD44 | CD3ζ ITAM

NK19-13b: Flag-CD19 scFv | CD8α Hinge | CD8α TM | CD44 | CD3ζ ITAM | 2A | mIL-15

NK19-14a: Flag-CD19 scFv | CD8α Hinge | CD8α TM | CD44 | OX40 | CD27 | CD3ζ ITAM NK19-14b: Flag-CD19 scFv | CD8α Hinge | CD8α TM | CD44 | OX40 | CD27 | CD3ζ ITAM | 2A | mIL-15

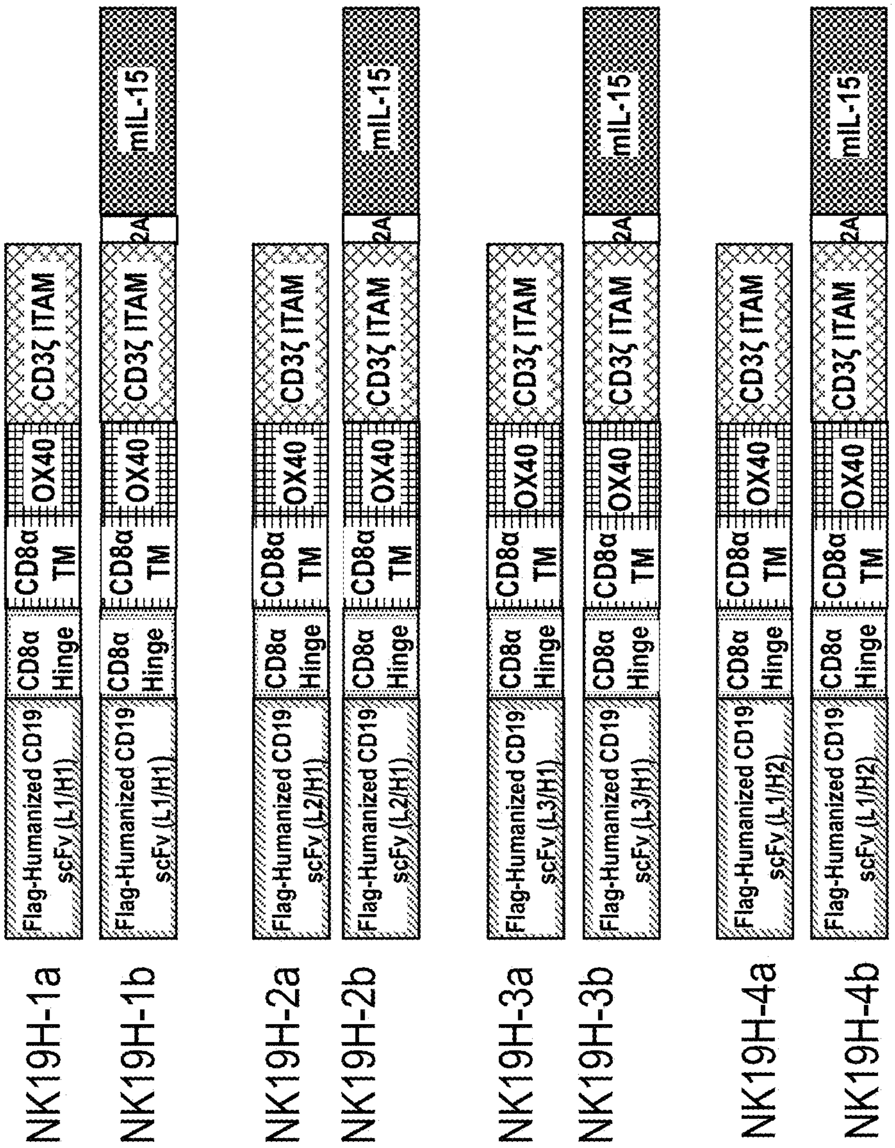

Figure 3D

NK19H-1a: Flag-Humanized CD19 scFv (L1/H1) | CD8α Hinge | CD8α TM | OX40 | CD3ζ ITAM
NK19H-1b: Flag-Humanized CD19 scFv (L1/H1) | CD8α Hinge | CD8α TM | OX40 | CD3ζ ITAM | 2A | mIL-15

NK19H-2a: Flag-Humanized CD19 scFv (L2/H1) | CD8α Hinge | CD8α TM | OX40 | CD3ζ ITAM
NK19H-2b: Flag-Humanized CD19 scFv (L2/H1) | CD8α Hinge | CD8α TM | OX40 | CD3ζ ITAM | 2A | mIL-15

NK19H-3a: Flag-Humanized CD19 scFv (L3/H1) | CD8α Hinge | CD8α TM | OX40 | CD3ζ ITAM
NK19H-3b: Flag-Humanized CD19 scFv (L3/H1) | CD8α Hinge | CD8α TM | OX40 | CD3ζ ITAM | 2A | mIL-15

NK19H-4a: Flag-Humanized CD19 scFv (L1/H2) | CD8α Hinge | CD8α TM | OX40 | CD3ζ ITAM
NK19H-4b: Flag-Humanized CD19 scFv (L1/H2) | CD8α Hinge | CD8α TM | OX40 | CD3ζ ITAM | 2A | mIL-15

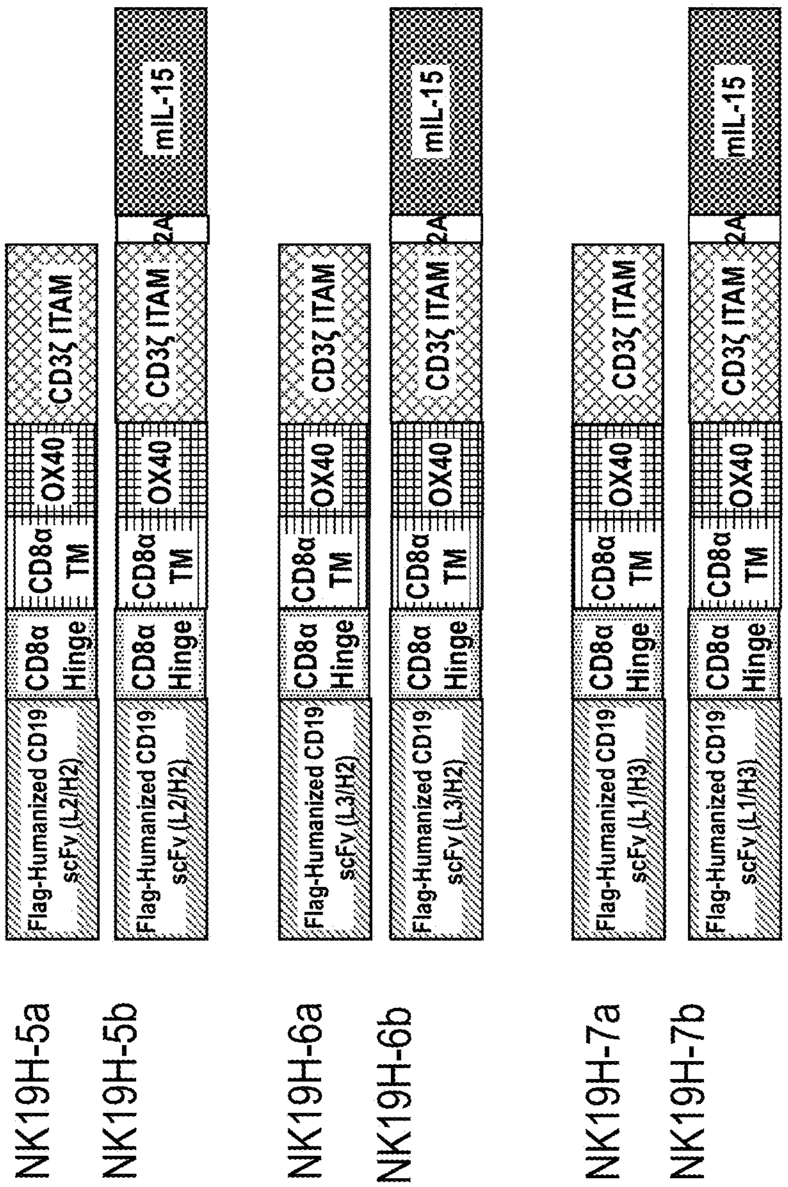

Figure 3E

NK19H-5a: Flag-Humanized CD19 scFv (L2/H2) | CD8α Hinge | CD8α TM | OX40 | CD3ζ ITAM NK19H-5b: Flag-Humanized CD19 scFv (L2/H2) | CD8α Hinge | CD8α TM | OX40 | CD3ζ ITAM | 2A | miL-15

NK19H-6a: Flag-Humanized CD19 scFv (L3/H2) | CD8α Hinge | CD8α TM | OX40 | CD3ζ ITAM NK19H-6b: Flag-Humanized CD19 scFv (L3/H2) | CD8α Hinge | CD8α TM | OX40 | CD3ζ ITAM | 2A | miL-15

NK19H-7a: Flag-Humanized CD19 scFv (L1/H3) | CD8α Hinge | CD8α TM | OX40 | CD3ζ ITAM NK19H-7b: Flag-Humanized CD19 scFv (L1/H3) | CD8α Hinge | CD8α TM | OX40 | CD3ζ ITAM | 2A | miL-15

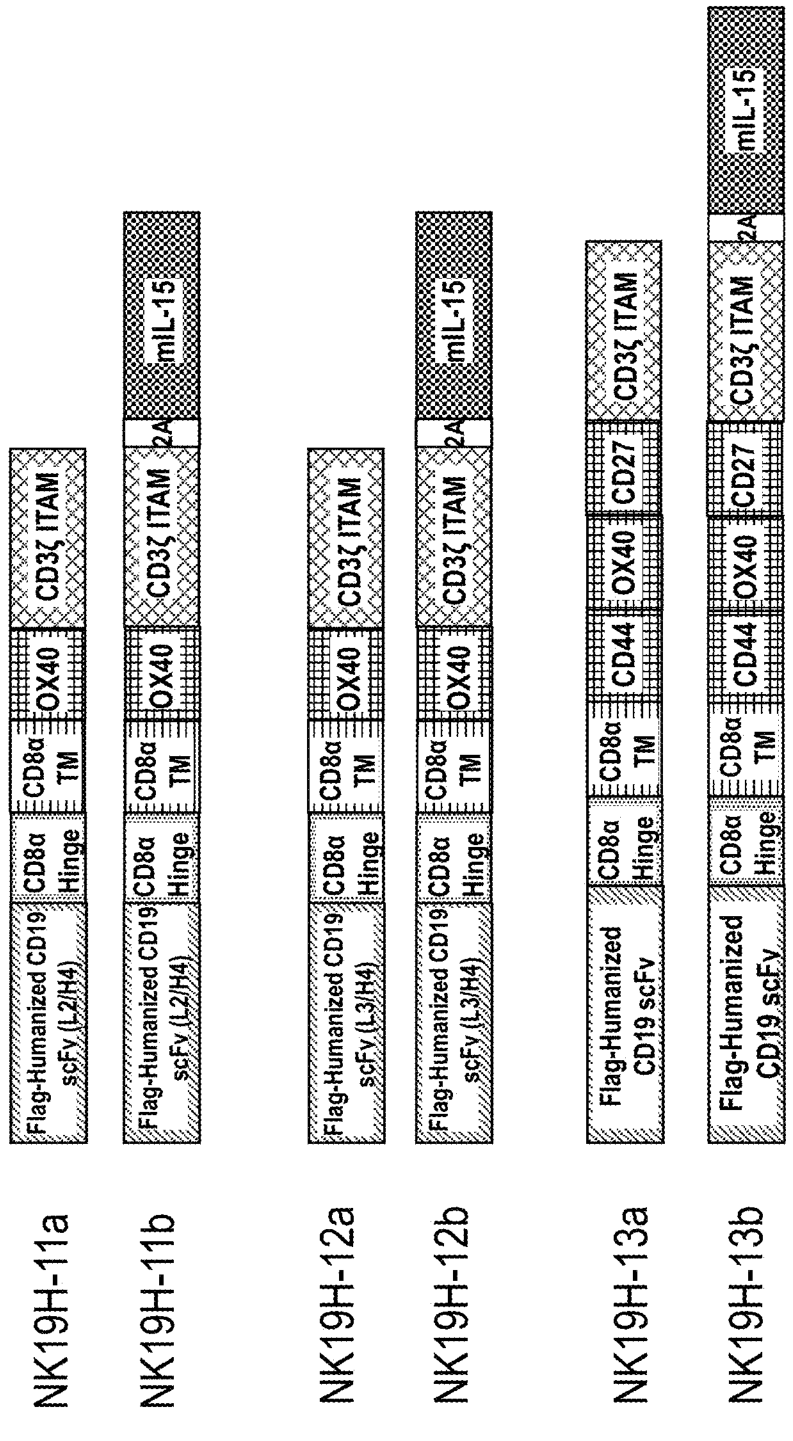

Figure 3F

NK19H-11a: Flag-Humanized CD19 scFv (L2/H4) | CD8α Hinge | CD8α TM | OX40 | CD3ζ ITAM NK19H-11b: Flag-Humanized CD19 scFv (L2/H4) | CD8α Hinge | CD8α TM | OX40 | CD3ζ ITAM | 2A | miL-15

NK19H-12a: Flag-Humanized CD19 scFv (L3/H4) | CD8α Hinge | CD8α TM | OX40 | CD3ζ ITAM NK19H-12b: Flag-Humanized CD19 scFv (L3/H4) | CD8α Hinge | CD8α TM | OX40 | CD3ζ ITAM | 2A | miL-15

NK19H-13a: Flag-Humanized CD19 scFv | CD8α Hinge | CD8α TM | CD44 | OX40 | CD27 | CD3ζ ITAM NK19H-13b: Flag-Humanized CD19 scFv | CD8α Hinge | CD8α TM | CD44 | OX40 | CD27 | CD3ζ ITAM | 2A | miL-15

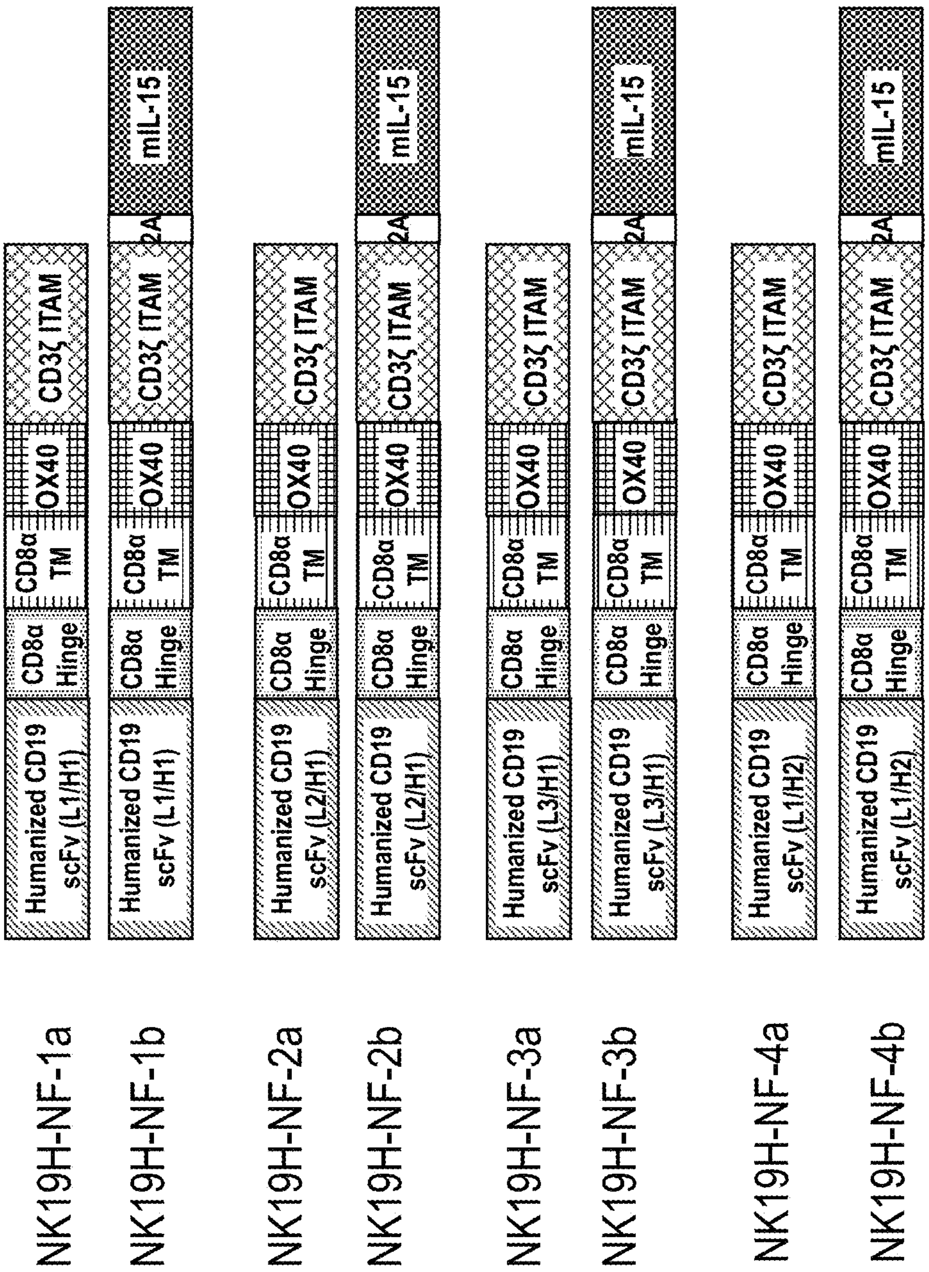

Figure 3G

NK19H-NF-1a: Humanized CD19 scFv (L1/H1) | CD8α Hinge | CD8α TM | OX40 | CD3ζ ITAM NK19H-NF-1b: Humanized CD19 scFv (L1/H1) | CD8α Hinge | CD8α TM | OX40 | CD3ζ ITAM | 2A | mIL-15

NK19H-NF-2a: Humanized CD19 scFv (L2/H1) | CD8α Hinge | CD8α TM | OX40 | CD3ζ ITAM NK19H-NF-2b: Humanized CD19 scFv (L2/H1) | CD8α Hinge | CD8α TM | OX40 | CD3ζ ITAM | 2A | mIL-15

NK19H-NF-3a: Humanized CD19 scFv (L3/H1) | CD8α Hinge | CD8α TM | OX40 | CD3ζ ITAM NK19H-NF-3b: Humanized CD19 scFv (L3/H1) | CD8α Hinge | CD8α TM | OX40 | CD3ζ ITAM | 2A | mIL-15

NK19H-NF-4a: Humanized CD19 scFv (L1/H2) | CD8α Hinge | CD8α TM | OX40 | CD3ζ ITAM NK19H-NF-4b: Humanized CD19 scFv (L1/H2) | CD8α Hinge | CD8α TM | OX40 | CD3ζ ITAM | 2A | mIL-15

NK19H-NF-5a: Humanized CD19 scFv (L2/H2) | CD8α Hinge | CD8α TM | OX40 | CD3ζ ITAM NK19H-NF-5b: Humanized CD19 scFv (L2/H2) | CD8α Hinge | CD8α TM | OX40 | CD3ζ ITAM | 2A | mIL-15

NK19H-NF-6a: Humanized CD19 scFv (L3/H2) | CD8α Hinge | CD8α TM | OX40 | CD3ζ ITAM NK19H-NF-6b: Humanized CD19 scFv (L3/H2) | CD8α Hinge | CD8α TM | OX40 | CD3ζ ITAM | 2A | mIL-15

NK19H-NF-7a: Humanized CD19 scFv (L1/H3) | CD8α Hinge | CD8α TM | OX40 | CD3ζ ITAM NK19H-NF-7b: Humanized CD19 scFv (L1/H3) | CD8α Hinge | CD8α TM | OX40 | CD3ζ ITAM | 2A | mIL-15

NK19H-NF-8a: Humanized CD19 scFv (L2/H3) | CD8α Hinge | CD8α TM | OX40 | CD3ζ ITAM NK19H-NF-8b: Humanized CD19 scFv (L2/H3) | CD8α Hinge | CD8α TM | OX40 | CD3ζ ITAM | 2A | mIL-15

NK19H-NF-9a: Humanized CD19 scFv (L3/H3) | CD8α Hinge | CD8α TM | OX40 | CD3ζ ITAM NK19H-NF-9b: Humanized CD19 scFv (L3/H3) | CD8α Hinge | CD8α TM | OX40 | CD3ζ ITAM | 2A | mIL-15

NK19H-NF-10a: Humanized CD19 scFv (L1/H4) | CD8α Hinge | CD8α TM | OX40 | CD3ζ ITAM NK19H-NF-10b: Humanized CD19 scFv (L1/H4) | CD8α Hinge | CD8α TM | OX40 | CD3ζ ITAM | 2A | mIL-15

NK19H-NF-11a: Humanized CD19 scFv (L2/H4) | CD8α Hinge | CD8α TM | OX40 | CD3ζ ITAM NK19H-NF-11b: Humanized CD19 scFv (L2/H4) | CD8α Hinge | CD8α TM | OX40 | CD3ζ ITAM | 2A | miL-15

NK19H-NF-12a: Humanized CD19 scFv (L3/H4) | CD8α Hinge | CD8α TM | OX40 | CD3ζ ITAM NK19H-NF-12b: Humanized CD19 scFv (L3/H4) | CD8α Hinge | CD8α TM | OX40 | CD3ζ ITAM | 2A | miL-15

NK19H-NF-13a: Humanized CD19 scFv | CD8α Hinge | CD8α TM | CD44 | OX40 | CD27 | CD3ζ ITAM NK19H-NF-13b: Humanized CD19 scFv | CD8α Hinge | CD8α TM | CD44 | OX40 | CD27 | CD3ζ ITAM | 2A | miL-15

Figure 11A-B
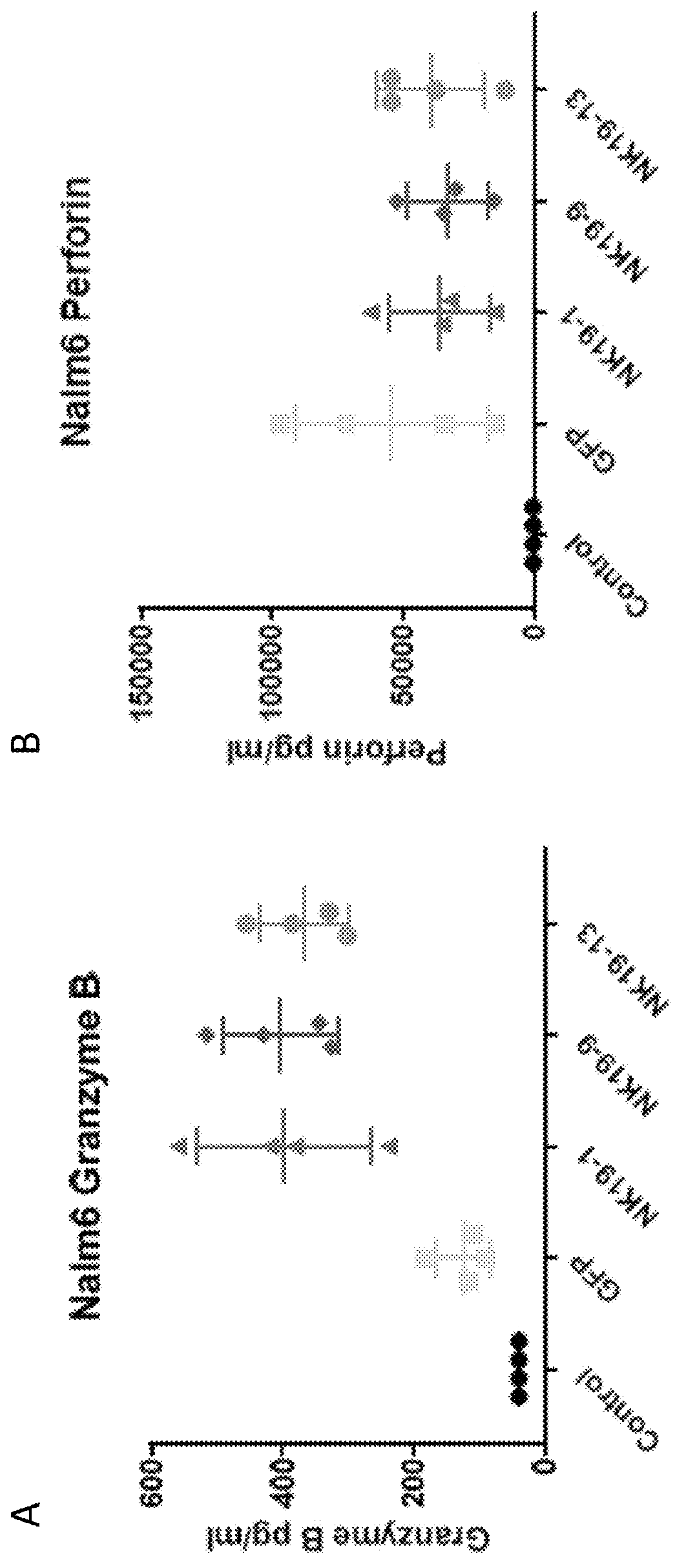

Figure 11C-D
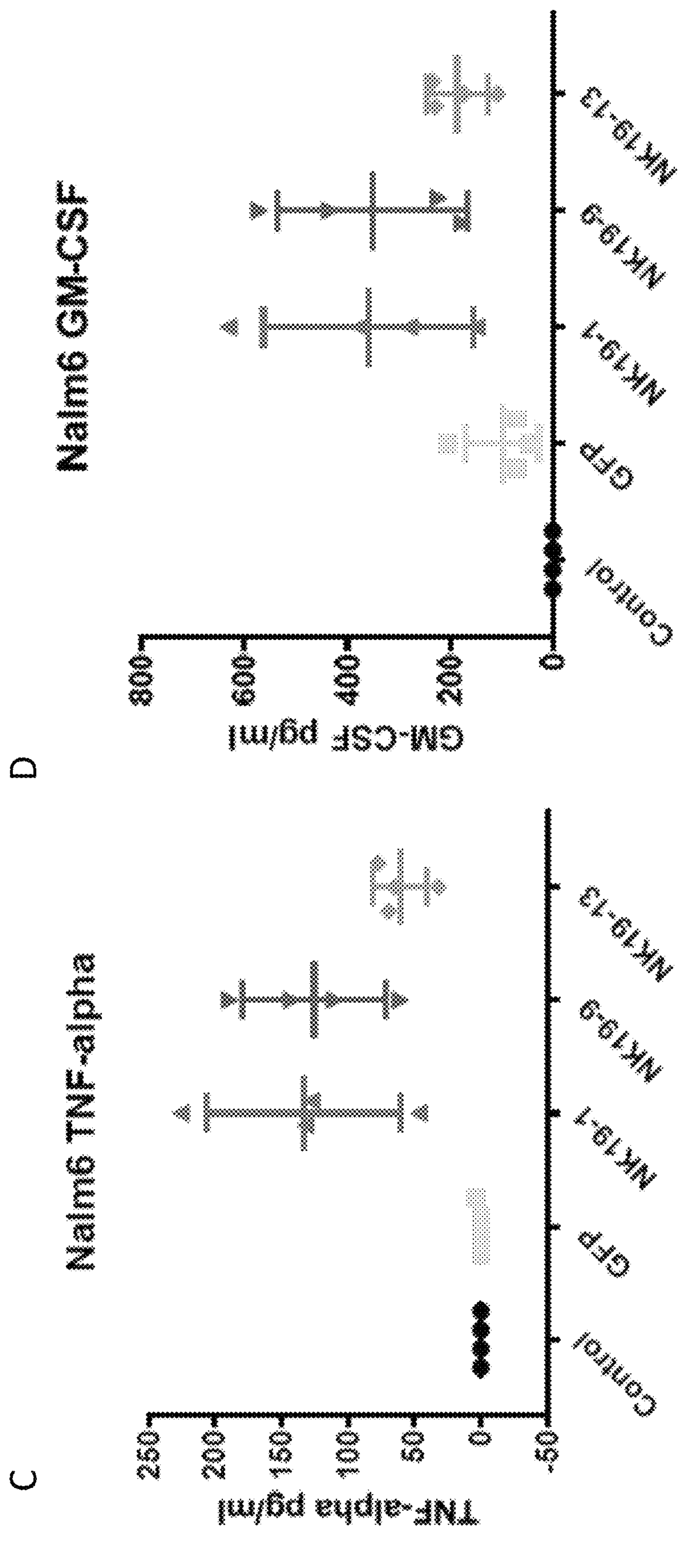

E

Figure 12A-B
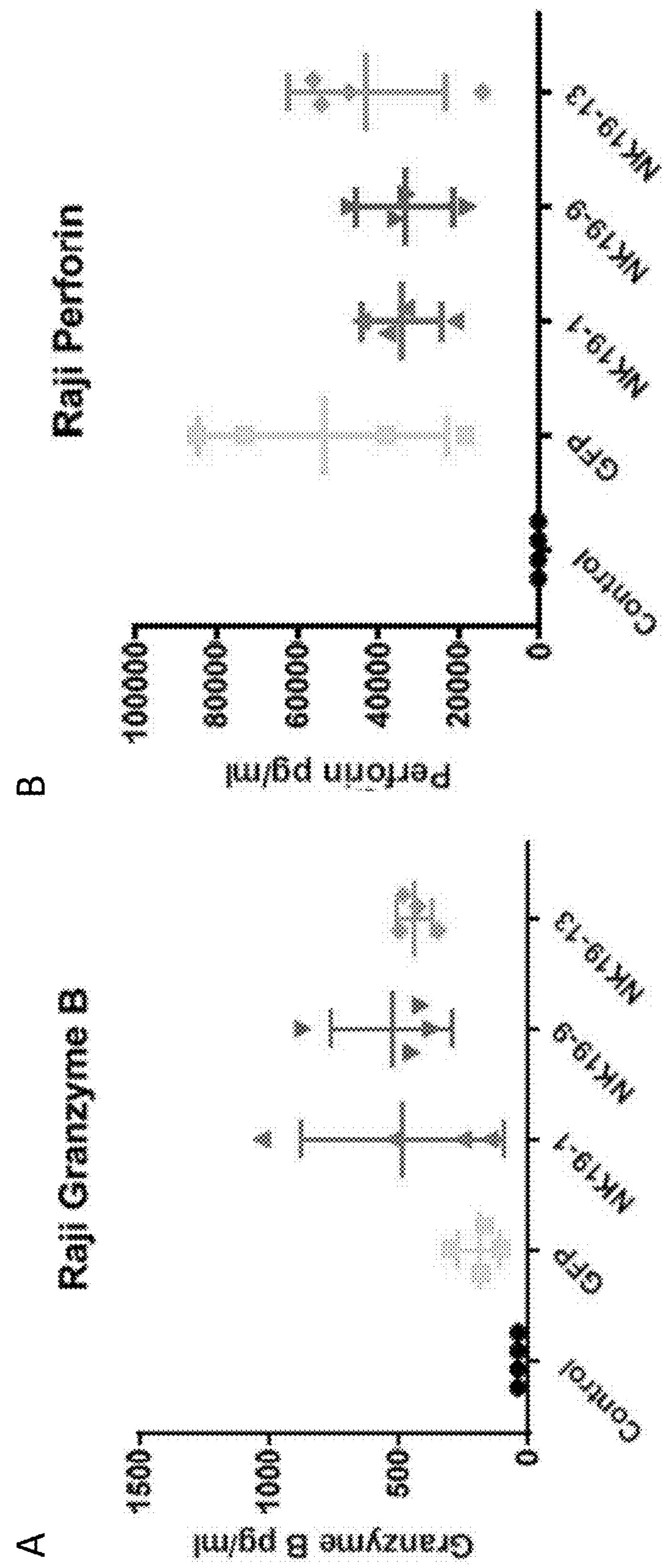

Figure 12C-D
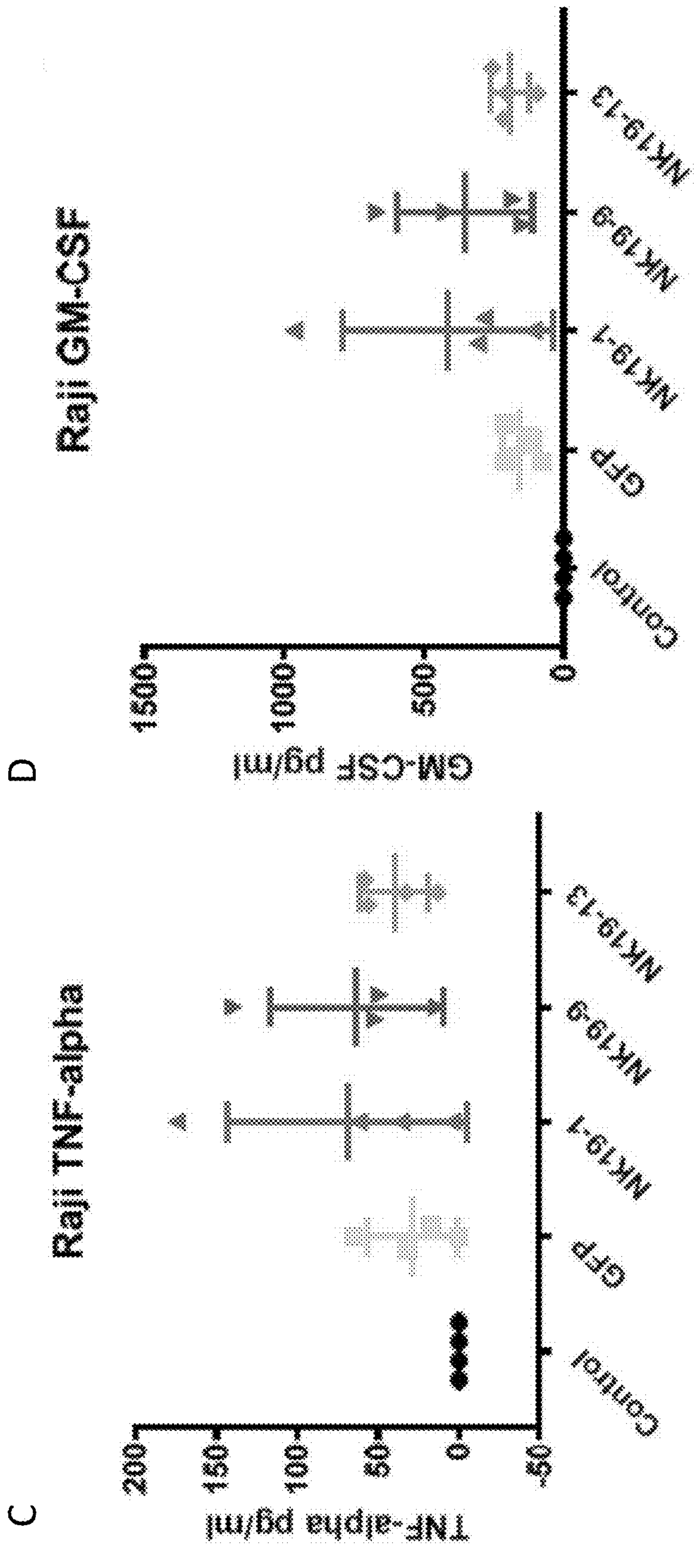

| MFI | Unheating | | | | Heating | | |
|---|---|---|---|---|---|---|---|
| | 0.5 | 0.25 | 0.125 | | 0.5 | 0.25 | 0.125 |
| H1L1 | 385 | 285 | 169 | H1L1 | 389 | 270 | 159 |
| H1L2 | 396 | 303 | 202 | H1L2 | 395 | 288 | 196 |
| H1L3 | 406 | 306 | 99.3 | H1L3 | 392 | 278 | 190 |
| H2L1 | 399 | 292 | 181 | H2L1 | 378 | 270 | 186 |
| H2L2 | 390 | 274 | 180 | H2L2 | 398 | 271 | 177 |
| H2L3 | 431 | 327 | 213 | H2L3 | 432 | 305 | 202 |
| H3L1 | 359 | 246 | 164 | H3L1 | 350 | 227 | 137 |
| H3L2 | 379 | 253 | 132 | H3L2 | 348 | 229 | 151 |
| H3L3 | 415 | 299 | 203 | H3L3 | 418 | 310 | 217 |
| H4L1 | 390 | 274 | 188 | H4L1 | 400 | 285 | 199 |
| H4L2 | 387 | 281 | 199 | H4L2 | 383 | 279 | 183 |
| H4L3 | 445 | 329 | 235 | H4L3 | 420 | 334 | 245 |
| H0L0 | 433 | 312 | 194 | H0L0 | 435 | 321 | 207 |

Media was changed 2X/week

SEQUENCE LISTING

```
<160> NUMBER OF SEQ ID NOS: 207

<210> SEQ ID NO 1
<211> LENGTH: 135
<212> TYPE: DNA
<213> ORGANISM: Homo sapiens
<220> FEATURE:
<221> NAME/KEY: misc_feature
<223> OTHER INFORMATION: CD8alpha hinge - DNA

<400> SEQUENCE: 1

accacgacgc cagcgccgcg accaccaaca ccggcgccca ccatcgcgtc gcagcccctg     60

tccctgcgcc cagaggcgtg ccggccagcg gcggggggcg cagtgcacac gagggggctg    120

gacttcgcct gtgat                                                     135


<210> SEQ ID NO 2
<211> LENGTH: 45
<212> TYPE: PRT
<213> ORGANISM: Homo sapiens
<220> FEATURE:
<221> NAME/KEY: MISC_FEATURE
<223> OTHER INFORMATION: CD8a hinge - protein

<400> SEQUENCE: 2

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp
        35                  40                  45


<210> SEQ ID NO 3
<211> LENGTH: 63
<212> TYPE: DNA
<213> ORGANISM: Homo sapiens
<220> FEATURE:
<221> NAME/KEY: misc_feature
<223> OTHER INFORMATION: CD8 TM - DNA

<400> SEQUENCE: 3

atctacatct gggcgccctt ggccgggact tgtggggtcc ttctcctgtc actggttatc     60

acc                                                                   63
```

<210> SEQ ID NO 4
<211> LENGTH: 21
<212> TYPE: PRT
<213> ORGANISM: Homo sapiens
<220> FEATURE:
<221> NAME/KEY: MISC_FEATURE
<223> OTHER INFORMATION: CD8 TM - protein

<400> SEQUENCE: 4

Ile Tyr Ile Trp Ala Pro Leu Ala Gly Thr Cys Gly Val Leu Leu Leu
1 5 10 15

Ser Leu Val Ile Thr
20

<210> SEQ ID NO 5
<211> LENGTH: 111
<212> TYPE: DNA
<213> ORGANISM: Homo sapiens
<220> FEATURE:
<221> NAME/KEY: misc_feature
<223> OTHER INFORMATION: OX40 - DNA

<400> SEQUENCE: 5
cggagggacc agaggctgcc ccccgatgcc cacaagcccc ctgggggagg cagtttccgg 60
acccccatcc aagaggagca ggccgacgcc cactccaccc tggccaagat c 111

<210> SEQ ID NO 6
<211> LENGTH: 37
<212> TYPE: PRT
<213> ORGANISM: Homo sapiens
<220> FEATURE:
<221> NAME/KEY: MISC_FEATURE
<223> OTHER INFORMATION: OX40 - protein

<400> SEQUENCE: 6

Arg Arg Asp Gln Arg Leu Pro Pro Asp Ala His Lys Pro Pro Gly Gly
1 5 10 15

Gly Ser Phe Arg Thr Pro Ile Gln Glu Glu Gln Ala Asp Ala His Ser
20 25 30

Thr Leu Ala Lys Ile
35

<210> SEQ ID NO 7
<211> LENGTH: 336
<212> TYPE: DNA
<213> ORGANISM: Homo sapiens
<220> FEATURE:
<221> NAME/KEY: misc_feature
<223> OTHER INFORMATION: CD3zeta - DNA

<400> SEQUENCE: 7
agagtgaagt tcagcaggag cgcagacgcc cccgcgtacc agcagggcca gaaccagctc 60
tataacgagc tcaatctagg acgaagagag gagtacgatg ttttggacaa gagacgtggc 120
cgggaccctg agatgggggg aaagccgaga aggaagaacc ctcaggaagg cctgtacaat 180
gaactgcaga aagataagat ggcggaggcc tacagtgaga ttgggatgaa aggcgagcgc 240
cggaggggca aggggcacga tggcctttac cagggtctca gtacagccac caaggacacc 300
tacgacgccc ttcacatgca ggccctgccc cctcgc 336

<210> SEQ ID NO 8
<211> LENGTH: 112
<212> TYPE: PRT

<213> ORGANISM: Homo sapiens
<220> FEATURE:
<221> NAME/KEY: MISC_FEATURE
<223> OTHER INFORMATION: CD3zeta - protein

<400> SEQUENCE: 8

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 9
<211> LENGTH: 63
<212> TYPE: DNA
<213> ORGANISM: Homo sapiens
<220> FEATURE:
<221> NAME/KEY: misc_feature
<223> OTHER INFORMATION: T2A - DNA

<400> SEQUENCE: 9
ggctctggcg agggaagggg ttccctgctt acttgcggcg acgtcgaaga gaatcccggt     60
ccg                                                                   63

<210> SEQ ID NO 10
<211> LENGTH: 21
<212> TYPE: PRT
<213> ORGANISM: Homo sapiens
<220> FEATURE:
<221> NAME/KEY: MISC_FEATURE
<223> OTHER INFORMATION: T2A - protein

<400> SEQUENCE: 10

Gly Ser Gly Glu Gly Arg Gly Ser Leu Leu Thr Cys Gly Asp Val Glu
1               5                   10                  15

Glu Asn Pro Gly Pro
            20

<210> SEQ ID NO 11
<211> LENGTH: 342
<212> TYPE: DNA
<213> ORGANISM: Homo sapiens
<220> FEATURE:
<221> NAME/KEY: misc_feature
<223> OTHER INFORMATION: IL15 - DNA

<400> SEQUENCE: 11
aactgggtca acgtgattag cgatttgaag aaaatcgagg accttataca gtctatgcat     60
attgacgcta cactgtatac tgagagtgat gtacacccgt cctgtaaggt aacggccatg    120
aaatgctttc ttctggagct ccaggtcatc agcttggagt ctggggacgc aagcatccac    180
gatacggttg aaaacctcat catccttgcg aacaactctc tctcatctaa tggaaacgtt    240

-continued

```
acagagagtg ggtgtaagga gtgcgaagag ttggaagaaa aaaacatcaa agaatttctt    300

caatccttcg ttcacatagt gcaaatgttc attaacacgt cc                       342


<210> SEQ ID NO 12
<211> LENGTH: 114
<212> TYPE: PRT
<213> ORGANISM: Homo sapiens
<220> FEATURE:
<221> NAME/KEY: MISC_FEATURE
<223> OTHER INFORMATION: IL15 - protein

<400> SEQUENCE: 12

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser


<210> SEQ ID NO 13
<211> LENGTH: 207
<212> TYPE: DNA
<213> ORGANISM: Homo sapiens
<220> FEATURE:
<221> NAME/KEY: misc_feature
<223> OTHER INFORMATION: CD8hinge/TM - DNA

<400> SEQUENCE: 13

actaccacac ccgccccgag gccacctacg ccggcaccga ctatcgccag tcaacccctc     60

tctctgcgcc ccgaggcttg ccggcctgcg gctggtgggg cggtccacac ccggggcctg    120

gattttgcgt gcgatatata catctgggca cctcttgccg gcacctgcgg agtgctgctt    180

ctctcactcg ttattacgct gtactgc                                        207


<210> SEQ ID NO 14
<211> LENGTH: 66
<212> TYPE: PRT
<213> ORGANISM: Homo sapiens
<220> FEATURE:
<221> NAME/KEY: MISC_FEATURE
<223> OTHER INFORMATION: CD8hinge/TM - protein

<400> SEQUENCE: 14

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp Ile Tyr Ile
        35                  40                  45

Trp Ala Pro Leu Ala Gly Thr Cys Gly Val Leu Leu Leu Ser Leu Val
    50                  55                  60
```

Ile Thr
65

<210> SEQ ID NO 15
<211> LENGTH: 30
<212> TYPE: DNA
<213> ORGANISM: Homo sapiens
<220> FEATURE:
<221> NAME/KEY: misc_feature
<223> OTHER INFORMATION: Linker 1 (used after FLAG tag) - DNA

<400> SEQUENCE: 15
ggcggtggtg gctctggtgg tggcggcagc 30

<210> SEQ ID NO 16
<211> LENGTH: 10
<212> TYPE: PRT
<213> ORGANISM: Homo sapiens
<220> FEATURE:
<221> NAME/KEY: MISC_FEATURE
<223> OTHER INFORMATION: Linker 1 (used after FLAG tag) - protein

<400> SEQUENCE: 16

Gly Gly Gly Gly Ser Gly Gly Gly Gly Ser
1 5 10

<210> SEQ ID NO 17
<211> LENGTH: 30
<212> TYPE: DNA
<213> ORGANISM: Homo sapiens
<220> FEATURE:
<221> NAME/KEY: misc_feature
<223> OTHER INFORMATION: Linker 2 - after neg. control binding domain -
DNA

<400> SEQUENCE: 17
ggccaggccg gctccggagg aggaggatcc 30

<210> SEQ ID NO 18
<211> LENGTH: 10
<212> TYPE: PRT
<213> ORGANISM: Homo sapiens
<220> FEATURE:
<221> NAME/KEY: MISC_FEATURE
<223> OTHER INFORMATION: Linker 2 - after neg. control binding domain -
Protein

<400> SEQUENCE: 18

Gly Gln Ala Gly Ser Gly Gly Gly Gly Ser
1 5 10

<210> SEQ ID NO 19
<211> LENGTH: 12
<212> TYPE: DNA
<213> ORGANISM: Homo sapiens
<220> FEATURE:
<221> NAME/KEY: misc_feature
<223> OTHER INFORMATION: Linker post scFv - DNA

<400> SEQUENCE: 19
ggccaggccg gc 12

<210> SEQ ID NO 20
<211> LENGTH: 4
<212> TYPE: PRT
<213> ORGANISM: Homo sapiens
<220> FEATURE:

-continued

<221> NAME/KEY: MISC_FEATURE
<223> OTHER INFORMATION: Linker post scFv - protein

<400> SEQUENCE: 20

Gly Gln Ala Gly
1

<210> SEQ ID NO 21
<211> LENGTH: 33
<212> TYPE: DNA
<213> ORGANISM: Homo sapiens
<220> FEATURE:
<221> NAME/KEY: misc_feature
<223> OTHER INFORMATION: Linker - DNA
<220> FEATURE:
<221> NAME/KEY: misc_feature
<223> OTHER INFORMATION: Misc Linker - DNA

<400> SEQUENCE: 21
ggcggcggcg gtagcggtgg tggcggctcc gga 33

<210> SEQ ID NO 22
<211> LENGTH: 11
<212> TYPE: PRT
<213> ORGANISM: Homo sapiens
<220> FEATURE:
<221> NAME/KEY: MISC_FEATURE
<223> OTHER INFORMATION: Misc Linker - protein

<400> SEQUENCE: 22

Gly Gly Gly Gly Ser Gly Gly Gly Gly Ser Gly
1 5 10

<210> SEQ ID NO 23
<211> LENGTH: 18
<212> TYPE: DNA
<213> ORGANISM: Homo sapiens
<220> FEATURE:
<221> NAME/KEY: misc_feature
<223> OTHER INFORMATION: Linker - DNA

<400> SEQUENCE: 23
ggccaggccg gctccgga 18

<210> SEQ ID NO 24
<211> LENGTH: 6
<212> TYPE: PRT
<213> ORGANISM: Homo sapiens
<220> FEATURE:
<221> NAME/KEY: MISC_FEATURE
<223> OTHER INFORMATION: Linker - protein

<400> SEQUENCE: 24

Gly Gln Ala Gly Ser Gly
1 5

<210> SEQ ID NO 25
<211> LENGTH: 405
<212> TYPE: DNA
<213> ORGANISM: Homo sapiens
<220> FEATURE:
<221> NAME/KEY: misc_feature
<223> OTHER INFORMATION: NKG2D Extracellular Fragment - DNA

<400> SEQUENCE: 25
ttattcaacc aagaagttca aattcccttg accgaaagtt actgtggccc atgtcctaaa 60
aactggatat gttacaaaaa taactgctac caatttttg atgagagtaa aaactggtat 120
gagagccagg cttcttgtat gtctcaaaat gccagccttc tgaaagtata cagcaaagag 180
gaccaggatt tacttaaact ggtgaagtca tatcattgga tgggactagt acacattcca 240
acaaatggat cttggcagtg ggaagatggc tccattctct cacccaacct actaacaata 300
attgaaatgc agaagggaga ctgtgcactc tatgcctcga gctttaaagg ctatatagaa 360
aactgttcaa ctccaaatac gtacatctgc atgcaaagga ctgtg 405

<210> SEQ ID NO 26
<211> LENGTH: 135
<212> TYPE: PRT
<213> ORGANISM: Homo sapiens
<220> FEATURE:
<221> NAME/KEY: MISC_FEATURE
<223> OTHER INFORMATION: NKG2D Extracellular Fragment - protein

<400> SEQUENCE: 26

```
Leu Phe Asn Gln Glu Val Gln Ile Pro Leu Thr Glu Ser Tyr Cys Gly
1               5                   10                  15

Pro Cys Pro Lys Asn Trp Ile Cys Tyr Lys Asn Asn Cys Tyr Gln Phe
            20                  25                  30

Phe Asp Glu Ser Lys Asn Trp Tyr Glu Ser Gln Ala Ser Cys Met Ser
        35                  40                  45

Gln Asn Ala Ser Leu Leu Lys Val Tyr Ser Lys Glu Asp Gln Asp Leu
    50                  55                  60

Leu Lys Leu Val Lys Ser Tyr His Trp Met Gly Leu Val His Ile Pro
65                  70                  75                  80

Thr Asn Gly Ser Trp Gln Trp Glu Asp Gly Ser Ile Leu Ser Pro Asn
                85                  90                  95

Leu Leu Thr Ile Ile Glu Met Gln Lys Gly Asp Cys Ala Leu Tyr Ala
            100                 105                 110

Ser Ser Phe Lys Gly Tyr Ile Glu Asn Cys Ser Thr Pro Asn Thr Tyr
        115                 120                 125

Ile Cys Met Gln Arg Thr Val
    130                 135
```

<210> SEQ ID NO 27
<211> LENGTH: 645
<212> TYPE: DNA
<213> ORGANISM: Homo sapiens
<220> FEATURE:
<221> NAME/KEY: misc_feature
<223> OTHER INFORMATION: Full Human NKG2D - DNA

<400> SEQUENCE: 27
gggtggattc gtggtcggag gtctcgacac agctgggaga tgagtgaatt tcataattat 60
aacttggatc tgaagaagag tgatttttca acacgatggc aaaagcaaag atgtccagta 120
gtcaaaagca aatgtagaga aaatgcatct ccattttttt tctgctgctt catcgctgta 180
gccatgggaa tccgtttcat tattatggta acaatatgga gtgctgtatt cctaaactca 240
ttattcaacc aagaagttca aattcccttg accgaaagtt actgtggccc atgtcctaaa 300
aactggatat gttacaaaaa taactgctac caatttttg atgagagtaa aaactggtat 360
gagagccagg cttcttgtat gtctcaaaat gccagccttc tgaaagtata cagcaaagag 420
gaccaggatt tacttaaact ggtgaagtca tatcattgga tgggactagt acacattcca 480
acaaatggat cttggcagtg ggaagatggc tccattctct cacccaacct actaacaata 540
attgaaatgc agaagggaga ctgtgcactc tatgcctcga gctttaaagg ctatatagaa 600
aactgttcaa ctccaaatac gtacatctgc atgcaaagga ctgtg 645

<210> SEQ ID NO 28
<211> LENGTH: 405
<212> TYPE: DNA
<213> ORGANISM: Homo sapiens
<220> FEATURE:
<221> NAME/KEY: misc_feature
<223> OTHER INFORMATION: Codon optimized human NKG2D fragment - DNA

<400> SEQUENCE: 28
ctgttcaatc aggaagtcca gatccccctg acagagtctt actgcggccc atgtcccaag 60
aactggatct gctacaagaa caattgttat cagttctttg acgagagcaa gaactggtat 120
gagtcccagg cctcttgcat gagccagaat gcctctctgc tgaaggtgta cagcaaggag 180
gaccaggatc tgctgaagct ggtgaagtcc tatcactgga tgggcctggt gcacatccct 240
acaaacggct cttggcagtg ggaggacggc tccatcctgt ctccaaatct gctgaccatc 300
atcgagatgc agaagggcga ttgcgccctg tacgccagct ccttcaaggg ctatatcgag 360
aactgctcca cacccaatac ctacatctgt atgcagagga ccgtg 405

<210> SEQ ID NO 29
<211> LENGTH: 126
<212> TYPE: DNA
<213> ORGANISM: Homo sapiens
<220> FEATURE:
<221> NAME/KEY: misc_feature
<223> OTHER INFORMATION: 4-1BB

<400> SEQUENCE: 29
aaacggggca gaaagaaact cctgtatata ttcaaacaac catttatgag accagtacaa 60
actactcaag aggaagatgg ctgtagctgc cgatttccag aagaagaaga aggaggatgt 120
gaactg 126

<210> SEQ ID NO 30
<211> LENGTH: 29
<212> TYPE: PRT
<213> ORGANISM: Homo sapiens
<220> FEATURE:
<221> NAME/KEY: MISC_FEATURE
<223> OTHER INFORMATION: Amino Acid Sequence CD28 Transmembrane domain

<400> SEQUENCE: 30

Phe Trp Val Leu Val Val Val Gly Gly Val Leu Ala Cys Tyr Ser Leu
1               5                   10                  15

Leu Val Thr Val Ala Phe Ile Ile Phe Trp Val Arg Ser
            20                  25

<210> SEQ ID NO 31
<211> LENGTH: 39
<212> TYPE: PRT
<213> ORGANISM: Homo sapiens
<220> FEATURE:
<221> NAME/KEY: MISC_FEATURE
<223> OTHER INFORMATION: Amino Acid Sequence CD28 IC domain

<400> SEQUENCE: 31

Lys Arg Ser Arg Leu Leu His Ser Asp Tyr Met Asn Met Thr Pro Arg
1               5                   10                  15

Arg Pro Gly Pro Thr Arg Lys His Tyr Gln Pro Tyr Ala Pro Pro Arg
            20                  25                  30

```
Asp Phe Ala Ala Tyr Arg Ser
        35


<210> SEQ ID NO 32
<211> LENGTH: 123
<212> TYPE: PRT
<213> ORGANISM: Homo sapiens
<220> FEATURE:
<221> NAME/KEY: MISC_FEATURE
<223> OTHER INFORMATION: VL Nicholson et al.

<400> SEQUENCE: 32

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr Arg Ala Asp Ala Ala
            100                 105                 110

Pro Thr Val Ser Ile Phe Pro Pro Ser Ser Asn
        115                 120


<210> SEQ ID NO 33
<211> LENGTH: 120
<212> TYPE: PRT
<213> ORGANISM: Homo sapiens
<220> FEATURE:
<221> NAME/KEY: MISC_FEATURE
<223> OTHER INFORMATION: VH Nicholson et al.

<400> SEQUENCE: 33

Glu Val Lys Leu Gln Glu Ser Gly Pro Gly Leu Val Ala Pro Ser Gln
1               5                   10                  15

Ser Leu Ser Val Thr Cys Thr Val Ser Gly Val Ser Leu Pro Asp Tyr
            20                  25                  30

Gly Val Ser Trp Ile Arg Gln Pro Pro Arg Lys Gly Leu Glu Trp Leu
        35                  40                  45

Gly Val Ile Trp Gly Ser Glu Thr Thr Tyr Tyr Asn Ser Ala Leu Lys
    50                  55                  60

Ser Arg Leu Thr Ile Ile Lys Asp Asn Ser Lys Ser Gln Val Phe Leu
65                  70                  75                  80

Lys Met Asn Ser Leu Gln Thr Asp Asp Thr Ala Ile Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Ser Val Thr Val Ser Ser
        115                 120


<210> SEQ ID NO 34
<211> LENGTH: 634
<212> TYPE: PRT
<213> ORGANISM: Homo sapiens
<220> FEATURE:
```

<221> NAME/KEY: MISC_FEATURE
<223> OTHER INFORMATION: PRT Artificial Sequence CD19R zeta chimeric receptor

<400> SEQUENCE: 34

Met Leu Leu Leu Val Thr Ser Leu Leu Leu Cys Glu Leu Pro His Pro
1 5 10 15

Ala Phe Leu Leu Ile Pro Asp Ile Gln Met Thr Gln Thr Thr Ser Ser
20 25 30

Leu Ser Ala Ser Leu Gly Asp Arg Val Thr Ile Ser Cys Arg Ala Ser
35 40 45

Gln Asp Ile Ser Lys Tyr Leu Asn Trp Tyr Gln Gln Lys Pro Asp Gly
50 55 60

Thr Val Lys Leu Leu Ile Tyr His Thr Ser Arg Leu His Ser Gly Val
65 70 75 80

Pro Ser Arg Phe Ser Gly Ser Gly Ser Gly Thr Asp Tyr Ser Leu Thr
85 90 95

Ile Ser Asn Leu Glu Gln Glu Asp Ile Ala Thr Tyr Phe Cys Gln Gln
100 105 110

Gly Asn Thr Leu Pro Tyr Thr Phe Gly Gly Gly Thr Lys Leu Glu Ile
115 120 125

Thr Gly Ser Thr Ser Gly Ser Gly Lys Pro Gly Ser Gly Glu Gly Ser
130 135 140

Thr Lys Gly Glu Val Lys Leu Gln Glu Ser Gly Pro Gly Leu Val Ala
145 150 155 160

Pro Ser Gln Ser Leu Ser Val Thr Cys Thr Val Ser Gly Val Ser Leu
165 170 175

Pro Asp Tyr Gly Val Ser Trp Ile Arg Gln Pro Pro Arg Lys Gly Leu
180 185 190

Glu Trp Leu Gly Val Ile Trp Gly Ser Glu Thr Thr Tyr Tyr Asn Ser
195 200 205

Ala Leu Lys Ser Arg Leu Thr Ile Ile Lys Asp Asn Ser Lys Ser Gln
210 215 220

Val Phe Leu Lys Met Asn Ser Leu Gln Thr Asp Asp Thr Ala Ile Tyr
225 230 235 240

Tyr Cys Ala Lys His Tyr Tyr Tyr Gly Gly Ser Tyr Ala Met Asp Tyr
245 250 255

Trp Gly Gln Gly Thr Ser Val Thr Val Ser Ser Val Glu Pro Lys Ser
260 265 270

Ser Asp Lys Thr His Thr Cys Pro Pro Cys Pro Ala Pro Glu Leu Leu
275 280 285

Gly Gly Pro Ser Val Phe Leu Phe Pro Pro Lys Pro Lys Asp Thr Leu
290 295 300

Met Ile Ser Arg Thr Pro Glu Val Thr Cys Val Val Val Asp Val Ser
305 310 315 320

His Glu Asp Pro Glu Val Lys Phe Asn Trp Tyr Val Asp Gly Val Glu
325 330 335

Val His Asn Ala Lys Thr Lys Pro Arg Glu Glu Gln Tyr Asn Ser Thr
340 345 350

Tyr Arg Val Val Ser Val Leu Thr Val Leu His Gln Asp Trp Leu Asn
355 360 365

Gly Lys Glu Tyr Lys Cys Lys Val Ser Asn Lys Ala Leu Pro Ala Pro
370 375 380

Ile Glu Lys Thr Ile Ser Lys Ala Lys Gly Gln Pro Arg Glu Pro Gln 385 390 395 400

Val Tyr Thr Leu Pro Pro Ser Arg Asp Glu Leu Thr Lys Asn Gln Val
405 410 415

Ser Leu Thr Cys Leu Val Lys Gly Phe Tyr Pro Ser Asp Ile Ala Val
420 425 430

Glu Trp Glu Ser Asn Gly Gln Pro Glu Asn Asn Tyr Lys Thr Thr Pro
435 440 445

Pro Val Leu Asp Ser Asp Gly Ser Phe Phe Leu Tyr Ser Lys Leu Thr
450 455 460

Val Asp Lys Ser Arg Trp Gln Gln Gly Asn Val Phe Ser Cys Ser Val
465 470 475 480

Met His Glu Ala Leu His Asn His Tyr Thr Gln Lys Ser Leu Ser Leu
485 490 495

Ser Pro Gly Lys Met Ala Leu Ile Val Leu Gly Gly Val Ala Gly Leu
500 505 510

Leu Leu Phe Ile Gly Leu Gly Ile Phe Phe Arg Val Lys Phe Ser Arg
515 520 525

Ser Ala Asp Ala Pro Ala Tyr Gln Gln Gly Gln Asn Gln Leu Tyr Asn
530 535 540

Glu Leu Asn Leu Gly Arg Arg Glu Glu Tyr Asp Val Leu Asp Lys Arg
545 550 555 560

Arg Gly Arg Asp Pro Glu Met Gly Gly Lys Pro Arg Arg Lys Asn Pro
565 570 575

Gln Glu Gly Leu Tyr Asn Glu Leu Gln Lys Asp Lys Met Ala Glu Ala
580 585 590

Tyr Ser Glu Ile Gly Met Lys Gly Glu Arg Arg Arg Gly Lys Gly His
595 600 605

Asp Gly Leu Tyr Gln Gly Leu Ser Thr Ala Thr Lys Asp Thr Tyr Asp
610 615 620

Ala Leu His Met Gln Ala Leu Pro Pro Arg
625 630

<210> SEQ ID NO 35
<211> LENGTH: 120
<212> TYPE: PRT
<213> ORGANISM: Homo sapiens
<220> FEATURE:
<221> NAME/KEY: MISC_FEATURE
<223> OTHER INFORMATION: anti-CD19 scFv HCV

<400> SEQUENCE: 35

Glu Val Gln Leu Val Glu Ser Gly Gly Gly Leu Val Gln Pro Gly Gly
1 5 10 15

Ser Leu Arg Leu Ser Cys Ala Ala Ser Gly Val Ser Leu Pro Asp Tyr
20 25 30

Gly Val Ser Trp Val Arg Gln Ala Pro Gly Lys Gly Leu Glu Trp Val
35 40 45

Ser Val Ile Trp Gly Ser Glu Thr Thr Tyr Tyr Asn Ser Ala Leu Lys
50 55 60

Ser Arg Phe Thr Ile Ser Arg Asp Asn Ala Lys Asn Ser Leu Tyr Leu
65 70 75 80

Gln Met Asn Ser Leu Arg Ala Glu Asp Thr Ala Val Tyr Tyr Cys Ala
85 90 95

Lys His Tyr Tyr Tyr Gly Gly Ser Tyr Ala Met Asp Tyr Trp Gly Gln
100 105 110

```
Gly Thr Leu Val Thr Val Ser Ser
        115                 120


<210> SEQ ID NO 36
<211> LENGTH: 107
<212> TYPE: PRT
<213> ORGANISM: Homo sapiens
<220> FEATURE:
<221> NAME/KEY: MISC_FEATURE
<223> OTHER INFORMATION: anti-CD19 scFv HCV

<400> SEQUENCE: 36

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Lys Tyr
            20                  25                  30

Leu Asn Trp Tyr Gln Gln Lys Pro Gly Lys Ala Pro Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Asn Thr Leu Pro Tyr
                85                  90                  95

Thr Phe Gly Gln Gly Thr Lys Val Glu Ile Lys
            100                 105


<210> SEQ ID NO 37
<211> LENGTH: 11
<212> TYPE: PRT
<213> ORGANISM: Homo sapiens
<220> FEATURE:
<221> NAME/KEY: MISC_FEATURE
<223> OTHER INFORMATION: LC CDR1

<400> SEQUENCE: 37

Arg Ala Ser Gln Asp Ile Ser Lys Tyr Leu Asn
1               5                   10


<210> SEQ ID NO 38
<211> LENGTH: 7
<212> TYPE: PRT
<213> ORGANISM: Homo sapiens
<220> FEATURE:
<221> NAME/KEY: MISC_FEATURE
<223> OTHER INFORMATION: LC CDR2

<400> SEQUENCE: 38

His Thr Ser Arg Leu His Ser
1               5


<210> SEQ ID NO 39
<211> LENGTH: 9
<212> TYPE: PRT
<213> ORGANISM: Homo sapiens
<220> FEATURE:
<221> NAME/KEY: MISC_FEATURE
<223> OTHER INFORMATION: LC CDR3

<400> SEQUENCE: 39

Gln Gln Gly Asn Thr Leu Pro Tyr Thr
1               5


<210> SEQ ID NO 40
```

<211> LENGTH: 10
<212> TYPE: PRT
<213> ORGANISM: Homo sapiens
<220> FEATURE:
<221> NAME/KEY: MISC_FEATURE
<223> OTHER INFORMATION: HC CDR1

<400> SEQUENCE: 40

Gly Val Ser Leu Pro Asp Tyr Gly Val Ser
1 5 10

<210> SEQ ID NO 41
<211> LENGTH: 16
<212> TYPE: PRT
<213> ORGANISM: Homo sapiens
<220> FEATURE:
<221> NAME/KEY: MISC_FEATURE
<223> OTHER INFORMATION: HC CDR2

<400> SEQUENCE: 41

Val Ile Trp Gly Ser Glu Thr Thr Tyr Tyr Ser Ser Ser Leu Lys Ser
1 5 10 15

<210> SEQ ID NO 42
<211> LENGTH: 16
<212> TYPE: PRT
<213> ORGANISM: Homo sapiens
<220> FEATURE:
<221> NAME/KEY: MISC_FEATURE
<223> OTHER INFORMATION: HC CDR2 - alternative

<400> SEQUENCE: 42

Val Ile Trp Gly Ser Glu Thr Thr Tyr Tyr Gln Ser Ser Leu Lys Ser
1 5 10 15

<210> SEQ ID NO 43
<211> LENGTH: 16
<212> TYPE: PRT
<213> ORGANISM: Homo sapiens
<220> FEATURE:
<221> NAME/KEY: MISC_FEATURE
<223> OTHER INFORMATION: HC CDR2 - alternative 2

<400> SEQUENCE: 43

Val Ile Trp Gly Ser Glu Thr Thr Tyr Tyr Asn Ser Ser Leu Lys Ser
1 5 10 15

<210> SEQ ID NO 44
<211> LENGTH: 12
<212> TYPE: PRT
<213> ORGANISM: Homo sapiens
<220> FEATURE:
<221> NAME/KEY: MISC_FEATURE
<223> OTHER INFORMATION: HC CDR3

<400> SEQUENCE: 44

His Tyr Tyr Tyr Gly Gly Ser Tyr Ala Met Asp Tyr
1 5 10

<210> SEQ ID NO 45
<211> LENGTH: 107
<212> TYPE: PRT
<213> ORGANISM: Homo sapiens
<220> FEATURE:
<221> NAME/KEY: MISC_FEATURE
<223> OTHER INFORMATION: Light chain variable region 1

<400> SEQUENCE: 45

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Lys Tyr
            20                  25                  30

Leu Asn Trp Tyr Gln Gln Lys Pro Asp Gln Ala Pro Lys Leu Leu Ile
        35                  40                  45

Lys His Thr Ser Arg Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Gly Asn Thr Leu Pro Tyr
                85                  90                  95

Thr Phe Gly Gln Gly Thr Lys Leu Glu Ile Lys
            100                 105


<210> SEQ ID NO 46
<211> LENGTH: 107
<212> TYPE: PRT
<213> ORGANISM: Homo sapiens
<220> FEATURE:
<221> NAME/KEY: MISC_FEATURE
<223> OTHER INFORMATION: Light chain variable region 2

<400> SEQUENCE: 46

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Lys Tyr
            20                  25                  30

Leu Asn Trp Tyr Gln Gln Lys Pro Gly Lys Ala Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Lys
            100                 105


<210> SEQ ID NO 47
<211> LENGTH: 107
<212> TYPE: PRT
<213> ORGANISM: Homo sapiens
<220> FEATURE:
<221> NAME/KEY: MISC_FEATURE
<223> OTHER INFORMATION: Light chain variable region 3

<400> SEQUENCE: 47

Asp Ile Gln Met Thr Gln Ser Pro Ser Phe Leu Ser Ala Ser Val Gly
1               5                   10                  15

Asp Arg Val Thr Ile Thr Cys Arg Ala Ser Gln Asp Ile Ser Lys Tyr
            20                  25                  30

Leu Asn Trp Tyr Gln Gln Lys Pro Asp Gln Ala Pro Lys Leu Leu Ile
        35                  40                  45

Lys His Thr Ser Arg Leu His Ser Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80
```

Glu Asp Ile Ala Thr Tyr Tyr Cys Gln Gln Gly Asn Thr Leu Pro Tyr
85 90 95

Thr Phe Gly Gln Gly Thr Lys Leu Glu Ile Lys
100 105

<210> SEQ ID NO 48
<211> LENGTH: 107
<212> TYPE: PRT
<213> ORGANISM: Homo sapiens
<220> FEATURE:
<221> NAME/KEY: MISC_FEATURE
<223> OTHER INFORMATION: Light chain variable region 4

<400> SEQUENCE: 48

Asp Ile Gln Met Thr Gln Ser Pro Ser Thr Leu Ser Ala Ser Val Gly
1 5 10 15

Asp Arg Val Thr Ile Thr Cys Arg Ala Ser Gln Asp Ile Ser Lys Tyr
20 25 30

Leu Asn Trp Tyr Gln Gln Lys Pro Asp Gln Ala Pro Lys Leu Leu Ile
35 40 45

Lys His Thr Ser Arg Leu His Ser Gly Val Pro Ser Arg Phe Ser Gly
50 55 60

Ser Gly Ser Gly Thr Asp Phe Thr Phe Thr Ile Ser Ser Leu Gln Pro
65 70 75 80

Glu Asp Ile Ala Thr Tyr Tyr Cys Gln Gln Gly Asn Thr Leu Pro Tyr
85 90 95

Thr Phe Gly Gln Gly Thr Lys Leu Glu Ile Lys
100 105

<210> SEQ ID NO 49
<211> LENGTH: 120
<212> TYPE: PRT
<213> ORGANISM: Homo sapiens
<220> FEATURE:
<221> NAME/KEY: MISC_FEATURE
<223> OTHER INFORMATION: Heavy chain variable region 1

<400> SEQUENCE: 49

Glu Val Gln Leu Val Glu Ser Gly Gly Gly Leu Val Gln Pro Gly Arg
1 5 10 15

Ser Leu Arg Leu Ser Cys Thr Ala Ser Gly Val Ser Leu Pro Asp Tyr
20 25 30

Gly Val Ser Trp Ile Arg Gln Pro Pro Gly Lys Gly Leu Glu Trp Ile
35 40 45

Gly Val Ile Trp Gly Ser Glu Thr Thr Tyr Tyr Asn Ser Ala Leu Lys
50 55 60

Ser Arg Phe Thr Ile Ser Arg Asp Asn Ser Lys Asn Thr Leu Tyr Leu
65 70 75 80

Gln Met Asn Ser Leu Arg Ala Glu Asp Thr Ala Val Tyr Tyr Cys Ala
85 90 95

Lys His Tyr Tyr Tyr Gly Gly Ser Tyr Ala Met Asp Tyr Trp Gly Gln
100 105 110

Gly Thr Leu Val Thr Val Ser Ser
115 120

<210> SEQ ID NO 50
<211> LENGTH: 120
<212> TYPE: PRT
<213> ORGANISM: Homo sapiens
<220> FEATURE:

<221> NAME/KEY: MISC_FEATURE
<223> OTHER INFORMATION: Heavy chain variable region 2

<400> SEQUENCE: 50

Gln Val Gln Leu Gln Glu Ser Gly Pro Gly Leu Val Lys Pro Ser Glu
1 5 10 15

Thr Leu Ser Val Thr Cys Thr Val Ser Gly Val Ser Leu Pro Asp Tyr
20 25 30

Gly Val Ser Trp Ile Arg Gln Pro Pro Gly Lys Gly Leu Glu Trp Leu
35 40 45

Gly Val Ile Trp Gly Ser Glu Thr Thr Tyr Tyr Asn Ser Ala Leu Lys
50 55 60

Ser Arg Leu Thr Ile Ser Lys Asp Thr Ser Lys Asn Gln Val Phe Leu
65 70 75 80

Lys Met Ser Ser Leu Thr Ala Ala Asp Thr Ala Ile Tyr Tyr Cys Ala
85 90 95

Lys His Tyr Tyr Tyr Gly Gly Ser Tyr Ala Met Asp Tyr Trp Gly Gln
100 105 110

Gly Thr Leu Val Thr Val Ser Ser
115 120

<210> SEQ ID NO 51
<211> LENGTH: 120
<212> TYPE: PRT
<213> ORGANISM: Homo sapiens
<220> FEATURE:
<221> NAME/KEY: MISC_FEATURE
<223> OTHER INFORMATION: Heavy chain variable region 3

<400> SEQUENCE: 51

Glu Val Gln Leu Val Glu Ser Gly Gly Gly Leu Val Gln Pro Gly Arg
1 5 10 15

Ser Leu Arg Leu Ser Cys Thr Ala Ser Gly Val Ser Leu Pro Asp Tyr
20 25 30

Gly Val Ser Trp Val Arg Gln Pro Pro Gly Lys Gly Leu Glu Trp Ile
35 40 45

Gly Val Ile Trp Gly Ser Glu Thr Thr Tyr Tyr Asn Ser Ala Leu Lys
50 55 60

Ser Arg Phe Thr Ile Ser Arg Asp Asn Ser Lys Asn Thr Leu Tyr Leu
65 70 75 80

Gln Met Asn Ser Leu Arg Ala Glu Asp Thr Ala Val Tyr Tyr Cys Ala
85 90 95

Lys His Tyr Tyr Tyr Gly Gly Ser Tyr Ala Met Asp Tyr Trp Gly Gln
100 105 110

Gly Thr Leu Val Thr Val Ser Ser
115 120

<210> SEQ ID NO 52
<211> LENGTH: 120
<212> TYPE: PRT
<213> ORGANISM: Homo sapiens
<220> FEATURE:
<221> NAME/KEY: MISC_FEATURE
<223> OTHER INFORMATION: Heavy chain variable region 4

<400> SEQUENCE: 52

Gln Val Gln Leu Gln Glu Ser Gly Pro Gly Leu Val Lys Pro Ser Gly
1 5 10 15

Thr Leu Ser Leu Thr Cys Ala Val Ser Gly Val Ser Leu Pro Asp Tyr

```
            20                  25                  30

Gly Val Ser Trp Ile Arg Gln Pro Pro Gly Lys Gly Leu Glu Trp Ile
        35                  40                  45

Gly Val Ile Trp Gly Ser Glu Thr Thr Tyr Tyr Asn Ser Ala Leu Lys
    50                  55                  60

Ser Arg Val Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Leu Val Thr Val Ser Ser
        115                 120
```

<210> SEQ ID NO 53
<211> LENGTH: 8
<212> TYPE: PRT
<213> ORGANISM: Homo sapiens
<220> FEATURE:
<221> NAME/KEY: MISC_FEATURE
<223> OTHER INFORMATION: LC CDR1

<400> SEQUENCE: 53

```
Arg Ala Ser Gln Asp Ile Ser Lys
1               5
```

<210> SEQ ID NO 54
<211> LENGTH: 7
<212> TYPE: PRT
<213> ORGANISM: Homo sapiens
<220> FEATURE:
<221> NAME/KEY: MISC_FEATURE
<223> OTHER INFORMATION: LC CDR2

<400> SEQUENCE: 54

```
Ile Tyr His Thr Ser Arg Leu
1               5
```

<210> SEQ ID NO 55
<211> LENGTH: 9
<212> TYPE: PRT
<213> ORGANISM: Homo sapiens
<220> FEATURE:
<221> NAME/KEY: MISC_FEATURE
<223> OTHER INFORMATION: LC CDR3

<400> SEQUENCE: 55

```
Gln Gln Gly Asn Thr Leu Pro Tyr Thr
1               5
```

<210> SEQ ID NO 56
<211> LENGTH: 10
<212> TYPE: PRT
<213> ORGANISM: Homo sapiens
<220> FEATURE:
<221> NAME/KEY: MISC_FEATURE
<223> OTHER INFORMATION: HC CDR1

<400> SEQUENCE: 56

```
Gly Val Ser Leu Pro Asp Tyr Gly Val Ser
1               5                   10
```

<210> SEQ ID NO 57
<211> LENGTH: 14

<212> TYPE: PRT
<213> ORGANISM: Homo sapiens
<220> FEATURE:
<221> NAME/KEY: MISC_FEATURE
<223> OTHER INFORMATION: HC CDR2

<400> SEQUENCE: 57

Val Ile Trp Gly Ser Glu Thr Thr Tyr Tyr Asn Ser Ala Leu
1 5 10

<210> SEQ ID NO 58
<211> LENGTH: 12
<212> TYPE: PRT
<213> ORGANISM: Homo sapiens
<220> FEATURE:
<221> NAME/KEY: MISC_FEATURE
<223> OTHER INFORMATION: HC CDR3

<400> SEQUENCE: 58

His Tyr Tyr Tyr Gly Gly Ser Tyr Ala Met Asp Tyr
1 5 10

<210> SEQ ID NO 59
<211> LENGTH: 2210
<212> TYPE: DNA
<213> ORGANISM: Homo sapiens
<220> FEATURE:
<221> NAME/KEY: misc_feature
<223> OTHER INFORMATION: NK19-1b DNA

<400> SEQUENCE: 59
ggatccgaat tcgccgccac catggcctta ccagtgaccg ccttgctcct gccgctggcc 60
ttgctgctcc acgccgccag gccggactac aaagacgatg acgataaagg cggtggtggc 120
tctggtggtg gcggcagcga catccagatg acacagacta catcctccct gtctgcctct 180
ctgggagaca gagtcaccat cagttgcagg gcaagtcagg acattagtaa atatttaaat 240
tggtatcagc agaaaccaga tggaactgtt aaactcctga tctaccatac atcaagatta 300
cactcaggag tcccatcaag gttcagtggc agtgggtctg gaacagatta ttctctcacc 360
attagcaacc tggagcaaga agatattgcc acttactttt gccaacaggg taatacgctt 420
ccgtacacgt tcggaggggg gaccaagctg gagatcacag gtggcggtgg ctcgggcggt 480
ggtgggtcgg gtggcggcgg atctgaggtg aaactgcagg agtcaggacc tggcctggtg 540
gcgccctcac agagcctgtc cgtcacatgc actgtctcag gggtctcatt acccgactat 600
ggtgtaagct ggattcgcca gcctccacga aagggtctgg agtggctggg agtaatatgg 660
ggtagtgaaa ccacatacta taattcagct ctcaaatcca gactgaccat catcaaggac 720
aactccaaga gccaagtttt cttaaaaatg aacagtctgc aaactgatga cacagccatt 780
tactactgtg ccaaacatta ttactacggt ggtagctatg ctatggacta ctggggccaa 840
ggaacctcag tcaccgtctc ctcaaccacg acgccagcgc cgcgaccacc aacaccggcg 900
cccaccatcg cgtcgcagcc cctgtccctg cgcccagagg cgtgccggcc agcggcgggg 960
ggcgcagtgc acacgagggg gctggacttc gcctgtgata tctacatctg ggcgcccttg 1020
gccgggactt gtggggtcct tctcctgtca ctggttatca ccctttactg ccggagggac 1080
cagaggctgc cccccgatgc ccacaagccc cctgggggag gcagtttccg gacccccatc 1140
caagaggagc aggccgacgc ccactccacc ctggccaaga tcagagtgaa gttcagcagg 1200
agcgcagacg cccccgcgta ccagcagggc cagaaccagc tctataacga gctcaatcta 1260
ggacgaagag aggagtacga tgttttggac aagagacgtg gccgggaccc tgagatgggg 1320

-continued

```
ggaaagccga gaaggaagaa ccctcaggaa ggcctgtaca atgaactgca gaaagataag   1380

atggcggagg cctacagtga gattgggatg aaaggcgagc gccggagggg caaggggcac   1440

gatggccttt accagggtct cagtacagcc accaaggaca cctacgacgc ccttcacatg   1500

caggccctgc cccctcgcgg ctctggcgag ggaaggggtt ccctgcttac ttgcggcgac   1560

gtcgaagaga atcccggtcc gatggccctc ccagtaactg ccctcctttt gcccctcgca   1620

ctccttcttc atgccgctcg ccccaactgg gtcaacgtga ttagcgattt gaagaaaatc   1680

gaggacctta tacagtctat gcatattgac gctacactgt atactgagag tgatgtacac   1740

ccgtcctgta aggtaacggc catgaaatgc tttcttctgg agctccaggt catcagcttg   1800

gagtctgggg acgcaagcat ccacgatacg gttgaaaacc tcatcatcct tgcgaacaac   1860

tctctctcat ctaatggaaa cgttacagag agtgggtgta aggagtgcga agagttggaa   1920

gaaaaaaaca tcaaagaatt tcttcaatcc ttcgttcaca tagtgcaaat gttcattaac   1980

acgtccacta ccacacccgc cccgaggcca cctacgccgg caccgactat cgccagtcaa   2040

cccctctctc tgcgccccga ggcttgccgg cctgcggctg gtggggcggt ccacacccgg   2100

ggcctggatt ttgcgtgcga tatatacatc tgggcacctc ttgccggcac ctgcggagtg   2160

ctgcttctct cactcgttat tacgctgtac tgctaagcgg ccgcgtcgac              2210
```

<210> SEQ ID NO 60
<211> LENGTH: 724
<212> TYPE: PRT
<213> ORGANISM: Homo sapiens
<220> FEATURE:
<221> NAME/KEY: MISC_FEATURE
<223> OTHER INFORMATION: NK19-1b Protein

<400> SEQUENCE: 60

```
Met Ala Leu Pro Val Thr Ala Leu Leu Leu Pro Leu Ala Leu Leu Leu
1               5                   10                  15

His Ala Ala Arg Pro Asp Tyr Lys Asp Asp Asp Asp Lys Gly Gly Gly
            20                  25                  30

Gly Ser Gly Gly Gly Gly Ser Asp Ile Gln Met Thr Gln Thr Thr Ser
        35                  40                  45

Ser Leu Ser Ala Ser Leu Gly Asp Arg Val Thr Ile Ser Cys Arg Ala
    50                  55                  60

Ser Gln Asp Ile Ser Lys Tyr Leu Asn Trp Tyr Gln Gln Lys Pro Asp
65                  70                  75                  80

Gly Thr Val Lys Leu Leu Ile Tyr His Thr Ser Arg Leu His Ser Gly
                85                  90                  95

Val Pro Ser Arg Phe Ser Gly Ser Gly Ser Gly Thr Asp Tyr Ser Leu
            100                 105                 110

Thr Ile Ser Asn Leu Glu Gln Glu Asp Ile Ala Thr Tyr Phe Cys Gln
        115                 120                 125

Gln Gly Asn Thr Leu Pro Tyr Thr Phe Gly Gly Gly Thr Lys Leu Glu
    130                 135                 140

Ile Thr Gly Gly Gly Gly Ser Gly Gly Gly Gly Ser Gly Gly Gly Gly
145                 150                 155                 160

Ser Glu Val Lys Leu Gln Glu Ser Gly Pro Gly Leu Val Ala Pro Ser
                165                 170                 175

Gln Ser Leu Ser Val Thr Cys Thr Val Ser Gly Val Ser Leu Pro Asp
            180                 185                 190

Tyr Gly Val Ser Trp Ile Arg Gln Pro Pro Arg Lys Gly Leu Glu Trp
```

```
        195                 200                 205

Leu Gly Val Ile Trp Gly Ser Glu Thr Thr Tyr Tyr Asn Ser Ala Leu
    210                 215                 220

Lys Ser Arg Leu Thr Ile Ile Lys Asp Asn Ser Lys Ser Gln Val Phe
225                 230                 235                 240

Leu Lys Met Asn Ser Leu Gln Thr Asp Asp Thr Ala Ile Tyr Tyr Cys
                245                 250                 255

Ala Lys His Tyr Tyr Tyr Gly Gly Ser Tyr Ala Met Asp Tyr Trp Gly
            260                 265                 270

Gln Gly Thr Ser Val Thr Val Ser Ser Thr Thr Thr Pro Ala Pro Arg
        275                 280                 285

Pro Pro Thr Pro Ala Pro Thr Ile Ala Ser Gln Pro Leu Ser Leu Arg
    290                 295                 300

Pro Glu Ala Cys Arg Pro Ala Ala Gly Gly Ala Val His Thr Arg Gly
305                 310                 315                 320

Leu Asp Phe Ala Cys Asp Ile Tyr Ile Trp Ala Pro Leu Ala Gly Thr
                325                 330                 335

Cys Gly Val Leu Leu Leu Ser Leu Val Ile Thr Leu Tyr Cys Arg Arg
            340                 345                 350

Asp Gln Arg Leu Pro Pro Asp Ala His Lys Pro Pro Gly Gly Gly Ser
        355                 360                 365

Phe Arg Thr Pro Ile Gln Glu Glu Gln Ala Asp Ala His Ser Thr Leu
    370                 375                 380

Ala Lys Ile Arg Val Lys Phe Ser Arg Ser Ala Asp Ala Pro Ala Tyr
385                 390                 395                 400

Gln Gln Gly Gln Asn Gln Leu Tyr Asn Glu Leu Asn Leu Gly Arg Arg
                405                 410                 415

Glu Glu Tyr Asp Val Leu Asp Lys Arg Arg Gly Arg Asp Pro Glu Met
            420                 425                 430

Gly Gly Lys Pro Arg Arg Lys Asn Pro Gln Glu Gly Leu Tyr Asn Glu
        435                 440                 445

Leu Gln Lys Asp Lys Met Ala Glu Ala Tyr Ser Glu Ile Gly Met Lys
    450                 455                 460

Gly Glu Arg Arg Arg Gly Lys Gly His Asp Gly Leu Tyr Gln Gly Leu
465                 470                 475                 480

Ser Thr Ala Thr Lys Asp Thr Tyr Asp Ala Leu His Met Gln Ala Leu
                485                 490                 495

Pro Pro Arg Gly Ser Gly Glu Gly Arg Gly Ser Leu Leu Thr Cys Gly
            500                 505                 510

Asp Val Glu Glu Asn Pro Gly Pro Met Ala Leu Pro Val Thr Ala Leu
        515                 520                 525

Leu Leu Pro Leu Ala Leu Leu Leu His Ala Ala Arg Pro Asn Trp Val
    530                 535                 540

Asn Val Ile Ser Asp Leu Lys Lys Ile Glu Asp Leu Ile Gln Ser Met
545                 550                 555                 560

His Ile Asp Ala Thr Leu Tyr Thr Glu Ser Asp Val His Pro Ser Cys
                565                 570                 575

Lys Val Thr Ala Met Lys Cys Phe Leu Leu Glu Leu Gln Val Ile Ser
            580                 585                 590

Leu Glu Ser Gly Asp Ala Ser Ile His Asp Thr Val Glu Asn Leu Ile
        595                 600                 605

Ile Leu Ala Asn Asn Ser Leu Ser Ser Asn Gly Asn Val Thr Glu Ser
    610                 615                 620
```

```
Gly Cys Lys Glu Cys Glu Glu Leu Glu Glu Lys Asn Ile Lys Glu Phe
625                 630                 635                 640

Leu Gln Ser Phe Val His Ile Val Gln Met Phe Ile Asn Thr Ser Thr
                645                 650                 655

Thr Thr Pro Ala Pro Arg Pro Pro Thr Pro Ala Pro Thr Ile Ala Ser
            660                 665                 670

Gln Pro Leu Ser Leu Arg Pro Glu Ala Cys Arg Pro Ala Ala Gly Gly
        675                 680                 685

Ala Val His Thr Arg Gly Leu Asp Phe Ala Cys Asp Ile Tyr Ile Trp
    690                 695                 700

Ala Pro Leu Ala Gly Thr Cys Gly Val Leu Leu Leu Ser Leu Val Ile
705                 710                 715                 720

Thr Leu Tyr Cys


<210> SEQ ID NO 61
<211> LENGTH: 2231
<212> TYPE: DNA
<213> ORGANISM: Homo sapiens
<220> FEATURE:
<221> NAME/KEY: misc_feature
<223> OTHER INFORMATION: NK19-2b DNA

<400> SEQUENCE: 61

ggatccgaat tcgccgccac catggcctta ccagtgaccg ccttgctcct gccgctggcc      60

ttgctgctcc acgccgccag gccggactac aaagacgatg acgataaagg cggtggtggc     120

tctggtggtg gcggcagcga catccagatg acacagacta catcctccct gtctgcctct     180

ctgggagaca gagtcaccat cagttgcagg gcaagtcagg acattagtaa atatttaaat     240

tggtatcagc agaaaccaga tggaactgtt aaactcctga tctaccatac atcaagatta     300

cactcaggag tcccatcaag gttcagtggc agtgggtctg gaacagatta ttctctcacc     360

attagcaacc tggagcaaga agatattgcc acttactttt gccaacaggg taatacgctt     420

ccgtacacgt tcggaggggg gaccaagctg gagatcacag gtggcggtgg ctcgggcggt     480

ggtgggtcgg gtggcggcgg atctgaggtg aaactgcagg agtcaggacc tggcctggtg     540

gcgccctcac agagcctgtc cgtcacatgc actgtctcag gggtctcatt acccgactat     600

ggtgtaagct ggattcgcca gcctccacga aagggtctgg agtggctggg agtaatatgg     660

ggtagtgaaa ccacatacta taattcagct ctcaaatcca gactgaccat catcaaggac     720

aactccaaga gccaagtttt cttaaaaatg aacagtctgc aaactgatga cacagccatt     780

tactactgtg ccaaacatta ttactacggt ggtagctatg ctatggacta ctggggccaa     840

ggaacctcag tcaccgtctc ctcaaccacg acgccagcgc cgcgaccacc aacaccggcg     900

cccaccatcg cgtcgcagcc cctgtccctg cgcccagagg cgtgccggcc agcggcgggg     960

ggcgcagtgc acacgagggg gctggacttc gcctgtgatt tttgggtgct ggtggtggtt    1020

ggtggagtcc tggcttgcta tagcttgcta gtaacagtgg cctttattat tttctgggtg    1080

aggagtaaga ggagcaggct cctgcacagt gactacatga acatgactcc ccgccgcccc    1140

gggcccaccc gcaagcatta ccagccctat gccccaccac gcgacttcgc agcctatcgc    1200

tccagagtga agttcagcag gagcgcagac gcccccgcgt accagcaggg ccagaaccag    1260

ctctataacg agctcaatct aggacgaaga gaggagtacg atgttttgga caagagacgt    1320

ggccgggacc ctgagatggg gggaaagccg agaaggaaga accctcagga aggcctgtac    1380

aatgaactgc agaaagataa gatggcggag gcctacagtg agattgggat gaaaggcgag    1440
```

```
cgccggaggg gcaaggggca cgatggcctt taccagggtc tcagtacagc caccaaggac   1500

acctacgacg cccttcacat gcaggccctg ccccctcgcg gctctggcga gggaaggggt   1560

tccctgctta cttgcggcga cgtcgaagag aatcccggtc cgatggccct cccagtaact   1620

gccctccttt tgcccctcgc actccttctt catgccgctc gccccaactg ggtcaacgtg   1680

attagcgatt tgaagaaaat cgaggacctt atacagtcta tgcatattga cgctacactg   1740

tatactgaga gtgatgtaca cccgtcctgt aaggtaacgg ccatgaaatg ctttcttctg   1800

gagctccagg tcatcagctt ggagtctggg gacgcaagca tccacgatac ggttgaaaac   1860

ctcatcatcc ttgcgaacaa ctctctctca tctaatggaa acgttacaga gagtgggtgt   1920

aaggagtgcg aagagttgga agaaaaaaac atcaaagaat ttcttcaatc cttcgttcac   1980

atagtgcaaa tgttcattaa cacgtccact accacacccg ccccgaggcc acctacgccg   2040

gcaccgacta tcgccagtca acccctctct ctgcgccccg aggcttgccg gcctgcggct   2100

ggtggggcgg tccacacccg gggcctggat tttgcgtgcg atatatacat ctgggcacct   2160

cttgccggca cctgcggagt gctgcttctc tcactcgtta ttacgctgta ctgctaagcg   2220

gccgcgtcga c                                                         2231


<210> SEQ ID NO 62
<211> LENGTH: 731
<212> TYPE: PRT
<213> ORGANISM: Homo sapiens
<220> FEATURE:
<221> NAME/KEY: MISC_FEATURE
<223> OTHER INFORMATION: NK19-2b Protein

<400> SEQUENCE: 62

Met Ala Leu Pro Val Thr Ala Leu Leu Leu Pro Leu Ala Leu Leu Leu
1               5                   10                  15

His Ala Ala Arg Pro Asp Tyr Lys Asp Asp Asp Asp Lys Gly Gly Gly
            20                  25                  30

Gly Ser Gly Gly Gly Gly Ser Asp Ile Gln Met Thr Gln Thr Thr Ser
        35                  40                  45

Ser Leu Ser Ala Ser Leu Gly Asp Arg Val Thr Ile Ser Cys Arg Ala
    50                  55                  60

Ser Gln Asp Ile Ser Lys Tyr Leu Asn Trp Tyr Gln Gln Lys Pro Asp
65                  70                  75                  80

Gly Thr Val Lys Leu Leu Ile Tyr His Thr Ser Arg Leu His Ser Gly
                85                  90                  95

Val Pro Ser Arg Phe Ser Gly Ser Gly Ser Gly Thr Asp Tyr Ser Leu
            100                 105                 110

Thr Ile Ser Asn Leu Glu Gln Glu Asp Ile Ala Thr Tyr Phe Cys Gln
        115                 120                 125

Gln Gly Asn Thr Leu Pro Tyr Thr Phe Gly Gly Gly Thr Lys Leu Glu
    130                 135                 140

Ile Thr Gly Gly Gly Gly Ser Gly Gly Gly Gly Ser Gly Gly Gly Gly
145                 150                 155                 160

Ser Glu Val Lys Leu Gln Glu Ser Gly Pro Gly Leu Val Ala Pro Ser
                165                 170                 175

Gln Ser Leu Ser Val Thr Cys Thr Val Ser Gly Val Ser Leu Pro Asp
            180                 185                 190

Tyr Gly Val Ser Trp Ile Arg Gln Pro Pro Arg Lys Gly Leu Glu Trp
        195                 200                 205
```

-continued

```
Leu Gly Val Ile Trp Gly Ser Glu Thr Thr Tyr Tyr Asn Ser Ala Leu
    210                 215                 220

Lys Ser Arg Leu Thr Ile Ile Lys Asp Asn Ser Lys Ser Gln Val Phe
225                 230                 235                 240

Leu Lys Met Asn Ser Leu Gln Thr Asp Asp Thr Ala Ile Tyr Tyr Cys
                245                 250                 255

Ala Lys His Tyr Tyr Tyr Gly Gly Ser Tyr Ala Met Asp Tyr Trp Gly
            260                 265                 270

Gln Gly Thr Ser Val Thr Val Ser Ser Thr Thr Thr Pro Ala Pro Arg
        275                 280                 285

Pro Pro Thr Pro Ala Pro Thr Ile Ala Ser Gln Pro Leu Ser Leu Arg
    290                 295                 300

Pro Glu Ala Cys Arg Pro Ala Ala Gly Gly Ala Val His Thr Arg Gly
305                 310                 315                 320

Leu Asp Phe Ala Cys Asp Phe Trp Val Leu Val Val Val Gly Gly Val
                325                 330                 335

Leu Ala Cys Tyr Ser Leu Leu Val Thr Val Ala Phe Ile Ile Phe Trp
            340                 345                 350

Val Arg Ser Lys Arg Ser Arg Leu Leu His Ser Asp Tyr Met Asn Met
        355                 360                 365

Thr Pro Arg Arg Pro Gly Pro Thr Arg Lys His Tyr Gln Pro Tyr Ala
    370                 375                 380

Pro Pro Arg Asp Phe Ala Ala Tyr Arg Ser Arg Val Lys Phe Ser Arg
385                 390                 395                 400

Ser Ala Asp Ala Pro Ala Tyr Gln Gln Gly Gln Asn Gln Leu Tyr Asn
                405                 410                 415

Glu Leu Asn Leu Gly Arg Arg Glu Glu Tyr Asp Val Leu Asp Lys Arg
            420                 425                 430

Arg Gly Arg Asp Pro Glu Met Gly Gly Lys Pro Arg Arg Lys Asn Pro
        435                 440                 445

Gln Glu Gly Leu Tyr Asn Glu Leu Gln Lys Asp Lys Met Ala Glu Ala
    450                 455                 460

Tyr Ser Glu Ile Gly Met Lys Gly Glu Arg Arg Arg Gly Lys Gly His
465                 470                 475                 480

Asp Gly Leu Tyr Gln Gly Leu Ser Thr Ala Thr Lys Asp Thr Tyr Asp
                485                 490                 495

Ala Leu His Met Gln Ala Leu Pro Pro Arg Gly Ser Gly Glu Gly Arg
            500                 505                 510

Gly Ser Leu Leu Thr Cys Gly Asp Val Glu Glu Asn Pro Gly Pro Met
        515                 520                 525

Ala Leu Pro Val Thr Ala Leu Leu Leu Pro Leu Ala Leu Leu Leu His
    530                 535                 540

Ala Ala Arg Pro Asn Trp Val Asn Val Ile Ser Asp Leu Lys Lys Ile
545                 550                 555                 560

Glu Asp Leu Ile Gln Ser Met His Ile Asp Ala Thr Leu Tyr Thr Glu
                565                 570                 575

Ser Asp Val His Pro Ser Cys Lys Val Thr Ala Met Lys Cys Phe Leu
            580                 585                 590

Leu Glu Leu Gln Val Ile Ser Leu Glu Ser Gly Asp Ala Ser Ile His
        595                 600                 605

Asp Thr Val Glu Asn Leu Ile Ile Leu Ala Asn Asn Ser Leu Ser Ser
    610                 615                 620

Asn Gly Asn Val Thr Glu Ser Gly Cys Lys Glu Cys Glu Glu Leu Glu
```

-continued 625 630 635 640

Glu Lys Asn Ile Lys Glu Phe Leu Gln Ser Phe Val His Ile Val Gln
645 650 655

Met Phe Ile Asn Thr Ser Thr Thr Thr Pro Ala Pro Arg Pro Pro Thr
660 665 670

Pro Ala Pro Thr Ile Ala Ser Gln Pro Leu Ser Leu Arg Pro Glu Ala
675 680 685

Cys Arg Pro Ala Ala Gly Gly Ala Val His Thr Arg Gly Leu Asp Phe
690 695 700

Ala Cys Asp Ile Tyr Ile Trp Ala Pro Leu Ala Gly Thr Cys Gly Val
705 710 715 720

Leu Leu Leu Ser Leu Val Ile Thr Leu Tyr Cys
725 730

<210> SEQ ID NO 63
<211> LENGTH: 2213
<212> TYPE: DNA
<213> ORGANISM: Homo sapiens
<220> FEATURE:
<221> NAME/KEY: misc_feature
<223> OTHER INFORMATION: NK19-3b DNA

<400> SEQUENCE: 63
ggatccgaat tcgccgccac catggcctta ccagtgaccg ccttgctcct gccgctggcc 60
ttgctgctcc acgccgccag gccggactac aaagacgatg acgataaagg cggtggtggc 120
tctggtggtg gcggcagcga catccagatg acacagacta catcctccct gtctgcctct 180
ctgggagaca gagtcaccat cagttgcagg gcaagtcagg acattagtaa atatttaaat 240
tggtatcagc agaaaccaga tggaactgtt aaactcctga tctaccatac atcaagatta 300
cactcaggag tcccatcaag gttcagtggc agtgggtctg gaacagatta ttctctcacc 360
attagcaacc tggagcaaga agatattgcc acttactttt gccaacaggg taatacgctt 420
ccgtacacgt tcggaggggg gaccaagctg gagatcacag gtggcggtgg ctcgggcggt 480
ggtgggtcgg gtggcggcgg atctgaggtg aaactgcagg agtcaggacc tggcctggtg 540
gcgccctcac agagcctgtc cgtcacatgc actgtctcag gggtctcatt acccgactat 600
ggtgtaagct ggattcgcca gcctccacga aagggtctgg agtggctggg agtaatatgg 660
ggtagtgaaa ccacatacta taattcagct ctcaaatcca gactgaccat catcaaggac 720
aactccaaga gccaagtttt cttaaaaatg aacagtctgc aaactgatga cacagccatt 780
tactactgtg ccaaacatta ttactacggt ggtagctatg ctatggacta ctggggccaa 840
ggaacctcag tcaccgtctc ctcaaccacg acgccagcgc cgcgaccacc aacaccggcg 900
cccaccatcg cgtcgcagcc cctgtccctg cgcccagagg cgtgccggcc agcggcgggg 960
ggcgcagtgc acacgagggg gctggacttc gcctgtgata tctacatctg ggcgcccttg 1020
gccgggactt gtggggtcct tctcctgtca ctggttatca ccctttactg ctgttggctt 1080
acaaaaaaga agtattcatc cagtgtgcac gaccctaacg gtgaatacat gttcatgaga 1140
gcagtgaaca cagccaaaaa atctagactc acagatgtga ccctaagagt gaagttcagc 1200
aggagcgcag acgcccccgc gtaccagcag ggccagaacc agctctataa cgagctcaat 1260
ctaggacgaa gagaggagta cgatgttttg gacaagagac gtggccggga ccctgagatg 1320
gggggaaagc cgagaaggaa gaaccctcag gaaggcctgt acaatgaact gcagaaagat 1380
aagatggcgg aggcctacag tgagattggg atgaaaggcg agcgccggag gggcaagggg 1440
cacgatggcc tttaccaggg tctcagtaca gccaccaagg acacctacga cgcccttcac 1500
atgcaggccc tgccccctcg cggctctggc gagggaaggg gttccctgct tacttgcggc 1560
gacgtcgaag agaatcccgg tccgatggcc ctcccagtaa ctgccctcct tttgcccctc 1620
gcactccttc ttcatgccgc tcgccccaac tgggtcaacg tgattagcga tttgaagaaa 1680
atcgaggacc ttatacagtc tatgcatatt gacgctacac tgtatactga gagtgatgta 1740
cacccgtcct gtaaggtaac ggccatgaaa tgctttcttc tggagctcca ggtcatcagc 1800
ttggagtctg gggacgcaag catccacgat acggttgaaa acctcatcat ccttgcgaac 1860
aactctctct catctaatgg aaacgttaca gagagtgggt gtaaggagtg cgaagagttg 1920
gaagaaaaaa acatcaaaga atttcttcaa tccttcgttc acatagtgca aatgttcatt 1980
aacacgtcca ctaccacacc cgccccgagg ccacctacgc cggcaccgac tatcgccagt 2040
caacccctct ctctgcgccc cgaggcttgc cggcctgcgg ctggtggggc ggtccacacc 2100
cggggcctgg attttgcgtg cgatatatac atctgggcac ctcttgccgg cacctgcgga 2160
gtgctgcttc tctcactcgt tattacgctg tactgctaag cggccgcgtc gac 2213

<210> SEQ ID NO 64
<211> LENGTH: 725
<212> TYPE: PRT
<213> ORGANISM: Homo sapiens
<220> FEATURE:
<221> NAME/KEY: MISC_FEATURE
<223> OTHER INFORMATION: NK19-3b Protein

<400> SEQUENCE: 64

Met Ala Leu Pro Val Thr Ala Leu Leu Leu Pro Leu Ala Leu Leu Leu
1 5 10 15

His Ala Ala Arg Pro Asp Tyr Lys Asp Asp Asp Asp Lys Gly Gly Gly
20 25 30

Gly Ser Gly Gly Gly Gly Ser Asp Ile Gln Met Thr Gln Thr Thr Ser
35 40 45

Ser Leu Ser Ala Ser Leu Gly Asp Arg Val Thr Ile Ser Cys Arg Ala
50 55 60

Ser Gln Asp Ile Ser Lys Tyr Leu Asn Trp Tyr Gln Gln Lys Pro Asp
65 70 75 80

Gly Thr Val Lys Leu Leu Ile Tyr His Thr Ser Arg Leu His Ser Gly
85 90 95

Val Pro Ser Arg Phe Ser Gly Ser Gly Ser Gly Thr Asp Tyr Ser Leu
100 105 110

Thr Ile Ser Asn Leu Glu Gln Glu Asp Ile Ala Thr Tyr Phe Cys Gln
115 120 125

Gln Gly Asn Thr Leu Pro Tyr Thr Phe Gly Gly Gly Thr Lys Leu Glu
130 135 140

Ile Thr Gly Gly Gly Gly Ser Gly Gly Gly Gly Ser Gly Gly Gly Gly
145 150 155 160

Ser Glu Val Lys Leu Gln Glu Ser Gly Pro Gly Leu Val Ala Pro Ser
165 170 175

Gln Ser Leu Ser Val Thr Cys Thr Val Ser Gly Val Ser Leu Pro Asp
180 185 190

Tyr Gly Val Ser Trp Ile Arg Gln Pro Pro Arg Lys Gly Leu Glu Trp
195 200 205

Leu Gly Val Ile Trp Gly Ser Glu Thr Thr Tyr Tyr Asn Ser Ala Leu
210 215 220

-continued

```
Lys Ser Arg Leu Thr Ile Ile Lys Asp Asn Ser Lys Ser Gln Val Phe
225                 230                 235                 240

Leu Lys Met Asn Ser Leu Gln Thr Asp Asp Thr Ala Ile Tyr Tyr Cys
                245                 250                 255

Ala Lys His Tyr Tyr Tyr Gly Gly Ser Tyr Ala Met Asp Tyr Trp Gly
            260                 265                 270

Gln Gly Thr Ser Val Thr Val Ser Ser Thr Thr Thr Pro Ala Pro Arg
        275                 280                 285

Pro Pro Thr Pro Ala Pro Thr Ile Ala Ser Gln Pro Leu Ser Leu Arg
    290                 295                 300

Pro Glu Ala Cys Arg Pro Ala Ala Gly Gly Ala Val His Thr Arg Gly
305                 310                 315                 320

Leu Asp Phe Ala Cys Asp Ile Tyr Ile Trp Ala Pro Leu Ala Gly Thr
                325                 330                 335

Cys Gly Val Leu Leu Leu Ser Leu Val Ile Thr Leu Tyr Cys Cys Trp
            340                 345                 350

Leu Thr Lys Lys Lys Tyr Ser Ser Ser Val His Asp Pro Asn Gly Glu
        355                 360                 365

Tyr Met Phe Met Arg Ala Val Asn Thr Ala Lys Lys Ser Arg Leu Thr
    370                 375                 380

Asp Val Thr Leu Arg Val Lys Phe Ser Arg Ser Ala Asp Ala Pro Ala
385                 390                 395                 400

Tyr Gln Gln Gly Gln Asn Gln Leu Tyr Asn Glu Leu Asn Leu Gly Arg
                405                 410                 415

Arg Glu Glu Tyr Asp Val Leu Asp Lys Arg Arg Gly Arg Asp Pro Glu
            420                 425                 430

Met Gly Gly Lys Pro Arg Arg Lys Asn Pro Gln Glu Gly Leu Tyr Asn
        435                 440                 445

Glu Leu Gln Lys Asp Lys Met Ala Glu Ala Tyr Ser Glu Ile Gly Met
    450                 455                 460

Lys Gly Glu Arg Arg Arg Gly Lys Gly His Asp Gly Leu Tyr Gln Gly
465                 470                 475                 480

Leu Ser Thr Ala Thr Lys Asp Thr Tyr Asp Ala Leu His Met Gln Ala
                485                 490                 495

Leu Pro Pro Arg Gly Ser Gly Glu Gly Arg Gly Ser Leu Leu Thr Cys
            500                 505                 510

Gly Asp Val Glu Glu Asn Pro Gly Pro Met Ala Leu Pro Val Thr Ala
        515                 520                 525

Leu Leu Leu Pro Leu Ala Leu Leu Leu His Ala Ala Arg Pro Asn Trp
    530                 535                 540

Val Asn Val Ile Ser Asp Leu Lys Lys Ile Glu Asp Leu Ile Gln Ser
545                 550                 555                 560

Met His Ile Asp Ala Thr Leu Tyr Thr Glu Ser Asp Val His Pro Ser
                565                 570                 575

Cys Lys Val Thr Ala Met Lys Cys Phe Leu Leu Glu Leu Gln Val Ile
            580                 585                 590

Ser Leu Glu Ser Gly Asp Ala Ser Ile His Asp Thr Val Glu Asn Leu
        595                 600                 605

Ile Ile Leu Ala Asn Asn Ser Leu Ser Ser Asn Gly Asn Val Thr Glu
    610                 615                 620

Ser Gly Cys Lys Glu Cys Glu Glu Leu Glu Glu Lys Asn Ile Lys Glu
625                 630                 635                 640

Phe Leu Gln Ser Phe Val His Ile Val Gln Met Phe Ile Asn Thr Ser
```

-continued

```
                645                 650                 655

Thr Thr Thr Pro Ala Pro Arg Pro Pro Thr Pro Ala Pro Thr Ile Ala
            660                 665                 670

Ser Gln Pro Leu Ser Leu Arg Pro Glu Ala Cys Arg Pro Ala Ala Gly
        675                 680                 685

Gly Ala Val His Thr Arg Gly Leu Asp Phe Ala Cys Asp Ile Tyr Ile
    690                 695                 700

Trp Ala Pro Leu Ala Gly Thr Cys Gly Val Leu Leu Leu Ser Leu Val
705                 710                 715                 720

Ile Thr Leu Tyr Cys
                725


<210> SEQ ID NO 65
<211> LENGTH: 2357
<212> TYPE: DNA
<213> ORGANISM: Homo sapiens
<220> FEATURE:
<221> NAME/KEY: misc_feature
<223> OTHER INFORMATION: NK19-4b DNA

<400> SEQUENCE: 65

ggatccgaat tcgccgccac catggcctta ccagtgaccg ccttgctcct gccgctggcc     60

ttgctgctcc acgccgccag gccggactac aaagacgatg acgataaagg cggtggtggc    120

tctggtggtg gcggcagcga catccagatg acacagacta catcctccct gtctgcctct    180

ctgggagaca gagtcaccat cagttgcagg gcaagtcagg acattagtaa atatttaaat    240

tggtatcagc agaaaccaga tggaactgtt aaactcctga tctaccatac atcaagatta    300

cactcaggag tcccatcaag gttcagtggc agtgggtctg gaacagatta ttctctcacc    360

attagcaacc tggagcaaga agatattgcc acttactttt gccaacaggg taatacgctt    420

ccgtacacgt tcggaggggg gaccaagctg gagatcacag gtggcggtgg ctcgggcggt    480

ggtgggtcgg gtggcggcgg atctgaggtg aaactgcagg agtcaggacc tggcctggtg    540

gcgccctcac agagcctgtc cgtcacatgc actgtctcag gggtctcatt acccgactat    600

ggtgtaagct ggattcgcca gcctccacga aagggtctgg agtggctggg agtaatatgg    660

ggtagtgaaa ccacatacta taattcagct ctcaaatcca gactgaccat catcaaggac    720

aactccaaga gccaagtttt cttaaaaatg aacagtctgc aaactgatga cacagccatt    780

tactactgtg ccaaacatta ttactacggt ggtagctatg ctatggacta ctggggccaa    840

ggaacctcag tcaccgtctc ctcaaccacg acgccagcgc cgcgaccacc aacaccggcg    900

cccaccatcg cgtcgcagcc cctgtccctg cgcccagagg cgtgccggcc agcggcgggg    960

ggcgcagtgc acacgagggg gctggacttc gcctgtgatt tttgggtgct ggtggtggtt   1020

ggtggagtcc tggcttgcta tagcttgcta gtaacagtgg cctttattat tttctgggtg   1080

aggagtaaga ggagcaggct cctgcacagt gactacatga acatgactcc ccgccgcccc   1140

gggcccaccc gcaagcatta ccagccctat gccccaccac gcgacttcgc agcctatcgc   1200

tccaaacggg gcagaaagaa actcctgtat atattcaaac aaccatttat gagaccagta   1260

caaactactc aagaggaaga tggctgtagc tgccgatttc cagaagaaga agaaggagga   1320

tgtgaactga gagtgaagtt cagcaggagc gcagacgccc ccgcgtacca gcagggccag   1380

aaccagctct ataacgagct caatctagga cgaagagagg agtacgatgt tttggacaag   1440

agacgtggcc gggaccctga gatgggggga aagccgagaa ggaagaaccc tcaggaaggc   1500

ctgtacaatg aactgcagaa agataagatg gcggaggcct acagtgagat tgggatgaaa   1560
```

-continued

```
ggcgagcgcc ggaggggcaa ggggcacgat ggcctttacc agggtctcag tacagccacc   1620

aaggacacct acgacgccct tcacatgcag gccctgcccc ctcgcggctc tggcgaggga   1680

aggggttccc tgcttacttg cggcgacgtc gaagagaatc ccggtccgat ggccctccca   1740

gtaactgccc tccttttgcc cctcgcactc cttcttcatg ccgctcgccc caactgggtc   1800

aacgtgatta gcgatttgaa gaaaatcgag gaccttatac agtctatgca tattgacgct   1860

acactgtata ctgagagtga tgtacacccg tcctgtaagg taacggccat gaaatgcttt   1920

cttctggagc tccaggtcat cagcttggag tctggggacg caagcatcca cgatacggtt   1980

gaaaacctca tcatccttgc gaacaactct ctctcatcta atggaaacgt tacagagagt   2040

gggtgtaagg agtgcgaaga gttggaagaa aaaaacatca aagaatttct tcaatccttc   2100

gttcacatag tgcaaatgtt cattaacacg tccactacca cacccgcccc gaggccacct   2160

acgccggcac cgactatcgc cagtcaaccc ctctctctgc gccccgaggc ttgccggcct   2220

gcggctggtg gggcggtcca cacccggggc ctggattttg cgtgcgatat atacatctgg   2280

gcacctcttg ccggcacctg cggagtgctg cttctctcac tcgttattac gctgtactgc   2340

taagcggccg cgtcgac                                                  2357
```

<210> SEQ ID NO 66
<211> LENGTH: 773
<212> TYPE: PRT
<213> ORGANISM: Homo sapiens
<220> FEATURE:
<221> NAME/KEY: MISC_FEATURE
<223> OTHER INFORMATION: NK19-4b Protein

<400> SEQUENCE: 66

```
Met Ala Leu Pro Val Thr Ala Leu Leu Leu Pro Leu Ala Leu Leu Leu
1               5                   10                  15

His Ala Ala Arg Pro Asp Tyr Lys Asp Asp Asp Asp Lys Gly Gly Gly
            20                  25                  30

Gly Ser Gly Gly Gly Gly Ser Asp Ile Gln Met Thr Gln Thr Thr Ser
        35                  40                  45

Ser Leu Ser Ala Ser Leu Gly Asp Arg Val Thr Ile Ser Cys Arg Ala
    50                  55                  60

Ser Gln Asp Ile Ser Lys Tyr Leu Asn Trp Tyr Gln Gln Lys Pro Asp
65                  70                  75                  80

Gly Thr Val Lys Leu Leu Ile Tyr His Thr Ser Arg Leu His Ser Gly
                85                  90                  95

Val Pro Ser Arg Phe Ser Gly Ser Gly Ser Gly Thr Asp Tyr Ser Leu
            100                 105                 110

Thr Ile Ser Asn Leu Glu Gln Glu Asp Ile Ala Thr Tyr Phe Cys Gln
        115                 120                 125

Gln Gly Asn Thr Leu Pro Tyr Thr Phe Gly Gly Gly Thr Lys Leu Glu
    130                 135                 140

Ile Thr Gly Gly Gly Gly Ser Gly Gly Gly Gly Ser Gly Gly Gly Gly
145                 150                 155                 160

Ser Glu Val Lys Leu Gln Glu Ser Gly Pro Gly Leu Val Ala Pro Ser
                165                 170                 175

Gln Ser Leu Ser Val Thr Cys Thr Val Ser Gly Val Ser Leu Pro Asp
            180                 185                 190

Tyr Gly Val Ser Trp Ile Arg Gln Pro Pro Arg Lys Gly Leu Glu Trp
        195                 200                 205
```

-continued

```
Leu Gly Val Ile Trp Gly Ser Glu Thr Thr Tyr Tyr Asn Ser Ala Leu
    210                 215                 220

Lys Ser Arg Leu Thr Ile Ile Lys Asp Asn Ser Lys Ser Gln Val Phe
225                 230                 235                 240

Leu Lys Met Asn Ser Leu Gln Thr Asp Asp Thr Ala Ile Tyr Tyr Cys
                245                 250                 255

Ala Lys His Tyr Tyr Tyr Gly Gly Ser Tyr Ala Met Asp Tyr Trp Gly
            260                 265                 270

Gln Gly Thr Ser Val Thr Val Ser Ser Thr Thr Thr Pro Ala Pro Arg
        275                 280                 285

Pro Pro Thr Pro Ala Pro Thr Ile Ala Ser Gln Pro Leu Ser Leu Arg
    290                 295                 300

Pro Glu Ala Cys Arg Pro Ala Ala Gly Gly Ala Val His Thr Arg Gly
305                 310                 315                 320

Leu Asp Phe Ala Cys Asp Phe Trp Val Leu Val Val Val Gly Gly Val
                325                 330                 335

Leu Ala Cys Tyr Ser Leu Leu Val Thr Val Ala Phe Ile Ile Phe Trp
            340                 345                 350

Val Arg Ser Lys Arg Ser Arg Leu Leu His Ser Asp Tyr Met Asn Met
        355                 360                 365

Thr Pro Arg Arg Pro Gly Pro Thr Arg Lys His Tyr Gln Pro Tyr Ala
    370                 375                 380

Pro Pro Arg Asp Phe Ala Ala Tyr Arg Ser Lys Arg Gly Arg Lys Lys
385                 390                 395                 400

Leu Leu Tyr Ile Phe Lys Gln Pro Phe Met Arg Pro Val Gln Thr Thr
                405                 410                 415

Gln Glu Glu Asp Gly Cys Ser Cys Arg Phe Pro Glu Glu Glu Glu Gly
            420                 425                 430

Gly Cys Glu Leu Arg Val Lys Phe Ser Arg Ser Ala Asp Ala Pro Ala
        435                 440                 445

Tyr Gln Gln Gly Gln Asn Gln Leu Tyr Asn Glu Leu Asn Leu Gly Arg
    450                 455                 460

Arg Glu Glu Tyr Asp Val Leu Asp Lys Arg Arg Gly Arg Asp Pro Glu
465                 470                 475                 480

Met Gly Gly Lys Pro Arg Arg Lys Asn Pro Gln Glu Gly Leu Tyr Asn
                485                 490                 495

Glu Leu Gln Lys Asp Lys Met Ala Glu Ala Tyr Ser Glu Ile Gly Met
            500                 505                 510

Lys Gly Glu Arg Arg Arg Gly Lys Gly His Asp Gly Leu Tyr Gln Gly
        515                 520                 525

Leu Ser Thr Ala Thr Lys Asp Thr Tyr Asp Ala Leu His Met Gln Ala
    530                 535                 540

Leu Pro Pro Arg Gly Ser Gly Glu Gly Arg Gly Ser Leu Leu Thr Cys
545                 550                 555                 560

Gly Asp Val Glu Glu Asn Pro Gly Pro Met Ala Leu Pro Val Thr Ala
                565                 570                 575

Leu Leu Leu Pro Leu Ala Leu Leu Leu His Ala Ala Arg Pro Asn Trp
            580                 585                 590

Val Asn Val Ile Ser Asp Leu Lys Lys Ile Glu Asp Leu Ile Gln Ser
        595                 600                 605

Met His Ile Asp Ala Thr Leu Tyr Thr Glu Ser Asp Val His Pro Ser
    610                 615                 620

Cys Lys Val Thr Ala Met Lys Cys Phe Leu Leu Glu Leu Gln Val Ile
```

-continued

```
625                 630                 635                 640

Ser Leu Glu Ser Gly Asp Ala Ser Ile His Asp Thr Val Glu Asn Leu
                645                 650                 655

Ile Ile Leu Ala Asn Asn Ser Leu Ser Ser Asn Gly Asn Val Thr Glu
            660                 665                 670

Ser Gly Cys Lys Glu Cys Glu Glu Leu Glu Glu Lys Asn Ile Lys Glu
        675                 680                 685

Phe Leu Gln Ser Phe Val His Ile Val Gln Met Phe Ile Asn Thr Ser
    690                 695                 700

Thr Thr Thr Pro Ala Pro Arg Pro Pro Thr Pro Ala Pro Thr Ile Ala
705                 710                 715                 720

Ser Gln Pro Leu Ser Leu Arg Pro Glu Ala Cys Arg Pro Ala Ala Gly
                725                 730                 735

Gly Ala Val His Thr Arg Gly Leu Asp Phe Ala Cys Asp Ile Tyr Ile
            740                 745                 750

Trp Ala Pro Leu Ala Gly Thr Cys Gly Val Leu Leu Leu Ser Leu Val
        755                 760                 765

Ile Thr Leu Tyr Cys
    770
```

<210> SEQ ID NO 67
<211> LENGTH: 2201
<212> TYPE: DNA
<213> ORGANISM: Homo sapiens
<220> FEATURE:
<221> NAME/KEY: misc_feature
<223> OTHER INFORMATION: NK19-5b DNA

<400> SEQUENCE: 67

```
ggatccgaat tcgccgccac catggcctta ccagtgaccg ccttgctcct gccgctggcc     60

ttgctgctcc acgccgccag gccggactac aaagacgatg acgataaagg cggtggtggc    120

tctggtggtg gcggcagcga catccagatg acacagacta catcctccct gtctgcctct    180

ctgggagaca gagtcaccat cagttgcagg gcaagtcagg acattagtaa atatttaaat    240

tggtatcagc agaaaccaga tggaactgtt aaactcctga tctaccatac atcaagatta    300

cactcaggag tcccatcaag gttcagtggc agtgggtctg gaacagatta ttctctcacc    360

attagcaacc tggagcaaga agatattgcc acttactttt gccaacaggg taatacgctt    420

ccgtacacgt tcggaggggg gaccaagctg gagatcacag gtggcggtgg ctcgggcggt    480

ggtgggtcgg gtggcggcgg atctgaggtg aaactgcagg agtcaggacc tggcctggtg    540

gcgccctcac agagcctgtc cgtcacatgc actgtctcag gggtctcatt acccgactat    600

ggtgtaagct ggattcgcca gcctccacga aagggtctgg agtggctggg agtaatatgg    660

ggtagtgaaa ccacatacta taattcagct ctcaaatcca gactgaccat catcaaggac    720

aactccaaga gccaagtttt cttaaaaatg aacagtctgc aaactgatga cacagccatt    780

tactactgtg ccaaacatta ttactacggt ggtagctatg ctatggacta ctggggccaa    840

ggaacctcag tcaccgtctc ctcaaccacg acgccagcgc cgcgaccacc aacaccggcg    900

cccaccatcg cgtcgcagcc cctgtccctg cgcccagagg cgtgccggcc agcggcgggg    960

ggcgcagtgc acacgagggg gctggacttc gcctgtgatc cattttttt ctgctgcttc   1020

atcgctgtag ccatgggaat ccgtttcatt attatggtaa cacggaggga ccagaggctg   1080

ccccccgatg cccacaagcc ccctgggga ggcagtttcc ggacccccat ccaagaggag   1140

caggccgacg cccactccac cctggccaag atcagagtga agttcagcag gagcgcagac   1200
```

```
gcccccgcgt accagcaggg ccagaaccag ctctataacg agctcaatct aggacgaaga   1260

gaggagtacg atgttttgga caagagacgt ggccgggacc ctgagatggg gggaaagccg   1320

agaaggaaga accctcagga aggcctgtac aatgaactgc agaaagataa gatggcggag   1380

gcctacagtg agattgggat gaaaggcgag cgccggaggg gcaaggggca cgatggcctt   1440

taccagggtc tcagtacagc caccaaggac acctacgacg cccttcacat gcaggccctg   1500

ccccctcgcg gctctggcga gggaaggggt tccctgctta cttgcggcga cgtcgaagag   1560

aatcccggtc cgatggccct cccagtaact gccctccttt tgcccctcgc actccttctt   1620

catgccgctc gccccaactg ggtcaacgtg attagcgatt tgaagaaaat cgaggacctt   1680

atacagtcta tgcatattga cgctacactg tatactgaga gtgatgtaca cccgtcctgt   1740

aaggtaacgg ccatgaaatg ctttcttctg gagctccagg tcatcagctt ggagtctggg   1800

gacgcaagca tccacgatac ggttgaaaac ctcatcatcc ttgcgaacaa ctctctctca   1860

tctaatggaa acgttacaga gagtgggtgt aaggagtgcg aagagttgga agaaaaaaac   1920

atcaaagaat ttcttcaatc cttcgttcac atagtgcaaa tgttcattaa cacgtccact   1980

accacacccg ccccgaggcc acctacgccg gcaccgacta tcgccagtca acccctctct   2040

ctgcgccccg aggcttgccg gcctgcggct ggtggggcgg tccacacccg gggcctggat   2100

tttgcgtgcg atatatacat ctgggcacct cttgccggca cctgcggagt gctgcttctc   2160

tcactcgtta ttacgctgta ctgctaagcg gccgcgtcga c                         2201
```

```
<210> SEQ ID NO 68
<211> LENGTH: 721
<212> TYPE: PRT
<213> ORGANISM: Homo sapiens
<220> FEATURE:
<221> NAME/KEY: MISC_FEATURE
<223> OTHER INFORMATION: NK19-5b Protein

<400> SEQUENCE: 68

Met Ala Leu Pro Val Thr Ala Leu Leu Leu Pro Leu Ala Leu Leu Leu
1               5                   10                  15

His Ala Ala Arg Pro Asp Tyr Lys Asp Asp Asp Asp Lys Gly Gly Gly
            20                  25                  30

Gly Ser Gly Gly Gly Gly Ser Asp Ile Gln Met Thr Gln Thr Thr Ser
        35                  40                  45

Ser Leu Ser Ala Ser Leu Gly Asp Arg Val Thr Ile Ser Cys Arg Ala
    50                  55                  60

Ser Gln Asp Ile Ser Lys Tyr Leu Asn Trp Tyr Gln Gln Lys Pro Asp
65                  70                  75                  80

Gly Thr Val Lys Leu Leu Ile Tyr His Thr Ser Arg Leu His Ser Gly
                85                  90                  95

Val Pro Ser Arg Phe Ser Gly Ser Gly Ser Gly Thr Asp Tyr Ser Leu
            100                 105                 110

Thr Ile Ser Asn Leu Glu Gln Glu Asp Ile Ala Thr Tyr Phe Cys Gln
        115                 120                 125

Gln Gly Asn Thr Leu Pro Tyr Thr Phe Gly Gly Gly Thr Lys Leu Glu
    130                 135                 140

Ile Thr Gly Gly Gly Gly Ser Gly Gly Gly Gly Ser Gly Gly Gly Gly
145                 150                 155                 160

Ser Glu Val Lys Leu Gln Glu Ser Gly Pro Gly Leu Val Ala Pro Ser
                165                 170                 175
```

-continued

```
Gln Ser Leu Ser Val Thr Cys Thr Val Ser Gly Val Ser Leu Pro Asp
            180                 185                 190

Tyr Gly Val Ser Trp Ile Arg Gln Pro Pro Arg Lys Gly Leu Glu Trp
        195                 200                 205

Leu Gly Val Ile Trp Gly Ser Glu Thr Thr Tyr Tyr Asn Ser Ala Leu
    210                 215                 220

Lys Ser Arg Leu Thr Ile Ile Lys Asp Asn Ser Lys Ser Gln Val Phe
225                 230                 235                 240

Leu Lys Met Asn Ser Leu Gln Thr Asp Asp Thr Ala Ile Tyr Tyr Cys
                245                 250                 255

Ala Lys His Tyr Tyr Tyr Gly Gly Ser Tyr Ala Met Asp Tyr Trp Gly
            260                 265                 270

Gln Gly Thr Ser Val Thr Val Ser Ser Thr Thr Thr Pro Ala Pro Arg
        275                 280                 285

Pro Pro Thr Pro Ala Pro Thr Ile Ala Ser Gln Pro Leu Ser Leu Arg
    290                 295                 300

Pro Glu Ala Cys Arg Pro Ala Ala Gly Gly Ala Val His Thr Arg Gly
305                 310                 315                 320

Leu Asp Phe Ala Cys Asp Pro Phe Phe Phe Cys Cys Phe Ile Ala Val
                325                 330                 335

Ala Met Gly Ile Arg Phe Ile Ile Met Val Thr Arg Arg Asp Gln Arg
            340                 345                 350

Leu Pro Pro Asp Ala His Lys Pro Pro Gly Gly Gly Ser Phe Arg Thr
        355                 360                 365

Pro Ile Gln Glu Glu Gln Ala Asp Ala His Ser Thr Leu Ala Lys Ile
    370                 375                 380

Arg Val Lys Phe Ser Arg Ser Ala Asp Ala Pro Ala Tyr Gln Gln Gly
385                 390                 395                 400

Gln Asn Gln Leu Tyr Asn Glu Leu Asn Leu Gly Arg Arg Glu Glu Tyr
                405                 410                 415

Asp Val Leu Asp Lys Arg Arg Gly Arg Asp Pro Glu Met Gly Gly Lys
            420                 425                 430

Pro Arg Arg Lys Asn Pro Gln Glu Gly Leu Tyr Asn Glu Leu Gln Lys
        435                 440                 445

Asp Lys Met Ala Glu Ala Tyr Ser Glu Ile Gly Met Lys Gly Glu Arg
    450                 455                 460

Arg Arg Gly Lys Gly His Asp Gly Leu Tyr Gln Gly Leu Ser Thr Ala
465                 470                 475                 480

Thr Lys Asp Thr Tyr Asp Ala Leu His Met Gln Ala Leu Pro Pro Arg
                485                 490                 495

Gly Ser Gly Glu Gly Arg Gly Ser Leu Leu Thr Cys Gly Asp Val Glu
            500                 505                 510

Glu Asn Pro Gly Pro Met Ala Leu Pro Val Thr Ala Leu Leu Leu Pro
        515                 520                 525

Leu Ala Leu Leu Leu His Ala Ala Arg Pro Asn Trp Val Asn Val Ile
    530                 535                 540

Ser Asp Leu Lys Lys Ile Glu Asp Leu Ile Gln Ser Met His Ile Asp
545                 550                 555                 560

Ala Thr Leu Tyr Thr Glu Ser Asp Val His Pro Ser Cys Lys Val Thr
                565                 570                 575

Ala Met Lys Cys Phe Leu Leu Glu Leu Gln Val Ile Ser Leu Glu Ser
            580                 585                 590

Gly Asp Ala Ser Ile His Asp Thr Val Glu Asn Leu Ile Ile Leu Ala
```

595 600 605

Asn Asn Ser Leu Ser Ser Asn Gly Asn Val Thr Glu Ser Gly Cys Lys
610 615 620

Glu Cys Glu Glu Leu Glu Glu Lys Asn Ile Lys Glu Phe Leu Gln Ser
625 630 635 640

Phe Val His Ile Val Gln Met Phe Ile Asn Thr Ser Thr Thr Thr Pro
645 650 655

Ala Pro Arg Pro Pro Thr Pro Ala Pro Thr Ile Ala Ser Gln Pro Leu
660 665 670

Ser Leu Arg Pro Glu Ala Cys Arg Pro Ala Ala Gly Gly Ala Val His
675 680 685

Thr Arg Gly Leu Asp Phe Ala Cys Asp Ile Tyr Ile Trp Ala Pro Leu
690 695 700

Ala Gly Thr Cys Gly Val Leu Leu Leu Ser Leu Val Ile Thr Leu Tyr
705 710 715 720

Cys

<210> SEQ ID NO 69
<211> LENGTH: 1805
<212> TYPE: DNA
<213> ORGANISM: Homo sapiens
<220> FEATURE:
<221> NAME/KEY: misc_feature
<223> OTHER INFORMATION: NK19-6b DNA

<400> SEQUENCE: 69
ggatccgaat tcgccgccac catggcctta ccagtgaccg ccttgctcct gccgctggcc 60
ttgctgctcc acgccgccag gccggactac aaagacgatg acgataaagg cggtggtggc 120
tctggtggtg gcggcagcga catccagatg acacagacta catcctccct gtctgcctct 180
ctgggagaca gagtcaccat cagttgcagg gcaagtcagg acattagtaa atatttaaat 240
tggtatcagc agaaaccaga tggaactgtt aaactcctga tctaccatac atcaagatta 300
cactcaggag tcccatcaag gttcagtggc agtgggtctg gaacagatta ttctctcacc 360
attagcaacc tggagcaaga agatattgcc acttactttt gccaacaggg taatacgctt 420
ccgtacacgt tcggaggggg gaccaagctg gagatcacaa ccacgacgcc agcgccgcga 480
ccaccaacac cggcgcccac catcgcgtcg cagcccctgt ccctgcgccc agaggcgtgc 540
cggccagcgg cggggggcgc agtgcacacg agggggctgg acttcgcctg tgatatctac 600
atctgggcgc ccttggccgg gacttgtggg gtccttctcc tgtcactggt tatcaccctt 660
tactgccgga gggaccagag gctgcccccc gatgcccaca agccccctgg gggaggcagt 720
ttccggaccc ccatccaaga ggagcaggcc gacgcccact ccaccctggc caagatcaga 780
gtgaagttca gcaggagcgc agacgccccc gcgtaccagc agggccagaa ccagctctat 840
aacgagctca atctaggacg aagagaggag tacgatgttt tggacaagag acgtggccgg 900
gaccctgaga tgggggggaaa gccgagaagg aagaaccctc aggaaggcct gtacaatgaa 960
ctgcagaaag ataagatggc ggaggcctac agtgagattg ggatgaaagg cgagcgccgg 1020
aggggcaagg ggcacgatgg cctttaccag ggtctcagta cagccaccaa ggacacctac 1080
gacgcccttc acatgcaggc cctgcccct cgcggctctg gcgagggaag gggttccctg 1140
cttacttgcg gcgacgtcga agagaatccc ggtccgatgg ccctcccagt aactgccctc 1200
cttttgcccc tcgcactcct tcttcatgcc gctcgcccca actgggtcaa cgtgattagc 1260
gatttgaaga aaatcgagga ccttatacag tctatgcata ttgacgctac actgtatact 1320

```
gagagtgatg tacacccgtc ctgtaaggta acggccatga aatgctttct tctggagctc   1380

caggtcatca gcttggagtc tggggacgca agcatccacg atacggttga aaacctcatc   1440

atccttgcga acaactctct ctcatctaat ggaaacgtta cagagagtgg gtgtaaggag   1500

tgcgaagagt tggaagaaaa aaacatcaaa gaatttcttc aatccttcgt tcacatagtg   1560

caaatgttca ttaacacgtc cactaccaca cccgccccga ggccacctac gccggcaccg   1620

actatcgcca gtcaacccct ctctctgcgc cccgaggctt gccggcctgc ggctggtggg   1680

gcggtccaca cccggggcct ggattttgcg tgcgatatat acatctgggc acctcttgcc   1740

ggcacctgcg gagtgctgct tctctcactc gttattacgc tgtactgcta agcggccgcg   1800

tcgac                                                               1805
```

```
<210> SEQ ID NO 70
<211> LENGTH: 589
<212> TYPE: PRT
<213> ORGANISM: Homo sapiens
<220> FEATURE:
<221> NAME/KEY: MISC_FEATURE
<223> OTHER INFORMATION: NK19-6b Protein

<400> SEQUENCE: 70

Met Ala Leu Pro Val Thr Ala Leu Leu Leu Pro Leu Ala Leu Leu Leu
1               5                   10                  15

His Ala Ala Arg Pro Asp Tyr Lys Asp Asp Asp Asp Lys Gly Gly Gly
            20                  25                  30

Gly Ser Gly Gly Gly Gly Ser Asp Ile Gln Met Thr Gln Thr Thr Ser
        35                  40                  45

Ser Leu Ser Ala Ser Leu Gly Asp Arg Val Thr Ile Ser Cys Arg Ala
    50                  55                  60

Ser Gln Asp Ile Ser Lys Tyr Leu Asn Trp Tyr Gln Gln Lys Pro Asp
65                  70                  75                  80

Gly Thr Val Lys Leu Leu Ile Tyr His Thr Ser Arg Leu His Ser Gly
                85                  90                  95

Val Pro Ser Arg Phe Ser Gly Ser Gly Ser Gly Thr Asp Tyr Ser Leu
            100                 105                 110

Thr Ile Ser Asn Leu Glu Gln Glu Asp Ile Ala Thr Tyr Phe Cys Gln
        115                 120                 125

Gln Gly Asn Thr Leu Pro Tyr Thr Phe Gly Gly Gly Thr Lys Leu Glu
    130                 135                 140

Ile Thr Thr Thr Thr Pro Ala Pro Arg Pro Pro Thr Pro Ala Pro Thr
145                 150                 155                 160

Ile Ala Ser Gln Pro Leu Ser Leu Arg Pro Glu Ala Cys Arg Pro Ala
                165                 170                 175

Ala Gly Gly Ala Val His Thr Arg Gly Leu Asp Phe Ala Cys Asp Ile
            180                 185                 190

Tyr Ile Trp Ala Pro Leu Ala Gly Thr Cys Gly Val Leu Leu Leu Ser
        195                 200                 205

Leu Val Ile Thr Leu Tyr Cys Arg Arg Asp Gln Arg Leu Pro Pro Asp
    210                 215                 220

Ala His Lys Pro Pro Gly Gly Gly Ser Phe Arg Thr Pro Ile Gln Glu
225                 230                 235                 240

Glu Gln Ala Asp Ala His Ser Thr Leu Ala Lys Ile Arg Val Lys Phe
                245                 250                 255

Ser Arg Ser Ala Asp Ala Pro Ala Tyr Gln Gln Gly Gln Asn Gln Leu
```

-continued

```
            260                 265                 270

Tyr Asn Glu Leu Asn Leu Gly Arg Arg Glu Glu Tyr Asp Val Leu Asp
        275                 280                 285

Lys Arg Arg Gly Arg Asp Pro Glu Met Gly Gly Lys Pro Arg Arg Lys
    290                 295                 300

Asn Pro Gln Glu Gly Leu Tyr Asn Glu Leu Gln Lys Asp Lys Met Ala
305                 310                 315                 320

Glu Ala Tyr Ser Glu Ile Gly Met Lys Gly Glu Arg Arg Arg Gly Lys
                325                 330                 335

Gly His Asp Gly Leu Tyr Gln Gly Leu Ser Thr Ala Thr Lys Asp Thr
            340                 345                 350

Tyr Asp Ala Leu His Met Gln Ala Leu Pro Pro Arg Gly Ser Gly Glu
        355                 360                 365

Gly Arg Gly Ser Leu Leu Thr Cys Gly Asp Val Glu Glu Asn Pro Gly
    370                 375                 380

Pro Met Ala Leu Pro Val Thr Ala Leu Leu Leu Pro Leu Ala Leu Leu
385                 390                 395                 400

Leu His Ala Ala Arg Pro Asn Trp Val Asn Val Ile Ser Asp Leu Lys
                405                 410                 415

Lys Ile Glu Asp Leu Ile Gln Ser Met His Ile Asp Ala Thr Leu Tyr
            420                 425                 430

Thr Glu Ser Asp Val His Pro Ser Cys Lys Val Thr Ala Met Lys Cys
        435                 440                 445

Phe Leu Leu Glu Leu Gln Val Ile Ser Leu Glu Ser Gly Asp Ala Ser
    450                 455                 460

Ile His Asp Thr Val Glu Asn Leu Ile Ile Leu Ala Asn Asn Ser Leu
465                 470                 475                 480

Ser Ser Asn Gly Asn Val Thr Glu Ser Gly Cys Lys Glu Cys Glu Glu
                485                 490                 495

Leu Glu Glu Lys Asn Ile Lys Glu Phe Leu Gln Ser Phe Val His Ile
            500                 505                 510

Val Gln Met Phe Ile Asn Thr Ser Thr Thr Thr Pro Ala Pro Arg Pro
        515                 520                 525

Pro Thr Pro Ala Pro Thr Ile Ala Ser Gln Pro Leu Ser Leu Arg Pro
    530                 535                 540

Glu Ala Cys Arg Pro Ala Ala Gly Gly Ala Val His Thr Arg Gly Leu
545                 550                 555                 560

Asp Phe Ala Cys Asp Ile Tyr Ile Trp Ala Pro Leu Ala Gly Thr Cys
                565                 570                 575

Gly Val Leu Leu Leu Ser Leu Val Ile Thr Leu Tyr Cys
            580                 585
```

<210> SEQ ID NO 71
<211> LENGTH: 3347
<212> TYPE: DNA
<213> ORGANISM: Homo sapiens
<220> FEATURE:
<221> NAME/KEY: misc_feature
<223> OTHER INFORMATION: NK19-7b DNA

<400> SEQUENCE: 71

```
ggatccgaat tcgccgccac catggcctta ccagtgaccg ccttgctcct gccgctggcc      60

ttgctgctcc acgccgccag gccggactac aaagacgatg acgataaagg cggtggtggc     120

tctggtggtg gcggcagcga catccagatg acacagacta catcctccct gtctgcctct     180
```

-continued

```
ctgggagaca gagtcaccat cagttgcagg gcaagtcagg acattagtaa atatttaaat    240
tggtatcagc agaaaccaga tggaactgtt aaactcctga tctaccatac atcaagatta    300
cactcaggag tcccatcaag gttcagtggc agtgggtctg gaacagatta ttctctcacc    360
attagcaacc tggagcaaga agatattgcc acttactttt gccaacaggg taatacgctt    420
ccgtacacgt tcggaggggg gaccaagctg gagatcacag gtggcggtgg ctcgggcggt    480
ggtgggtcgg gtggcggcgg atctgaggtg aaactgcagg agtcaggacc tggcctggtg    540
gcgccctcac agagcctgtc cgtcacatgc actgtctcag gggtctcatt acccgactat    600
ggtgtaagct ggattcgcca gcctccacga aagggtctgg agtggctggg agtaatatgg    660
ggtagtgaaa ccacatacta taattcagct ctcaaatcca gactgaccat catcaaggac    720
aactccaaga gccaagtttt cttaaaaatg aacagtctgc aaactgatga cacagccatt    780
tactactgtg ccaaacatta ttactacggt ggtagctatg ctatggacta ctggggccaa    840
ggaacctcag tcaccgtctc ctcaaccacg acgccagcgc cgcgaccacc aacaccggcg    900
cccaccatcg cgtcgcagcc cctgtccctg cgcccagagg cgtgccggcc agcggcgggg    960
ggcgcagtgc acacgagggg gctggacttc gcctgtgata tctacatctg ggcgcccttg   1020
gccgggactt gtggggtcct tctcctgtca ctggttatca ccctttactg ccggagggac   1080
cagaggctgc cccccgatgc ccacaagccc cctgggggag gcagtttccg gacccccatc   1140
caagaggagc aggccgacgc ccactccacc ctggccaaga tcagagtgaa gttcagcagg   1200
agcgcagacg cccccgcgta ccagcagggc cagaaccagc tctataacga gctcaatcta   1260
ggacgaagag aggagtacga tgttttggac aagagacgtg gccgggaccc tgagatgggg   1320
ggaaagccga gaaggaagaa ccctcaggaa ggcctgtaca atgaactgca gaaagataag   1380
atggcggagg cctacagtga gattgggatg aaaggcgagc gccggagggg caaggggcac   1440
gatggccttt accagggtct cagtacagcc accaaggaca cctacgacgc ccttcacatg   1500
caggccctgc cccctcgcgg ctctggcgag ggaaggggtt ccctgcttac ttgcggcgac   1560
gtcgaagaga atcccggtcc gatggccctc ccagtaactg ccctcctttt gcccctcgca   1620
ctccttcttc atgccgctcg ccccaactgg gtcaacgtga ttagcgattt gaagaaaatc   1680
gaggacctta tacagtctat gcatattgac gctacactgt atactgagag tgatgtacac   1740
ccgtcctgta aggtaacggc catgaaatgc tttcttctgg agctccaggt catcagcttg   1800
gagtctgggg acgcaagcat ccacgatacg gttgaaaacc tcatcatcct tgcgaacaac   1860
tctctctcat ctaatggaaa cgttacagag agtgggtgta aggagtgcga agagttggaa   1920
gaaaaaaaca tcaaagaatt tcttcaatcc ttcgttcaca tagtgcaaat gttcattaac   1980
acgtccacta ccacacccgc cccgaggcca cctacgccgg caccgactat cgccagtcaa   2040
cccctctctc tgcgccccga ggcttgccgg cctgcggctg gtggggcggt ccacacccgg   2100
ggcctggatt ttgcgtgcga tatatacatc tgggcacctc ttgccggcac ctgcggagtg   2160
ctgcttctct cactcgttat tacgctgtac tgcggcagcg gcgccacaaa cttctctctg   2220
ctaaagcaag caggtgatgt tgaagaaaac cccgggccta tgcttctcct ggtgacaagc   2280
cttctgctct gtgagttacc acacccagca ttcctcctga tcccacgcaa agtgtgtaac   2340
ggaataggta ttggtgaatt taaagactca ctctccataa atgctacgaa tattaaacac   2400
ttcaaaaact gcacctccat cagtggcgat ctccacatcc tgccggtggc atttaggggt   2460
gactccttca cacatactcc tcctctggat ccacaggaac tggatattct gaaaaccgta   2520
aaggaaatca cagggttttt gctgattcag gcttggcctg aaaacaggac ggacctccat   2580
```

```
gcctttgaga acctagaaat catacgcggc aggaccaagc aacatggtca gttttctctt   2640

gcagtcgtca gcctgaacat aacatccttg ggattacgct ccctcaagga gataagtgat   2700

ggagatgtga taatttcagg aaacaaaaat ttgtgctatg caaatacaat aaactggaaa   2760

aaactgtttg ggacctccgg tcagaaaacc aaaattataa gcaacagagg tgaaaacagc   2820

tgcaaggcca caggccaggt ctgccatgcc ttgtgctccc ccgagggctg ctggggcccg   2880

gagcccaggg actgcgtctc ttgccggaat gtcagccgag gcagggaatg cgtggacaag   2940

tgcaaccttc tggagggtga gccaagggag tttgtggaga actctgagtg catacagtgc   3000

cacccagagt gcctgcctca ggccatgaac atcacctgca caggacgggg accagacaac   3060

tgtatccagt gtgcccacta cattgacggc ccccactgcg tcaagacctg cccggcagga   3120

gtcatgggag aaaacaacac cctggtctgg aagtacgcag acgccggcca tgtgtgccac   3180

ctgtgccatc caaactgcac ctacggatgc actgggccag gtcttgaagg ctgtccaacg   3240

aatgggccta agatcccgtc catcgccact gggatggtgg gggccctcct cttgctgctg   3300

gtggtggccc tggggatcgg cctcttcatg tgagcggccg cgtcgac                3347
```

<210> SEQ ID NO 72
<211> LENGTH: 1103
<212> TYPE: PRT
<213> ORGANISM: Homo sapiens
<220> FEATURE:
<221> NAME/KEY: MISC_FEATURE
<223> OTHER INFORMATION: NK19-7b Protein

<400> SEQUENCE: 72

```
Met Ala Leu Pro Val Thr Ala Leu Leu Leu Pro Leu Ala Leu Leu Leu
1               5                   10                  15

His Ala Ala Arg Pro Asp Tyr Lys Asp Asp Asp Asp Lys Gly Gly Gly
            20                  25                  30

Gly Ser Gly Gly Gly Gly Ser Asp Ile Gln Met Thr Gln Thr Thr Ser
        35                  40                  45

Ser Leu Ser Ala Ser Leu Gly Asp Arg Val Thr Ile Ser Cys Arg Ala
    50                  55                  60

Ser Gln Asp Ile Ser Lys Tyr Leu Asn Trp Tyr Gln Gln Lys Pro Asp
65                  70                  75                  80

Gly Thr Val Lys Leu Leu Ile Tyr His Thr Ser Arg Leu His Ser Gly
                85                  90                  95

Val Pro Ser Arg Phe Ser Gly Ser Gly Ser Gly Thr Asp Tyr Ser Leu
            100                 105                 110

Thr Ile Ser Asn Leu Glu Gln Glu Asp Ile Ala Thr Tyr Phe Cys Gln
        115                 120                 125

Gln Gly Asn Thr Leu Pro Tyr Thr Phe Gly Gly Gly Thr Lys Leu Glu
    130                 135                 140

Ile Thr Gly Gly Gly Gly Ser Gly Gly Gly Gly Ser Gly Gly Gly Gly
145                 150                 155                 160

Ser Glu Val Lys Leu Gln Glu Ser Gly Pro Gly Leu Val Ala Pro Ser
                165                 170                 175

Gln Ser Leu Ser Val Thr Cys Thr Val Ser Gly Val Ser Leu Pro Asp
            180                 185                 190

Tyr Gly Val Ser Trp Ile Arg Gln Pro Pro Arg Lys Gly Leu Glu Trp
        195                 200                 205

Leu Gly Val Ile Trp Gly Ser Glu Thr Thr Tyr Tyr Asn Ser Ala Leu
    210                 215                 220
```

-continued

```
Lys Ser Arg Leu Thr Ile Ile Lys Asp Asn Ser Lys Ser Gln Val Phe
225                 230                 235                 240

Leu Lys Met Asn Ser Leu Gln Thr Asp Asp Thr Ala Ile Tyr Tyr Cys
                245                 250                 255

Ala Lys His Tyr Tyr Tyr Gly Gly Ser Tyr Ala Met Asp Tyr Trp Gly
            260                 265                 270

Gln Gly Thr Ser Val Thr Val Ser Ser Thr Thr Thr Pro Ala Pro Arg
        275                 280                 285

Pro Pro Thr Pro Ala Pro Thr Ile Ala Ser Gln Pro Leu Ser Leu Arg
    290                 295                 300

Pro Glu Ala Cys Arg Pro Ala Ala Gly Gly Ala Val His Thr Arg Gly
305                 310                 315                 320

Leu Asp Phe Ala Cys Asp Ile Tyr Ile Trp Ala Pro Leu Ala Gly Thr
                325                 330                 335

Cys Gly Val Leu Leu Leu Ser Leu Val Ile Thr Leu Tyr Cys Arg Arg
            340                 345                 350

Asp Gln Arg Leu Pro Pro Asp Ala His Lys Pro Pro Gly Gly Gly Ser
        355                 360                 365

Phe Arg Thr Pro Ile Gln Glu Glu Gln Ala Asp Ala His Ser Thr Leu
    370                 375                 380

Ala Lys Ile Arg Val Lys Phe Ser Arg Ser Ala Asp Ala Pro Ala Tyr
385                 390                 395                 400

Gln Gln Gly Gln Asn Gln Leu Tyr Asn Glu Leu Asn Leu Gly Arg Arg
                405                 410                 415

Glu Glu Tyr Asp Val Leu Asp Lys Arg Arg Gly Arg Asp Pro Glu Met
            420                 425                 430

Gly Gly Lys Pro Arg Arg Lys Asn Pro Gln Glu Gly Leu Tyr Asn Glu
        435                 440                 445

Leu Gln Lys Asp Lys Met Ala Glu Ala Tyr Ser Glu Ile Gly Met Lys
    450                 455                 460

Gly Glu Arg Arg Arg Gly Lys Gly His Asp Gly Leu Tyr Gln Gly Leu
465                 470                 475                 480

Ser Thr Ala Thr Lys Asp Thr Tyr Asp Ala Leu His Met Gln Ala Leu
                485                 490                 495

Pro Pro Arg Gly Ser Gly Glu Gly Arg Gly Ser Leu Leu Thr Cys Gly
            500                 505                 510

Asp Val Glu Glu Asn Pro Gly Pro Met Ala Leu Pro Val Thr Ala Leu
        515                 520                 525

Leu Leu Pro Leu Ala Leu Leu Leu His Ala Ala Arg Pro Asn Trp Val
    530                 535                 540

Asn Val Ile Ser Asp Leu Lys Lys Ile Glu Asp Leu Ile Gln Ser Met
545                 550                 555                 560

His Ile Asp Ala Thr Leu Tyr Thr Glu Ser Asp Val His Pro Ser Cys
                565                 570                 575

Lys Val Thr Ala Met Lys Cys Phe Leu Leu Glu Leu Gln Val Ile Ser
            580                 585                 590

Leu Glu Ser Gly Asp Ala Ser Ile His Asp Thr Val Glu Asn Leu Ile
        595                 600                 605

Ile Leu Ala Asn Asn Ser Leu Ser Ser Asn Gly Asn Val Thr Glu Ser
    610                 615                 620

Gly Cys Lys Glu Cys Glu Glu Leu Glu Glu Lys Asn Ile Lys Glu Phe
625                 630                 635                 640
```

-continued

```
Leu Gln Ser Phe Val His Ile Val Gln Met Phe Ile Asn Thr Ser Thr
                645                 650                 655

Thr Thr Pro Ala Pro Arg Pro Pro Thr Pro Ala Pro Thr Ile Ala Ser
            660                 665                 670

Gln Pro Leu Ser Leu Arg Pro Glu Ala Cys Arg Pro Ala Ala Gly Gly
        675                 680                 685

Ala Val His Thr Arg Gly Leu Asp Phe Ala Cys Asp Ile Tyr Ile Trp
    690                 695                 700

Ala Pro Leu Ala Gly Thr Cys Gly Val Leu Leu Leu Ser Leu Val Ile
705                 710                 715                 720

Thr Leu Tyr Cys Gly Ser Gly Ala Thr Asn Phe Ser Leu Leu Lys Gln
                725                 730                 735

Ala Gly Asp Val Glu Glu Asn Pro Gly Pro Met Leu Leu Leu Val Thr
            740                 745                 750

Ser Leu Leu Leu Cys Glu Leu Pro His Pro Ala Phe Leu Leu Ile Pro
        755                 760                 765

Arg Lys Val Cys Asn Gly Ile Gly Ile Gly Glu Phe Lys Asp Ser Leu
    770                 775                 780

Ser Ile Asn Ala Thr Asn Ile Lys His Phe Lys Asn Cys Thr Ser Ile
785                 790                 795                 800

Ser Gly Asp Leu His Ile Leu Pro Val Ala Phe Arg Gly Asp Ser Phe
                805                 810                 815

Thr His Thr Pro Pro Leu Asp Pro Gln Glu Leu Asp Ile Leu Lys Thr
            820                 825                 830

Val Lys Glu Ile Thr Gly Phe Leu Leu Ile Gln Ala Trp Pro Glu Asn
        835                 840                 845

Arg Thr Asp Leu His Ala Phe Glu Asn Leu Glu Ile Ile Arg Gly Arg
    850                 855                 860

Thr Lys Gln His Gly Gln Phe Ser Leu Ala Val Val Ser Leu Asn Ile
865                 870                 875                 880

Thr Ser Leu Gly Leu Arg Ser Leu Lys Glu Ile Ser Asp Gly Asp Val
                885                 890                 895

Ile Ile Ser Gly Asn Lys Asn Leu Cys Tyr Ala Asn Thr Ile Asn Trp
            900                 905                 910

Lys Lys Leu Phe Gly Thr Ser Gly Gln Lys Thr Lys Ile Ile Ser Asn
        915                 920                 925

Arg Gly Glu Asn Ser Cys Lys Ala Thr Gly Gln Val Cys His Ala Leu
    930                 935                 940

Cys Ser Pro Glu Gly Cys Trp Gly Pro Glu Pro Arg Asp Cys Val Ser
945                 950                 955                 960

Cys Arg Asn Val Ser Arg Gly Arg Glu Cys Val Asp Lys Cys Asn Leu
                965                 970                 975

Leu Glu Gly Glu Pro Arg Glu Phe Val Glu Asn Ser Glu Cys Ile Gln
            980                 985                 990

Cys His Pro Glu Cys Leu Pro Gln  Ala Met Asn Ile Thr  Cys Thr Gly
        995                 1000                 1005

Arg Gly  Pro Asp Asn Cys Ile  Gln Cys Ala His Tyr  Ile Asp Gly
    1010                 1015                 1020

Pro His  Cys Val Lys Thr Cys  Pro Ala Gly Val Met  Gly Glu Asn
    1025                 1030                 1035

Asn Thr  Leu Val Trp Lys Tyr  Ala Asp Ala Gly His  Val Cys His
    1040                 1045                 1050

Leu Cys  His Pro Asn Cys Thr  Tyr Gly Cys Thr Gly  Pro Gly Leu
```

```
    1055                1060                1065

Glu Gly  Cys Pro Thr Asn Gly  Pro Lys Ile Pro Ser  Ile Ala Thr
    1070                1075                1080

Gly Met  Val Gly Ala Leu Leu  Leu Leu Leu Val Val  Ala Leu Gly
    1085                1090                1095

Ile Gly  Leu Phe Met
    1100
```

```
<210> SEQ ID NO 73
<211> LENGTH: 1844
<212> TYPE: DNA
<213> ORGANISM: Homo sapiens
<220> FEATURE:
<221> NAME/KEY: misc_feature
<223> OTHER INFORMATION: NK19-8b DNA

<400> SEQUENCE: 73

ggatccgaat tcgccgccac catggcctta ccagtgaccg ccttgctcct gccgctggcc     60
ttgctgctcc acgccgccag gccggactac aaagacgatg acgataaagg cggtggtggc    120
tctggtggtg gcggcagcga ggtgaaactg caggagtcag gacctggcct ggtggcgccc    180
tcacagagcc tgtccgtcac atgcactgtc tcaggggtct cattacccga ctatggtgta    240
agctggattc gccagcctcc acgaaagggt ctggagtggc tgggagtaat atggggtagt    300
gaaaccacat actataattc agctctcaaa tccagactga ccatcatcaa ggacaactcc    360
aagagccaag ttttcttaaa aatgaacagt ctgcaaactg atgacacagc catttactac    420
tgtgccaaac attattacta cggtggtagc tatgctatgg actactgggg ccaaggaacc    480
tcagtcaccg tctcctcaac cacgacgcca gcgccgcgac caccaacacc ggcgcccacc    540
atcgcgtcgc agcccctgtc cctgcgccca gaggcgtgcc ggccagcggc ggggggcgca    600
gtgcacacga gggggctgga cttcgcctgt gatatctaca tctgggcgcc cttggccggg    660
acttgtgggg tccttctcct gtcactggtt atcacccttt actgccggag ggaccagagg    720
ctgccccccg atgcccacaa gccccctggg ggaggcagtt tccggacccc catccaagag    780
gagcaggccg acgcccactc caccctggcc aagatcagag tgaagttcag caggagcgca    840
gacgcccccg cgtaccagca gggccagaac cagctctata acgagctcaa tctaggacga    900
agagaggagt acgatgtttt ggacaagaga cgtggccggg accctgagat ggggggaaag    960
ccgagaagga agaaccctca ggaaggcctg tacaatgaac tgcagaaaga taagatggcg   1020
gaggcctaca gtgagattgg gatgaaaggc gagcgccgga ggggcaaggg gcacgatggc   1080
ctttaccagg gtctcagtac agccaccaag gacacctacg acgcccttca catgcaggcc   1140
ctgccccctc gcggctctgg cgagggaagg ggttccctgc ttacttgcgg cgacgtcgaa   1200
gagaatcccg gtccgatggc cctcccagta actgccctcc ttttgcccct cgcactcctt   1260
cttcatgccg ctcgccccaa ctgggtcaac gtgattagcg atttgaagaa aatcgaggac   1320
cttatacagt ctatgcatat tgacgctaca ctgtatactg agagtgatgt acacccgtcc   1380
tgtaaggtaa cggccatgaa atgctttctt ctggagctcc aggtcatcag cttggagtct   1440
ggggacgcaa gcatccacga tacggttgaa aacctcatca tccttgcgaa caactctctc   1500
tcatctaatg gaaacgttac agagagtggg tgtaaggagt gcgaagagtt ggaagaaaaa   1560
aacatcaaag aatttcttca atccttcgtt cacatagtgc aaatgttcat taacacgtcc   1620
actaccacac ccgccccgag gccacctacg ccggcaccga ctatcgccag tcaacccctc   1680
tctctgcgcc ccgaggcttg ccggcctgcg gctggtgggg cggtccacac ccggggcctg   1740
```

```
gattttgcgt gcgatatata catctgggca cctcttgccg gcacctgcgg agtgctgctt   1800

ctctcactcg ttattacgct gtactgctaa gcggccgcgt cgac                    1844


<210> SEQ ID NO 74
<211> LENGTH: 602
<212> TYPE: PRT
<213> ORGANISM: Homo sapiens
<220> FEATURE:
<221> NAME/KEY: MISC_FEATURE
<223> OTHER INFORMATION: NK19-8b Protein

<400> SEQUENCE: 74

Met Ala Leu Pro Val Thr Ala Leu Leu Leu Pro Leu Ala Leu Leu Leu
1               5                   10                  15

His Ala Ala Arg Pro Asp Tyr Lys Asp Asp Asp Asp Lys Gly Gly Gly
            20                  25                  30

Gly Ser Gly Gly Gly Gly Ser Glu Val Lys Leu Gln Glu Ser Gly Pro
        35                  40                  45

Gly Leu Val Ala Pro Ser Gln Ser Leu Ser Val Thr Cys Thr Val Ser
    50                  55                  60

Gly Val Ser Leu Pro Asp Tyr Gly Val Ser Trp Ile Arg Gln Pro Pro
65                  70                  75                  80

Arg Lys Gly Leu Glu Trp Leu Gly Val Ile Trp Gly Ser Glu Thr Thr
                85                  90                  95

Tyr Tyr Asn Ser Ala Leu Lys Ser Arg Leu Thr Ile Ile Lys Asp Asn
            100                 105                 110

Ser Lys Ser Gln Val Phe Leu Lys Met Asn Ser Leu Gln Thr Asp Asp
        115                 120                 125

Thr Ala Ile Tyr Tyr Cys Ala Lys His Tyr Tyr Tyr Gly Gly Ser Tyr
    130                 135                 140

Ala Met Asp Tyr Trp Gly Gln Gly Thr Ser Val Thr Val Ser Ser Thr
145                 150                 155                 160

Thr Thr Pro Ala Pro Arg Pro Pro Thr Pro Ala Pro Thr Ile Ala Ser
                165                 170                 175

Gln Pro Leu Ser Leu Arg Pro Glu Ala Cys Arg Pro Ala Ala Gly Gly
            180                 185                 190

Ala Val His Thr Arg Gly Leu Asp Phe Ala Cys Asp Ile Tyr Ile Trp
        195                 200                 205

Ala Pro Leu Ala Gly Thr Cys Gly Val Leu Leu Leu Ser Leu Val Ile
    210                 215                 220

Thr Leu Tyr Cys Arg Arg Asp Gln Arg Leu Pro Pro Asp Ala His Lys
225                 230                 235                 240

Pro Pro Gly Gly Gly Ser Phe Arg Thr Pro Ile Gln Glu Glu Gln Ala
                245                 250                 255

Asp Ala His Ser Thr Leu Ala Lys Ile Arg Val Lys Phe Ser Arg Ser
            260                 265                 270

Ala Asp Ala Pro Ala Tyr Gln Gln Gly Gln Asn Gln Leu Tyr Asn Glu
        275                 280                 285

Leu Asn Leu Gly Arg Arg Glu Glu Tyr Asp Val Leu Asp Lys Arg Arg
    290                 295                 300

Gly Arg Asp Pro Glu Met Gly Gly Lys Pro Arg Arg Lys Asn Pro Gln
305                 310                 315                 320

Glu Gly Leu Tyr Asn Glu Leu Gln Lys Asp Lys Met Ala Glu Ala Tyr
                325                 330                 335
```

-continued

```
Ser Glu Ile Gly Met Lys Gly Glu Arg Arg Arg Gly Lys Gly His Asp
            340                 345                 350

Gly Leu Tyr Gln Gly Leu Ser Thr Ala Thr Lys Asp Thr Tyr Asp Ala
        355                 360                 365

Leu His Met Gln Ala Leu Pro Pro Arg Gly Ser Gly Glu Gly Arg Gly
    370                 375                 380

Ser Leu Leu Thr Cys Gly Asp Val Glu Glu Asn Pro Gly Pro Met Ala
385                 390                 395                 400

Leu Pro Val Thr Ala Leu Leu Leu Pro Leu Ala Leu Leu Leu His Ala
                405                 410                 415

Ala Arg Pro Asn Trp Val Asn Val Ile Ser Asp Leu Lys Lys Ile Glu
            420                 425                 430

Asp Leu Ile Gln Ser Met His Ile Asp Ala Thr Leu Tyr Thr Glu Ser
        435                 440                 445

Asp Val His Pro Ser Cys Lys Val Thr Ala Met Lys Cys Phe Leu Leu
    450                 455                 460

Glu Leu Gln Val Ile Ser Leu Glu Ser Gly Asp Ala Ser Ile His Asp
465                 470                 475                 480

Thr Val Glu Asn Leu Ile Ile Leu Ala Asn Asn Ser Leu Ser Ser Asn
                485                 490                 495

Gly Asn Val Thr Glu Ser Gly Cys Lys Glu Cys Glu Glu Leu Glu Glu
            500                 505                 510

Lys Asn Ile Lys Glu Phe Leu Gln Ser Phe Val His Ile Val Gln Met
        515                 520                 525

Phe Ile Asn Thr Ser Thr Thr Thr Pro Ala Pro Arg Pro Pro Thr Pro
    530                 535                 540

Ala Pro Thr Ile Ala Ser Gln Pro Leu Ser Leu Arg Pro Glu Ala Cys
545                 550                 555                 560

Arg Pro Ala Ala Gly Gly Ala Val His Thr Arg Gly Leu Asp Phe Ala
                565                 570                 575

Cys Asp Ile Tyr Ile Trp Ala Pro Leu Ala Gly Thr Cys Gly Val Leu
            580                 585                 590

Leu Leu Ser Leu Val Ile Thr Leu Tyr Cys
        595                 600
```

<210> SEQ ID NO 75
<211> LENGTH: 2243
<212> TYPE: DNA
<213> ORGANISM: Homo sapiens
<220> FEATURE:
<221> NAME/KEY: misc_feature
<223> OTHER INFORMATION: NK19-9b DNA

<400> SEQUENCE: 75

```
ggatccgaat tcgccgccac catggcctta ccagtgaccg ccttgctcct gccgctggcc      60

ttgctgctcc acgccgccag gccggactac aaagacgatg acgataaagg cggtggtggc     120

tctggtggtg gcggcagcga catccagatg acacagacta catcctccct gtctgcctct     180

ctgggagaca gagtcaccat cagttgcagg gcaagtcagg acattagtaa atatttaaat     240

tggtatcagc agaaaccaga tggaactgtt aaactcctga tctaccatac atcaagatta     300

cactcaggag tcccatcaag gttcagtggc agtgggtctg gaacagatta ttctctcacc     360

attagcaacc tggagcaaga agatattgcc acttactttt gccaacaggg taatacgctt     420

ccgtacacgt tcggaggggg gaccaagctg gagatcacag gtggcggtgg ctcgggcggt     480

ggtgggtcgg gtggcggcgg atctgaggtg aaactgcagg agtcaggacc tggcctggtg     540
```

```
gcgccctcac agagcctgtc cgtcacatgc actgtctcag ggtctcatt acccgactat    600

ggtgtaagct ggattcgcca gcctccacga aagggtctgg agtggctggg agtaatatgg    660

ggtagtgaaa ccacatacta taattcagct ctcaaatcca gactgaccat catcaaggac    720

aactccaaga gccaagtttt cttaaaaatg aacagtctgc aaactgatga cacagccatt    780

tactactgtg ccaaacatta ttactacggt ggtagctatg ctatggacta ctggggccaa    840

ggaacctcag tcaccgtctc ctcaaccacg acgccagcgc cgcgaccacc aacaccggcg    900

cccaccatcg cgtcgcagcc cctgtccctg cgcccagagg cgtgccggcc agcggcgggg    960

ggcgcagtgc acacgagggg gctggacttc gcctgtgata tctacatctg ggcgcccttg   1020

gccgggactt gtggggtcct tctcctgtca ctggttatca ccctttactg ccaacgaagg   1080

aaatatagat caaacaaagg agaaagtcct gtggagcctg cagagccttg tcgttacagc   1140

tgccccaggg aggaggaggg cagcaccatc cccatccagg aggattaccg aaaaccggag   1200

cctgcctgct cccccagagt gaagttcagc aggagcgcag acgcccccgc gtaccagcag   1260

ggccagaacc agctctataa cgagctcaat ctaggacgaa gagaggagta cgatgttttg   1320

gacaagagac gtggccggga ccctgagatg gggggaaagc cgagaaggaa gaaccctcag   1380

gaaggcctgt acaatgaact gcagaaagat aagatggcgg aggcctacag tgagattggg   1440

atgaaaggcg agcgccggag gggcaagggg cacgatggcc tttaccaggg tctcagtaca   1500

gccaccaagg acacctacga cgcccttcac atgcaggccc tgccccctcg cggctctggc   1560

gagggaaggg gttccctgct tacttgcggc gacgtcgaag agaatcccgg tccgatggcc   1620

ctcccagtaa ctgccctcct tttgcccctc gcactccttc ttcatgccgc tcgccccaac   1680

tgggtcaacg tgattagcga tttgaagaaa atcgaggacc ttatacagtc tatgcatatt   1740

gacgctacac tgtatactga gagtgatgta cacccgtcct gtaaggtaac ggccatgaaa   1800

tgctttcttc tggagctcca ggtcatcagc ttggagtctg gggacgcaag catccacgat   1860

acggttgaaa acctcatcat ccttgcgaac aactctctct catctaatgg aaacgttaca   1920

gagagtgggt gtaaggagtg cgaagagttg gaagaaaaaa acatcaaaga atttcttcaa   1980

tccttcgttc acatagtgca aatgttcatt aacacgtcca ctaccacacc cgccccgagg   2040

ccacctacgc cggcaccgac tatcgccagt caacccctct ctctgcgccc cgaggcttgc   2100

cggcctgcgg ctggtggggc ggtccacacc cggggcctgg attttgcgtg cgatatatac   2160

atctgggcac ctcttgccgg cacctgcgga gtgctgcttc tctcactcgt tattacgctg   2220

tactgctaag cggccgcgtc gac                                           2243
```

<210> SEQ ID NO 76
<211> LENGTH: 735
<212> TYPE: PRT
<213> ORGANISM: Homo sapiens
<220> FEATURE:
<221> NAME/KEY: MISC_FEATURE
<223> OTHER INFORMATION: NK19-9b Protein

<400> SEQUENCE: 76

```
Met Ala Leu Pro Val Thr Ala Leu Leu Leu Pro Leu Ala Leu Leu Leu
1               5                   10                  15

His Ala Ala Arg Pro Asp Tyr Lys Asp Asp Asp Asp Lys Gly Gly Gly
            20                  25                  30

Gly Ser Gly Gly Gly Gly Ser Asp Ile Gln Met Thr Gln Thr Thr Ser
        35                  40                  45
```

-continued

```
Ser Leu Ser Ala Ser Leu Gly Asp Arg Val Thr Ile Ser Cys Arg Ala
    50                  55                  60

Ser Gln Asp Ile Ser Lys Tyr Leu Asn Trp Tyr Gln Gln Lys Pro Asp
65                  70                  75                  80

Gly Thr Val Lys Leu Leu Ile Tyr His Thr Ser Arg Leu His Ser Gly
                85                  90                  95

Val Pro Ser Arg Phe Ser Gly Ser Gly Ser Gly Thr Asp Tyr Ser Leu
            100                 105                 110

Thr Ile Ser Asn Leu Glu Gln Glu Asp Ile Ala Thr Tyr Phe Cys Gln
        115                 120                 125

Gln Gly Asn Thr Leu Pro Tyr Thr Phe Gly Gly Gly Thr Lys Leu Glu
    130                 135                 140

Ile Thr Gly Gly Gly Gly Ser Gly Gly Gly Gly Ser Gly Gly Gly Gly
145                 150                 155                 160

Ser Glu Val Lys Leu Gln Glu Ser Gly Pro Gly Leu Val Ala Pro Ser
                165                 170                 175

Gln Ser Leu Ser Val Thr Cys Thr Val Ser Gly Val Ser Leu Pro Asp
            180                 185                 190

Tyr Gly Val Ser Trp Ile Arg Gln Pro Pro Arg Lys Gly Leu Glu Trp
        195                 200                 205

Leu Gly Val Ile Trp Gly Ser Glu Thr Thr Tyr Tyr Asn Ser Ala Leu
    210                 215                 220

Lys Ser Arg Leu Thr Ile Ile Lys Asp Asn Ser Lys Ser Gln Val Phe
225                 230                 235                 240

Leu Lys Met Asn Ser Leu Gln Thr Asp Asp Thr Ala Ile Tyr Tyr Cys
                245                 250                 255

Ala Lys His Tyr Tyr Tyr Gly Gly Ser Tyr Ala Met Asp Tyr Trp Gly
            260                 265                 270

Gln Gly Thr Ser Val Thr Val Ser Ser Thr Thr Thr Pro Ala Pro Arg
        275                 280                 285

Pro Pro Thr Pro Ala Pro Thr Ile Ala Ser Gln Pro Leu Ser Leu Arg
    290                 295                 300

Pro Glu Ala Cys Arg Pro Ala Ala Gly Gly Ala Val His Thr Arg Gly
305                 310                 315                 320

Leu Asp Phe Ala Cys Asp Ile Tyr Ile Trp Ala Pro Leu Ala Gly Thr
                325                 330                 335

Cys Gly Val Leu Leu Leu Ser Leu Val Ile Thr Leu Tyr Cys Gln Arg
            340                 345                 350

Arg Lys Tyr Arg Ser Asn Lys Gly Glu Ser Pro Val Glu Pro Ala Glu
        355                 360                 365

Pro Cys Arg Tyr Ser Cys Pro Arg Glu Glu Glu Gly Ser Thr Ile Pro
    370                 375                 380

Ile Gln Glu Asp Tyr Arg Lys Pro Glu Pro Ala Cys Ser Pro Arg Val
385                 390                 395                 400

Lys Phe Ser Arg Ser Ala Asp Ala Pro Ala Tyr Gln Gln Gly Gln Asn
                405                 410                 415

Gln Leu Tyr Asn Glu Leu Asn Leu Gly Arg Arg Glu Glu Tyr Asp Val
            420                 425                 430

Leu Asp Lys Arg Arg Gly Arg Asp Pro Glu Met Gly Gly Lys Pro Arg
        435                 440                 445

Arg Lys Asn Pro Gln Glu Gly Leu Tyr Asn Glu Leu Gln Lys Asp Lys
    450                 455                 460

Met Ala Glu Ala Tyr Ser Glu Ile Gly Met Lys Gly Glu Arg Arg Arg
```

-continued

```
465                 470                 475                 480

Gly Lys Gly His Asp Gly Leu Tyr Gln Gly Leu Ser Thr Ala Thr Lys
                485                 490                 495

Asp Thr Tyr Asp Ala Leu His Met Gln Ala Leu Pro Pro Arg Gly Ser
            500                 505                 510

Gly Glu Gly Arg Gly Ser Leu Leu Thr Cys Gly Asp Val Glu Glu Asn
        515                 520                 525

Pro Gly Pro Met Ala Leu Pro Val Thr Ala Leu Leu Leu Pro Leu Ala
    530                 535                 540

Leu Leu Leu His Ala Ala Arg Pro Asn Trp Val Asn Val Ile Ser Asp
545                 550                 555                 560

Leu Lys Lys Ile Glu Asp Leu Ile Gln Ser Met His Ile Asp Ala Thr
                565                 570                 575

Leu Tyr Thr Glu Ser Asp Val His Pro Ser Cys Lys Val Thr Ala Met
            580                 585                 590

Lys Cys Phe Leu Leu Glu Leu Gln Val Ile Ser Leu Glu Ser Gly Asp
        595                 600                 605

Ala Ser Ile His Asp Thr Val Glu Asn Leu Ile Ile Leu Ala Asn Asn
    610                 615                 620

Ser Leu Ser Ser Asn Gly Asn Val Thr Glu Ser Gly Cys Lys Glu Cys
625                 630                 635                 640

Glu Glu Leu Glu Glu Lys Asn Ile Lys Glu Phe Leu Gln Ser Phe Val
                645                 650                 655

His Ile Val Gln Met Phe Ile Asn Thr Ser Thr Thr Thr Pro Ala Pro
            660                 665                 670

Arg Pro Pro Thr Pro Ala Pro Thr Ile Ala Ser Gln Pro Leu Ser Leu
        675                 680                 685

Arg Pro Glu Ala Cys Arg Pro Ala Ala Gly Gly Ala Val His Thr Arg
    690                 695                 700

Gly Leu Asp Phe Ala Cys Asp Ile Tyr Ile Trp Ala Pro Leu Ala Gly
705                 710                 715                 720

Thr Cys Gly Val Leu Leu Leu Ser Leu Val Ile Thr Leu Tyr Cys
                725                 730                 735
```

```
<210> SEQ ID NO 77
<211> LENGTH: 2150
<212> TYPE: DNA
<213> ORGANISM: Homo sapiens
<220> FEATURE:
<221> NAME/KEY: misc_feature
<223> OTHER INFORMATION: NK19-10b DNA

<400> SEQUENCE: 77

ggatccgaat tcgccgccac catggcctta ccagtgaccg ccttgctcct gccgctggcc     60

ttgctgctcc acgccgccag gccggactac aaagacgatg acgataaagg cggtggtggc    120

tctggtggtg gcggcagcga catccagatg acacagacta catcctccct gtctgcctct    180

ctgggagaca gagtcaccat cagttgcagg gcaagtcagg acattagtaa atatttaaat    240

tggtatcagc agaaaccaga tggaactgtt aaactcctga tctaccatac atcaagatta    300

cactcaggag tcccatcaag gttcagtggc agtgggtctg gaacagatta ttctctcacc    360

attagcaacc tggagcaaga agatattgcc acttactttt gccaacaggg taatacgctt    420

ccgtacacgt tcggaggggg gaccaagctg gagatcacag gtggcggtgg ctcgggcggt    480

ggtgggtcgg gtggcggcgg atctgaggtg aaactgcagg agtcaggacc tggcctggtg    540
```

-continued

```
gcgccctcac agagcctgtc cgtcacatgc actgtctcag gggtctcatt acccgactat    600
ggtgtaagct ggattcgcca gcctccacga aagggtctgg agtggctggg agtaatatgg    660
ggtagtgaaa ccacatacta taattcagct ctcaaatcca gactgaccat catcaaggac    720
aactccaaga gccaagtttt cttaaaaatg aacagtctgc aaactgatga cacagccatt    780
tactactgtg ccaaacatta ttactacggt ggtagctatg ctatggacta ctggggccaa    840
ggaacctcag tcaccgtctc ctcaaccacg acgccagcgc cgcgaccacc aacaccggcg    900
cccaccatcg cgtcgcagcc cctgtccctg cgcccagagg cgtgccggcc agcggcgggg    960
ggcgcagtgc acacgagggg gctggacttc gcctgtgata tctacatctg ggcgcccttg   1020
gccgggactt gtggggtcct tctcctgtca ctggttatca ccctttactg catgccggag   1080
gagggttcgg gctgctcggt gcggcgcagg ccctatgggt gcagagtgaa gttcagcagg   1140
agcgcagacg cccccgcgta ccagcagggc cagaaccagc tctataacga gctcaatcta   1200
ggacgaagag aggagtacga tgttttggac aagagacgtg gccgggaccc tgagatgggg   1260
ggaaagccga gaaggaagaa ccctcaggaa ggcctgtaca atgaactgca gaaagataag   1320
atggcggagg cctacagtga gattgggatg aaaggcgagc gccggagggg caaggggcac   1380
gatggccttt accagggtct cagtacagcc accaaggaca cctacgacgc ccttcacatg   1440
caggccctgc cccctcgcgg ctctggcgag ggaaggggtt ccctgcttac ttgcggcgac   1500
gtcgaagaga atcccggtcc gatggccctc ccagtaactg ccctcctttt gcccctcgca   1560
ctccttcttc atgccgctcg ccccaactgg gtcaacgtga ttagcgattt gaagaaaatc   1620
gaggacctta tacagtctat gcatattgac gctacactgt atactgagag tgatgtacac   1680
ccgtcctgta aggtaacggc catgaaatgc tttcttctgg agctccaggt catcagcttg   1740
gagtctgggg acgcaagcat ccacgatacg gttgaaaacc tcatcatcct tgcgaacaac   1800
tctctctcat ctaatggaaa cgttacagag agtgggtgta aggagtgcga agagttggaa   1860
gaaaaaaaca tcaaagaatt tcttcaatcc ttcgttcaca tagtgcaaat gttcattaac   1920
acgtccacta ccacacccgc cccgaggcca cctacgccgg caccgactat cgccagtcaa   1980
cccctctctc tgcgccccga ggcttgccgg cctgcggctg gtggggcggt ccacacccgg   2040
ggcctggatt ttgcgtgcga tatatacatc tgggcacctc ttgccggcac ctgcggagtg   2100
ctgcttctct cactcgttat tacgctgtac tgctaagcgg ccgcgtcgac               2150
```

<210> SEQ ID NO 78
<211> LENGTH: 704
<212> TYPE: PRT
<213> ORGANISM: Homo sapiens
<220> FEATURE:
<221> NAME/KEY: MISC_FEATURE
<223> OTHER INFORMATION: NK19-10b Protein

<400> SEQUENCE: 78

```
Met Ala Leu Pro Val Thr Ala Leu Leu Leu Pro Leu Ala Leu Leu Leu
1               5                   10                  15

His Ala Ala Arg Pro Asp Tyr Lys Asp Asp Asp Asp Lys Gly Gly Gly
            20                  25                  30

Gly Ser Gly Gly Gly Gly Ser Asp Ile Gln Met Thr Gln Thr Thr Ser
        35                  40                  45

Ser Leu Ser Ala Ser Leu Gly Asp Arg Val Thr Ile Ser Cys Arg Ala
    50                  55                  60

Ser Gln Asp Ile Ser Lys Tyr Leu Asn Trp Tyr Gln Gln Lys Pro Asp
65                  70                  75                  80
```

-continued

```
Gly Thr Val Lys Leu Leu Ile Tyr His Thr Ser Arg Leu His Ser Gly
                85                  90                  95

Val Pro Ser Arg Phe Ser Gly Ser Gly Ser Gly Thr Asp Tyr Ser Leu
            100                 105                 110

Thr Ile Ser Asn Leu Glu Gln Glu Asp Ile Ala Thr Tyr Phe Cys Gln
        115                 120                 125

Gln Gly Asn Thr Leu Pro Tyr Thr Phe Gly Gly Gly Thr Lys Leu Glu
    130                 135                 140

Ile Thr Gly Gly Gly Gly Ser Gly Gly Gly Gly Ser Gly Gly Gly Gly
145                 150                 155                 160

Ser Glu Val Lys Leu Gln Glu Ser Gly Pro Gly Leu Val Ala Pro Ser
                165                 170                 175

Gln Ser Leu Ser Val Thr Cys Thr Val Ser Gly Val Ser Leu Pro Asp
            180                 185                 190

Tyr Gly Val Ser Trp Ile Arg Gln Pro Pro Arg Lys Gly Leu Glu Trp
        195                 200                 205

Leu Gly Val Ile Trp Gly Ser Glu Thr Thr Tyr Tyr Asn Ser Ala Leu
    210                 215                 220

Lys Ser Arg Leu Thr Ile Ile Lys Asp Asn Ser Lys Ser Gln Val Phe
225                 230                 235                 240

Leu Lys Met Asn Ser Leu Gln Thr Asp Asp Thr Ala Ile Tyr Tyr Cys
                245                 250                 255

Ala Lys His Tyr Tyr Tyr Gly Gly Ser Tyr Ala Met Asp Tyr Trp Gly
            260                 265                 270

Gln Gly Thr Ser Val Thr Val Ser Ser Thr Thr Thr Pro Ala Pro Arg
        275                 280                 285

Pro Pro Thr Pro Ala Pro Thr Ile Ala Ser Gln Pro Leu Ser Leu Arg
    290                 295                 300

Pro Glu Ala Cys Arg Pro Ala Ala Gly Gly Ala Val His Thr Arg Gly
305                 310                 315                 320

Leu Asp Phe Ala Cys Asp Ile Tyr Ile Trp Ala Pro Leu Ala Gly Thr
                325                 330                 335

Cys Gly Val Leu Leu Leu Ser Leu Val Ile Thr Leu Tyr Cys Met Pro
            340                 345                 350

Glu Glu Gly Ser Gly Cys Ser Val Arg Arg Arg Pro Tyr Gly Cys Arg
        355                 360                 365

Val Lys Phe Ser Arg Ser Ala Asp Ala Pro Ala Tyr Gln Gln Gly Gln
    370                 375                 380

Asn Gln Leu Tyr Asn Glu Leu Asn Leu Gly Arg Arg Glu Glu Tyr Asp
385                 390                 395                 400

Val Leu Asp Lys Arg Arg Gly Arg Asp Pro Glu Met Gly Gly Lys Pro
                405                 410                 415

Arg Arg Lys Asn Pro Gln Glu Gly Leu Tyr Asn Glu Leu Gln Lys Asp
            420                 425                 430

Lys Met Ala Glu Ala Tyr Ser Glu Ile Gly Met Lys Gly Glu Arg Arg
        435                 440                 445

Arg Gly Lys Gly His Asp Gly Leu Tyr Gln Gly Leu Ser Thr Ala Thr
    450                 455                 460

Lys Asp Thr Tyr Asp Ala Leu His Met Gln Ala Leu Pro Pro Arg Gly
465                 470                 475                 480

Ser Gly Glu Gly Arg Gly Ser Leu Leu Thr Cys Gly Asp Val Glu Glu
                485                 490                 495
```

```
Asn Pro Gly Pro Met Ala Leu Pro Val Thr Ala Leu Leu Leu Pro Leu
            500                 505                 510

Ala Leu Leu Leu His Ala Ala Arg Pro Asn Trp Val Asn Val Ile Ser
        515                 520                 525

Asp Leu Lys Lys Ile Glu Asp Leu Ile Gln Ser Met His Ile Asp Ala
    530                 535                 540

Thr Leu Tyr Thr Glu Ser Asp Val His Pro Ser Cys Lys Val Thr Ala
545                 550                 555                 560

Met Lys Cys Phe Leu Leu Glu Leu Gln Val Ile Ser Leu Glu Ser Gly
                565                 570                 575

Asp Ala Ser Ile His Asp Thr Val Glu Asn Leu Ile Ile Leu Ala Asn
            580                 585                 590

Asn Ser Leu Ser Ser Asn Gly Asn Val Thr Glu Ser Gly Cys Lys Glu
        595                 600                 605

Cys Glu Glu Leu Glu Glu Lys Asn Ile Lys Glu Phe Leu Gln Ser Phe
    610                 615                 620

Val His Ile Val Gln Met Phe Ile Asn Thr Ser Thr Thr Thr Pro Ala
625                 630                 635                 640

Pro Arg Pro Pro Thr Pro Ala Pro Thr Ile Ala Ser Gln Pro Leu Ser
                645                 650                 655

Leu Arg Pro Glu Ala Cys Arg Pro Ala Ala Gly Gly Ala Val His Thr
            660                 665                 670

Arg Gly Leu Asp Phe Ala Cys Asp Ile Tyr Ile Trp Ala Pro Leu Ala
        675                 680                 685

Gly Thr Cys Gly Val Leu Leu Leu Ser Leu Val Ile Thr Leu Tyr Cys
    690                 695                 700
```

<210> SEQ ID NO 79
<211> LENGTH: 2234
<212> TYPE: DNA
<213> ORGANISM: Homo sapiens
<220> FEATURE:
<221> NAME/KEY: misc_feature
<223> OTHER INFORMATION: NK19-11b DNA

<400> SEQUENCE: 79

```
ggatccgaat tcgccgccac catggcctta ccagtgaccg ccttgctcct gccgctggcc      60

ttgctgctcc acgccgccag gccggactac aaagacgatg acgataaagg cggtggtggc     120

tctggtggtg gcggcagcga catccagatg acacagacta catcctccct gtctgcctct     180

ctgggagaca gagtcaccat cagttgcagg gcaagtcagg acattagtaa atatttaaat     240

tggtatcagc agaaaccaga tggaactgtt aaactcctga tctaccatac atcaagatta     300

cactcaggag tcccatcaag gttcagtggc agtgggtctg gaacagatta ttctctcacc     360

attagcaacc tggagcaaga agatattgcc acttactttt gccaacaggg taatacgctt     420

ccgtacacgt tcggaggggg gaccaagctg gagatcacag gtggcggtgg ctcgggcggt     480

ggtgggtcgg gtggcggcgg atctgaggtg aaactgcagg agtcaggacc tggcctggtg     540

gcgccctcac agagcctgtc cgtcacatgc actgtctcag gggtctcatt acccgactat     600

ggtgtaagct ggattcgcca gcctccacga aagggtctgg agtggctggg agtaatatgg     660

ggtagtgaaa ccacatacta taattcagct ctcaaatcca gactgaccat catcaaggac     720

aactccaaga gccaagtttt cttaaaaatg aacagtctgc aaactgatga cacagccatt     780

tactactgtg ccaaacatta ttactacggt ggtagctatg ctatggacta ctggggccaa     840

ggaacctcag tcaccgtctc ctcaaccacg acgccagcgc cgcgaccacc aacaccggcg     900
```

cccaccatcg cgtcgcagcc cctgtccctg cgcccagagg cgtgccggcc agcggcgggg 960
ggcgcagtgc acacgagggg gctggacttc gcctgtgata tctacatctg ggcgcccttg 1020
gccgggactt gtggggtcct tctcctgtca ctggttatca ccctttactg catggaccaa 1080
caagcaatat atgctgagtt aaacttaccc acagactcag gcccagaaag ttcttcacct 1140
tcatctcttc ctcgggatgt ctgtcagggt tcaccttggc atcaatttgc cctgaaactt 1200
agctgtagag tgaagttcag caggagcgca gacgcccccg cgtaccagca gggccagaac 1260
cagctctata acgagctcaa tctaggacga agagaggagt acgatgtttt ggacaagaga 1320
cgtggccggg accctgagat ggggggaaag ccgagaagga agaaccctca ggaaggcctg 1380
tacaatgaac tgcagaaaga taagatggcg gaggcctaca gtgagattgg gatgaaaggc 1440
gagcgccgga ggggcaaggg gcacgatggc ctttaccagg gtctcagtac agccaccaag 1500
gacacctacg acgcccttca catgcaggcc ctgccccctc gcggctctgg cgagggaagg 1560
ggttccctgc ttacttgcgg cgacgtcgaa gagaatcccg gtccgatggc cctcccagta 1620
actgccctcc ttttgcccct cgcactcctt cttcatgccg ctcgccccaa ctgggtcaac 1680
gtgattagcg atttgaagaa aatcgaggac cttatacagt ctatgcatat tgacgctaca 1740
ctgtatactg agagtgatgt acacccgtcc tgtaaggtaa cggccatgaa atgctttctt 1800
ctggagctcc aggtcatcag cttggagtct ggggacgcaa gcatccacga tacggttgaa 1860
aacctcatca tccttgcgaa caactctctc tcatctaatg gaaacgttac agagagtggg 1920
tgtaaggagt gcgaagagtt ggaagaaaaa aacatcaaag aatttcttca atccttcgtt 1980
cacatagtgc aaatgttcat taacacgtcc actaccacac ccgccccgag gccacctacg 2040
ccggcaccga ctatcgccag tcaacccctc tctctgcgcc ccgaggcttg ccggcctgcg 2100
gctggtgggg cggtccacac ccggggcctg gattttgcgt gcgatatata catctgggca 2160
cctcttgccg gcacctgcgg agtgctgctt ctctcactcg ttattacgct gtactgctaa 2220
gcggccgcgt cgac 2234

<210> SEQ ID NO 80
<211> LENGTH: 732
<212> TYPE: PRT
<213> ORGANISM: Homo sapiens
<220> FEATURE:
<221> NAME/KEY: MISC_FEATURE
<223> OTHER INFORMATION: NK19-11b Protein

<400> SEQUENCE: 80

Met Ala Leu Pro Val Thr Ala Leu Leu Leu Pro Leu Ala Leu Leu Leu
1 5 10 15

His Ala Ala Arg Pro Asp Tyr Lys Asp Asp Asp Asp Lys Gly Gly Gly
20 25 30

Gly Ser Gly Gly Gly Gly Ser Asp Ile Gln Met Thr Gln Thr Thr Ser
35 40 45

Ser Leu Ser Ala Ser Leu Gly Asp Arg Val Thr Ile Ser Cys Arg Ala
50 55 60

Ser Gln Asp Ile Ser Lys Tyr Leu Asn Trp Tyr Gln Gln Lys Pro Asp
65 70 75 80

Gly Thr Val Lys Leu Leu Ile Tyr His Thr Ser Arg Leu His Ser Gly
85 90 95

Val Pro Ser Arg Phe Ser Gly Ser Gly Ser Gly Thr Asp Tyr Ser Leu
100 105 110

-continued

```
Thr Ile Ser Asn Leu Glu Gln Glu Asp Ile Ala Thr Tyr Phe Cys Gln
        115                 120                 125

Gln Gly Asn Thr Leu Pro Tyr Thr Phe Gly Gly Gly Thr Lys Leu Glu
    130                 135                 140

Ile Thr Gly Gly Gly Gly Ser Gly Gly Gly Gly Ser Gly Gly Gly Gly
145                 150                 155                 160

Ser Glu Val Lys Leu Gln Glu Ser Gly Pro Gly Leu Val Ala Pro Ser
                165                 170                 175

Gln Ser Leu Ser Val Thr Cys Thr Val Ser Gly Val Ser Leu Pro Asp
            180                 185                 190

Tyr Gly Val Ser Trp Ile Arg Gln Pro Pro Arg Lys Gly Leu Glu Trp
        195                 200                 205

Leu Gly Val Ile Trp Gly Ser Glu Thr Thr Tyr Tyr Asn Ser Ala Leu
    210                 215                 220

Lys Ser Arg Leu Thr Ile Ile Lys Asp Asn Ser Lys Ser Gln Val Phe
225                 230                 235                 240

Leu Lys Met Asn Ser Leu Gln Thr Asp Asp Thr Ala Ile Tyr Tyr Cys
                245                 250                 255

Ala Lys His Tyr Tyr Tyr Gly Gly Ser Tyr Ala Met Asp Tyr Trp Gly
            260                 265                 270

Gln Gly Thr Ser Val Thr Val Ser Ser Thr Thr Thr Pro Ala Pro Arg
        275                 280                 285

Pro Pro Thr Pro Ala Pro Thr Ile Ala Ser Gln Pro Leu Ser Leu Arg
    290                 295                 300

Pro Glu Ala Cys Arg Pro Ala Ala Gly Gly Ala Val His Thr Arg Gly
305                 310                 315                 320

Leu Asp Phe Ala Cys Asp Ile Tyr Ile Trp Ala Pro Leu Ala Gly Thr
                325                 330                 335

Cys Gly Val Leu Leu Leu Ser Leu Val Ile Thr Leu Tyr Cys Met Asp
            340                 345                 350

Gln Gln Ala Ile Tyr Ala Glu Leu Asn Leu Pro Thr Asp Ser Gly Pro
        355                 360                 365

Glu Ser Ser Ser Pro Ser Ser Leu Pro Arg Asp Val Cys Gln Gly Ser
    370                 375                 380

Pro Trp His Gln Phe Ala Leu Lys Leu Ser Cys Arg Val Lys Phe Ser
385                 390                 395                 400

Arg Ser Ala Asp Ala Pro Ala Tyr Gln Gln Gly Gln Asn Gln Leu Tyr
                405                 410                 415

Asn Glu Leu Asn Leu Gly Arg Arg Glu Glu Tyr Asp Val Leu Asp Lys
            420                 425                 430

Arg Arg Gly Arg Asp Pro Glu Met Gly Gly Lys Pro Arg Arg Lys Asn
        435                 440                 445

Pro Gln Glu Gly Leu Tyr Asn Glu Leu Gln Lys Asp Lys Met Ala Glu
    450                 455                 460

Ala Tyr Ser Glu Ile Gly Met Lys Gly Glu Arg Arg Arg Gly Lys Gly
465                 470                 475                 480

His Asp Gly Leu Tyr Gln Gly Leu Ser Thr Ala Thr Lys Asp Thr Tyr
                485                 490                 495

Asp Ala Leu His Met Gln Ala Leu Pro Pro Arg Gly Ser Gly Glu Gly
            500                 505                 510

Arg Gly Ser Leu Leu Thr Cys Gly Asp Val Glu Glu Asn Pro Gly Pro
        515                 520                 525

Met Ala Leu Pro Val Thr Ala Leu Leu Leu Pro Leu Ala Leu Leu Leu
```

-continued

```
    530                 535                 540

His Ala Ala Arg Pro Asn Trp Val Asn Val Ile Ser Asp Leu Lys Lys
545                 550                 555                 560

Ile Glu Asp Leu Ile Gln Ser Met His Ile Asp Ala Thr Leu Tyr Thr
                565                 570                 575

Glu Ser Asp Val His Pro Ser Cys Lys Val Thr Ala Met Lys Cys Phe
            580                 585                 590

Leu Leu Glu Leu Gln Val Ile Ser Leu Glu Ser Gly Asp Ala Ser Ile
        595                 600                 605

His Asp Thr Val Glu Asn Leu Ile Ile Leu Ala Asn Asn Ser Leu Ser
    610                 615                 620

Ser Asn Gly Asn Val Thr Glu Ser Gly Cys Lys Glu Cys Glu Glu Leu
625                 630                 635                 640

Glu Glu Lys Asn Ile Lys Glu Phe Leu Gln Ser Phe Val His Ile Val
                645                 650                 655

Gln Met Phe Ile Asn Thr Ser Thr Thr Thr Pro Ala Pro Arg Pro Pro
            660                 665                 670

Thr Pro Ala Pro Thr Ile Ala Ser Gln Pro Leu Ser Leu Arg Pro Glu
        675                 680                 685

Ala Cys Arg Pro Ala Ala Gly Gly Ala Val His Thr Arg Gly Leu Asp
    690                 695                 700

Phe Ala Cys Asp Ile Tyr Ile Trp Ala Pro Leu Ala Gly Thr Cys Gly
705                 710                 715                 720

Val Leu Leu Leu Ser Leu Val Ile Thr Leu Tyr Cys
                725                 730


<210> SEQ ID NO 81
<211> LENGTH: 2165
<212> TYPE: DNA
<213> ORGANISM: Homo sapiens
<220> FEATURE:
<221> NAME/KEY: misc_feature
<223> OTHER INFORMATION: NK19-12b DNA

<400> SEQUENCE: 81

ggatccgaat tcgccgccac catggcctta ccagtgaccg ccttgctcct gccgctggcc     60

ttgctgctcc acgccgccag gccggactac aaagacgatg acgataaagg cggtggtggc    120

tctggtggtg gcggcagcga catccagatg acacagacta catcctccct gtctgcctct    180

ctgggagaca gagtcaccat cagttgcagg gcaagtcagg acattagtaa atatttaaat    240

tggtatcagc agaaaccaga tggaactgtt aaactcctga tctaccatac atcaagatta    300

cactcaggag tcccatcaag gttcagtggc agtgggtctg gaacagatta ttctctcacc    360

attagcaacc tggagcaaga agatattgcc acttactttt gccaacaggg taatacgctt    420

ccgtacacgt tcggaggggg gaccaagctg gagatcacag gtggcggtgg ctcgggcggt    480

ggtgggtcgg gtggcggcgg atctgaggtg aaactgcagg agtcaggacc tggcctggtg    540

gcgccctcac agagcctgtc cgtcacatgc actgtctcag gggtctcatt acccgactat    600

ggtgtaagct ggattcgcca gcctccacga aagggtctgg agtggctggg agtaatatgg    660

ggtagtgaaa ccacatacta taattcagct ctcaaatcca gactgaccat catcaaggac    720

aactccaaga gccaagtttt cttaaaaatg aacagtctgc aaactgatga cacagccatt    780

tactactgtg ccaaacatta ttactacggt ggtagctatg ctatggacta ctggggccaa    840

ggaacctcag tcaccgtctc ctcaaccacg acgccagcgc cgcgaccacc aacaccggcg    900
```

cccaccatcg cgtcgcagcc cctgtccctg cgcccagagg cgtgccggcc agcggcgggg 960
ggcgcagtgc acacgagggg gctggacttc gcctgtgata tctacatctg ggcgcccttg 1020
gccgggactt gtggggtcct tctcctgtca ctggttatca ccctttactg catgatcgaa 1080
acatacaacc aaacttctcc ccgatctgcg gccactggac tgcccatcag catgaaaaga 1140
gtgaagttca gcaggagcgc agacgccccc gcgtaccagc agggccagaa ccagctctat 1200
aacgagctca atctaggacg aagagaggag tacgatgttt tggacaagag acgtggccgg 1260
gaccctgaga tgggggggaaa gccgagaagg aagaaccctc aggaaggcct gtacaatgaa 1320
ctgcagaaag ataagatggc ggaggcctac agtgagattg ggatgaaagg cgagcgccgg 1380
aggggcaagg ggcacgatgg cctttaccag ggtctcagta cagccaccaa ggacacctac 1440
gacgcccttc acatgcaggc cctgccccct cgcggctctg gcgagggaag gggttccctg 1500
cttacttgcg gcgacgtcga agagaatccc ggtccgatgg ccctcccagt aactgccctc 1560
cttttgcccc tcgcactcct tcttcatgcc gctcgcccca actgggtcaa cgtgattagc 1620
gatttgaaga aaatcgagga ccttatacag tctatgcata ttgacgctac actgtatact 1680
gagagtgatg tacacccgtc ctgtaaggta acggccatga aatgctttct tctggagctc 1740
caggtcatca gcttggagtc tggggacgca agcatccacg atacggttga aaacctcatc 1800
atccttgcga acaactctct ctcatctaat ggaaacgtta cagagagtgg gtgtaaggag 1860
tgcgaagagt tggaagaaaa aaacatcaaa gaatttcttc aatccttcgt tcacatagtg 1920
caaatgttca ttaacacgtc cactaccaca cccgccccga ggccacctac gccggcaccg 1980
actatcgcca gtcaacccct ctctctgcgc cccgaggctt gccggcctgc ggctggtggg 2040
gcggtccaca cccggggcct ggattttgcg tgcgatatat acatctgggc acctcttgcc 2100
ggcacctgcg gagtgctgct tctctcactc gttattacgc tgtactgcta agcggccgcg 2160
tcgac 2165

<210> SEQ ID NO 82
<211> LENGTH: 709
<212> TYPE: PRT
<213> ORGANISM: Homo sapiens
<220> FEATURE:
<221> NAME/KEY: MISC_FEATURE
<223> OTHER INFORMATION: NK19-12b Protein

<400> SEQUENCE: 82

Met Ala Leu Pro Val Thr Ala Leu Leu Leu Pro Leu Ala Leu Leu Leu
1 5 10 15

His Ala Ala Arg Pro Asp Tyr Lys Asp Asp Asp Asp Lys Gly Gly Gly
20 25 30

Gly Ser Gly Gly Gly Gly Ser Asp Ile Gln Met Thr Gln Thr Thr Ser
35 40 45

Ser Leu Ser Ala Ser Leu Gly Asp Arg Val Thr Ile Ser Cys Arg Ala
50 55 60

Ser Gln Asp Ile Ser Lys Tyr Leu Asn Trp Tyr Gln Gln Lys Pro Asp
65 70 75 80

Gly Thr Val Lys Leu Leu Ile Tyr His Thr Ser Arg Leu His Ser Gly
85 90 95

Val Pro Ser Arg Phe Ser Gly Ser Gly Ser Gly Thr Asp Tyr Ser Leu
100 105 110

Thr Ile Ser Asn Leu Glu Gln Glu Asp Ile Ala Thr Tyr Phe Cys Gln
115 120 125

```
Gln Gly Asn Thr Leu Pro Tyr Thr Phe Gly Gly Gly Thr Lys Leu Glu
    130                 135                 140

Ile Thr Gly Gly Gly Gly Ser Gly Gly Gly Gly Ser Gly Gly Gly Gly
145                 150                 155                 160

Ser Glu Val Lys Leu Gln Glu Ser Gly Pro Gly Leu Val Ala Pro Ser
                165                 170                 175

Gln Ser Leu Ser Val Thr Cys Thr Val Ser Gly Val Ser Leu Pro Asp
            180                 185                 190

Tyr Gly Val Ser Trp Ile Arg Gln Pro Pro Arg Lys Gly Leu Glu Trp
        195                 200                 205

Leu Gly Val Ile Trp Gly Ser Glu Thr Thr Tyr Tyr Asn Ser Ala Leu
    210                 215                 220

Lys Ser Arg Leu Thr Ile Ile Lys Asp Asn Ser Lys Ser Gln Val Phe
225                 230                 235                 240

Leu Lys Met Asn Ser Leu Gln Thr Asp Asp Thr Ala Ile Tyr Tyr Cys
                245                 250                 255

Ala Lys His Tyr Tyr Tyr Gly Gly Ser Tyr Ala Met Asp Tyr Trp Gly
            260                 265                 270

Gln Gly Thr Ser Val Thr Val Ser Ser Thr Thr Thr Pro Ala Pro Arg
        275                 280                 285

Pro Pro Thr Pro Ala Pro Thr Ile Ala Ser Gln Pro Leu Ser Leu Arg
    290                 295                 300

Pro Glu Ala Cys Arg Pro Ala Ala Gly Gly Ala Val His Thr Arg Gly
305                 310                 315                 320

Leu Asp Phe Ala Cys Asp Ile Tyr Ile Trp Ala Pro Leu Ala Gly Thr
                325                 330                 335

Cys Gly Val Leu Leu Leu Ser Leu Val Ile Thr Leu Tyr Cys Met Ile
            340                 345                 350

Glu Thr Tyr Asn Gln Thr Ser Pro Arg Ser Ala Ala Thr Gly Leu Pro
        355                 360                 365

Ile Ser Met Lys Arg Val Lys Phe Ser Arg Ser Ala Asp Ala Pro Ala
    370                 375                 380

Tyr Gln Gln Gly Gln Asn Gln Leu Tyr Asn Glu Leu Asn Leu Gly Arg
385                 390                 395                 400

Arg Glu Glu Tyr Asp Val Leu Asp Lys Arg Arg Gly Arg Asp Pro Glu
                405                 410                 415

Met Gly Gly Lys Pro Arg Arg Lys Asn Pro Gln Glu Gly Leu Tyr Asn
            420                 425                 430

Glu Leu Gln Lys Asp Lys Met Ala Glu Ala Tyr Ser Glu Ile Gly Met
        435                 440                 445

Lys Gly Glu Arg Arg Arg Gly Lys Gly His Asp Gly Leu Tyr Gln Gly
    450                 455                 460

Leu Ser Thr Ala Thr Lys Asp Thr Tyr Asp Ala Leu His Met Gln Ala
465                 470                 475                 480

Leu Pro Pro Arg Gly Ser Gly Glu Gly Arg Gly Ser Leu Leu Thr Cys
                485                 490                 495

Gly Asp Val Glu Glu Asn Pro Gly Pro Met Ala Leu Pro Val Thr Ala
            500                 505                 510

Leu Leu Leu Pro Leu Ala Leu Leu Leu His Ala Ala Arg Pro Asn Trp
        515                 520                 525

Val Asn Val Ile Ser Asp Leu Lys Lys Ile Glu Asp Leu Ile Gln Ser
    530                 535                 540

Met His Ile Asp Ala Thr Leu Tyr Thr Glu Ser Asp Val His Pro Ser
```

-continued 545 550 555 560

Cys Lys Val Thr Ala Met Lys Cys Phe Leu Leu Glu Leu Gln Val Ile
565 570 575

Ser Leu Glu Ser Gly Asp Ala Ser Ile His Asp Thr Val Glu Asn Leu
580 585 590

Ile Ile Leu Ala Asn Asn Ser Leu Ser Ser Asn Gly Asn Val Thr Glu
595 600 605

Ser Gly Cys Lys Glu Cys Glu Glu Leu Glu Glu Lys Asn Ile Lys Glu
610 615 620

Phe Leu Gln Ser Phe Val His Ile Val Gln Met Phe Ile Asn Thr Ser
625 630 635 640

Thr Thr Thr Pro Ala Pro Arg Pro Pro Thr Pro Ala Pro Thr Ile Ala
645 650 655

Ser Gln Pro Leu Ser Leu Arg Pro Glu Ala Cys Arg Pro Ala Ala Gly
660 665 670

Gly Ala Val His Thr Arg Gly Leu Asp Phe Ala Cys Asp Ile Tyr Ile
675 680 685

Trp Ala Pro Leu Ala Gly Thr Cys Gly Val Leu Leu Leu Ser Leu Val
690 695 700

Ile Thr Leu Tyr Cys
705

<210> SEQ ID NO 83
<211> LENGTH: 2315
<212> TYPE: DNA
<213> ORGANISM: Homo sapiens
<220> FEATURE:
<221> NAME/KEY: misc_feature
<223> OTHER INFORMATION: NK19-13b DNA

<400> SEQUENCE: 83
ggatccgaat tcgccgccac catggcctta ccagtgaccg ccttgctcct gccgctggcc 60
ttgctgctcc acgccgccag gccggactac aaagacgatg acgataaagg cggtggtggc 120
tctggtggtg gcggcagcga catccagatg acacagacta catcctccct gtctgcctct 180
ctgggagaca gagtcaccat cagttgcagg gcaagtcagg acattagtaa atatttaaat 240
tggtatcagc agaaaccaga tggaactgtt aaactcctga tctaccatac atcaagatta 300
cactcaggag tcccatcaag gttcagtggc agtgggtctg gaacagatta ttctctcacc 360
attagcaacc tggagcaaga agatattgcc acttactttt gccaacaggg taatacgctt 420
ccgtacacgt tcggaggggg gaccaagctg gagatcacag gtggcggtgg ctcgggcggt 480
ggtgggtcgg gtggcggcgg atctgaggtg aaactgcagg agtcaggacc tggcctggtg 540
gcgccctcac agagcctgtc cgtcacatgc actgtctcag gggtctcatt acccgactat 600
ggtgtaagct ggattcgcca gcctccacga aagggtctgg agtggctggg agtaatatgg 660
ggtagtgaaa ccacatacta taattcagct ctcaaatcca gactgaccat catcaaggac 720
aactccaaga gccaagtttt cttaaaaatg aacagtctgc aaactgatga cacagccatt 780
tactactgtg ccaaacatta ttactacggt ggtagctatg ctatggacta ctggggccaa 840
ggaacctcag tcaccgtctc ctcaaccacg acgccagcgc cgcgaccacc aacaccggcg 900
cccaccatcg cgtcgcagcc cctgtccctg cgcccagagg cgtgccggcc agcggcgggg 960
ggcgcagtgc acacgagggg gctggacttc gcctgtgata tctacatctg ggcgcccttg 1020
gccgggactt gtggggtcct tctcctgtca ctggttatca ccctttactg caacagtcga 1080

-continued

```
agaaggtgtg ggcagaagaa aaagctagtg atcaacagtg gcaatggagc tgtggaggac   1140

agaaagccaa gtggactcaa cggagaggcc agcaagtctc aggaaatggt gcatttggtg   1200

aacaaggagt cgtcagaaac tccagaccag tttatgacag ctgatgagac aaggaacctg   1260

cagaatgtgg acatgaagat tggggtgaga gtgaagttca gcaggagcgc agacgccccc   1320

gcgtaccagc agggccagaa ccagctctat aacgagctca atctaggacg aagagaggag   1380

tacgatgttt tggacaagag acgtggccgg gaccctgaga tggggggaaa gccgagaagg   1440

aagaaccctc aggaaggcct gtacaatgaa ctgcagaaag ataagatggc ggaggcctac   1500

agtgagattg ggatgaaagg cgagcgccgg aggggcaagg ggcacgatgg cctttaccag   1560

ggtctcagta cagccaccaa ggacacctac gacgcccttc acatgcaggc cctgccccct   1620

cgcggctctg gcgagggaag ggggttccctg cttacttgcg gcgacgtcga agagaatccc   1680

ggtccgatgg ccctcccagt aactgccctc cttttgcccc tcgcactcct tcttcatgcc   1740

gctcgcccca actgggtcaa cgtgattagc gatttgaaga aaatcgagga ccttatacag   1800

tctatgcata ttgacgctac actgtatact gagagtgatg tacacccgtc ctgtaaggta   1860

acggccatga aatgctttct tctggagctc caggtcatca gcttggagtc tggggacgca   1920

agcatccacg atacggttga aaacctcatc atccttgcga acaactctct ctcatctaat   1980

ggaaacgtta cagagagtgg gtgtaaggag tgcgaagagt tggaagaaaa aaacatcaaa   2040

gaatttcttc aatccttcgt tcacatagtg caaatgttca ttaacacgtc cactaccaca   2100

cccgccccga ggccacctac gccggcaccg actatcgcca gtcaacccct ctctctgcgc   2160

cccgaggctt gccggcctgc ggctggtggg gcggtccaca cccggggcct ggattttgcg   2220

tgcgatatat acatctgggc acctcttgcc ggcacctgcg gagtgctgct tctctcactc   2280

gttattacgc tgtactgcta agcggccgcg tcgac                              2315
```

```
<210> SEQ ID NO 84
<211> LENGTH: 759
<212> TYPE: PRT
<213> ORGANISM: Homo sapiens
<220> FEATURE:
<221> NAME/KEY: MISC_FEATURE
<223> OTHER INFORMATION: NK19-13b Protein

<400> SEQUENCE: 84

Met Ala Leu Pro Val Thr Ala Leu Leu Leu Pro Leu Ala Leu Leu Leu
1               5                   10                  15

His Ala Ala Arg Pro Asp Tyr Lys Asp Asp Asp Asp Lys Gly Gly Gly
            20                  25                  30

Gly Ser Gly Gly Gly Gly Ser Asp Ile Gln Met Thr Gln Thr Thr Ser
        35                  40                  45

Ser Leu Ser Ala Ser Leu Gly Asp Arg Val Thr Ile Ser Cys Arg Ala
    50                  55                  60

Ser Gln Asp Ile Ser Lys Tyr Leu Asn Trp Tyr Gln Gln Lys Pro Asp
65                  70                  75                  80

Gly Thr Val Lys Leu Leu Ile Tyr His Thr Ser Arg Leu His Ser Gly
                85                  90                  95

Val Pro Ser Arg Phe Ser Gly Ser Gly Ser Gly Thr Asp Tyr Ser Leu
            100                 105                 110

Thr Ile Ser Asn Leu Glu Gln Glu Asp Ile Ala Thr Tyr Phe Cys Gln
        115                 120                 125

Gln Gly Asn Thr Leu Pro Tyr Thr Phe Gly Gly Gly Thr Lys Leu Glu
    130                 135                 140
```

-continued

```
Ile Thr Gly Gly Gly Gly Ser Gly Gly Gly Gly Ser Gly Gly Gly Gly
145                 150                 155                 160

Ser Glu Val Lys Leu Gln Glu Ser Gly Pro Gly Leu Val Ala Pro Ser
                165                 170                 175

Gln Ser Leu Ser Val Thr Cys Thr Val Ser Gly Val Ser Leu Pro Asp
            180                 185                 190

Tyr Gly Val Ser Trp Ile Arg Gln Pro Pro Arg Lys Gly Leu Glu Trp
        195                 200                 205

Leu Gly Val Ile Trp Gly Ser Glu Thr Thr Tyr Tyr Asn Ser Ala Leu
    210                 215                 220

Lys Ser Arg Leu Thr Ile Ile Lys Asp Asn Ser Lys Ser Gln Val Phe
225                 230                 235                 240

Leu Lys Met Asn Ser Leu Gln Thr Asp Asp Thr Ala Ile Tyr Tyr Cys
                245                 250                 255

Ala Lys His Tyr Tyr Tyr Gly Gly Ser Tyr Ala Met Asp Tyr Trp Gly
            260                 265                 270

Gln Gly Thr Ser Val Thr Val Ser Ser Thr Thr Thr Pro Ala Pro Arg
        275                 280                 285

Pro Pro Thr Pro Ala Pro Thr Ile Ala Ser Gln Pro Leu Ser Leu Arg
    290                 295                 300

Pro Glu Ala Cys Arg Pro Ala Ala Gly Gly Ala Val His Thr Arg Gly
305                 310                 315                 320

Leu Asp Phe Ala Cys Asp Ile Tyr Ile Trp Ala Pro Leu Ala Gly Thr
                325                 330                 335

Cys Gly Val Leu Leu Leu Ser Leu Val Ile Thr Leu Tyr Cys Asn Ser
            340                 345                 350

Arg Arg Arg Cys Gly Gln Lys Lys Lys Leu Val Ile Asn Ser Gly Asn
        355                 360                 365

Gly Ala Val Glu Asp Arg Lys Pro Ser Gly Leu Asn Gly Glu Ala Ser
    370                 375                 380

Lys Ser Gln Glu Met Val His Leu Val Asn Lys Glu Ser Ser Glu Thr
385                 390                 395                 400

Pro Asp Gln Phe Met Thr Ala Asp Glu Thr Arg Asn Leu Gln Asn Val
                405                 410                 415

Asp Met Lys Ile Gly Val Arg Val Lys Phe Ser Arg Ser Ala Asp Ala
            420                 425                 430

Pro Ala Tyr Gln Gln Gly Gln Asn Gln Leu Tyr Asn Glu Leu Asn Leu
        435                 440                 445

Gly Arg Arg Glu Glu Tyr Asp Val Leu Asp Lys Arg Arg Gly Arg Asp
    450                 455                 460

Pro Glu Met Gly Gly Lys Pro Arg Arg Lys Asn Pro Gln Glu Gly Leu
465                 470                 475                 480

Tyr Asn Glu Leu Gln Lys Asp Lys Met Ala Glu Ala Tyr Ser Glu Ile
                485                 490                 495

Gly Met Lys Gly Glu Arg Arg Arg Gly Lys Gly His Asp Gly Leu Tyr
            500                 505                 510

Gln Gly Leu Ser Thr Ala Thr Lys Asp Thr Tyr Asp Ala Leu His Met
        515                 520                 525

Gln Ala Leu Pro Pro Arg Gly Ser Gly Glu Gly Arg Gly Ser Leu Leu
    530                 535                 540

Thr Cys Gly Asp Val Glu Glu Asn Pro Gly Pro Met Ala Leu Pro Val
545                 550                 555                 560
```

Thr Ala Leu Leu Leu Pro Leu Ala Leu Leu Leu His Ala Ala Arg Pro
565 570 575

Asn Trp Val Asn Val Ile Ser Asp Leu Lys Lys Ile Glu Asp Leu Ile
580 585 590

Gln Ser Met His Ile Asp Ala Thr Leu Tyr Thr Glu Ser Asp Val His
595 600 605

Pro Ser Cys Lys Val Thr Ala Met Lys Cys Phe Leu Leu Glu Leu Gln
610 615 620

Val Ile Ser Leu Glu Ser Gly Asp Ala Ser Ile His Asp Thr Val Glu
625 630 635 640

Asn Leu Ile Ile Leu Ala Asn Asn Ser Leu Ser Ser Asn Gly Asn Val
645 650 655

Thr Glu Ser Gly Cys Lys Glu Cys Glu Glu Leu Glu Glu Lys Asn Ile
660 665 670

Lys Glu Phe Leu Gln Ser Phe Val His Ile Val Gln Met Phe Ile Asn
675 680 685

Thr Ser Thr Thr Thr Pro Ala Pro Arg Pro Pro Thr Pro Ala Pro Thr
690 695 700

Ile Ala Ser Gln Pro Leu Ser Leu Arg Pro Glu Ala Cys Arg Pro Ala
705 710 715 720

Ala Gly Gly Ala Val His Thr Arg Gly Leu Asp Phe Ala Cys Asp Ile
725 730 735

Tyr Ile Trp Ala Pro Leu Ala Gly Thr Cys Gly Val Leu Leu Leu Ser
740 745 750

Leu Val Ile Thr Leu Tyr Cys
755

<210> SEQ ID NO 85
<211> LENGTH: 6488
<212> TYPE: DNA
<213> ORGANISM: Homo sapiens
<220> FEATURE:
<221> NAME/KEY: misc_feature
<223> OTHER INFORMATION: NK19 DNA

<400> SEQUENCE: 85
atgaaagacc ccacctgtag gtttggcaag ctagcttaag taacgccatt ttgcaaggca 60
tggaaaatac ataactgaga atagagaagt tcagatcaag gttaggaaca gagagacagc 120
agaatatggg ccaaacagga tatctgtggt aagcagttcc tgccccggct cagggccaag 180
aacagatggt ccccagatgc ggtcccgccc tcagcagttt ctagagaacc atcagatgtt 240
tccagggtgc cccaaggacc tgaaatgacc ctgtgcctta tttgaactaa ccaatcagtt 300
cgcttctcgc ttctgttcgc gcgcttctgc tccccgagct caataaaaga gcccacaacc 360
cctcactcgg cgcgccagtc ctccgataga ctgcgtcgcc cgggtacccg tattcccaat 420
aaagcctctt gctgtttgca tccgaatcgt ggactcgctg atccttggga gggtctcctc 480
agattgattg actgcccacc tcgggggtct ttcatttgga ggttccaccg agatttggag 540
acccctgccc agggaccacc gacccccccg ccgggaggta agctggccag cggtcgtttc 600
gtgtctgtct ctgtctttgt gcgtgtttgt gccggcatct aatgtttgcg cctgcgtctg 660
tactagttag ctaactagct ctgtatctgg cggacccgtg gtggaactga cgagttctga 720
acacccggcc gcaaccctgg gagacgtccc agggactttg ggggccgttt ttgtggcccg 780
acctgaggaa gggagtcgat gtggaatccg accccgtcag gatatgtggt tctggtagga 840
gacgagaacc taaaacagtt cccgcctccg tctgaatttt tgctttcggt ttggaaccga 900

-continued

```
agccgcgcgt cttgtctgct gcagcgctgc agcatcgttc tgtgttgtct ctgtctgact    960
gtgtttctgt atttgtctga aaattagggc cagactgtta ccactccctt aagtttgacc   1020
ttaggtcact ggaaagatgt cgagcggatc gctcacaacc agtcggtaga tgtcaagaag   1080
agacgttggg ttaccttctg ctctgcagaa tggccaacct ttaacgtcgg atggccgcga   1140
gacggcacct ttaaccgaga cctcatcacc caggttaaga tcaaggtctt ttcacctggc   1200
ccgcatggac acccagacca ggtcccctac atcgtgacct gggaagcctt ggcttttgac   1260
ccccctccct gggtcaagcc ctttgtacac cctaagcctc cgcctcctct tcctccatcc   1320
gccccgtctc tcccccttga acctcctcgt tcgaccccgc ctcgatcctc cctttatcca   1380
gccctcactc cttctctagg cgccggaatt cgttaacctc gagcgggatc aattccgccc   1440
ccccccctaac gttactggcc gaagccgctt ggaataaggc cggtgtgcgt ttgtctatat   1500
gttattttcc accatattgc cgtcttttgg caatgtgagg gcccggaaac ctggccctgt   1560
cttcttgacg agcattccta ggggtctttc ccctctcgcc aaaggaatgc aaggtctgtt   1620
gaatgtcgtg aaggaagcag ttcctctgga agcttcttga agacaaacaa cgtctgtagc   1680
gaccctttgc aggcagcgga acccccccacc tggcgacagg tgcctctgcg gccaaaagcc   1740
acgtgtataa gatacacctg caaaggcggc acaaccccag tgccacgttg tgagttggat   1800
agttgtggaa agagtcaaat ggctctcctc aagcgtattc aacaaggggc tgaaggatgc   1860
ccagaaggta ccccattgta tgggatctga tctggggcct cggtgcacat gctttacatg   1920
tgtttagtcg aggttaaaaa aacgtctagg ccccccgaac cacggggacg tggttttcct   1980
ttgaaaaaca cgataatacc atggtgagca agggcgagga gctgttcacc ggggtggtgc   2040
ccatcctggt cgagctggac ggcgacgtaa acggccacaa gttcagcgtg tccggcgagg   2100
gcgagggcga tgccacctac ggcaagctga ccctgaagtt catctgcacc accggcaagc   2160
tgcccgtgcc ctggcccacc ctcgtgacca ccctgaccta cggcgtgcag tgcttcagcc   2220
gctaccccga ccacatgaag cagcacgact tcttcaagtc cgccatgccc gaaggctacg   2280
tccaggagcg caccatcttc ttcaaggacg acggcaacta caagacccgc gccgaggtga   2340
agttcgaggg cgacaccctg gtgaaccgca tcgagctgaa gggcatcgac ttcaaggagg   2400
acggcaacat cctggggcac aagctggagt acaactacaa cagccacaac gtctatatca   2460
tggccgacaa gcagaagaac ggcatcaagg tgaacttcaa gatccgccac aacatcgagg   2520
acggcagcgt gcagctcgcc gaccactacc agcagaacac ccccatcggc gacggccccg   2580
tgctgctgcc cgacaaccac tacctgagca cccagtccgc cctgagcaaa gaccccaacg   2640
agaagcgcga tcacatggtc ctgctggagt tcgtgaccgc cgccgggatc actctcggca   2700
tggacgagct gtacaagtaa agcggccgcg actctagagt cgacctgcag gcatgcaagc   2760
ttcaggtagc cggctaacgt taacaaccgg tacctctaga actatagcta gcatgcgcaa   2820
atttaaagcg ctgatatcga taaaataaaa gattttattt agtctccaga aaaagggggg   2880
aatgaaagac cccacctgta ggtttggcaa gctagcttaa gtaacgccat tttgcaaggc   2940
atggaaaata cataactgag aatagagaag ttcagatcaa ggttaggaac agagagacag   3000
cagaatatgg gccaaacagg atatctgtgg taagcagttc ctgccccggc tcagggccaa   3060
gaacagatgg tccccagatg cggtcccgcc ctcagcagtt tctagagaac catcagatgt   3120
ttccagggtg ccccaaggac ctgaaatgac cctgtgcctt atttgaacta accaatcagt   3180
tcgcttctcg cttctgttcg cgcgcttctg ctccccgagc tcaataaaag agcccacaac   3240
```

-continued

```
ccctcactcg gcgcgccagt cctccgatag actgcgtcgc ccgggtaccc gtgtatccaa   3300
taaaccctct tgcagttgca tccgacttgt ggtctcgctg ttccttggga gggtctcctc   3360
tgagtgattg actacccgtc agcgggggtc tttcatgggt aacagtttct tgaagttgga   3420
gaacaacatt ctgagggtag gagtcgaata ttaagtaatc ctgactcaat tagccactgt   3480
tttgaatcca catactccaa tactcctgaa atagttcatt atggacagcg cagaaagagc   3540
tggggagaat tgtgaaattg ttatccgctc acaattccac acaacatacg agccggaagc   3600
ataaagtgta aagcctgggg tgcctaatga gtgagctaac tcacattaat tgcgttgcgc   3660
tcactgcccg ctttccagtc gggaaacctg tcgtgccagc tgcattaatg aatcggccaa   3720
cgcgcgggga gaggcggttt gcgtattggg cgctcttccg cttcctcgct cactgactcg   3780
ctgcgctcgg tcgttcggct gcggcgagcg gtatcagctc actcaaaggc ggtaatacgg   3840
ttatccacag aatcagggga taacgcagga aagaacatgt gagcaaaagg ccagcaaaag   3900
gccaggaacc gtaaaaaggc cgcgttgctg gcgtttttcc ataggctccg cccccctgac   3960
gagcatcaca aaaatcgacg ctcaagtcag aggtggcgaa acccgacagg actataaaga   4020
taccaggcgt ttccccctgg aagctccctc gtgcgctctc ctgttccgac cctgccgctt   4080
accggatacc tgtccgcctt tctcccttcg ggaagcgtgg cgctttctca tagctcacgc   4140
tgtaggtatc tcagttcggt gtaggtcgtt cgctccaagc tgggctgtgt gcacgaaccc   4200
cccgttcagc ccgaccgctg cgccttatcc ggtaactatc gtcttgagtc caacccggta   4260
agacacgact tatcgccact ggcagcagcc actggtaaca ggattagcag agcgaggtat   4320
gtaggcggtg ctacagagtt cttgaagtgg tggcctaact acggctacac tagaagaaca   4380
gtatttggta tctgcgctct gctgaagcca gttaccttcg gaaaaagagt tggtagctct   4440
tgatccggca aacaaaccac cgctggtagc ggtggttttt ttgtttgcaa gcagcagatt   4500
acgcgcagaa aaaaaggatc tcaagaagat cctttgatct tttctacggg gtctgacgct   4560
cagtggaacg aaaactcacg ttaagggatt ttggtcatga gattatcaaa aaggatcttc   4620
acctagatcc ttttaaatta aaaatgaagt tttaaatcaa tctaaagtat atatgagtaa   4680
acttggtctg acagttacca atgcttaatc agtgaggcac ctatctcagc gatctgtcta   4740
tttcgttcat ccatagttgc ctgactcccc gtcgtgtaga taactacgat acgggagggc   4800
ttaccatctg gccccagtgc tgcaatgata ccgcgagacc cacgctcacc ggctccagat   4860
ttatcagcaa taaaccagcc agccggaagg gccgagcgca gaagtggtcc tgcaacttta   4920
tccgcctcca tccagtctat taattgttgc cgggaagcta gagtaagtag ttcgccagtt   4980
aatagtttgc gcaacgttgt tgccattgct acaggcatcg tggtgtcacg ctcgtcgttt   5040
ggtatggctt cattcagctc cggttcccaa cgatcaaggc gagttacatg atcccccatg   5100
ttgtgcaaaa aagcggttag ctccttcggt cctccgatcg ttgtcagaag taagttggcc   5160
gcagtgttat cactcatggt tatggcagca ctgcataatt ctcttactgt catgccatcc   5220
gtaagatgct tttctgtgac tggtgagtac tcaaccaagt cattctgaga atagtgtatg   5280
cggcgaccga gttgctcttg cccggcgtca atacgggata ataccgcgcc acatagcaga   5340
actttaaaag tgctcatcat tggaaaacgt tcttcggggc gaaaactctc aaggatctta   5400
ccgctgttga gatccagttc gatgtaaccc actcgtgcac ccaactgatc ttcagcatct   5460
tttactttca ccagcgtttc tgggtgagca aaaacaggaa ggcaaaatgc cgcaaaaaag   5520
ggaataaggg cgacacggaa atgttgaata ctcatactct tcctttttca atattattga   5580
agcatttatc agggttattg tctcatgagc ggatacatat ttgaatgtat ttagaaaaat   5640
```

aaacaaatag gggttccgcg cacatttccc cgaaaagtgc cacctgacgt ctaagaaacc 5700
attattatca tgacattaac ctataaaaat aggcgtatca cgaggccctt tcgtctcgcg 5760
cgtttcggtg atgacggtga aaacctctga cacatgcagc tcccggagac ggtcacagct 5820
tgtctgtaag cggatgccgg gagcagacaa gcccgtcagg gcgcgtcagc gggtgttggc 5880
gggtgtcggg gctggcttaa ctatgcggca tcagagcaga ttgtactgag agtgcaccat 5940
atgcggtgtg aaataccgca cagatgcgta aggagaaaat accgcatcag gcgccattcg 6000
ccattcaggc tgcgcaactg ttgggaaggg cgatcggtgc gggcctcttc gctattacgc 6060
cagctggcga aagggggatg tgctgcaagg cgattaagtt gggtaacgcc agggttttcc 6120
cagtcacgac gttgtaaaac gacggcgcaa ggaatggtgc atgcaaggag atggcgccca 6180
acagtccccc ggccacgggg cctgccacca tacccacgcc gaaacaagcg ctcatgagcc 6240
cgaagtggcg agcccgatct tccccatcgg tgatgtcggc gatataggcg ccagcaaccg 6300
cacctgtggc gccggtgatg ccggccacga tgcgtccggc gtagaggcga ttagtccaat 6360
ttgttaaaga caggatatca gtggtccagg ctctagtttt gactcaacaa tatcaccagc 6420
tgaagcctat agagtacgag ccatagataa aataaaagat tttatttagt ctccagaaaa 6480
aggggga 6488

<210> SEQ ID NO 86
<211> LENGTH: 486
<212> TYPE: PRT
<213> ORGANISM: Homo sapiens
<220> FEATURE:
<221> NAME/KEY: MISC_FEATURE
<223> OTHER INFORMATION: NK19 PROTEIN

<400> SEQUENCE: 86

Met Ala Leu Pro Val Thr Ala Leu Leu Leu Pro Leu Ala Leu Leu Leu
1 5 10 15

His Ala Ala Arg Pro Asp Ile Gln Met Thr Gln Thr Thr Ser Ser Leu
20 25 30

Ser Ala Ser Leu Gly Asp Arg Val Thr Ile Ser Cys Arg Ala Ser Gln
35 40 45

Asp Ile Ser Lys Tyr Leu Asn Trp Tyr Gln Gln Lys Pro Asp Gly Thr
50 55 60

Val Lys Leu Leu Ile Tyr His Thr Ser Arg Leu His Ser Gly Val Pro
65 70 75 80

Ser Arg Phe Ser Gly Ser Gly Ser Gly Thr Asp Tyr Ser Leu Thr Ile
85 90 95

Ser Asn Leu Glu Gln Glu Asp Ile Ala Thr Tyr Phe Cys Gln Gln Gly
100 105 110

Asn Thr Leu Pro Tyr Thr Phe Gly Gly Gly Thr Lys Leu Glu Ile Thr
115 120 125

Gly Gly Gly Gly Ser Gly Gly Gly Gly Ser Gly Gly Gly Gly Ser Glu
130 135 140

Val Lys Leu Gln Glu Ser Gly Pro Gly Leu Val Ala Pro Ser Gln Ser
145 150 155 160

Leu Ser Val Thr Cys Thr Val Ser Gly Val Ser Leu Pro Asp Tyr Gly
165 170 175

Val Ser Trp Ile Arg Gln Pro Pro Arg Lys Gly Leu Glu Trp Leu Gly
180 185 190

Val Ile Trp Gly Ser Glu Thr Thr Tyr Tyr Asn Ser Ala Leu Lys Ser

-continued

```
        195                 200                 205

Arg Leu Thr Ile Ile Lys Asp Asn Ser Lys Ser Gln Val Phe Leu Lys
    210                 215                 220

Met Asn Ser Leu Gln Thr Asp Asp Thr Ala Ile Tyr Tyr Cys Ala Lys
225                 230                 235                 240

His Tyr Tyr Tyr Gly Gly Ser Tyr Ala Met Asp Tyr Trp Gly Gln Gly
                245                 250                 255

Thr Ser Val Thr Val Ser Ser Thr Thr Thr Pro Ala Pro Arg Pro Pro
            260                 265                 270

Thr Pro Ala Pro Thr Ile Ala Ser Gln Pro Leu Ser Leu Arg Pro Glu
        275                 280                 285

Ala Cys Arg Pro Ala Ala Gly Gly Ala Val His Thr Arg Gly Leu Asp
    290                 295                 300

Phe Ala Cys Asp Ile Tyr Ile Trp Ala Pro Leu Ala Gly Thr Cys Gly
305                 310                 315                 320

Val Leu Leu Leu Ser Leu Val Ile Thr Leu Tyr Cys Lys Arg Gly Arg
                325                 330                 335

Lys Lys Leu Leu Tyr Ile Phe Lys Gln Pro Phe Met Arg Pro Val Gln
            340                 345                 350

Thr Thr Gln Glu Glu Asp Gly Cys Ser Cys Arg Phe Pro Glu Glu Glu
        355                 360                 365

Glu Gly Gly Cys Glu Leu Arg Val Lys Phe Ser Arg Ser Ala Asp Ala
    370                 375                 380

Pro Ala Tyr Gln Gln Gly Gln Asn Gln Leu Tyr Asn Glu Leu Asn Leu
385                 390                 395                 400

Gly Arg Arg Glu Glu Tyr Asp Val Leu Asp Lys Arg Arg Gly Arg Asp
                405                 410                 415

Pro Glu Met Gly Gly Lys Pro Arg Arg Lys Asn Pro Gln Glu Gly Leu
            420                 425                 430

Tyr Asn Glu Leu Gln Lys Asp Lys Met Ala Glu Ala Tyr Ser Glu Ile
        435                 440                 445

Gly Met Lys Gly Glu Arg Arg Arg Gly Lys Gly His Asp Gly Leu Tyr
    450                 455                 460

Gln Gly Leu Ser Thr Ala Thr Lys Asp Thr Tyr Asp Ala Leu His Met
465                 470                 475                 480

Gln Ala Leu Pro Pro Arg
                485
```

<210> SEQ ID NO 87
<211> LENGTH: 6488
<212> TYPE: DNA
<213> ORGANISM: Homo sapiens
<220> FEATURE:
<221> NAME/KEY: misc_feature
<223> OTHER INFORMATION: MSCV-IRES-GFP expression plasmid

<400> SEQUENCE: 87

```
atgaaagacc ccacctgtag gtttggcaag ctagcttaag taacgccatt ttgcaaggca      60

tggaaaatac ataactgaga atagagaagt tcagatcaag gttaggaaca gagagacagc     120

agaatatggg ccaaacagga tatctgtggt aagcagttcc tgccccggct cagggccaag     180

aacagatggt ccccagatgc ggtcccgccc tcagcagttt ctagagaacc atcagatgtt     240

tccagggtgc cccaaggacc tgaaatgacc ctgtgcctta tttgaactaa ccaatcagtt     300

cgcttctcgc ttctgttcgc gcgcttctgc tccccgagct caataaaaga gcccacaacc     360
```

-continued

```
cctcactcgg cgcgccagtc ctccgataga ctgcgtcgcc cgggtacccg tattcccaat    420
aaagcctctt gctgtttgca tccgaatcgt ggactcgctg atccttggga gggtctcctc    480
agattgattg actgcccacc tcgggggtct ttcatttgga ggttccaccg agatttggag    540
acccctgccc agggaccacc gacccccccg ccgggaggta agctggccag cggtcgtttc    600
gtgtctgtct ctgtctttgt gcgtgtttgt gccggcatct aatgtttgcg cctgcgtctg    660
tactagttag ctaactagct ctgtatctgg cggacccgtg gtggaactga cgagttctga    720
acacccggcc gcaaccctgg gagacgtccc agggactttg ggggccgttt ttgtggcccg    780
acctgaggaa gggagtcgat gtggaatccg accccgtcag gatatgtggt tctggtagga    840
gacgagaacc taaaacagtt cccgcctccg tctgaatttt tgctttcggt ttggaaccga    900
agccgcgcgt cttgtctgct gcagcgctgc agcatcgttc tgtgttgtct ctgtctgact    960
gtgtttctgt atttgtctga aaattagggc cagactgtta ccactccctt aagtttgacc   1020
ttaggtcact ggaaagatgt cgagcggatc gctcacaacc agtcggtaga tgtcaagaag   1080
agacgttggg ttaccttctg ctctgcagaa tggccaacct ttaacgtcgg atggccgcga   1140
gacggcacct ttaaccgaga cctcatcacc caggttaaga tcaaggtctt ttcacctggc   1200
ccgcatggac acccagacca ggtcccctac atcgtgacct gggaagcctt ggcttttgac   1260
ccccctccct gggtcaagcc ctttgtacac cctaagcctc cgcctcctct tcctccatcc   1320
gccccgtctc tccccccttga acctcctcgt tcgaccccgc ctcgatcctc cctttatcca   1380
gccctcactc cttctctagg cgccggaatt cgttaacctc gagcgggatc aattccgccc   1440
ccccccctaac gttactggcc gaagccgctt ggaataaggc cggtgtgcgt ttgtctatat   1500
gttattttcc accatattgc cgtcttttgg caatgtgagg gcccggaaac ctggccctgt   1560
cttcttgacg agcattccta ggggtctttc ccctctcgcc aaaggaatgc aaggtctgtt   1620
gaatgtcgtg aaggaagcag ttcctctgga agcttcttga agacaaacaa cgtctgtagc   1680
gaccctttgc aggcagcgga accccccacc tggcgacagg tgcctctgcg gccaaaagcc   1740
acgtgtataa gatacacctg caaaggcggc acaaccccag tgccacgttg tgagttggat   1800
agttgtggaa agagtcaaat ggctctcctc aagcgtattc aacaaggggc tgaaggatgc   1860
ccagaaggta ccccattgta tgggatctga tctggggcct cggtgcacat gctttacatg   1920
tgtttagtcg aggttaaaaa aacgtctagg ccccccgaac cacggggacg tggttttcct   1980
ttgaaaaaca cgataatacc atggtgagca agggcgagga gctgttcacc ggggtggtgc   2040
ccatcctggt cgagctggac ggcgacgtaa acggccacaa gttcagcgtg tccggcgagg   2100
gcgagggcga tgccacctac ggcaagctga ccctgaagtt catctgcacc accggcaagc   2160
tgcccgtgcc ctggcccacc ctcgtgacca ccctgaccta cggcgtgcag tgcttcagcc   2220
gctaccccga ccacatgaag cagcacgact tcttcaagtc cgccatgccc gaaggctacg   2280
tccaggagcg caccatcttc ttcaaggacg acggcaacta caagacccgc gccgaggtga   2340
agttcgaggg cgacaccctg gtgaaccgca tcgagctgaa gggcatcgac ttcaaggagg   2400
acggcaacat cctggggcac aagctggagt acaactacaa cagccacaac gtctatatca   2460
tggccgacaa gcagaagaac ggcatcaagg tgaacttcaa gatccgccac aacatcgagg   2520
acggcagcgt gcagctcgcc gaccactacc agcagaacac ccccatcggc gacggccccg   2580
tgctgctgcc cgacaaccac tacctgagca cccagtccgc cctgagcaaa gaccccaacg   2640
agaagcgcga tcacatggtc ctgctggagt tcgtgaccgc cgccgggatc actctcggca   2700
tggacgagct gtacaagtaa agcggccgcg actctagagt cgacctgcag gcatgcaagc   2760
```

```
ttcaggtagc cggctaacgt taacaaccgg tacctctaga actatagcta gcatgcgcaa   2820
atttaaagcg ctgatatcga taaaataaaa gattttattt agtctccaga aaaagggggg   2880
aatgaaagac cccacctgta ggtttggcaa gctagcttaa gtaacgccat tttgcaaggc   2940
atggaaaata cataactgag aatagagaag ttcagatcaa ggttaggaac agagagacag   3000
cagaatatgg gccaaacagg atatctgtgg taagcagttc ctgccccggc tcagggccaa   3060
gaacagatgg tccccagatg cggtcccgcc ctcagcagtt tctagagaac catcagatgt   3120
ttccagggtg ccccaaggac ctgaaatgac cctgtgcctt atttgaacta accaatcagt   3180
tcgcttctcg cttctgttcg cgcgcttctg ctccccgagc tcaataaaag agcccacaac   3240
ccctcactcg gcgcgccagt cctccgatag actgcgtcgc ccgggtaccc gtgtatccaa   3300
taaaccctct tgcagttgca tccgacttgt ggtctcgctg ttccttggga gggtctcctc   3360
tgagtgattg actacccgtc agcgggggtc tttcatgggt aacagtttct tgaagttgga   3420
gaacaacatt ctgagggtag gagtcgaata ttaagtaatc ctgactcaat tagccactgt   3480
tttgaatcca catactccaa tactcctgaa atagttcatt atggacagcg cagaaagagc   3540
tggggagaat tgtgaaattg ttatccgctc acaattccac acaacatacg agccggaagc   3600
ataaagtgta aagcctgggg tgcctaatga gtgagctaac tcacattaat tgcgttgcgc   3660
tcactgcccg ctttccagtc gggaaacctg tcgtgccagc tgcattaatg aatcggccaa   3720
cgcgcgggga gaggcggttt gcgtattggg cgctcttccg cttcctcgct cactgactcg   3780
ctgcgctcgg tcgttcggct gcggcgagcg gtatcagctc actcaaaggc ggtaatacgg   3840
ttatccacag aatcagggga taacgcagga aagaacatgt gagcaaaagg ccagcaaaag   3900
gccaggaacc gtaaaaaggc cgcgttgctg gcgtttttcc ataggctccg cccccctgac   3960
gagcatcaca aaaatcgacg ctcaagtcag aggtggcgaa acccgacagg actataaaga   4020
taccaggcgt ttccccctgg aagctccctc gtgcgctctc ctgttccgac cctgccgctt   4080
accggatacc tgtccgcctt tctcccttcg ggaagcgtgg cgctttctca tagctcacgc   4140
tgtaggtatc tcagttcggt gtaggtcgtt cgctccaagc tgggctgtgt gcacgaaccc   4200
cccgttcagc ccgaccgctg cgccttatcc ggtaactatc gtcttgagtc caacccggta   4260
agacacgact tatcgccact ggcagcagcc actggtaaca ggattagcag agcgaggtat   4320
gtaggcggtg ctacagagtt cttgaagtgg tggcctaact acggctacac tagaagaaca   4380
gtatttggta tctgcgctct gctgaagcca gttaccttcg gaaaaagagt tggtagctct   4440
tgatccggca aacaaaccac cgctggtagc ggtggttttt ttgtttgcaa gcagcagatt   4500
acgcgcagaa aaaaaggatc tcaagaagat cctttgatct tttctacggg gtctgacgct   4560
cagtggaacg aaaactcacg ttaagggatt ttggtcatga gattatcaaa aaggatcttc   4620
acctagatcc ttttaaatta aaaatgaagt tttaaatcaa tctaaagtat atatgagtaa   4680
acttggtctg acagttacca atgcttaatc agtgaggcac ctatctcagc gatctgtcta   4740
tttcgttcat ccatagttgc ctgactcccc gtcgtgtaga taactacgat acgggagggc   4800
ttaccatctg gccccagtgc tgcaatgata ccgcgagacc cacgctcacc ggctccagat   4860
ttatcagcaa taaaccagcc agccggaagg gccgagcgca gaagtggtcc tgcaacttta   4920
tccgcctcca tccagtctat taattgttgc cgggaagcta gagtaagtag ttcgccagtt   4980
aatagtttgc gcaacgttgt tgccattgct acaggcatcg tggtgtcacg ctcgtcgttt   5040
ggtatggctt cattcagctc cggttcccaa cgatcaaggc gagttacatg atcccccatg   5100
```

-continued

```
ttgtgcaaaa aagcggttag ctccttcggt cctccgatcg ttgtcagaag taagttggcc   5160

gcagtgttat cactcatggt tatggcagca ctgcataatt ctcttactgt catgccatcc   5220

gtaagatgct tttctgtgac tggtgagtac tcaaccaagt cattctgaga atagtgtatg   5280

cggcgaccga gttgctcttg cccggcgtca atacgggata ataccgcgcc acatagcaga   5340

actttaaaag tgctcatcat tggaaaacgt tcttcggggc gaaaactctc aaggatctta   5400

ccgctgttga gatccagttc gatgtaaccc actcgtgcac ccaactgatc ttcagcatct   5460

tttactttca ccagcgtttc tgggtgagca aaaacaggaa ggcaaaatgc cgcaaaaaag   5520

ggaataaggg cgacacggaa atgttgaata ctcatactct tcctttttca atattattga   5580

agcatttatc agggttattg tctcatgagc ggatacatat ttgaatgtat ttagaaaaat   5640

aaacaaatag gggttccgcg cacatttccc cgaaaagtgc cacctgacgt ctaagaaacc   5700

attattatca tgacattaac ctataaaaat aggcgtatca cgaggccctt tcgtctcgcg   5760

cgtttcggtg atgacggtga aaacctctga cacatgcagc tcccggagac ggtcacagct   5820

tgtctgtaag cggatgccgg gagcagacaa gcccgtcagg gcgcgtcagc gggtgttggc   5880

gggtgtcggg gctggcttaa ctatgcggca tcagagcaga ttgtactgag agtgcaccat   5940

atgcggtgtg aaataccgca cagatgcgta aggagaaaat accgcatcag gcgccattcg   6000

ccattcaggc tgcgcaactg ttgggaaggg cgatcggtgc gggcctcttc gctattacgc   6060

cagctggcga aagggggatg tgctgcaagg cgattaagtt gggtaacgcc agggttttcc   6120

cagtcacgac gttgtaaaac gacggcgcaa ggaatggtgc atgcaaggag atggcgccca   6180

acagtccccc ggccacgggg cctgccacca tacccacgcc gaaacaagcg ctcatgagcc   6240

cgaagtggcg agcccgatct tccccatcgg tgatgtcggc gatataggcg ccagcaaccg   6300

cacctgtggc gccggtgatg ccggccacga tgcgtccggc gtagaggcga ttagtccaat   6360

ttgttaaaga caggatatca gtggtccagg ctctagtttt gactcaacaa tatcaccagc   6420

tgaagcctat agagtacgag ccatagataa aataaaagat tttatttagt ctccagaaaa   6480

aggggggga                                                           6488


<210> SEQ ID NO 88
<211> LENGTH: 117
<212> TYPE: PRT
<213> ORGANISM: Homo sapiens
<220> FEATURE:
<221> NAME/KEY: MISC_FEATURE
<223> OTHER INFORMATION: anti CLDN6 heavy chain

<400> SEQUENCE: 88

Glu Val Gln Leu Gln Gln Ser Gly Pro Glu Leu Val Lys Pro Gly Ala
1               5                   10                  15

Ser Met Lys Ile Ser Cys Lys Ala Ser Gly Tyr Ser Phe Thr Gly Tyr
            20                  25                  30

Thr Met Asn Trp Val Lys Gln Ser His Gly Lys Asn Leu Glu Trp Ile
        35                  40                  45

Gly Leu Ile Asn Pro Tyr Asn Gly Gly Thr Ile Tyr Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Leu Ser Leu Thr Ser Glu Asp Ser Ala Val Tyr Tyr Cys
                85                  90                  95

Ala Arg Asp Tyr Gly Phe Val Leu Asp Tyr Trp Gly Gln Gly Thr Thr
            100                 105                 110
```

```
Leu Thr Val Ser Ser
        115


<210> SEQ ID NO 89
<211> LENGTH: 107
<212> TYPE: PRT
<213> ORGANISM: Homo sapiens
<220> FEATURE:
<221> NAME/KEY: MISC_FEATURE
<223> OTHER INFORMATION: anti CLDN6 light chain 1

<400> SEQUENCE: 89

Gln Ile Val Leu Thr Gln Ser Pro Ala Ile Met Ser Ala Ser Pro Gly
1               5                   10                  15

Glu Lys Val Thr Ile Thr Cys Ser Ala Ser Ser Ser Val Ser Tyr Leu
            20                  25                  30

His Trp Phe Gln Gln Lys Pro Gly Thr Ser Pro Lys Leu Trp Val Tyr
        35                  40                  45

Ser Thr Ser Asn Leu Pro Ser Gly Val Pro Ala Arg Phe Gly Gly Ser
    50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Arg Ser Ile Tyr Pro Pro Trp
                85                  90                  95

Thr Phe Gly Gly Gly Thr Lys Leu Glu Ile Lys
            100                 105


<210> SEQ ID NO 90
<211> LENGTH: 107
<212> TYPE: PRT
<213> ORGANISM: Homo sapiens
<220> FEATURE:
<221> NAME/KEY: MISC_FEATURE
<223> OTHER INFORMATION: anti CLDN6 light chain 2

<400> SEQUENCE: 90

Gln Ile Val Leu Thr Gln Ser Pro Ser Ile Met Ser Val Ser Pro Gly
1               5                   10                  15

Glu Lys Val Thr Ile Thr Cys Ser Ala Ser Ser Ser Val Ser Tyr Met
            20                  25                  30

His Trp Phe Gln Gln Lys Pro Gly Thr Ser Pro Lys Leu Gly Ile Tyr
        35                  40                  45

Ser Thr Ser Asn Leu Ala Ser Gly Val Pro Ala Arg Phe Ser Gly Arg
    50                  55                  60

Gly Ser Gly Thr Ser Tyr Ser Leu Thr Ile Ser Arg Val Ala Ala Glu
65                  70                  75                  80

Asp Ala Ala Thr Tyr Tyr Cys Gln Gln Arg Ser Asn Tyr Pro Pro Trp
                85                  90                  95

Thr Phe Gly Gly Gly Thr Lys Leu Glu Ile Lys
            100                 105


<210> SEQ ID NO 91
<211> LENGTH: 107
<212> TYPE: PRT
<213> ORGANISM: Homo sapiens
<220> FEATURE:
<221> NAME/KEY: MISC_FEATURE
<223> OTHER INFORMATION: anti CLDN6 light chain 3

<400> SEQUENCE: 91
```

```
Gln Ile Val Leu Thr Gln Ser Pro Ser Ile Met Ser Val Ser Pro Gly
1               5                   10                  15

Glu Lys Val Thr Ile Thr Cys Ser Ala Ser Ser Ser Val Ser Tyr Met
            20                  25                  30

His Trp Phe Gln Gln Lys Pro Gly Thr Ser Pro Lys Leu Ser Ile Tyr
        35                  40                  45

Ser Thr Ser Asn Leu Ala Ser Gly Val Pro Ala Arg Phe Ser Gly Arg
    50                  55                  60

Gly Ser Gly Thr Ser Tyr Ser Leu Thr Ile Ser Arg Val Ala Ala Glu
65                  70                  75                  80

Asp Ala Ala Thr Tyr Tyr Cys Gln Gln Arg Ser Asn Tyr Pro Pro Trp
                85                  90                  95

Thr Phe Gly Gly Gly Thr Lys Leu Glu Ile Lys
            100                 105
```

<210> SEQ ID NO 92
<211> LENGTH: 8
<212> TYPE: PRT
<213> ORGANISM: Homo sapiens
<220> FEATURE:
<221> NAME/KEY: MISC_FEATURE
<223> OTHER INFORMATION: anti CLDN6 heavy chain CDR1

<400> SEQUENCE: 92

```
Gly Tyr Ser Phe Thr Gly Tyr Thr
1               5
```

<210> SEQ ID NO 93
<211> LENGTH: 8
<212> TYPE: PRT
<213> ORGANISM: Homo sapiens
<220> FEATURE:
<221> NAME/KEY: MISC_FEATURE
<223> OTHER INFORMATION: anti CLDN6 heavy chain CDR2

<400> SEQUENCE: 93

```
Ile Asn Pro Tyr Asn Gly Gly Thr
1               5
```

<210> SEQ ID NO 94
<211> LENGTH: 10
<212> TYPE: PRT
<213> ORGANISM: Homo sapiens
<220> FEATURE:
<221> NAME/KEY: MISC_FEATURE
<223> OTHER INFORMATION: anti CLDN6 heavy chain CDR3

<400> SEQUENCE: 94

```
Ala Arg Asp Tyr Gly Phe Val Leu Asp Tyr
1               5                   10
```

<210> SEQ ID NO 95
<211> LENGTH: 5
<212> TYPE: PRT
<213> ORGANISM: Homo sapiens
<220> FEATURE:
<221> NAME/KEY: MISC_FEATURE
<223> OTHER INFORMATION: anti CLDN6 light chain 1 CDR1

<400> SEQUENCE: 95

```
Ser Ser Val Ser Tyr
1               5
```

<210> SEQ ID NO 96

<211> LENGTH: 3
<212> TYPE: PRT
<213> ORGANISM: Homo sapiens
<220> FEATURE:
<221> NAME/KEY: MISC_FEATURE
<223> OTHER INFORMATION: anti CLDN6 light chain 1 CDR2

<400> SEQUENCE: 96

Ser Thr Ser
1

<210> SEQ ID NO 97
<211> LENGTH: 8
<212> TYPE: PRT
<213> ORGANISM: Homo sapiens
<220> FEATURE:
<221> NAME/KEY: MISC_FEATURE
<223> OTHER INFORMATION: anti CLDN6 light chain 1 CDR3

<400> SEQUENCE: 97

Gln Gln Arg Ser Ile Tyr Pro Pro
1 5

<210> SEQ ID NO 98
<211> LENGTH: 5
<212> TYPE: PRT
<213> ORGANISM: Homo sapiens
<220> FEATURE:
<221> NAME/KEY: MISC_FEATURE
<223> OTHER INFORMATION: anti CLDN6 light chain 2 CDR1

<400> SEQUENCE: 98

Ser Ser Val Ser Tyr
1 5

<210> SEQ ID NO 99
<211> LENGTH: 3
<212> TYPE: PRT
<213> ORGANISM: Homo sapiens
<220> FEATURE:
<221> NAME/KEY: MISC_FEATURE
<223> OTHER INFORMATION: anti CLDN6 light chain 2 CDR2

<400> SEQUENCE: 99

Ser Thr Ser
1

<210> SEQ ID NO 100
<211> LENGTH: 8
<212> TYPE: PRT
<213> ORGANISM: Homo sapiens
<220> FEATURE:
<221> NAME/KEY: MISC_FEATURE
<223> OTHER INFORMATION: anti CLDN6 light chain 2 CDR3

<400> SEQUENCE: 100

Gln Gln Arg Ser Asn Tyr Pro Pro
1 5

<210> SEQ ID NO 101
<211> LENGTH: 5
<212> TYPE: PRT
<213> ORGANISM: Homo sapiens
<220> FEATURE:
<221> NAME/KEY: MISC_FEATURE
<223> OTHER INFORMATION: anti CLDN6 LC CDR1

<400> SEQUENCE: 101

```
Ser Ser Val Ser Tyr
1               5


<210> SEQ ID NO 102
<211> LENGTH: 3
<212> TYPE: PRT
<213> ORGANISM: Homo sapiens
<220> FEATURE:
<221> NAME/KEY: MISC_FEATURE
<223> OTHER INFORMATION: anti CLDN6 LC3 CDR2

<400> SEQUENCE: 102

Ser Thr Ser
1


<210> SEQ ID NO 103
<211> LENGTH: 8
<212> TYPE: PRT
<213> ORGANISM: Homo sapiens
<220> FEATURE:
<221> NAME/KEY: MISC_FEATURE
<223> OTHER INFORMATION: anti CLDN6 LC3 CDR3

<400> SEQUENCE: 103

Gln Gln Arg Ser Asn Tyr Pro Pro
1               5


<210> SEQ ID NO 104
<211> LENGTH: 120
<212> TYPE: PRT
<213> ORGANISM: Homo sapiens
<220> FEATURE:
<221> NAME/KEY: MISC_FEATURE
<223> OTHER INFORMATION: anti CD19 heavy chain variable region

<400> SEQUENCE: 104

Gln Val Gln Leu Val Gln Ser Gly Gly Gly Val Val Gln Pro Gly Arg
1               5                   10                  15

Ser Leu Arg Leu Ser Cys Ala Ala Ser Gly Val Ser Leu Pro Asp Tyr
            20                  25                  30

Gly Val Ser Trp Val Arg Gln Ala Pro Gly Lys Gly Leu Glu Trp Val
        35                  40                  45

Ala Val Ile Trp Gly Ser Glu Thr Thr Tyr Tyr Asn Ser Ala Leu Lys
    50                  55                  60

Ser Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Leu Val Thr Val Ser Ser
        115                 120


<210> SEQ ID NO 105
<211> LENGTH: 107
<212> TYPE: PRT
<213> ORGANISM: Homo sapiens
<220> FEATURE:
<221> NAME/KEY: MISC_FEATURE
<223> OTHER INFORMATION: anti CD19 light chain variable region

<400> SEQUENCE: 105

Asp Ile Gln Met Thr Gln Ser Pro Ser Ser Leu Ser Ala Ser Val Gly
1               5                   10                  15
```

```
Asp Arg Val Thr Ile Thr Cys Arg Ala Ser Gln Asp Ile Ser Lys Tyr
            20                  25                  30

Leu Asn Trp Tyr Gln Gln Lys Pro Gly Lys Ala Ile Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Ala Thr Leu Pro Tyr
                85                  90                  95

Thr Phe Gly Pro Gly Thr Lys Val Asp Ile Lys
            100                 105


<210> SEQ ID NO 106
<211> LENGTH: 450
<212> TYPE: PRT
<213> ORGANISM: Homo sapiens
<220> FEATURE:
<221> NAME/KEY: MISC_FEATURE
<223> OTHER INFORMATION: anti CD19 heavy chain variable

<400> SEQUENCE: 106

Gln Val Gln Leu Val Gln Ser Gly Gly Gly Val Val Gln Pro Gly Arg
1               5                   10                  15

Ser Leu Arg Leu Ser Cys Ala Ala Ser Gly Val Ser Leu Pro Asp Tyr
            20                  25                  30

Gly Val Ser Trp Val Arg Gln Ala Pro Gly Lys Gly Leu Glu Trp Val
        35                  40                  45

Ala Val Ile Trp Gly Ser Glu Thr Thr Tyr Tyr Asn Ser Ala Leu Lys
    50                  55                  60

Ser Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
```

```
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450


<210> SEQ ID NO 107
<211> LENGTH: 214
<212> TYPE: PRT
<213> ORGANISM: Homo sapiens
<220> FEATURE:
<221> NAME/KEY: MISC_FEATURE
<223> OTHER INFORMATION: anti CD19 light chain variable

<400> SEQUENCE: 107

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Lys Tyr
            20                  25                  30

Leu Asn Trp Tyr Gln Gln Lys Pro Gly Lys Ala Ile Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Ala Thr Leu Pro Tyr
                85                  90                  95

Thr Phe Gly Pro Gly Thr Lys Val Asp Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160
```

-continued

```
Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 108
<211> LENGTH: 11
<212> TYPE: PRT
<213> ORGANISM: Homo sapiens
<220> FEATURE:
<221> NAME/KEY: MISC_FEATURE
<223> OTHER INFORMATION: anti CD19 LCCDR1

<400> SEQUENCE: 108

```
Arg Ala Ser Gln Asp Ile Ser Lys Tyr Leu Asn
1               5                   10
```

<210> SEQ ID NO 109
<211> LENGTH: 7
<212> TYPE: PRT
<213> ORGANISM: Homo sapiens
<220> FEATURE:
<221> NAME/KEY: MISC_FEATURE
<223> OTHER INFORMATION: anti CD19 LCCDR2

<400> SEQUENCE: 109

```
His Thr Ser Arg Leu His Ser
1               5
```

<210> SEQ ID NO 110
<211> LENGTH: 9
<212> TYPE: PRT
<213> ORGANISM: Homo sapiens
<220> FEATURE:
<221> NAME/KEY: MISC_FEATURE
<223> OTHER INFORMATION: anti CD19 LCCDR3

<400> SEQUENCE: 110

```
Gln Gln Gly Asn Thr Leu Pro Tyr Thr
1               5
```

<210> SEQ ID NO 111
<211> LENGTH: 10
<212> TYPE: PRT
<213> ORGANISM: Homo sapiens
<220> FEATURE:
<221> NAME/KEY: MISC_FEATURE
<223> OTHER INFORMATION: anti CD19 HCCDR1

<400> SEQUENCE: 111

```
Gly Val Ser Leu Pro Asp Tyr Gly Val Ser
1               5                   10
```

<210> SEQ ID NO 112
<211> LENGTH: 16
<212> TYPE: PRT
<213> ORGANISM: Homo sapiens
<220> FEATURE:
<221> NAME/KEY: MISC_FEATURE
<223> OTHER INFORMATION: anti CD19 HCCDR2

<400> SEQUENCE: 112

-continued

Val Ile Trp Gly Ser Glu Thr Thr Tyr Tyr Ser Ser Ser Leu Lys Ser
1 5 10 15

<210> SEQ ID NO 113
<211> LENGTH: 16
<212> TYPE: PRT
<213> ORGANISM: Homo sapiens
<220> FEATURE:
<221> NAME/KEY: MISC_FEATURE
<223> OTHER INFORMATION: anti CD19 HCCDR2

<400> SEQUENCE: 113

Val Ile Trp Gly Ser Glu Thr Thr Tyr Tyr Gln Ser Ser Leu Lys Ser
1 5 10 15

<210> SEQ ID NO 114
<211> LENGTH: 16
<212> TYPE: PRT
<213> ORGANISM: Homo sapiens
<220> FEATURE:
<221> NAME/KEY: MISC_FEATURE
<223> OTHER INFORMATION: anti CD19 HCCDR2

<400> SEQUENCE: 114

Val Ile Trp Gly Ser Glu Thr Thr Tyr Tyr Asn Ser Ser Leu Lys Ser
1 5 10 15

<210> SEQ ID NO 115
<211> LENGTH: 12
<212> TYPE: PRT
<213> ORGANISM: Homo sapiens
<220> FEATURE:
<221> NAME/KEY: MISC_FEATURE
<223> OTHER INFORMATION: anti CD19 HCCDR3

<400> SEQUENCE: 115

His Tyr Tyr Tyr Gly Gly Ser Tyr Ala Met Asp Tyr
1 5 10

<210> SEQ ID NO 116
<211> LENGTH: 242
<212> TYPE: PRT
<213> ORGANISM: Homo sapiens
<220> FEATURE:
<221> NAME/KEY: MISC_FEATURE
<223> OTHER INFORMATION: antiCD19CAR

<400> SEQUENCE: 116

Glu Ile Val Met Thr Gln Ser Pro Ala Thr Leu Ser Leu Ser Pro Gly
1 5 10 15

Glu Arg Ala Thr Leu Ser Cys Arg Ala Ser Gln Asp Ile Ser Lys Tyr
20 25 30

Leu Asn Trp Tyr Gln Gln Lys Pro Gly Gln Ala Pro Arg Leu Leu Ile
35 40 45

Tyr His Thr Ser Arg Leu His Ser Gly Ile Pro Ala Arg Phe Ser Gly
50 55 60

Ser Gly Ser Gly Thr Asp Tyr Thr Leu Thr Ile Ser Ser Leu Gln Pro
65 70 75 80

Glu Asp Phe Ala Val Tyr Phe Cys Gln Gln Gly Asn Thr Leu Pro Tyr
85 90 95

Thr Phe Gly Gln Gly Thr Lys Leu Glu Ile Lys Gly Gly Gly Gly Ser
100 105 110

Gly Gly Gly Gly Ser Gly Gly Gly Gly Ser Gln Val Gln Leu Gln Glu
115 120 125

Ser Gly Pro Gly Leu Val Lys Pro Ser Glu Thr Leu Ser Leu Thr Cys
    130                 135                 140

Thr Val Ser Gly Val Ser Leu Pro Asp Tyr Gly Val Ser Trp Ile Arg
145                 150                 155                 160

Gln Pro Pro Gly Lys Gly Leu Glu Trp Ile Gly Val Ile Trp Gly Ser
                165                 170                 175

Glu Thr Thr Tyr Tyr Gln Ser Ser Leu Lys Ser Arg Val Thr Ile Ser
            180                 185                 190

Lys Asp Asn Ser Lys Asn Gln Val Ser Leu Lys Leu Ser Ser Val Thr
        195                 200                 205

Ala Ala Asp Thr Ala Val Tyr Tyr Cys Ala Lys His Tyr Tyr Tyr Gly
    210                 215                 220

Gly Ser Tyr Ala Met Asp Tyr Trp Gly Gln Gly Thr Leu Val Thr Val
225                 230                 235                 240

Ser Ser

<210> SEQ ID NO 117
<211> LENGTH: 107
<212> TYPE: PRT
<213> ORGANISM: Homo sapiens
<220> FEATURE:
<221> NAME/KEY: MISC_FEATURE
<223> OTHER INFORMATION: huFMC63VLv1

<400> SEQUENCE: 117

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Lys Tyr
            20                  25                  30

Leu Asn Trp Tyr Gln Gln Lys Pro Gly Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Ile Ala Thr Tyr Tyr Cys Gln Gln Gly Asn Thr Leu Pro Tyr
                85                  90                  95

Thr Phe Gly Gly Gly Thr Lys Leu Glu Ile Thr
            100                 105

<210> SEQ ID NO 118
<211> LENGTH: 107
<212> TYPE: PRT
<213> ORGANISM: Homo sapiens
<220> FEATURE:
<221> NAME/KEY: MISC_FEATURE
<223> OTHER INFORMATION: HUFMC63VLV2

<400> SEQUENCE: 118

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Lys Tyr
            20                  25                  30

Leu Asn Trp Tyr Gln Gln Lys Pro Gly Gly Thr Val Lys Leu Leu Ile
        35                  40                  45

Tyr His Thr Ser Arg Leu His Ser Gly Val Pro Ser Arg Phe Ser Gly
    50                  55                  60

```
Ser Gly Ser Gly Thr Asp Phe Thr Leu Thr Ile Ser Ser Leu Gln Pro
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr
            100                 105


<210> SEQ ID NO 119
<211> LENGTH: 107
<212> TYPE: PRT
<213> ORGANISM: Homo sapiens
<220> FEATURE:
<221> NAME/KEY: MISC_FEATURE
<223> OTHER INFORMATION: HUFMC63VLV3

<400> SEQUENCE: 119

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr
            100                 105


<210> SEQ ID NO 120
<211> LENGTH: 120
<212> TYPE: PRT
<213> ORGANISM: Homo sapiens
<220> FEATURE:
<221> NAME/KEY: MISC_FEATURE
<223> OTHER INFORMATION: HUFMC63VHV1

<400> SEQUENCE: 120

Gln Val Gln Leu Gln Glu Ser Gly Pro Gly Leu Val Lys Pro Ser Gln
1               5                   10                  15

Thr Leu Ser Leu Thr Cys Thr Val Ser Gly Val Ser Leu Pro Asp Tyr
            20                  25                  30

Gly Val Ser Trp Ile Arg Gln Pro Pro Gly Lys Gly Leu Glu Trp Ile
        35                  40                  45

Gly Val Ile Trp Gly Ser Glu Thr Thr Tyr Tyr Asn Ser Ala Leu Lys
    50                  55                  60

Ser Arg Leu Thr Ile Ser Lys Asp Asn Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Ser Val Thr Val Ser Ser
        115                 120


<210> SEQ ID NO 121
<211> LENGTH: 120
```

<212> TYPE: PRT
<213> ORGANISM: Homo sapiens
<220> FEATURE:
<221> NAME/KEY: MISC_FEATURE
<223> OTHER INFORMATION: HUFMC63VHV2

<400> SEQUENCE: 121

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Val Ser Leu Pro Asp Tyr
            20                  25                  30

Gly Val Ser Trp Ile Arg Gln Pro Pro Gly Lys Gly Leu Glu Trp Leu
        35                  40                  45

Gly Val Ile Trp Gly Ser Glu Thr Thr Tyr Tyr Asn Ser Ala Leu Lys
    50                  55                  60

Ser Arg Leu Thr Ile Ser Lys Asp Asn Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Ser Val Thr Val Ser Ser
        115                 120
```

<210> SEQ ID NO 122
<211> LENGTH: 120
<212> TYPE: PRT
<213> ORGANISM: Homo sapiens
<220> FEATURE:
<221> NAME/KEY: MISC_FEATURE
<223> OTHER INFORMATION: HUFMC63VHV3

<400> SEQUENCE: 122

```
Gln Val Gln Leu Gln Glu Ser Gly Pro Gly Leu Val Lys Pro Ser Gln
1               5                   10                  15

Thr Leu Ser Val Thr Cys Thr Val Ser Gly Val Ser Leu Pro Asp Tyr
            20                  25                  30

Gly Val Ser Trp Ile Arg Gln Pro Pro Gly Lys Gly Leu Glu Trp Leu
        35                  40                  45

Gly Val Ile Trp Gly Ser Glu Thr Thr Tyr Tyr Asn Ser Ala Leu Lys
    50                  55                  60

Ser Arg Leu Thr Ile Ser Lys Asp Asn Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Ser Val Thr Val Ser Ser
        115                 120
```

<210> SEQ ID NO 123
<211> LENGTH: 120
<212> TYPE: PRT
<213> ORGANISM: Homo sapiens
<220> FEATURE:
<221> NAME/KEY: MISC_FEATURE
<223> OTHER INFORMATION: HUFMC63VHV4

<400> SEQUENCE: 123

```
Gln Val Gln Leu Gln Glu Ser Gly Pro Gly Leu Val Lys Pro Ser Gln
```

```
1               5                   10                  15

Thr Leu Ser Val Thr Cys Thr Val Ser Gly Val Ser Leu Pro Asp Tyr
            20                  25                  30

Gly Val Ser Trp Ile Arg Gln Pro Pro Arg Lys Gly Leu Glu Trp Leu
        35                  40                  45

Gly Val Ile Trp Gly Ser Glu Thr Thr Tyr Tyr Asn Ser Ala Leu Lys
    50                  55                  60

Ser Arg Leu Thr Ile Ser Lys Asp Asn Ser Lys Ser Gln Val Ser Leu
65                  70                  75                  80

Lys Met Ser Ser Val Thr Ala Ala Asp Thr Ala Ile Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Ser Val Thr Val Ser Ser
        115                 120


<210> SEQ ID NO 124
<211> LENGTH: 11
<212> TYPE: PRT
<213> ORGANISM: Homo sapiens
<220> FEATURE:
<221> NAME/KEY: MISC_FEATURE
<223> OTHER INFORMATION: huFMC63VLv1 CDR1

<400> SEQUENCE: 124

Arg Ala Ser Gln Asp Ile Ser Lys Tyr Leu Asn
1               5                   10


<210> SEQ ID NO 125
<211> LENGTH: 7
<212> TYPE: PRT
<213> ORGANISM: Homo sapiens
<220> FEATURE:
<221> NAME/KEY: MISC_FEATURE
<223> OTHER INFORMATION: huFMC63VLv1 CDR2

<400> SEQUENCE: 125

His Thr Ser Arg Leu His Ser
1               5


<210> SEQ ID NO 126

<400> SEQUENCE: 126

000


<210> SEQ ID NO 127
<211> LENGTH: 11
<212> TYPE: PRT
<213> ORGANISM: Homo sapiens
<220> FEATURE:
<221> NAME/KEY: MISC_FEATURE
<223> OTHER INFORMATION: HUFMC63VLV2 CDR1

<400> SEQUENCE: 127

Arg Ala Ser Gln Asp Ile Ser Lys Tyr Leu Asn
1               5                   10


<210> SEQ ID NO 128
<211> LENGTH: 7
<212> TYPE: PRT
<213> ORGANISM: Homo sapiens
<220> FEATURE:
<221> NAME/KEY: MISC_FEATURE
```

<223> OTHER INFORMATION: HUFMC63VLV2 CDR2

<400> SEQUENCE: 128

His Thr Ser Arg Leu His Ser
1               5

<210> SEQ ID NO 129
<211> LENGTH: 9
<212> TYPE: PRT
<213> ORGANISM: Homo sapiens
<220> FEATURE:
<221> NAME/KEY: MISC_FEATURE
<223> OTHER INFORMATION: HUFMC63VLV2 CDR3

<400> SEQUENCE: 129

Gln Gln Gly Asn Thr Leu Pro Tyr Thr
1               5

<210> SEQ ID NO 130
<211> LENGTH: 11
<212> TYPE: PRT
<213> ORGANISM: Homo sapiens
<220> FEATURE:
<221> NAME/KEY: MISC_FEATURE
<223> OTHER INFORMATION: HUFMC63VLV3 CDR1

<400> SEQUENCE: 130

Arg Ala Ser Gln Asp Ile Ser Lys Tyr Leu Asn
1               5                   10

<210> SEQ ID NO 131
<211> LENGTH: 7
<212> TYPE: PRT
<213> ORGANISM: Homo sapiens
<220> FEATURE:
<221> NAME/KEY: MISC_FEATURE
<223> OTHER INFORMATION: HUFMC63VLV3 CDR2

<400> SEQUENCE: 131

His Thr Ser Arg Leu His Ser
1               5

<210> SEQ ID NO 132
<211> LENGTH: 9
<212> TYPE: PRT
<213> ORGANISM: Homo sapiens
<220> FEATURE:
<221> NAME/KEY: MISC_FEATURE
<223> OTHER INFORMATION: HUFMC63VLV3 CDR3

<400> SEQUENCE: 132

Gln Gln Gly Asn Thr Leu Pro Tyr Thr
1               5

<210> SEQ ID NO 133
<211> LENGTH: 10
<212> TYPE: PRT
<213> ORGANISM: Homo sapiens
<220> FEATURE:
<221> NAME/KEY: MISC_FEATURE
<223> OTHER INFORMATION: HUFMC63VHV1 CDR1

<400> SEQUENCE: 133

Gly Val Ser Leu Pro Asp Tyr Gly Val Ser
1               5                   10

<210> SEQ ID NO 134

<211> LENGTH: 16
<212> TYPE: PRT
<213> ORGANISM: Homo sapiens
<220> FEATURE:
<221> NAME/KEY: MISC_FEATURE
<223> OTHER INFORMATION: HUFMC63VHV1 CDR2

<400> SEQUENCE: 134

Val Ile Trp Gly Ser Glu Thr Thr Tyr Tyr Asn Ser Ala Leu Lys Ser
1 5 10 15

<210> SEQ ID NO 135
<211> LENGTH: 12
<212> TYPE: PRT
<213> ORGANISM: Homo sapiens
<220> FEATURE:
<221> NAME/KEY: MISC_FEATURE
<223> OTHER INFORMATION: HUFMC63VHV1 CDR3

<400> SEQUENCE: 135

His Tyr Tyr Tyr Gly Gly Ser Tyr Ala Met Asp Tyr
1 5 10

<210> SEQ ID NO 136
<211> LENGTH: 10
<212> TYPE: PRT
<213> ORGANISM: Homo sapiens
<220> FEATURE:
<221> NAME/KEY: MISC_FEATURE
<223> OTHER INFORMATION: HUFMC63VHV2 CDR1

<400> SEQUENCE: 136

Gly Val Ser Leu Pro Asp Tyr Gly Val Ser
1 5 10

<210> SEQ ID NO 137
<211> LENGTH: 16
<212> TYPE: PRT
<213> ORGANISM: Homo sapiens
<220> FEATURE:
<221> NAME/KEY: MISC_FEATURE
<223> OTHER INFORMATION: HUFMC63VHV2 CDR2

<400> SEQUENCE: 137

Val Ile Trp Gly Ser Glu Thr Thr Tyr Tyr Asn Ser Ala Leu Lys Ser
1 5 10 15

<210> SEQ ID NO 138
<211> LENGTH: 12
<212> TYPE: PRT
<213> ORGANISM: Homo sapiens
<220> FEATURE:
<221> NAME/KEY: MISC_FEATURE
<223> OTHER INFORMATION: HUFMC63VHV2 CDR3

<400> SEQUENCE: 138

His Tyr Tyr Tyr Gly Gly Ser Tyr Ala Met Asp Tyr
1 5 10

<210> SEQ ID NO 139
<211> LENGTH: 10
<212> TYPE: PRT
<213> ORGANISM: Homo sapiens
<220> FEATURE:
<221> NAME/KEY: MISC_FEATURE
<223> OTHER INFORMATION: HUFMC63VHV3 CDR1

<400> SEQUENCE: 139

Gly Val Ser Leu Pro Asp Tyr Gly Val Ser
1 5 10

<210> SEQ ID NO 140
<211> LENGTH: 16
<212> TYPE: PRT
<213> ORGANISM: Homo sapiens
<220> FEATURE:
<221> NAME/KEY: MISC_FEATURE
<223> OTHER INFORMATION: HUFMC63VHV3 CDR2

<400> SEQUENCE: 140

Val Ile Trp Gly Ser Glu Thr Thr Tyr Tyr Asn Ser Ala Leu Lys Ser
1 5 10 15

<210> SEQ ID NO 141
<211> LENGTH: 12
<212> TYPE: PRT
<213> ORGANISM: Homo sapiens
<220> FEATURE:
<221> NAME/KEY: MISC_FEATURE
<223> OTHER INFORMATION: HUFMC63VHV3 CDR3

<400> SEQUENCE: 141

His Tyr Tyr Tyr Gly Gly Ser Tyr Ala Met Asp Tyr
1 5 10

<210> SEQ ID NO 142
<211> LENGTH: 10
<212> TYPE: PRT
<213> ORGANISM: Homo sapiens
<220> FEATURE:
<221> NAME/KEY: MISC_FEATURE
<223> OTHER INFORMATION: HUFMC63VHV4 CDR1

<400> SEQUENCE: 142

Gly Val Ser Leu Pro Asp Tyr Gly Val Ser
1 5 10

<210> SEQ ID NO 143
<211> LENGTH: 16
<212> TYPE: PRT
<213> ORGANISM: Homo sapiens
<220> FEATURE:
<221> NAME/KEY: MISC_FEATURE
<223> OTHER INFORMATION: HUFMC63VHV4 CDR2

<400> SEQUENCE: 143

Val Ile Trp Gly Ser Glu Thr Thr Tyr Tyr Asn Ser Ala Leu Lys Ser
1 5 10 15

<210> SEQ ID NO 144
<211> LENGTH: 12
<212> TYPE: PRT
<213> ORGANISM: Homo sapiens
<220> FEATURE:
<221> NAME/KEY: MISC_FEATURE
<223> OTHER INFORMATION: HUFMC63VHV4 CDR3

<400> SEQUENCE: 144

His Tyr Tyr Tyr Gly Gly Ser Tyr Ala Met Asp Tyr
1 5 10

<210> SEQ ID NO 145
<211> LENGTH: 1122
<212> TYPE: DNA
<213> ORGANISM: Homo sapiens
<220> FEATURE:

<221> NAME/KEY: misc_feature
<223> OTHER INFORMATION: DNA NKG2D-Ox40-CD3z

<400> SEQUENCE: 145

```
atggccttac cagtgaccgc cttgctcctg ccgctggcct tgctgctcca cgccgccagg     60

ccgttattca accaagaagt tcaaattccc ttgaccgaaa gttactgtgg cccatgtcct    120

aaaaactgga tatgttacaa aaataactgc taccaatttt ttgatgagag taaaaactgg    180

tatgagagcc aggcttcttg tatgtctcaa aatgccagcc ttctgaaagt atacagcaaa    240

gaggaccagg atttacttaa actggtgaag tcatatcatt ggatgggact agtacacatt    300

ccaacaaatg gatcttggca gtgggaagat ggctccattc tctcacccaa cctactaaca    360

ataattgaaa tgcagaaggg agactgtgca ctctatgcct cgagctttaa aggctatata    420

gaaaactgtt caactccaaa tacgtacatc tgcatgcaaa ggactgtgac cacgacgcca    480

gcgccgcgac caccaacacc ggcgcccacc atcgcgtcgc agcccctgtc cctgcgccca    540

gaggcgtgcc ggccagcggc ggggggcgca gtgcacacga gggggctgga cttcgcctgt    600

gatatctaca tctgggcgcc cttggccggg acttgtgggg tccttctcct gtcactggtt    660

atcacccttt actgccggag ggaccagagg ctgccccccg atgcccacaa gccccctggg    720

ggaggcagtt tccggacccc catccaagag gagcaggccg acgcccactc caccctggcc    780

aagatcagag tgaagttcag caggagcgca gacgcccccg cgtaccagca gggccagaac    840

cagctctata acgagctcaa tctaggacga agagaggagt acgatgtttt ggacaagaga    900

cgtggccggg accctgagat ggggggaaag ccgagaagga agaaccctca ggaaggcctg    960

tacaatgaac tgcagaaaga taagatggcg gaggcctaca gtgagattgg gatgaaaggc   1020

gagcgccgga ggggcaaggg gcacgatggc ctttaccagg gtctcagtac agccaccaag   1080

gacacctacg acgcccttca catgcaggcc ctgccccctc gc                      1122
```

<210> SEQ ID NO 146
<211> LENGTH: 341
<212> TYPE: PRT
<213> ORGANISM: Homo sapiens
<220> FEATURE:
<221> NAME/KEY: MISC_FEATURE
<223> OTHER INFORMATION: Amino Acid NKG2D-OX40-CD3z

<400> SEQUENCE: 146

```
Met Ala Leu Pro Val Thr Ala Leu Leu Leu Pro Leu Ala Leu Leu Leu
1               5                   10                  15

His Ala Ala Arg Pro Leu Phe Asn Gln Glu Val Gln Ile Pro Leu Thr
            20                  25                  30

Glu Ser Tyr Cys Gly Pro Cys Pro Lys Asn Trp Ile Cys Tyr Lys Asn
        35                  40                  45

Asn Cys Tyr Gln Phe Phe Asp Glu Ser Lys Asn Trp Tyr Glu Ser Gln
    50                  55                  60

Ala Ser Cys Met Ser Gln Asn Ala Ser Leu Leu Lys Val Tyr Ser Lys
65                  70                  75                  80

Glu Asp Gln Asp Leu Leu Lys Leu Val Lys Ser Tyr His Trp Met Gly
                85                  90                  95

Leu Val His Ile Pro Thr Asn Gly Ser Trp Gln Trp Glu Asp Gly Ser
            100                 105                 110

Ile Leu Ser Pro Asn Leu Leu Thr Ile Ile Glu Met Gln Lys Gly Asp
        115                 120                 125

Cys Ala Leu Tyr Ala Ser Ser Phe Lys Gly Tyr Ile Glu Asn Cys Ser
```

```
    130                 135                 140

Thr Pro Asn Thr Tyr Ile Cys Met Gln Arg Thr Val Glu Ser Lys Tyr
145                 150                 155                 160

Gly Pro Pro Cys Pro Ser Cys Pro Ile Tyr Ile Trp Ala Pro Leu Ala
                165                 170                 175

Gly Thr Cys Gly Val Leu Leu Leu Ser Leu Val Ile Thr Leu Tyr Cys
            180                 185                 190

Arg Arg Asp Gln Arg Leu Pro Pro Asp Ala His Lys Pro Pro Gly Gly
        195                 200                 205

Gly Ser Phe Arg Thr Pro Ile Gln Glu Glu Gln Ala Asp Ala His Ser
    210                 215                 220

Thr Leu Ala Lys Ile Arg Val Lys Phe Ser Arg Ser Ala Asp Ala Pro
225                 230                 235                 240

Ala Tyr Gln Gln Gly Gln Asn Gln Leu Tyr Asn Glu Leu Asn Leu Gly
                245                 250                 255

Arg Arg Glu Glu Tyr Asp Val Leu Asp Lys Arg Arg Gly Arg Asp Pro
            260                 265                 270

Glu Met Gly Gly Lys Pro Arg Arg Lys Asn Pro Gln Glu Gly Leu Tyr
        275                 280                 285

Asn Glu Leu Gln Lys Asp Lys Met Ala Glu Ala Tyr Ser Glu Ile Gly
    290                 295                 300

Met Lys Gly Glu Arg Arg Arg Gly Lys Gly His Asp Gly Leu Tyr Gln
305                 310                 315                 320

Gly Leu Ser Thr Ala Thr Lys Asp Thr Tyr Asp Ala Leu His Met Gln
                325                 330                 335

Ala Leu Pro Pro Arg
            340
```

<210> SEQ ID NO 147
<211> LENGTH: 1467
<212> TYPE: DNA
<213> ORGANISM: Homo sapiens
<220> FEATURE:
<221> NAME/KEY: misc_feature
<223> OTHER INFORMATION: DNA Sequence FMC63_CD28_CAR

<400> SEQUENCE: 147

```
atgcttctcc tggtgacaag ccttctttac cacacccagc attcctcctg atcccagaca     60

tccagataca tcctccctgt ctgcctctct gggagacaga gtcaccgggc aagtcaggac    120

attagtaaat atttaaattg gtatcagctc tgtgagtgac acagacatca gttgcagcag    180

aaaccagatg gaactgttaa actcctgatc taccatacat caagattaca ctcaggagtc    240

ccatcaaggt tcagtggcag tgggtctgga acagattatt ctctcaccat tagcaacctg    300

gagcaagaag atattgccac ttacttttgc caacagggta atacgcttcc gtacacgttc    360

ggaggggga ctaagttgga aataacaggc tccacctctg gatccggcaa gcccggatct    420

ggcgagggat ccaccaaggg cgaggtgaaa ctgcaggagt caggacctgg cctggtggcg    480

ccctcacaga gcctgtccgt cacatgcact gtctcagggg tctcattacc cgactatggt    540

gtaagctgga ttcgccagcc tccacgaaag ggtctggagt ggctgggagt aatatggggt    600

agtgaaacca catactataa ttcagctctc aaatccagac tgaccatcat caaggacaac    660

tccaagagcc aagttttctt aaaaatgaac agtctgcaaa ctgatgacac agccatttac    720

tactgtgcca aacattatta ctacggtggt agctatgcta tggactactg gggtcaagga    780

acctcagtca ccgtctcctc agcggccgca attgaagtta tgtatcctcc tccttaccta    840
```

gacaatgaga agagcaatgg aaccattatc catgtgaaag ggaaacacct ttgtccaagt 900
cccctatttc ccggaccttc taagcccttt tgggtgctgg tggtggttgg gggagtcctg 960
gcttgctata gcttgctagt aacagtggcc tttattattt tctgggtgag gagtaagagg 1020
agcaggctcc tgcacagtga ctacatgaac atgactcccc gccgccccgg gcccacccgc 1080
aagcattacc agccctatgc cccaccacgc gacttcgcag cctatcgctc cagagtgaag 1140
ttcagcagga gcgcagacgc ccccgcgtac cagcagggcc agaaccagct ctataacgag 1200
ctcaatctag gacgaagaga ggagtacgat gttttggaca agagacgtgg ccgggaccct 1260
gagatggggg gaaagccgag aaggaagaac cctcaggaag gcctgtacaa tgaactgcag 1320
aaagataaga tggcggaggc ctacagtgag attgggatga aaggcgagcg ccggaggggc 1380
aaggggcacg atggccttta ccagggtctc agtacagcca ccaaggacac ctacgacgcc 1440
cttcacatgc aggccctgcc ccctcgc 1467

<210> SEQ ID NO 148
<211> LENGTH: 331
<212> TYPE: DNA
<213> ORGANISM: Homo sapiens
<220> FEATURE:
<221> NAME/KEY: misc_feature
<223> OTHER INFORMATION: DNA Sequence FCM63 Light Chain

<400> SEQUENCE: 148
gacatccaga tacatcctcc ctgtctgcct ctctgggaga cagagtcacc gggcaagtca 60
ggacattagt aaatatttaa attggtatca gctctgtgag tgacacagac atcagttgca 120
gcagaaacca gatggaactg ttaaactcct gatctaccat acatcaagat tacactcagg 180
agtcccatca aggttcagtg gcagtgggtc tggaacagat tattctctca ccattagcaa 240
cctggagcaa gaagatattg ccacttactt ttgccaacag ggtaatacgc ttccgtacac 300
gttcggaggg gggactaagt tggaaataac a 331

<210> SEQ ID NO 149
<211> LENGTH: 54
<212> TYPE: DNA
<213> ORGANISM: Homo sapiens
<220> FEATURE:
<221> NAME/KEY: misc_feature
<223> OTHER INFORMATION: DNA Sequence FMC63 Linker

<400> SEQUENCE: 149
ggctccacct ctggatccgg caagcccgga tctggcgagg gatccaccaa gggc 54

<210> SEQ ID NO 150
<211> LENGTH: 360
<212> TYPE: DNA
<213> ORGANISM: Homo sapiens
<220> FEATURE:
<221> NAME/KEY: misc_feature
<223> OTHER INFORMATION: DNA Sequence FMC63 Heavy Chain

<400> SEQUENCE: 150
gaggtgaaac tgcaggagtc aggacctggc ctggtggcgc cctcacagag cctgtccgtc 60
acatgcactg tctcaggggt ctcattaccc gactatggtg taagctggat tcgccagcct 120
ccacgaaagg gtctggagtg gctgggagta atatggggta gtgaaaccac atactataat 180
tcagctctca aatccagact gaccatcatc aaggacaact ccaagagcca agttttctta 240
aaaatgaaca gtctgcaaac tgatgacaca gccatttact actgtgccaa acattattac 300
tacggtggta gctatgctat ggactactgg ggtcaaggaa cctcagtcac cgtctcctca 360

<210> SEQ ID NO 151
<211> LENGTH: 117
<212> TYPE: DNA
<213> ORGANISM: Homo sapiens
<220> FEATURE:
<221> NAME/KEY: misc_feature
<223> OTHER INFORMATION: DNA Sequence CD28 spacer

<400> SEQUENCE: 151
attgaagtta tgtatcctcc tccttaccta gacaatgaga agagcaatgg aaccattatc 60
catgtgaaag ggaaacacct ttgtccaagt cccctatttc ccggaccttc taagccc 117

<210> SEQ ID NO 152
<211> LENGTH: 81
<212> TYPE: DNA
<213> ORGANISM: Homo sapiens
<220> FEATURE:
<221> NAME/KEY: misc_feature
<223> OTHER INFORMATION: DNA Sequence transmembrane region

<400> SEQUENCE: 152
ttttgggtgc tggtggtggt tgggggagtc ctggcttgct atagcttgct agtaacagtg 60
gcctttatta ttttctgggt g 81

<210> SEQ ID NO 153
<211> LENGTH: 123
<212> TYPE: DNA
<213> ORGANISM: Homo sapiens
<220> FEATURE:
<221> NAME/KEY: misc_feature
<223> OTHER INFORMATION: DNA Sequence CD28 Co-stim

<400> SEQUENCE: 153
aggagtaaga ggagcaggct cctgcacagt gactacatga acatgactcc ccgccgcccc 60
gggcccaccc gcaagcatta ccagccctat gccccaccac gcgacttcgc agcctatcgc 120
tcc 123

<210> SEQ ID NO 154
<211> LENGTH: 336
<212> TYPE: DNA
<213> ORGANISM: Homo sapiens
<220> FEATURE:
<221> NAME/KEY: misc_feature
<223> OTHER INFORMATION: CD3zeta [repeat]

<400> SEQUENCE: 154
agagtgaagt tcagcaggag cgcagacgcc cccgcgtacc agcagggcca gaaccagctc 60
tataacgagc tcaatctagg acgaagagag gagtacgatg ttttggacaa gagacgtggc 120
cgggaccctg agatgggggg aaagccgaga aggaagaacc ctcaggaagg cctgtacaat 180
gaactgcaga aagataagat ggcggaggcc tacagtgaga ttgggatgaa aggcgagcgc 240
cggaggggca aggggcacga tggcctttac cagggtctca gtacagccac caaggacacc 300
tacgacgccc ttcacatgca ggccctgccc cctcgc 336

<210> SEQ ID NO 155
<211> LENGTH: 342
<212> TYPE: DNA
<213> ORGANISM: Homo sapiens
<220> FEATURE:

<221> NAME/KEY: misc_feature
<223> OTHER INFORMATION: Coding sequence for mbIL15

<400> SEQUENCE: 155
aactgggtca acgtgattag cgatttgaag aaaatcgagg accttataca gtctatgcat 60
attgacgcta cactgtatac tgagagtgat gtacacccgt cctgtaaggt aacggccatg 120
aaatgctttc ttctggagct ccaggtcatc agcttggagt ctggggacgc aagcatccac 180
gatacggttg aaaacctcat catccttgcg aacaactctc tctcatctaa tggaaacgtt 240
acagagagtg ggtgtaagga gtgcgaagag ttggaagaaa aaaacatcaa agaatttctt 300
caatccttcg ttcacatagt gcaaatgttc attaacacgt cc 342

<210> SEQ ID NO 156
<211> LENGTH: 135
<212> TYPE: DNA
<213> ORGANISM: Homo sapiens
<220> FEATURE:
<221> NAME/KEY: misc_feature
<223> OTHER INFORMATION: DNA seq of cd hinge rev. trans from No: 157

<400> SEQUENCE: 156
accaccaccc cggcgccgcg cccgccgacc ccggcgccga ccattgcgag ccagccgctg 60
agcctgcgcc cggaagcgtg ccgcccggcg gcgggcggcg cggtgcatac ccgcggcctg 120
gattttgcgt gcgat 135

<210> SEQ ID NO 157
<211> LENGTH: 45
<212> TYPE: PRT
<213> ORGANISM: Homo sapiens
<220> FEATURE:
<221> NAME/KEY: MISC_FEATURE
<223> OTHER INFORMATION: Amino Acid CD8 Hinge

<400> SEQUENCE: 157

Thr Thr Thr Pro Ala Pro Arg Pro Pro Thr Pro Ala Pro Thr Ile Ala
1 5 10 15

Ser Gln Pro Leu Ser Leu Arg Pro Glu Ala Cys Arg Pro Ala Ala Gly
20 25 30

Gly Ala Val His Thr Arg Gly Leu Asp Phe Ala Cys Asp
35 40 45

<210> SEQ ID NO 158
<211> LENGTH: 72
<212> TYPE: DNA
<213> ORGANISM: Homo sapiens
<220> FEATURE:
<221> NAME/KEY: misc_feature
<223> OTHER INFORMATION: DNA seq of CD8 TM rev trans from No: 159

<400> SEQUENCE: 158
atttatattt gggcgccgct ggcgggcacc tgcggcgtgc tgctgctgag cctggtgatt 60
accctgtatt gc 72

<210> SEQ ID NO 159
<211> LENGTH: 24
<212> TYPE: PRT
<213> ORGANISM: Homo sapiens
<220> FEATURE:
<221> NAME/KEY: MISC_FEATURE
<223> OTHER INFORMATION: AA Sequence CD8 TM

<400> SEQUENCE: 159

```
Ile Tyr Ile Trp Ala Pro Leu Ala Gly Thr Cys Gly Val Leu Leu Leu
1               5                   10                  15

Ser Leu Val Ile Thr Leu Tyr Cys
            20


<210> SEQ ID NO 160
<211> LENGTH: 2204
<212> TYPE: DNA
<213> ORGANISM: Homo sapiens
<220> FEATURE:
<221> NAME/KEY: misc_feature
<223> OTHER INFORMATION: DNA NK19H-1

<400> SEQUENCE: 160

gaattcgccg ccaccatggc cttaccagtg accgccttgc tcctgccgct ggccttgctg     60

ctccacgccg ccaggccgga ctacaaagac gatgacgata aaggcggtgg tggctctggt    120

ggtggcggca gcgatattca gatgacccag agcccgagca gcctgagcgc gagcgtgggc    180

gatcgcgtga ccattacctg ccgcgcgagc caggatatta gcaaatatct gaactggtat    240

cagcagaaac cgggcggcac cgtgaaactg ctgatttatc ataccagccg cctgcatagc    300

ggcgtgccga gccgctttag cggcagcggc agcggcaccg attttaccct gaccattagc    360

agcctgcagc cggaagatat tgcgacctat tattgccagc agggcaacac cctgccgtat    420

acctttggcg gcggcaccaa actggaaatt accggtggcg gtggctcggg cggtggtggg    480

tcgggtggcg gcggatctca ggtgcagctg caggaaagcg gcccgggcct ggtgaaaccg    540

agccagaccc tgagcctgac ctgcaccgtg agcggcgtga gcctgccgga ttatggcgtg    600

agctggattc gccagccgcc gggcaaaggc ctggaatgga ttggcgtgat ttggggcagc    660

gaaaccacct attataacag cgcgctgaaa agccgcctga ccattagcaa agataacagc    720

aaaaaccagg tgagcctgaa actgagcagc gtgaccgcgg cggataccgc ggtgtattat    780

tgcgcgaaac attattatta tggcggcagc tatgcgatgg attattgggg ccagggcacc    840

agcgtgaccg tgagcagcac cacgacgcca gcgccgcgac caccaacacc ggcgcccacc    900

atcgcgtcgc agcccctgtc cctgcgccca gaggcgtgcc ggccagcggc ggggggcgca    960

gtgcacacga gggggctgga cttcgcctgt gatatctaca tctgggcgcc cttggccggg   1020

acttgtgggg tccttctcct gtcactggtt atcacccttt actgccggag ggaccagagg   1080

ctgccccccg atgcccacaa gccccctggg ggaggcagtt tccggacccc catccaagag   1140

gagcaggccg acgcccactc caccctggcc aagatcagag tgaagttcag caggagcgca   1200

gacgcccccg cgtaccagca gggccagaac cagctctata acgagctcaa tctaggacga   1260

agagaggagt acgatgtttt ggacaagaga cgtggccggg accctgagat ggggggaaag   1320

ccgagaagga agaaccctca ggaaggcctg tacaatgaac tgcagaaaga taagatggcg   1380

gaggcctaca gtgagattgg gatgaaaggc gagcgccgga ggggcaaggg gcacgatggc   1440

ctttaccagg gtctcagtac agccaccaag gacacctacg acgcccttca catgcaggcc   1500

ctgccccctc gcggctctgg cgagggaagg ggttccctgc ttacttgcgg cgacgtcgaa   1560

gagaatcccg gtccgatggc cctcccagta actgccctcc ttttgcccct cgcactcctt   1620

cttcatgccg ctcgccccaa ctgggtcaac gtgattagcg atttgaagaa aatcgaggac   1680

cttatacagt ctatgcatat tgacgctaca ctgtatactg agagtgatgt acacccgtcc   1740

tgtaaggtaa cggccatgaa atgctttctt ctggagctcc aggtcatcag cttggagtct   1800

ggggacgcaa gcatccacga tacggttgaa aacctcatca tccttgcgaa caactctctc   1860
```

```
tcatctaatg gaaacgttac agagagtggg tgtaaggagt gcgaagagtt ggaagaaaaa   1920

aacatcaaag aatttcttca atccttcgtt cacatagtgc aaatgttcat taacacgtcc   1980

actaccacac ccgccccgag gccacctacg ccggcaccga ctatcgccag tcaacccctc   2040

tctctgcgcc ccgaggcttg ccggcctgcg gctggtgggg cggtccacac ccggggcctg   2100

gattttgcgt gcgatatata catctgggca cctcttgccg gcacctgcgg agtgctgctt   2160

ctctcactcg ttattacgct gtactgctaa gcggccgcgt cgac                    2204


<210> SEQ ID NO 161
<211> LENGTH: 724
<212> TYPE: PRT
<213> ORGANISM: Homo sapiens
<220> FEATURE:
<221> NAME/KEY: MISC_FEATURE
<223> OTHER INFORMATION: AA NK19H-1

<400> SEQUENCE: 161

Met Ala Leu Pro Val Thr Ala Leu Leu Leu Pro Leu Ala Leu Leu Leu
1               5                   10                  15

His Ala Ala Arg Pro Asp Tyr Lys Asp Asp Asp Asp Lys Gly Gly Gly
            20                  25                  30

Gly Ser Gly Gly Gly Gly Ser Asp Ile Gln Met Thr Gln Ser Pro Ser
        35                  40                  45

Ser Leu Ser Ala Ser Val Gly Asp Arg Val Thr Ile Thr Cys Arg Ala
    50                  55                  60

Ser Gln Asp Ile Ser Lys Tyr Leu Asn Trp Tyr Gln Gln Lys Pro Gly
65                  70                  75                  80

Gly Thr Val Lys Leu Leu Ile Tyr His Thr Ser Arg Leu His Ser Gly
                85                  90                  95

Val Pro Ser Arg Phe Ser Gly Ser Gly Ser Gly Thr Asp Phe Thr Leu
            100                 105                 110

Thr Ile Ser Ser Leu Gln Pro Glu Asp Ile Ala Thr Tyr Tyr Cys Gln
        115                 120                 125

Gln Gly Asn Thr Leu Pro Tyr Thr Phe Gly Gly Gly Thr Lys Leu Glu
    130                 135                 140

Ile Thr Gly Gly Gly Gly Ser Gly Gly Gly Gly Ser Gly Gly Gly Gly
145                 150                 155                 160

Ser Gln Val Gln Leu Gln Glu Ser Gly Pro Gly Leu Val Lys Pro Ser
                165                 170                 175

Gln Thr Leu Ser Leu Thr Cys Thr Val Ser Gly Val Ser Leu Pro Asp
            180                 185                 190

Tyr Gly Val Ser Trp Ile Arg Gln Pro Pro Gly Lys Gly Leu Glu Trp
        195                 200                 205

Ile Gly Val Ile Trp Gly Ser Glu Thr Thr Tyr Tyr Asn Ser Ala Leu
    210                 215                 220

Lys Ser Arg Leu Thr Ile Ser Lys Asp Asn Ser Lys Asn Gln Val Ser
225                 230                 235                 240

Leu Lys Leu Ser Ser Val Thr Ala Ala Asp Thr Ala Val Tyr Tyr Cys
                245                 250                 255

Ala Lys His Tyr Tyr Tyr Gly Gly Ser Tyr Ala Met Asp Tyr Trp Gly
            260                 265                 270

Gln Gly Thr Ser Val Thr Val Ser Ser Thr Thr Thr Pro Ala Pro Arg
        275                 280                 285

Pro Pro Thr Pro Ala Pro Thr Ile Ala Ser Gln Pro Leu Ser Leu Arg
```

```
    290                 295                 300

Pro Glu Ala Cys Arg Pro Ala Ala Gly Gly Ala Val His Thr Arg Gly
305                 310                 315                 320

Leu Asp Phe Ala Cys Asp Ile Tyr Ile Trp Ala Pro Leu Ala Gly Thr
                325                 330                 335

Cys Gly Val Leu Leu Leu Ser Leu Val Ile Thr Leu Tyr Cys Arg Arg
            340                 345                 350

Asp Gln Arg Leu Pro Pro Asp Ala His Lys Pro Pro Gly Gly Gly Ser
        355                 360                 365

Phe Arg Thr Pro Ile Gln Glu Glu Gln Ala Asp Ala His Ser Thr Leu
    370                 375                 380

Ala Lys Ile Arg Val Lys Phe Ser Arg Ser Ala Asp Ala Pro Ala Tyr
385                 390                 395                 400

Gln Gln Gly Gln Asn Gln Leu Tyr Asn Glu Leu Asn Leu Gly Arg Arg
                405                 410                 415

Glu Glu Tyr Asp Val Leu Asp Lys Arg Arg Gly Arg Asp Pro Glu Met
            420                 425                 430

Gly Gly Lys Pro Arg Arg Lys Asn Pro Gln Glu Gly Leu Tyr Asn Glu
        435                 440                 445

Leu Gln Lys Asp Lys Met Ala Glu Ala Tyr Ser Glu Ile Gly Met Lys
    450                 455                 460

Gly Glu Arg Arg Arg Gly Lys Gly His Asp Gly Leu Tyr Gln Gly Leu
465                 470                 475                 480

Ser Thr Ala Thr Lys Asp Thr Tyr Asp Ala Leu His Met Gln Ala Leu
                485                 490                 495

Pro Pro Arg Gly Ser Gly Glu Gly Arg Gly Ser Leu Leu Thr Cys Gly
            500                 505                 510

Asp Val Glu Glu Asn Pro Gly Pro Met Ala Leu Pro Val Thr Ala Leu
        515                 520                 525

Leu Leu Pro Leu Ala Leu Leu Leu His Ala Ala Arg Pro Asn Trp Val
    530                 535                 540

Asn Val Ile Ser Asp Leu Lys Lys Ile Glu Asp Leu Ile Gln Ser Met
545                 550                 555                 560

His Ile Asp Ala Thr Leu Tyr Thr Glu Ser Asp Val His Pro Ser Cys
                565                 570                 575

Lys Val Thr Ala Met Lys Cys Phe Leu Leu Glu Leu Gln Val Ile Ser
            580                 585                 590

Leu Glu Ser Gly Asp Ala Ser Ile His Asp Thr Val Glu Asn Leu Ile
        595                 600                 605

Ile Leu Ala Asn Asn Ser Leu Ser Ser Asn Gly Asn Val Thr Glu Ser
    610                 615                 620

Gly Cys Lys Glu Cys Glu Glu Leu Glu Glu Lys Asn Ile Lys Glu Phe
625                 630                 635                 640

Leu Gln Ser Phe Val His Ile Val Gln Met Phe Ile Asn Thr Ser Thr
                645                 650                 655

Thr Thr Pro Ala Pro Arg Pro Pro Thr Pro Ala Pro Thr Ile Ala Ser
            660                 665                 670

Gln Pro Leu Ser Leu Arg Pro Glu Ala Cys Arg Pro Ala Ala Gly Gly
        675                 680                 685

Ala Val His Thr Arg Gly Leu Asp Phe Ala Cys Asp Ile Tyr Ile Trp
    690                 695                 700

Ala Pro Leu Ala Gly Thr Cys Gly Val Leu Leu Leu Ser Leu Val Ile
705                 710                 715                 720
```

Thr Leu Tyr Cys

<210> SEQ ID NO 162
<211> LENGTH: 2187
<212> TYPE: DNA
<213> ORGANISM: Homo sapiens
<220> FEATURE:
<221> NAME/KEY: misc_feature
<223> OTHER INFORMATION: DNA NK19H-2

<400> SEQUENCE: 162
gaattcgccg ccaccatggc cttaccagtg accgccttgc tcctgccgct ggccttgctg 60
ctccacgccg ccaggccgga ctacaaagac gatgacgata aaggcggtgg tggctctggt 120
ggtggcggca gcgatattca gatgacccag agcccgagca gcctgagcgc gagcgtgggc 180
gatcgcgtga ccattacctg ccgcgcgagc caggatatta gcaaatatct gaactggtat 240
cagcagaaac cgggcggcac cgtgaaactg ctgatttatc ataccagccg cctgcatagc 300
ggcgtgccga gccgctttag cggcagcggc agcggcaccg attttaccct gaccattagc 360
agcctgcagc cggaagatat tgcgacctat ttttgccagc agggcaacac cctgccgtat 420
acctttggcg gcggcaccaa actggaaatt accggtggcg gtggctcggg cggtggtggg 480
tcgggtggcg gcggatctca ggtgcagctg caggaaagcg gcccgggcct ggtgaaaccg 540
agccagaccc tgagcctgac ctgcaccgtg agcggcgtga gcctgccgga ttatggcgtg 600
agctggattc gccagccgcc gggcaaaggc ctggaatgga ttggcgtgat ttggggcagc 660
gaaaccacct attataacag cgcgctgaaa agccgcctga ccattagcaa agataacagc 720
aaaaaccagg tgagcctgaa actgagcagc gtgaccgcgg cggataccgc ggtgtattat 780
tgcgcgaaac attattatta tggcggcagc tatgcgatgg attattgggg ccagggcacc 840
agcgtgaccg tgagcagcac cacgacgcca gcgccgcgac caccaacacc ggcgcccacc 900
atcgcgtcgc agcccctgtc cctgcgccca gaggcgtgcc ggccagcggc ggggggcgca 960
gtgcacacga gggggctgga cttcgcctgt gatatctaca tctgggcgcc cttggccggg 1020
acttgtgggg tccttctcct gtcactggtt atcacccttt actgccggag ggaccagagg 1080 ctgcccccg atgcccacaa gccccctggg ggaggcagtt tccggacccc catccaagag 1140
gagcaggccg acgcccactc caccctggcc aagatcagag tgaagttcag caggagcgca 1200
gacgcccccg cgtaccagca gggccagaac cagctctata acgagctcaa tctaggacga 1260
agagaggagt acgatgtttt ggacaagaga cgtggccggg accctgagat gggggggaaag 1320 ccgagaagga agaaccctca ggaaggcctg tacaatgaac tgcagaaaga taagatggcg 1380
gaggcctaca gtgagattgg gatgaaaggc gagcgccgga ggggcaaggg gcacgatggc 1440
ctttaccagg gtctcagtac agccaccaag gacacctacg acgcccttca catgcaggcc 1500
ctgccccctc gcggctctgg cgagggaagg ggttccctgc ttacttgcgg cgacgtcgaa 1560
gagaatcccg gtccgatggc cctcccagta actgccctcc ttttgcccct cgcactcctt 1620
cttcatgccg ctcgccccaa ctgggtcaac gtgattagcg atttgaagaa aatcgaggac 1680
cttatacagt ctatgcatat tgacgctaca ctgtatactg agagtgatgt acacccgtcc 1740
tgtaaggtaa cggccatgaa atgctttctt ctggagctcc aggtcatcag cttggagtct 1800
ggggacgcaa gcatccacga tacggttgaa aacctcatca tccttgcgaa caactctctc 1860
tcatctaatg gaaacgttac agagagtggg tgtaaggagt gcgaagagtt ggaagaaaaa 1920
aacatcaaag aatttcttca atccttcgtt cacatagtgc aaatgttcat taacacgtcc 1980

```
actaccacac ccgccccgag gccacctacg ccggcaccga ctatcgccag tcaacccctc   2040

tctctgcgcc ccgaggcttg ccggcctgcg gctggtgggg cggtccacac ccggggcctg   2100

gattttgcgt gcgatatata catctgggca cctcttgccg gcacctgcgg agtgctgctt   2160

ctctcactcg ttattacgct gtactgc                                       2187


<210> SEQ ID NO 163
<211> LENGTH: 724
<212> TYPE: PRT
<213> ORGANISM: Homo sapiens
<220> FEATURE:
<221> NAME/KEY: MISC_FEATURE
<223> OTHER INFORMATION: AA NK19H-2

<400> SEQUENCE: 163

Met Ala Leu Pro Val Thr Ala Leu Leu Leu Pro Leu Ala Leu Leu Leu
1               5                   10                  15

His Ala Ala Arg Pro Asp Tyr Lys Asp Asp Asp Asp Lys Gly Gly Gly
            20                  25                  30

Gly Ser Gly Gly Gly Gly Ser Asp Ile Gln Met Thr Gln Ser Pro Ser
        35                  40                  45

Ser Leu Ser Ala Ser Val Gly Asp Arg Val Thr Ile Thr Cys Arg Ala
    50                  55                  60

Ser Gln Asp Ile Ser Lys Tyr Leu Asn Trp Tyr Gln Gln Lys Pro Gly
65                  70                  75                  80

Gly Thr Val Lys Leu Leu Ile Tyr His Thr Ser Arg Leu His Ser Gly
                85                  90                  95

Val Pro Ser Arg Phe Ser Gly Ser Gly Ser Gly Thr Asp Phe Thr Leu
            100                 105                 110

Thr Ile Ser Ser Leu Gln Pro Glu Asp Ile Ala Thr Tyr Phe Cys Gln
        115                 120                 125

Gln Gly Asn Thr Leu Pro Tyr Thr Phe Gly Gly Gly Thr Lys Leu Glu
    130                 135                 140

Ile Thr Gly Gly Gly Gly Ser Gly Gly Gly Gly Ser Gly Gly Gly Gly
145                 150                 155                 160

Ser Gln Val Gln Leu Gln Glu Ser Gly Pro Gly Leu Val Lys Pro Ser
                165                 170                 175

Gln Thr Leu Ser Leu Thr Cys Thr Val Ser Gly Val Ser Leu Pro Asp
            180                 185                 190

Tyr Gly Val Ser Trp Ile Arg Gln Pro Pro Gly Lys Gly Leu Glu Trp
        195                 200                 205

Ile Gly Val Ile Trp Gly Ser Glu Thr Thr Tyr Tyr Asn Ser Ala Leu
    210                 215                 220

Lys Ser Arg Leu Thr Ile Ser Lys Asp Asn Ser Lys Asn Gln Val Ser
225                 230                 235                 240

Leu Lys Leu Ser Ser Val Thr Ala Ala Asp Thr Ala Val Tyr Tyr Cys
                245                 250                 255

Ala Lys His Tyr Tyr Tyr Gly Gly Ser Tyr Ala Met Asp Tyr Trp Gly
            260                 265                 270

Gln Gly Thr Ser Val Thr Val Ser Ser Thr Thr Thr Pro Ala Pro Arg
        275                 280                 285

Pro Pro Thr Pro Ala Pro Thr Ile Ala Ser Gln Pro Leu Ser Leu Arg
    290                 295                 300

Pro Glu Ala Cys Arg Pro Ala Ala Gly Gly Ala Val His Thr Arg Gly
305                 310                 315                 320
```

```
Leu Asp Phe Ala Cys Asp Ile Tyr Ile Trp Ala Pro Leu Ala Gly Thr
                325                 330                 335

Cys Gly Val Leu Leu Leu Ser Leu Val Ile Thr Leu Tyr Cys Arg Arg
            340                 345                 350

Asp Gln Arg Leu Pro Pro Asp Ala His Lys Pro Pro Gly Gly Gly Ser
        355                 360                 365

Phe Arg Thr Pro Ile Gln Glu Glu Gln Ala Asp Ala His Ser Thr Leu
    370                 375                 380

Ala Lys Ile Arg Val Lys Phe Ser Arg Ser Ala Asp Ala Pro Ala Tyr
385                 390                 395                 400

Gln Gln Gly Gln Asn Gln Leu Tyr Asn Glu Leu Asn Leu Gly Arg Arg
                405                 410                 415

Glu Glu Tyr Asp Val Leu Asp Lys Arg Arg Gly Arg Asp Pro Glu Met
            420                 425                 430

Gly Gly Lys Pro Arg Arg Lys Asn Pro Gln Glu Gly Leu Tyr Asn Glu
        435                 440                 445

Leu Gln Lys Asp Lys Met Ala Glu Ala Tyr Ser Glu Ile Gly Met Lys
    450                 455                 460

Gly Glu Arg Arg Arg Gly Lys Gly His Asp Gly Leu Tyr Gln Gly Leu
465                 470                 475                 480

Ser Thr Ala Thr Lys Asp Thr Tyr Asp Ala Leu His Met Gln Ala Leu
                485                 490                 495

Pro Pro Arg Gly Ser Gly Glu Gly Arg Gly Ser Leu Leu Thr Cys Gly
            500                 505                 510

Asp Val Glu Glu Asn Pro Gly Pro Met Ala Leu Pro Val Thr Ala Leu
        515                 520                 525

Leu Leu Pro Leu Ala Leu Leu Leu His Ala Ala Arg Pro Asn Trp Val
    530                 535                 540

Asn Val Ile Ser Asp Leu Lys Lys Ile Glu Asp Leu Ile Gln Ser Met
545                 550                 555                 560

His Ile Asp Ala Thr Leu Tyr Thr Glu Ser Asp Val His Pro Ser Cys
                565                 570                 575

Lys Val Thr Ala Met Lys Cys Phe Leu Leu Glu Leu Gln Val Ile Ser
            580                 585                 590

Leu Glu Ser Gly Asp Ala Ser Ile His Asp Thr Val Glu Asn Leu Ile
        595                 600                 605

Ile Leu Ala Asn Asn Ser Leu Ser Ser Asn Gly Asn Val Thr Glu Ser
    610                 615                 620

Gly Cys Lys Glu Cys Glu Glu Leu Glu Glu Lys Asn Ile Lys Glu Phe
625                 630                 635                 640

Leu Gln Ser Phe Val His Ile Val Gln Met Phe Ile Asn Thr Ser Thr
                645                 650                 655

Thr Thr Pro Ala Pro Arg Pro Pro Thr Pro Ala Pro Thr Ile Ala Ser
            660                 665                 670

Gln Pro Leu Ser Leu Arg Pro Glu Ala Cys Arg Pro Ala Ala Gly Gly
        675                 680                 685

Ala Val His Thr Arg Gly Leu Asp Phe Ala Cys Asp Ile Tyr Ile Trp
    690                 695                 700

Ala Pro Leu Ala Gly Thr Cys Gly Val Leu Leu Leu Ser Leu Val Ile
705                 710                 715                 720

Thr Leu Tyr Cys
```

<210> SEQ ID NO 164
<211> LENGTH: 2204
<212> TYPE: DNA
<213> ORGANISM: Homo sapiens
<220> FEATURE:
<221> NAME/KEY: misc_feature
<223> OTHER INFORMATION: DNA NK19H-3

<400> SEQUENCE: 164

```
gaattcgccg ccaccatggc cttaccagtg accgccttgc tcctgccgct ggccttgctg     60

ctccacgccg ccaggccgga ctacaaagac gatgacgata aaggcggtgg tggctctggt    120

ggtggcggca gcgatattca gatgacccag agcccgagca gcctgagcgc gagcgtgggc    180

gatcgcgtga ccattacctg ccgcgcgagc caggatatta gcaaatatct gaactggtat    240

cagcagaaac cggatggcac cgtgaaactg ctgatttatc ataccagccg cctgcatagc    300

ggcgtgccga gccgctttag cggcagcggc agcggcaccg attataccct gaccattagc    360

agcctgcagc cggaagatat tgcgacctat ttttgccagc agggcaacac cctgccgtat    420

acctttggcg gcggcaccaa actggaaatt accggtggcg gtggctcggg cggtggtggg    480

tcgggtggcg gcggatctca ggtgcagctg caggaaagcg gcccgggcct ggtgaaaccg    540

agccagaccc tgagcctgac ctgcaccgtg agcggcgtga gcctgccgga ttatggcgtg    600

agctggattc gccagccgcc gggcaaaggc ctggaatgga ttggcgtgat ttggggcagc    660

gaaaccacct attataacag cgcgctgaaa agccgcctga ccattagcaa agataacagc    720

aaaaaccagg tgagcctgaa actgagcagc gtgaccgcgg cggataccgc ggtgtattat    780

tgcgcgaaac attattatta tggcggcagc tatgcgatgg attattgggg ccagggcacc    840

agcgtgaccg tgagcagcac cacgacgcca gcgccgcgac caccaacacc ggcgcccacc    900

atcgcgtcgc agcccctgtc cctgcgccca gaggcgtgcc ggccagcggc ggggggcgca    960

gtgcacacga gggggctgga cttcgcctgt gatatctaca tctgggcgcc cttggccggg   1020

acttgtgggg tccttctcct gtcactggtt atcacccttt actgccggag ggaccagagg   1080

ctgccccccg atgcccacaa gccccctggg ggaggcagtt tccggacccc catccaagag   1140

gagcaggccg acgcccactc caccctggcc aagatcagag tgaagttcag caggagcgca   1200

gacgcccccg cgtaccagca gggccagaac cagctctata acgagctcaa tctaggacga   1260

agagaggagt acgatgtttt ggacaagaga cgtggccggg accctgagat ggggggaaag   1320

ccgagaagga agaaccctca ggaaggcctg tacaatgaac tgcagaaaga taagatggcg   1380

gaggcctaca gtgagattgg gatgaaaggc gagcgccgga ggggcaaggg gcacgatggc   1440

ctttaccagg gtctcagtac agccaccaag gacacctacg acgcccttca catgcaggcc   1500

ctgccccctc gcggctctgg cgagggaagg ggttccctgc ttacttgcgg cgacgtcgaa   1560

gagaatcccg gtccgatggc cctcccagta actgccctcc ttttgcccct cgcactcctt   1620

cttcatgccg ctcgccccaa ctgggtcaac gtgattagcg atttgaagaa aatcgaggac   1680

cttatacagt ctatgcatat tgacgctaca ctgtatactg agagtgatgt acacccgtcc   1740

tgtaaggtaa cggccatgaa atgctttctt ctggagctcc aggtcatcag cttggagtct   1800

ggggacgcaa gcatccacga tacggttgaa aacctcatca tccttgcgaa caactctctc   1860

tcatctaatg gaaacgttac agagagtggg tgtaaggagt gcgaagagtt ggaagaaaaa   1920

aacatcaaag aatttcttca atccttcgtt cacatagtgc aaatgttcat taacacgtcc   1980

actaccacac ccgccccgag gccacctacg ccggcaccga ctatcgccag tcaacccctc   2040

tctctgcgcc ccgaggcttg ccggcctgcg gctggtgggg cggtccacac ccggggcctg   2100
```

gattttgcgt gcgatatata catctgggca cctcttgccg gcacctgcgg agtgctgctt 2160
ctctcactcg ttattacgct gtactgctaa gcggccgcgt cgac 2204

<210> SEQ ID NO 165
<211> LENGTH: 724
<212> TYPE: PRT
<213> ORGANISM: Homo sapiens
<220> FEATURE:
<221> NAME/KEY: MISC_FEATURE
<223> OTHER INFORMATION: AA NK19H-3

<400> SEQUENCE: 165

Met Ala Leu Pro Val Thr Ala Leu Leu Leu Pro Leu Ala Leu Leu Leu
1 5 10 15

His Ala Ala Arg Pro Asp Tyr Lys Asp Asp Asp Asp Lys Gly Gly Gly
20 25 30

Gly Ser Gly Gly Gly Gly Ser Asp Ile Gln Met Thr Gln Ser Pro Ser
35 40 45

Ser Leu Ser Ala Ser Val Gly Asp Arg Val Thr Ile Thr Cys Arg Ala
50 55 60

Ser Gln Asp Ile Ser Lys Tyr Leu Asn Trp Tyr Gln Gln Lys Pro Asp
65 70 75 80

Gly Thr Val Lys Leu Leu Ile Tyr His Thr Ser Arg Leu His Ser Gly
85 90 95

Val Pro Ser Arg Phe Ser Gly Ser Gly Ser Gly Thr Asp Tyr Thr Leu
100 105 110

Thr Ile Ser Ser Leu Gln Pro Glu Asp Ile Ala Thr Tyr Phe Cys Gln
115 120 125

Gln Gly Asn Thr Leu Pro Tyr Thr Phe Gly Gly Gly Thr Lys Leu Glu
130 135 140

Ile Thr Gly Gly Gly Gly Ser Gly Gly Gly Gly Ser Gly Gly Gly Gly
145 150 155 160

Ser Gln Val Gln Leu Gln Glu Ser Gly Pro Gly Leu Val Lys Pro Ser
165 170 175

Gln Thr Leu Ser Leu Thr Cys Thr Val Ser Gly Val Ser Leu Pro Asp
180 185 190

Tyr Gly Val Ser Trp Ile Arg Gln Pro Pro Gly Lys Gly Leu Glu Trp
195 200 205

Ile Gly Val Ile Trp Gly Ser Glu Thr Thr Tyr Tyr Asn Ser Ala Leu
210 215 220

Lys Ser Arg Leu Thr Ile Ser Lys Asp Asn Ser Lys Asn Gln Val Ser
225 230 235 240

Leu Lys Leu Ser Ser Val Thr Ala Ala Asp Thr Ala Val Tyr Tyr Cys
245 250 255

Ala Lys His Tyr Tyr Tyr Gly Gly Ser Tyr Ala Met Asp Tyr Trp Gly
260 265 270

Gln Gly Thr Ser Val Thr Val Ser Ser Thr Thr Thr Pro Ala Pro Arg
275 280 285

Pro Pro Thr Pro Ala Pro Thr Ile Ala Ser Gln Pro Leu Ser Leu Arg
290 295 300

Pro Glu Ala Cys Arg Pro Ala Ala Gly Gly Ala Val His Thr Arg Gly
305 310 315 320

Leu Asp Phe Ala Cys Asp Ile Tyr Ile Trp Ala Pro Leu Ala Gly Thr
325 330 335

```
Cys Gly Val Leu Leu Leu Ser Leu Val Ile Thr Leu Tyr Cys Arg Arg
            340                 345                 350

Asp Gln Arg Leu Pro Pro Asp Ala His Lys Pro Pro Gly Gly Gly Ser
        355                 360                 365

Phe Arg Thr Pro Ile Gln Glu Glu Gln Ala Asp Ala His Ser Thr Leu
    370                 375                 380

Ala Lys Ile Arg Val Lys Phe Ser Arg Ser Ala Asp Ala Pro Ala Tyr
385                 390                 395                 400

Gln Gln Gly Gln Asn Gln Leu Tyr Asn Glu Leu Asn Leu Gly Arg Arg
                405                 410                 415

Glu Glu Tyr Asp Val Leu Asp Lys Arg Arg Gly Arg Asp Pro Glu Met
            420                 425                 430

Gly Gly Lys Pro Arg Arg Lys Asn Pro Gln Glu Gly Leu Tyr Asn Glu
        435                 440                 445

Leu Gln Lys Asp Lys Met Ala Glu Ala Tyr Ser Glu Ile Gly Met Lys
    450                 455                 460

Gly Glu Arg Arg Arg Gly Lys Gly His Asp Gly Leu Tyr Gln Gly Leu
465                 470                 475                 480

Ser Thr Ala Thr Lys Asp Thr Tyr Asp Ala Leu His Met Gln Ala Leu
                485                 490                 495

Pro Pro Arg Gly Ser Gly Glu Gly Arg Gly Ser Leu Leu Thr Cys Gly
            500                 505                 510

Asp Val Glu Glu Asn Pro Gly Pro Met Ala Leu Pro Val Thr Ala Leu
        515                 520                 525

Leu Leu Pro Leu Ala Leu Leu Leu His Ala Ala Arg Pro Asn Trp Val
    530                 535                 540

Asn Val Ile Ser Asp Leu Lys Lys Ile Glu Asp Leu Ile Gln Ser Met
545                 550                 555                 560

His Ile Asp Ala Thr Leu Tyr Thr Glu Ser Asp Val His Pro Ser Cys
                565                 570                 575

Lys Val Thr Ala Met Lys Cys Phe Leu Leu Glu Leu Gln Val Ile Ser
            580                 585                 590

Leu Glu Ser Gly Asp Ala Ser Ile His Asp Thr Val Glu Asn Leu Ile
        595                 600                 605

Ile Leu Ala Asn Asn Ser Leu Ser Ser Asn Gly Asn Val Thr Glu Ser
    610                 615                 620

Gly Cys Lys Glu Cys Glu Glu Leu Glu Glu Lys Asn Ile Lys Glu Phe
625                 630                 635                 640

Leu Gln Ser Phe Val His Ile Val Gln Met Phe Ile Asn Thr Ser Thr
                645                 650                 655

Thr Thr Pro Ala Pro Arg Pro Pro Thr Pro Ala Pro Thr Ile Ala Ser
            660                 665                 670

Gln Pro Leu Ser Leu Arg Pro Glu Ala Cys Arg Pro Ala Ala Gly Gly
        675                 680                 685

Ala Val His Thr Arg Gly Leu Asp Phe Ala Cys Asp Ile Tyr Ile Trp
    690                 695                 700

Ala Pro Leu Ala Gly Thr Cys Gly Val Leu Leu Leu Ser Leu Val Ile
705                 710                 715                 720

Thr Leu Tyr Cys
```

<210> SEQ ID NO 166
<211> LENGTH: 2204
<212> TYPE: DNA
<213> ORGANISM: Homo sapiens
<220> FEATURE:
<221> NAME/KEY: misc_feature
<223> OTHER INFORMATION: DNA NK19H-4

<400> SEQUENCE: 166
gaattcgccg ccaccatggc cttaccagtg accgccttgc tcctgccgct ggccttgctg 60
ctccacgccg ccaggccgga ctacaaagac gatgacgata aaggcggtgg tggctctggt 120
ggtggcggca gcgatattca gatgacccag agcccgagca gcctgagcgc gagcgtgggc 180
gatcgcgtga ccattacctg ccgcgcgagc caggatatta gcaaatatct gaactggtat 240
cagcagaaac cgggcggcac cgtgaaactg ctgatttatc ataccagccg cctgcatagc 300
ggcgtgccga gccgctttag cggcagcggc agcggcaccg attttaccct gaccattagc 360
agcctgcagc cggaagatat tgcgacctat tattgccagc agggcaacac cctgccgtat 420
acctttggcg gcggcaccaa actggaaatt accggtggcg gtggctcggg cggtggtggg 480
tcgggtggcg gcggatctca ggtgcagctg caggaaagcg gcccgggcct ggtgaaaccg 540
agccagaccc tgagcctgac ctgcaccgtg agcggcgtga gcctgccgga ttatggcgtg 600
agctggattc gccagccgcc gggcaaaggc ctggaatggc tgggcgtgat ttggggcagc 660
gaaaccacct attataacag cgcgctgaaa agccgcctga ccattagcaa agataacagc 720
aaaagccagg tgagcctgaa actgagcagc gtgaccgcgg cggataccgc ggtgtattat 780
tgcgcgaaac attattatta tggcggcagc tatgcgatgg attattgggg ccagggcacc 840
agcgtgaccg tgagcagcac cacgacgcca gcgccgcgac caccaacacc ggcgcccacc 900
atcgcgtcgc agcccctgtc cctgcgccca gaggcgtgcc ggccagcggc ggggggcgca 960
gtgcacacga gggggctgga cttcgcctgt gatatctaca tctgggcgcc cttggccggg 1020
acttgtgggg tccttctcct gtcactggtt atcacccttt actgccggag ggaccagagg 1080
ctgccccccg atgcccacaa gccccctggg ggaggcagtt tccggacccc catccaagag 1140
gagcaggccg acgcccactc caccctggcc aagatcagag tgaagttcag caggagcgca 1200
gacgcccccg cgtaccagca gggccagaac cagctctata acgagctcaa tctaggacga 1260
agagaggagt acgatgtttt ggacaagaga cgtggccggg accctgagat gggggggaaag 1320 ccgagaagga agaaccctca ggaaggcctg tacaatgaac tgcagaaaga taagatggcg 1380
gaggcctaca gtgagattgg gatgaaaggc gagcgccgga ggggcaaggg gcacgatggc 1440
ctttaccagg gtctcagtac agccaccaag gacacctacg acgcccttca catgcaggcc 1500
ctgccccctc gcggctctgg cgagggaagg ggttccctgc ttacttgcgg cgacgtcgaa 1560
gagaatcccg gtccgatggc cctcccagta actgccctcc ttttgcccct cgcactcctt 1620
cttcatgccg ctcgccccaa ctgggtcaac gtgattagcg atttgaagaa aatcgaggac 1680
cttatacagt ctatgcatat tgacgctaca ctgtatactg agagtgatgt acacccgtcc 1740
tgtaaggtaa cggccatgaa atgctttctt ctggagctcc aggtcatcag cttggagtct 1800
ggggacgcaa gcatccacga tacggttgaa aacctcatca tccttgcgaa caactctctc 1860
tcatctaatg gaaacgttac agagagtggg tgtaaggagt gcgaagagtt ggaagaaaaa 1920
aacatcaaag aatttcttca atccttcgtt cacatagtgc aaatgttcat taacacgtcc 1980
actaccacac ccgccccgag gccacctacg ccggcaccga ctatcgccag tcaacccctc 2040
tctctgcgcc ccgaggcttg ccggcctgcg gctggtgggg cggtccacac ccggggcctg 2100
gattttgcgt gcgatatata catctgggca cctcttgccg gcacctgcgg agtgctgctt 2160
ctctcactcg ttattacgct gtactgctaa gcggccgcgt cgac 2204

<210> SEQ ID NO 167
<211> LENGTH: 724
<212> TYPE: PRT
<213> ORGANISM: Homo sapiens
<220> FEATURE:
<221> NAME/KEY: MISC_FEATURE
<223> OTHER INFORMATION: AA NK19H-4

<400> SEQUENCE: 167

Met Ala Leu Pro Val Thr Ala Leu Leu Leu Pro Leu Ala Leu Leu Leu
1 5 10 15

His Ala Ala Arg Pro Asp Tyr Lys Asp Asp Asp Asp Lys Gly Gly Gly
20 25 30

Gly Ser Gly Gly Gly Gly Ser Asp Ile Gln Met Thr Gln Ser Pro Ser
35 40 45

Ser Leu Ser Ala Ser Val Gly Asp Arg Val Thr Ile Thr Cys Arg Ala
50 55 60

Ser Gln Asp Ile Ser Lys Tyr Leu Asn Trp Tyr Gln Gln Lys Pro Gly
65 70 75 80

Gly Thr Val Lys Leu Leu Ile Tyr His Thr Ser Arg Leu His Ser Gly
85 90 95

Val Pro Ser Arg Phe Ser Gly Ser Gly Ser Gly Thr Asp Phe Thr Leu
100 105 110

Thr Ile Ser Ser Leu Gln Pro Glu Asp Ile Ala Thr Tyr Tyr Cys Gln
115 120 125

Gln Gly Asn Thr Leu Pro Tyr Thr Phe Gly Gly Gly Thr Lys Leu Glu
130 135 140

Ile Thr Gly Gly Gly Gly Ser Gly Gly Gly Gly Ser Gly Gly Gly Gly
145 150 155 160

Ser Gln Val Gln Leu Gln Glu Ser Gly Pro Gly Leu Val Lys Pro Ser
165 170 175

Gln Thr Leu Ser Leu Thr Cys Thr Val Ser Gly Val Ser Leu Pro Asp
180 185 190

Tyr Gly Val Ser Trp Ile Arg Gln Pro Pro Gly Lys Gly Leu Glu Trp
195 200 205

Leu Gly Val Ile Trp Gly Ser Glu Thr Thr Tyr Tyr Asn Ser Ala Leu
210 215 220

Lys Ser Arg Leu Thr Ile Ser Lys Asp Asn Ser Lys Ser Gln Val Ser
225 230 235 240

Leu Lys Leu Ser Ser Val Thr Ala Ala Asp Thr Ala Val Tyr Tyr Cys
245 250 255

Ala Lys His Tyr Tyr Tyr Gly Gly Ser Tyr Ala Met Asp Tyr Trp Gly
260 265 270

Gln Gly Thr Ser Val Thr Val Ser Ser Thr Thr Thr Pro Ala Pro Arg
275 280 285

Pro Pro Thr Pro Ala Pro Thr Ile Ala Ser Gln Pro Leu Ser Leu Arg
290 295 300

Pro Glu Ala Cys Arg Pro Ala Ala Gly Gly Ala Val His Thr Arg Gly
305 310 315 320

Leu Asp Phe Ala Cys Asp Ile Tyr Ile Trp Ala Pro Leu Ala Gly Thr
325 330 335

Cys Gly Val Leu Leu Leu Ser Leu Val Ile Thr Leu Tyr Cys Arg Arg
340 345 350

Asp Gln Arg Leu Pro Pro Asp Ala His Lys Pro Pro Gly Gly Gly Ser

```
        355                 360                 365

Phe Arg Thr Pro Ile Gln Glu Glu Gln Ala Asp Ala His Ser Thr Leu
    370                 375                 380

Ala Lys Ile Arg Val Lys Phe Ser Arg Ser Ala Asp Ala Pro Ala Tyr
385                 390                 395                 400

Gln Gln Gly Gln Asn Gln Leu Tyr Asn Glu Leu Asn Leu Gly Arg Arg
                405                 410                 415

Glu Glu Tyr Asp Val Leu Asp Lys Arg Arg Gly Arg Asp Pro Glu Met
            420                 425                 430

Gly Gly Lys Pro Arg Arg Lys Asn Pro Gln Glu Gly Leu Tyr Asn Glu
        435                 440                 445

Leu Gln Lys Asp Lys Met Ala Glu Ala Tyr Ser Glu Ile Gly Met Lys
    450                 455                 460

Gly Glu Arg Arg Arg Gly Lys Gly His Asp Gly Leu Tyr Gln Gly Leu
465                 470                 475                 480

Ser Thr Ala Thr Lys Asp Thr Tyr Asp Ala Leu His Met Gln Ala Leu
                485                 490                 495

Pro Pro Arg Gly Ser Gly Glu Gly Arg Gly Ser Leu Leu Thr Cys Gly
            500                 505                 510

Asp Val Glu Glu Asn Pro Gly Pro Met Ala Leu Pro Val Thr Ala Leu
        515                 520                 525

Leu Leu Pro Leu Ala Leu Leu Leu His Ala Ala Arg Pro Asn Trp Val
    530                 535                 540

Asn Val Ile Ser Asp Leu Lys Lys Ile Glu Asp Leu Ile Gln Ser Met
545                 550                 555                 560

His Ile Asp Ala Thr Leu Tyr Thr Glu Ser Asp Val His Pro Ser Cys
                565                 570                 575

Lys Val Thr Ala Met Lys Cys Phe Leu Leu Glu Leu Gln Val Ile Ser
            580                 585                 590

Leu Glu Ser Gly Asp Ala Ser Ile His Asp Thr Val Glu Asn Leu Ile
        595                 600                 605

Ile Leu Ala Asn Asn Ser Leu Ser Ser Asn Gly Asn Val Thr Glu Ser
    610                 615                 620

Gly Cys Lys Glu Cys Glu Glu Leu Glu Glu Lys Asn Ile Lys Glu Phe
625                 630                 635                 640

Leu Gln Ser Phe Val His Ile Val Gln Met Phe Ile Asn Thr Ser Thr
                645                 650                 655

Thr Thr Pro Ala Pro Arg Pro Pro Thr Pro Ala Pro Thr Ile Ala Ser
            660                 665                 670

Gln Pro Leu Ser Leu Arg Pro Glu Ala Cys Arg Pro Ala Ala Gly Gly
        675                 680                 685

Ala Val His Thr Arg Gly Leu Asp Phe Ala Cys Asp Ile Tyr Ile Trp
    690                 695                 700

Ala Pro Leu Ala Gly Thr Cys Gly Val Leu Leu Leu Ser Leu Val Ile
705                 710                 715                 720

Thr Leu Tyr Cys
```

```
<210> SEQ ID NO 168
<211> LENGTH: 2204
<212> TYPE: DNA
<213> ORGANISM: Homo sapiens
<220> FEATURE:
<221> NAME/KEY: misc_feature
<223> OTHER INFORMATION: DNA NK19H-5
```

<400> SEQUENCE: 168

```
gaattcgccg ccaccatggc cttaccagtg accgccttgc tcctgccgct ggccttgctg     60
ctccacgccg ccaggccgga ctacaaagac gatgacgata aaggcggtgg tggctctggt    120
ggtggcggca gcgatattca gatgacccag agcccgagca gcctgagcgc gagcgtgggc    180
gatcgcgtga ccattacctg ccgcgcgagc caggatatta gcaaatatct gaactggtat    240
cagcagaaac cgggcggcac cgtgaaactg ctgatttatc ataccagccg cctgcatagc    300
ggcgtgccga gccgctttag cggcagcggc agcggcaccg attttaccct gaccattagc    360
agcctgcagc cggaagatat tgcgacctat ttttgccagc agggcaacac cctgccgtat    420
acctttggcg gcggcaccaa actggaaatt accggtggcg gtggctcggg cggtggtggg    480
tcgggtggcg gcggatctca ggtgcagctg caggaaagcg gcccgggcct ggtgaaaccg    540
agccagaccc tgagcctgac ctgcaccgtg agcggcgtga gcctgccgga ttatggcgtg    600
agctggattc gccagccgcc gggcaaaggc ctggaatggc tgggcgtgat ttggggcagc    660
gaaaccacct attataacag cgcgctgaaa agccgcctga ccattagcaa agataacagc    720
aaaagccagg tgagcctgaa actgagcagc gtgaccgcgg cggataccgc ggtgtattat    780
tgcgcgaaac attattatta tggcggcagc tatgcgatgg attattgggg ccagggcacc    840
agcgtgaccg tgagcagcac cacgacgcca gcgccgcgac caccaacacc ggcgcccacc    900
atcgcgtcgc agcccctgtc cctgcgccca gaggcgtgcc ggccagcggc ggggggcgca    960
gtgcacacga gggggctgga cttcgcctgt gatatctaca tctgggcgcc cttggccggg   1020
acttgtgggg tccttctcct gtcactggtt atcacccttt actgccggag ggaccagagg   1080
ctgccccccg atgcccacaa gccccctggg ggaggcagtt tccggacccc catccaagag   1140
gagcaggccg acgcccactc caccctggcc aagatcagag tgaagttcag caggagcgca   1200
gacgcccccg cgtaccagca gggccagaac cagctctata acgagctcaa tctaggacga   1260
agagaggagt acgatgtttt ggacaagaga cgtggccggg accctgagat ggggggaaag   1320
ccgagaagga agaaccctca ggaaggcctg tacaatgaac tgcagaaaga taagatggcg   1380
gaggcctaca gtgagattgg gatgaaaggc gagcgccgga ggggcaaggg gcacgatggc   1440
ctttaccagg gtctcagtac agccaccaag gacacctacg acgcccttca catgcaggcc   1500
ctgccccctc gcggctctgg cgagggaagg ggttccctgc ttacttgcgg cgacgtcgaa   1560
gagaatcccg gtccgatggc cctcccagta actgccctcc ttttgcccct cgcactcctt   1620
cttcatgccg ctcgccccaa ctgggtcaac gtgattagcg atttgaagaa aatcgaggac   1680
cttatacagt ctatgcatat tgacgctaca ctgtatactg agagtgatgt acacccgtcc   1740
tgtaaggtaa cggccatgaa atgctttctt ctggagctcc aggtcatcag cttggagtct   1800
ggggacgcaa gcatccacga tacggttgaa aacctcatca tccttgcgaa caactctctc   1860
tcatctaatg gaaacgttac agagagtggg tgtaaggagt gcgaagagtt ggaagaaaaa   1920
aacatcaaag aatttcttca atccttcgtt cacatagtgc aaatgttcat taacacgtcc   1980
actaccacac ccgccccgag gccacctacg ccggcaccga ctatcgccag tcaacccctc   2040
tctctgcgcc ccgaggcttg ccggcctgcg gctggtgggg cggtccacac ccggggcctg   2100
gattttgcgt gcgatatata catctgggca cctcttgccg gcacctgcgg agtgctgctt   2160
ctctcactcg ttattacgct gtactgctaa gcggccgcgt cgac                     2204
```

<210> SEQ ID NO 169
<211> LENGTH: 724

<212> TYPE: PRT
<213> ORGANISM: Homo sapiens
<220> FEATURE:
<221> NAME/KEY: MISC_FEATURE
<223> OTHER INFORMATION: AA NK19H-5

<400> SEQUENCE: 169

```
Met Ala Leu Pro Val Thr Ala Leu Leu Leu Pro Leu Ala Leu Leu Leu
1               5                   10                  15

His Ala Ala Arg Pro Asp Tyr Lys Asp Asp Asp Asp Lys Gly Gly Gly
            20                  25                  30

Gly Ser Gly Gly Gly Gly Ser Asp Ile Gln Met Thr Gln Ser Pro Ser
        35                  40                  45

Ser Leu Ser Ala Ser Val Gly Asp Arg Val Thr Ile Thr Cys Arg Ala
    50                  55                  60

Ser Gln Asp Ile Ser Lys Tyr Leu Asn Trp Tyr Gln Gln Lys Pro Gly
65                  70                  75                  80

Gly Thr Val Lys Leu Leu Ile Tyr His Thr Ser Arg Leu His Ser Gly
                85                  90                  95

Val Pro Ser Arg Phe Ser Gly Ser Gly Ser Gly Thr Asp Phe Thr Leu
            100                 105                 110

Thr Ile Ser Ser Leu Gln Pro Glu Asp Ile Ala Thr Tyr Phe Cys Gln
        115                 120                 125

Gln Gly Asn Thr Leu Pro Tyr Thr Phe Gly Gly Gly Thr Lys Leu Glu
    130                 135                 140

Ile Thr Gly Gly Gly Gly Ser Gly Gly Gly Gly Ser Gly Gly Gly Gly
145                 150                 155                 160

Ser Gln Val Gln Leu Gln Glu Ser Gly Pro Gly Leu Val Lys Pro Ser
                165                 170                 175

Gln Thr Leu Ser Leu Thr Cys Thr Val Ser Gly Val Ser Leu Pro Asp
            180                 185                 190

Tyr Gly Val Ser Trp Ile Arg Gln Pro Pro Gly Lys Gly Leu Glu Trp
        195                 200                 205

Leu Gly Val Ile Trp Gly Ser Glu Thr Thr Tyr Tyr Asn Ser Ala Leu
    210                 215                 220

Lys Ser Arg Leu Thr Ile Ser Lys Asp Asn Ser Lys Ser Gln Val Ser
225                 230                 235                 240

Leu Lys Leu Ser Ser Val Thr Ala Ala Asp Thr Ala Val Tyr Tyr Cys
                245                 250                 255

Ala Lys His Tyr Tyr Tyr Gly Gly Ser Tyr Ala Met Asp Tyr Trp Gly
            260                 265                 270

Gln Gly Thr Ser Val Thr Val Ser Ser Thr Thr Thr Pro Ala Pro Arg
        275                 280                 285

Pro Pro Thr Pro Ala Pro Thr Ile Ala Ser Gln Pro Leu Ser Leu Arg
    290                 295                 300

Pro Glu Ala Cys Arg Pro Ala Ala Gly Gly Ala Val His Thr Arg Gly
305                 310                 315                 320

Leu Asp Phe Ala Cys Asp Ile Tyr Ile Trp Ala Pro Leu Ala Gly Thr
                325                 330                 335

Cys Gly Val Leu Leu Leu Ser Leu Val Ile Thr Leu Tyr Cys Arg Arg
            340                 345                 350

Asp Gln Arg Leu Pro Pro Asp Ala His Lys Pro Pro Gly Gly Ser
        355                 360                 365

Phe Arg Thr Pro Ile Gln Glu Glu Gln Ala Asp Ala His Ser Thr Leu
    370                 375                 380
```

```
Ala Lys Ile Arg Val Lys Phe Ser Arg Ser Ala Asp Ala Pro Ala Tyr
385                 390                 395                 400

Gln Gln Gly Gln Asn Gln Leu Tyr Asn Glu Leu Asn Leu Gly Arg Arg
                405                 410                 415

Glu Glu Tyr Asp Val Leu Asp Lys Arg Arg Gly Arg Asp Pro Glu Met
            420                 425                 430

Gly Gly Lys Pro Arg Arg Lys Asn Pro Gln Glu Gly Leu Tyr Asn Glu
        435                 440                 445

Leu Gln Lys Asp Lys Met Ala Glu Ala Tyr Ser Glu Ile Gly Met Lys
    450                 455                 460

Gly Glu Arg Arg Arg Gly Lys Gly His Asp Gly Leu Tyr Gln Gly Leu
465                 470                 475                 480

Ser Thr Ala Thr Lys Asp Thr Tyr Asp Ala Leu His Met Gln Ala Leu
                485                 490                 495

Pro Pro Arg Gly Ser Gly Glu Gly Arg Gly Ser Leu Leu Thr Cys Gly
            500                 505                 510

Asp Val Glu Glu Asn Pro Gly Pro Met Ala Leu Pro Val Thr Ala Leu
        515                 520                 525

Leu Leu Pro Leu Ala Leu Leu Leu His Ala Ala Arg Pro Asn Trp Val
    530                 535                 540

Asn Val Ile Ser Asp Leu Lys Lys Ile Glu Asp Leu Ile Gln Ser Met
545                 550                 555                 560

His Ile Asp Ala Thr Leu Tyr Thr Glu Ser Asp Val His Pro Ser Cys
                565                 570                 575

Lys Val Thr Ala Met Lys Cys Phe Leu Leu Glu Leu Gln Val Ile Ser
            580                 585                 590

Leu Glu Ser Gly Asp Ala Ser Ile His Asp Thr Val Glu Asn Leu Ile
        595                 600                 605

Ile Leu Ala Asn Asn Ser Leu Ser Ser Asn Gly Asn Val Thr Glu Ser
    610                 615                 620

Gly Cys Lys Glu Cys Glu Glu Leu Glu Glu Lys Asn Ile Lys Glu Phe
625                 630                 635                 640

Leu Gln Ser Phe Val His Ile Val Gln Met Phe Ile Asn Thr Ser Thr
                645                 650                 655

Thr Thr Pro Ala Pro Arg Pro Pro Thr Pro Ala Pro Thr Ile Ala Ser
            660                 665                 670

Gln Pro Leu Ser Leu Arg Pro Glu Ala Cys Arg Pro Ala Ala Gly Gly
        675                 680                 685

Ala Val His Thr Arg Gly Leu Asp Phe Ala Cys Asp Ile Tyr Ile Trp
    690                 695                 700

Ala Pro Leu Ala Gly Thr Cys Gly Val Leu Leu Leu Ser Leu Val Ile
705                 710                 715                 720

Thr Leu Tyr Cys
```

<210> SEQ ID NO 170
<211> LENGTH: 2204
<212> TYPE: DNA
<213> ORGANISM: Homo sapiens
<220> FEATURE:
<221> NAME/KEY: misc_feature
<223> OTHER INFORMATION: DNA NK19H-6

<400> SEQUENCE: 170

```
gaattcgccg ccaccatggc cttaccagtg accgccttgc tcctgccgct ggccttgctg     60
```

```
ctccacgccg ccaggccgga ctacaaagac gatgacgata aaggcggtgg tggctctggt    120
ggtggcggca gcgacatcca gatgacacag agcccgtcct ccctgtctgc ctctgtggga    180
gacagagtca ccatcacctg cagggcaagt caggacatta gtaaatattt aaattggtat    240
cagcagaaac cagacggaac tgttaaactc ctgatctacc atacatcaag attacactca    300
ggagtcccat caaggttcag tggcagtggg tctggaacag attacaccct caccattagc    360
agcctgcaac cggaagatat tgccacttac ttctgccaac agggtaatac gcttccgtac    420
acgttcggag gggggaccaa gctggagatc acaggtggcg gtggctcggg cggtggtggg    480
tcgggtggcg gcggatctca ggtgcagctg caggagtcag gacctggcct ggtgaaaccc    540
tcacagactc tgtccctgac atgcactgtc tcaggggtct cattacccga ctatggtgta    600
agctggattc gccagcctcc aggtaagggt ctggagtggc tgggagtaat atggggtagt    660
gaaaccacat actataattc agctctcaaa tccagactga ccatctccaa ggacaactcc    720
aagagccaag tttccttaaa attaagtagt gttactgctg ctgacacagc cgtctactac    780
tgtgccaaac attattacta cggtggtagc tatgctatgg actactgggg ccaaggaacc    840
tcagtcaccg tctcctcaac cacgacgcca gcgccgcgac caccaacacc ggcgcccacc    900
atcgcgtcgc agcccctgtc cctgcgccca gaggcgtgcc ggccagcggc ggggggcgca    960
gtgcacacga gggggctgga cttcgcctgt gatatctaca tctgggcgcc cttggccggg   1020
acttgtgggg tccttctcct gtcactggtt atcacccttt actgccggag ggaccagagg   1080
ctgccccccg atgcccacaa gccccctggg ggaggcagtt tccggacccc catccaagag   1140
gagcaggccg acgcccactc caccctggcc aagatcagag tgaagttcag caggagcgca   1200
gacgcccccg cgtaccagca gggccagaac cagctctata acgagctcaa tctaggacga   1260
agagaggagt acgatgtttt ggacaagaga cgtggccggg accctgagat gggggggaaag   1320
ccgagaagga agaaccctca ggaaggcctg tacaatgaac tgcagaaaga taagatggcg   1380
gaggcctaca gtgagattgg gatgaaaggc gagcgccgga ggggcaaggg gcacgatggc   1440
ctttaccagg gtctcagtac agccaccaag gacacctacg acgcccttca catgcaggcc   1500
ctgccccctc gcggctctgg cgagggaagg ggttccctgc ttacttgcgg cgacgtcgaa   1560
gagaatcccg gtccgatggc cctcccagta actgccctcc ttttgcccct cgcactcctt   1620
cttcatgccg ctcgccccaa ctgggtcaac gtgattagcg atttgaagaa aatcgaggac   1680
cttatacagt ctatgcatat tgacgctaca ctgtatactg agagtgatgt acacccgtcc   1740
tgtaaggtaa cggccatgaa atgctttctt ctggagctcc aggtcatcag cttggagtct   1800
ggggacgcaa gcatccacga tacggttgaa aacctcatca tccttgcgaa caactctctc   1860
tcatctaatg gaaacgttac agagagtggg tgtaaggagt gcgaagagtt ggaagaaaaa   1920
aacatcaaag aatttcttca atccttcgtt cacatagtgc aaatgttcat taacacgtcc   1980
actaccacac ccgccccgag gccacctacg ccggcaccga ctatcgccag tcaacccctc   2040
tctctgcgcc ccgaggcttg ccggcctgcg gctggtgggg cggtccacac ccggggcctg   2100
gattttgcgt gcgatatata catctgggca cctcttgccg gcacctgcgg agtgctgctt   2160
ctctcactcg ttattacgct gtactgctaa gcggccgcgt cgac                    2204
```

<210> SEQ ID NO 171
<211> LENGTH: 724
<212> TYPE: PRT
<213> ORGANISM: Homo sapiens
<220> FEATURE:
<221> NAME/KEY: MISC_FEATURE

<223> OTHER INFORMATION: AA NK19H-6

<400> SEQUENCE: 171

```
Met Ala Leu Pro Val Thr Ala Leu Leu Leu Pro Leu Ala Leu Leu Leu
1               5                   10                  15

His Ala Ala Arg Pro Asp Tyr Lys Asp Asp Asp Asp Lys Gly Gly Gly
            20                  25                  30

Gly Ser Gly Gly Gly Gly Ser Asp Ile Gln Met Thr Gln Ser Pro Ser
        35                  40                  45

Ser Leu Ser Ala Ser Val Gly Asp Arg Val Thr Ile Thr Cys Arg Ala
    50                  55                  60

Ser Gln Asp Ile Ser Lys Tyr Leu Asn Trp Tyr Gln Gln Lys Pro Asp
65                  70                  75                  80

Gly Thr Val Lys Leu Leu Ile Tyr His Thr Ser Arg Leu His Ser Gly
                85                  90                  95

Val Pro Ser Arg Phe Ser Gly Ser Gly Ser Gly Thr Asp Tyr Thr Leu
            100                 105                 110

Thr Ile Ser Ser Leu Gln Pro Glu Asp Ile Ala Thr Tyr Phe Cys Gln
        115                 120                 125

Gln Gly Asn Thr Leu Pro Tyr Thr Phe Gly Gly Gly Thr Lys Leu Glu
    130                 135                 140

Ile Thr Gly Gly Gly Gly Ser Gly Gly Gly Gly Ser Gly Gly Gly Gly
145                 150                 155                 160

Ser Gln Val Gln Leu Gln Glu Ser Gly Pro Gly Leu Val Lys Pro Ser
                165                 170                 175

Gln Thr Leu Ser Leu Thr Cys Thr Val Ser Gly Val Ser Leu Pro Asp
            180                 185                 190

Tyr Gly Val Ser Trp Ile Arg Gln Pro Pro Gly Lys Gly Leu Glu Trp
        195                 200                 205

Leu Gly Val Ile Trp Gly Ser Glu Thr Thr Tyr Tyr Asn Ser Ala Leu
    210                 215                 220

Lys Ser Arg Leu Thr Ile Ser Lys Asp Asn Ser Lys Ser Gln Val Ser
225                 230                 235                 240

Leu Lys Leu Ser Ser Val Thr Ala Ala Asp Thr Ala Val Tyr Tyr Cys
                245                 250                 255

Ala Lys His Tyr Tyr Tyr Gly Gly Ser Tyr Ala Met Asp Tyr Trp Gly
            260                 265                 270

Gln Gly Thr Ser Val Thr Val Ser Ser Thr Thr Thr Pro Ala Pro Arg
        275                 280                 285

Pro Pro Thr Pro Ala Pro Thr Ile Ala Ser Gln Pro Leu Ser Leu Arg
    290                 295                 300

Pro Glu Ala Cys Arg Pro Ala Ala Gly Gly Ala Val His Thr Arg Gly
305                 310                 315                 320

Leu Asp Phe Ala Cys Asp Ile Tyr Ile Trp Ala Pro Leu Ala Gly Thr
                325                 330                 335

Cys Gly Val Leu Leu Leu Ser Leu Val Ile Thr Leu Tyr Cys Arg Arg
            340                 345                 350

Asp Gln Arg Leu Pro Pro Asp Ala His Lys Pro Pro Gly Gly Gly Ser
        355                 360                 365

Phe Arg Thr Pro Ile Gln Glu Glu Gln Ala Asp Ala His Ser Thr Leu
    370                 375                 380

Ala Lys Ile Arg Val Lys Phe Ser Arg Ser Ala Asp Ala Pro Ala Tyr
385                 390                 395                 400
```

```
Gln Gln Gly Gln Asn Gln Leu Tyr Asn Glu Leu Asn Leu Gly Arg Arg
                405                 410                 415

Glu Glu Tyr Asp Val Leu Asp Lys Arg Arg Gly Arg Asp Pro Glu Met
            420                 425                 430

Gly Gly Lys Pro Arg Arg Lys Asn Pro Gln Glu Gly Leu Tyr Asn Glu
        435                 440                 445

Leu Gln Lys Asp Lys Met Ala Glu Ala Tyr Ser Glu Ile Gly Met Lys
    450                 455                 460

Gly Glu Arg Arg Arg Gly Lys Gly His Asp Gly Leu Tyr Gln Gly Leu
465                 470                 475                 480

Ser Thr Ala Thr Lys Asp Thr Tyr Asp Ala Leu His Met Gln Ala Leu
                485                 490                 495

Pro Pro Arg Gly Ser Gly Glu Gly Arg Gly Ser Leu Leu Thr Cys Gly
            500                 505                 510

Asp Val Glu Glu Asn Pro Gly Pro Met Ala Leu Pro Val Thr Ala Leu
        515                 520                 525

Leu Leu Pro Leu Ala Leu Leu Leu His Ala Ala Arg Pro Asn Trp Val
    530                 535                 540

Asn Val Ile Ser Asp Leu Lys Lys Ile Glu Asp Leu Ile Gln Ser Met
545                 550                 555                 560

His Ile Asp Ala Thr Leu Tyr Thr Glu Ser Asp Val His Pro Ser Cys
                565                 570                 575

Lys Val Thr Ala Met Lys Cys Phe Leu Leu Glu Leu Gln Val Ile Ser
            580                 585                 590

Leu Glu Ser Gly Asp Ala Ser Ile His Asp Thr Val Glu Asn Leu Ile
        595                 600                 605

Ile Leu Ala Asn Asn Ser Leu Ser Ser Asn Gly Asn Val Thr Glu Ser
    610                 615                 620

Gly Cys Lys Glu Cys Glu Glu Leu Glu Glu Lys Asn Ile Lys Glu Phe
625                 630                 635                 640

Leu Gln Ser Phe Val His Ile Val Gln Met Phe Ile Asn Thr Ser Thr
                645                 650                 655

Thr Thr Pro Ala Pro Arg Pro Pro Thr Pro Ala Pro Thr Ile Ala Ser
            660                 665                 670

Gln Pro Leu Ser Leu Arg Pro Glu Ala Cys Arg Pro Ala Ala Gly Gly
        675                 680                 685

Ala Val His Thr Arg Gly Leu Asp Phe Ala Cys Asp Ile Tyr Ile Trp
    690                 695                 700

Ala Pro Leu Ala Gly Thr Cys Gly Val Leu Leu Leu Ser Leu Val Ile
705                 710                 715                 720

Thr Leu Tyr Cys


<210> SEQ ID NO 172
<211> LENGTH: 2204
<212> TYPE: DNA
<213> ORGANISM: Homo sapiens
<220> FEATURE:
<221> NAME/KEY: misc_feature
<223> OTHER INFORMATION: DNA NK19H-7

<400> SEQUENCE: 172

gaattcgccg ccaccatggc cttaccagtg accgccttgc tcctgccgct ggccttgctg      60

ctccacgccg ccaggccgga ctacaaagac gatgacgata aaggcggtgg tggctctggt     120

ggtggcggca gcgacatcca gatgacacag agcccgtcct ccctgtctgc ctctgtggga     180
```

-continued

```
gacagagtca ccatcacctg cagggcaagt caggacatta gtaaatattt aaattggtat    240
cagcagaaac caggtggaac tgttaaactc ctgatctacc atacatcaag attacactca    300
ggagtcccat caaggttcag tggcagtggg tctggaacag atttcaccct caccattagc    360
agcctgcaac cggaagatat tgccacttac tactgccaac agggtaatac gcttccgtac    420
acgttcggag gggggaccaa gctggagatc acaggtggcg gtggctcggg cggtggtggg    480
tcgggtggcg gcggatctca ggtgcagctg caggagtcag gacctggcct ggtgaaaccc    540
tcacagactc tgtccgtgac atgcactgtc tcaggggtct cattacccga ctatggtgta    600
agctggattc gccagcctcc aggtaagggt ctggagtggc tgggagtaat atggggtagt    660
gaaaccacat actataattc agctctcaaa tccagactga ccatctccaa ggacaactcc    720
aagagccaag tttccttaaa attaagtagt gttactgctg ctgacacagc cgtctactac    780
tgtgccaaac attattacta cggtggtagc tatgctatgg actactgggg ccaaggaacc    840
tcagtcaccg tctcctcaac cacgacgcca gcgccgcgac caccaacacc ggcgcccacc    900
atcgcgtcgc agcccctgtc cctgcgccca gaggcgtgcc ggccagcggc ggggggcgca    960
gtgcacacga gggggctgga cttcgcctgt gatatctaca tctgggcgcc cttggccggg   1020
acttgtgggg tccttctcct gtcactggtt atcacccttt actgccggag ggaccagagg   1080
ctgccccccg atgcccacaa gccccctggg ggaggcagtt tccggacccc catccaagag   1140
gagcaggccg acgcccactc caccctggcc aagatcagag tgaagttcag caggagcgca   1200
gacgcccccg cgtaccagca gggccagaac cagctctata acgagctcaa tctaggacga   1260
agagaggagt acgatgtttt ggacaagaga cgtggccggg accctgagat ggggggaaag   1320
ccgagaagga agaaccctca ggaaggcctg tacaatgaac tgcagaaaga taagatggcg   1380
gaggcctaca gtgagattgg gatgaaaggc gagcgccgga ggggcaaggg gcacgatggc   1440
ctttaccagg gtctcagtac agccaccaag gacacctacg acgcccttca catgcaggcc   1500
ctgccccctc gcggctctgg cgagggaagg ggttccctgc ttacttgcgg cgacgtcgaa   1560
gagaatcccg gtccgatggc cctcccagta actgccctcc ttttgcccct cgcactcctt   1620
cttcatgccg ctcgccccaa ctgggtcaac gtgattagcg atttgaagaa aatcgaggac   1680
cttatacagt ctatgcatat tgacgctaca ctgtatactg agagtgatgt acacccgtcc   1740
tgtaaggtaa cggccatgaa atgctttctt ctggagctcc aggtcatcag cttggagtct   1800
ggggacgcaa gcatccacga tacggttgaa aacctcatca tccttgcgaa caactctctc   1860
tcatctaatg gaaacgttac agagagtggg tgtaaggagt gcgaagagtt ggaagaaaaa   1920
aacatcaaag aatttcttca atccttcgtt cacatagtgc aaatgttcat taacacgtcc   1980
actaccacac ccgccccgag gccacctacg ccggcaccga ctatcgccag tcaacccctc   2040
tctctgcgcc ccgaggcttg ccggcctgcg gctggtgggg cggtccacac ccggggcctg   2100
gattttgcgt gcgatatata catctgggca cctcttgccg gcacctgcgg agtgctgctt   2160
ctctcactcg ttattacgct gtactgctaa gcggccgcgt cgac                    2204
```

<210> SEQ ID NO 173
<211> LENGTH: 724
<212> TYPE: PRT
<213> ORGANISM: Homo sapiens
<220> FEATURE:
<221> NAME/KEY: MISC_FEATURE
<223> OTHER INFORMATION: AA NK19H-7

<400> SEQUENCE: 173

-continued

```
Met Ala Leu Pro Val Thr Ala Leu Leu Leu Pro Leu Ala Leu Leu Leu
1               5                   10                  15

His Ala Ala Arg Pro Asp Tyr Lys Asp Asp Asp Asp Lys Gly Gly Gly
            20                  25                  30

Gly Ser Gly Gly Gly Gly Ser Asp Ile Gln Met Thr Gln Ser Pro Ser
        35                  40                  45

Ser Leu Ser Ala Ser Val Gly Asp Arg Val Thr Ile Thr Cys Arg Ala
    50                  55                  60

Ser Gln Asp Ile Ser Lys Tyr Leu Asn Trp Tyr Gln Gln Lys Pro Gly
65                  70                  75                  80

Gly Thr Val Lys Leu Leu Ile Tyr His Thr Ser Arg Leu His Ser Gly
                85                  90                  95

Val Pro Ser Arg Phe Ser Gly Ser Gly Ser Gly Thr Asp Phe Thr Leu
            100                 105                 110

Thr Ile Ser Ser Leu Gln Pro Glu Asp Ile Ala Thr Tyr Tyr Cys Gln
        115                 120                 125

Gln Gly Asn Thr Leu Pro Tyr Thr Phe Gly Gly Gly Thr Lys Leu Glu
    130                 135                 140

Ile Thr Gly Gly Gly Gly Ser Gly Gly Gly Gly Ser Gly Gly Gly Gly
145                 150                 155                 160

Ser Gln Val Gln Leu Gln Glu Ser Gly Pro Gly Leu Val Lys Pro Ser
                165                 170                 175

Gln Thr Leu Ser Val Thr Cys Thr Val Ser Gly Val Ser Leu Pro Asp
            180                 185                 190

Tyr Gly Val Ser Trp Ile Arg Gln Pro Pro Gly Lys Gly Leu Glu Trp
        195                 200                 205

Leu Gly Val Ile Trp Gly Ser Glu Thr Thr Tyr Tyr Asn Ser Ala Leu
    210                 215                 220

Lys Ser Arg Leu Thr Ile Ser Lys Asp Asn Ser Lys Ser Gln Val Ser
225                 230                 235                 240

Leu Lys Leu Ser Ser Val Thr Ala Ala Asp Thr Ala Val Tyr Tyr Cys
                245                 250                 255

Ala Lys His Tyr Tyr Tyr Gly Gly Ser Tyr Ala Met Asp Tyr Trp Gly
            260                 265                 270

Gln Gly Thr Ser Val Thr Val Ser Ser Thr Thr Thr Pro Ala Pro Arg
        275                 280                 285

Pro Pro Thr Pro Ala Pro Thr Ile Ala Ser Gln Pro Leu Ser Leu Arg
    290                 295                 300

Pro Glu Ala Cys Arg Pro Ala Ala Gly Gly Ala Val His Thr Arg Gly
305                 310                 315                 320

Leu Asp Phe Ala Cys Asp Ile Tyr Ile Trp Ala Pro Leu Ala Gly Thr
                325                 330                 335

Cys Gly Val Leu Leu Leu Ser Leu Val Ile Thr Leu Tyr Cys Arg Arg
            340                 345                 350

Asp Gln Arg Leu Pro Pro Asp Ala His Lys Pro Pro Gly Gly Gly Ser
        355                 360                 365

Phe Arg Thr Pro Ile Gln Glu Glu Gln Ala Asp Ala His Ser Thr Leu
    370                 375                 380

Ala Lys Ile Arg Val Lys Phe Ser Arg Ser Ala Asp Ala Pro Ala Tyr
385                 390                 395                 400

Gln Gln Gly Gln Asn Gln Leu Tyr Asn Glu Leu Asn Leu Gly Arg Arg
                405                 410                 415

Glu Glu Tyr Asp Val Leu Asp Lys Arg Arg Gly Arg Asp Pro Glu Met
```

```
            420                 425                 430

Gly Gly Lys Pro Arg Arg Lys Asn Pro Gln Glu Gly Leu Tyr Asn Glu
        435                 440                 445

Leu Gln Lys Asp Lys Met Ala Glu Ala Tyr Ser Glu Ile Gly Met Lys
    450                 455                 460

Gly Glu Arg Arg Arg Gly Lys Gly His Asp Gly Leu Tyr Gln Gly Leu
465                 470                 475                 480

Ser Thr Ala Thr Lys Asp Thr Tyr Asp Ala Leu His Met Gln Ala Leu
                485                 490                 495

Pro Pro Arg Gly Ser Gly Glu Gly Arg Gly Ser Leu Leu Thr Cys Gly
            500                 505                 510

Asp Val Glu Glu Asn Pro Gly Pro Met Ala Leu Pro Val Thr Ala Leu
        515                 520                 525

Leu Leu Pro Leu Ala Leu Leu Leu His Ala Ala Arg Pro Asn Trp Val
    530                 535                 540

Asn Val Ile Ser Asp Leu Lys Lys Ile Glu Asp Leu Ile Gln Ser Met
545                 550                 555                 560

His Ile Asp Ala Thr Leu Tyr Thr Glu Ser Asp Val His Pro Ser Cys
                565                 570                 575

Lys Val Thr Ala Met Lys Cys Phe Leu Leu Glu Leu Gln Val Ile Ser
            580                 585                 590

Leu Glu Ser Gly Asp Ala Ser Ile His Asp Thr Val Glu Asn Leu Ile
        595                 600                 605

Ile Leu Ala Asn Asn Ser Leu Ser Ser Asn Gly Asn Val Thr Glu Ser
    610                 615                 620

Gly Cys Lys Glu Cys Glu Glu Leu Glu Glu Lys Asn Ile Lys Glu Phe
625                 630                 635                 640

Leu Gln Ser Phe Val His Ile Val Gln Met Phe Ile Asn Thr Ser Thr
                645                 650                 655

Thr Thr Pro Ala Pro Arg Pro Pro Thr Pro Ala Pro Thr Ile Ala Ser
            660                 665                 670

Gln Pro Leu Ser Leu Arg Pro Glu Ala Cys Arg Pro Ala Ala Gly Gly
        675                 680                 685

Ala Val His Thr Arg Gly Leu Asp Phe Ala Cys Asp Ile Tyr Ile Trp
    690                 695                 700

Ala Pro Leu Ala Gly Thr Cys Gly Val Leu Leu Leu Ser Leu Val Ile
705                 710                 715                 720

Thr Leu Tyr Cys


<210> SEQ ID NO 174
<211> LENGTH: 2204
<212> TYPE: DNA
<213> ORGANISM: Homo sapiens
<220> FEATURE:
<221> NAME/KEY: misc_feature
<223> OTHER INFORMATION: DNA NK19H-8

<400> SEQUENCE: 174

gaattcgccg ccaccatggc cttaccagtg accgccttgc tcctgccgct ggccttgctg      60

ctccacgccg ccaggccgga ctacaaagac gatgacgata aaggcggtgg tggctctggt     120

ggtggcggca gcgacatcca gatgacacag agcccgtcct ccctgtctgc ctctgtggga     180

gacagagtca ccatcacctg cagggcaagt caggacatta gtaaatattt aaattggtat     240

cagcagaaac caggtggaac tgttaaactc ctgatctacc atacatcaag attacactca     300
```

-continued

```
ggagtcccat caaggttcag tggcagtggg tctggaacag atttcaccct caccattagc    360
agcctgcaac cggaagatat tgccacttac ttctgccaac agggtaatac gcttccgtac    420
acgttcggag gggggaccaa gctggagatc acaggtggcg gtggctcggg cggtggtggg    480
tcgggtggcg gcggatctca ggtgcagctg caggagtcag gacctggcct ggtgaaaccc    540
tcacagactc tgtccgtgac atgcactgtc tcaggggtct cattacccga ctatggtgta    600
agctggattc gccagcctcc aggtaagggt ctggagtggc tgggagtaat atggggtagt    660
gaaaccacat actataattc agctctcaaa tccagactga ccatctccaa ggacaactcc    720
aagagccaag tttccttaaa attaagtagt gttactgctg ctgacacagc cgtctactac    780
tgtgccaaac attattacta cggtggtagc tatgctatgg actactgggg ccaaggaacc    840
tcagtcaccg tctcctcaac cacgacgcca gcgccgcgac caccaacacc ggcgcccacc    900
atcgcgtcgc agcccctgtc cctgcgccca gaggcgtgcc ggccagcggc ggggggcgca    960
gtgcacacga gggggctgga cttcgcctgt gatatctaca tctgggcgcc cttggccggg   1020
acttgtgggg tccttctcct gtcactggtt atcacccttt actgccggag ggaccagagg   1080
ctgccccccg atgcccacaa gccccctggg ggaggcagtt tccggacccc catccaagag   1140
gagcaggccg acgcccactc caccctggcc aagatcagag tgaagttcag caggagcgca   1200
gacgcccccg cgtaccagca gggccagaac cagctctata acgagctcaa tctaggacga   1260
agagaggagt acgatgtttt ggacaagaga cgtggccggg accctgagat ggggggaaag   1320
ccgagaagga agaaccctca ggaaggcctg tacaatgaac tgcagaaaga taagatggcg   1380
gaggcctaca gtgagattgg gatgaaaggc gagcgccgga ggggcaaggg gcacgatggc   1440
ctttaccagg gtctcagtac agccaccaag gacacctacg acgcccttca catgcaggcc   1500
ctgccccctc gcggctctgg cgagggaagg ggttccctgc ttacttgcgg cgacgtcgaa   1560
gagaatcccg gtccgatggc cctcccagta actgccctcc ttttgcccct cgcactcctt   1620
cttcatgccg ctcgccccaa ctgggtcaac gtgattagcg atttgaagaa aatcgaggac   1680
cttatacagt ctatgcatat tgacgctaca ctgtatactg agagtgatgt acacccgtcc   1740
tgtaaggtaa cggccatgaa atgctttctt ctggagctcc aggtcatcag cttggagtct   1800
ggggacgcaa gcatccacga tacggttgaa aacctcatca tccttgcgaa caactctctc   1860
tcatctaatg gaaacgttac agagagtggg tgtaaggagt gcgaagagtt ggaagaaaaa   1920
aacatcaaag aatttcttca atccttcgtt cacatagtgc aaatgttcat taacacgtcc   1980
actaccacac ccgccccgag gccacctacg ccggcaccga ctatcgccag tcaacccctc   2040
tctctgcgcc ccgaggcttg ccggcctgcg gctggtgggg cggtccacac ccggggcctg   2100
gattttgcgt gcgatatata catctgggca cctcttgccg gcacctgcgg agtgctgctt   2160
ctctcactcg ttattacgct gtactgctaa gcggccgcgt cgac                    2204
```

<210> SEQ ID NO 175
<211> LENGTH: 724
<212> TYPE: PRT
<213> ORGANISM: Homo sapiens
<220> FEATURE:
<221> NAME/KEY: MISC_FEATURE
<223> OTHER INFORMATION: AA NK19H-8

<400> SEQUENCE: 175

```
Met Ala Leu Pro Val Thr Ala Leu Leu Leu Pro Leu Ala Leu Leu Leu
1               5                   10                  15

His Ala Ala Arg Pro Asp Tyr Lys Asp Asp Asp Asp Lys Gly Gly Gly
```

-continued

```
            20                  25                  30

Gly Ser Gly Gly Gly Gly Ser Asp Ile Gln Met Thr Gln Ser Pro Ser
        35                  40                  45

Ser Leu Ser Ala Ser Val Gly Asp Arg Val Thr Ile Thr Cys Arg Ala
    50                  55                  60

Ser Gln Asp Ile Ser Lys Tyr Leu Asn Trp Tyr Gln Gln Lys Pro Gly
65                  70                  75                  80

Gly Thr Val Lys Leu Leu Ile Tyr His Thr Ser Arg Leu His Ser Gly
                85                  90                  95

Val Pro Ser Arg Phe Ser Gly Ser Gly Ser Gly Thr Asp Phe Thr Leu
            100                 105                 110

Thr Ile Ser Ser Leu Gln Pro Glu Asp Ile Ala Thr Tyr Phe Cys Gln
        115                 120                 125

Gln Gly Asn Thr Leu Pro Tyr Thr Phe Gly Gly Gly Thr Lys Leu Glu
    130                 135                 140

Ile Thr Gly Gly Gly Gly Ser Gly Gly Gly Gly Ser Gly Gly Gly Gly
145                 150                 155                 160

Ser Gln Val Gln Leu Gln Glu Ser Gly Pro Gly Leu Val Lys Pro Ser
                165                 170                 175

Gln Thr Leu Ser Val Thr Cys Thr Val Ser Gly Val Ser Leu Pro Asp
            180                 185                 190

Tyr Gly Val Ser Trp Ile Arg Gln Pro Pro Gly Lys Gly Leu Glu Trp
        195                 200                 205

Leu Gly Val Ile Trp Gly Ser Glu Thr Thr Tyr Tyr Asn Ser Ala Leu
    210                 215                 220

Lys Ser Arg Leu Thr Ile Ser Lys Asp Asn Ser Lys Ser Gln Val Ser
225                 230                 235                 240

Leu Lys Leu Ser Ser Val Thr Ala Ala Asp Thr Ala Val Tyr Tyr Cys
                245                 250                 255

Ala Lys His Tyr Tyr Tyr Gly Gly Ser Tyr Ala Met Asp Tyr Trp Gly
            260                 265                 270

Gln Gly Thr Ser Val Thr Val Ser Ser Thr Thr Thr Pro Ala Pro Arg
        275                 280                 285

Pro Pro Thr Pro Ala Pro Thr Ile Ala Ser Gln Pro Leu Ser Leu Arg
    290                 295                 300

Pro Glu Ala Cys Arg Pro Ala Ala Gly Gly Ala Val His Thr Arg Gly
305                 310                 315                 320

Leu Asp Phe Ala Cys Asp Ile Tyr Ile Trp Ala Pro Leu Ala Gly Thr
                325                 330                 335

Cys Gly Val Leu Leu Leu Ser Leu Val Ile Thr Leu Tyr Cys Arg Arg
            340                 345                 350

Asp Gln Arg Leu Pro Pro Asp Ala His Lys Pro Pro Gly Gly Gly Ser
        355                 360                 365

Phe Arg Thr Pro Ile Gln Glu Glu Gln Ala Asp Ala His Ser Thr Leu
    370                 375                 380

Ala Lys Ile Arg Val Lys Phe Ser Arg Ser Ala Asp Ala Pro Ala Tyr
385                 390                 395                 400

Gln Gln Gly Gln Asn Gln Leu Tyr Asn Glu Leu Asn Leu Gly Arg Arg
                405                 410                 415

Glu Glu Tyr Asp Val Leu Asp Lys Arg Arg Gly Arg Asp Pro Glu Met
            420                 425                 430

Gly Gly Lys Pro Arg Arg Lys Asn Pro Gln Glu Gly Leu Tyr Asn Glu
        435                 440                 445
```

```
Leu Gln Lys Asp Lys Met Ala Glu Ala Tyr Ser Glu Ile Gly Met Lys
    450                 455                 460

Gly Glu Arg Arg Arg Gly Lys Gly His Asp Gly Leu Tyr Gln Gly Leu
465                 470                 475                 480

Ser Thr Ala Thr Lys Asp Thr Tyr Asp Ala Leu His Met Gln Ala Leu
                485                 490                 495

Pro Pro Arg Gly Ser Gly Glu Gly Arg Gly Ser Leu Leu Thr Cys Gly
            500                 505                 510

Asp Val Glu Glu Asn Pro Gly Pro Met Ala Leu Pro Val Thr Ala Leu
        515                 520                 525

Leu Leu Pro Leu Ala Leu Leu Leu His Ala Ala Arg Pro Asn Trp Val
    530                 535                 540

Asn Val Ile Ser Asp Leu Lys Lys Ile Glu Asp Leu Ile Gln Ser Met
545                 550                 555                 560

His Ile Asp Ala Thr Leu Tyr Thr Glu Ser Asp Val His Pro Ser Cys
                565                 570                 575

Lys Val Thr Ala Met Lys Cys Phe Leu Leu Glu Leu Gln Val Ile Ser
            580                 585                 590

Leu Glu Ser Gly Asp Ala Ser Ile His Asp Thr Val Glu Asn Leu Ile
        595                 600                 605

Ile Leu Ala Asn Asn Ser Leu Ser Ser Asn Gly Asn Val Thr Glu Ser
    610                 615                 620

Gly Cys Lys Glu Cys Glu Glu Leu Glu Glu Lys Asn Ile Lys Glu Phe
625                 630                 635                 640

Leu Gln Ser Phe Val His Ile Val Gln Met Phe Ile Asn Thr Ser Thr
                645                 650                 655

Thr Thr Pro Ala Pro Arg Pro Pro Thr Pro Ala Pro Thr Ile Ala Ser
            660                 665                 670

Gln Pro Leu Ser Leu Arg Pro Glu Ala Cys Arg Pro Ala Ala Gly Gly
        675                 680                 685

Ala Val His Thr Arg Gly Leu Asp Phe Ala Cys Asp Ile Tyr Ile Trp
    690                 695                 700

Ala Pro Leu Ala Gly Thr Cys Gly Val Leu Leu Leu Ser Leu Val Ile
705                 710                 715                 720

Thr Leu Tyr Cys


<210> SEQ ID NO 176
<211> LENGTH: 2204
<212> TYPE: DNA
<213> ORGANISM: Homo sapiens
<220> FEATURE:
<221> NAME/KEY: misc_feature
<223> OTHER INFORMATION: DNA NK19H-9

<400> SEQUENCE: 176

gaattcgccg ccaccatggc cttaccagtg accgccttgc tcctgccgct ggccttgctg      60

ctccacgccg ccaggccgga ctacaaagac gatgacgata aaggcggtgg tggctctggt     120

ggtggcggca gcgacatcca gatgacacag agcccgtcct ccctgtctgc ctctgtggga     180

gacagagtca ccatcacctg cagggcaagt caggacatta gtaaatattt aaattggtat     240

cagcagaaac cagacggaac tgttaaactc ctgatctacc atacatcaag attacactca     300

ggagtcccat caaggttcag tggcagtggg tctggaacag attacaccct caccattagc     360

agcctgcaac cggaagatat tgccacttac ttctgccaac agggtaatac gcttccgtac     420
```

```
acgttcggag gggggaccaa gctggagatc acaggtggcg gtggctcggg cggtggtggg    480
tcgggtggcg gcggatctca ggtgcagctg caggagtcag gacctggcct ggtgaaaccc    540
tcacagactc tgtccgtgac atgcactgtc tcaggggtct cattacccga ctatggtgta    600
agctggattc gccagcctcc aggtaagggt ctggagtggc tgggagtaat atggggtagt    660
gaaaccacat actataattc agctctcaaa tccagactga ccatctccaa ggacaactcc    720
aagagccaag tttccttaaa attaagtagt gttactgctg ctgacacagc cgtctactac    780
tgtgccaaac attattacta cggtggtagc tatgctatgg actactgggg ccaaggaacc    840
tcagtcaccg tctcctcaac cacgacgcca gcgccgcgac caccaacacc ggcgcccacc    900
atcgcgtcgc agcccctgtc cctgcgccca gaggcgtgcc ggccagcggc ggggggcgca    960
gtgcacacga gggggctgga cttcgcctgt gatatctaca tctgggcgcc cttggccggg   1020
acttgtgggg tccttctcct gtcactggtt atcacccttt actgccggag ggaccagagg   1080
ctgcccccg atgcccacaa gcccctggg ggaggcagtt tccggacccc catccaagag   1140
gagcaggccg acgcccactc caccctggcc aagatcagag tgaagttcag caggagcgca   1200
gacgcccccg cgtaccagca gggccagaac cagctctata acgagctcaa tctaggacga   1260
agagaggagt acgatgtttt ggacaagaga cgtggccggg accctgagat ggggggaaag   1320
ccgagaagga agaaccctca ggaaggcctg tacaatgaac tgcagaaaga taagatggcg   1380
gaggcctaca gtgagattgg gatgaaaggc gagcgccgga ggggcaaggg gcacgatggc   1440
ctttaccagg gtctcagtac agccaccaag gacacctacg acgcccttca catgcaggcc   1500
ctgccccctc gcggctctgg cgagggaagg ggttccctgc ttacttgcgg cgacgtcgaa   1560
gagaatcccg gtccgatggc cctcccagta actgccctcc ttttgcccct cgcactcctt   1620
cttcatgccg ctcgccccaa ctgggtcaac gtgattagcg atttgaagaa aatcgaggac   1680
cttatacagt ctatgcatat tgacgctaca ctgtatactg agagtgatgt acacccgtcc   1740
tgtaaggtaa cggccatgaa atgctttctt ctggagctcc aggtcatcag cttggagtct   1800
ggggacgcaa gcatccacga tacggttgaa aacctcatca tccttgcgaa caactctctc   1860
tcatctaatg gaaacgttac agagagtggg tgtaaggagt gcgaagagtt ggaagaaaaa   1920
aacatcaaag aatttcttca atccttcgtt cacatagtgc aaatgttcat taacacgtcc   1980
actaccacac ccgccccgag gccacctacg ccggcaccga ctatcgccag tcaacccctc   2040
tctctgcgcc ccgaggcttg ccggcctgcg gctggtgggg cggtccacac ccggggcctg   2100
gattttgcgt gcgatatata catctgggca cctcttgccg gcacctgcgg agtgctgctt   2160
ctctcactcg ttattacgct gtactgctaa gcggccgcgt cgac                    2204
```

<210> SEQ ID NO 177
<211> LENGTH: 724
<212> TYPE: PRT
<213> ORGANISM: Homo sapiens
<220> FEATURE:
<221> NAME/KEY: MISC_FEATURE
<223> OTHER INFORMATION: AA NK19H-9

<400> SEQUENCE: 177

```
Met Ala Leu Pro Val Thr Ala Leu Leu Leu Pro Leu Ala Leu Leu Leu
1               5                   10                  15

His Ala Ala Arg Pro Asp Tyr Lys Asp Asp Asp Asp Lys Gly Gly Gly
            20                  25                  30

Gly Ser Gly Gly Gly Gly Ser Asp Ile Gln Met Thr Gln Ser Pro Ser
        35                  40                  45
```

```
Ser Leu Ser Ala Ser Val Gly Asp Arg Val Thr Ile Thr Cys Arg Ala
    50                  55                  60

Ser Gln Asp Ile Ser Lys Tyr Leu Asn Trp Tyr Gln Gln Lys Pro Asp
65                  70                  75                  80

Gly Thr Val Lys Leu Leu Ile Tyr His Thr Ser Arg Leu His Ser Gly
                85                  90                  95

Val Pro Ser Arg Phe Ser Gly Ser Gly Ser Gly Thr Asp Tyr Thr Leu
            100                 105                 110

Thr Ile Ser Ser Leu Gln Pro Glu Asp Ile Ala Thr Tyr Phe Cys Gln
        115                 120                 125

Gln Gly Asn Thr Leu Pro Tyr Thr Phe Gly Gly Gly Thr Lys Leu Glu
    130                 135                 140

Ile Thr Gly Gly Gly Gly Ser Gly Gly Gly Gly Ser Gly Gly Gly Gly
145                 150                 155                 160

Ser Gln Val Gln Leu Gln Glu Ser Gly Pro Gly Leu Val Lys Pro Ser
                165                 170                 175

Gln Thr Leu Ser Val Thr Cys Thr Val Ser Gly Val Ser Leu Pro Asp
            180                 185                 190

Tyr Gly Val Ser Trp Ile Arg Gln Pro Pro Gly Lys Gly Leu Glu Trp
        195                 200                 205

Leu Gly Val Ile Trp Gly Ser Glu Thr Thr Tyr Tyr Asn Ser Ala Leu
    210                 215                 220

Lys Ser Arg Leu Thr Ile Ser Lys Asp Asn Ser Lys Ser Gln Val Ser
225                 230                 235                 240

Leu Lys Leu Ser Ser Val Thr Ala Ala Asp Thr Ala Val Tyr Tyr Cys
                245                 250                 255

Ala Lys His Tyr Tyr Tyr Gly Gly Ser Tyr Ala Met Asp Tyr Trp Gly
            260                 265                 270

Gln Gly Thr Ser Val Thr Val Ser Ser Thr Thr Thr Pro Ala Pro Arg
        275                 280                 285

Pro Pro Thr Pro Ala Pro Thr Ile Ala Ser Gln Pro Leu Ser Leu Arg
    290                 295                 300

Pro Glu Ala Cys Arg Pro Ala Ala Gly Gly Ala Val His Thr Arg Gly
305                 310                 315                 320

Leu Asp Phe Ala Cys Asp Ile Tyr Ile Trp Ala Pro Leu Ala Gly Thr
                325                 330                 335

Cys Gly Val Leu Leu Leu Ser Leu Val Ile Thr Leu Tyr Cys Arg Arg
            340                 345                 350

Asp Gln Arg Leu Pro Pro Asp Ala His Lys Pro Pro Gly Gly Gly Ser
        355                 360                 365

Phe Arg Thr Pro Ile Gln Glu Glu Gln Ala Asp Ala His Ser Thr Leu
    370                 375                 380

Ala Lys Ile Arg Val Lys Phe Ser Arg Ser Ala Asp Ala Pro Ala Tyr
385                 390                 395                 400

Gln Gln Gly Gln Asn Gln Leu Tyr Asn Glu Leu Asn Leu Gly Arg Arg
                405                 410                 415

Glu Glu Tyr Asp Val Leu Asp Lys Arg Arg Gly Arg Asp Pro Glu Met
            420                 425                 430

Gly Gly Lys Pro Arg Arg Lys Asn Pro Gln Glu Gly Leu Tyr Asn Glu
        435                 440                 445

Leu Gln Lys Asp Lys Met Ala Glu Ala Tyr Ser Glu Ile Gly Met Lys
    450                 455                 460
```

Gly Glu Arg Arg Arg Gly Lys Gly His Asp Gly Leu Tyr Gln Gly Leu
465 470 475 480

Ser Thr Ala Thr Lys Asp Thr Tyr Asp Ala Leu His Met Gln Ala Leu
485 490 495

Pro Pro Arg Gly Ser Gly Glu Gly Arg Gly Ser Leu Leu Thr Cys Gly
500 505 510

Asp Val Glu Glu Asn Pro Gly Pro Met Ala Leu Pro Val Thr Ala Leu
515 520 525

Leu Leu Pro Leu Ala Leu Leu Leu His Ala Ala Arg Pro Asn Trp Val
530 535 540

Asn Val Ile Ser Asp Leu Lys Lys Ile Glu Asp Leu Ile Gln Ser Met
545 550 555 560

His Ile Asp Ala Thr Leu Tyr Thr Glu Ser Asp Val His Pro Ser Cys
565 570 575

Lys Val Thr Ala Met Lys Cys Phe Leu Leu Glu Leu Gln Val Ile Ser
580 585 590

Leu Glu Ser Gly Asp Ala Ser Ile His Asp Thr Val Glu Asn Leu Ile
595 600 605

Ile Leu Ala Asn Asn Ser Leu Ser Ser Asn Gly Asn Val Thr Glu Ser
610 615 620

Gly Cys Lys Glu Cys Glu Glu Leu Glu Glu Lys Asn Ile Lys Glu Phe
625 630 635 640

Leu Gln Ser Phe Val His Ile Val Gln Met Phe Ile Asn Thr Ser Thr
645 650 655

Thr Thr Pro Ala Pro Arg Pro Pro Thr Pro Ala Pro Thr Ile Ala Ser
660 665 670

Gln Pro Leu Ser Leu Arg Pro Glu Ala Cys Arg Pro Ala Ala Gly Gly
675 680 685

Ala Val His Thr Arg Gly Leu Asp Phe Ala Cys Asp Ile Tyr Ile Trp
690 695 700

Ala Pro Leu Ala Gly Thr Cys Gly Val Leu Leu Leu Ser Leu Val Ile
705 710 715 720

Thr Leu Tyr Cys

<210> SEQ ID NO 178
<211> LENGTH: 2204
<212> TYPE: DNA
<213> ORGANISM: Homo sapiens
<220> FEATURE:
<221> NAME/KEY: misc_feature
<223> OTHER INFORMATION: DNA NK19H-10

<400> SEQUENCE: 178
gaattcgccg ccaccatggc cttaccagtg accgccttgc tcctgccgct ggccttgctg 60
ctccacgccg ccaggccgga ctacaaagac gatgacgata aaggcggtgg tggctctggt 120
ggtggcggca gcgatattca gatgacccag agcccgagca gcctgagcgc gagcgtgggc 180
gatcgcgtga ccattacctg ccgcgcgagc caggatatta gcaaatatct gaactggtat 240
cagcagaaac cgggcggcac cgtgaaactg ctgatttatc ataccagccg cctgcatagc 300
ggcgtgccga gccgctttag cggcagcggc agcggcaccg attttaccct gaccattagc 360
agcctgcagc cggaagatat tgcgacctat tattgccagc agggcaacac cctgccgtat 420
acctttggcg gcggcaccaa actggaaatt accggtggcg gtggctcggg cggtggtggg 480
tcgggtggcg gcggatctca ggtgcagctg caggaaagcg gcccgggcct ggtgaaaccg 540

-continued

```
agccagaccc tgagcgtgac ctgcaccgtg agcggcgtga gcctgccgga ttatggcgtg    600

agctggattc gccagccgcc gcgcaaaggc ctggaatggc tgggcgtgat ttggggcagc    660

gaaaccacct attataacag cgcgctgaaa agccgcctga ccattagcaa agataacagc    720

aaaagccagg tgagcctgaa aatgagcagc gtgaccgcgg cggataccgc gatttattat    780

tgcgcgaaac attattatta tggcggcagc tatgcgatgg attattgggg ccagggcacc    840

agcgtgaccg tgagcagcac cacgacgcca gcgccgcgac caccaacacc ggcgcccacc    900

atcgcgtcgc agcccctgtc cctgcgccca gaggcgtgcc ggccagcggc ggggggcgca    960

gtgcacacga gggggctgga cttcgcctgt gatatctaca tctgggcgcc cttggccggg   1020

acttgtgggg tccttctcct gtcactggtt atcacccttt actgccggag ggaccagagg   1080

ctgccccccg atgcccacaa gccccctggg ggaggcagtt tccggacccc catccaagag   1140

gagcaggccg acgcccactc caccctggcc aagatcagag tgaagttcag caggagcgca   1200

gacgcccccg cgtaccagca gggccagaac cagctctata acgagctcaa tctaggacga   1260

agagaggagt acgatgtttt ggacaagaga cgtggccggg accctgagat ggggggaaag   1320

ccgagaagga agaaccctca ggaaggcctg tacaatgaac tgcagaaaga taagatggcg   1380

gaggcctaca gtgagattgg gatgaaaggc gagcgccgga ggggcaaggg gcacgatggc   1440

ctttaccagg gtctcagtac agccaccaag gacacctacg acgcccttca catgcaggcc   1500

ctgccccctc gcggctctgg cgagggaagg ggttccctgc ttacttgcgg cgacgtcgaa   1560

gagaatcccg gtccgatggc cctcccagta actgccctcc ttttgcccct cgcactcctt   1620

cttcatgccg ctcgccccaa ctgggtcaac gtgattagcg atttgaagaa aatcgaggac   1680

cttatacagt ctatgcatat tgacgctaca ctgtatactg agagtgatgt acacccgtcc   1740

tgtaaggtaa cggccatgaa atgctttctt ctggagctcc aggtcatcag cttggagtct   1800

ggggacgcaa gcatccacga tacggttgaa aacctcatca tccttgcgaa caactctctc   1860

tcatctaatg gaaacgttac agagagtggg tgtaaggagt gcgaagagtt ggaagaaaaa   1920

aacatcaaag aatttcttca atccttcgtt cacatagtgc aaatgttcat taacacgtcc   1980

actaccacac ccgccccgag gccacctacg ccggcaccga ctatcgccag tcaacccctc   2040

tctctgcgcc ccgaggcttg ccggcctgcg gctggtgggg cggtccacac ccggggcctg   2100

gattttgcgt gcgatatata catctgggca cctcttgccg gcacctgcgg agtgctgctt   2160

ctctcactcg ttattacgct gtactgctaa gcggccgcgt cgac                    2204
```

<210> SEQ ID NO 179
<211> LENGTH: 724
<212> TYPE: PRT
<213> ORGANISM: Homo sapiens
<220> FEATURE:
<221> NAME/KEY: MISC_FEATURE
<223> OTHER INFORMATION: AA NK19H-10

<400> SEQUENCE: 179

```
Met Ala Leu Pro Val Thr Ala Leu Leu Leu Pro Leu Ala Leu Leu Leu
1               5                   10                  15

His Ala Ala Arg Pro Asp Tyr Lys Asp Asp Asp Asp Lys Gly Gly Gly
            20                  25                  30

Gly Ser Gly Gly Gly Gly Ser Asp Ile Gln Met Thr Gln Ser Pro Ser
        35                  40                  45

Ser Leu Ser Ala Ser Val Gly Asp Arg Val Thr Ile Thr Cys Arg Ala
    50                  55                  60
```

```
Ser Gln Asp Ile Ser Lys Tyr Leu Asn Trp Tyr Gln Gln Lys Pro Gly
65                  70                  75                  80

Gly Thr Val Lys Leu Leu Ile Tyr His Thr Ser Arg Leu His Ser Gly
                85                  90                  95

Val Pro Ser Arg Phe Ser Gly Ser Gly Ser Gly Thr Asp Phe Thr Leu
            100                 105                 110

Thr Ile Ser Ser Leu Gln Pro Glu Asp Ile Ala Thr Tyr Tyr Cys Gln
        115                 120                 125

Gln Gly Asn Thr Leu Pro Tyr Thr Phe Gly Gly Gly Thr Lys Leu Glu
    130                 135                 140

Ile Thr Gly Gly Gly Gly Ser Gly Gly Gly Gly Ser Gly Gly Gly Gly
145                 150                 155                 160

Ser Gln Val Gln Leu Gln Glu Ser Gly Pro Gly Leu Val Lys Pro Ser
                165                 170                 175

Gln Thr Leu Ser Val Thr Cys Thr Val Ser Gly Val Ser Leu Pro Asp
            180                 185                 190

Tyr Gly Val Ser Trp Ile Arg Gln Pro Pro Arg Lys Gly Leu Glu Trp
        195                 200                 205

Leu Gly Val Ile Trp Gly Ser Glu Thr Thr Tyr Tyr Asn Ser Ala Leu
    210                 215                 220

Lys Ser Arg Leu Thr Ile Ser Lys Asp Asn Ser Lys Ser Gln Val Ser
225                 230                 235                 240

Leu Lys Met Ser Ser Val Thr Ala Ala Asp Thr Ala Ile Tyr Tyr Cys
                245                 250                 255

Ala Lys His Tyr Tyr Tyr Gly Gly Ser Tyr Ala Met Asp Tyr Trp Gly
            260                 265                 270

Gln Gly Thr Ser Val Thr Val Ser Ser Thr Thr Thr Pro Ala Pro Arg
        275                 280                 285

Pro Pro Thr Pro Ala Pro Thr Ile Ala Ser Gln Pro Leu Ser Leu Arg
    290                 295                 300

Pro Glu Ala Cys Arg Pro Ala Ala Gly Gly Ala Val His Thr Arg Gly
305                 310                 315                 320

Leu Asp Phe Ala Cys Asp Ile Tyr Ile Trp Ala Pro Leu Ala Gly Thr
                325                 330                 335

Cys Gly Val Leu Leu Leu Ser Leu Val Ile Thr Leu Tyr Cys Arg Arg
            340                 345                 350

Asp Gln Arg Leu Pro Pro Asp Ala His Lys Pro Pro Gly Gly Gly Ser
        355                 360                 365

Phe Arg Thr Pro Ile Gln Glu Glu Gln Ala Asp Ala His Ser Thr Leu
    370                 375                 380

Ala Lys Ile Arg Val Lys Phe Ser Arg Ser Ala Asp Ala Pro Ala Tyr
385                 390                 395                 400

Gln Gln Gly Gln Asn Gln Leu Tyr Asn Glu Leu Asn Leu Gly Arg Arg
                405                 410                 415

Glu Glu Tyr Asp Val Leu Asp Lys Arg Arg Gly Arg Asp Pro Glu Met
            420                 425                 430

Gly Gly Lys Pro Arg Arg Lys Asn Pro Gln Glu Gly Leu Tyr Asn Glu
        435                 440                 445

Leu Gln Lys Asp Lys Met Ala Glu Ala Tyr Ser Glu Ile Gly Met Lys
    450                 455                 460

Gly Glu Arg Arg Arg Gly Lys Gly His Asp Gly Leu Tyr Gln Gly Leu
465                 470                 475                 480

Ser Thr Ala Thr Lys Asp Thr Tyr Asp Ala Leu His Met Gln Ala Leu
```

```
                485                 490                 495

Pro Pro Arg Gly Ser Gly Glu Gly Arg Gly Ser Leu Leu Thr Cys Gly
            500                 505                 510

Asp Val Glu Glu Asn Pro Gly Pro Met Ala Leu Pro Val Thr Ala Leu
        515                 520                 525

Leu Leu Pro Leu Ala Leu Leu Leu His Ala Ala Arg Pro Asn Trp Val
    530                 535                 540

Asn Val Ile Ser Asp Leu Lys Lys Ile Glu Asp Leu Ile Gln Ser Met
545                 550                 555                 560

His Ile Asp Ala Thr Leu Tyr Thr Glu Ser Asp Val His Pro Ser Cys
                565                 570                 575

Lys Val Thr Ala Met Lys Cys Phe Leu Leu Glu Leu Gln Val Ile Ser
            580                 585                 590

Leu Glu Ser Gly Asp Ala Ser Ile His Asp Thr Val Glu Asn Leu Ile
        595                 600                 605

Ile Leu Ala Asn Asn Ser Leu Ser Ser Asn Gly Asn Val Thr Glu Ser
    610                 615                 620

Gly Cys Lys Glu Cys Glu Glu Leu Glu Glu Lys Asn Ile Lys Glu Phe
625                 630                 635                 640

Leu Gln Ser Phe Val His Ile Val Gln Met Phe Ile Asn Thr Ser Thr
                645                 650                 655

Thr Thr Pro Ala Pro Arg Pro Pro Thr Pro Ala Pro Thr Ile Ala Ser
            660                 665                 670

Gln Pro Leu Ser Leu Arg Pro Glu Ala Cys Arg Pro Ala Ala Gly Gly
        675                 680                 685

Ala Val His Thr Arg Gly Leu Asp Phe Ala Cys Asp Ile Tyr Ile Trp
    690                 695                 700

Ala Pro Leu Ala Gly Thr Cys Gly Val Leu Leu Leu Ser Leu Val Ile
705                 710                 715                 720

Thr Leu Tyr Cys


<210> SEQ ID NO 180
<211> LENGTH: 2204
<212> TYPE: DNA
<213> ORGANISM: Homo sapiens
<220> FEATURE:
<221> NAME/KEY: misc_feature
<223> OTHER INFORMATION: DNA NK19H-11

<400> SEQUENCE: 180

gaattcgccg ccaccatggc cttaccagtg accgccttgc tcctgccgct ggccttgctg     60

ctccacgccg ccaggccgga ctacaaagac gatgacgata aaggcggtgg tggctctggt    120

ggtggcggca gcgatattca gatgacccag agcccgagca gcctgagcgc gagcgtgggc    180

gatcgcgtga ccattacctg ccgcgcgagc caggatatta gcaaatatct gaactggtat    240

cagcagaaac cgggcggcac cgtgaaactg ctgatttatc ataccagccg cctgcatagc    300

ggcgtgccga gccgctttag cggcagcggc agcggcaccg attttaccct gaccattagc    360

agcctgcagc cggaagatat tgcgacctat ttttgccagc agggcaacac cctgccgtat    420

acctttggcg gcggcaccaa actggaaatt accggtggcg gtggctcggg cggtggtggg    480

tcgggtggcg gcggatctca ggtgcagctg caggaaagcg gcccgggcct ggtgaaaccg    540

agccagaccc tgagcgtgac ctgcaccgtg agcggcgtga gcctgccgga ttatggcgtg    600

agctggattc gccagccgcc gcgcaaaggc ctggaatggc tgggcgtgat ttggggcagc    660
```

-continued

```
gaaaccacct attataacag cgcgctgaaa agccgcctga ccattagcaa agataacagc    720

aaaagccagg tgagcctgaa aatgagcagc gtgaccgcgg cggataccgc gatttattat    780

tgcgcgaaac attattatta tggcggcagc tatgcgatgg attattgggg ccagggcacc    840

agcgtgaccg tgagcagcac cacgacgcca gcgccgcgac caccaacacc ggcgcccacc    900

atcgcgtcgc agcccctgtc cctgcgccca gaggcgtgcc ggccagcggc ggggggcgca    960

gtgcacacga gggggctgga cttcgcctgt gatatctaca tctgggcgcc cttggccggg   1020

acttgtgggg tccttctcct gtcactggtt atcacccttt actgccggag ggaccagagg   1080

ctgccccccg atgcccacaa gccccctggg ggaggcagtt tccggacccc catccaagag   1140

gagcaggccg acgcccactc caccctggcc aagatcagag tgaagttcag caggagcgca   1200

gacgcccccg cgtaccagca gggccagaac cagctctata acgagctcaa tctaggacga   1260

agagaggagt acgatgtttt ggacaagaga cgtggccggg accctgagat ggggggaaag   1320

ccgagaagga agaaccctca ggaaggcctg tacaatgaac tgcagaaaga taagatggcg   1380

gaggcctaca gtgagattgg gatgaaaggc gagcgccgga ggggcaaggg gcacgatggc   1440

ctttaccagg gtctcagtac agccaccaag gacacctacg acgcccttca catgcaggcc   1500

ctgccccctc gcggctctgg cgagggaagg ggttccctgc ttacttgcgg cgacgtcgaa   1560

gagaatcccg gtccgatggc cctcccagta actgccctcc ttttgcccct cgcactcctt   1620

cttcatgccg ctcgccccaa ctgggtcaac gtgattagcg atttgaagaa aatcgaggac   1680

cttatacagt ctatgcatat tgacgctaca ctgtatactg agagtgatgt acacccgtcc   1740

tgtaaggtaa cggccatgaa atgctttctt ctggagctcc aggtcatcag cttggagtct   1800

ggggacgcaa gcatccacga tacggttgaa aacctcatca tccttgcgaa caactctctc   1860

tcatctaatg gaaacgttac agagagtggg tgtaaggagt gcgaagagtt ggaagaaaaa   1920

aacatcaaag aatttcttca atccttcgtt cacatagtgc aaatgttcat taacacgtcc   1980

actaccacac ccgccccgag gccacctacg ccggcaccga ctatcgccag tcaacccctc   2040

tctctgcgcc ccgaggcttg ccggcctgcg gctggtgggg cggtccacac ccggggcctg   2100

gattttgcgt gcgatatata catctgggca cctcttgccg gcacctgcgg agtgctgctt   2160

ctctcactcg ttattacgct gtactgctaa gcggccgcgt cgac                    2204
```

```
<210> SEQ ID NO 181
<211> LENGTH: 724
<212> TYPE: PRT
<213> ORGANISM: Homo sapiens
<220> FEATURE:
<221> NAME/KEY: MISC_FEATURE
<223> OTHER INFORMATION: AA NK19H-11

<400> SEQUENCE: 181

Met Ala Leu Pro Val Thr Ala Leu Leu Leu Pro Leu Ala Leu Leu Leu
1               5                   10                  15

His Ala Ala Arg Pro Asp Tyr Lys Asp Asp Asp Asp Lys Gly Gly Gly
            20                  25                  30

Gly Ser Gly Gly Gly Gly Ser Asp Ile Gln Met Thr Gln Ser Pro Ser
        35                  40                  45

Ser Leu Ser Ala Ser Val Gly Asp Arg Val Thr Ile Thr Cys Arg Ala
    50                  55                  60

Ser Gln Asp Ile Ser Lys Tyr Leu Asn Trp Tyr Gln Gln Lys Pro Gly
65                  70                  75                  80

Gly Thr Val Lys Leu Leu Ile Tyr His Thr Ser Arg Leu His Ser Gly
```

-continued

```
                85                  90                  95

Val Pro Ser Arg Phe Ser Gly Ser Gly Ser Gly Thr Asp Phe Thr Leu
            100                 105                 110

Thr Ile Ser Ser Leu Gln Pro Glu Asp Ile Ala Thr Tyr Phe Cys Gln
        115                 120                 125

Gln Gly Asn Thr Leu Pro Tyr Thr Phe Gly Gly Gly Thr Lys Leu Glu
    130                 135                 140

Ile Thr Gly Gly Gly Gly Ser Gly Gly Gly Gly Ser Gly Gly Gly Gly
145                 150                 155                 160

Ser Gln Val Gln Leu Gln Glu Ser Gly Pro Gly Leu Val Lys Pro Ser
                165                 170                 175

Gln Thr Leu Ser Val Thr Cys Thr Val Ser Gly Val Ser Leu Pro Asp
            180                 185                 190

Tyr Gly Val Ser Trp Ile Arg Gln Pro Pro Arg Lys Gly Leu Glu Trp
        195                 200                 205

Leu Gly Val Ile Trp Gly Ser Glu Thr Thr Tyr Tyr Asn Ser Ala Leu
    210                 215                 220

Lys Ser Arg Leu Thr Ile Ser Lys Asp Asn Ser Lys Ser Gln Val Ser
225                 230                 235                 240

Leu Lys Met Ser Ser Val Thr Ala Ala Asp Thr Ala Ile Tyr Tyr Cys
                245                 250                 255

Ala Lys His Tyr Tyr Tyr Gly Gly Ser Tyr Ala Met Asp Tyr Trp Gly
            260                 265                 270

Gln Gly Thr Ser Val Thr Val Ser Ser Thr Thr Thr Pro Ala Pro Arg
        275                 280                 285

Pro Pro Thr Pro Ala Pro Thr Ile Ala Ser Gln Pro Leu Ser Leu Arg
    290                 295                 300

Pro Glu Ala Cys Arg Pro Ala Ala Gly Gly Ala Val His Thr Arg Gly
305                 310                 315                 320

Leu Asp Phe Ala Cys Asp Ile Tyr Ile Trp Ala Pro Leu Ala Gly Thr
                325                 330                 335

Cys Gly Val Leu Leu Leu Ser Leu Val Ile Thr Leu Tyr Cys Arg Arg
            340                 345                 350

Asp Gln Arg Leu Pro Pro Asp Ala His Lys Pro Pro Gly Gly Gly Ser
        355                 360                 365

Phe Arg Thr Pro Ile Gln Glu Glu Gln Ala Asp Ala His Ser Thr Leu
    370                 375                 380

Ala Lys Ile Arg Val Lys Phe Ser Arg Ser Ala Asp Ala Pro Ala Tyr
385                 390                 395                 400

Gln Gln Gly Gln Asn Gln Leu Tyr Asn Glu Leu Asn Leu Gly Arg Arg
                405                 410                 415

Glu Glu Tyr Asp Val Leu Asp Lys Arg Arg Gly Arg Asp Pro Glu Met
            420                 425                 430

Gly Gly Lys Pro Arg Arg Lys Asn Pro Gln Glu Gly Leu Tyr Asn Glu
        435                 440                 445

Leu Gln Lys Asp Lys Met Ala Glu Ala Tyr Ser Glu Ile Gly Met Lys
    450                 455                 460

Gly Glu Arg Arg Arg Gly Lys Gly His Asp Gly Leu Tyr Gln Gly Leu
465                 470                 475                 480

Ser Thr Ala Thr Lys Asp Thr Tyr Asp Ala Leu His Met Gln Ala Leu
                485                 490                 495

Pro Pro Arg Gly Ser Gly Glu Gly Arg Gly Ser Leu Leu Thr Cys Gly
            500                 505                 510
```

```
Asp Val Glu Glu Asn Pro Gly Pro Met Ala Leu Pro Val Thr Ala Leu
        515                 520                 525

Leu Leu Pro Leu Ala Leu Leu Leu His Ala Ala Arg Pro Asn Trp Val
    530                 535                 540

Asn Val Ile Ser Asp Leu Lys Lys Ile Glu Asp Leu Ile Gln Ser Met
545                 550                 555                 560

His Ile Asp Ala Thr Leu Tyr Thr Glu Ser Asp Val His Pro Ser Cys
                565                 570                 575

Lys Val Thr Ala Met Lys Cys Phe Leu Leu Glu Leu Gln Val Ile Ser
            580                 585                 590

Leu Glu Ser Gly Asp Ala Ser Ile His Asp Thr Val Glu Asn Leu Ile
        595                 600                 605

Ile Leu Ala Asn Asn Ser Leu Ser Ser Asn Gly Asn Val Thr Glu Ser
    610                 615                 620

Gly Cys Lys Glu Cys Glu Glu Leu Glu Glu Lys Asn Ile Lys Glu Phe
625                 630                 635                 640

Leu Gln Ser Phe Val His Ile Val Gln Met Phe Ile Asn Thr Ser Thr
                645                 650                 655

Thr Thr Pro Ala Pro Arg Pro Pro Thr Pro Ala Pro Thr Ile Ala Ser
            660                 665                 670

Gln Pro Leu Ser Leu Arg Pro Glu Ala Cys Arg Pro Ala Ala Gly Gly
        675                 680                 685

Ala Val His Thr Arg Gly Leu Asp Phe Ala Cys Asp Ile Tyr Ile Trp
    690                 695                 700

Ala Pro Leu Ala Gly Thr Cys Gly Val Leu Leu Leu Ser Leu Val Ile
705                 710                 715                 720

Thr Leu Tyr Cys
```

<210> SEQ ID NO 182
<211> LENGTH: 2204
<212> TYPE: DNA
<213> ORGANISM: Homo sapiens
<220> FEATURE:
<221> NAME/KEY: misc_feature
<223> OTHER INFORMATION: DNA NK19H-12

<400> SEQUENCE: 182

```
gaattcgccg ccaccatggc cttaccagtg accgccttgc tcctgccgct ggccttgctg     60

ctccacgccg ccaggccgga ctacaaagac gatgacgata aaggcggtgg tggctctggt    120

ggtggcggca gcgatattca gatgacccag agcccgagca gcctgagcgc gagcgtgggc    180

gatcgcgtga ccattacctg ccgcgcgagc caggatatta gcaaatatct gaactggtat    240

cagcagaaac cggatggcac cgtgaaactg ctgatttatc ataccagccg cctgcatagc    300

ggcgtgccga gccgctttag cggcagcggc agcggcaccg attataccct gaccattagc    360

agcctgcagc cggaagatat tgcgacctat ttttgccagc agggcaacac cctgccgtat    420

acctttggcg gcggcaccaa actggaaatt accggtggcg gtggctcggg cggtggtggg    480

tcgggtggcg gcggatctca ggtgcagctg caggaaagcg gcccgggcct ggtgaaaccg    540

agccagaccc tgagcgtgac ctgcaccgtg agcggcgtga gcctgccgga ttatggcgtg    600

agctggattc gccagccgcc gcgcaaaggc ctggaatggc tgggcgtgat ttggggcagc    660

gaaaccacct attataacag cgcgctgaaa agccgcctga ccattagcaa agataacagc    720

aaaagccagg tgagcctgaa aatgagcagc gtgaccgcgg cggataccgc gatttattat    780
```

-continued

```
tgcgcgaaac attattatta tggcggcagc tatgcgatgg attattgggg ccagggcacc    840

agcgtgaccg tgagcagcac cacgacgcca gcgccgcgac caccaacacc ggcgcccacc    900

atcgcgtcgc agcccctgtc cctgcgccca gaggcgtgcc ggccagcggc ggggggcgca    960

gtgcacacga gggggctgga cttcgcctgt gatatctaca tctgggcgcc cttggccggg   1020

acttgtgggg tccttctcct gtcactggtt atcacccttt actgccggag ggaccagagg   1080

ctgccccccg atgcccacaa gccccctggg ggaggcagtt tccggacccc catccaagag   1140

gagcaggccg acgcccactc caccctggcc aagatcagag tgaagttcag caggagcgca   1200

gacgcccccg cgtaccagca gggccagaac cagctctata acgagctcaa tctaggacga   1260

agagaggagt acgatgtttt ggacaagaga cgtggccggg accctgagat gggggggaaag   1320

ccgagaagga agaaccctca ggaaggcctg tacaatgaac tgcagaaaga taagatggcg   1380

gaggcctaca gtgagattgg gatgaaaggc gagcgccgga ggggcaaggg gcacgatggc   1440

ctttaccagg gtctcagtac agccaccaag gacacctacg acgcccttca catgcaggcc   1500

ctgccccctc gcggctctgg cgagggaagg ggttccctgc ttacttgcgg cgacgtcgaa   1560

gagaatcccg gtccgatggc cctcccagta actgccctcc ttttgcccct cgcactcctt   1620

cttcatgccg ctcgccccaa ctgggtcaac gtgattagcg atttgaagaa aatcgaggac   1680

cttatacagt ctatgcatat tgacgctaca ctgtatactg agagtgatgt acacccgtcc   1740

tgtaaggtaa cggccatgaa atgctttctt ctggagctcc aggtcatcag cttggagtct   1800

ggggacgcaa gcatccacga tacggttgaa aacctcatca tccttgcgaa caactctctc   1860

tcatctaatg gaaacgttac agagagtggg tgtaaggagt gcgaagagtt ggaagaaaaa   1920

aacatcaaag aatttcttca atccttcgtt cacatagtgc aaatgttcat taacacgtcc   1980

actaccacac ccgccccgag gccacctacg ccggcaccga ctatcgccag tcaacccctc   2040

tctctgcgcc ccgaggcttg ccggcctgcg gctggtgggg cggtccacac ccggggcctg   2100

gattttgcgt gcgatatata catctgggca cctcttgccg gcacctgcgg agtgctgctt   2160

ctctcactcg ttattacgct gtactgctaa gcggccgcgt cgac                     2204
```

<210> SEQ ID NO 183
<211> LENGTH: 724
<212> TYPE: PRT
<213> ORGANISM: Homo sapiens
<220> FEATURE:
<221> NAME/KEY: MISC_FEATURE
<223> OTHER INFORMATION: AA NK19H-12

<400> SEQUENCE: 183

```
Met Ala Leu Pro Val Thr Ala Leu Leu Leu Pro Leu Ala Leu Leu Leu
1               5                   10                  15

His Ala Ala Arg Pro Asp Tyr Lys Asp Asp Asp Asp Lys Gly Gly Gly
            20                  25                  30

Gly Ser Gly Gly Gly Gly Ser Asp Ile Gln Met Thr Gln Ser Pro Ser
        35                  40                  45

Ser Leu Ser Ala Ser Val Gly Asp Arg Val Thr Ile Thr Cys Arg Ala
    50                  55                  60

Ser Gln Asp Ile Ser Lys Tyr Leu Asn Trp Tyr Gln Gln Lys Pro Asp
65                  70                  75                  80

Gly Thr Val Lys Leu Leu Ile Tyr His Thr Ser Arg Leu His Ser Gly
                85                  90                  95

Val Pro Ser Arg Phe Ser Gly Ser Gly Ser Gly Thr Asp Tyr Thr Leu
            100                 105                 110
```

-continued

```
Thr Ile Ser Ser Leu Gln Pro Glu Asp Ile Ala Thr Tyr Phe Cys Gln
        115                 120                 125

Gln Gly Asn Thr Leu Pro Tyr Thr Phe Gly Gly Gly Thr Lys Leu Glu
    130                 135                 140

Ile Thr Gly Gly Gly Gly Ser Gly Gly Gly Gly Ser Gly Gly Gly Gly
145                 150                 155                 160

Ser Gln Val Gln Leu Gln Glu Ser Gly Pro Gly Leu Val Lys Pro Ser
                165                 170                 175

Gln Thr Leu Ser Val Thr Cys Thr Val Ser Gly Val Ser Leu Pro Asp
            180                 185                 190

Tyr Gly Val Ser Trp Ile Arg Gln Pro Pro Arg Lys Gly Leu Glu Trp
        195                 200                 205

Leu Gly Val Ile Trp Gly Ser Glu Thr Thr Tyr Tyr Asn Ser Ala Leu
    210                 215                 220

Lys Ser Arg Leu Thr Ile Ser Lys Asp Asn Ser Lys Ser Gln Val Ser
225                 230                 235                 240

Leu Lys Met Ser Ser Val Thr Ala Ala Asp Thr Ala Ile Tyr Tyr Cys
                245                 250                 255

Ala Lys His Tyr Tyr Tyr Gly Gly Ser Tyr Ala Met Asp Tyr Trp Gly
            260                 265                 270

Gln Gly Thr Ser Val Thr Val Ser Ser Thr Thr Thr Pro Ala Pro Arg
        275                 280                 285

Pro Pro Thr Pro Ala Pro Thr Ile Ala Ser Gln Pro Leu Ser Leu Arg
    290                 295                 300

Pro Glu Ala Cys Arg Pro Ala Ala Gly Gly Ala Val His Thr Arg Gly
305                 310                 315                 320

Leu Asp Phe Ala Cys Asp Ile Tyr Ile Trp Ala Pro Leu Ala Gly Thr
                325                 330                 335

Cys Gly Val Leu Leu Leu Ser Leu Val Ile Thr Leu Tyr Cys Arg Arg
            340                 345                 350

Asp Gln Arg Leu Pro Pro Asp Ala His Lys Pro Pro Gly Gly Gly Ser
        355                 360                 365

Phe Arg Thr Pro Ile Gln Glu Glu Gln Ala Asp Ala His Ser Thr Leu
    370                 375                 380

Ala Lys Ile Arg Val Lys Phe Ser Arg Ser Ala Asp Ala Pro Ala Tyr
385                 390                 395                 400

Gln Gln Gly Gln Asn Gln Leu Tyr Asn Glu Leu Asn Leu Gly Arg Arg
                405                 410                 415

Glu Glu Tyr Asp Val Leu Asp Lys Arg Arg Gly Arg Asp Pro Glu Met
            420                 425                 430

Gly Gly Lys Pro Arg Arg Lys Asn Pro Gln Glu Gly Leu Tyr Asn Glu
        435                 440                 445

Leu Gln Lys Asp Lys Met Ala Glu Ala Tyr Ser Glu Ile Gly Met Lys
    450                 455                 460

Gly Glu Arg Arg Arg Gly Lys Gly His Asp Gly Leu Tyr Gln Gly Leu
465                 470                 475                 480

Ser Thr Ala Thr Lys Asp Thr Tyr Asp Ala Leu His Met Gln Ala Leu
                485                 490                 495

Pro Pro Arg Gly Ser Gly Glu Gly Arg Gly Ser Leu Leu Thr Cys Gly
            500                 505                 510

Asp Val Glu Glu Asn Pro Gly Pro Met Ala Leu Pro Val Thr Ala Leu
        515                 520                 525
```

```
Leu Leu Pro Leu Ala Leu Leu Leu His Ala Ala Arg Pro Asn Trp Val
    530                 535                 540

Asn Val Ile Ser Asp Leu Lys Lys Ile Glu Asp Leu Ile Gln Ser Met
545                 550                 555                 560

His Ile Asp Ala Thr Leu Tyr Thr Glu Ser Asp Val His Pro Ser Cys
                565                 570                 575

Lys Val Thr Ala Met Lys Cys Phe Leu Leu Glu Leu Gln Val Ile Ser
            580                 585                 590

Leu Glu Ser Gly Asp Ala Ser Ile His Asp Thr Val Glu Asn Leu Ile
        595                 600                 605

Ile Leu Ala Asn Asn Ser Leu Ser Ser Asn Gly Asn Val Thr Glu Ser
    610                 615                 620

Gly Cys Lys Glu Cys Glu Glu Leu Glu Glu Lys Asn Ile Lys Glu Phe
625                 630                 635                 640

Leu Gln Ser Phe Val His Ile Val Gln Met Phe Ile Asn Thr Ser Thr
                645                 650                 655

Thr Thr Pro Ala Pro Arg Pro Pro Thr Pro Ala Pro Thr Ile Ala Ser
            660                 665                 670

Gln Pro Leu Ser Leu Arg Pro Glu Ala Cys Arg Pro Ala Ala Gly Gly
        675                 680                 685

Ala Val His Thr Arg Gly Leu Asp Phe Ala Cys Asp Ile Tyr Ile Trp
    690                 695                 700

Ala Pro Leu Ala Gly Thr Cys Gly Val Leu Leu Leu Ser Leu Val Ile
705                 710                 715                 720

Thr Leu Tyr Cys


<210> SEQ ID NO 184
<211> LENGTH: 2150
<212> TYPE: DNA
<213> ORGANISM: Homo sapiens
<220> FEATURE:
<221> NAME/KEY: misc_feature
<223> OTHER INFORMATION: DNA NK19H-NF-1

<400> SEQUENCE: 184

gaattcgccg ccaccatggc cttaccagtg accgccttgc tcctgccgct ggccttgctg     60

ctccacgccg ccaggccgga tattcagatg acccagagcc cgagcagcct gagcgcgagc    120

gtgggcgatc gcgtgaccat tacctgccgc gcgagccagg atattagcaa atatctgaac    180

tggtatcagc agaaaccggg cggcaccgtg aaactgctga tttatcatac cagccgcctg    240

catagcggcg tgccgagccg ctttagcggc agcggcagcg gcaccgattt taccctgacc    300

attagcagcc tgcagccgga agatattgcg acctattatt gccagcaggg caacaccctg    360

ccgtatacct ttggcggcgg caccaaactg gaaattaccg gtggcggtgg ctcgggcggt    420

ggtgggtcgg gtggcggcgg atctcaggtg cagctgcagg aaagcggccc gggcctggtg    480

aaaccgagcc agaccctgag cctgacctgc accgtgagcg gcgtgagcct gccggattat    540

ggcgtgagct ggattcgcca gccgccgggc aaaggcctgg aatggattgg cgtgatttgg    600

ggcagcgaaa ccacctatta taacagcgcg ctgaaaagcc gcctgaccat tagcaaagat    660

aacagcaaaa accaggtgag cctgaaactg agcagcgtga ccgcggcgga taccgcggtg    720

tattattgcg cgaaacatta ttattatggc ggcagctatg cgatggatta ttggggccag    780

ggcaccagcg tgaccgtgag cagcaccacg acgccagcgc cgcgaccacc aacaccggcg    840

cccaccatcg cgtcgcagcc cctgtccctg cgcccagagg cgtgccggcc agcggcgggg    900
```

```
ggcgcagtgc acacgagggg gctggacttc gcctgtgata tctacatctg ggcgcccttg     960
gccgggactt gtggggtcct tctcctgtca ctggttatca ccctttactg ccggagggac    1020
cagaggctgc cccccgatgc ccacaagccc cctgggggag gcagtttccg gacccccatc    1080
caagaggagc aggccgacgc ccactccacc ctggccaaga tcagagtgaa gttcagcagg    1140
agcgcagacg cccccgcgta ccagcagggc cagaaccagc tctataacga gctcaatcta    1200
ggacgaagag aggagtacga tgttttggac aagagacgtg gccgggaccc tgagatgggg    1260
ggaaagccga gaaggaagaa ccctcaggaa ggcctgtaca atgaactgca gaaagataag    1320
atggcggagg cctacagtga gattgggatg aaaggcgagc gccggagggg caaggggcac    1380
gatggccttt accagggtct cagtacagcc accaaggaca cctacgacgc ccttcacatg    1440
caggccctgc cccctcgcgg ctctggcgag ggaaggggtt ccctgcttac ttgcggcgac    1500
gtcgaagaga atcccggtcc gatggccctc ccagtaactg ccctcctttt gccccctcgca    1560
ctccttcttc atgccgctcg ccccaactgg gtcaacgtga ttagcgattt gaagaaaatc    1620
gaggacctta tacagtctat gcatattgac gctacactgt atactgagag tgatgtacac    1680
ccgtcctgta aggtaacggc catgaaatgc tttcttctgg agctccaggt catcagcttg    1740
gagtctgggg acgcaagcat ccacgatacg gttgaaaacc tcatcatcct tgcgaacaac    1800
tctctctcat ctaatggaaa cgttacagag agtgggtgta aggagtgcga agagttggaa    1860
gaaaaaaaca tcaaagaatt tcttcaatcc ttcgttcaca tagtgcaaat gttcattaac    1920
acgtccacta ccacacccgc cccgaggcca cctacgccgg caccgactat cgccagtcaa    1980
cccctctctc tgcgccccga ggcttgccgg cctgcggctg gtggggcggt ccacacccgg    2040
ggcctggatt ttgcgtgcga tatatacatc tgggcacctc ttgccggcac ctgcggagtg    2100
ctgcttctct cactcgttat tacgctgtac tgctaagcgg ccgcgtcgac                2150
```

<210> SEQ ID NO 185
<211> LENGTH: 706
<212> TYPE: PRT
<213> ORGANISM: Homo sapiens
<220> FEATURE:
<221> NAME/KEY: MISC_FEATURE
<223> OTHER INFORMATION: AA NK19H-NF-1

<400> SEQUENCE: 185

```
Met Ala Leu Pro Val Thr Ala Leu Leu Leu Pro Leu Ala Leu Leu Leu
1               5                   10                  15

His Ala Ala Arg Pro Asp Ile Gln Met Thr Gln Ser Pro Ser Ser Leu
            20                  25                  30

Ser Ala Ser Val Gly Asp Arg Val Thr Ile Thr Cys Arg Ala Ser Gln
        35                  40                  45

Asp Ile Ser Lys Tyr Leu Asn Trp Tyr Gln Gln Lys Pro Gly Gly Thr
    50                  55                  60

Val Lys Leu Leu Ile Tyr His Thr Ser Arg Leu His Ser Gly Val Pro
65                  70                  75                  80

Ser Arg Phe Ser Gly Ser Gly Ser Gly Thr Asp Phe Thr Leu Thr Ile
                85                  90                  95

Ser Ser Leu Gln Pro Glu Asp Ile Ala Thr Tyr Tyr Cys Gln Gln Gly
            100                 105                 110

Asn Thr Leu Pro Tyr Thr Phe Gly Gly Gly Thr Lys Leu Glu Ile Thr
        115                 120                 125

Gly Gly Gly Gly Ser Gly Gly Gly Gly Ser Gly Gly Gly Gly Ser Gln
    130                 135                 140
```

-continued

Val Gln Leu Gln Glu Ser Gly Pro Gly Leu Val Lys Pro Ser Gln Thr
145 150 155 160

Leu Ser Leu Thr Cys Thr Val Ser Gly Val Ser Leu Pro Asp Tyr Gly
165 170 175

Val Ser Trp Ile Arg Gln Pro Pro Gly Lys Gly Leu Glu Trp Ile Gly
180 185 190

Val Ile Trp Gly Ser Glu Thr Thr Tyr Tyr Asn Ser Ala Leu Lys Ser
195 200 205

Arg Leu Thr Ile Ser Lys Asp Asn Ser Lys Asn Gln Val Ser Leu Lys
210 215 220

Leu Ser Ser Val Thr Ala Ala Asp Thr Ala Val Tyr Tyr Cys Ala Lys
225 230 235 240

His Tyr Tyr Tyr Gly Gly Ser Tyr Ala Met Asp Tyr Trp Gly Gln Gly
245 250 255

Thr Ser Val Thr Val Ser Ser Thr Thr Thr Pro Ala Pro Arg Pro Pro
260 265 270

Thr Pro Ala Pro Thr Ile Ala Ser Gln Pro Leu Ser Leu Arg Pro Glu
275 280 285

Ala Cys Arg Pro Ala Ala Gly Gly Ala Val His Thr Arg Gly Leu Asp
290 295 300

Phe Ala Cys Asp Ile Tyr Ile Trp Ala Pro Leu Ala Gly Thr Cys Gly
305 310 315 320

Val Leu Leu Leu Ser Leu Val Ile Thr Leu Tyr Cys Arg Arg Asp Gln
325 330 335

Arg Leu Pro Pro Asp Ala His Lys Pro Pro Gly Gly Gly Ser Phe Arg
340 345 350

Thr Pro Ile Gln Glu Glu Gln Ala Asp Ala His Ser Thr Leu Ala Lys
355 360 365

Ile Arg Val Lys Phe Ser Arg Ser Ala Asp Ala Pro Ala Tyr Gln Gln
370 375 380

Gly Gln Asn Gln Leu Tyr Asn Glu Leu Asn Leu Gly Arg Arg Glu Glu
385 390 395 400

Tyr Asp Val Leu Asp Lys Arg Arg Gly Arg Asp Pro Glu Met Gly Gly
405 410 415

Lys Pro Arg Arg Lys Asn Pro Gln Glu Gly Leu Tyr Asn Glu Leu Gln
420 425 430

Lys Asp Lys Met Ala Glu Ala Tyr Ser Glu Ile Gly Met Lys Gly Glu
435 440 445

Arg Arg Arg Gly Lys Gly His Asp Gly Leu Tyr Gln Gly Leu Ser Thr
450 455 460

Ala Thr Lys Asp Thr Tyr Asp Ala Leu His Met Gln Ala Leu Pro Pro
465 470 475 480

Arg Gly Ser Gly Glu Gly Arg Gly Ser Leu Leu Thr Cys Gly Asp Val
485 490 495

Glu Glu Asn Pro Gly Pro Met Ala Leu Pro Val Thr Ala Leu Leu Leu
500 505 510

Pro Leu Ala Leu Leu Leu His Ala Ala Arg Pro Asn Trp Val Asn Val
515 520 525

Ile Ser Asp Leu Lys Lys Ile Glu Asp Leu Ile Gln Ser Met His Ile
530 535 540

Asp Ala Thr Leu Tyr Thr Glu Ser Asp Val His Pro Ser Cys Lys Val
545 550 555 560

-continued

```
Thr Ala Met Lys Cys Phe Leu Leu Glu Leu Gln Val Ile Ser Leu Glu
                565                 570                 575

Ser Gly Asp Ala Ser Ile His Asp Thr Val Glu Asn Leu Ile Ile Leu
            580                 585                 590

Ala Asn Asn Ser Leu Ser Ser Asn Gly Asn Val Thr Glu Ser Gly Cys
        595                 600                 605

Lys Glu Cys Glu Glu Leu Glu Glu Lys Asn Ile Lys Glu Phe Leu Gln
    610                 615                 620

Ser Phe Val His Ile Val Gln Met Phe Ile Asn Thr Ser Thr Thr Thr
625                 630                 635                 640

Pro Ala Pro Arg Pro Pro Thr Pro Ala Pro Thr Ile Ala Ser Gln Pro
                645                 650                 655

Leu Ser Leu Arg Pro Glu Ala Cys Arg Pro Ala Ala Gly Gly Ala Val
            660                 665                 670

His Thr Arg Gly Leu Asp Phe Ala Cys Asp Ile Tyr Ile Trp Ala Pro
        675                 680                 685

Leu Ala Gly Thr Cys Gly Val Leu Leu Leu Ser Leu Val Ile Thr Leu
    690                 695                 700

Tyr Cys
705
```

<210> SEQ ID NO 186
<211> LENGTH: 2150
<212> TYPE: DNA
<213> ORGANISM: Homo sapiens
<220> FEATURE:
<221> NAME/KEY: misc_feature
<223> OTHER INFORMATION: DNA NK19H-NF-2

<400> SEQUENCE: 186

```
gaattcgccg ccaccatggc cttaccagtg accgccttgc tcctgccgct ggccttgctg     60
ctccacgccg ccaggccgga tattcagatg acccagagcc cgagcagcct gagcgcgagc    120
gtgggcgatc gcgtgaccat tacctgccgc gcgagccagg atattagcaa atatctgaac    180
tggtatcagc agaaaccggg cggcaccgtg aaactgctga tttatcatac cagccgcctg    240
catagcggcg tgccgagccg ctttagcggc agcggcagcg gcaccgattt taccctgacc    300
attagcagcc tgcagccgga agatattgcg acctattttt gccagcaggg caacaccctg    360
ccgtatacct ttggcggcgg caccaaactg gaaattaccg gtggcggtgg ctcgggcggt    420
ggtgggtcgg gtggcggcgg atctcaggtg cagctgcagg aaagcggccc gggcctggtg    480
aaaccgagcc agaccctgag cctgacctgc accgtgagcg gcgtgagcct gccggattat    540
ggcgtgagct ggattcgcca gccgccgggc aaaggcctgg aatggattgg cgtgatttgg    600
ggcagcgaaa ccacctatta taacagcgcg ctgaaaagcc gcctgaccat tagcaaagat    660
aacagcaaaa accaggtgag cctgaaactg agcagcgtga ccgcggcgga taccgcggtg    720
tattattgcg cgaaacatta ttattatggc ggcagctatg cgatggatta ttggggccag    780
ggcaccagcg tgaccgtgag cagcaccacg acgccagcgc cgcgaccacc aacaccggcg    840
cccaccatcg cgtcgcagcc cctgtccctg cgcccagagg cgtgccggcc agcggcgggg    900
ggcgcagtgc acacgagggg gctggacttc gcctgtgata tctacatctg ggcgcccttg    960
gccgggactt gtggggtcct tctcctgtca ctggttatca ccctttactg ccggagggac   1020
cagaggctgc cccccgatgc ccacaagccc cctgggggag gcagtttccg gacccccatc   1080
caagaggagc aggccgacgc ccactccacc ctggccaaga tcagagtgaa gttcagcagg   1140
```

```
agcgcagacg cccccgcgta ccagcagggc cagaaccagc tctataacga gctcaatcta   1200

ggacgaagag aggagtacga tgttttggac aagagacgtg gccgggaccc tgagatgggg   1260

ggaaagccga gaaggaagaa ccctcaggaa ggcctgtaca atgaactgca gaaagataag   1320

atggcggagg cctacagtga gattgggatg aaaggcgagc gccggagggg caaggggcac   1380

gatggccttt accagggtct cagtacagcc accaaggaca cctacgacgc ccttcacatg   1440

caggccctgc cccctcgcgg ctctggcgag ggaaggggtt ccctgcttac ttgcggcgac   1500

gtcgaagaga atcccggtcc gatggccctc ccagtaactg ccctcctttt gcccctcgca   1560

ctccttcttc atgccgctcg ccccaactgg gtcaacgtga ttagcgattt gaagaaaatc   1620

gaggacctta tacagtctat gcatattgac gctacactgt atactgagag tgatgtacac   1680

ccgtcctgta aggtaacggc catgaaatgc tttcttctgg agctccaggt catcagcttg   1740

gagtctgggg acgcaagcat ccacgatacg gttgaaaacc tcatcatcct tgcgaacaac   1800

tctctctcat ctaatggaaa cgttacagag agtgggtgta aggagtgcga agagttggaa   1860

gaaaaaaaca tcaaagaatt tcttcaatcc ttcgttcaca tagtgcaaat gttcattaac   1920

acgtccacta ccacacccgc cccgaggcca cctacgccgg caccgactat cgccagtcaa   1980

cccctctctc tgcgccccga ggcttgccgg cctgcggctg gtggggcggt ccacacccgg   2040

ggcctggatt ttgcgtgcga tatatacatc tgggcacctc ttgccggcac ctgcggagtg   2100

ctgcttctct cactcgttat tacgctgtac tgctaagcgg ccgcgtcgac              2150
```

```
<210> SEQ ID NO 187
<211> LENGTH: 706
<212> TYPE: PRT
<213> ORGANISM: Homo sapiens
<220> FEATURE:
<221> NAME/KEY: MISC_FEATURE
<223> OTHER INFORMATION: AA NK19H-NF-2

<400> SEQUENCE: 187

Met Ala Leu Pro Val Thr Ala Leu Leu Leu Pro Leu Ala Leu Leu Leu
1               5                   10                  15

His Ala Ala Arg Pro Asp Ile Gln Met Thr Gln Ser Pro Ser Ser Leu
            20                  25                  30

Ser Ala Ser Val Gly Asp Arg Val Thr Ile Thr Cys Arg Ala Ser Gln
        35                  40                  45

Asp Ile Ser Lys Tyr Leu Asn Trp Tyr Gln Gln Lys Pro Gly Gly Thr
    50                  55                  60

Val Lys Leu Leu Ile Tyr His Thr Ser Arg Leu His Ser Gly Val Pro
65                  70                  75                  80

Ser Arg Phe Ser Gly Ser Gly Ser Gly Thr Asp Phe Thr Leu Thr Ile
                85                  90                  95

Ser Ser Leu Gln Pro Glu Asp Ile Ala Thr Tyr Phe Cys Gln Gln Gly
            100                 105                 110

Asn Thr Leu Pro Tyr Thr Phe Gly Gly Gly Thr Lys Leu Glu Ile Thr
        115                 120                 125

Gly Gly Gly Gly Ser Gly Gly Gly Gly Ser Gly Gly Gly Gly Ser Gln
    130                 135                 140

Val Gln Leu Gln Glu Ser Gly Pro Gly Leu Val Lys Pro Ser Gln Thr
145                 150                 155                 160

Leu Ser Leu Thr Cys Thr Val Ser Gly Val Ser Leu Pro Asp Tyr Gly
                165                 170                 175

Val Ser Trp Ile Arg Gln Pro Pro Gly Lys Gly Leu Glu Trp Ile Gly
```

-continued

```
            180                 185                 190

Val Ile Trp Gly Ser Glu Thr Thr Tyr Tyr Asn Ser Ala Leu Lys Ser
        195                 200                 205

Arg Leu Thr Ile Ser Lys Asp Asn Ser Lys Asn Gln Val Ser Leu Lys
    210                 215                 220

Leu Ser Ser Val Thr Ala Ala Asp Thr Ala Val Tyr Tyr Cys Ala Lys
225                 230                 235                 240

His Tyr Tyr Tyr Gly Gly Ser Tyr Ala Met Asp Tyr Trp Gly Gln Gly
                245                 250                 255

Thr Ser Val Thr Val Ser Ser Thr Thr Thr Pro Ala Pro Arg Pro Pro
            260                 265                 270

Thr Pro Ala Pro Thr Ile Ala Ser Gln Pro Leu Ser Leu Arg Pro Glu
        275                 280                 285

Ala Cys Arg Pro Ala Ala Gly Gly Ala Val His Thr Arg Gly Leu Asp
    290                 295                 300

Phe Ala Cys Asp Ile Tyr Ile Trp Ala Pro Leu Ala Gly Thr Cys Gly
305                 310                 315                 320

Val Leu Leu Leu Ser Leu Val Ile Thr Leu Tyr Cys Arg Arg Asp Gln
                325                 330                 335

Arg Leu Pro Pro Asp Ala His Lys Pro Pro Gly Gly Gly Ser Phe Arg
            340                 345                 350

Thr Pro Ile Gln Glu Glu Gln Ala Asp Ala His Ser Thr Leu Ala Lys
        355                 360                 365

Ile Arg Val Lys Phe Ser Arg Ser Ala Asp Ala Pro Ala Tyr Gln Gln
    370                 375                 380

Gly Gln Asn Gln Leu Tyr Asn Glu Leu Asn Leu Gly Arg Arg Glu Glu
385                 390                 395                 400

Tyr Asp Val Leu Asp Lys Arg Arg Gly Arg Asp Pro Glu Met Gly Gly
                405                 410                 415

Lys Pro Arg Arg Lys Asn Pro Gln Glu Gly Leu Tyr Asn Glu Leu Gln
            420                 425                 430

Lys Asp Lys Met Ala Glu Ala Tyr Ser Glu Ile Gly Met Lys Gly Glu
        435                 440                 445

Arg Arg Arg Gly Lys Gly His Asp Gly Leu Tyr Gln Gly Leu Ser Thr
    450                 455                 460

Ala Thr Lys Asp Thr Tyr Asp Ala Leu His Met Gln Ala Leu Pro Pro
465                 470                 475                 480

Arg Gly Ser Gly Glu Gly Arg Gly Ser Leu Leu Thr Cys Gly Asp Val
                485                 490                 495

Glu Glu Asn Pro Gly Pro Met Ala Leu Pro Val Thr Ala Leu Leu Leu
            500                 505                 510

Pro Leu Ala Leu Leu Leu His Ala Ala Arg Pro Asn Trp Val Asn Val
        515                 520                 525

Ile Ser Asp Leu Lys Lys Ile Glu Asp Leu Ile Gln Ser Met His Ile
    530                 535                 540

Asp Ala Thr Leu Tyr Thr Glu Ser Asp Val His Pro Ser Cys Lys Val
545                 550                 555                 560

Thr Ala Met Lys Cys Phe Leu Leu Glu Leu Gln Val Ile Ser Leu Glu
                565                 570                 575

Ser Gly Asp Ala Ser Ile His Asp Thr Val Glu Asn Leu Ile Ile Leu
            580                 585                 590

Ala Asn Asn Ser Leu Ser Ser Asn Gly Asn Val Thr Glu Ser Gly Cys
        595                 600                 605
```

```
Lys Glu Cys Glu Glu Leu Glu Glu Lys Asn Ile Lys Glu Phe Leu Gln
    610                 615                 620

Ser Phe Val His Ile Val Gln Met Phe Ile Asn Thr Ser Thr Thr Thr
625                 630                 635                 640

Pro Ala Pro Arg Pro Pro Thr Pro Ala Pro Thr Ile Ala Ser Gln Pro
                645                 650                 655

Leu Ser Leu Arg Pro Glu Ala Cys Arg Pro Ala Ala Gly Gly Ala Val
            660                 665                 670

His Thr Arg Gly Leu Asp Phe Ala Cys Asp Ile Tyr Ile Trp Ala Pro
        675                 680                 685

Leu Ala Gly Thr Cys Gly Val Leu Leu Leu Ser Leu Val Ile Thr Leu
    690                 695                 700

Tyr Cys
705
```

<210> SEQ ID NO 188
<211> LENGTH: 2150
<212> TYPE: DNA
<213> ORGANISM: Homo sapiens
<220> FEATURE:
<221> NAME/KEY: misc_feature
<223> OTHER INFORMATION: DNA NK19H-NF-3

<400> SEQUENCE: 188

```
gaattcgccg ccaccatggc cttaccagtg accgccttgc tcctgccgct ggccttgctg     60

ctccacgccg ccaggccgga tattcagatg acccagagcc cgagcagcct gagcgcgagc    120

gtgggcgatc gcgtgaccat tacctgccgc gcgagccagg atattagcaa atatctgaac    180

tggtatcagc agaaaccgga tggcaccgtg aaactgctga tttatcatac cagccgcctg    240

catagcggcg tgccgagccg ctttagcggc agcggcagcg gcaccgatta taccctgacc    300

attagcagcc tgcagccgga agatattgcg acctattttt gccagcaggg caacaccctg    360

ccgtatacct ttggcggcgg caccaaactg gaaattaccg gtggcggtgg ctcgggcggt    420

ggtgggtcgg gtggcggcgg atctcaggtg cagctgcagg aaagcggccc gggcctggtg    480

aaaccgagcc agaccctgag cctgacctgc accgtgagcg gcgtgagcct gccggattat    540

ggcgtgagct ggattcgcca gccgccgggc aaaggcctgg aatggattgg cgtgatttgg    600

ggcagcgaaa ccacctatta taacagcgcg ctgaaaagcc gcctgaccat tagcaaagat    660

aacagcaaaa accaggtgag cctgaaactg agcagcgtga ccgcggcgga taccgcggtg    720

tattattgcg cgaaacatta ttattatggc ggcagctatg cgatggatta ttggggccag    780

ggcaccagcg tgaccgtgag cagcaccacg acgccagcgc cgcgaccacc aacaccggcg    840

cccaccatcg cgtcgcagcc cctgtccctg cgcccagagg cgtgccggcc agcggcgggg    900

ggcgcagtgc acacgagggg gctggacttc gcctgtgata tctacatctg ggcgcccttg    960

gccgggactt gtggggtcct tctcctgtca ctggttatca ccctttactg ccggagggac   1020

cagaggctgc cccccgatgc ccacaagccc cctgggggag gcagtttccg gacccccatc   1080

caagaggagc aggccgacgc ccactccacc ctggccaaga tcagagtgaa gttcagcagg   1140

agcgcagacg cccccgcgta ccagcagggc cagaaccagc tctataacga gctcaatcta   1200

ggacgaagag aggagtacga tgttttggac aagagacgtg gccgggaccc tgagatgggg   1260

ggaaagccga gaaggaagaa ccctcaggaa ggcctgtaca atgaactgca gaaagataag   1320

atggcggagg cctacagtga gattgggatg aaaggcgagc gccggagggg caaggggcac   1380
```

gatggccttt accagggtct cagtacagcc accaaggaca cctacgacgc ccttcacatg 1440
caggccctgc cccctcgcgg ctctggcgag ggaaggggtt ccctgcttac ttgcggcgac 1500
gtcgaagaga atcccggtcc gatggccctc ccagtaactg ccctcctttt gcccctcgca 1560
ctccttcttc atgccgctcg ccccaactgg gtcaacgtga ttagcgattt gaagaaaatc 1620
gaggacctta tacagtctat gcatattgac gctacactgt atactgagag tgatgtacac 1680
ccgtcctgta aggtaacggc catgaaatgc tttcttctgg agctccaggt catcagcttg 1740
gagtctgggg acgcaagcat ccacgatacg gttgaaaacc tcatcatcct tgcgaacaac 1800
tctctctcat ctaatggaaa cgttacagag agtgggtgta aggagtgcga agagttggaa 1860
gaaaaaaaca tcaaagaatt tcttcaatcc ttcgttcaca tagtgcaaat gttcattaac 1920
acgtccacta ccacacccgc cccgaggcca cctacgccgg caccgactat cgccagtcaa 1980
cccctctctc tgcgccccga ggcttgccgg cctgcggctg gtggggcggt ccacacccgg 2040
ggcctggatt ttgcgtgcga tatatacatc tgggcacctc ttgccggcac ctgcggagtg 2100
ctgcttctct cactcgttat tacgctgtac tgctaagcgg ccgcgtcgac 2150

<210> SEQ ID NO 189
<211> LENGTH: 706
<212> TYPE: PRT
<213> ORGANISM: Homo sapiens
<220> FEATURE:
<221> NAME/KEY: MISC_FEATURE
<223> OTHER INFORMATION: AA NK19H-NF-3

<400> SEQUENCE: 189

Met Ala Leu Pro Val Thr Ala Leu Leu Leu Pro Leu Ala Leu Leu Leu
1 5 10 15

His Ala Ala Arg Pro Asp Ile Gln Met Thr Gln Ser Pro Ser Ser Leu
20 25 30

Ser Ala Ser Val Gly Asp Arg Val Thr Ile Thr Cys Arg Ala Ser Gln
35 40 45

Asp Ile Ser Lys Tyr Leu Asn Trp Tyr Gln Gln Lys Pro Asp Gly Thr
50 55 60

Val Lys Leu Leu Ile Tyr His Thr Ser Arg Leu His Ser Gly Val Pro
65 70 75 80

Ser Arg Phe Ser Gly Ser Gly Ser Gly Thr Asp Tyr Thr Leu Thr Ile
85 90 95

Ser Ser Leu Gln Pro Glu Asp Ile Ala Thr Tyr Phe Cys Gln Gln Gly
100 105 110

Asn Thr Leu Pro Tyr Thr Phe Gly Gly Gly Thr Lys Leu Glu Ile Thr
115 120 125

Gly Gly Gly Gly Ser Gly Gly Gly Gly Ser Gly Gly Gly Gly Ser Gln
130 135 140

Val Gln Leu Gln Glu Ser Gly Pro Gly Leu Val Lys Pro Ser Gln Thr
145 150 155 160

Leu Ser Leu Thr Cys Thr Val Ser Gly Val Ser Leu Pro Asp Tyr Gly
165 170 175

Val Ser Trp Ile Arg Gln Pro Pro Gly Lys Gly Leu Glu Trp Ile Gly
180 185 190

Val Ile Trp Gly Ser Glu Thr Thr Tyr Tyr Asn Ser Ala Leu Lys Ser
195 200 205

Arg Leu Thr Ile Ser Lys Asp Asn Ser Lys Asn Gln Val Ser Leu Lys
210 215 220

-continued

Leu Ser Ser Val Thr Ala Ala Asp Thr Ala Val Tyr Tyr Cys Ala Lys
225 230 235 240

His Tyr Tyr Tyr Gly Gly Ser Tyr Ala Met Asp Tyr Trp Gly Gln Gly
245 250 255

Thr Ser Val Thr Val Ser Ser Thr Thr Thr Pro Ala Pro Arg Pro Pro
260 265 270

Thr Pro Ala Pro Thr Ile Ala Ser Gln Pro Leu Ser Leu Arg Pro Glu
275 280 285

Ala Cys Arg Pro Ala Ala Gly Gly Ala Val His Thr Arg Gly Leu Asp
290 295 300

Phe Ala Cys Asp Ile Tyr Ile Trp Ala Pro Leu Ala Gly Thr Cys Gly
305 310 315 320

Val Leu Leu Leu Ser Leu Val Ile Thr Leu Tyr Cys Arg Arg Asp Gln
325 330 335

Arg Leu Pro Pro Asp Ala His Lys Pro Pro Gly Gly Gly Ser Phe Arg
340 345 350

Thr Pro Ile Gln Glu Glu Gln Ala Asp Ala His Ser Thr Leu Ala Lys
355 360 365

Ile Arg Val Lys Phe Ser Arg Ser Ala Asp Ala Pro Ala Tyr Gln Gln
370 375 380

Gly Gln Asn Gln Leu Tyr Asn Glu Leu Asn Leu Gly Arg Arg Glu Glu
385 390 395 400

Tyr Asp Val Leu Asp Lys Arg Arg Gly Arg Asp Pro Glu Met Gly Gly
405 410 415

Lys Pro Arg Arg Lys Asn Pro Gln Glu Gly Leu Tyr Asn Glu Leu Gln
420 425 430

Lys Asp Lys Met Ala Glu Ala Tyr Ser Glu Ile Gly Met Lys Gly Glu
435 440 445

Arg Arg Arg Gly Lys Gly His Asp Gly Leu Tyr Gln Gly Leu Ser Thr
450 455 460

Ala Thr Lys Asp Thr Tyr Asp Ala Leu His Met Gln Ala Leu Pro Pro
465 470 475 480

Arg Gly Ser Gly Glu Gly Arg Gly Ser Leu Leu Thr Cys Gly Asp Val
485 490 495

Glu Glu Asn Pro Gly Pro Met Ala Leu Pro Val Thr Ala Leu Leu Leu
500 505 510

Pro Leu Ala Leu Leu Leu His Ala Ala Arg Pro Asn Trp Val Asn Val
515 520 525

Ile Ser Asp Leu Lys Lys Ile Glu Asp Leu Ile Gln Ser Met His Ile
530 535 540

Asp Ala Thr Leu Tyr Thr Glu Ser Asp Val His Pro Ser Cys Lys Val
545 550 555 560

Thr Ala Met Lys Cys Phe Leu Leu Glu Leu Gln Val Ile Ser Leu Glu
565 570 575

Ser Gly Asp Ala Ser Ile His Asp Thr Val Glu Asn Leu Ile Ile Leu
580 585 590

Ala Asn Asn Ser Leu Ser Ser Asn Gly Asn Val Thr Glu Ser Gly Cys
595 600 605

Lys Glu Cys Glu Glu Leu Glu Glu Lys Asn Ile Lys Glu Phe Leu Gln
610 615 620

Ser Phe Val His Ile Val Gln Met Phe Ile Asn Thr Ser Thr Thr Thr
625 630 635 640

Pro Ala Pro Arg Pro Pro Thr Pro Ala Pro Thr Ile Ala Ser Gln Pro

-continued

```
                645                 650                 655

Leu Ser Leu Arg Pro Glu Ala Cys Arg Pro Ala Ala Gly Gly Ala Val
            660                 665                 670

His Thr Arg Gly Leu Asp Phe Ala Cys Asp Ile Tyr Ile Trp Ala Pro
        675                 680                 685

Leu Ala Gly Thr Cys Gly Val Leu Leu Leu Ser Leu Val Ile Thr Leu
    690                 695                 700

Tyr Cys
705


<210> SEQ ID NO 190
<211> LENGTH: 2150
<212> TYPE: DNA
<213> ORGANISM: Homo sapiens
<220> FEATURE:
<221> NAME/KEY: misc_feature
<223> OTHER INFORMATION: DNA NK19H-NF-4

<400> SEQUENCE: 190

gaattcgccg ccaccatggc cttaccagtg accgccttgc tcctgccgct ggccttgctg     60

ctccacgccg ccaggccgga tattcagatg acccagagcc cgagcagcct gagcgcgagc    120

gtgggcgatc gcgtgaccat tacctgccgc gcgagccagg atattagcaa atatctgaac    180

tggtatcagc agaaaccggg cggcaccgtg aaactgctga tttatcatac cagccgcctg    240

catagcggcg tgccgagccg ctttagcggc agcggcagcg gcaccgattt taccctgacc    300

attagcagcc tgcagccgga agatattgcg acctattatt gccagcaggg caacaccctg    360

ccgtatacct ttggcggcgg caccaaactg gaaattaccg gtggcggtgg ctcgggcggt    420

ggtgggtcgg gtggcggcgg atctcaggtg cagctgcagg aaagcggccc gggcctggtg    480

aaaccgagcc agaccctgag cctgacctgc accgtgagcg gcgtgagcct gccggattat    540

ggcgtgagct ggattcgcca gccgccgggc aaaggcctgg aatggctggg cgtgatttgg    600

ggcagcgaaa ccacctatta taacagcgcg ctgaaaagcc gcctgaccat tagcaaagat    660

aacagcaaaa gccaggtgag cctgaaactg agcagcgtga ccgcggcgga taccgcggtg    720

tattattgcg cgaaacatta ttattatggc ggcagctatg cgatggatta ttggggccag    780

ggcaccagcg tgaccgtgag cagcaccacg acgccagcgc cgcgaccacc aacaccggcg    840

cccaccatcg cgtcgcagcc cctgtccctg cgcccagagg cgtgccggcc agcggcgggg    900

ggcgcagtgc acacgagggg gctggacttc gcctgtgata tctacatctg ggcgcccttg    960

gccgggactt gtggggtcct tctcctgtca ctggttatca ccctttactg ccggagggac   1020

cagaggctgc cccccgatgc ccacaagccc cctgggggag gcagtttccg gacccccatc   1080

caagaggagc aggccgacgc ccactccacc ctggccaaga tcagagtgaa gttcagcagg   1140

agcgcagacg cccccgcgta ccagcagggc cagaaccagc tctataacga gctcaatcta   1200

ggacgaagag aggagtacga tgttttggac aagagacgtg gccgggaccc tgagatgggg   1260

ggaaagccga gaaggaagaa ccctcaggaa ggcctgtaca atgaactgca gaaagataag   1320

atggcggagg cctacagtga gattgggatg aaaggcgagc gccggagggg caaggggcac   1380

gatggccttt accagggtct cagtacagcc accaaggaca cctacgacgc ccttcacatg   1440

caggccctgc cccctcgcgg ctctggcgag ggaaggggtt ccctgcttac ttgcggcgac   1500

gtcgaagaga atcccggtcc gatggccctc ccagtaactg ccctcctttt gcccctcgca   1560

ctccttcttc atgccgctcg ccccaactgg gtcaacgtga ttagcgattt gaagaaaatc   1620
```

-continued gaggacctta tacagtctat gcatattgac gctacactgt atactgagag tgatgtacac 1680
ccgtcctgta aggtaacggc catgaaatgc tttcttctgg agctccaggt catcagcttg 1740
gagtctgggg acgcaagcat ccacgatacg gttgaaaacc tcatcatcct tgcgaacaac 1800
tctctctcat ctaatggaaa cgttacagag agtgggtgta aggagtgcga agagttggaa 1860
gaaaaaaaca tcaaagaatt tcttcaatcc ttcgttcaca tagtgcaaat gttcattaac 1920
acgtccacta ccacacccgc cccgaggcca cctacgccgg caccgactat cgccagtcaa 1980
cccctctctc tgcgccccga ggcttgccgg cctgcggctg gtggggcggt ccacacccgg 2040
ggcctggatt ttgcgtgcga tatatacatc tgggcacctc ttgccggcac ctgcggagtg 2100
ctgcttctct cactcgttat tacgctgtac tgctaagcgg ccgcgtcgac 2150

<210> SEQ ID NO 191
<211> LENGTH: 706
<212> TYPE: PRT
<213> ORGANISM: Homo sapiens
<220> FEATURE:
<221> NAME/KEY: MISC_FEATURE
<223> OTHER INFORMATION: AA NK19H-NF-4

<400> SEQUENCE: 191

Met Ala Leu Pro Val Thr Ala Leu Leu Leu Pro Leu Ala Leu Leu Leu
1 5 10 15

His Ala Ala Arg Pro Asp Ile Gln Met Thr Gln Ser Pro Ser Ser Leu
20 25 30

Ser Ala Ser Val Gly Asp Arg Val Thr Ile Thr Cys Arg Ala Ser Gln
35 40 45

Asp Ile Ser Lys Tyr Leu Asn Trp Tyr Gln Gln Lys Pro Gly Gly Thr
50 55 60

Val Lys Leu Leu Ile Tyr His Thr Ser Arg Leu His Ser Gly Val Pro
65 70 75 80

Ser Arg Phe Ser Gly Ser Gly Ser Gly Thr Asp Phe Thr Leu Thr Ile
85 90 95

Ser Ser Leu Gln Pro Glu Asp Ile Ala Thr Tyr Tyr Cys Gln Gln Gly
100 105 110

Asn Thr Leu Pro Tyr Thr Phe Gly Gly Gly Thr Lys Leu Glu Ile Thr
115 120 125

Gly Gly Gly Gly Ser Gly Gly Gly Gly Ser Gly Gly Gly Gly Ser Gln
130 135 140

Val Gln Leu Gln Glu Ser Gly Pro Gly Leu Val Lys Pro Ser Gln Thr
145 150 155 160

Leu Ser Leu Thr Cys Thr Val Ser Gly Val Ser Leu Pro Asp Tyr Gly
165 170 175

Val Ser Trp Ile Arg Gln Pro Pro Gly Lys Gly Leu Glu Trp Leu Gly
180 185 190

Val Ile Trp Gly Ser Glu Thr Thr Tyr Tyr Asn Ser Ala Leu Lys Ser
195 200 205

Arg Leu Thr Ile Ser Lys Asp Asn Ser Lys Ser Gln Val Ser Leu Lys
210 215 220

Leu Ser Ser Val Thr Ala Ala Asp Thr Ala Val Tyr Tyr Cys Ala Lys
225 230 235 240

His Tyr Tyr Tyr Gly Gly Ser Tyr Ala Met Asp Tyr Trp Gly Gln Gly
245 250 255

Thr Ser Val Thr Val Ser Ser Thr Thr Thr Pro Ala Pro Arg Pro Pro
260 265 270

-continued

Thr Pro Ala Pro Thr Ile Ala Ser Gln Pro Leu Ser Leu Arg Pro Glu
275 280 285

Ala Cys Arg Pro Ala Ala Gly Gly Ala Val His Thr Arg Gly Leu Asp
290 295 300

Phe Ala Cys Asp Ile Tyr Ile Trp Ala Pro Leu Ala Gly Thr Cys Gly
305 310 315 320

Val Leu Leu Leu Ser Leu Val Ile Thr Leu Tyr Cys Arg Arg Asp Gln
325 330 335

Arg Leu Pro Pro Asp Ala His Lys Pro Pro Gly Gly Gly Ser Phe Arg
340 345 350

Thr Pro Ile Gln Glu Glu Gln Ala Asp Ala His Ser Thr Leu Ala Lys
355 360 365

Ile Arg Val Lys Phe Ser Arg Ser Ala Asp Ala Pro Ala Tyr Gln Gln
370 375 380

Gly Gln Asn Gln Leu Tyr Asn Glu Leu Asn Leu Gly Arg Arg Glu Glu
385 390 395 400

Tyr Asp Val Leu Asp Lys Arg Arg Gly Arg Asp Pro Glu Met Gly Gly
405 410 415

Lys Pro Arg Arg Lys Asn Pro Gln Glu Gly Leu Tyr Asn Glu Leu Gln
420 425 430

Lys Asp Lys Met Ala Glu Ala Tyr Ser Glu Ile Gly Met Lys Gly Glu
435 440 445

Arg Arg Arg Gly Lys Gly His Asp Gly Leu Tyr Gln Gly Leu Ser Thr
450 455 460

Ala Thr Lys Asp Thr Tyr Asp Ala Leu His Met Gln Ala Leu Pro Pro
465 470 475 480

Arg Gly Ser Gly Glu Gly Arg Gly Ser Leu Leu Thr Cys Gly Asp Val
485 490 495

Glu Glu Asn Pro Gly Pro Met Ala Leu Pro Val Thr Ala Leu Leu Leu
500 505 510

Pro Leu Ala Leu Leu Leu His Ala Ala Arg Pro Asn Trp Val Asn Val
515 520 525

Ile Ser Asp Leu Lys Lys Ile Glu Asp Leu Ile Gln Ser Met His Ile
530 535 540

Asp Ala Thr Leu Tyr Thr Glu Ser Asp Val His Pro Ser Cys Lys Val
545 550 555 560

Thr Ala Met Lys Cys Phe Leu Leu Glu Leu Gln Val Ile Ser Leu Glu
565 570 575

Ser Gly Asp Ala Ser Ile His Asp Thr Val Glu Asn Leu Ile Ile Leu
580 585 590

Ala Asn Asn Ser Leu Ser Ser Asn Gly Asn Val Thr Glu Ser Gly Cys
595 600 605

Lys Glu Cys Glu Glu Leu Glu Glu Lys Asn Ile Lys Glu Phe Leu Gln
610 615 620

Ser Phe Val His Ile Val Gln Met Phe Ile Asn Thr Ser Thr Thr Thr
625 630 635 640

Pro Ala Pro Arg Pro Pro Thr Pro Ala Pro Thr Ile Ala Ser Gln Pro
645 650 655

Leu Ser Leu Arg Pro Glu Ala Cys Arg Pro Ala Ala Gly Gly Ala Val
660 665 670

His Thr Arg Gly Leu Asp Phe Ala Cys Asp Ile Tyr Ile Trp Ala Pro
675 680 685

Leu Ala Gly Thr Cys Gly Val Leu Leu Leu Ser Leu Val Ile Thr Leu
690 695 700

Tyr Cys
705

<210> SEQ ID NO 192
<211> LENGTH: 2153
<212> TYPE: DNA
<213> ORGANISM: Homo sapiens
<220> FEATURE:
<221> NAME/KEY: misc_feature
<223> OTHER INFORMATION: DNA NK19H-NF-5

<400> SEQUENCE: 192
gaattcgccg ccaccatggc cttaccagtg accgccttgc tcctgccgct ggccttgctg 60
ctccacgccg ccaggccgga tattcagatg acccagagcc cgagcagcct gagcgcgagc 120
gtgggcgatc gcgtgaccat tacctgccgc gcgagccagg atattagcaa atatctgaac 180
tggtatcagc agaaaccggg cggcaccgtg aaactgctga tttatcatac cagccgcctg 240
catagcggcg tgccgagccg ctttagcggc agcggcagcg gcaccgattt taccctgacc 300
attagcagcc tgcagccgga agatattgcg acctattttt gccagcaggg caacaccctg 360
ccgtatacct ttggcggcgg caccaaactg gaaattaccg gtggcggtgg ctcgggcggt 420
ggtgggtcgg gtggcggcgg atctcaggtg cagctgcagg agtcaggacc tggcctggtg 480
aaaccctcac agactctgtc cctgacatgc actgtctcag ggtctcatt acccgactat 540 ggtgtaagct ggattcgcca gcctccaggt aagggtctgg agtggctggg agtaatatgg 600
ggtagtgaaa ccacatacta taattcagct ctcaaatcca gactgaccat ctccaaggac 660
aactccaaga gccaagtttc cttaaaatta agtagtgtta ctgctgctga cacagccgtc 720
tactactgtg ccaaacatta ttactacggt ggtagctatg ctatggacta ctggggccaa 780
ggaacctcag tcaccgtctc ctcaaccacg acgccagcgc cgcgaccacc aacaccggcg 840
cccaccatcg cgtcgcagcc cctgtccctg cgcccagagg cgtgccggcc agcggcgggg 900
ggcgcagtgc acacgagggg gctggacttc gcctgtgata tctacatctg ggcgcccttg 960
gccgggactt gtggggtcct tctcctgtca ctggttatca ccctttactg ccggagggac 1020
cagaggctgc cccccgatgc ccacaagccc cctgggggag gcagtttccg gacccccatc 1080
caagaggagc aggccgacgc ccactccacc ctggccaaga tcagagtgaa gttcagcaga 1140
tctagcgcag acgcccccgc gtaccagcag ggccagaacc agctctataa cgagctcaat 1200
ctaggacgaa gagaggagta cgatgttttg gacaagagac gtggccggga ccctgagatg 1260
gggggaaagc cgagaaggaa gaaccctcag gaaggcctgt acaatgaact gcagaaagat 1320
aagatggcgg aggcctacag tgagattggg atgaaaggcg agcgccggag gggcaagggg 1380
cacgatggcc tttaccaggg tctcagtaca gccaccaagg acacctacga cgcccttcac 1440
atgcaggccc tgccccctcg cggctctggc gagggaaggg gttccctgct tacttgcggc 1500
gacgtcgaag agaatcccgg tccgatggcc ctcccagtaa ctgccctcct tttgcccctc 1560
gcactccttc ttcatgccgc tcgccccaac tgggtcaacg tgattagcga tttgaagaaa 1620
atcgaggacc ttatacagtc tatgcatatt gacgctacac tgtatactga gagtgatgta 1680
cacccgtcct gtaaggtaac ggccatgaaa tgctttcttc tggagctcca ggtcatcagc 1740
ttggagtctg ggacgcaag catccacgat acggttgaaa acctcatcat ccttgcgaac 1800
aactctctct catctaatgg aaacgttaca gagagtgggt gtaaggagtg cgaagagttg 1860

-continued

```
gaagaaaaaa acatcaaaga atttcttcaa tccttcgttc acatagtgca aatgttcatt   1920

aacacgtcca ctaccacacc cgccccgagg ccacctacgc cggcaccgac tatcgccagt   1980

caacccctct ctctgcgccc cgaggcttgc cggcctgcgg ctggtggggc ggtccacacc   2040

cggggcctgg attttgcgtg cgatatatac atctgggcac ctcttgccgg cacctgcgga   2100

gtgctgcttc tctcactcgt tattacgctg tactgctaag cggccgcgtc gac          2153


<210> SEQ ID NO 193
<211> LENGTH: 707
<212> TYPE: PRT
<213> ORGANISM: Homo sapiens
<220> FEATURE:
<221> NAME/KEY: MISC_FEATURE
<223> OTHER INFORMATION: AA NK19H-NF-5

<400> SEQUENCE: 193

Met Ala Leu Pro Val Thr Ala Leu Leu Leu Pro Leu Ala Leu Leu Leu
1               5                   10                  15

His Ala Ala Arg Pro Asp Ile Gln Met Thr Gln Ser Pro Ser Ser Leu
            20                  25                  30

Ser Ala Ser Val Gly Asp Arg Val Thr Ile Thr Cys Arg Ala Ser Gln
        35                  40                  45

Asp Ile Ser Lys Tyr Leu Asn Trp Tyr Gln Gln Lys Pro Gly Gly Thr
    50                  55                  60

Val Lys Leu Leu Ile Tyr His Thr Ser Arg Leu His Ser Gly Val Pro
65                  70                  75                  80

Ser Arg Phe Ser Gly Ser Gly Ser Gly Thr Asp Phe Thr Leu Thr Ile
                85                  90                  95

Ser Ser Leu Gln Pro Glu Asp Ile Ala Thr Tyr Phe Cys Gln Gln Gly
            100                 105                 110

Asn Thr Leu Pro Tyr Thr Phe Gly Gly Gly Thr Lys Leu Glu Ile Thr
        115                 120                 125

Gly Gly Gly Gly Ser Gly Gly Gly Gly Ser Gly Gly Gly Gly Ser Gln
    130                 135                 140

Val Gln Leu Gln Glu Ser Gly Pro Gly Leu Val Lys Pro Ser Gln Thr
145                 150                 155                 160

Leu Ser Leu Thr Cys Thr Val Ser Gly Val Ser Leu Pro Asp Tyr Gly
                165                 170                 175

Val Ser Trp Ile Arg Gln Pro Pro Gly Lys Gly Leu Glu Trp Leu Gly
            180                 185                 190

Val Ile Trp Gly Ser Glu Thr Thr Tyr Tyr Asn Ser Ala Leu Lys Ser
        195                 200                 205

Arg Leu Thr Ile Ser Lys Asp Asn Ser Lys Ser Gln Val Ser Leu Lys
    210                 215                 220

Leu Ser Ser Val Thr Ala Ala Asp Thr Ala Val Tyr Tyr Cys Ala Lys
225                 230                 235                 240

His Tyr Tyr Tyr Gly Gly Ser Tyr Ala Met Asp Tyr Trp Gly Gln Gly
                245                 250                 255

Thr Ser Val Thr Val Ser Ser Thr Thr Thr Pro Ala Pro Arg Pro Pro
            260                 265                 270

Thr Pro Ala Pro Thr Ile Ala Ser Gln Pro Leu Ser Leu Arg Pro Glu
        275                 280                 285

Ala Cys Arg Pro Ala Ala Gly Gly Ala Val His Thr Arg Gly Leu Asp
    290                 295                 300

Phe Ala Cys Asp Ile Tyr Ile Trp Ala Pro Leu Ala Gly Thr Cys Gly
```

```
305                 310                 315                 320

Val Leu Leu Leu Ser Leu Val Ile Thr Leu Tyr Cys Arg Arg Asp Gln
                325                 330                 335

Arg Leu Pro Pro Asp Ala His Lys Pro Pro Gly Gly Gly Ser Phe Arg
            340                 345                 350

Thr Pro Ile Gln Glu Glu Gln Ala Asp Ala His Ser Thr Leu Ala Lys
        355                 360                 365

Ile Arg Val Lys Phe Ser Arg Ser Ser Ala Asp Ala Pro Ala Tyr Gln
    370                 375                 380

Gln Gly Gln Asn Gln Leu Tyr Asn Glu Leu Asn Leu Gly Arg Arg Glu
385                 390                 395                 400

Glu Tyr Asp Val Leu Asp Lys Arg Arg Gly Arg Asp Pro Glu Met Gly
                405                 410                 415

Gly Lys Pro Arg Arg Lys Asn Pro Gln Glu Gly Leu Tyr Asn Glu Leu
            420                 425                 430

Gln Lys Asp Lys Met Ala Glu Ala Tyr Ser Glu Ile Gly Met Lys Gly
        435                 440                 445

Glu Arg Arg Arg Gly Lys Gly His Asp Gly Leu Tyr Gln Gly Leu Ser
    450                 455                 460

Thr Ala Thr Lys Asp Thr Tyr Asp Ala Leu His Met Gln Ala Leu Pro
465                 470                 475                 480

Pro Arg Gly Ser Gly Glu Gly Arg Gly Ser Leu Leu Thr Cys Gly Asp
                485                 490                 495

Val Glu Glu Asn Pro Gly Pro Met Ala Leu Pro Val Thr Ala Leu Leu
            500                 505                 510

Leu Pro Leu Ala Leu Leu Leu His Ala Ala Arg Pro Asn Trp Val Asn
        515                 520                 525

Val Ile Ser Asp Leu Lys Lys Ile Glu Asp Leu Ile Gln Ser Met His
    530                 535                 540

Ile Asp Ala Thr Leu Tyr Thr Glu Ser Asp Val His Pro Ser Cys Lys
545                 550                 555                 560

Val Thr Ala Met Lys Cys Phe Leu Leu Glu Leu Gln Val Ile Ser Leu
                565                 570                 575

Glu Ser Gly Asp Ala Ser Ile His Asp Thr Val Glu Asn Leu Ile Ile
            580                 585                 590

Leu Ala Asn Asn Ser Leu Ser Ser Asn Gly Asn Val Thr Glu Ser Gly
        595                 600                 605

Cys Lys Glu Cys Glu Glu Leu Glu Glu Lys Asn Ile Lys Glu Phe Leu
    610                 615                 620

Gln Ser Phe Val His Ile Val Gln Met Phe Ile Asn Thr Ser Thr Thr
625                 630                 635                 640

Thr Pro Ala Pro Arg Pro Pro Thr Pro Ala Pro Thr Ile Ala Ser Gln
                645                 650                 655

Pro Leu Ser Leu Arg Pro Glu Ala Cys Arg Pro Ala Ala Gly Gly Ala
            660                 665                 670

Val His Thr Arg Gly Leu Asp Phe Ala Cys Asp Ile Tyr Ile Trp Ala
        675                 680                 685

Pro Leu Ala Gly Thr Cys Gly Val Leu Leu Leu Ser Leu Val Ile Thr
    690                 695                 700

Leu Tyr Cys
705
```

<210> SEQ ID NO 194

<211> LENGTH: 2150
<212> TYPE: DNA
<213> ORGANISM: Homo sapiens
<220> FEATURE:
<221> NAME/KEY: misc_feature
<223> OTHER INFORMATION: DNA NK19H-NF-6

<400> SEQUENCE: 194

```
gaattcgccg ccaccatggc cttaccagtg accgccttgc tcctgccgct ggccttgctg     60
ctccacgccg ccaggccgga catccagatg acacagagcc cgtcctccct gtctgcctct    120
gtgggagaca gagtcaccat cacctgcagg gcaagtcagg acattagtaa atatttaaat    180
tggtatcagc agaaaccaga cggaactgtt aaactcctga tctaccatac atcaagatta    240
cactcaggag tcccatcaag gttcagtggc agtgggtctg gaacagatta caccctcacc    300
attagcagcc tgcaaccgga agatattgcc acttacttct gccaacaggg taatacgctt    360
ccgtacacgt tcggaggggg gaccaagctg gagatcacag gtggcggtgg ctcgggcggt    420
ggtgggtcgg gtggcggcgg atctcaggtg cagctgcagg agtcaggacc tggcctggtg    480
aaaccctcac agactctgtc cctgacatgc actgtctcag ggtctcatt acccgactat    540
ggtgtaagct ggattcgcca gcctccaggt aagggtctgg agtggctggg agtaatatgg    600
ggtagtgaaa ccacatacta taattcagct ctcaaatcca gactgaccat ctccaaggac    660
aactccaaga gccaagtttc cttaaaatta agtagtgtta ctgctgctga cacagccgtc    720
tactactgtg ccaaacatta ttactacggt ggtagctatg ctatggacta ctggggccaa    780
ggaacctcag tcaccgtctc ctcaaccacg acgccagcgc cgcgaccacc aacaccggcg    840
cccaccatcg cgtcgcagcc cctgtccctg cgcccagagg cgtgccggcc agcggcgggg    900
ggcgcagtgc acacgagggg gctggacttc gcctgtgata tctacatctg ggcgcccttg    960
gccgggactt gtggggtcct tctcctgtca ctggttatca ccctttactg ccggagggac   1020
cagaggctgc cccccgatgc ccacaagccc cctgggggag gcagtttccg gacccccatc   1080
caagaggagc aggccgacgc ccactccacc ctggccaaga tcagagtgaa gttcagcagg   1140
agcgcagacg cccccgcgta ccagcagggc cagaaccagc tctataacga gctcaatcta   1200
ggacgaagag aggagtacga tgttttggac aagagacgtg gccgggaccc tgagatgggg   1260
ggaaagccga gaaggaagaa ccctcaggaa ggcctgtaca atgaactgca gaaagataag   1320
atggcggagg cctacagtga gattgggatg aaaggcgagc gccggagggg caaggggcac   1380
gatggccttt accagggtct cagtacagcc accaaggaca cctacgacgc ccttcacatg   1440
caggccctgc cccctcgcgg ctctggcgag ggaaggggtt ccctgcttac ttgcggcgac   1500
gtcgaagaga atcccggtcc gatggccctc ccagtaactg ccctcctttt gcccctcgca   1560
ctccttcttc atgccgctcg ccccaactgg gtcaacgtga ttagcgattt gaagaaaatc   1620
gaggacctta tacagtctat gcatattgac gctacactgt atactgagag tgatgtacac   1680
ccgtcctgta aggtaacggc catgaaatgc tttcttctgg agctccaggt catcagcttg   1740
gagtctgggg acgcaagcat ccacgatacg gttgaaaacc tcatcatcct tgcgaacaac   1800
tctctctcat ctaatggaaa cgttacagag agtgggtgta aggagtgcga agagttggaa   1860
gaaaaaaaca tcaaagaatt tcttcaatcc ttcgttcaca tagtgcaaat gttcattaac   1920
acgtccacta ccacacccgc cccgaggcca cctacgccgg caccgactat cgccagtcaa   1980
cccctctctc tgcgccccga ggcttgccgg cctgcggctg gtggggcggt ccacacccgg   2040
ggcctggatt ttgcgtgcga tatatacatc tgggcacctc ttgccggcac ctgcggagtg   2100
```

ctgcttctct cactcgttat tacgctgtac tgctaagcgg ccgcgtcgac 2150

<210> SEQ ID NO 195
<211> LENGTH: 706
<212> TYPE: PRT
<213> ORGANISM: Homo sapiens
<220> FEATURE:
<221> NAME/KEY: MISC_FEATURE
<223> OTHER INFORMATION: AA NK19H-NF-6

<400> SEQUENCE: 195

Met Ala Leu Pro Val Thr Ala Leu Leu Leu Pro Leu Ala Leu Leu Leu
1 5 10 15

His Ala Ala Arg Pro Asp Ile Gln Met Thr Gln Ser Pro Ser Ser Leu
20 25 30

Ser Ala Ser Val Gly Asp Arg Val Thr Ile Thr Cys Arg Ala Ser Gln
35 40 45

Asp Ile Ser Lys Tyr Leu Asn Trp Tyr Gln Gln Lys Pro Asp Gly Thr
50 55 60

Val Lys Leu Leu Ile Tyr His Thr Ser Arg Leu His Ser Gly Val Pro
65 70 75 80

Ser Arg Phe Ser Gly Ser Gly Ser Gly Thr Asp Tyr Thr Leu Thr Ile
85 90 95

Ser Ser Leu Gln Pro Glu Asp Ile Ala Thr Tyr Phe Cys Gln Gln Gly
100 105 110

Asn Thr Leu Pro Tyr Thr Phe Gly Gly Gly Thr Lys Leu Glu Ile Thr
115 120 125

Gly Gly Gly Gly Ser Gly Gly Gly Gly Ser Gly Gly Gly Gly Ser Gln
130 135 140

Val Gln Leu Gln Glu Ser Gly Pro Gly Leu Val Lys Pro Ser Gln Thr
145 150 155 160

Leu Ser Leu Thr Cys Thr Val Ser Gly Val Ser Leu Pro Asp Tyr Gly
165 170 175

Val Ser Trp Ile Arg Gln Pro Pro Gly Lys Gly Leu Glu Trp Leu Gly
180 185 190

Val Ile Trp Gly Ser Glu Thr Thr Tyr Tyr Asn Ser Ala Leu Lys Ser
195 200 205

Arg Leu Thr Ile Ser Lys Asp Asn Ser Lys Ser Gln Val Ser Leu Lys
210 215 220

Leu Ser Ser Val Thr Ala Ala Asp Thr Ala Val Tyr Tyr Cys Ala Lys
225 230 235 240

His Tyr Tyr Tyr Gly Gly Ser Tyr Ala Met Asp Tyr Trp Gly Gln Gly
245 250 255

Thr Ser Val Thr Val Ser Ser Thr Thr Thr Pro Ala Pro Arg Pro Pro
260 265 270

Thr Pro Ala Pro Thr Ile Ala Ser Gln Pro Leu Ser Leu Arg Pro Glu
275 280 285

Ala Cys Arg Pro Ala Ala Gly Gly Ala Val His Thr Arg Gly Leu Asp
290 295 300

Phe Ala Cys Asp Ile Tyr Ile Trp Ala Pro Leu Ala Gly Thr Cys Gly
305 310 315 320

Val Leu Leu Leu Ser Leu Val Ile Thr Leu Tyr Cys Arg Arg Asp Gln
325 330 335

Arg Leu Pro Pro Asp Ala His Lys Pro Pro Gly Gly Gly Ser Phe Arg
340 345 350

-continued

```
Thr Pro Ile Gln Glu Glu Gln Ala Asp Ala His Ser Thr Leu Ala Lys
        355                 360                 365

Ile Arg Val Lys Phe Ser Arg Ser Ala Asp Ala Pro Ala Tyr Gln Gln
    370                 375                 380

Gly Gln Asn Gln Leu Tyr Asn Glu Leu Asn Leu Gly Arg Arg Glu Glu
385                 390                 395                 400

Tyr Asp Val Leu Asp Lys Arg Arg Gly Arg Asp Pro Glu Met Gly Gly
                405                 410                 415

Lys Pro Arg Arg Lys Asn Pro Gln Glu Gly Leu Tyr Asn Glu Leu Gln
            420                 425                 430

Lys Asp Lys Met Ala Glu Ala Tyr Ser Glu Ile Gly Met Lys Gly Glu
        435                 440                 445

Arg Arg Arg Gly Lys Gly His Asp Gly Leu Tyr Gln Gly Leu Ser Thr
    450                 455                 460

Ala Thr Lys Asp Thr Tyr Asp Ala Leu His Met Gln Ala Leu Pro Pro
465                 470                 475                 480

Arg Gly Ser Gly Glu Gly Arg Gly Ser Leu Leu Thr Cys Gly Asp Val
                485                 490                 495

Glu Glu Asn Pro Gly Pro Met Ala Leu Pro Val Thr Ala Leu Leu Leu
            500                 505                 510

Pro Leu Ala Leu Leu Leu His Ala Ala Arg Pro Asn Trp Val Asn Val
        515                 520                 525

Ile Ser Asp Leu Lys Lys Ile Glu Asp Leu Ile Gln Ser Met His Ile
    530                 535                 540

Asp Ala Thr Leu Tyr Thr Glu Ser Asp Val His Pro Ser Cys Lys Val
545                 550                 555                 560

Thr Ala Met Lys Cys Phe Leu Leu Glu Leu Gln Val Ile Ser Leu Glu
                565                 570                 575

Ser Gly Asp Ala Ser Ile His Asp Thr Val Glu Asn Leu Ile Ile Leu
            580                 585                 590

Ala Asn Asn Ser Leu Ser Ser Asn Gly Asn Val Thr Glu Ser Gly Cys
        595                 600                 605

Lys Glu Cys Glu Glu Leu Glu Glu Lys Asn Ile Lys Glu Phe Leu Gln
    610                 615                 620

Ser Phe Val His Ile Val Gln Met Phe Ile Asn Thr Ser Thr Thr Thr
625                 630                 635                 640

Pro Ala Pro Arg Pro Pro Thr Pro Ala Pro Thr Ile Ala Ser Gln Pro
                645                 650                 655

Leu Ser Leu Arg Pro Glu Ala Cys Arg Pro Ala Ala Gly Gly Ala Val
            660                 665                 670

His Thr Arg Gly Leu Asp Phe Ala Cys Asp Ile Tyr Ile Trp Ala Pro
        675                 680                 685

Leu Ala Gly Thr Cys Gly Val Leu Leu Leu Ser Leu Val Ile Thr Leu
    690                 695                 700

Tyr Cys
705
```

<210> SEQ ID NO 196
<211> LENGTH: 2150
<212> TYPE: DNA
<213> ORGANISM: Homo sapiens
<220> FEATURE:
<221> NAME/KEY: misc_feature
<223> OTHER INFORMATION: DNA NK19H-NF-7

<400> SEQUENCE: 196

-continued gaattcgccg ccaccatggc cttaccagtg accgccttgc tcctgccgct ggccttgctg 60
ctccacgccg ccaggccgga catccagatg acacagagcc cgtcctccct gtctgcctct 120
gtgggagaca gagtcaccat cacctgcagg gcaagtcagg acattagtaa atatttaaat 180
tggtatcagc agaaaccagg tggaactgtt aaactcctga tctaccatac atcaagatta 240
cactcaggag tcccatcaag gttcagtggc agtgggtctg gaacagattt caccctcacc 300
attagcagcc tgcaaccgga agatattgcc acttactact gccaacaggg taatacgctt 360
ccgtacacgt tcggaggggg gaccaagctg gagatcacag gtggcggtgg ctcgggcggt 420
ggtgggtcgg gtggcggcgg atctcaggtg cagctgcagg agtcaggacc tggcctggtg 480
aaaccctcac agactctgtc cgtgacatgc actgtctcag ggtctcatt acccgactat 540 ggtgtaagct ggattcgcca gcctccaggt aagggtctgg agtggctggg agtaatatgg 600
ggtagtgaaa ccacatacta taattcagct ctcaaatcca gactgaccat ctccaaggac 660
aactccaaga gccaagtttc cttaaaatta agtagtgtta ctgctgctga cacagccgtc 720
tactactgtg ccaaacatta ttactacggt ggtagctatg ctatggacta ctggggccaa 780
ggaacctcag tcaccgtctc ctcaaccacg acgccagcgc cgcgaccacc aacaccggcg 840
cccaccatcg cgtcgcagcc cctgtccctg cgcccagagg cgtgccggcc agcggcgggg 900
ggcgcagtgc acacgagggg gctggacttc gcctgtgata tctacatctg ggcgcccttg 960
gccgggactt gtggggtcct tctcctgtca ctggttatca ccctttactg ccggagggac 1020
cagaggctgc cccccgatgc ccacaagccc cctgggggag gcagtttccg gacccccatc 1080
caagaggagc aggccgacgc ccactccacc ctggccaaga tcagagtgaa gttcagcagg 1140
agcgcagacg cccccgcgta ccagcagggc cagaaccagc tctataacga gctcaatcta 1200
ggacgaagag aggagtacga tgttttggac aagagacgtg gccgggaccc tgagatgggg 1260
ggaaagccga gaaggaagaa ccctcaggaa ggcctgtaca atgaactgca gaaagataag 1320
atggcggagg cctacagtga gattgggatg aaaggcgagc gccggagggg caaggggcac 1380
gatggccttt accagggtct cagtacagcc accaaggaca cctacgacgc ccttcacatg 1440
caggccctgc cccctcgcgg ctctggcgag ggaaggggtt ccctgcttac ttgcggcgac 1500
gtcgaagaga atcccggtcc gatggccctc ccagtaactg ccctcctttt gcccctcgca 1560
ctccttcttc atgccgctcg ccccaactgg gtcaacgtga ttagcgattt gaagaaaatc 1620
gaggacctta tacagtctat gcatattgac gctacactgt atactgagag tgatgtacac 1680
ccgtcctgta aggtaacggc catgaaatgc tttcttctgg agctccaggt catcagcttg 1740
gagtctgggg acgcaagcat ccacgatacg gttgaaaacc tcatcatcct tgcgaacaac 1800
tctctctcat ctaatggaaa cgttacagag agtgggtgta aggagtgcga agagttggaa 1860
gaaaaaaaca tcaaagaatt tcttcaatcc ttcgttcaca tagtgcaaat gttcattaac 1920
acgtccacta ccacacccgc cccgaggcca cctacgccgg caccgactat cgccagtcaa 1980
cccctctctc tgcgccccga ggcttgccgg cctgcggctg gtggggcggt ccacacccgg 2040
ggcctggatt ttgcgtgcga tatatacatc tgggcacctc ttgccggcac ctgcggagtg 2100
ctgcttctct cactcgttat tacgctgtac tgctaagcgg ccgcgtcgac 2150

<210> SEQ ID NO 197
<211> LENGTH: 706
<212> TYPE: PRT
<213> ORGANISM: Homo sapiens
<220> FEATURE:

```
<221> NAME/KEY: MISC_FEATURE
<223> OTHER INFORMATION: AA NK19H-NF-7

<400> SEQUENCE: 197

Met Ala Leu Pro Val Thr Ala Leu Leu Leu Pro Leu Ala Leu Leu Leu
1               5                   10                  15

His Ala Ala Arg Pro Asp Ile Gln Met Thr Gln Ser Pro Ser Ser Leu
            20                  25                  30

Ser Ala Ser Val Gly Asp Arg Val Thr Ile Thr Cys Arg Ala Ser Gln
        35                  40                  45

Asp Ile Ser Lys Tyr Leu Asn Trp Tyr Gln Gln Lys Pro Gly Gly Thr
    50                  55                  60

Val Lys Leu Leu Ile Tyr His Thr Ser Arg Leu His Ser Gly Val Pro
65                  70                  75                  80

Ser Arg Phe Ser Gly Ser Gly Ser Gly Thr Asp Phe Thr Leu Thr Ile
                85                  90                  95

Ser Ser Leu Gln Pro Glu Asp Ile Ala Thr Tyr Tyr Cys Gln Gln Gly
            100                 105                 110

Asn Thr Leu Pro Tyr Thr Phe Gly Gly Gly Thr Lys Leu Glu Ile Thr
        115                 120                 125

Gly Gly Gly Gly Ser Gly Gly Gly Gly Ser Gly Gly Gly Gly Ser Gln
    130                 135                 140

Val Gln Leu Gln Glu Ser Gly Pro Gly Leu Val Lys Pro Ser Gln Thr
145                 150                 155                 160

Leu Ser Val Thr Cys Thr Val Ser Gly Val Ser Leu Pro Asp Tyr Gly
                165                 170                 175

Val Ser Trp Ile Arg Gln Pro Pro Gly Lys Gly Leu Glu Trp Leu Gly
            180                 185                 190

Val Ile Trp Gly Ser Glu Thr Thr Tyr Tyr Asn Ser Ala Leu Lys Ser
        195                 200                 205

Arg Leu Thr Ile Ser Lys Asp Asn Ser Lys Ser Gln Val Ser Leu Lys
    210                 215                 220

Leu Ser Ser Val Thr Ala Ala Asp Thr Ala Val Tyr Tyr Cys Ala Lys
225                 230                 235                 240

His Tyr Tyr Tyr Gly Gly Ser Tyr Ala Met Asp Tyr Trp Gly Gln Gly
                245                 250                 255

Thr Ser Val Thr Val Ser Ser Thr Thr Thr Pro Ala Pro Arg Pro Pro
            260                 265                 270

Thr Pro Ala Pro Thr Ile Ala Ser Gln Pro Leu Ser Leu Arg Pro Glu
        275                 280                 285

Ala Cys Arg Pro Ala Ala Gly Gly Ala Val His Thr Arg Gly Leu Asp
    290                 295                 300

Phe Ala Cys Asp Ile Tyr Ile Trp Ala Pro Leu Ala Gly Thr Cys Gly
305                 310                 315                 320

Val Leu Leu Leu Ser Leu Val Ile Thr Leu Tyr Cys Arg Arg Asp Gln
                325                 330                 335

Arg Leu Pro Pro Asp Ala His Lys Pro Pro Gly Gly Gly Ser Phe Arg
            340                 345                 350

Thr Pro Ile Gln Glu Glu Gln Ala Asp Ala His Ser Thr Leu Ala Lys
        355                 360                 365

Ile Arg Val Lys Phe Ser Arg Ser Ala Asp Ala Pro Ala Tyr Gln Gln
    370                 375                 380

Gly Gln Asn Gln Leu Tyr Asn Glu Leu Asn Leu Gly Arg Arg Glu Glu
385                 390                 395                 400
```

-continued

```
Tyr Asp Val Leu Asp Lys Arg Arg Gly Arg Asp Pro Glu Met Gly Gly
                405                 410                 415

Lys Pro Arg Arg Lys Asn Pro Gln Glu Gly Leu Tyr Asn Glu Leu Gln
            420                 425                 430

Lys Asp Lys Met Ala Glu Ala Tyr Ser Glu Ile Gly Met Lys Gly Glu
        435                 440                 445

Arg Arg Arg Gly Lys Gly His Asp Gly Leu Tyr Gln Gly Leu Ser Thr
    450                 455                 460

Ala Thr Lys Asp Thr Tyr Asp Ala Leu His Met Gln Ala Leu Pro Pro
465                 470                 475                 480

Arg Gly Ser Gly Glu Gly Arg Gly Ser Leu Leu Thr Cys Gly Asp Val
                485                 490                 495

Glu Glu Asn Pro Gly Pro Met Ala Leu Pro Val Thr Ala Leu Leu Leu
            500                 505                 510

Pro Leu Ala Leu Leu Leu His Ala Ala Arg Pro Asn Trp Val Asn Val
        515                 520                 525

Ile Ser Asp Leu Lys Lys Ile Glu Asp Leu Ile Gln Ser Met His Ile
    530                 535                 540

Asp Ala Thr Leu Tyr Thr Glu Ser Asp Val His Pro Ser Cys Lys Val
545                 550                 555                 560

Thr Ala Met Lys Cys Phe Leu Leu Glu Leu Gln Val Ile Ser Leu Glu
                565                 570                 575

Ser Gly Asp Ala Ser Ile His Asp Thr Val Glu Asn Leu Ile Ile Leu
            580                 585                 590

Ala Asn Asn Ser Leu Ser Ser Asn Gly Asn Val Thr Glu Ser Gly Cys
        595                 600                 605

Lys Glu Cys Glu Glu Leu Glu Glu Lys Asn Ile Lys Glu Phe Leu Gln
    610                 615                 620

Ser Phe Val His Ile Val Gln Met Phe Ile Asn Thr Ser Thr Thr Thr
625                 630                 635                 640

Pro Ala Pro Arg Pro Pro Thr Pro Ala Pro Thr Ile Ala Ser Gln Pro
                645                 650                 655

Leu Ser Leu Arg Pro Glu Ala Cys Arg Pro Ala Ala Gly Gly Ala Val
            660                 665                 670

His Thr Arg Gly Leu Asp Phe Ala Cys Asp Ile Tyr Ile Trp Ala Pro
        675                 680                 685

Leu Ala Gly Thr Cys Gly Val Leu Leu Leu Ser Leu Val Ile Thr Leu
    690                 695                 700

Tyr Cys
705
```

<210> SEQ ID NO 198
<211> LENGTH: 2150
<212> TYPE: DNA
<213> ORGANISM: Homo sapiens
<220> FEATURE:
<221> NAME/KEY: misc_feature
<223> OTHER INFORMATION: DNA NK19H-NF-8

<400> SEQUENCE: 198

```
gaattcgccg ccaccatggc cttaccagtg accgccttgc tcctgccgct ggccttgctg     60

ctccacgccg ccaggccgga catccagatg acacagagcc cgtcctccct gtctgcctct    120

gtgggagaca gagtcaccat cacctgcagg gcaagtcagg acattagtaa atatttaaat    180

tggtatcagc agaaaccagg tggaactgtt aaactcctga tctaccatac atcaagatta    240
```

cactcaggag tcccatcaag gttcagtggc agtgggtctg gaacagattt caccctcacc 300
attagcagcc tgcaaccgga agatattgcc acttacttct gccaacaggg taatacgctt 360
ccgtacacgt tcggaggggg gaccaagctg gagatcacag gtggcggtgg ctcgggcggt 420
ggtgggtcgg gtggcggcgg atctcaggtg cagctgcagg agtcaggacc tggcctggtg 480
aaaccctcac agactctgtc cgtgacatgc actgtctcag ggtctcatt acccgactat 540 ggtgtaagct ggattcgcca gcctccaggt aagggtctgg agtggctggg agtaatatgg 600
ggtagtgaaa ccacatacta taattcagct ctcaaatcca gactgaccat ctccaaggac 660
aactccaaga gccaagtttc cttaaaatta agtagtgtta ctgctgctga cacagccgtc 720
tactactgtg ccaaacatta ttactacggt ggtagctatg ctatggacta ctggggccaa 780
ggaacctcag tcaccgtctc ctcaaccacg acgccagcgc cgcgaccacc aacaccggcg 840
cccaccatcg cgtcgcagcc cctgtccctg cgcccagagg cgtgccggcc agcggcgggg 900
ggcgcagtgc acacgagggg gctggacttc gcctgtgata tctacatctg ggcgcccttg 960
gccgggactt gtggggtcct tctcctgtca ctggttatca ccctttactg ccggagggac 1020
cagaggctgc cccccgatgc ccacaagccc cctgggggag gcagtttccg gacccccatc 1080
caagaggagc aggccgacgc ccactccacc ctggccaaga tcagagtgaa gttcagcagg 1140
agcgcagacg cccccgcgta ccagcagggc cagaaccagc tctataacga gctcaatcta 1200
ggacgaagag aggagtacga tgttttggac aagagacgtg gccgggaccc tgagatgggg 1260
ggaaagccga gaaggaagaa ccctcaggaa ggcctgtaca atgaactgca gaaagataag 1320
atggcggagg cctacagtga gattgggatg aaaggcgagc gccggagggg caaggggcac 1380
gatggccttt accagggtct cagtacagcc accaaggaca cctacgacgc ccttcacatg 1440
caggccctgc cccctcgcgg ctctggcgag ggaaggggtt ccctgcttac ttgcggcgac 1500
gtcgaagaga atcccggtcc gatggccctc ccagtaactg ccctcctttt gcccctcgca 1560
ctccttcttc atgccgctcg ccccaactgg gtcaacgtga ttagcgattt gaagaaaatc 1620
gaggacctta tacagtctat gcatattgac gctacactgt atactgagag tgatgtacac 1680
ccgtcctgta aggtaacggc catgaaatgc tttcttctgg agctccaggt catcagcttg 1740
gagtctgggg acgcaagcat ccacgatacg gttgaaaacc tcatcatcct tgcgaacaac 1800
tctctctcat ctaatggaaa cgttacagag agtgggtgta aggagtgcga agagttggaa 1860
gaaaaaaaca tcaaagaatt tcttcaatcc ttcgttcaca tagtgcaaat gttcattaac 1920
acgtccacta ccacacccgc cccgaggcca cctacgccgg caccgactat cgccagtcaa 1980
cccctctctc tgcgccccga ggcttgccgg cctgcggctg gtggggcggt ccacacccgg 2040
ggcctggatt ttgcgtgcga tatatacatc tgggcacctc ttgccggcac ctgcggagtg 2100
ctgcttctct cactcgttat tacgctgtac tgctaagcgg ccgcgtcgac 2150

<210> SEQ ID NO 199
<211> LENGTH: 706
<212> TYPE: PRT
<213> ORGANISM: Homo sapiens
<220> FEATURE:
<221> NAME/KEY: MISC_FEATURE
<223> OTHER INFORMATION: AA NK19H-NF-8

<400> SEQUENCE: 199

Met Ala Leu Pro Val Thr Ala Leu Leu Leu Pro Leu Ala Leu Leu Leu
1 5 10 15

-continued

```
His Ala Ala Arg Pro Asp Ile Gln Met Thr Gln Ser Pro Ser Ser Leu
            20                  25                  30

Ser Ala Ser Val Gly Asp Arg Val Thr Ile Thr Cys Arg Ala Ser Gln
        35                  40                  45

Asp Ile Ser Lys Tyr Leu Asn Trp Tyr Gln Gln Lys Pro Gly Gly Thr
    50                  55                  60

Val Lys Leu Leu Ile Tyr His Thr Ser Arg Leu His Ser Gly Val Pro
65                  70                  75                  80

Ser Arg Phe Ser Gly Ser Gly Ser Gly Thr Asp Phe Thr Leu Thr Ile
                85                  90                  95

Ser Ser Leu Gln Pro Glu Asp Ile Ala Thr Tyr Phe Cys Gln Gln Gly
            100                 105                 110

Asn Thr Leu Pro Tyr Thr Phe Gly Gly Gly Thr Lys Leu Glu Ile Thr
        115                 120                 125

Gly Gly Gly Gly Ser Gly Gly Gly Gly Ser Gly Gly Gly Gly Ser Gln
    130                 135                 140

Val Gln Leu Gln Glu Ser Gly Pro Gly Leu Val Lys Pro Ser Gln Thr
145                 150                 155                 160

Leu Ser Val Thr Cys Thr Val Ser Gly Val Ser Leu Pro Asp Tyr Gly
                165                 170                 175

Val Ser Trp Ile Arg Gln Pro Pro Gly Lys Gly Leu Glu Trp Leu Gly
            180                 185                 190

Val Ile Trp Gly Ser Glu Thr Thr Tyr Tyr Asn Ser Ala Leu Lys Ser
        195                 200                 205

Arg Leu Thr Ile Ser Lys Asp Asn Ser Lys Ser Gln Val Ser Leu Lys
    210                 215                 220

Leu Ser Ser Val Thr Ala Ala Asp Thr Ala Val Tyr Tyr Cys Ala Lys
225                 230                 235                 240

His Tyr Tyr Tyr Gly Gly Ser Tyr Ala Met Asp Tyr Trp Gly Gln Gly
                245                 250                 255

Thr Ser Val Thr Val Ser Ser Thr Thr Thr Pro Ala Pro Arg Pro Pro
            260                 265                 270

Thr Pro Ala Pro Thr Ile Ala Ser Gln Pro Leu Ser Leu Arg Pro Glu
        275                 280                 285

Ala Cys Arg Pro Ala Ala Gly Gly Ala Val His Thr Arg Gly Leu Asp
    290                 295                 300

Phe Ala Cys Asp Ile Tyr Ile Trp Ala Pro Leu Ala Gly Thr Cys Gly
305                 310                 315                 320

Val Leu Leu Leu Ser Leu Val Ile Thr Leu Tyr Cys Arg Arg Asp Gln
                325                 330                 335

Arg Leu Pro Pro Asp Ala His Lys Pro Pro Gly Gly Gly Ser Phe Arg
            340                 345                 350

Thr Pro Ile Gln Glu Glu Gln Ala Asp Ala His Ser Thr Leu Ala Lys
        355                 360                 365

Ile Arg Val Lys Phe Ser Arg Ser Ala Asp Ala Pro Ala Tyr Gln Gln
    370                 375                 380

Gly Gln Asn Gln Leu Tyr Asn Glu Leu Asn Leu Gly Arg Arg Glu Glu
385                 390                 395                 400

Tyr Asp Val Leu Asp Lys Arg Arg Gly Arg Asp Pro Glu Met Gly Gly
                405                 410                 415

Lys Pro Arg Arg Lys Asn Pro Gln Glu Gly Leu Tyr Asn Glu Leu Gln
            420                 425                 430

Lys Asp Lys Met Ala Glu Ala Tyr Ser Glu Ile Gly Met Lys Gly Glu
```

-continued

```
        435                 440                 445

Arg Arg Arg Gly Lys Gly His Asp Gly Leu Tyr Gln Gly Leu Ser Thr
    450                 455                 460

Ala Thr Lys Asp Thr Tyr Asp Ala Leu His Met Gln Ala Leu Pro Pro
465                 470                 475                 480

Arg Gly Ser Gly Glu Gly Arg Gly Ser Leu Leu Thr Cys Gly Asp Val
                485                 490                 495

Glu Glu Asn Pro Gly Pro Met Ala Leu Pro Val Thr Ala Leu Leu Leu
            500                 505                 510

Pro Leu Ala Leu Leu Leu His Ala Ala Arg Pro Asn Trp Val Asn Val
        515                 520                 525

Ile Ser Asp Leu Lys Lys Ile Glu Asp Leu Ile Gln Ser Met His Ile
    530                 535                 540

Asp Ala Thr Leu Tyr Thr Glu Ser Asp Val His Pro Ser Cys Lys Val
545                 550                 555                 560

Thr Ala Met Lys Cys Phe Leu Leu Glu Leu Gln Val Ile Ser Leu Glu
                565                 570                 575

Ser Gly Asp Ala Ser Ile His Asp Thr Val Glu Asn Leu Ile Ile Leu
            580                 585                 590

Ala Asn Asn Ser Leu Ser Ser Asn Gly Asn Val Thr Glu Ser Gly Cys
        595                 600                 605

Lys Glu Cys Glu Glu Leu Glu Glu Lys Asn Ile Lys Glu Phe Leu Gln
    610                 615                 620

Ser Phe Val His Ile Val Gln Met Phe Ile Asn Thr Ser Thr Thr Thr
625                 630                 635                 640

Pro Ala Pro Arg Pro Pro Thr Pro Ala Pro Thr Ile Ala Ser Gln Pro
                645                 650                 655

Leu Ser Leu Arg Pro Glu Ala Cys Arg Pro Ala Ala Gly Gly Ala Val
            660                 665                 670

His Thr Arg Gly Leu Asp Phe Ala Cys Asp Ile Tyr Ile Trp Ala Pro
        675                 680                 685

Leu Ala Gly Thr Cys Gly Val Leu Leu Leu Ser Leu Val Ile Thr Leu
    690                 695                 700

Tyr Cys
705
```

<210> SEQ ID NO 200
<211> LENGTH: 2150
<212> TYPE: DNA
<213> ORGANISM: Homo sapiens
<220> FEATURE:
<221> NAME/KEY: misc_feature
<223> OTHER INFORMATION: DNA NK19H-NF-9

<400> SEQUENCE: 200

```
gaattcgccg ccaccatggc cttaccagtg accgccttgc tcctgccgct ggccttgctg     60

ctccacgccg ccaggccgga catccagatg acacagagcc cgtcctccct gtctgcctct    120

gtgggagaca gagtcaccat cacctgcagg gcaagtcagg acattagtaa atatttaaat    180

tggtatcagc agaaaccaga cggaactgtt aaactcctga tctaccatac atcaagatta    240

cactcaggag tcccatcaag gttcagtggc agtgggtctg gaacagatta caccctcacc    300

attagcagcc tgcaaccgga agatattgcc acttacttct gccaacaggg taatacgctt    360

ccgtacacgt tcggaggggg gaccaagctg gagatcacag gtggcggtgg ctcgggcggt    420

ggtgggtcgg gtggcggcgg atctcaggtg cagctgcagg agtcaggacc tggcctggtg    480
```

aaaccctcac agactctgtc cgtgacatgc actgtctcag gggtctcatt acccgactat 540
ggtgtaagct ggattcgcca gcctccaggt aagggtctgg agtggctggg agtaatatgg 600
ggtagtgaaa ccacatacta taattcagct ctcaaatcca gactgaccat ctccaaggac 660
aactccaaga gccaagtttc cttaaaatta agtagtgtta ctgctgctga cacagccgtc 720
tactactgtg ccaaacatta ttactacggt ggtagctatg ctatggacta ctggggccaa 780
ggaacctcag tcaccgtctc ctcaaccacg acgccagcgc cgcgaccacc aacaccggcg 840
cccaccatcg cgtcgcagcc cctgtccctg cgcccagagg cgtgccggcc agcggcgggg 900
ggcgcagtgc acacgagggg gctggacttc gcctgtgata tctacatctg ggcgcccttg 960
gccgggactt gtggggtcct tctcctgtca ctggttatca ccctttactg ccggagggac 1020
cagaggctgc cccccgatgc ccacaagccc cctgggggag gcagtttccg gacccccatc 1080
caagaggagc aggccgacgc ccactccacc ctggccaaga tcagagtgaa gttcagcagg 1140
agcgcagacg cccccgcgta ccagcagggc cagaaccagc tctataacga gctcaatcta 1200
ggacgaagag aggagtacga tgttttggac aagagacgtg gccgggaccc tgagatgggg 1260
ggaaagccga gaaggaagaa ccctcaggaa ggcctgtaca atgaactgca gaaagataag 1320
atggcggagg cctacagtga gattgggatg aaaggcgagc gccggagggg caaggggcac 1380
gatggccttt accagggtct cagtacagcc accaaggaca cctacgacgc ccttcacatg 1440
caggccctgc cccctcgcgg ctctggcgag ggaaggggtt ccctgcttac ttgcggcgac 1500
gtcgaagaga atcccggtcc gatggccctc ccagtaactg ccctcctttt gccccctcgca 1560 ctccttcttc atgccgctcg ccccaactgg gtcaacgtga ttagcgattt gaagaaaatc 1620
gaggacctta tacagtctat gcatattgac gctacactgt atactgagag tgatgtacac 1680
ccgtcctgta aggtaacggc catgaaatgc tttcttctgg agctccaggt catcagcttg 1740
gagtctgggg acgcaagcat ccacgatacg gttgaaaacc tcatcatcct tgcgaacaac 1800
tctctctcat ctaatggaaa cgttacagag agtgggtgta aggagtgcga agagttggaa 1860
gaaaaaaaca tcaaagaatt tcttcaatcc ttcgttcaca tagtgcaaat gttcattaac 1920
acgtccacta ccacacccgc cccgaggcca cctacgccgg caccgactat cgccagtcaa 1980
cccctctctc tgcgccccga ggcttgccgg cctgcggctg gtggggcggt ccacacccgg 2040
ggcctggatt ttgcgtgcga tatatacatc tgggcacctc ttgccggcac ctgcggagtg 2100
ctgcttctct cactcgttat tacgctgtac tgctaagcgg ccgcgtcgac 2150

<210> SEQ ID NO 201
<211> LENGTH: 706
<212> TYPE: PRT
<213> ORGANISM: Homo sapiens
<220> FEATURE:
<221> NAME/KEY: MISC_FEATURE
<223> OTHER INFORMATION: AA NK19H-NF-9

<400> SEQUENCE: 201

Met Ala Leu Pro Val Thr Ala Leu Leu Leu Pro Leu Ala Leu Leu Leu
1 5 10 15

His Ala Ala Arg Pro Asp Ile Gln Met Thr Gln Ser Pro Ser Ser Leu
20 25 30

Ser Ala Ser Val Gly Asp Arg Val Thr Ile Thr Cys Arg Ala Ser Gln
35 40 45

Asp Ile Ser Lys Tyr Leu Asn Trp Tyr Gln Gln Lys Pro Asp Gly Thr
50 55 60

Val Lys Leu Leu Ile Tyr His Thr Ser Arg Leu His Ser Gly Val Pro
65 70 75 80

Ser Arg Phe Ser Gly Ser Gly Ser Gly Thr Asp Tyr Thr Leu Thr Ile
85 90 95

Ser Ser Leu Gln Pro Glu Asp Ile Ala Thr Tyr Phe Cys Gln Gln Gly
100 105 110

Asn Thr Leu Pro Tyr Thr Phe Gly Gly Gly Thr Lys Leu Glu Ile Thr
115 120 125

Gly Gly Gly Gly Ser Gly Gly Gly Gly Ser Gly Gly Gly Gly Ser Gln
130 135 140

Val Gln Leu Gln Glu Ser Gly Pro Gly Leu Val Lys Pro Ser Gln Thr
145 150 155 160

Leu Ser Val Thr Cys Thr Val Ser Gly Val Ser Leu Pro Asp Tyr Gly
165 170 175

Val Ser Trp Ile Arg Gln Pro Pro Gly Lys Gly Leu Glu Trp Leu Gly
180 185 190

Val Ile Trp Gly Ser Glu Thr Thr Tyr Tyr Asn Ser Ala Leu Lys Ser
195 200 205

Arg Leu Thr Ile Ser Lys Asp Asn Ser Lys Ser Gln Val Ser Leu Lys
210 215 220

Leu Ser Ser Val Thr Ala Ala Asp Thr Ala Val Tyr Tyr Cys Ala Lys
225 230 235 240

His Tyr Tyr Tyr Gly Gly Ser Tyr Ala Met Asp Tyr Trp Gly Gln Gly
245 250 255

Thr Ser Val Thr Val Ser Ser Thr Thr Thr Pro Ala Pro Arg Pro Pro
260 265 270

Thr Pro Ala Pro Thr Ile Ala Ser Gln Pro Leu Ser Leu Arg Pro Glu
275 280 285

Ala Cys Arg Pro Ala Ala Gly Gly Ala Val His Thr Arg Gly Leu Asp
290 295 300

Phe Ala Cys Asp Ile Tyr Ile Trp Ala Pro Leu Ala Gly Thr Cys Gly
305 310 315 320

Val Leu Leu Leu Ser Leu Val Ile Thr Leu Tyr Cys Arg Arg Asp Gln
325 330 335

Arg Leu Pro Pro Asp Ala His Lys Pro Pro Gly Gly Gly Ser Phe Arg
340 345 350

Thr Pro Ile Gln Glu Glu Gln Ala Asp Ala His Ser Thr Leu Ala Lys
355 360 365

Ile Arg Val Lys Phe Ser Arg Ser Ala Asp Ala Pro Ala Tyr Gln Gln
370 375 380

Gly Gln Asn Gln Leu Tyr Asn Glu Leu Asn Leu Gly Arg Arg Glu Glu
385 390 395 400

Tyr Asp Val Leu Asp Lys Arg Arg Gly Arg Asp Pro Glu Met Gly Gly
405 410 415

Lys Pro Arg Arg Lys Asn Pro Gln Glu Gly Leu Tyr Asn Glu Leu Gln
420 425 430

Lys Asp Lys Met Ala Glu Ala Tyr Ser Glu Ile Gly Met Lys Gly Glu
435 440 445

Arg Arg Arg Gly Lys Gly His Asp Gly Leu Tyr Gln Gly Leu Ser Thr
450 455 460

Ala Thr Lys Asp Thr Tyr Asp Ala Leu His Met Gln Ala Leu Pro Pro
465 470 475 480

-continued

```
Arg Gly Ser Gly Glu Gly Arg Gly Ser Leu Leu Thr Cys Gly Asp Val
                485                 490                 495

Glu Glu Asn Pro Gly Pro Met Ala Leu Pro Val Thr Ala Leu Leu Leu
            500                 505                 510

Pro Leu Ala Leu Leu Leu His Ala Ala Arg Pro Asn Trp Val Asn Val
        515                 520                 525

Ile Ser Asp Leu Lys Lys Ile Glu Asp Leu Ile Gln Ser Met His Ile
    530                 535                 540

Asp Ala Thr Leu Tyr Thr Glu Ser Asp Val His Pro Ser Cys Lys Val
545                 550                 555                 560

Thr Ala Met Lys Cys Phe Leu Leu Glu Leu Gln Val Ile Ser Leu Glu
                565                 570                 575

Ser Gly Asp Ala Ser Ile His Asp Thr Val Glu Asn Leu Ile Ile Leu
            580                 585                 590

Ala Asn Asn Ser Leu Ser Ser Asn Gly Asn Val Thr Glu Ser Gly Cys
        595                 600                 605

Lys Glu Cys Glu Glu Leu Glu Glu Lys Asn Ile Lys Glu Phe Leu Gln
    610                 615                 620

Ser Phe Val His Ile Val Gln Met Phe Ile Asn Thr Ser Thr Thr Thr
625                 630                 635                 640

Pro Ala Pro Arg Pro Pro Thr Pro Ala Pro Thr Ile Ala Ser Gln Pro
                645                 650                 655

Leu Ser Leu Arg Pro Glu Ala Cys Arg Pro Ala Ala Gly Gly Ala Val
            660                 665                 670

His Thr Arg Gly Leu Asp Phe Ala Cys Asp Ile Tyr Ile Trp Ala Pro
        675                 680                 685

Leu Ala Gly Thr Cys Gly Val Leu Leu Leu Ser Leu Val Ile Thr Leu
    690                 695                 700

Tyr Cys
705
```

<210> SEQ ID NO 202
<211> LENGTH: 2150
<212> TYPE: DNA
<213> ORGANISM: Homo sapiens
<220> FEATURE:
<221> NAME/KEY: misc_feature
<223> OTHER INFORMATION: DNA NK19H-NF-10

<400> SEQUENCE: 202

```
gaattcgccg ccaccatggc cttaccagtg accgccttgc tcctgccgct ggccttgctg      60

ctccacgccg ccaggccgga tattcagatg acccagagcc cgagcagcct gagcgcgagc     120

gtgggcgatc gcgtgaccat tacctgccgc gcgagccagg atattagcaa atatctgaac     180

tggtatcagc agaaaccggg cggcaccgtg aaactgctga tttatcatac cagccgcctg     240

catagcggcg tgccgagccg ctttagcggc agcggcagcg gcaccgattt taccctgacc     300

attagcagcc tgcagccgga agatattgcg acctattatt gccagcaggg caacaccctg     360

ccgtatacct ttggcggcgg caccaaactg gaaattaccg gtggcggtgg ctcgggcggt     420

ggtgggtcgg gtggcggcgg atctcaggtg cagctgcagg aaagcggccc gggcctggtg     480

aaaccgagcc agaccctgag cgtgacctgc accgtgagcg gcgtgagcct gccggattat     540

ggcgtgagct ggattcgcca gccgccgcgc aaaggcctgg aatggctggg cgtgatttgg     600

ggcagcgaaa ccacctatta taacagcgcg ctgaaaagcc gcctgaccat tagcaaagat     660

aacagcaaaa gccaggtgag cctgaaaatg agcagcgtga ccgcggcgga taccgcgatt     720
```

tattattgcg cgaaacatta ttattatggc ggcagctatg cgatggatta ttggggccag 780
ggcaccagcg tgaccgtgag cagcaccacg acgccagcgc cgcgaccacc aacaccggcg 840
cccaccatcg cgtcgcagcc cctgtccctg cgcccagagg cgtgccggcc agcggcgggg 900
ggcgcagtgc acacgagggg gctggacttc gcctgtgata tctacatctg ggcgcccttg 960
gccgggactt gtggggtcct tctcctgtca ctggttatca ccctttactg ccggagggac 1020
cagaggctgc cccccgatgc ccacaagccc cctgggggag gcagtttccg gacccccatc 1080
caagaggagc aggccgacgc ccactccacc ctggccaaga tcagagtgaa gttcagcagg 1140
agcgcagacg cccccgcgta ccagcagggc cagaaccagc tctataacga gctcaatcta 1200
ggacgaagag aggagtacga tgttttggac aagagacgtg gccgggaccc tgagatgggg 1260
ggaaagccga gaaggaagaa ccctcaggaa ggcctgtaca atgaactgca gaaagataag 1320
atggcggagg cctacagtga gattgggatg aaaggcgagc gccggagggg caaggggcac 1380
gatggccttt accagggtct cagtacagcc accaaggaca cctacgacgc ccttcacatg 1440
caggccctgc cccctcgcgg ctctggcgag ggaaggggtt ccctgcttac ttgcggcgac 1500
gtcgaagaga atcccggtcc gatggccctc ccagtaactg ccctcctttt gcccctcgca 1560
ctccttcttc atgccgctcg ccccaactgg gtcaacgtga ttagcgattt gaagaaaatc 1620
gaggacctta tacagtctat gcatattgac gctacactgt atactgagag tgatgtacac 1680
ccgtcctgta aggtaacggc catgaaatgc tttcttctgg agctccaggt catcagcttg 1740
gagtctgggg acgcaagcat ccacgatacg gttgaaaacc tcatcatcct tgcgaacaac 1800
tctctctcat ctaatggaaa cgttacagag agtgggtgta aggagtgcga agagttggaa 1860
gaaaaaaaca tcaaagaatt tcttcaatcc ttcgttcaca tagtgcaaat gttcattaac 1920
acgtccacta ccacacccgc cccgaggcca cctacgccgg caccgactat cgccagtcaa 1980
cccctctctc tgcgccccga ggcttgccgg cctgcggctg gtggggcggt ccacacccgg 2040
ggcctggatt ttgcgtgcga tatatacatc tgggcacctc ttgccggcac ctgcggagtg 2100
ctgcttctct cactcgttat tacgctgtac tgctaagcgg ccgcgtcgac 2150

<210> SEQ ID NO 203
<211> LENGTH: 706
<212> TYPE: PRT
<213> ORGANISM: Homo sapiens
<220> FEATURE:
<221> NAME/KEY: MISC_FEATURE
<223> OTHER INFORMATION: AA NK19H-NF-10

<400> SEQUENCE: 203

Met Ala Leu Pro Val Thr Ala Leu Leu Leu Pro Leu Ala Leu Leu Leu
1               5                   10                  15

His Ala Ala Arg Pro Asp Ile Gln Met Thr Gln Ser Pro Ser Ser Leu
            20                  25                  30

Ser Ala Ser Val Gly Asp Arg Val Thr Ile Thr Cys Arg Ala Ser Gln
        35                  40                  45

Asp Ile Ser Lys Tyr Leu Asn Trp Tyr Gln Gln Lys Pro Gly Gly Thr
    50                  55                  60

Val Lys Leu Leu Ile Tyr His Thr Ser Arg Leu His Ser Gly Val Pro
65                  70                  75                  80

Ser Arg Phe Ser Gly Ser Gly Ser Gly Thr Asp Phe Thr Leu Thr Ile
                85                  90                  95

Ser Ser Leu Gln Pro Glu Asp Ile Ala Thr Tyr Tyr Cys Gln Gln Gly

```
            100                 105                 110

Asn Thr Leu Pro Tyr Thr Phe Gly Gly Gly Thr Lys Leu Glu Ile Thr
        115                 120                 125

Gly Gly Gly Gly Ser Gly Gly Gly Gly Ser Gly Gly Gly Gly Ser Gln
    130                 135                 140

Val Gln Leu Gln Glu Ser Gly Pro Gly Leu Val Lys Pro Ser Gln Thr
145                 150                 155                 160

Leu Ser Val Thr Cys Thr Val Ser Gly Val Ser Leu Pro Asp Tyr Gly
                165                 170                 175

Val Ser Trp Ile Arg Gln Pro Pro Arg Lys Gly Leu Glu Trp Leu Gly
            180                 185                 190

Val Ile Trp Gly Ser Glu Thr Thr Tyr Tyr Asn Ser Ala Leu Lys Ser
        195                 200                 205

Arg Leu Thr Ile Ser Lys Asp Asn Ser Lys Ser Gln Val Ser Leu Lys
    210                 215                 220

Met Ser Ser Val Thr Ala Ala Asp Thr Ala Ile Tyr Tyr Cys Ala Lys
225                 230                 235                 240

His Tyr Tyr Tyr Gly Gly Ser Tyr Ala Met Asp Tyr Trp Gly Gln Gly
                245                 250                 255

Thr Ser Val Thr Val Ser Ser Thr Thr Thr Pro Ala Pro Arg Pro Pro
            260                 265                 270

Thr Pro Ala Pro Thr Ile Ala Ser Gln Pro Leu Ser Leu Arg Pro Glu
        275                 280                 285

Ala Cys Arg Pro Ala Ala Gly Gly Ala Val His Thr Arg Gly Leu Asp
    290                 295                 300

Phe Ala Cys Asp Ile Tyr Ile Trp Ala Pro Leu Ala Gly Thr Cys Gly
305                 310                 315                 320

Val Leu Leu Leu Ser Leu Val Ile Thr Leu Tyr Cys Arg Arg Asp Gln
                325                 330                 335

Arg Leu Pro Pro Asp Ala His Lys Pro Pro Gly Gly Gly Ser Phe Arg
            340                 345                 350

Thr Pro Ile Gln Glu Glu Gln Ala Asp Ala His Ser Thr Leu Ala Lys
        355                 360                 365

Ile Arg Val Lys Phe Ser Arg Ser Ala Asp Ala Pro Ala Tyr Gln Gln
    370                 375                 380

Gly Gln Asn Gln Leu Tyr Asn Glu Leu Asn Leu Gly Arg Arg Glu Glu
385                 390                 395                 400

Tyr Asp Val Leu Asp Lys Arg Arg Gly Arg Asp Pro Glu Met Gly Gly
                405                 410                 415

Lys Pro Arg Arg Lys Asn Pro Gln Glu Gly Leu Tyr Asn Glu Leu Gln
            420                 425                 430

Lys Asp Lys Met Ala Glu Ala Tyr Ser Glu Ile Gly Met Lys Gly Glu
        435                 440                 445

Arg Arg Arg Gly Lys Gly His Asp Gly Leu Tyr Gln Gly Leu Ser Thr
    450                 455                 460

Ala Thr Lys Asp Thr Tyr Asp Ala Leu His Met Gln Ala Leu Pro Pro
465                 470                 475                 480

Arg Gly Ser Gly Glu Gly Arg Gly Ser Leu Leu Thr Cys Gly Asp Val
                485                 490                 495

Glu Glu Asn Pro Gly Pro Met Ala Leu Pro Val Thr Ala Leu Leu Leu
            500                 505                 510

Pro Leu Ala Leu Leu Leu His Ala Ala Arg Pro Asn Trp Val Asn Val
        515                 520                 525
```

```
Ile Ser Asp Leu Lys Lys Ile Glu Asp Leu Ile Gln Ser Met His Ile
    530                 535                 540

Asp Ala Thr Leu Tyr Thr Glu Ser Asp Val His Pro Ser Cys Lys Val
545                 550                 555                 560

Thr Ala Met Lys Cys Phe Leu Leu Glu Leu Gln Val Ile Ser Leu Glu
                565                 570                 575

Ser Gly Asp Ala Ser Ile His Asp Thr Val Glu Asn Leu Ile Ile Leu
            580                 585                 590

Ala Asn Asn Ser Leu Ser Ser Asn Gly Asn Val Thr Glu Ser Gly Cys
        595                 600                 605

Lys Glu Cys Glu Glu Leu Glu Glu Lys Asn Ile Lys Glu Phe Leu Gln
    610                 615                 620

Ser Phe Val His Ile Val Gln Met Phe Ile Asn Thr Ser Thr Thr Thr
625                 630                 635                 640

Pro Ala Pro Arg Pro Pro Thr Pro Ala Pro Thr Ile Ala Ser Gln Pro
                645                 650                 655

Leu Ser Leu Arg Pro Glu Ala Cys Arg Pro Ala Ala Gly Gly Ala Val
            660                 665                 670

His Thr Arg Gly Leu Asp Phe Ala Cys Asp Ile Tyr Ile Trp Ala Pro
        675                 680                 685

Leu Ala Gly Thr Cys Gly Val Leu Leu Leu Ser Leu Val Ile Thr Leu
    690                 695                 700

Tyr Cys
705
```

<210> SEQ ID NO 204
<211> LENGTH: 2150
<212> TYPE: DNA
<213> ORGANISM: Homo sapiens
<220> FEATURE:
<221> NAME/KEY: misc_feature
<223> OTHER INFORMATION: DNA NK19H-NF-11

<400> SEQUENCE: 204

```
gaattcgccg ccaccatggc cttaccagtg accgccttgc tcctgccgct ggccttgctg     60
ctccacgccg ccaggccgga tattcagatg acccagagcc cgagcagcct gagcgcgagc    120
gtgggcgatc gcgtgaccat tacctgccgc gcgagccagg atattagcaa atatctgaac    180
tggtatcagc agaaaccggg cggcaccgtg aaactgctga tttatcatac cagccgcctg    240
catagcggcg tgccgagccg ctttagcggc agcggcagcg gcaccgattt taccctgacc    300
attagcagcc tgcagccgga agatattgcg acctattttt gccagcaggg caacaccctg    360
ccgtatacct ttggcggcgg caccaaactg gaaattaccg gtggcggtgg ctcgggcggt    420
ggtgggtcgg gtggcggcgg atctcaggtg cagctgcagg aaagcggccc gggcctggtg    480
aaaccgagcc agaccctgag cgtgacctgc accgtgagcg gcgtgagcct gccggattat    540
ggcgtgagct ggattcgcca gccgccgcgc aaaggcctgg aatggctggg cgtgatttgg    600
ggcagcgaaa ccacctatta taacagcgcg ctgaaaagcc gcctgaccat tagcaaagat    660
aacagcaaaa gccaggtgag cctgaaaatg agcagcgtga ccgcggcgga taccgcgatt    720
tattattgcg cgaaacatta ttattatggc ggcagctatg cgatggatta ttggggccag    780
ggcaccagcg tgaccgtgag cagcaccacg acgccagcgc cgcgaccacc aacaccggcg    840
cccaccatcg cgtcgcagcc cctgtccctg cgcccagagg cgtgccggcc agcggcgggg    900
ggcgcagtgc acacgagggg gctggacttc gcctgtgata tctacatctg ggcgcccttg    960
```

gccgggactt gtggggtcct tctcctgtca ctggttatca ccctttactg ccggagggac 1020
cagaggctgc cccccgatgc ccacaagccc cctgggggag gcagtttccg gacccccatc 1080
caagaggagc aggccgacgc ccactccacc ctggccaaga tcagagtgaa gttcagcagg 1140
agcgcagacg cccccgcgta ccagcagggc cagaaccagc tctataacga gctcaatcta 1200
ggacgaagag aggagtacga tgttttggac aagagacgtg gccgggaccc tgagatgggg 1260
ggaaagccga gaaggaagaa ccctcaggaa ggcctgtaca atgaactgca gaaagataag 1320
atggcggagg cctacagtga gattgggatg aaaggcgagc gccggagggg caaggggcac 1380
gatggccttt accagggtct cagtacagcc accaaggaca cctacgacgc ccttcacatg 1440
caggccctgc cccctcgcgg ctctggcgag ggaaggggtt ccctgcttac ttgcggcgac 1500
gtcgaagaga atcccggtcc gatggccctc ccagtaactg ccctcctttt gcccctcgca 1560
ctccttcttc atgccgctcg ccccaactgg gtcaacgtga ttagcgattt gaagaaaatc 1620
gaggacctta tacagtctat gcatattgac gctacactgt atactgagag tgatgtacac 1680
ccgtcctgta aggtaacggc catgaaatgc tttcttctgg agctccaggt catcagcttg 1740
gagtctgggg acgcaagcat ccacgatacg gttgaaaacc tcatcatcct tgcgaacaac 1800
tctctctcat ctaatggaaa cgttacagag agtgggtgta aggagtgcga agagttggaa 1860
gaaaaaaaca tcaaagaatt tcttcaatcc ttcgttcaca tagtgcaaat gttcattaac 1920
acgtccacta ccacacccgc cccgaggcca cctacgccgg caccgactat cgccagtcaa 1980
cccctctctc tgcgccccga ggcttgccgg cctgcggctg gtggggcggt ccacacccgg 2040
ggcctggatt ttgcgtgcga tatatacatc tgggcacctc ttgccggcac ctgcggagtg 2100
ctgcttctct cactcgttat tacgctgtac tgctaagcgg ccgcgtcgac 2150

<210> SEQ ID NO 205
<211> LENGTH: 706
<212> TYPE: PRT
<213> ORGANISM: Homo sapiens
<220> FEATURE:
<221> NAME/KEY: MISC_FEATURE
<223> OTHER INFORMATION: AA NK19H-NF-11

<400> SEQUENCE: 205

Met Ala Leu Pro Val Thr Ala Leu Leu Leu Pro Leu Ala Leu Leu Leu
1               5                   10                  15

His Ala Ala Arg Pro Asp Ile Gln Met Thr Gln Ser Pro Ser Ser Leu
            20                  25                  30

Ser Ala Ser Val Gly Asp Arg Val Thr Ile Thr Cys Arg Ala Ser Gln
        35                  40                  45

Asp Ile Ser Lys Tyr Leu Asn Trp Tyr Gln Gln Lys Pro Gly Gly Thr
    50                  55                  60

Val Lys Leu Leu Ile Tyr His Thr Ser Arg Leu His Ser Gly Val Pro
65                  70                  75                  80

Ser Arg Phe Ser Gly Ser Gly Ser Gly Thr Asp Phe Thr Leu Thr Ile
                85                  90                  95

Ser Ser Leu Gln Pro Glu Asp Ile Ala Thr Tyr Phe Cys Gln Gln Gly
            100                 105                 110

Asn Thr Leu Pro Tyr Thr Phe Gly Gly Gly Thr Lys Leu Glu Ile Thr
        115                 120                 125

Gly Gly Gly Gly Ser Gly Gly Gly Gly Ser Gly Gly Gly Gly Ser Gln
    130                 135                 140

-continued

```
Val Gln Leu Gln Glu Ser Gly Pro Gly Leu Val Lys Pro Ser Gln Thr
145                 150                 155                 160

Leu Ser Val Thr Cys Thr Val Ser Gly Val Ser Leu Pro Asp Tyr Gly
                165                 170                 175

Val Ser Trp Ile Arg Gln Pro Pro Arg Lys Gly Leu Glu Trp Leu Gly
            180                 185                 190

Val Ile Trp Gly Ser Glu Thr Thr Tyr Tyr Asn Ser Ala Leu Lys Ser
        195                 200                 205

Arg Leu Thr Ile Ser Lys Asp Asn Ser Lys Ser Gln Val Ser Leu Lys
    210                 215                 220

Met Ser Ser Val Thr Ala Ala Asp Thr Ala Ile Tyr Tyr Cys Ala Lys
225                 230                 235                 240

His Tyr Tyr Tyr Gly Gly Ser Tyr Ala Met Asp Tyr Trp Gly Gln Gly
                245                 250                 255

Thr Ser Val Thr Val Ser Ser Thr Thr Thr Pro Ala Pro Arg Pro Pro
            260                 265                 270

Thr Pro Ala Pro Thr Ile Ala Ser Gln Pro Leu Ser Leu Arg Pro Glu
        275                 280                 285

Ala Cys Arg Pro Ala Ala Gly Gly Ala Val His Thr Arg Gly Leu Asp
    290                 295                 300

Phe Ala Cys Asp Ile Tyr Ile Trp Ala Pro Leu Ala Gly Thr Cys Gly
305                 310                 315                 320

Val Leu Leu Leu Ser Leu Val Ile Thr Leu Tyr Cys Arg Arg Asp Gln
                325                 330                 335

Arg Leu Pro Pro Asp Ala His Lys Pro Pro Gly Gly Gly Ser Phe Arg
            340                 345                 350

Thr Pro Ile Gln Glu Glu Gln Ala Asp Ala His Ser Thr Leu Ala Lys
        355                 360                 365

Ile Arg Val Lys Phe Ser Arg Ser Ala Asp Ala Pro Ala Tyr Gln Gln
    370                 375                 380

Gly Gln Asn Gln Leu Tyr Asn Glu Leu Asn Leu Gly Arg Arg Glu Glu
385                 390                 395                 400

Tyr Asp Val Leu Asp Lys Arg Arg Gly Arg Asp Pro Glu Met Gly Gly
                405                 410                 415

Lys Pro Arg Arg Lys Asn Pro Gln Glu Gly Leu Tyr Asn Glu Leu Gln
            420                 425                 430

Lys Asp Lys Met Ala Glu Ala Tyr Ser Glu Ile Gly Met Lys Gly Glu
        435                 440                 445

Arg Arg Arg Gly Lys Gly His Asp Gly Leu Tyr Gln Gly Leu Ser Thr
    450                 455                 460

Ala Thr Lys Asp Thr Tyr Asp Ala Leu His Met Gln Ala Leu Pro Pro
465                 470                 475                 480

Arg Gly Ser Gly Glu Gly Arg Gly Ser Leu Leu Thr Cys Gly Asp Val
                485                 490                 495

Glu Glu Asn Pro Gly Pro Met Ala Leu Pro Val Thr Ala Leu Leu Leu
            500                 505                 510

Pro Leu Ala Leu Leu Leu His Ala Ala Arg Pro Asn Trp Val Asn Val
        515                 520                 525

Ile Ser Asp Leu Lys Lys Ile Glu Asp Leu Ile Gln Ser Met His Ile
    530                 535                 540

Asp Ala Thr Leu Tyr Thr Glu Ser Asp Val His Pro Ser Cys Lys Val
545                 550                 555                 560

Thr Ala Met Lys Cys Phe Leu Leu Glu Leu Gln Val Ile Ser Leu Glu
```

```
                565                 570                 575

Ser Gly Asp Ala Ser Ile His Asp Thr Val Glu Asn Leu Ile Ile Leu
            580                 585                 590

Ala Asn Asn Ser Leu Ser Ser Asn Gly Asn Val Thr Glu Ser Gly Cys
        595                 600                 605

Lys Glu Cys Glu Glu Leu Glu Glu Lys Asn Ile Lys Glu Phe Leu Gln
    610                 615                 620

Ser Phe Val His Ile Val Gln Met Phe Ile Asn Thr Ser Thr Thr Thr
625                 630                 635                 640

Pro Ala Pro Arg Pro Pro Thr Pro Ala Pro Thr Ile Ala Ser Gln Pro
                645                 650                 655

Leu Ser Leu Arg Pro Glu Ala Cys Arg Pro Ala Ala Gly Gly Ala Val
            660                 665                 670

His Thr Arg Gly Leu Asp Phe Ala Cys Asp Ile Tyr Ile Trp Ala Pro
        675                 680                 685

Leu Ala Gly Thr Cys Gly Val Leu Leu Leu Ser Leu Val Ile Thr Leu
    690                 695                 700

Tyr Cys
705
```

<210> SEQ ID NO 206
<211> LENGTH: 2150
<212> TYPE: DNA
<213> ORGANISM: Homo sapiens
<220> FEATURE:
<221> NAME/KEY: misc_feature
<223> OTHER INFORMATION: DNA NK19H-NF-12

<400> SEQUENCE: 206

```
gaattcgccg ccaccatggc cttaccagtg accgccttgc tcctgccgct ggccttgctg     60

ctccacgccg ccaggccgga tattcagatg acccagagcc cgagcagcct gagcgcgagc    120

gtgggcgatc gcgtgaccat tacctgccgc gcgagccagg atattagcaa atatctgaac    180

tggtatcagc agaaaccgga tggcaccgtg aaactgctga tttatcatac cagccgcctg    240

catagcggcg tgccgagccg ctttagcggc agcggcagcg gcaccgatta taccctgacc    300

attagcagcc tgcagccgga agatattgcg acctattttt gccagcaggg caacaccctg    360

ccgtatacct ttggcggcgg caccaaactg gaaattaccg gtggcggtgg ctcgggcggt    420

ggtgggtcgg gtggcggcgg atctcaggtg cagctgcagg aaagcggccc gggcctggtg    480

aaaccgagcc agaccctgag cgtgacctgc accgtgagcg gcgtgagcct gccggattat    540

ggcgtgagct ggattcgcca gccgccgcgc aaaggcctgg aatggctggg cgtgatttgg    600

ggcagcgaaa ccacctatta taacagcgcg ctgaaaagcc gcctgaccat tagcaaagat    660

aacagcaaaa gccaggtgag cctgaaaatg agcagcgtga ccgcggcgga taccgcgatt    720

tattattgcg cgaaacatta ttattatggc ggcagctatg cgatggatta ttggggccag    780

ggcaccagcg tgaccgtgag cagcaccacg acgccagcgc cgcgaccacc aacaccggcg    840

cccaccatcg cgtcgcagcc cctgtccctg cgcccagagg cgtgccggcc agcggcgggg    900

ggcgcagtgc acacgagggg gctggacttc gcctgtgata tctacatctg ggcgcccttg    960

gccgggactt gtggggtcct tctcctgtca ctggttatca ccctttactg ccggagggac   1020

cagaggctgc cccccgatgc ccacaagccc cctgggggag gcagtttccg gacccccatc   1080

caagaggagc aggccgacgc ccactccacc ctggccaaga tcagagtgaa gttcagcagg   1140

agcgcagacg cccccgcgta ccagcagggc cagaaccagc tctataacga gctcaatcta   1200
```

```
ggacgaagag aggagtacga tgttttggac aagagacgtg gccgggaccc tgagatgggg   1260

ggaaagccga gaaggaagaa ccctcaggaa ggcctgtaca atgaactgca gaaagataag   1320

atggcggagg cctacagtga gattgggatg aaaggcgagc gccggagggg caaggggcac   1380

gatggccttt accagggtct cagtacagcc accaaggaca cctacgacgc ccttcacatg   1440

caggccctgc cccctcgcgg ctctggcgag ggaaggggtt ccctgcttac ttgcggcgac   1500

gtcgaagaga atcccggtcc gatggccctc ccagtaactg ccctcctttt gcccctcgca   1560

ctccttcttc atgccgctcg ccccaactgg gtcaacgtga ttagcgattt gaagaaaatc   1620

gaggacctta tacagtctat gcatattgac gctacactgt atactgagag tgatgtacac   1680

ccgtcctgta aggtaacggc catgaaatgc tttcttctgg agctccaggt catcagcttg   1740

gagtctgggg acgcaagcat ccacgatacg gttgaaaacc tcatcatcct tgcgaacaac   1800

tctctctcat ctaatggaaa cgttacagag agtgggtgta aggagtgcga agagttggaa   1860

gaaaaaaaca tcaaagaatt tcttcaatcc ttcgttcaca tagtgcaaat gttcattaac   1920

acgtccacta ccacacccgc cccgaggcca cctacgccgg caccgactat cgccagtcaa   1980

cccctctctc tgcgccccga ggcttgccgg cctgcggctg gtggggcggt ccacacccgg   2040

ggcctggatt ttgcgtgcga tatatacatc tgggcacctc ttgccggcac ctgcggagtg   2100

ctgcttctct cactcgttat tacgctgtac tgctaagcgg ccgcgtcgac              2150
```

<210> SEQ ID NO 207
<211> LENGTH: 706
<212> TYPE: PRT
<213> ORGANISM: Homo sapiens
<220> FEATURE:
<221> NAME/KEY: MISC_FEATURE
<223> OTHER INFORMATION: AA NK19H-NF-12

<400> SEQUENCE: 207

```
Met Ala Leu Pro Val Thr Ala Leu Leu Leu Pro Leu Ala Leu Leu Leu
1               5                   10                  15

His Ala Ala Arg Pro Asp Ile Gln Met Thr Gln Ser Pro Ser Ser Leu
            20                  25                  30

Ser Ala Ser Val Gly Asp Arg Val Thr Ile Thr Cys Arg Ala Ser Gln
        35                  40                  45

Asp Ile Ser Lys Tyr Leu Asn Trp Tyr Gln Gln Lys Pro Asp Gly Thr
    50                  55                  60

Val Lys Leu Leu Ile Tyr His Thr Ser Arg Leu His Ser Gly Val Pro
65                  70                  75                  80

Ser Arg Phe Ser Gly Ser Gly Ser Gly Thr Asp Tyr Thr Leu Thr Ile
                85                  90                  95

Ser Ser Leu Gln Pro Glu Asp Ile Ala Thr Tyr Phe Cys Gln Gln Gly
            100                 105                 110

Asn Thr Leu Pro Tyr Thr Phe Gly Gly Gly Thr Lys Leu Glu Ile Thr
        115                 120                 125

Gly Gly Gly Gly Ser Gly Gly Gly Gly Ser Gly Gly Gly Gly Ser Gln
    130                 135                 140

Val Gln Leu Gln Glu Ser Gly Pro Gly Leu Val Lys Pro Ser Gln Thr
145                 150                 155                 160

Leu Ser Val Thr Cys Thr Val Ser Gly Val Ser Leu Pro Asp Tyr Gly
                165                 170                 175

Val Ser Trp Ile Arg Gln Pro Pro Arg Lys Gly Leu Glu Trp Leu Gly
            180                 185                 190
```

```
Val Ile Trp Gly Ser Glu Thr Thr Tyr Tyr Asn Ser Ala Leu Lys Ser
        195                 200                 205

Arg Leu Thr Ile Ser Lys Asp Asn Ser Lys Ser Gln Val Ser Leu Lys
    210                 215                 220

Met Ser Ser Val Thr Ala Ala Asp Thr Ala Ile Tyr Tyr Cys Ala Lys
225                 230                 235                 240

His Tyr Tyr Tyr Gly Gly Ser Tyr Ala Met Asp Tyr Trp Gly Gln Gly
                245                 250                 255

Thr Ser Val Thr Val Ser Ser Thr Thr Thr Pro Ala Pro Arg Pro Pro
            260                 265                 270

Thr Pro Ala Pro Thr Ile Ala Ser Gln Pro Leu Ser Leu Arg Pro Glu
        275                 280                 285

Ala Cys Arg Pro Ala Ala Gly Gly Ala Val His Thr Arg Gly Leu Asp
    290                 295                 300

Phe Ala Cys Asp Ile Tyr Ile Trp Ala Pro Leu Ala Gly Thr Cys Gly
305                 310                 315                 320

Val Leu Leu Leu Ser Leu Val Ile Thr Leu Tyr Cys Arg Arg Asp Gln
                325                 330                 335

Arg Leu Pro Pro Asp Ala His Lys Pro Pro Gly Gly Gly Ser Phe Arg
            340                 345                 350

Thr Pro Ile Gln Glu Glu Gln Ala Asp Ala His Ser Thr Leu Ala Lys
        355                 360                 365

Ile Arg Val Lys Phe Ser Arg Ser Ala Asp Ala Pro Ala Tyr Gln Gln
    370                 375                 380

Gly Gln Asn Gln Leu Tyr Asn Glu Leu Asn Leu Gly Arg Arg Glu Glu
385                 390                 395                 400

Tyr Asp Val Leu Asp Lys Arg Arg Gly Arg Asp Pro Glu Met Gly Gly
                405                 410                 415

Lys Pro Arg Arg Lys Asn Pro Gln Glu Gly Leu Tyr Asn Glu Leu Gln
            420                 425                 430

Lys Asp Lys Met Ala Glu Ala Tyr Ser Glu Ile Gly Met Lys Gly Glu
        435                 440                 445

Arg Arg Arg Gly Lys Gly His Asp Gly Leu Tyr Gln Gly Leu Ser Thr
    450                 455                 460

Ala Thr Lys Asp Thr Tyr Asp Ala Leu His Met Gln Ala Leu Pro Pro
465                 470                 475                 480

Arg Gly Ser Gly Glu Gly Arg Gly Ser Leu Leu Thr Cys Gly Asp Val
                485                 490                 495

Glu Glu Asn Pro Gly Pro Met Ala Leu Pro Val Thr Ala Leu Leu Leu
            500                 505                 510

Pro Leu Ala Leu Leu Leu His Ala Ala Arg Pro Asn Trp Val Asn Val
        515                 520                 525

Ile Ser Asp Leu Lys Lys Ile Glu Asp Leu Ile Gln Ser Met His Ile
    530                 535                 540

Asp Ala Thr Leu Tyr Thr Glu Ser Asp Val His Pro Ser Cys Lys Val
545                 550                 555                 560

Thr Ala Met Lys Cys Phe Leu Leu Glu Leu Gln Val Ile Ser Leu Glu
                565                 570                 575

Ser Gly Asp Ala Ser Ile His Asp Thr Val Glu Asn Leu Ile Ile Leu
            580                 585                 590

Ala Asn Asn Ser Leu Ser Ser Asn Gly Asn Val Thr Glu Ser Gly Cys
        595                 600                 605
```

-continued

```
Lys Glu Cys Glu Glu Leu Glu Glu Lys Asn Ile Lys Glu Phe Leu Gln
    610                 615                 620

Ser Phe Val His Ile Val Gln Met Phe Ile Asn Thr Ser Thr Thr Thr
625                 630                 635                 640

Pro Ala Pro Arg Pro Pro Thr Pro Ala Pro Thr Ile Ala Ser Gln Pro
                645                 650                 655

Leu Ser Leu Arg Pro Glu Ala Cys Arg Pro Ala Ala Gly Gly Ala Val
            660                 665                 670

His Thr Arg Gly Leu Asp Phe Ala Cys Asp Ile Tyr Ile Trp Ala Pro
        675                 680                 685

Leu Ala Gly Thr Cys Gly Val Leu Leu Leu Ser Leu Val Ile Thr Leu
    690                 695                 700

Tyr Cys
705
```

CD19-DIRECTED CHIMERIC ANTIGEN RECEPTORS AND USES THEREOF IN IMMUNOTHERAPY

RELATED CASES

This application is a continuation of U.S. patent application Ser. No. 17/089,449, filed Nov. 4, 2020, now issued as U.S. Pat. No. 11,253,547, which is a continuation of International Patent Application No. PCT/US2020/020824, filed Mar. 3, 2020, which claims the priority to U.S. Provisional Patent Application Nos. 62/814,180, filed Mar. 5, 2019, 62/895,910, filed Sep. 4, 2019, and 62/932,165, filed Nov. 7, 2019, the entire contents of each of which is incorporated by reference herein.

FIELD

Some embodiments of the methods and compositions provided herein relate to CD19-directed receptors. In some, embodiments the receptors are chimeric. Some embodiments include methods of use of the chimeric receptors in immunotherapy.

BACKGROUND

As further knowledge is gained about various cancers and what characteristics a cancerous cell has that can be used to specifically distinguish that cell from a healthy cell, therapeutics are under development that leverage the distinct features of a cancerous cell. Immunotherapies that employ engineered immune cells are one approach to treating cancers.

INCORPORATION BY REFERENCE OF MATERIAL IN ASCII TEXT FILE

This application incorporates by reference the Sequence Listing contained in the following ASCII text file being submitted concurrently herewith: File Name: NKT033C4_ST25.txt; created Jan. 7, 2022, 445,480 bytes in size.

SUMMARY

Immunotherapy presents a new technological advancement in the treatment of disease, wherein immune cells are engineered to express certain targeting and/or effector molecules that specifically identify and react to diseased or damaged cells. This represents a promising advance due, at least in part, to the potential for specifically targeting diseased or damaged cells, as opposed to more traditional approaches, such as chemotherapy, where all cells are impacted, and the desired outcome is that sufficient healthy cells survive to allow the patient to live. One immunotherapy approach is the recombinant expression of chimeric receptors in immune cells to achieve the targeted recognition and destruction of aberrant cells of interest.

In several embodiments, there is provided herein an immune cell, and also populations of immune cells, that expresses a CD19-directed chimeric receptor, the chimeric receptor comprising an extracellular anti-CD19 binding moiety, a hinge and/or transmembrane domain, and an intracellular signaling domain. Also provided for herein are polynucleotides (as well as vectors for transfecting cells with the same) encoding a CD19-directed chimeric antigen receptor, the chimeric antigen receptor comprising an extracellular anti-CD19 binding moiety, a hinge and/or transmembrane domain, and an intracellular signaling domain.

In several embodiments, there is provided a polynucleotide encoding a CD19-directed chimeric antigen receptor, the chimeric antigen receptor comprising an extracellular anti-CD19 binding moiety, wherein the anti-CD19 binding moiety comprises a variable heavy (VH) domain of a single chain Fragment variable (scFv) and a variable light (VL) domain of a scFv, a hinge, a transmembrane domain, and an intracellular signaling domain, and wherein the intracellular signaling domain comprises an OX40 subdomain, a CD3 zeta subdomain.

In several embodiments, there is provided a polynucleotide encoding a CD19-directed chimeric antigen receptor, the chimeric antigen receptor comprising an extracellular anti-CD19 binding moiety, wherein the anti-CD19 binding moiety comprises a variable heavy (VH) domain of a single chain Fragment variable (scFv) and a variable light (VL) domain of a scFv, wherein the encoded VH domain comprises at least one heavy chain complementarity determining region (CDR) selected from the group consisting of SEQ ID NO: 133, SEQ ID NO: 134, and SEQ ID NO: 135, wherein the encoded VL domain comprises at least one light chain complementarity determining region (CDR) selected from the group consisting of SEQ ID NO: 127, SEQ ID NO: 128, and SEQ ID NO: 129, a hinge domain, a transmembrane domain, an intracellular signaling domain, and wherein the intracellular signaling domain comprises an OX40 subdomain and a CD3 zeta subdomain.

In several embodiments, the polynucleotide also encodes membrane-bound interleukin-15 (mbIL15). However, in some embodiments, a separate polynucleotide is used to encode the mbIL15. In several embodiments, the transmembrane domain is derived from or comprises a CD8 alpha transmembrane domain. In several embodiments, the CD8 alpha transmembrane domain is encoded by SEQ ID NO: 3. In several embodiments, the hinge is derived from or comprises a CD8 alpha hinge. In several embodiments, the CD8 alpha hinge is encoded by SEQ ID NO: 1. In several embodiments, the OX40 subdomain is encoded by a sequence having at least 90% (e.g., 90-95%, 95%, 96%, 97%, 98%, or 99%) sequence identity to SEQ ID NO. 5. In several embodiments, the CD3 zeta subdomain is encoded by a sequence having at least 90% (e.g., 90-95%, 95%, 96%, 97%, 98%, or 99%) sequence identity to SEQ ID NO. 7. In several embodiments, the mbIL15 is encoded by a sequence having at least 90% (e.g., 90-95%, 95%, 96%, 97%, 98%, or 99%) sequence identity to SEQ ID NO. 11. In several embodiments, the OX40 domain is encoded by SEQ ID NO: 5, the CD3 zeta subdomain is encoded by SEQ ID NO. 7 and/or mbIL15 (whether encoded separately or bicistronically) is encoded by SEQ ID NO: 11. In several embodiments, the encoded OX40 subdomain comprises the amino acid sequence of SEQ ID NO: 6, the encoded CD3 zeta subdomain comprises the amino acid sequence of SEQ ID NO: 8, and/or the encoded mbIL15 (whether encoded separately or bicistronically) comprises the amino acid sequence of SEQ ID NO: 12.

In several embodiments, the VH domain comprises a VH domain selected from SEQ ID NO: 120, SEQ ID NO: 121, SEQ ID NO: 122, and SEQ ID NO: 123, and wherein the VL domain comprises a VL domain selected from SEQ ID NO: 117, SEQ ID NO: 118, and SEQ ID NO: 119. In several embodiments, the polynucleotide encodes a VL domain comprising at least one light chain complementarity determining region (CDR) selected from the group consisting of SEQ ID NO: 127, SEQ ID NO: 128, and SEQ ID NO: 129.

In several embodiments, the polynucleotide encodes a VH domain comprising at least one heavy chain complementarity determining region (CDR) selected from the group consisting of SEQ ID NO: 133, SEQ ID NO: 134, and SEQ ID NO: 135. In several embodiments, the polynucleotide is designed (e.g., engineered) to reduce potential antigenicity of the encoded protein and/or enhance one or more characteristics of the encoded protein (e.g., target recognition and/or binding characteristics) Thus, according to several embodiments, the anti-CD19 binding moiety does not comprise certain sequences. For example, according to several embodiments the polynucleotide does not encode one or more of SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52. SEQ ID NO: 53, SEQ ID NO: 54, or SEQ ID NO: 55. In several embodiments, the encoded VH domain comprises an amino acid sequence at having at least 90% (e.g., 90-95%, 95%, 96%, 97%, 98%, or 99%) sequence identity to SEQ ID NO: 120. In several embodiments, the encoded VH domain comprises the amino acid sequence of SEQ ID NO: 120. In several embodiments, the encoded VL domain comprises an amino acid sequence at having at least 90% (e.g., 90-95%, 95%, 96%, 97%, 98%, or 99%) sequence identity to SEQ ID NO: 118. In several embodiments, the encoded VL domain comprises the amino acid sequence of SEQ ID NO: 118. In several embodiments, VH domain is derived from a parent amino acid sequence and is modified from the parent sequence. For example, mutations, truncations, extensions, conservative substitutions, or other modifications are introduced to increase the affinity of the domain for its target, increase the avidity for the target, and/or reduce potential antigenicity of the sequence. In several embodiments, the VH domain results from humanization of the VH domain amino acid sequence set forth in SEQ ID NO: 33. Likewise, in several embodiments, the VL domain results from humanization of the VL domain amino acid sequence set forth in SEQ ID NO: 32. In several embodiments, the polynucleotide encodes a CD19-directed chimeric antigen receptor having at least is encoded by a sequence having at least 90% (e.g., 90-95%, 95%, 96%, 97%, 98%, or 99%) sequence identity to the amino acid sequence set forth in SEQ ID NO: 187. In several embodiments, the polynucleotide encodes a CD19-directed chimeric antigen receptor comprising the amino acid sequence set forth in SEQ ID NO: 187.

In several embodiments, the polynucleotide does not encode or otherwise comprise a DAP10 domain. In several embodiments, the polynucleotide does not encode or otherwise comprise a DAP12 domain. In several embodiments, the intracellular signaling domain comprises additional subdomains, that advantageously enhance generation of cytotoxic signals by cells expressing the constructs. In several embodiments, the polynucleotide further encodes one or more of CD44 and CD27 as signaling subdomains. In several embodiments, the polynucleotide optionally further encodes a detection tag or other moiety (e.g., marker) that allows for detection of expression of the protein(s) encoded by the polynucleotide by host cells.

There are also provided for herein uses of the disclosed polynucleotides in the manufacture of a medicament for enhancing NK cell cytotoxicity in a mammal in need thereof, in the manufacture of a medicament for treating cancer in a mammal in need thereof and/or for the treatment of cancer in a mammal in need thereof.

There are also provided for herein engineered immune cells that express the CD19-directed chimeric antigen receptors encoded by the polynucleotides disclosed herein. In several embodiments, the engineered immune cells are natural killer (NK) cell. In some embodiments, the engineered cells are T cells, though combinations of NK cell and T cells (and optionally other immune cell types) are used in some embodiments. In several embodiments, the immune cells are allogeneic with respect to a subject receiving the cells. There are also provided for herein the use of immune cells that express the CD19-directed chimeric antigen receptors encoded by the polynucleotides disclosed herein for the treatment of cancer in a mammal in need thereof. There are also provided for herein the use of immune cells that express the CD19-directed chimeric antigen receptors encoded by the polynucleotides disclosed herein for the manufacture of a medicament for the treatment of cancer in a mammal in need thereof.

In several embodiments, there are provided methods for treating cancer using the polynucleotides disclosed herein. For example, in several embodiments the methods comprise administering to a subject having a cancer a composition comprising a population of immune cells expressing CD19-directed chimeric antigen receptors as disclosed herein. In several embodiments, the CAR comprises an extracellular anti-CD19 binding moiety, wherein the anti-CD19 binding moiety comprises a variable heavy (VH) domain of a single chain Fragment variable (scFv) and a variable light (VL) domain of a scFv, a hinge, such as a CD8 alpha hinge, a transmembrane domain, such as a CD8 alpha transmembrane domain; and an intracellular signaling domain comprising an OX40 subdomain and a CD3 zeta subdomain, and wherein the cell also expresses membrane-bound interleukin-15 (mbIL15). In several embodiments, the OX40 subdomain is encoded by a sequence having at least 95% sequence identity to SEQ ID NO. 5, the CD3 zeta subdomain is encoded by a sequence having at least 95% sequence identity to SEQ ID NO. 7, and/or the mbIL15 is encoded by a sequence having at least 95% sequence identity to SEQ ID NO. 11. In several embodiments, the encoded VH domain comprises an amino acid sequence having at least 95% sequence identity to SEQ ID NO: 120, wherein the encoded VL domain comprises an amino acid sequence having at least 95% sequence identity to SEQ ID NO: 118. In several embodiments, the polynucleotide encodes a CD19-directed chimeric antigen receptor having at least 95% sequence identity to the amino acid sequence set forth in SEQ ID NO: 187. As discussed above, in several embodiments, the immune cells expressing such CD19 CAR constructs are natural killer (NK) cells. In some embodiments, the immune cells are T cells. In several embodiments, combinations of NK and T cells (and optionally other immune cells) are used. In several embodiments, the cells are allogeneic cells originating from a donor that is not the subject. In several embodiments, the cells are autologous cells originating the subject. Mixtures of allogeneic and autologous cells may also be used, in some embodiments. In several embodiments, the administered population comprises about $2\times10^6$ cells per kilogram of body weight of the subject. In several embodiments, the administration is intravenous. In several embodiments, the method further comprises administering one or more doses of interleukin 2 to the subject. In several embodiments, the methods also involve the administration of another therapy to the subject. For example, in several embodiments, the methods involve administering a chemotherapy treatment to the subject prior to the administration of the cells. In several embodiments, the chemotherapy treatment induces lymphodepletion in the subject. In some embodiments, the subject is administered a combination of cyclophosphamide and fludarabine prior to administration of the cells. In several embodiments, the cyclophosphamide is administered in a dose between about 400 and about 600 mg/m$^2$. In several embodiments, the fludarabine is administered in a dose between about 25 and 25 mg/m$^2$. In several embodiments, the lymphodepleting chemotherapy is administered several days prior to administration of engineered immune cells and optionally administered multiple times. For example, in several embodiments the lymphodepleting chemotherapy is administered on at least the fifth, fourth, and/or third day prior to administration of engineered immune cells disclosed herein.

In several embodiments there is provided a polynucleotide encoding a humanized CD19-directed chimeric antigen receptor, the chimeric antigen receptor comprising a humanized anti-CD19 binding moiety, a co-stimulatory domain, and a signaling domain. In several embodiments, the co-stimulatory domain comprises OX40. In several embodiments, the humanized anti-CD19-binding moiety comprises a humanized scFv, wherein one or more of the heavy and light chains have been humanized. In several embodiments, one or more of the CDRs on the heavy and/or light chains have been humanized. For example, in several embodiments, there is provided a polynucleotide encoding a humanized CD19-directed chimeric antigen receptor, the chimeric antigen receptor comprising an extracellular anti-CD19 binding moiety, wherein the anti-CD19 binding moiety comprises a heavy chain variable (VH) domain and a and a light chain variable (VL) domain, the VH domain comprising a VH domain selected from SEQ ID NO: 120, SEQ ID NO: 121, SEQ ID NO: 122, and SEQ ID NO: 123 and the VL domain comprising a VL domain selected from SEQ ID NO: 117, SEQ ID NO: 118, and SEQ ID NO: 119, a hinge and/or transmembrane domain, an intracellular signaling domain.

In several embodiments, there is provided a polynucleotide encoding a humanized chimeric antigen receptor (CAR), wherein the CAR comprises a single chain antibody or single chain antibody fragment which comprises a humanized anti-CD19 binding domain, a transmembrane domain, a primary intracellular signaling domain comprising a native intracellular signaling domain of CD3-zeta, or a functional fragment thereof, and a costimulatory domain comprising a native intracellular signaling domain of a protein selected from the group consisting of OX40, CD27, CD28, ICOS, and 4-1 BB, or a functional fragment thereof, wherein said anti-CD19 binding domain comprises a light chain complementary determining region 1 (LC CDR1) of SEQ ID NO: 124, 127, or 130, a light chain complementary determining region 2 (LC CDR2) of SEQ ID NO: 125, 128, or 131, and a light chain complementary determining region 3 (LC CDR3) of SEQ ID NO: 126, 129, or 132, and a heavy chain complementary determining region 1 (HC CDR1) of SEQ ID NO: 133, 136, 139, or 142, a heavy chain complementary determining region 2 (HC CDR2) of SEQ ID NO: 134, 137, 140, or 143, and a heavy chain complementary determining region 3 (HC CDR3) of SEQ ID NO: 135, 138, 141, or 144.

In several embodiments, there is provided a polynucleotide encoding a humanized CD19-directed chimeric antigen receptor, the chimeric antigen receptor comprising an extracellular anti-CD19 binding moiety, wherein the anti-CD19 binding moiety comprises a humanized scFv sequence comprising a variable light (VL) domain of SEQ ID NO: 117, a hinge and/or transmembrane domain, and an intracellular signaling domain. In several embodiments, the polynucleotide encodes the humanized chimeric antigen receptor of SEQ ID NO: 161, SEQ ID NO: 167, SEQ ID NO: 173, SEQ ID NO: 179, SEQ ID NO: 185, SEQ ID NO: 191, SEQ ID NO: 197, or SEQ ID NO: 203.

In several embodiments, there is provided a polynucleotide encoding a humanized CD19-directed chimeric antigen receptor, the chimeric antigen receptor comprising an extracellular anti-CD19 binding moiety, wherein the anti-CD19 binding moiety comprises a humanized scFv sequence comprising a variable light (VL) domain of SEQ ID NO: 118, a hinge and/or transmembrane domain, and an intracellular signaling domain. In several embodiments, the polynucleotide encodes the humanized chimeric antigen receptor of SEQ ID NO: 163, SEQ ID NO: 169, SEQ ID NO: 175, SEQ ID NO: 181, SEQ ID NO: 187, SEQ ID NO: 193, SEQ ID NO: 199, or SEQ ID NO: 205.

In several embodiments, there is provided a polynucleotide encoding a humanized CD19-directed chimeric antigen receptor, the chimeric antigen receptor comprising an extracellular anti-CD19 binding moiety, wherein the anti-CD19 binding moiety comprises a humanized scFv sequence comprising a variable light (VL) domain of SEQ ID NO: 119, a hinge and/or transmembrane domain, and an intracellular signaling domain. In several embodiments, the polynucleotide encodes the humanized chimeric antigen receptor of SEQ ID NO: 165, SEQ ID NO: 171, SEQ ID NO: 177, SEQ ID NO: 183, SEQ ID NO: 189, SEQ ID NO: 195, SEQ ID NO: 201, or SEQ ID NO: 207.

In several embodiments, there is provided a polynucleotide encoding a humanized CD19-directed chimeric antigen receptor, the chimeric antigen receptor comprising an extracellular anti-CD19 binding moiety, wherein the anti-CD19 binding moiety comprises a humanized scFv sequence comprising a variable heavy (VH) domain of SEQ ID NO: 120, a hinge and/or transmembrane domain, and an intracellular signaling domain. In several embodiments, the polynucleotide encodes the humanized chimeric antigen receptor of SEQ ID NO: 161, SEQ ID NO: 163, SEQ ID NO: 165, SEQ ID NO: 185, SEQ ID NO: 187, or SEQ ID NO: 189.

In several embodiments, there is provided a polynucleotide encoding a humanized CD19-directed chimeric antigen receptor, the chimeric antigen receptor comprising an extracellular anti-CD19 binding moiety, wherein the anti-CD19 binding moiety comprises a humanized scFv sequence comprising a variable heavy (VH) domain of SEQ ID NO: 121, a hinge and/or transmembrane domain, and an intracellular signaling domain. In several embodiments, the polynucleotide encodes the humanized chimeric antigen receptor of SEQ ID NO: 167, SEQ ID NO: 169, SEQ ID NO: 171, SEQ ID NO: 191, SEQ ID NO: 193, or SEQ ID NO: 195.

In several embodiments, there is provided a polynucleotide encoding a humanized CD19-directed chimeric antigen receptor, the chimeric antigen receptor comprising an extracellular anti-CD19 binding moiety, wherein the anti-CD19 binding moiety comprises a humanized scFv sequence comprising a variable heavy (VH) domain of SEQ ID NO: 122, a hinge and/or transmembrane domain, and an intracellular signaling domain. In several embodiments, the polynucleotide encodes the humanized chimeric antigen receptor of SEQ ID NO: 173, SEQ ID NO: 175, SEQ ID NO: 177, SEQ ID NO: 197, SEQ ID NO: 199, or SEQ ID NO: 201.

In several embodiments, there is provided a polynucleotide encoding a humanized CD19-directed chimeric antigen receptor, the chimeric antigen receptor comprising an extracellular anti-CD19 binding moiety, wherein the anti-CD19 binding moiety comprises a humanized scFv sequence comprising a variable heavy (VH) domain of SEQ ID NO: 123, a hinge and/or transmembrane domain, and an intracellular signaling domain. In several embodiments, the polynucleotide encodes the humanized chimeric antigen receptor of SEQ ID NO: 179, SEQ ID NO: 181, SEQ ID NO: 183, SEQ ID NO: 203, SEQ ID NO: 205, or SEQ ID NO: 207.

In several embodiments, the provided polynucleotides also encode membrane-bound interleukin-15 (mbIL15).

In several embodiments, the intracellular signaling domain comprises an OX40 subdomain. However, in several embodiments the intracellular signaling domain comprises one or more of an OX40 subdomain, a CD28 subdomain, an iCOS subdomain, a CD28-41 BB subdomain, a CD27 subdomain, a CD44 subdomain, or combinations thereof.

In several embodiments, the chimeric antigen receptor comprises a hinge and a transmembrane domain, wherein the hinge is a CD8 alpha hinge, wherein the transmembrane domain is either a CD8 alpha or an NKG2D transmembrane domain. In several embodiments, the intracellular signaling domain comprises a CD3zeta domain.

In several embodiments, the polynucleotide does not encode SEQ ID NO: 112, 113, or 114. In several embodiments the polynucleotide does not encode SEQ ID NO: 116.

In several embodiments, there are provided engineered NK cells, engineered T cells, and/or mixed populations of NK cells and T cells that express one or more of the humanized CD19-directed chimeric antigen receptors provided for herein.

Also provided are methods for treating cancer in a subject comprising administering to a subject having cancer the engineered NK and/or T cells expressing chimeric antigen receptors as disclosed herein. Also provided for are the use of the polynucleotides provided for herein for the treatment of cancer as well as use of the polynucleotides provided for herein in the manufacture of a medicament for the treatment of cancer.

Also provided for herein, in several embodiments, is a polynucleotide encoding a CD19-directed chimeric antigen receptor, the chimeric antigen receptor comprising an extracellular anti-CD19 binding moiety, wherein the anti-CD19 binding moiety comprises a scFv, a transmembrane domain, and an intracellular signaling domain, wherein the intracellular signaling domain comprises a CD28 co-stimulatory domain and a CD3 zeta signaling domain.

Also provided for herein, in several embodiments, is a polynucleotide encoding a CD19-directed chimeric antigen receptor, the chimeric antigen receptor comprising an extracellular anti-CD19 binding moiety, wherein the anti-CD19 binding moiety comprises a scFv, a hinge, wherein the hinge is a CD8 alpha hinge, a transmembrane domain, and an intracellular signaling domain, wherein the intracellular signaling domain comprises a CD3 zeta ITAM.

Also provided for herein, in several embodiments, is a polynucleotide encoding a CD19-directed chimeric antigen receptor, the chimeric antigen receptor comprising an extracellular anti-CD19 binding moiety, wherein the anti-CD19 binding moiety comprises a variable heavy chain of a scFv or a variable light chain of a scFv, a hinge, wherein the hinge is a CD8 alpha hinge, a transmembrane domain, wherein the transmembrane domain comprises a CD8 alpha transmembrane domain, and an intracellular signaling domain, wherein the intracellular signaling domain comprises a CD3 zeta ITAM.

In several embodiments, the transmembrane domain comprises a CD8 alpha transmembrane domain. In several embodiments, the transmembrane domain comprises an NKG2D transmembrane domain. In several embodiments, the transmembrane domain comprises a CD28 transmembrane domain.

In several embodiments the intracellular signaling domain comprises or further comprises a CD28 signaling domain. In several embodiments, the intracellular signaling domain comprises or further comprises a 4-1 BB signaling domain. In several embodiments, the intracellular signaling domain comprises an or further comprises OX40 domain. In several embodiments, the intracellular signaling domain comprises or further comprises a 4-1 BB signaling domain. In several embodiments, the intracellular signaling domain comprises or further comprises a domain selected from ICOS, CD70, CD161, CD40L, CD44, and combinations thereof.

In several embodiments, the polynucleotide also encodes a truncated epidermal growth factor receptor (EGFRt). In several embodiments, the EGFRt is expressed in a cell as a soluble factor. In several embodiments, the EGFRt is expressed in a membrane bound form. In several embodiments, the EGFRt operates to provide a "suicide switch" function in the engineered NK cells. In several embodiments, the polynucleotide also encodes membrane-bound interleukin-15 (mbIL15). Also provided for herein are engineered immune cells (e.g., NK or T cells, or mixtures thereof) that express a CD19-directed chimeric antigen receptor encoded by a polynucleotide disclosed herein. Further provided are methods for treating cancer in a subject comprising administering to a subject having cancer engineered immune cells expressing the chimeric antigen receptors disclosed herein. In several embodiments, there is provided the use of the polynucleotides disclosed herein in the treatment of cancer and/or in the manufacture of a medicament for the treatment of cancer.

In several embodiments, the anti-CD19 binding moiety comprises a heavy chain variable (VH) domain and a light chain variable (VL) domain. In several embodiments, the VH domain has at least 95% (e.g., 95, 96, 97, 98, or 99%) identity to the VH domain amino acid sequence set forth in SEQ ID NO: 33. In several embodiments, the VL domain has at least 95% (e.g., 95, 96, 97, 98, or 99%) identity to the VL domain amino acid sequence set forth in SEQ ID NO: 32. In several embodiments, the anti-CD19 binding moiety is derived from the VH and/or VL sequences of SEQ ID NO: 33 or 32. For example, in several embodiments, the VH and VL sequences for SEQ ID NO: 33 and/or 32 are subject to a humanization campaign and therefore are expressed more readily and/or less immunogenic when administered to human subjects. Thus, in several embodiments, the anti-CD19 binding moiety does not comprise SEQ ID NO: 32 and/or SEQ ID NO: 33. In several embodiments, the anti-CD19 binding moiety comprises a scFv that targets CD19 wherein the scFv comprises a heavy chain variable region comprising the sequence of SEQ ID NO. 35 or a sequence at least 95% (e.g., 95, 96, 97, 98, or 99%) identical to SEQ ID NO: 35. In several embodiments, the anti-CD19 binding moiety comprises an scFv that targets CD19 comprises a light chain variable region comprising the sequence of SEQ ID NO. 36 or a sequence at least 95% identical (e.g., 95, 96, 97, 98, or 99%) to SEQ ID NO: 36. In several embodiments, the anti-CD19 binding moiety comprises a light chain CDR comprising a first, second and third complementarity determining region (LC CDR1, LC CDR2, and LC CDR3, respectively) and/or a heavy chain CDR comprising a first, second and third complementarity determining region (HC CDR1, HC CDR2, and HC CDR3, respectively). Depending on the embodiment, various combinations of the LC CDRs and HC CDRs are used. For example, in one embodiment the anti-CD19 binding moiety comprises LC CDR1, LC CDR3, HC CD2, and HC, CDR3. Other combinations are used in some embodiments. In several embodiments, the LC CDR1 comprises the sequence of SEQ ID NO. 37 or a sequence at least about 95% homologous to the sequence of SEQ NO. 37. In several embodiments, the LC CDR2 comprises the sequence of SEQ ID NO. 38 or a or a sequence at least about 95% (e.g., 96, 97, 98, or 99%) homologous to the sequence of SEQ NO. 38. In several embodiments, the LC CDR3 comprises the sequence of SEQ ID NO. 39 or a sequence at least about 95% homologous to the sequence of SEQ NO. 39. In several embodiments, the HC CDR1 comprises the sequence of SEQ ID NO. 40 or a sequence at least about 95% homologous to the sequence of SEQ NO. 40. In several embodiments, the HC CDR2 comprises the sequence of SEQ ID NO. 41, 42, or 43 or a sequence at least about 95% homologous to the sequence of SEQ NO. 41, 42, or 43. In several embodiments, the HC CDR3 comprises the sequence of SEQ ID NO. 44 or a sequence at least about 95% (e.g., 96, 97, 98, 99 or 99%) homologous to the sequence of SEQ NO. 44.

In several embodiments, there is also provided an anti-CD19 binding moiety that comprises a light chain variable region (VL) and a heavy chain variable region (HL), the VL region comprising a first, second and third complementarity determining region (VL CDR1, VL CDR2, and VL CDR3, respectively and the VH region comprising a first, second and third complementarity determining region (VH CDR1, VH CDR2, and VH CDR3, respectively. In several embodiments, the VL region comprises the sequence of SEQ ID NO. 45, 46, 47, or 48 or a sequence at least about 95% (e.g., 96, 97, 98, 99 or 99%) homologous to the sequence of SEQ NO. 45, 46, 47, or 48. In several embodiments, the VH region comprises the sequence of SEQ ID NO. 49, 50, 51 or 52 or a sequence at least about 95% (e.g., 96, 97, 98, 99 or 99%) homologous to the sequence of SEQ NO. 49, 50, 51 or 52.

In several embodiments, there is also provided an anti-CD19 binding moiety that comprises a light chain CDR comprising a first, second and third complementarity determining region (LC CDR1, LC CDR2, and LC CDR3, respectively. In several embodiments, the anti-CD19 binding moiety further comprises a heavy chain CDR comprising a first, second and third complementarity determining region (HC CDR1, HC CDR2, and HC CDR3, respectively. In several embodiments, the LC CDR1 comprises the sequence of SEQ ID NO. 53 or a sequence at least about 95% homologous to the sequence of SEQ NO. 53. In several embodiments, the LC CDR2 comprises the sequence of SEQ ID NO. 54 or a sequence at least about 95% homologous to the sequence of SEQ NO. 54. In several embodiments, the LC CDR3 comprises the sequence of SEQ ID NO. 55 or a sequence at least about 95% homologous to the sequence of SEQ NO. 55. In several embodiments, the HC CDR1 comprises the sequence of SEQ ID NO. 56 or a sequence at least about 95% homologous to the sequence of SEQ NO. 56. In several embodiments, the HC CDR2 comprises the sequence of SEQ ID NO. 57 or a sequence at least about 95% homologous to the sequence of SEQ NO. 57. In several embodiments, the HC CDR3 comprises the sequence of SEQ ID NO. 58 or a sequence at least about 95% homologous to the sequence of SEQ NO. 58. In several embodiments, the anti-CD19 binding moiety (and thus the resultant CAR) is engineered to not include certain sequences, such as, for example, those that may cause increased risk of immunogenicity and/or side effects, such as cytokine release syndrome. Thus, according to several embodiments, the anti-CD19 binding moiety does not comprise one or more of SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52. SEQ ID NO: 53, SEQ ID NO: 54, SEQ ID NO: 55, SEQ ID NO: 32, or SEQ ID NO: 33.

In several embodiments, the intracellular signaling domain of the chimeric receptor comprises an OX40 subdomain. In several embodiments, the intracellular signaling domain further comprises a CD3zeta subdomain. In several embodiments, the OX40 subdomain comprises the amino acid sequence of SEQ ID NO: 16 (or a sequence at least about 95% homologous to the sequence of SEQ ID NO. 16) and the CD3zeta subdomain comprises the amino acid sequence of SEQ ID NO: 8 (or a sequence at least about 95% homologous to the sequence of SEQ ID NO: 8).

In several embodiments, the hinge domain comprises a CD8a hinge domain. In several embodiments, the CD8a hinge domain, comprises the amino acid sequence of SEQ ID NO: 2 or a sequence at least about 95% homologous to the sequence of SEQ ID NO: 2).

In several embodiments, the immune cell also expresses membrane-bound interleukin-15 (mbIL15). In several embodiments, the mbIL15 comprises the amino acid sequence of SEQ ID NO: 12 or a sequence at least about 95% homologous to the sequence of SEQ ID NO: 12.

In several embodiments, wherein the chimeric receptor further comprises an extracellular domain of an NKG2D receptor. In several embodiments, the immune cell expresses a second chimeric receptor comprising an extracellular domain of an NKG2D receptor, a transmembrane domain, a cytotoxic signaling complex and optionally, mbIL15. In several embodiments, the extracellular domain of the NKG2D receptor comprises a functional fragment of NKG2D comprising the amino acid sequence of SEQ ID NO: 26 or a sequence at least about 95% homologous to the sequence of SEQ ID NO: 26. In various embodiments, the immune cell engineered to express the chimeric antigen receptor and/or chimeric receptors disclosed herein is an NK cell. In some embodiments, T cells are used. In several embodiments, combinations of NK and T cells (and/or other immune cells) are used.

In several embodiments, there are provided herein methods of treating cancer in a subject comprising administering to the subject having an engineered immune cell targeting CD19 as disclosed herein. Also provided for herein is the use of an immune cell targeting CD19 as disclosed herein for the treatment of cancer. Likewise, there is provided for herein the use of an immune cell targeting CD19 as disclosed herein in the preparation of a medicament for the treatment of cancer. In several embodiments, the cancer treated is acute lymphocytic leukemia.

Some embodiments of the methods and compositions described herein relate to an immune cell. In some embodiments, the immune cell expresses a CD19-directed chimeric receptor comprising an extracellular anti-CD19 moiety, a hinge and/or transmembrane domain, and/or an intracellular signaling domain. In some embodiments, the immune cell is a natural killer (NK) cell. In some embodiments, the immune cell is a T cell.

In some embodiments, the hinge domain comprises a CD8a hinge domain. In some embodiments, the hinge domain comprises an Ig4 SH domain.

In some embodiments, the transmembrane domain comprises a CD8a transmembrane domain. In some embodiments, the transmembrane domain comprises a CD28 transmembrane domain. In some embodiments, the transmembrane domain comprises a CD3 transmembrane domain.

In some embodiments, the signaling domain comprises an OX40 signaling domain. In some embodiments, the signaling domain comprises a 4-1 BB signaling domain. In some embodiments, the signaling domain comprises a CD28 signaling domain. In some embodiments, the signaling domain comprises an NKp80 signaling domain. In some embodiments, the signaling domain comprises a CD16 IC signaling domain. In some embodiments, the signaling domain comprises a CD3zeta or CD3ζ ITAM signaling domain. In some embodiments, the signaling domain comprises an mbIL-15 signaling domain. In some embodiments, the signaling domain comprises a 2A cleavage domain. In some embodiments, the mIL-15 signaling domain is separated from the rest or another portion of the CD19-directed chimeric receptor by a 2A cleavage domain.

Some embodiments relate to a method comprising administering an immune cell as described herein to a subject in need. In some embodiments, the subject has cancer. In some embodiments, the administration treats, inhibits, or prevents progression of the cancer.

BRIEF DESCRIPTION OF THE DRAWINGS

FIG. 1A includes depictions of non-limiting examples of CD19-directed chimeric receptors.

FIG. 3A also includes depictions of non-limiting examples of CD19-directed chimeric receptors.

FIG. 3D also includes depictions of non-limiting examples of CD19-directed chimeric receptors comprising humanized CD19 binding domains.

FIG. 3F also includes depictions of non-limiting examples of CD19-directed chimeric receptors comprising humanized CD19 binding domains.

FIG. 3G also includes depictions of non-limiting examples of CD19-directed chimeric receptors comprising humanized CD19 binding domains without a tag sequence.

FIGS. 11A-11E depict data related to cytokine release by NK cells expressing various CD19-directed chimeric receptors when co-cultured with Nalm6 cells. FIG. 11A depicts Granzyme B release. FIG. 11B depicts perforin release. FIG. 11C depicts TNF-alpha release. FIG. 11D depicts GM-CSF release. FIG. 11E depicts interferon gamma release.

FIGS. 12A-12E depict data related to cytokine release by NK cells expressing various CD19-directed chimeric receptors when co-cultured with Raji cells. FIG. 12A depicts Granzyme B release. FIG. 12B depicts perforin release. FIG. 12C depicts TNF-alpha release. FIG. 12D depicts GM-CSF release. FIG. 12E depicts interferon gamma release.

FIG. 15 depicts data related to selected functional characteristics of selected humanized anti-CD19 CAR constructs.

FIG. 19A shows data related to the cytotoxicity of NK cells from a first donor engineered to express selected humanized CD19 CAR constructs disclosed herein against Raji cells with addition of the Raji cells to the NK cell culture at day 7 and again at day 14. FIG. 19B shows data related to the cytotoxicity of NK cells from a first donor engineered to express selected humanized CD19 CAR constructs disclosed herein against Nalm6 cells with addition of the Nalm6 cells to the NK cell culture at day 7 and again at day 14. FIG. 19C shows data related to the cytotoxicity of NK cells from a second donor engineered to express selected humanized CD19 CAR constructs disclosed herein against Raji cells with addition of the Raji cells to the NK cell culture at day 7 and again at day 14. FIG. 19D shows data related to the cytotoxicity of NK cells from a second donor engineered to express selected humanized CD19 CAR constructs disclosed herein against Nalm6 cells with addition of the Nalm6 cells to the NK cell culture at day 7 and again at day 14.

FIG. 20A shows fluorescence data from expression of non-limiting examples of humanized anti-CD19 CAR constructs from two donors 10 days post-transduction. FIG. 20B shows data related to the percentage of cells expressing CD19 (indicative of the efficiency of expression of the given anti-CD19 CAR.

FIG. 21A shows data related to the cytotoxicity of NK cells (from the first of the two donors of FIG. 20) engineered to express selected humanized CD19 CAR constructs disclosed herein against Raji cells with addition of the Raji cells to the NK cell culture at day 7 and again at day 14. FIG. 21B shows data related to the cytotoxicity of NK cells (from the second of the two donors of FIG. 20) engineered to express selected humanized CD19 CAR constructs disclosed herein against Raji cells with addition of the Raji cells to the NK cell culture at day 7 and again at day 14.

FIG. 22A shows interferon gamma release. FIG. 22B shows GM-CSF release. FIG. 22C shows tumor necrosis factor release. FIG. 22D shows perforin release. FIG. 22E shows granzyme release.

FIG. 23A shows the analysis of survival of NK cells from a first donor engineered to express the indicated non-limiting embodiments of anti-CD19 CAR constructs at days 7, 13, 19, and 26 post-transduction. FIG. 23B shows the analysis of survival of NK cells from a second donor engineered to express the indicated non-limiting embodiments of anti-CD19 CAR constructs at days 7, 13, 19, and 26 post-transduction. FIG. 23C shows the analysis of survival of NK cells from a third donor engineered to express the indicated non-limiting embodiments of anti-CD19 CAR constructs at days 11, 19, and 26 post-transduction. FIG. 23D shows the analysis of survival of NK cells from a fourth donor engineered to express the indicated non-limiting embodiments of anti-CD19 CAR constructs at days 11, 19, and 26 post-transduction. For each experiment, media was changed twice per week.

FIG. 25A shows GFP transduced NK cells as a control. FIG. 25B shows CD19 expression in NK cells transduced with NK19-1. FIG. 25C shows CD19 expression in NK cells transduced with NK19H-1. FIG. 25D shows CD19 expression in NK cells transduced with NK19H-2. FIG. 25E shows CD19 expression in NK cells transduced with NK19H-3. FIG. 25F shows CD19 expression in NK cells transduced with NK19H-4. FIG. 25G shows CD19 expression in NK cells transduced with NK19H-5. FIG. 25H shows CD19 expression in NK cells transduced with NK19H-11. FIG. 25I shows CD19 expression in NK cells transduced with NK19H-12.

FIG. 26A shows data related to the cytotoxicity of NK cells (from a first donor) engineered to express selected humanized CD19 CAR constructs disclosed herein against Raji cells with addition of the Raji cells to the NK cell culture at day 7 and again at day 14. FIG. 26B shows data related to the cytotoxicity of NK cells (from the first donor) engineered to express selected humanized CD19 CAR constructs disclosed herein against Nalm6 cells with addition of the Nalm6 cells to the NK cell culture at day 7 and again at day 14. FIG. 26C shows data related to the cytotoxicity of NK cells (from a second donor) engineered to express selected humanized CD19 CAR constructs disclosed herein against Raji cells with addition of the Raji cells to the NK cell culture at day 7 and again at day 14. FIG. 26D shows data related to the cytotoxicity of NK cells (from the second donor) engineered to express selected humanized CD19 CAR constructs disclosed herein against Nalm6 cells with addition of the Nalm6 cells to the NK cell culture at day 7 and again at day 14.

FIG. 27A shows flow cytometry data for NK cells from a donor that were engineered to express various non-limiting anti-CD19 CAR constructs disclosed herein. FIG. 27B shows corresponding data from NK cells isolated from an additional donor.

FIG. 28A shows the Raji cell count over time when exposed (at 1:1 E:T ratio) to NK cells (from the first donor of FIG. 27) expressing the non-limiting examples of anti-CD19 CAR constructs indicated. FIG. 28B shows the Raji cell count over time when exposed (at 1:1 E:T ratio) to NK cells (from the second donor of FIG. 27) expressing the non-limiting examples of anti-CD19 CAR constructs indicated.

FIG. 29A shows a schematic depiction of an experimental protocol for assessing the effectiveness of CD19-directed CAR constructs in vivo. FIG. 29B shows in vivo bioluminescent imaging of mice having been administered NALM6 tumor cells and treated with the indicated construct. FIG. 29C shows a line graph of the bioluminescent data collected from FIG. 29B. FIG. 29D is a survival curve showing the days that animals in each treatment group survived. FIG. 29E shows the relative expression level of the indicated constructs by NK cells, as measured by the MFI of a tag included in the CD19 CAR construct.

FIG. 30A shows data related to the expression of the indicated constructs as a percentage of all CD56 positive cells in a blood sample from mice 15 days post-NK cell administration (e.g., as per the schematic in FIG. 29A). FIG. 30B shows data related to expression of the indicated constructs as a percentage of cells that are both CD56 positive and express a Flag tag (as part of the CD19 CAR construct), also at 15 days post-NK cell administration. FIG. 30C shows data related to detection of GFP+ tumor cells in samples from animals treated with the indicated constructs, also at day 15 post-NK cell administration. FIGS. 30D, 30E, and 30F show corresponding data at 32 days post-NK cell administration.

FIG. 31A shows data related to the expressing of selected non-flag tagged humanized anti CD19 CAR constructs over time. FIG. 31B shows corresponding data in terms of the detected mean fluorescent intensity for the indicated constructs.

FIG. 32A shows data at 10 days after inception of co-culture with Raji cells. FIG. 32B shows data related to Raji at the final time point, 14 days. FIG. 32C shows data related to Nalm6 cells at 10 days. FIG. 32D shows data related to Nalm6 cells at 14 days.

FIG. 33A shows expression of interferon gamma by NK cells expressing the indicated constructs after co-culturing with Raji cells. FIG. 33B shows expression of GM-CSF by NK cells expressing the indicated constructs after co-culturing with Raji cells. FIG. 33C shows expression of tumor necrosis factor alpha by NK cells expressing the indicated constructs after co-culturing with Raji cells. FIG. 33D shows expression of perforin by NK cells expressing the indicated constructs after co-culturing with Raji cells. FIG. 33E shows expression of granzyme B by NK cells expressing the indicated constructs after co-culturing with Raji cells. FIG. 33F shows expression of interferon gamma by NK cells expressing the indicated constructs after co-culturing with Nalm6 cells. FIG. 33G shows expression of GM-CSF by NK cells expressing the indicated constructs after co-culturing with Nalm6 cells. FIG. 33H shows expression of tumor necrosis factor alpha by NK cells expressing the indicated constructs after co-culturing with Nalm6 cells. FIG. 33I shows expression of perforin by NK cells expressing the indicated constructs after co-culturing with Nalm6 cells. FIG. 33J shows expression of granzyme B by NK cells expressing the indicated constructs after co-culturing with Nalm6 cells.

FIG. 35A shows a schematic depiction of an experimental protocol for assessing the effectiveness of humanized, non-tagged, CD19-directed CAR constructs in vivo. FIG. 35B shows in vivo bioluminescent imaging of mice having been administered NALM6 tumor cells and treated with the indicated construct. FIG. 35C shows a line graph of the bioluminescent data collected from FIG. 35B. FIG. 35D shows the relative expression level of the indicated constructs by NK cells, as measured by detection of a CD19-Fc fusion protein that binds to the CD19 CAR construct.

FIG. 36A shows data related to the expression of the indicated constructs as a percentage of all CD56 positive cells in a blood sample from mice 13 days post-NK cell administration (e.g., as per the schematic in FIG. 35A). FIG. 36B shows data related to detection of CD19+ tumor cells in samples from animals treated with the indicated constructs, also at 13 days post-NK cell administration. FIG. 36C shows data related to detection of GFP+ tumor cells in samples from animals treated with the indicated constructs, also at 13 days post-NK cell administration. FIGS. 36D, 36E, and 36F show corresponding data at 27 days post-NK cell administration.

FIG. 37A shows a schematic depiction of an experimental protocol for assessing the effectiveness of humanized, NK cells expressing various CD19-directed CAR constructs in vivo. The various experimental groups tested are as indicated. For cells with an "IL12/IL18" designation, the cells were expanded in the presence of soluble IL12 and/or IL18, as described in in U.S. Provisional Patent Application No. 62/881,311, filed Jul. 31, 2019 and Application No. 62/932,342, filed Nov. 7, 2019, each of which is incorporated in its entirety by reference herein. FIGS. 37B and 37C show bioluminescence data from animals dosed with Nalm6 tumor cells and treated with the indicated construct.

FIG. 38A shows bioluminescence (as photon/second flux) from animals receiving untransduced NK cells. FIG. 38B shows flux measured in animals receiving PBS as a vehicle. FIG. 38C shows flux measured in animals receiving previously frozen NK cells expressing the NK19 NF2 CAR (as a non-limiting example of a CAR). FIG. 38D shows flux measured in animals receiving previously frozen NK cells expressing the NK19 NF2 CAR (as a non-limiting example of a CAR) expanded using IL12 and/or IL18. FIG. 38E and FIG. 38F show flux measured in animals receiving fresh NK cells expressing the NK19 NF2 CAR (as a non-limiting example of a CAR). FIG. 38G and FIG. 38H show flux measured in animals receiving previously fresh NK cells expressing the NK19 NF2 CAR (as a non-limiting example of a CAR) expanded using IL12 and/or IL18. FIG. 38I shows a line graph depicting the bioluminescence measured in the various groups over the first 30 days post-tumor inoculation. FIG. 38J shows a line graph depicting the bioluminescence measured in the various groups over the first 56 days post-tumor inoculation.

DETAILED DESCRIPTION

Figure 1B:
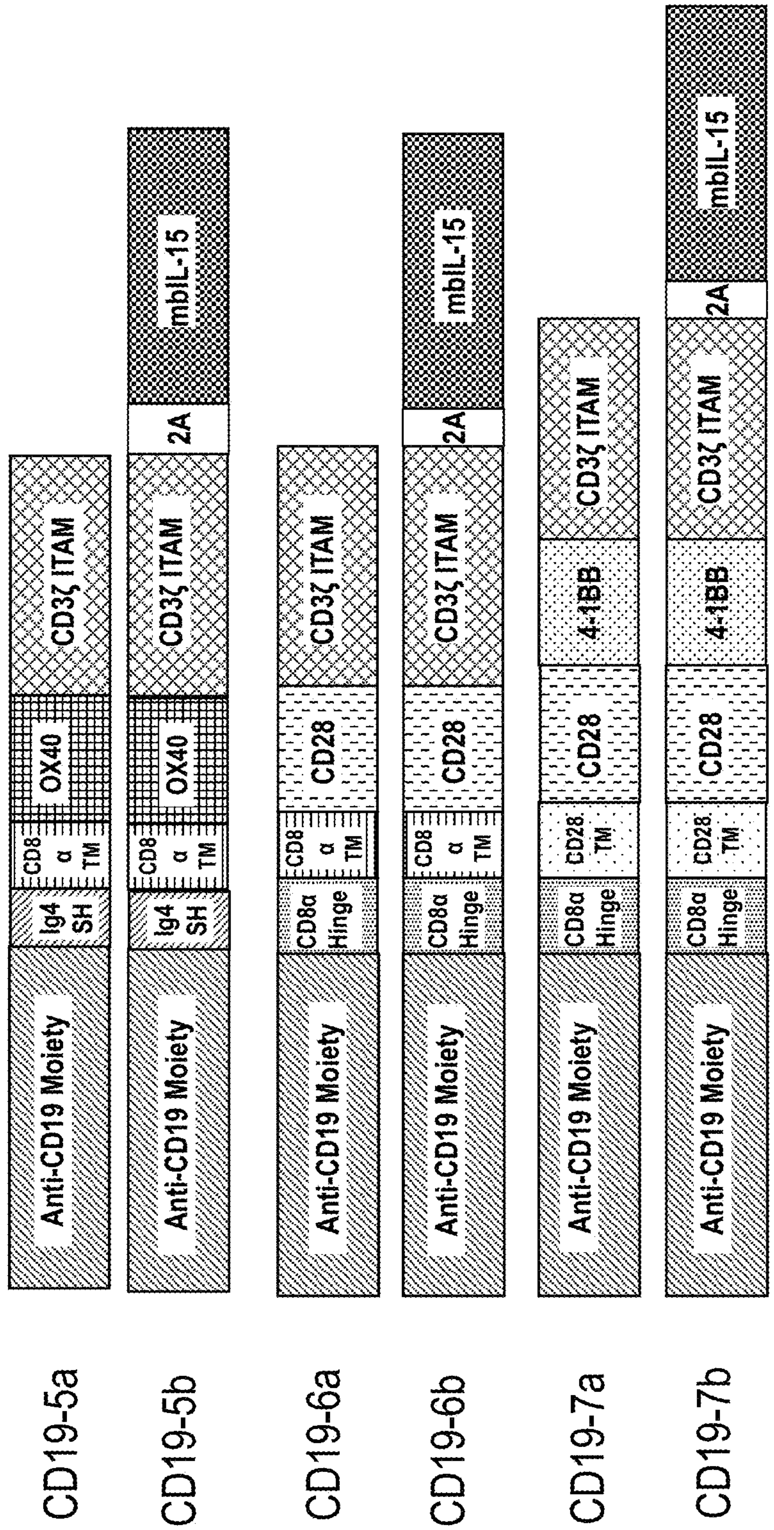
FIG. 1B includes depictions of additional non-limiting examples of CD19-directed chimeric receptors.

Some embodiments of the methods and compositions provided herein relate to CD19-directed chimeric receptors. In some embodiments, the receptors are expressed on a cell as described herein. Some embodiments include methods of use of the compositions or cells in immunotherapy.

The term "anticancer effect" refers to a biological effect which can be manifested by various means, including but not limited to, a decrease in tumor volume, a decrease in the number of cancer cells, a decrease in the number of metastases, an increase in life expectancy, decrease in cancer cell proliferation, decrease in cancer cell survival, or amelioration of various physiological symptoms associated with the cancerous condition. An "anticancer effect" can also be manifested by the ability of the SIRs in prevention of the occurrence of cancer in the first place.

Cell Types

Some embodiments of the methods and compositions provided herein relate to a cell such as an immune cell. For example, an immune cell may be engineered to include a chimeric receptor such as a CD19-directed chimeric receptor, or engineered to include a nucleic acid encoding said chimeric receptor as described herein.

Traditional anti-cancer therapies relied on a surgical approach, radiation therapy, chemotherapy, or combinations of these methods. As research led to a greater understanding of some of the mechanisms of certain cancers, this knowledge was leveraged to develop targeted cancer therapies. Targeted therapy is a cancer treatment that employs certain drugs that target specific genes or proteins found in cancer cells or cells supporting cancer growth, (like blood vessel cells) to reduce or arrest cancer cell growth. More recently, genetic engineering has enabled approaches to be developed that harness certain aspects of the immune system to fight cancers. In some cases, a patient's own immune cells are modified to specifically eradicate that patient's type of cancer. Various types of immune cells can be used, such as T cells or Natural Killer (NK cells), as described in more detail below.

To facilitate cancer immunotherapies, there are provided for herein polynucleotides, polypeptides, and vectors that encode chimeric antigen receptors (CAR) that comprise a target binding moiety (e.g., an extracellular binder of a ligand, or a CD19-directed chimeric receptor, expressed by a cancer cell) and a cytotoxic signaling complex. For example, some embodiments include a polynucleotide, polypeptide, or vector that encodes a CD19-directed chimeric receptor to facilitate targeting of an immune cell to a cancer and exerting cytotoxic effects on the cancer cell. Also provided are engineered immune cells (e.g., T cells or NK cells) expressing such CARs. There are also provided herein, in several embodiments, polynucleotides, polypeptides, and vectors that encode a construct comprising an extracellular domain comprising two or more subdomains, e.g., first CD19-targeting subdomain comprising a CD19 binding moiety as disclosed herein and a second subdomain comprising a C-type lectin-like receptor and a cytotoxic signaling complex. Also provided are engineered immune cells (e.g., T cells or NK cells) expressing such bi-specific constructs. Engineered immune cells (e.g., T cells or NK cells) expressing multi-specific constructs and/or having the ability to bind a plurality of target markers are also provided. Methods of treating cancer and other uses of such cells for cancer immunotherapy are also provided for herein.

Engineered Cells for Immunotherapy

In several embodiments, cells of the immune system are engineered to have enhanced cytotoxic effects against target cells, such as tumor cells. For example, a cell of the immune system may be engineered to include a CD19-directed chimeric receptor as described herein. In several embodiments, white blood cells or leukocytes, are used, since their native function is to defend the body against growth of abnormal cells and infectious disease. There are a variety of types of white bloods cells that serve specific roles in the human immune system, and are therefore a preferred starting point for the engineering of cells disclosed herein. White blood cells include granulocytes and agranulocytes (presence or absence of granules in the cytoplasm, respectively). Granulocytes include basophils, eosinophils, neutrophils, and mast cells. Agranulocytes include lymphocytes and monocytes. Cells such as those that follow or are otherwise described herein may be engineered to include a chimeric receptor such as a CD19-directed chimeric receptor, or a nucleic acid encoding the chimeric receptor and/or engineered to co-express a membrane-bound interleukin 15 (mbIL15) co-stimulatory domain.

Monocytes for Immunotherapy

Monocytes are a subtype of leukocyte. Monocytes can differentiate into macrophages and myeloid lineage dendritic cells. Monocytes are associated with the adaptive immune system and serve the main functions of phagocytosis, antigen presentation, and cytokine production. Phagocytosis is the process of uptake cellular material, or entire cells, followed by digestion and destruction of the engulfed cellular material. In several embodiments, monocytes are used in connection with one or more additional engineered cells as disclosed herein. Some embodiments of the methods and compositions described herein relate to a monocyte that includes a CD19-directed chimeric receptor, or a nucleic acid encoding the CD19-directed chimeric receptor. Several embodiments of the methods and compositions disclosed herein relate to monocytes engineered to express a CD19-directed chimeric receptor and a membrane-bound interleukin 15 (mbIL15) co-stimulatory domain.

Lymphocytes for Immunotherapy

Lymphocytes, the other primary sub-type of leukocyte include T cells (cell-mediated, cytotoxic adaptive immunity), natural killer cells (cell-mediated, cytotoxic innate immunity), and B cells (humoral, antibody-driven adaptive immunity). While B cells are engineered according to several embodiments, disclosed herein, several embodiments also relate to engineered T cells or engineered NK cells (mixtures of T cells and NK cells are used in some embodiments). Some embodiments of the methods and compositions described herein relate to a lymphocyte that includes a CD19-directed chimeric receptor, or a nucleic acid encoding the CD19-directed chimeric receptor. Several embodiments of the methods and compositions disclosed herein relate to lymphocytes engineered to express a CD19-directed chimeric receptor and a membrane-bound interleukin 15 (mbIL15) co-stimulatory domain.

T Cells for Immunotherapy

T cells are distinguishable from other lymphocytes subtypes (e.g., B cells or NK cells) based on the presence of a T-cell receptor on the cell surface. T cells can be divided into various different subtypes, including effector T cells, helper T cells, cytotoxic T cells, memory T cells, regulatory T cells, natural killer T cell, mucosal associated invariant T cells and gamma delta T cells. In some embodiments, a specific subtype of T cell is engineered. In some embodiments, a mixed pool of T cell subtypes is engineered. In some embodiments, there is no specific selection of a type of T cells to be engineered to express the cytotoxic receptor complexes disclosed herein. In several embodiments, specific techniques, such as use of cytokine stimulation are used to enhance expansion/collection of T cells with a specific marker profile. For example, in several embodiments, activation of certain human T cells, e.g. CD4+ T cells, CD8+ T cells is achieved through use of CD3 and/or CD28 as stimulatory molecules. In several embodiments, there is provided a method of treating or preventing cancer or an infectious disease, comprising administering a therapeutically effective amount of T cells expressing the cytotoxic receptor complex and/or a homing moiety as described herein. In several embodiments, the engineered T cells are autologous cells, while in some embodiments, the T cells are allogeneic cells. Some embodiments of the methods and compositions described herein relate to a T cell that includes a CD19-directed chimeric receptor, or a nucleic acid encoding the CD19-directed chimeric receptor. Several embodiments of the methods and compositions disclosed herein relate to T-cells engineered to express a CD19-directed chimeric receptor and a membrane-bound interleukin 15 (mbIL15) co-stimulatory domain.

NK Cells for Immunotherapy

In several embodiments, there is provided a method of treating or preventing cancer or an infectious disease, comprising administering a therapeutically effective amount of natural killer (NK) cells expressing the cytotoxic receptor complex and/or a homing moiety as described herein. In several embodiments, the engineered NK cells are autologous cells, while in some embodiments, the NK cells are allogeneic cells. In several embodiments, NK cells are preferred because the natural cytotoxic potential of NK cells is relatively high. In several embodiments, it is unexpectedly beneficial that the engineered cells disclosed herein can further upregulate the cytotoxic activity of NK cells, leading to an even more effective activity against target cells (e.g., tumor or other diseased cells). Some embodiments of the methods and compositions described herein relate to an NK that includes a CD19-directed chimeric receptor, or a nucleic acid encoding the CD19-directed chimeric receptor. Several embodiments of the methods and compositions disclosed herein relate to NK cells engineered to express a CD19-directed chimeric receptor and a membrane-bound interleukin 15 (mbIL15) co-stimulatory domain.

Hematopoietic Stem Cells for Cancer Immunotherapy

In some embodiments, hematopoietic stem cells (HSCs) are used in the methods of immunotherapy disclosed herein. In several embodiments, the cells are engineered to express a homing moiety and/or a cytotoxic receptor complex. HSCs are used, in several embodiments, to leverage their ability to engraft for long-term blood cell production, which could result in a sustained source of targeted anti-cancer effector cells, for example to combat cancer remissions. In several embodiments, this ongoing production helps to offset anergy or exhaustion of other cell types, for example due to the tumor microenvironment. In several embodiments allogeneic HSCs are used, while in some embodiments, autologous HSCs are used. In several embodiments, HSCs are used in combination with one or more additional engineered cell type disclosed herein. Some embodiments of the methods and compositions described herein relate to a stem cell, such as a hematopoietic stem cell, that includes a CD19-directed chimeric receptor, or a nucleic acid encoding the CD19-directed chimeric receptor. Several embodiments of the methods and compositions disclosed herein relate to stem cells, such as hematopoietic stem cells that are engineered to express a CD19-directed chimeric receptor and a membrane-bound interleukin 15 (mbIL15) co-stimulatory domain.

Extracellular Domains (Tumor Binder)

Some embodiments of the compositions and methods described herein relate to a chimeric receptor, such as a CD19-directed chimeric receptor, that includes an extracellular domain. In some embodiments, the extracellular domain comprises a tumor-binding domain (also referred to as an antigen-binding protein or antigen-binding domain) as described herein. in some embodiments, the antigen-binding domain is derived from or comprises wild-type or non-wild-type sequence of an antibody, an antibody fragment, an scFv, a Fv, a Fab, a (Fab')2, a single domain antibody (SDAB), a vH or vL domain, a camelid VHH domain, or a non-immunoglobulin scaffold such as a DARPIN, an affibody, an affilin, an adnectin, an affitin, a repebody, a fynomer, an alphabody, an avimer, an atrimer, a centyrin, a pronectin, an anticalin, a kunitz domain, an Armadillo repeat protein, an autoantigen, a receptor or a ligand. In some embodiments, the tumor-binding domain contains more than one antigen binding domain. In embodiments, the antigen-binding domain is operably linked directly or via an optional linker to the NH2-terminal end of a TCR domain (e.g. constant chains of TCR-alpha, TCR-beta1, TCR-beta2, preTCR-alpha, pre-TCR-alpha-Del48, TCR-gamma, or TCR-delta)

Antigen-Binding Proteins

There are provided, in several embodiments, antigen-binding proteins. As used herein, the term “antigen-binding protein” shall be given its ordinary meaning, and shall also refer to a protein comprising an antigen-binding fragment that binds to an antigen and, optionally, a scaffold or framework portion that allows the antigen-binding fragment to adopt a conformation that promotes binding of the antigen-binding protein to the antigen. In some embodiments, the antigen is a cancer antigen (e.g., CD19) or a fragment thereof. In some embodiments, the antigen-binding fragment comprises at least one CDR from an antibody that binds to the antigen. In some embodiments, the antigen-binding fragment comprises all three CDRs from the heavy chain of an antibody that binds to the antigen or from the light chain of an antibody that binds to the antigen. In still some embodiments, the antigen-binding fragment comprises all six CDRs from an antibody that binds to the antigen (three from the heavy chain and three from the light chain). In several embodiments, the antigen-binding fragment comprises one, two, three, four, five, or six CDRs from an antibody that binds to the antigen, and in several embodiments, the CDRs can be any combination of heavy and/or light chain CDRs. The antigen-binding fragment in some embodiments is an antibody fragment.

Nonlimiting examples of antigen-binding proteins include antibodies, antibody fragments (e.g., an antigen-binding fragment of an antibody), antibody derivatives, and antibody analogs. Further specific examples include, but are not limited to, a single-chain variable fragment (scFv), a nanobody (e.g. VH domain of camelid heavy chain antibodies; VHH fragment), a Fab fragment, a Fab' fragment, a F(ab')2 fragment, a Fv fragment, a Fd fragment, and a complementarity determining region (CDR) fragment. These molecules can be derived from any mammalian source, such as human, mouse, rat, rabbit, or pig, dog, or camelid. Antibody fragments may compete for binding of a target antigen with an intact (e.g., native) antibody and the fragments may be produced by the modification of intact antibodies (e.g. enzymatic or chemical cleavage) or synthesized de novo using recombinant DNA technologies or peptide synthesis. The antigen-binding protein can comprise, for example, an alternative protein scaffold or artificial scaffold with grafted CDRs or CDR derivatives. Such scaffolds include, but are not limited to, antibody-derived scaffolds comprising mutations introduced to, for example, stabilize the three-dimensional structure of the antigen-binding protein as well as wholly synthetic scaffolds comprising, for example, a biocompatible polymer. In addition, peptide antibody mimetics ("PAMs") can be used, as well as scaffolds based on antibody mimetics utilizing fibronectin components as a scaffold.

In some embodiments, the antigen-binding protein comprises one or more antibody fragments incorporated into a single polypeptide chain or into multiple polypeptide chains. For instance, antigen-binding proteins can include, but are not limited to, a diabody; an intrabody; a domain antibody (single VL or VH domain or two or more VH domains joined by a peptide linker); a maxibody (2 scFvs fused to Fc region); a triabody; a tetrabody; a minibody (scFv fused to CH3 domain); a peptibody (one or more peptides attached to an Fc region); a linear antibody (a pair of tandem Fd segments (VH-CH1-VH-CH1) which, together with complementary light chain polypeptides, form a pair of antigen binding regions); a small modular immunopharmaceutical; and immunoglobulin fusion proteins (e.g. IgG-scFv, IgG-Fab, 2scFv-IgG, 4scFv-IgG, VH-IgG, IgG-VH, and Fab-scFv-Fc).

In some embodiments, the antigen-binding protein has the structure of an immunoglobulin. As used herein, the term "immunoglobulin" shall be given its ordinary meaning, and shall also refer to a tetrameric molecule, with each tetramer comprising two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function.

Within light and heavy chains, the variable (V) and constant regions (C) are joined by a "J" region of about 12 or more amino acids, with the heavy chain also including a "D" region of about 10 more amino acids. The variable regions of each light/heavy chain pair form the antibody binding site such that an intact immunoglobulin has two binding sites.

Immunoglobulin chains exhibit the same general structure of relatively conserved framework regions (FR) joined by three hypervariable regions, also called complementarity determining regions or CDRs. From N-terminus to C-terminus, both light and heavy chains comprise the domains FR1, CDR1, FR2, CDR2, FR3, CDR3 and FR4.

Human light chains are classified as kappa and lambda light chains. An antibody "light chain", refers to the smaller of the two types of polypeptide chains present in antibody molecules in their naturally occurring conformations. Kappa (K) and lambda (A) light chains refer to the two major antibody light chain isotypes. A light chain may include a polypeptide comprising, from amino terminus to carboxyl terminus, a single immunoglobulin light chain variable region (VL) and a single immunoglobulin light chain constant domain (CL).

Heavy chains are classified as mu (A delta (A), gamma (γ), alpha (a), and epsilon (E), and define the antibody's isotype as IgM, IgD, IgG, IgA, and IgE, respectively. An antibody "heavy chain" refers to the larger of the two types of polypeptide chains present in antibody molecules in their naturally occurring conformations, and which normally determines the class to which the antibody belongs. A heavy chain may include a polypeptide comprising, from amino terminus to carboxyl terminus, a single immunoglobulin heavy chain variable region (VH), an immunoglobulin heavy chain constant domain 1 (CH1), an immunoglobulin hinge region, an immunoglobulin heavy chain constant domain 2 (CH2), an immunoglobulin heavy chain constant domain 3 (CH3), and optionally an immunoglobulin heavy chain constant domain 4 (CH4).

The IgG-class is further divided into subclasses, namely, IgG1, IgG2, IgG3, and IgG4. The IgA-class is further divided into subclasses, namely IgA1 and IgA2. The IgM has subclasses including, but not limited to, IgM1 and IgM2. The heavy chains in IgG, IgA, and IgD antibodies have three domains (CH1, CH2, and CH3), whereas the heavy chains in IgM and IgE antibodies have four domains (CH1, CH2, CH3, and CH4). The immunoglobulin heavy chain constant domains can be from any immunoglobulin isotype, including subtypes. The antibody chains are linked together via inter-polypeptide disulfide bonds between the CL domain and the CH1 domain (e.g., between the light and heavy chain) and between the hinge regions of the antibody heavy chains.

In some embodiments, the antigen-binding protein is an antibody. The term "antibody", as used herein, refers to a protein, or polypeptide sequence derived from an immunoglobulin molecule which specifically binds with an antigen. Antibodies can be monoclonal, or polyclonal, multiple or single chain, or intact immunoglobulins, and may be derived from natural sources or from recombinant sources. Antibodies can be tetramers of immunoglobulin molecules. The antibody may be "humanized", "chimeric" or non-human. An antibody may include an intact immunoglobulin of any isotype, and includes, for instance, chimeric, humanized, human, and bispecific antibodies. An intact antibody will generally comprise at least two full-length heavy chains and two full-length light chains. Antibody sequences can be derived solely from a single species, or can be "chimeric," that is, different portions of the antibody can be derived from two different species as described further below. Unless otherwise indicated, the term "antibody" also includes antibodies comprising two substantially full-length heavy chains and two substantially full-length light chains provided the antibodies retain the same or similar binding and/or function as the antibody comprised of two full length light and heavy chains. For example, antibodies having 1, 2, 3, 4, or 5 amino acid residue substitutions, insertions or deletions at the N-terminus and/or C-terminus of the heavy and/or light chains are included in the definition provided that the antibodies retain the same or similar binding and/or function as the antibodies comprising two full length heavy chains and two full length light chains. Examples of antibodies include monoclonal antibodies, polyclonal antibodies, chimeric antibodies, humanized antibodies, human antibodies, bispecific antibodies, and synthetic antibodies. There is provided, in some embodiments, monoclonal and polyclonal antibodies. As used herein, the term “polyclonal antibody” shall be given its ordinary meaning, and shall also refer to a population of antibodies that are typically widely varied in composition and binding specificity. As used herein, the term “monoclonal antibody” (“mAb”) shall be given its ordinary meaning, and shall also refer to one or more of a population of antibodies having identical sequences. Monoclonal antibodies bind to the antigen at a particular epitope on the antigen.

In some embodiments, the antigen-binding protein is a fragment or antigen-binding fragment of an antibody. The term “antibody fragment” refers to at least one portion of an antibody, that retains the ability to specifically interact with (e.g., by binding, steric hindrance, stabilizing/destabilizing, spatial distribution) an epitope of an antigen. Examples of antibody fragments include, but are not limited to, Fab, Fab', F(ab')2, Fv fragments, scFv antibody fragments, disulfide-linked Fvs (sdFv), a Fd fragment consisting of the VH and CHI domains, linear antibodies, single domain antibodies such as sdAb (either vL or vH), camelid vHH domains, multi-specific antibodies formed from antibody fragments such as a bivalent fragment comprising two Fab fragments linked by a disulfide bridge at the hinge region, and an isolated CDR or other epitope binding fragments of an antibody. An antigen binding fragment can also be incorporated into single domain antibodies, maxibodies, minibodies, nanobodies, intrabodies, diabodies, triabodies, tetrabodies, v-NAR and bis-scFv (see, e.g., Hollinger and Hudson, Nature Biotechnology 23: 1126-1136, 2005). Antigen binding fragments can also be grafted into scaffolds based on polypeptides such as a fibronectin type III (Fn3)(see U.S. Pat. No. 6,703,199, which describes fibronectin polypeptide mini bodies). An antibody fragment may include a Fab, Fab', F(ab')2, and/or Fv fragment that contains at least one CDR of an immunoglobulin that is sufficient to confer specific antigen binding to a cancer antigen (e.g., CD19). Antibody fragments may be produced by recombinant DNA techniques or by enzymatic or chemical cleavage of intact antibodies.

In some embodiments, Fab fragments are provided. A Fab fragment is a monovalent fragment having the VL, VH, CL and CH1 domains; a F(ab')2 fragment is a bivalent fragment having two Fab fragments linked by a disulfide bridge at the hinge region; a Fd fragment has the VH and CH1 domains; an Fv fragment has the VL and VH domains of a single arm of an antibody; and a dAb fragment has a VH domain, a VL domain, or an antigen-binding fragment of a VH or VL domain. In some embodiments, these antibody fragments can be incorporated into single domain antibodies, single-chain antibodies, maxibodies, minibodies, intrabodies, diabodies, triabodies, tetrabodies, v-NAR and bis-scFv. In some embodiments, the antibodies comprise at least one CDR as described herein.

There is also provided for herein, in several embodiments, single-chain variable fragments. As used herein, the term “single-chain variable fragment” (“scFv”) shall be given its ordinary meaning, and shall also refer to a fusion protein in which a VL and a VH region are joined via a linker (e.g., a synthetic sequence of amino acid residues) to form a continuous protein chain wherein the linker is long enough to allow the protein chain to fold back on itself and form a monovalent antigen binding site). For the sake of clarity, unless otherwise indicated as such, a “single-chain variable fragment” is not an antibody or an antibody fragment as defined herein. Diabodies are bivalent antibodies comprising two polypeptide chains, wherein each polypeptide chain comprises VH and VL domains joined by a linker that is configured to reduce or not allow for pairing between two domains on the same chain, thus allowing each domain to pair with a complementary domain on another polypeptide chain. According to several embodiments, if the two polypeptide chains of a diabody are identical, then a diabody resulting from their pairing will have two identical antigen binding sites. Polypeptide chains having different sequences can be used to make a diabody with two different antigen binding sites. Similarly, tribodies and tetrabodies are antibodies comprising three and four polypeptide chains, respectively, and forming three and four antigen binding sites, respectively, which can be the same or different.

In several embodiments, the antigen-binding protein comprises one or more CDRs. As used herein, the term “CDR” shall be given its ordinary meaning, and shall also refer to the complementarity determining region (also termed “minimal recognition units” or “hypervariable region”) within antibody variable sequences. The CDRs permit the antigen-binding protein to specifically bind to a particular antigen of interest. There are three heavy chain variable region CDRs (CDRH1, CDRH2 and CDRH3) and three light chain variable region CDRs (CDRL1, CDRL2 and CDRL3). The CDRs in each of the two chains typically are aligned by the framework regions to form a structure that binds specifically to a specific epitope or domain on the target protein. From N-terminus to C-terminus, naturally-occurring light and heavy chain variable regions both typically conform to the following order of these elements: FR1, CDR1, FR2, CDR2, FR3, CDR3 and FR4. A numbering system has been devised for assigning numbers to amino acids that occupy positions in each of these domains. This numbering system is defined in Kabat Sequences of Proteins of Immunological Interest (1987 and 1991, NIH, Bethesda, MD), or Chothia & Lesk, 1987, J. Mol. Biol. 196:901-917; Chothia et al., 1989, Nature 342:878-883. Complementarity determining regions (CDRs) and framework regions (FR) of a given antibody may be identified using this system. Other numbering systems for the amino acids in immunoglobulin chains include IMGT® (the international ImMunoGeneTics information system; Lefranc et al, Dev. Comp. Immunol. 29:185-203; 2005) and AHo (Honegger and Pluckthun, J. Mol. Biol. 309(3):657-670; 2001). One or more CDRs may be incorporated into a molecule either covalently or noncovalently to make it an antigen-binding protein. In several embodiments, the antigen-binding proteins provided herein comprise a heavy chain variable region selected from SEQ ID NO: 104 and SEQ ID NO: 106. In several embodiments, the antigen-binding proteins provided herein comprise a light chain variable region selected from SEQ ID NO: 105 and SEQ ID NO: 107.

In several embodiments, the antigen-binding protein has been modified from its original sequence, for example for purposes of improving expression, function, or reducing a potential immune response to the antigen-binding protein by a host. In several embodiments, the antigen-binding protein comprises a light chain variable region selected from SEQ ID NO: 117, SEQ ID NO: 118, and SEQ ID NO: 119 and/or sequences having at least 90% identity and/or homology (e.g., 90-95%, 95%, 96%, 97%, 98%, 99%). In several embodiments, the light chain variable region differs in sequence from SEQ ID NO: 117, SEQ ID NO: 118, or SEQ ID NO: 119 by more than 5% (e.g., by 5-7%, 5-10%, 10-20% or higher) with ligand-binding function (or other functionality) being similar, substantially similar or the same as SEQ ID NO: 117, SEQ ID NO: 118, or SEQ ID NO: 119. In several embodiments, the antigen-binding protein comprises a heavy chain variable region selected from SEQ ID NO: 120, SEQ ID NO: 121, SEQ ID NO: 122, and SEQ ID NO: 123 and/or sequences having at least 90% identity and/or homology (e.g., 90-95%, 95%, 96%, 97%, 98%, 99%). In several embodiments, the heavy chain variable region differs in sequence from SEQ ID NO: 120, SEQ ID NO: 121, SEQ ID NO: 122, or SEQ ID NO: 123 by more than 5% (e.g., by 5-7%, 5-10%, 10-20% or higher) with ligand-binding function (or other functionality) being similar, substantially similar or the same as SEQ ID NO: 120, SEQ ID NO: 121, SEQ ID NO: 122, or SEQ ID NO: 123. Depending on the embodiment, any combination of heavy and light chain regions may be used (e.g., in assembling a scFv). In several embodiments, the antigen-binding protein comprises one or more CDRs selected from SEQ ID NO: 124, SEQ ID NO: 125, SEQ ID NO: 126, SEQ ID NO: 127, SEQ ID NO: 128, SEQ ID NO: 129, SEQ ID NO: 130, SEQ ID NO: 131, SEQ ID NO: 132, SEQ ID NO: 133, SEQ ID NO: 134, SEQ ID NO: 134, SEQ ID NO: 136, SEQ ID NO: 137, SEQ ID NO: 138, SEQ ID NO: 139, SEQ ID NO: 140, SEQ ID NO: 141, SEQ ID NO: 142, SEQ ID NO: 143, and SEQ ID NO: 144.

In additional embodiments, the CDRs are selected from SEQ ID NO: 108, SEQ ID NO: 109, SEQ ID NO: 110, SEQ ID NO: 111, SEQ ID NO: 112, SEQ ID NO: 113, SEQ ID NO: 114, and SEQ ID NO: 115, in any combination. In one embodiment, the CDRs are assembled to generate a CAR directed to CD19 and comprising SEQ ID NO: 116.

In several embodiments, the antigen-binding protein comprises a heavy chain having the sequence of SEQ ID NO: 88. In several embodiments, that heavy chain is coupled with (e.g., as an scFv), one of the light chains of SEQ ID NO: 89, SEQ ID NO: 90, and/or SEQ ID NO: 91. In several embodiments, the antigen-binding protein comprises one of more CDRs selected from SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, and SEQ ID NO: 100.

In several embodiments, the antigen-binding protein comprises a light chain region of an FMC63 antibody that has the sequence of SEQ ID NO: 150. In several embodiments, the antigen-binding protein comprises a light chain region of an FMC63 antibody that has the sequence of SEQ ID NO: 148. In several embodiments, linkers are used between heavy and light chains, and in some embodiments, the linker comprises the sequence of SEQ ID NO: 149. In several embodiments, such heavy and light chains are used in conjunction with a CD28 co-stimulatory domain, such as that of SEQ ID NO: 153. Often a spacer is used to separate component parts of a CAR. For example, in several embodiments, a spacer is used comprising the sequence of SEQ ID NO: 151. In several embodiments, a transmembrane domain having the sequence of SEQ ID NO: 152 is used. In several embodiments, the CAR comprises a nucleic acid sequence that shares at least about 90%, at least about 94%, at least about 95%, at least about 96%, at least about 97%, at least about 98%, or at least about 99%, sequence identity, homology and/or functional equivalence with SEQ ID NO: 147.

In some embodiments, the antigen-binding proteins provided herein comprise one or more CDR(s) as part of a larger polypeptide chain. In some embodiments, the antigen-binding proteins covalently link the one or more CDR(s) to another polypeptide chain. In some embodiments, the antigen-binding proteins incorporate the one or more CDR(s) noncovalently. In some embodiments, the antigen-binding proteins may comprise at least one of the CDRs described herein incorporated into a biocompatible framework structure. In some embodiments, the biocompatible framework structure comprises a polypeptide or portion thereof that is sufficient to form a conformationally stable structural support, or framework, or scaffold, which is able to display one or more sequences of amino acids that bind to an antigen (e.g., CDRs, a variable region, etc.) in a localized surface region. Such structures can be a naturally occurring polypeptide or polypeptide "fold" (a structural motif), or can have one or more modifications, such as additions, deletions and/or substitutions of amino acids, relative to a naturally occurring polypeptide or fold. Depending on the embodiment, the scaffolds can be derived from a polypeptide of a variety of different species (or of more than one species), such as a human, a non-human primate or other mammal, other vertebrate, invertebrate, plant, bacteria or virus.

Depending on the embodiment, the biocompatible framework structures are based on protein scaffolds or skeletons other than immunoglobulin domains. In some such embodiments, those framework structures are based on fibronectin, ankyrin, lipocalin, neocarzinostain, cytochrome b, CP1 zinc finger, PST1, coiled coil, LACI-D1, Z domain and/or tendamistat domains.

There is also provided, in some embodiments, antigen-binding proteins with more than one binding site. In several embodiments, the binding sites are identical to one another while in some embodiments the binding sites are different from one another. For example, an antibody typically has two identical binding sites, while a "bispecific" or "bifunctional" antibody has two different binding sites. The two binding sites of a bispecific antigen-binding protein or antibody will bind to two different epitopes, which can reside on the same or different protein targets. In several embodiments, this is particularly advantageous, as a bispecific chimeric antigen receptor can impart to an engineered cell the ability to target multiple tumor markers. For example, CD19 and an additional tumor marker, such as CD123, NKG2D or any other marker disclosed herein or appreciated in the art as a tumor specific antigen or tumor associated antigen.

As used herein, the term "chimeric antibody" shall be given its ordinary meaning, and shall also refer to an antibody that contains one or more regions from one antibody and one or more regions from one or more other antibodies. In some embodiments, one or more of the CDRs are derived from an anti-cancer antigen (e.g., CD19) antibody. In several embodiments, all of the CDRs are derived from an anti-cancer antigen antibody (such as an anti-CD19 antibody). In some embodiments, the CDRs from more than one anti-cancer antigen antibodies are mixed and matched in a chimeric antibody. For instance, a chimeric antibody may comprise a CDR1 from the light chain of a first anti-cancer antigen antibody, a CDR2 and a CDR3 from the light chain of a second anti-cancer antigen antibody, and the CDRs from the heavy chain from a third anti-cancer antigen antibody. Further, the framework regions of antigen-binding proteins disclosed herein may be derived from one of the same anti-cancer antigen (e.g., CD19) antibodies, from one or more different antibodies, such as a human antibody, or from a humanized antibody. In one example of a chimeric antibody, a portion of the heavy and/or light chain is identical with, homologous to, or derived from an antibody from a particular species or belonging to a particular antibody class or subclass, while the remainder of the chain(s) is/are identical with, homologous to, or derived from an antibody or antibodies from another species or belonging to another antibody class or subclass. Also provided herein are fragments of such antibodies that exhibit the desired biological activity.

In some embodiments, an antigen-binding protein is provided comprising a heavy chain variable domain having at least 90% identity to the VH domain amino acid sequence set forth in SEQ ID NO: 33. In some embodiments, the antigen-binding protein comprises a heavy chain variable domain having at least 95% identity to the VH domain amino acid sequence set forth in SEQ ID NO: 33. In some embodiments, the antigen-binding protein comprises a heavy chain variable domain having at least 96, 97, 98, or 99% identity to the VH domain amino acid sequence set forth in SEQ ID NO: 33. In several embodiments, the heavy chain variable domain may have one or more additional mutations (e.g., for purposes of humanization) in the VH domain amino acid sequence set forth in SEQ ID NO: 33, but retains specific binding to a cancer antigen (e.g., CD19). In several embodiments, the heavy chain variable domain may have one or more additional mutations in the VH domain amino acid sequence set forth in SEQ ID NO: 33, but has improved specific binding to a cancer antigen (e.g., CD19).

In some embodiments, the antigen-binding protein comprises a light chain variable domain having at least 90% identity to the VL domain amino acid sequence set forth in SEQ ID NO: 32. In some embodiments, the antigen-binding protein comprises a light chain variable domain having at least 95% identity to the VL domain amino acid sequence set forth in SEQ ID NO: 32. In some embodiments, the antigen-binding protein comprises a light chain variable domain having at least 96, 97, 98, or 99% identity to the VL domain amino acid sequence set forth in SEQ ID NO: 32. In several embodiments, the light chain variable domain may have one or more additional mutations (e.g., for purposes of humanization) in the VL domain amino acid sequence set forth in SEQ ID NO: 32, but retains specific binding to a cancer antigen (e.g., CD19). In several embodiments, the light chain variable domain may have one or more additional mutations in the VL domain amino acid sequence set forth in SEQ ID NO: 32, but has improved specific binding to a cancer antigen (e.g., CD19).

In some embodiments, the antigen-binding protein comprises a heavy chain variable domain having at least 90% identity to the VH domain amino acid sequence set forth in SEQ ID NO: 33, and a light chain variable domain having at least 90% identity to the VL domain amino acid sequence set forth in SEQ ID NO: 32. In some embodiments, the antigen-binding protein comprises a heavy chain variable domain having at least 95% identity to the VH domain amino acid sequence set forth in SEQ ID NO: 33, and a light chain variable domain having at least 95% identity to the VL domain amino acid sequence set forth in SEQ ID NO: 32. In some embodiments, the antigen-binding protein comprises a heavy chain variable domain having at least 96, 97, 98, or 99% identity to the VH domain amino acid sequence set forth in SEQ ID NO: 33, and a light chain variable domain having at least 96, 97, 98, or 99% identity to the VL domain amino acid sequence set forth in SEQ ID NO: 32.

In some embodiments, the antigen-binding protein comprises a heavy chain variable domain having the VH domain amino acid sequence set forth in SEQ ID NO: 33, and a light chain variable domain having the VL domain amino acid sequence set forth in SEQ ID NO: 32. In some embodiments, the light-chain variable domain comprises a sequence of amino acids that is at least 70%, 75%, 80%, 85%, 90%, 91%, 92%, 93%, 94%, 95%, 96%, 97%, 98%, 99% or 100% identical to the sequence of a light chain variable domain of SEQ ID NO: 32. In some embodiments, the light-chain variable domain comprises a sequence of amino acids that is at least 70%, 75%, 80%, 85%, 90%, 91%, 92%, 93%, 94%, 95%, 96%, 97%, 98%, 99% or 100% identical to the sequence of a heavy chain variable domain in accordance with SEQ ID NO: 33.

In some embodiments, the light chain variable domain comprises a sequence of amino acids that is encoded by a nucleotide sequence that is at least 70%, 75%, 80%, 85%, 90%, 91%, 92%, 93%, 94%, 95%, 96%, 97%, 98%, 99% or 100% identical to the polynucleotide sequence SEQ ID NO: 32. In some embodiments, the light chain variable domain comprises a sequence of amino acids that is encoded by a polynucleotide that hybridizes under moderately stringent conditions to the complement of a polynucleotide that encodes a light chain variable domain in accordance with the sequence in SEQ ID NO: 32. In some embodiments, the light chain variable domain comprises a sequence of amino acids that is encoded by a polynucleotide that hybridizes under stringent conditions to the complement of a polynucleotide that encodes a light chain variable domain in accordance with the sequence in SEQ ID NO: 32.

In some embodiments, the heavy chain variable domain comprises a sequence of amino acids that is at least 70%, 75%, 80%, 85%, 90%, 91%, 92%, 93%, 94%, 95%, 96%, 97%, 98%, 99% or 100% identical to the sequence of a heavy chain variable domain in accordance with the sequence of SEQ ID NO: 33. In some embodiments, the heavy chain variable domain comprises a sequence of amino acids that is encoded by a polynucleotide that hybridizes under moderately stringent conditions to the complement of a polynucleotide that encodes a heavy chain variable domain in accordance with the sequence of SEQ ID NO: 33. In some embodiments, the heavy chain variable domain comprises a sequence of amino acids that is encoded by a polynucleotide that hybridizes under stringent conditions to the complement of a polynucleotide that encodes a heavy chain variable domain in accordance with the sequence of SEQ ID NO: 33.

In several embodiments, additional anti-CD19 binding constructs are provided. For example, in several embodiments, there is provided an scFv that targets CD19 wherein the scFv comprises a heavy chain variable region comprising the sequence of SEQ ID NO. 35. In some embodiments, the antigen-binding protein comprises a heavy chain variable domain having at least 95% identity to the HCV domain amino acid sequence set forth in SEQ ID NO: 35. In some embodiments, the antigen-binding protein comprises a heavy chain variable domain having at least 96, 97, 98, or 99% identity to the HCV domain amino acid sequence set forth in SEQ ID NO: 35. In several embodiments, the heavy chain variable domain may have one or more additional mutations (e.g., for purposes of humanization) in the HCV domain amino acid sequence set forth in SEQ ID NO: 35, but retains specific binding to a cancer antigen (e.g., CD19). In several embodiments, the heavy chain variable domain may have one or more additional mutations in the HCV domain amino acid sequence set forth in SEQ ID NO: 35, but has improved specific binding to a cancer antigen (e.g., CD19).

Additionally, in several embodiments, an scFv that targets CD19 comprises a light chain variable region comprising the sequence of SEQ ID NO. 36. In some embodiments, the antigen-binding protein comprises a light chain variable domain having at least 95% identity to the LCV domain amino acid sequence set forth in SEQ ID NO: 36. In some embodiments, the antigen-binding protein comprises a light chain variable domain having at least 96, 97, 98, or 99% identity to the LCV domain amino acid sequence set forth in SEQ ID NO: 36. In several embodiments, the light chain variable domain may have one or more additional mutations (e.g., for purposes of humanization) in the LCV domain amino acid sequence set forth in SEQ ID NO: 36, but retains specific binding to a cancer antigen (e.g., CD19). In several embodiments, the light chain variable domain may have one or more additional mutations in the LCV domain amino acid sequence set forth in SEQ ID NO: 36, but has improved specific binding to a cancer antigen (e.g., CD19).

In several embodiments, there is also provided an anti-CD19 binding moiety that comprises a light chain CDR comprising a first, second and third complementarity determining region (LC CDR1, LC CDR2, and LC CDR3, respectively. In several embodiments, the anti-CD19 binding moiety further comprises a heavy chain CDR comprising a first, second and third complementarity determining region (HC CDR1, HC CDR2, and HC CDR3, respectively. In several embodiments, the LC CDR1 comprises the sequence of SEQ ID NO. 37. In several embodiments, the LC CDR1 comprises an amino acid sequence with at least about 85%, about 90%, about 95%, or about 98% homology to the sequence of SEQ NO. 37. In several embodiments, the LC CDR2 comprises the sequence of SEQ ID NO. 38. In several embodiments, the LC CDR2 comprises an amino acid sequence with at least about 85%, about 90%, about 95%, or about 98% homology to the sequence of SEQ NO. 38. In several embodiments, the LC CDR3 comprises the sequence of SEQ ID NO. 39. In several embodiments, the LC CDR3 comprises an amino acid sequence with at least about 85%, about 90%, about 95%, or about 98% homology to the sequence of SEQ NO. 39. In several embodiments, the HC CDR1 comprises the sequence of SEQ ID NO. 40. In several embodiments, the HC CDR1 comprises an amino acid sequence with at least about 85%, about 90%, about 95%, or about 98% homology to the sequence of SEQ NO. 40. In several embodiments, the HC CDR2 comprises the sequence of SEQ ID NO. 41, 42, or 43. In several embodiments, the HC CDR2 comprises an amino acid sequence with at least about 85%, about 90%, about 95%, or about 98% homology to the sequence of SEQ NO. 41, 42, or 43. In several embodiments, the HC CDR3 comprises the sequence of SEQ ID NO. 44. In several embodiments, the HC CDR3 comprises an amino acid sequence with at least about 85%, about 90%, about 95%, or about 98% homology to the sequence of SEQ NO. 44.

In several embodiments, there is also provided an anti-CD19 binding moiety that comprises a light chain variable region (VL) and a heavy chain variable region (HL), the VL region comprising a first, second and third complementarity determining region (VL CDR1, VL CDR2, and VL CDR3, respectively and the VH region comprising a first, second and third complementarity determining region (VH CDR1, VH CDR2, and VH CDR3, respectively. In several embodiments, the VL region comprises the sequence of SEQ ID NO. 45, 46, 47, or 48. In several embodiments, the VL region comprises an amino acid sequence with at least about 85%, about 90%, about 95%, or about 98% homology to the sequence of SEQ NO. 45, 46, 47, or 48. In several embodiments, the VH region comprises the sequence of SEQ ID NO. 49, 50, 51 or 52. In several embodiments, the VH region comprises an amino acid sequence with at least about 85%, about 90%, about 95%, or about 98% homology to the sequence of SEQ NO. 49, 50, 51 or 52.

In several embodiments, there is also provided an anti-CD19 binding moiety that comprises a light chain CDR comprising a first, second and third complementarity determining region (LC CDR1, LC CDR2, and LC CDR3, respectively. In several embodiments, the anti-CD19 binding moiety further comprises a heavy chain CDR comprising a first, second and third complementarity determining region (HC CDR1, HC CDR2, and HC CDR3, respectively. In several embodiments, the LC CDR1 comprises the sequence of SEQ ID NO. 53. In several embodiments, the LC CDR1 comprises an amino acid sequence with at least about 85%, about 90%, about 95%, or about 98% homology to the sequence of SEQ NO. 53. In several embodiments, the LC CDR2 comprises the sequence of SEQ ID NO. 54. In several embodiments, the LC CDR2 comprises an amino acid sequence with at least about 85%, about 90%, about 95%, or about 98% homology to the sequence of SEQ NO. 54. In several embodiments, the LC CDR3 comprises the sequence of SEQ ID NO. 55. In several embodiments, the LC CDR3 comprises an amino acid sequence with at least about 85%, about 90%, about 95%, or about 98% homology to the sequence of SEQ NO. 55. In several embodiments, the HC CDR1 comprises the sequence of SEQ ID NO. 56. In several embodiments, the HC CDR1 comprises an amino acid sequence with at least about 85%, about 90%, about 95%, or about 98% homology to the sequence of SEQ NO. 56. In several embodiments, the HC CDR2 comprises the sequence of SEQ ID NO. 57. In several embodiments, the HC CDR2 comprises an amino acid sequence with at least about 85%, about 90%, about 95%, or about 98% homology to the sequence of SEQ NO. 57. In several embodiments, the HC CDR3 comprises the sequence of SEQ ID NO. 58. In several embodiments, the HC CDR3 comprises an amino acid sequence with at least about 85%, about 90%, about 95%, or about 98% homology to the sequence of SEQ NO. 58.

Additional anti-CD19 binding moieties are known in the art, such as those disclosed in, for example, U.S. Pat. No. 8,399,645, US Patent Publication No. 2018/0153977, US Patent Publication No. 2014/0271635, US Patent Publication No. 2018/0251514, and US Patent Publication No. 2018/0312588, the entirety of each of which is incorporated by reference herein.

Natural Killer Group Domains that Bind Tumor Ligands

In several embodiments, engineered immune cells such as NK cells are leveraged for their ability to recognize and destroy tumor cells. For example, an engineered NK cell may include a CD19-directed chimeric receptor or a nucleic acid encoding said chimeric receptor. NK cells express both inhibitory and activating receptors on the cell surface. Inhibitory receptors bind self-molecules expressed on the surface of healthy cells (thus preventing immune responses against "self" cells), while the activating receptors bind ligands expressed on abnormal cells, such as tumor cells. When the balance between inhibitory and activating receptor activation is in favor of activating receptors, NK cell activation occurs and target (e.g., tumor) cells are lysed.

Natural killer Group 2 member D (NKG2D) is an NK cell activating receptor that recognizes a variety of ligands expressed on cells. The surface expression of various NKG2D ligands is generally low in healthy cells but is upregulated upon, for example, malignant transformation. Non-limiting examples of ligands recognized by NKG2D include, but are not limited to, MICA, MICB, ULBP1, ULBP2, ULBP3, ULBP4, ULBP5, and ULBP6, as well as other molecules expressed on target cells that control the cytolytic or cytotoxic function of NK cells. In several embodiments, T cells are engineered to express an extracellular domain to binds to one or more tumor ligands and activate the T cell. For example, in several embodiments, T cells are engineered to express an NKG2D receptor as the binder/activation moiety. In several embodiments, engineered cells as disclosed herein are engineered to express another member of the NKG2 family, e.g., NKG2A, NKG2C, and/or NKG2E. Combinations of such receptors are engineered in some embodiments. Moreover, in several embodiments, other receptors are expressed, such as the Killer-cell immunoglobulin-like receptors (KIRs).

In several embodiments, cells are engineered to express a cytotoxic receptor complex comprising a full length NKG2D as an extracellular component to recognize ligands on the surface of tumor cells (e.g., liver cells). In one embodiment, full length NKG2D has the nucleic acid sequence of SEQ ID NO: 27. In several embodiments, the full length NKG2D, or functional fragment thereof is human NKG2D.

In several embodiments, cells are engineered to express a cytotoxic receptor complex comprising a functional fragment of NKG2D as an extracellular component to recognize ligands on the surface of tumor cells or other diseased cells. In one embodiment, the functional fragment of NKG2D has the nucleic acid sequence of SEQ ID NO: 25. In several embodiments, the fragment of NKG2D is at least 70%, at least 75%, at least 80%, at least 85%, at least 90%, or at least 95% homologous with full-length wild-type NKG2D. In several embodiments, the fragment may have one or more additional mutations from SEQ ID NO: 25, but retains, or in some embodiments, has enhanced, ligand-binding function. In several embodiments, the functional fragment of NKG2D comprises the amino acid sequence of SEQ ID NO: 26. In several embodiments, the NKG2D fragment is provided as a dimer, trimer, or other concatameric format, such embodiments providing enhanced ligand-binding activity. In several embodiments, the sequence encoding the NKG2D fragment is optionally fully or partially codon optimized. In one embodiment, a sequence encoding a codon optimized NKG2D fragment comprises the sequence of SEQ ID NO: 28. Advantageously, according to several embodiments, the functional fragment lacks its native transmembrane or intracellular domains but retains its ability to bind ligands of NKG2D as well as transduce activation signals upon ligand binding. A further advantage of such fragments is that expression of DAP10 to localize NKG2D to the cell membrane is not required. Thus, in several embodiments, the cytotoxic receptor complex encoded by the polypeptides disclosed herein does not comprise DAP10. In several embodiments, immune cells, such as NK or T cells, are engineered to express one or more chimeric receptors that target CD19 and an NGG2D ligand. Such cells, in several embodiments, also co-express mbIL15.

In several embodiments, the cytotoxic receptor complexes are configured to dimerize. Dimerization may comprise homodimers or heterodimers, depending on the embodiment. In several embodiments, dimerization results in improved ligand recognition by the cytotoxic receptor complexes (and hence the NK cells expressing the receptor), resulting in a reduction in (or lack) of adverse toxic effects. In several embodiments, the cytotoxic receptor complexes employ internal dimers, or repeats of one or more component subunits. For example, in several embodiments, the cytotoxic receptor complexes may optionally comprise a first NKG2D extracellular domain coupled to a second NKG2D extracellular domain, and a transmembrane/signaling region (or a separate transmembrane region along with a separate signaling region).

In several embodiments, the various domains/subdomains are separated by a linker such as, a GS3 linker (SEQ ID NO: 15 and 16, nucleotide and protein, respectively) is used (or a GSn linker). Other linkers used according to various embodiments disclosed herein include, but are not limited to those encoded by SEQ ID NO: 17, 19, 21 or 23. This provides the potential to separate the various component parts of the receptor complex along the polynucleotide, which can enhance expression, stability, and/or functionality of the receptor complex.

Cytotoxic Signaling Complex

Some embodiments of the compositions and methods described herein relate to a chimeric receptor, such as a CD19-directed chimeric receptor, that includes a cytotoxic signaling complex. As disclosed herein, according to several embodiments, the provided cytotoxic receptor complexes comprise one or more transmembrane and/or intracellular domains that initiate cytotoxic signaling cascades upon the extracellular domain(s) binding to ligands on the surface of target cells. Certain embodiments disclosed herein relate to chimeric antigen receptor constructs wherein the tumor-targeting domain (or CD19-directed domain) is coupled to a cytotoxic signaling complex.

In several embodiments, the cytotoxic signaling complex comprises at least one transmembrane domain, at least one co-stimulatory domain, and/or at least one signaling domain. In some embodiments, more than one component part makes up a given domain—e.g., a co-stimulatory domain may comprise two subdomains. Moreover, in some embodiments, a domain may serve multiple functions, for example, a transmembrane domain may also serve to provide signaling function.

Transmembrane Domains

Some embodiments of the compositions and methods described herein relate to a chimeric receptor, such as a CD19-directed chimeric receptor, that includes a transmembrane domain. Some embodiments include a transmembrane domain from NKG2D or another transmembrane protein. In several embodiments in which a transmembrane domain is employed, the portion of the transmembrane protein employed retains at least a portion of its normal transmembrane domain.

In several embodiments, however, the transmembrane domain comprises at least a portion of CD8, a transmembrane glycoprotein normally expressed on both T cells and NK cells. In several embodiments, the transmembrane domain comprises CD8a. In several embodiments, the transmembrane domain is referred to as a "hinge". In several embodiments, the "hinge" of CD8a has the nucleic acid sequence of SEQ ID NO: 1. In several embodiments, the CD8a hinge is truncated or modified and is at least 70%, at least 75%, at least 80%, at least 85%, at least 90%, at least 95% homologous with the CD8a having the sequence of SEQ ID NO: 1. In several embodiments, the "hinge" of CD8a comprises the amino acid sequence of SEQ ID NO: 2. In several embodiments, the CD8a can be truncated or modified, such that it is at least 70%, at least 75%, at least 80%, at least 85%, at least 90%, at least 95% homologous with the sequence of SEQ ID NO: 2.

In several embodiments, the transmembrane domain comprises a CD8a transmembrane region. In several embodiments, the CD8a transmembrane domain has the nucleic acid sequence of SEQ ID NO: 3. In several embodiments, the CD8a hinge is truncated or modified and is at least 70%, at least 75%, at least 80%, at least 85%, at least 90%, at least 95% homologous with the CD8a having the sequence of SEQ ID NO: 3. In several embodiments, the CD8a transmembrane domain comprises the amino acid sequence of SEQ ID NO: 4. In several embodiments, the CD8a hinge is truncated or modified and is at least 70%, at least 75%, at least 80%, at least 85%, at least 90%, at least 95% homologous with the CD8a having the sequence of SEQ ID NO: 4.

Taken together in several embodiments, the CD8 hinge/transmembrane complex is encoded by the nucleic acid sequence of SEQ ID NO: 13. In several embodiments, the CD8 hinge/transmembrane complex is truncated or modified and is at least 70%, at least 75%, at least 80%, at least 85%, at least 90%, at least 95% homologous with the CD8 hinge/transmembrane complex having the sequence of SEQ ID NO: 13. In several embodiments, the CD8 hinge/transmembrane complex comprises the amino acid sequence of SEQ ID NO: 14. In several embodiments, the CD8 hinge/transmembrane complex hinge is truncated or modified and is at least 70%, at least 75%, at least 80%, at least 85%, at least 90%, at least 95% homologous with the CD8 hinge/transmembrane complex having the sequence of SEQ ID NO: 14.

In some embodiments, the transmembrane domain comprises a CD28 transmembrane domain or a fragment thereof. In several embodiments, the CD28 transmembrane domain comprises the amino acid sequence of SEQ ID NO: 30. In several embodiments, the CD28 transmembrane domain complex hinge is truncated or modified and is at least 70%, at least 75%, at least 80%, at least 85%, at least 90%, at least 95% homologous with the CD28 transmembrane domain having the sequence of SEQ ID NO: 30.

Co-Stimulatory Domains

Some embodiments of the compositions and methods described herein relate to a chimeric receptor, such as a CD19-directed chimeric receptor, that includes a co-stimulatory domain. In addition the various the transmembrane domains and signaling domain (and the combination transmembrane/signaling domains), additional co-activating molecules can be provided, in several embodiments. These can be certain molecules that, for example, further enhance activity of the immune cells. Cytokines may be used in some embodiments. For example, certain interleukins, such as IL-2 and/or IL-15 as non-limiting examples, are used. In some embodiments, the immune cells for therapy are engineered to express such molecules as a secreted form. In additional embodiments, such co-stimulatory domains are engineered to be membrane bound, acting as autocrine stimulatory molecules (or even as paracrine stimulators to neighboring cells delivered). In several embodiments, NK cells are engineered to express membrane-bound interleukin 15 (mbIL15). In such embodiments, mbIL15 expression on the NK enhances the cytotoxic effects of the engineered NK cell by enhancing the proliferation and/or longevity of the NK cells. In several embodiments, mbIL15 has the nucleic acid sequence of SEQ ID NO: 11. In several embodiments, mbIL15 can be truncated or modified, such that it is at least 70%, at least 75%, at least 80%, at least 85%, at least 90%, at least 95% homologous with the sequence of SEQ ID NO: 11. In several embodiments, the mbIL15 comprises the amino acid sequence of SEQ ID NO: 12. In several embodiments, the mbIL15 is truncated or modified and is at least 70%, at least 75%, at least 80%, at least 85%, at least 90%, at least 95% homologous with the mbIL15 having the sequence of SEQ ID NO: 12.

In some embodiments, the CD19-directed chimeric receptor or engineered cytotoxic receptor complex is encoded by a polynucleotide that includes one or more cytosolic protease cleavage sites, for example a T2A cleavage site, a P2A cleavage site, an E2A cleavage site, and/or a F2A cleavage site. Such sites are recognized and cleaved by a cytosolic protease, which can result in separation (and separate expression) of the various component parts of the receptor encoded by the polynucleotide. As a result, depending on the embodiment, the various constituent parts of a CD19-directed chimeric receptor or engineered cytotoxic receptor complex can be delivered to an NK cell or T cell in a single vector or by multiple vectors. Thus, as shown schematically, in the Figures, a construct can be encoded by a single polynucleotide, but also include a cleavage site, such that downstream elements of the constructs are expressed by the cells as a separate protein (as is the case in some embodiments with IL-15). In several embodiments, a T2A cleavage site is used. In several embodiments, a T2A cleavage site has the nucleic acid sequence of SEQ ID NO: 9. In several embodiments, T2A cleavage site can be truncated or modified, such that it is at least 70%, at least 75%, at least 80%, at least 85%, at least 90%, at least 95% homologous with the sequence of SEQ ID NO: 9. In several embodiments, the T2A cleavage site comprises the amino acid sequence of SEQ ID NO: 10. In several embodiments, the T2A cleavage site is truncated or modified and is at least 70%, at least 75%, at least 80%, at least 85%, at least 90%, at least 95% homologous with the T2A cleavage site having the sequence of SEQ ID NO: 10.

Signaling Domains

Some embodiments of the compositions and methods described herein relate to a chimeric receptor, such as a CD19-directed chimeric receptor, that includes a signaling domain. For example, immune cells engineered according to several embodiments disclosed herein may comprise at least one subunit of the CD3 T cell receptor complex (or a fragment thereof). In several embodiments, the signaling domain comprises the CD3 zeta subunit. In several embodiments, the CD3 zeta is encoded by the nucleic acid sequence of SEQ ID NO: 7. In several embodiments, the CD3 zeta can be truncated or modified, such that it is at least 70%, at least 75%, at least 80%, at least 85%, at least 90%, at least 95% homologous with the CD3 zeta having the sequence of SEQ ID NO: 7. In several embodiments, the CD3 zeta domain comprises the amino acid sequence of SEQ ID NO: 8. In several embodiments, the CD3 zeta domain is truncated or modified and is at least 70%, at least 75%, at least 80%, at least 85%, at least 90%, at least 95% homologous with the CD3 zeta domain having the sequence of SEQ ID NO: 8.

In several embodiments, unexpectedly enhanced signaling is achieved through the use of multiple signaling domains whose activities act synergistically. For example, in several embodiments, the signaling domain further comprises an OX40 domain. In several embodiments, the OX40 domain is an intracellular signaling domain. In several embodiments, the OX40 intracellular signaling domain has the nucleic acid sequence of SEQ ID NO: 5. In several embodiments, the OX40 intracellular signaling domain can be truncated or modified, such that it is at least 70%, at least 75%, at least 80%, at least 85%, at least 90%, at least 95% homologous with the OX40 having the sequence of SEQ ID NO: 5. In several embodiments, the OX40 intracellular signaling domain comprises the amino acid sequence of SEQ ID NO: 16. In several embodiments, the OX40 intracellular signaling domain is truncated or modified and is at least 70%, at least 75%, at least 80%, at least 85%, at least 90%, at least 95% homologous with the OX40 intracellular signaling domain having the sequence of SEQ ID NO: 6. In several embodiments, OX40 is used as the sole transmembrane/signaling domain in the construct, however, in several embodiments, OX40 can be used with one or more other domains. For example, combinations of OX40 and CD3zeta are used in some embodiments. By way of further example, combinations of CD28, OX40, 4-1 BB, and/or CD3zeta are used in some embodiments.

In several embodiments, the signaling domain comprises a 4-1BB domain. In several embodiments, the 4-1 BB domain is an intracellular signaling domain. In several embodiments, the 4-1 BB intracellular signaling domain comprises the amino acid sequence of SEQ ID NO: 29. In several embodiments, the 4-1 BB intracellular signaling domain is truncated or modified and is at least 70%, at least 75%, at least 80%, at least 85%, at least 90%, at least 95% homologous with the 4-1BB intracellular signaling domain having the sequence of SEQ ID NO: 29. In several embodiments, 4-1 BB is used as the sole transmembrane/signaling domain in the construct, however, in several embodiments, 4-1BB can be used with one or more other domains. For example, combinations of 4-1 BB and CD3zeta are used in some embodiments. By way of further example, combinations of CD28, OX40, 4-1 BB, and/or CD3zeta are used in some embodiments.

In several embodiments, the signaling domain comprises a CD28 domain. In several embodiments the CD28 domain is an intracellular signaling domain. In several embodiments, the CD28 intracellular signaling domain comprises the amino acid sequence of SEQ ID NO: 31. In several embodiments, the CD28 intracellular signaling domain is truncated or modified and is at least 70%, at least 75%, at least 80%, at least 85%, at least 90%, at least 95% homologous with the CD28 intracellular signaling domain having the sequence of SEQ ID NO: 31. In several embodiments, CD28 is used as the sole transmembrane/signaling domain in the construct, however, in several embodiments, CD28 can be used with one or more other domains. For example, combinations of CD28 and CD3zeta are used in some embodiments. By way of further example, combinations of CD28, OX40, 4-1 BB, and/or CD3zeta are used in some embodiments.

Cytotoxic Receptor Complex Constructs

Some embodiments of the compositions and methods described herein relate to a chimeric receptor, such as a CD19-directed chimeric receptor, that comprises a cytotoxic receptor complex or cytotoxic receptor complex construct. In line with the above, a variety of cytotoxic receptor complexes (also referred to as cytotoxic receptors) are provided for herein. The expression of these complexes in immune cells, such as T cells and/or NK cells, allows the targeting and destruction of particular target cells, such as cancerous cells. Non-limiting examples of such cytotoxic receptor complexes are discussed in more detail below.

Chimeric Antigen Receptor Cytotoxic Receptor Complex Constructs

Figure 2:
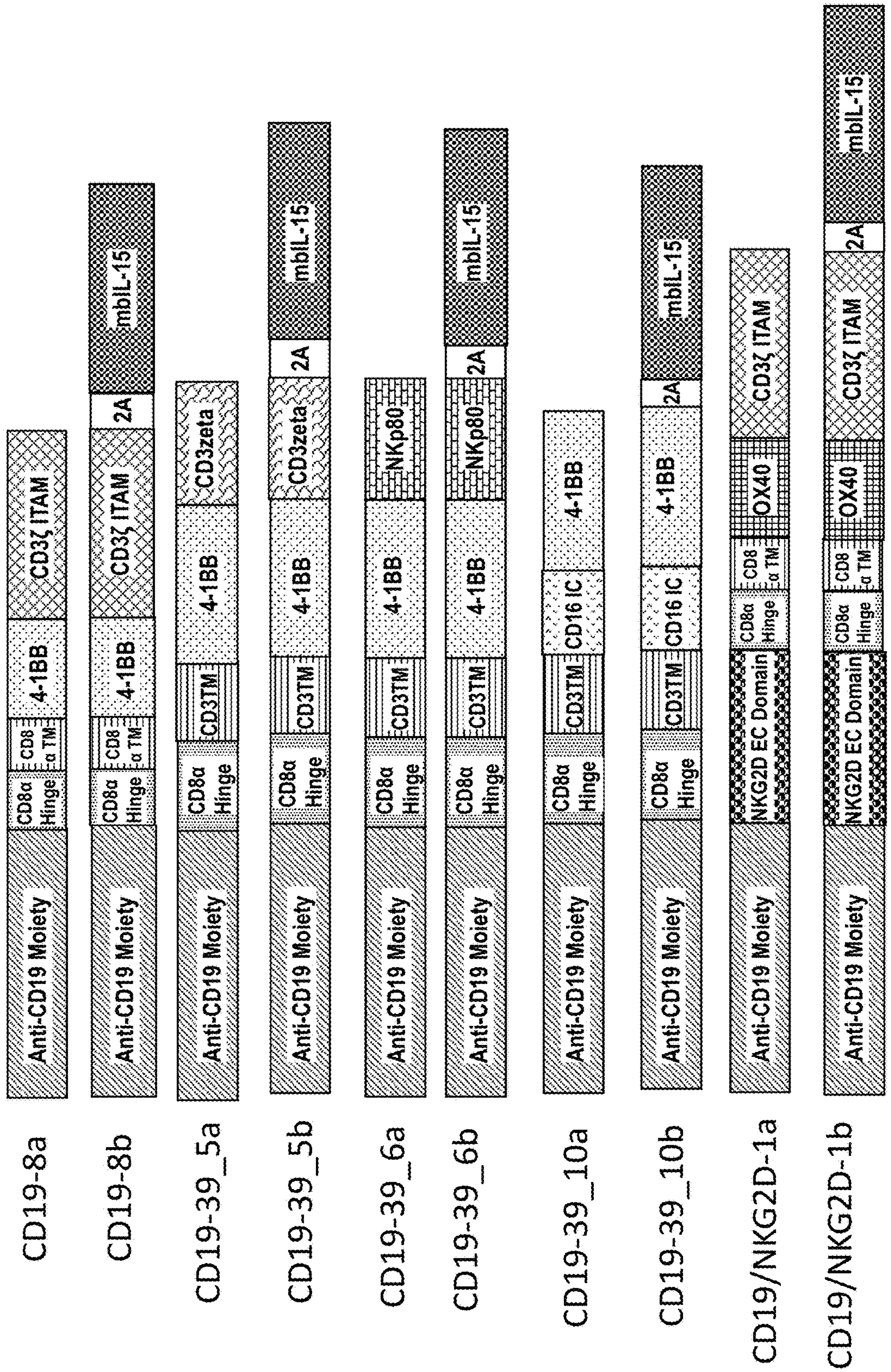
FIG. 2 also includes depictions of non-limiting examples of CD19-directed chimeric receptors.

In several embodiments, there are provided for herein a variety of cytotoxic receptor complexes (also referred to as cytotoxic receptors) are provided for herein with the general structure of a chimeric antigen receptor. FIGS. 1A, 1B, and 2 schematically depict non-limiting schematics of constructs that include an anti-CD19 moiety that binds to tumor antigens or tumor-associated antigens expressed on the surface of cancer cells and activates the engineered cell expressing the chimeric antigen receptor. As shown in the figures, several embodiments of the chimeric receptor include an anti-CD19 moiety, a CD8a hinge domain, an Ig4 SH domain (or hinge), a CD8a transmembrane domain, a CD28 transmembrane domain, an OX40 domain, a 4-1BB domain, a CD28 domain, a CD3ζ ITAM domain or subdomain, a CD3zeta domain, an NKp80 domain, a CD16 IC domain, a 2A cleavage site, and a membrane-bound IL-15 domain (though, as above, in several embodiments soluble IL-15 is used). In several embodiments, the binding and activation functions are engineered to be performed by separate domains. Several embodiments relate to complexes with more than one anti-CD19 moiety or other binder/activation moiety. In some embodiments, the binder/activation moiety targets other markers besides CD19, such as a cancer target described herein. In several embodiments, the general structure of the chimeric antigen receptor construct includes a hinge and/or transmembrane domain. These may, in some embodiments, be fulfilled by a single domain, or a plurality of subdomains may be used, in several embodiments. The receptor complex further comprises a signaling domain, which transduces signals after binding of the homing moiety to the target cell, ultimately leading to the cytotoxic effects on the target cell. In several embodiments, the complex further comprises a co-stimulatory domain, which operates, synergistically, in several embodiments, to enhance the function of the signaling domain. Expression of these complexes in immune cells, such as T cells and/or NK cells, allows the targeting and destruction of particular target cells, such as cancerous cells that express CD19. Some such receptor complexes comprise an extracellular domain comprising an anti-CD19 moiety, or CD19-binding moiety, that binds CD19 on the surface of target cells and activates the engineered cell. The CD3zeta ITAM subdomain may act in concert as a signaling domain. The IL-15 domain, e.g., mbIL-15 domain, may acting as a co-stimulatory domain. The IL-15 domain, e.g. mbIL-15 domain, may render immune cells (e.g., NK or T cells) expressing it particularly efficacious against target tumor cells. It shall be appreciated that the IL-15 domain, such as an mbIL-15 domain, can, in accordance with several embodiments, be encoded on a separate construct. Additionally, each of the components may be encoded in one or more separate constructs. In some embodiments, the cytotoxic receptor or CD19-directed receptor comprises a sequence of amino acids that is at least 70%, 75%, 80%, 85%, 90%, 91%, 92%, 93%, 94%, 95%, 96%, 97%, 98%, 99% or 100%, or a range defined by any two of the aforementioned percentages, identical to the sequence of SEQ ID NO: 34.

In one embodiment, there is provided a polynucleotide encoding an anti-CD19moiety/CD8hinge-CD8TM/OX40/CD3zeta chimeric antigen receptor complex (see FIG. 1A, CD19-1a). The polynucleotide comprises or is composed of an anti-CD19 moiety, a CD8a hinge, a CD8a transmembrane domain, an OX40 domain, and a CD3zeta domain as described herein. In several embodiments, this receptor complex is encoded by a nucleic acid molecule comprising a sequence obtained from a combination of sequences disclosed herein, or comprises an amino acid sequence obtained from a combination of sequences disclosed herein. In several embodiments, the encoding nucleic acid sequence, or the amino acid sequence, comprises a sequence in accordance with one or more SEQ ID NOS as described herein, such as those included herein as examples of constituent parts. In several embodiments, the encoding nucleic acid sequence, or the amino acid sequence, comprises a sequence that shares at least about 90%, at least about 94%, at least about 95%, at least about 96%, at least about 97%, at least about 98%, or at least about 99%, sequence identity, homology and/or functional equivalence with a sequence resulting from the combination one or more SEQ ID NOS as described herein.

In several embodiments, there is provided a polynucleotide encoding an anti-CD19moiety/CD8hinge-CD8TM/

OX40/CD3zeta/2A/mIL-15 chimeric antigen receptor complex (see FIG. 1A, CD19-1b). The polynucleotide comprises or is composed of an anti-CD19 moiety, a CD8a hinge, a CD8a transmembrane domain, an OX40 domain, a CD3zeta domain, a 2A cleavage site, and an mIL-15 domain as described herein. In several embodiments, this receptor complex is encoded by a nucleic acid molecule comprising a sequence obtained from a combination of sequences disclosed herein, or comprises an amino acid sequence obtained from a combination of sequences disclosed herein. In several embodiments, the encoding nucleic acid sequence, or the amino acid sequence, comprises a sequence in accordance with one or more SEQ ID NOS as described herein, such as those included herein as examples of constituent parts. In several embodiments, the encoding nucleic acid sequence, or the amino acid sequence, comprises a sequence that shares at least about 90%, at least about 94%, at least about 95%, at least about 96%, at least about 97%, at least about 98%, or at least about 99%, sequence identity, homology and/or functional equivalence with a sequence resulting from the combination one or more SEQ ID NOS as described herein.

In several embodiments, there is provided a polynucleotide encoding an anti-CD19moiety/Ig4SH-CD8TM/4-1BB/CD3zeta chimeric antigen receptor complex (see FIG. 1A, CD19-2a). The polynucleotide comprises or is composed of an anti-CD19 moiety, a Ig4 SH domain, a CD8a transmembrane domain, a 4-1BB domain, and a CD3zeta domain as described herein. In several embodiments, this receptor complex is encoded by a nucleic acid molecule comprising a sequence obtained from a combination of sequences disclosed herein, or comprises an amino acid sequence obtained from a combination of sequences disclosed herein. In several embodiments, the encoding nucleic acid sequence, or the amino acid sequence, comprises a sequence in accordance with one or more SEQ ID NOS as described herein, such as those included herein as examples of constituent parts. In several embodiments, the encoding nucleic acid sequence, or the amino acid sequence, comprises a sequence that shares at least about 90%, at least about 94%, at least about 95%, at least about 96%, at least about 97%, at least about 98%, or at least about 99%, sequence identity, homology and/or functional equivalence with a sequence resulting from the combination one or more SEQ ID NOS as described herein.

In several embodiments, there is provided a polynucleotide encoding an anti-CD19moiety/Ig4SH-CD8TM/4-1BB/CD3zeta/2A/mIL-15 chimeric antigen receptor complex (see FIG. 1A, CD19-2b). The polynucleotide comprises or is composed of an anti-CD19 moiety, a Ig4 SH domain, a CD8a transmembrane domain, a 4-1 BB domain, a CD3zeta domain, a 2A cleavage site, and an mIL-15 domain as described herein. In several embodiments, this receptor complex is encoded by a nucleic acid molecule comprising a sequence obtained from a combination of sequences disclosed herein, or comprises an amino acid sequence obtained from a combination of sequences disclosed herein. In several embodiments, the encoding nucleic acid sequence, or the amino acid sequence, comprises a sequence in accordance with one or more SEQ ID NOS as described herein, such as those included herein as examples of constituent parts. In several embodiments, the encoding nucleic acid sequence, or the amino acid sequence, comprises a sequence that shares at least about 90%, at least about 94%, at least about 95%, at least about 96%, at least about 97%, at least about 98%, or at least about 99%, sequence identity, homology and/or functional equivalence with a sequence resulting from the combination one or more SEQ ID NOS as described herein.

In several embodiments, there is provided a polynucleotide encoding an anti-CD19moiety/CD8hinge-CD28TM/CD28/CD3zeta chimeric antigen receptor complex (see FIG. 1A, CD19-3a). The polynucleotide comprises or is composed of an anti-CD19 moiety, a CD8a hinge, a CD28 transmembrane domain, a CD28 domain, and a CD3zeta domain as described herein. In several embodiments, this receptor complex is encoded by a nucleic acid molecule comprising a sequence obtained from a combination of sequences disclosed herein, or comprises an amino acid sequence obtained from a combination of sequences disclosed herein. In several embodiments, the encoding nucleic acid sequence, or the amino acid sequence, comprises a sequence in accordance with one or more SEQ ID NOS as described herein, such as those included herein as examples of constituent parts. In several embodiments, the encoding nucleic acid sequence, or the amino acid sequence, comprises a sequence that shares at least about 90%, at least about 94%, at least about 95%, at least about 96%, at least about 97%, at least about 98%, or at least about 99%, sequence identity, homology and/or functional equivalence with a sequence resulting from the combination one or more SEQ ID NOS as described herein.

In several embodiments, there is provided a polynucleotide encoding an anti-CD19moiety/CD8hinge-CD28TM/CD28/CD3zeta/2A/mIL-15 chimeric antigen receptor complex (see FIG. 1A, CD19-3b). The polynucleotide comprises or is composed of an anti-CD19 moiety, a CD8a hinge, a CD28 transmembrane domain, a CD28 domain, a CD3zeta domain, a 2A cleavage site, and an mIL-15 domain as described herein. In several embodiments, this receptor complex is encoded by a nucleic acid molecule comprising a sequence obtained from a combination of sequences disclosed herein, or comprises an amino acid sequence obtained from a combination of sequences disclosed herein. In several embodiments, the encoding nucleic acid sequence, or the amino acid sequence, comprises a sequence in accordance with one or more SEQ ID NOS as described herein, such as those included herein as examples of constituent parts. In several embodiments, the encoding nucleic acid sequence, or the amino acid sequence, comprises a sequence that shares at least about 90%, at least about 94%, at least about 95%, at least about 96%, at least about 97%, at least about 98%, or at least about 99%, sequence identity, homology and/or functional equivalence with a sequence resulting from the combination one or more SEQ ID NOS as described herein.

In several embodiments, there is provided a polynucleotide encoding an anti-CD19moiety/Ig4SH-CD28TM/CD28/CD3zeta chimeric antigen receptor complex (see FIG. 1A, CD19-4a). The polynucleotide comprises or is composed of an anti-CD19 moiety, an Ig4 SH domain, a CD28 transmembrane domain, a CD28 domain, and a CD3zeta domain as described herein. In several embodiments, this receptor complex is encoded by a nucleic acid molecule comprising a sequence obtained from a combination of sequences disclosed herein, or comprises an amino acid sequence obtained from a combination of sequences disclosed herein. In several embodiments, the encoding nucleic acid sequence, or the amino acid sequence, comprises a sequence in accordance with one or more SEQ ID NOS as described herein, such as those included herein as examples of constituent parts. In several embodiments, the encoding nucleic acid sequence, or the amino acid sequence, comprises a sequence that shares at least about 90%, at least about 94%, at least about 95%, at least about 96%, at least about 97%, at least about 98%, or at least about 99%, sequence identity, homology and/or functional equivalence with a sequence resulting from the combination one or more SEQ ID NOS as described herein.

In several embodiments, there is provided a polynucleotide encoding an anti-CD19moiety/Ig4SH-CD28TM/CD28/CD3zeta/2A/mIL-15 chimeric antigen receptor complex (see FIG. 1A, CD19-4b). The polynucleotide comprises or is composed of an anti-CD19 moiety, an Ig4 SH domain, a CD28 transmembrane domain, a CD28 domain, a CD3zeta domain, a 2A cleavage site, and an mIL-15 domain as described herein. In several embodiments, this receptor complex is encoded by a nucleic acid molecule comprising a sequence obtained from a combination of sequences disclosed herein, or comprises an amino acid sequence obtained from a combination of sequences disclosed herein. In several embodiments, the encoding nucleic acid sequence, or the amino acid sequence, comprises a sequence in accordance with one or more SEQ ID NOS as described herein, such as those included herein as examples of constituent parts. In several embodiments, the encoding nucleic acid sequence, or the amino acid sequence, comprises a sequence that shares at least about 90%, at least about 94%, at least about 95%, at least about 96%, at least about 97%, at least about 98%, or at least about 99%, sequence identity, homology and/or functional equivalence with a sequence resulting from the combination one or more SEQ ID NOS as described herein.

In several embodiments, there is provided a polynucleotide encoding an anti-CD19moiety/Ig4SH-CD8TM/OX40/CD3zeta chimeric antigen receptor complex (see FIG. 2A, CD19-5a). The polynucleotide comprises or is composed of an anti-CD19 moiety, a Ig4 SH domain, a CD8a transmembrane domain, an OX40 domain, and a CD3zeta domain as described herein. In several embodiments, this receptor complex is encoded by a nucleic acid molecule comprising a sequence obtained from a combination of sequences disclosed herein, or comprises an amino acid sequence obtained from a combination of sequences disclosed herein. In several embodiments, the encoding nucleic acid sequence, or the amino acid sequence, comprises a sequence in accordance with one or more SEQ ID NOS as described herein, such as those included herein as examples of constituent parts. In several embodiments, the encoding nucleic acid sequence, or the amino acid sequence, comprises a sequence that shares at least about 90%, at least about 94%, at least about 95%, at least about 96%, at least about 97%, at least about 98%, or at least about 99%, sequence identity, homology and/or functional equivalence with a sequence resulting from the combination one or more SEQ ID NOS as described herein.

In several embodiments, there is provided a polynucleotide encoding an anti-CD19moiety/Ig4SH-CD8TM/OX40/CD3zeta/2A/mIL-15 chimeric antigen receptor complex (see FIG. 2A, CD19-5b). The polynucleotide comprises or is composed of an anti-CD19 moiety, a Ig4 SH domain, a CD8a transmembrane domain, an OX40 domain, a CD3zeta domain, a 2A cleavage site, and an mIL-15 domain as described herein. In several embodiments, this receptor complex is encoded by a nucleic acid molecule comprising a sequence obtained from a combination of sequences disclosed herein, or comprises an amino acid sequence obtained from a combination of sequences disclosed herein. In several embodiments, the encoding nucleic acid sequence, or the amino acid sequence, comprises a sequence in accordance with one or more SEQ ID NOS as described herein, such as those included herein as examples of constituent parts. In several embodiments, the encoding nucleic acid sequence, or the amino acid sequence, comprises a sequence that shares at least about 90%, at least about 94%, at least about 95%, at least about 96%, at least about 97%, at least about 98%, or at least about 99%, sequence identity, homology and/or functional equivalence with a sequence resulting from the combination one or more SEQ ID NOS as described herein.

In several embodiments, there is provided a polynucleotide encoding an anti-CD19moiety/CD8hinge-CD3αTM/CD28/CD3zeta chimeric antigen receptor complex (see FIG. 1B, CD19-6a). The polynucleotide comprises or is composed of an anti-CD19 moiety, a CD8a hinge, a CD3a transmembrane domain, a CD28 domain, and a CD3zeta domain as described herein. In several embodiments, this receptor complex is encoded by a nucleic acid molecule comprising a sequence obtained from a combination of sequences disclosed herein, or comprises an amino acid sequence obtained from a combination of sequences disclosed herein. In several embodiments, the encoding nucleic acid sequence, or the amino acid sequence, comprises a sequence in accordance with one or more SEQ ID NOS as described herein, such as those included herein as examples of constituent parts. In several embodiments, the encoding nucleic acid sequence, or the amino acid sequence, comprises a sequence that shares at least about 90%, at least about 94%, at least about 95%, at least about 96%, at least about 97%, at least about 98%, or at least about 99%, sequence identity, homology and/or functional equivalence with a sequence resulting from the combination one or more SEQ ID NOS as described herein.

In several embodiments, there is provided a polynucleotide encoding an anti-CD19moiety/CD8hinge-CD3αTM/CD28/CD3zeta/2A/mIL-15 chimeric antigen receptor complex (see FIG. 1B, CD19-6b). The polynucleotide comprises or is composed of an anti-CD19 moiety, a CD8a hinge, a CD3a transmembrane domain, a CD28 domain, a CD3zeta domain, a 2A cleavage site, and an mIL-15 domain as described herein. In several embodiments, this receptor complex is encoded by a nucleic acid molecule comprising a sequence obtained from a combination of sequences disclosed herein, or comprises an amino acid sequence obtained from a combination of sequences disclosed herein. In several embodiments, the encoding nucleic acid sequence, or the amino acid sequence, comprises a sequence in accordance with one or more SEQ ID NOS as described herein, such as those included herein as examples of constituent parts. In several embodiments, the encoding nucleic acid sequence, or the amino acid sequence, comprises a sequence that shares at least about 90%, at least about 94%, at least about 95%, at least about 96%, at least about 97%, at least about 98%, or at least about 99%, sequence identity, homology and/or functional equivalence with a sequence resulting from the combination one or more SEQ ID NOS as described herein.

In several embodiments, there is provided a polynucleotide encoding an anti-CD19moiety/CD8hinge-CD28TM/CD28/4-1BB/CD3zeta chimeric antigen receptor complex (see FIG. 1B, CD19-7a). The polynucleotide comprises or is composed of an anti-CD19 moiety, a CD8a hinge, a CD28 transmembrane domain, a CD28 domain, a 4-1 BB domain, and a CD3zeta domain as described herein. In several embodiments, this receptor complex is encoded by a nucleic acid molecule comprising a sequence obtained from a combination of sequences disclosed herein, or comprises an amino acid sequence obtained from a combination of sequences disclosed herein. In several embodiments, the encoding nucleic acid sequence, or the amino acid sequence, comprises a sequence in accordance with one or more SEQ ID NOS as described herein, such as those included herein as examples of constituent parts. In several embodiments, the encoding nucleic acid sequence, or the amino acid sequence, comprises a sequence that shares at least about 90%, at least about 94%, at least about 95%, at least about 96%, at least about 97%, at least about 98%, or at least about 99%, sequence identity, homology and/or functional equivalence with a sequence resulting from the combination one or more SEQ ID NOS as described herein.

In several embodiments, there is provided a polynucleotide encoding an anti-CD19moiety/CD8hinge-CD28TM/CD28/4-1BB/CD3zeta/2A/mIL-15 chimeric antigen receptor complex (see FIG. 1B, CD19-7b). The polynucleotide comprises or is composed of an anti-CD19 moiety, a CD8a hinge, a CD28 transmembrane domain, a CD28 domain, a 4-1BB domain, a CD3zeta domain, a 2A cleavage site, and an mIL-15 domain as described herein. In several embodiments, this receptor complex is encoded by a nucleic acid molecule comprising a sequence obtained from a combination of sequences disclosed herein, or comprises an amino acid sequence obtained from a combination of sequences disclosed herein. In several embodiments, the encoding nucleic acid sequence, or the amino acid sequence, comprises a sequence in accordance with one or more SEQ ID NOS as described herein, such as those included herein as examples of constituent parts. In several embodiments, the encoding nucleic acid sequence, or the amino acid sequence, comprises a sequence that shares at least about 90%, at least about 94%, at least about 95%, at least about 96%, at least about 97%, at least about 98%, or at least about 99%, sequence identity, homology and/or functional equivalence with a sequence resulting from the combination one or more SEQ ID NOS as described herein.

In several embodiments, there is provided a polynucleotide encoding an anti-CD19moiety/CD8 alpha hinge/CD8 alpha TM/4-1BB/CD3zeta chimeric antigen receptor complex (see FIG. 2, CD19-8a). The polynucleotide comprises or is composed of an anti-CD19 moiety, a CD8a hinge, a CD8a transmembrane domain, a 4-1 BB domain, and a CD3zeta domain as described herein. In several embodiments, this receptor complex is encoded by a nucleic acid molecule comprising a sequence obtained from a combination of sequences disclosed herein, or comprises an amino acid sequence obtained from a combination of sequences disclosed herein. In several embodiments, the encoding nucleic acid sequence, or the amino acid sequence, comprises a sequence in accordance with one or more SEQ ID NOS as described herein, such as those included herein as examples of constituent parts. In several embodiments, the encoding nucleic acid sequence, or the amino acid sequence, comprises a sequence that shares at least about 90%, at least about 94%, at least about 95%, at least about 96%, at least about 97%, at least about 98%, or at least about 99%, sequence identity, homology and/or functional equivalence with a sequence resulting from the combination one or more SEQ ID NOS as described herein.

In several embodiments, there is provided a polynucleotide encoding an anti-CD19moiety/CD8 alpha hinge/CD8 alpha TM/4-1BB/CD3zeta/2A/mIL-15 chimeric antigen receptor complex (see FIG. 2, CD19-8b). The polynucleotide comprises or is composed of an anti-CD19 moiety, a CD8a hinge, a CD8a transmembrane domain, a 4-1 BB domain, a CD3zeta domain, a 2A cleavage site, and an mIL-15 domain as described herein. In several embodiments, this receptor complex is encoded by a nucleic acid molecule comprising a sequence obtained from a combination of sequences disclosed herein, or comprises an amino acid sequence obtained from a combination of sequences disclosed herein. In several embodiments, the encoding nucleic acid sequence, or the amino acid sequence, comprises a sequence in accordance with one or more SEQ ID NOS as described herein, such as those included herein as examples of constituent parts. In several embodiments, the encoding nucleic acid sequence, or the amino acid sequence, comprises a sequence that shares at least about 90%, at least about 94%, at least about 95%, at least about 96%, at least about 97%, at least about 98%, or at least about 99%, sequence identity, homology and/or functional equivalence with a sequence resulting from the combination one or more SEQ ID NOS as described herein.

In several embodiments, there is provided a polynucleotide encoding an anti-CD19moiety/CD8 alpha hinge/CD3 TM/4-1 BB/CD3zeta chimeric antigen receptor complex (see FIG. 2, CD19-39_5a). The polynucleotide comprises or is composed of an anti-CD19 moiety, a CD8a hinge, a CD3 transmembrane domain, a 4-1BB domain, and a CD3zeta domain as described herein. In several embodiments, this receptor complex is encoded by a nucleic acid molecule comprising a sequence obtained from a combination of sequences disclosed herein, or comprises an amino acid sequence obtained from a combination of sequences disclosed herein. In several embodiments, the encoding nucleic acid sequence, or the amino acid sequence, comprises a sequence in accordance with one or more SEQ ID NOS as described herein, such as those included herein as examples of constituent parts. In several embodiments, the encoding nucleic acid sequence, or the amino acid sequence, comprises a sequence that shares at least about 90%, at least about 94%, at least about 95%, at least about 96%, at least about 97%, at least about 98%, or at least about 99%, sequence identity, homology and/or functional equivalence with a sequence resulting from the combination one or more SEQ ID NOS as described herein.

In several embodiments, there is provided a polynucleotide encoding an anti-CD19moiety/CD8 alpha hinge/CD3 TM/4-1BB/CD3zeta/2A/mIL-15 chimeric antigen receptor complex (see FIG. 2, CD19-39_5b). The polynucleotide comprises or is composed of an anti-CD19 moiety, a CD8a hinge, a CD8a transmembrane domain, a 4-1 BB domain, a CD3zeta domain, a 2A cleavage site, and an mIL-15 domain as described herein. In several embodiments, this receptor complex is encoded by a nucleic acid molecule comprising a sequence obtained from a combination of sequences disclosed herein, or comprises an amino acid sequence obtained from a combination of sequences disclosed herein. In several embodiments, the encoding nucleic acid sequence, or the amino acid sequence, comprises a sequence in accordance with one or more SEQ ID NOS as described herein, such as those included herein as examples of constituent parts. In several embodiments, the encoding nucleic acid sequence, or the amino acid sequence, comprises a sequence that shares at least about 90%, at least about 94%, at least about 95%, at least about 96%, at least about 97%, at least about 98%, or at least about 99%, sequence identity, homology and/or functional equivalence with a sequence resulting from the combination one or more SEQ ID NOS as described herein.

In several embodiments, there is provided a polynucleotide encoding an anti-CD19moiety/CD8 alpha hinge/CD3 TM/4-1BB/NKp80 chimeric antigen receptor complex (see FIG. 2, CD19-39_6a). The polynucleotide comprises or is composed of an anti-CD19 moiety, a CD8a hinge, a CD3 transmembrane domain, a 4-1BB domain, and an NKp80 domain as described herein. In several embodiments, this receptor complex is encoded by a nucleic acid molecule comprising a sequence obtained from a combination of sequences disclosed herein, or comprises an amino acid sequence obtained from a combination of sequences disclosed herein. In several embodiments, the encoding nucleic acid sequence, or the amino acid sequence, comprises a sequence in accordance with one or more SEQ ID NOS as described herein, such as those included herein as examples of constituent parts. In several embodiments, the encoding nucleic acid sequence, or the amino acid sequence, comprises a sequence that shares at least about 90%, at least about 94%, at least about 95%, at least about 96%, at least about 97%, at least about 98%, or at least about 99%, sequence identity, homology and/or functional equivalence with a sequence resulting from the combination one or more SEQ ID NOS as described herein.

In several embodiments, there is provided a polynucleotide encoding an anti-CD19moiety/CD8 alpha hinge/CD3 TM/4-1BB/NKp80/2A/mIL-15 chimeric antigen receptor complex (see FIG. 2, CD19-39_6b). The polynucleotide comprises or is composed of an anti-CD19 moiety, a CD8a hinge, a CD8a transmembrane domain, a 4-1 BB domain, an NKp80 domain, a 2A cleavage site, and an mIL-15 domain as described herein. In several embodiments, this receptor complex is encoded by a nucleic acid molecule comprising a sequence obtained from a combination of sequences disclosed herein, or comprises an amino acid sequence obtained from a combination of sequences disclosed herein. In several embodiments, the encoding nucleic acid sequence, or the amino acid sequence, comprises a sequence in accordance with one or more SEQ ID NOS as described herein, such as those included herein as examples of constituent parts. In several embodiments, the encoding nucleic acid sequence, or the amino acid sequence, comprises a sequence that shares at least about 90%, at least about 94%, at least about 95%, at least about 96%, at least about 97%, at least about 98%, or at least about 99%, sequence identity, homology and/or functional equivalence with a sequence resulting from the combination one or more SEQ ID NOS as described herein.

In several embodiments, there is provided a polynucleotide encoding an anti-CD19moiety/CD8 alpha hinge/CD3 TM/CD16 intracellular domain/4-1BB chimeric antigen receptor complex (see FIG. 2, CD19-39_10a). The polynucleotide comprises or is composed of an anti-CD19 moiety, a CD8a hinge, a CD3 transmembrane domain, CD16 intracellular domain, and a 4-1 BB domain as described herein. In several embodiments, this receptor complex is encoded by a nucleic acid molecule comprising a sequence obtained from a combination of sequences disclosed herein, or comprises an amino acid sequence obtained from a combination of sequences disclosed herein. In several embodiments, the encoding nucleic acid sequence, or the amino acid sequence, comprises a sequence in accordance with one or more SEQ ID NOS as described herein, such as those included herein as examples of constituent parts. In several embodiments, the encoding nucleic acid sequence, or the amino acid sequence, comprises a sequence that shares at least about 90%, at least about 94%, at least about 95%, at least about 96%, at least about 97%, at least about 98%, or at least about 99%, sequence identity, homology and/or functional equivalence with a sequence resulting from the combination one or more SEQ ID NOS as described herein.

In several embodiments, there is provided a polynucleotide encoding an anti-CD19moiety/CD8 alpha hinge/CD3 TM/CD16/4-1BB/2A/mIL-15 chimeric antigen receptor complex (see FIG. 2, CD19-39_10b). The polynucleotide comprises or is composed of an anti-CD19 moiety, a CD8a hinge, a CD8a transmembrane domain, a CD16 intracellular domain, a 4-1 BB domain, a 2A cleavage site, and an mIL-15 domain as described herein. In several embodiments, this receptor complex is encoded by a nucleic acid molecule comprising a sequence obtained from a combination of sequences disclosed herein, or comprises an amino acid sequence obtained from a combination of sequences disclosed herein. In several embodiments, the encoding nucleic acid sequence, or the amino acid sequence, comprises a sequence in accordance with one or more SEQ ID NOS as described herein, such as those included herein as examples of constituent parts. In several embodiments, the encoding nucleic acid sequence, or the amino acid sequence, comprises a sequence that shares at least about 90%, at least about 94%, at least about 95%, at least about 96%, at least about 97%, at least about 98%, or at least about 99%, sequence identity, homology and/or functional equivalence with a sequence resulting from the combination one or more SEQ ID NOS as described herein.

In several embodiments, there is provided a polynucleotide encoding an anti-CD19moiety/NKG2D Extracellular Domain/CD8hinge-CD8TM/OX40/CD3zeta chimeric antigen receptor complex (see FIG. 2, CD19/NKG2D-1a). The polynucleotide comprises or is composed of an anti-CD19 moiety, an NKG2D extracellular domain (either full length or a fragment), a CD8a hinge, a CD8a transmembrane domain, an OX40 domain, and a CD3zeta domain as described herein. In several embodiments, this receptor complex is encoded by a nucleic acid molecule comprising a sequence obtained from a combination of sequences disclosed herein, or comprises an amino acid sequence obtained from a combination of sequences disclosed herein. In several embodiments, the encoding nucleic acid sequence, or the amino acid sequence, comprises a sequence in accordance with one or more SEQ ID NOS as described herein, such as those included herein as examples of constituent parts. In several embodiments, the encoding nucleic acid sequence, or the amino acid sequence, comprises a sequence that shares at least about 90%, at least about 94%, at least about 95%, at least about 96%, at least about 97%, at least about 98%, or at least about 99%, sequence identity, homology and/or functional equivalence with a sequence resulting from the combination one or more SEQ ID NOS as described herein.

In several embodiments, there is provided a polynucleotide encoding an anti-CD19moiety/NKG2D EC Domain/CD8hinge-CD8TM/OX40/CD3zeta/2A/mIL-15 chimeric antigen receptor complex (see FIG. 2, CD19/NKG2D-1b). The polynucleotide comprises or is composed of an anti-CD19 moiety, an NKG2D extracellular domain (either full length or a fragment), a CD8a hinge, a CD8a transmembrane domain, an OX40 domain, a CD3zeta domain, a 2A cleavage site, and an mIL-15 domain as described herein. In several embodiments, this receptor complex is encoded by a nucleic acid molecule comprising a sequence obtained from a combination of sequences disclosed herein, or comprises an amino acid sequence obtained from a combination of sequences disclosed herein. In several embodiments, the encoding nucleic acid sequence, or the amino acid sequence, comprises a sequence in accordance with one or more SEQ ID NOS as described herein, such as those included herein as examples of constituent parts. In several embodiments, the encoding nucleic acid sequence, or the amino acid sequence, comprises a sequence that shares at least about 90%, at least about 94%, at least about 95%, at least about 96%, at least about 97%, at least about 98%, or at least about 99%, sequence identity, homology and/or functional equivalence with a sequence resulting from the combination one or more SEQ ID NOS as described herein.

In several embodiments, there is provided a polynucleotide encoding an anti-CD19moiety/CD8hinge/CD8TM/4-1BB/CD3zeta/mbIL15 chimeric antigen receptor complex (see FIG. 3A, NK19). The polynucleotide comprises or is composed of an anti-CD19 scFv, a CD8a hinge, a CD8a transmembrane domain, a 4-1BB domain, and a CD3zeta domain. In several embodiments, this receptor complex is encoded by a nucleic acid molecule having the sequence of SEQ ID NO: 85. In several embodiments, a nucleic acid sequence encoding an NK19 chimeric antigen receptor comprises a sequence that shares at least about 90%, at least about 94%, at least about 95%, at least about 96%, at least about 97%, at least about 98%, or at least about 99%, sequence identity, homology and/or functional equivalence with SEQ ID NO: 85. In several embodiments, the chimeric receptor comprises the amino acid sequence of SEQ ID NO: 86. In several embodiments, a NK19 chimeric antigen receptor comprises an amino acid sequence that shares at least about 90%, at least about 94%, at least about 95%, at least about 96%, at least about 97%, at least about 98%, or at least about 99%, sequence identity, homology and/or functional equivalence with SEQ ID NO: 86. Schematically depicted and used in several embodiments, there is provided an NK19 construct that lacks an mbIL15 domain (FIG. 3A, NK19 opt.)

In several embodiments, there is provided a polynucleotide encoding an anti-CD19moiety/CD8hinge/CD8TM/OX40/CD3zeta chimeric antigen receptor complex (see FIG. 3A, NK19-1a). The polynucleotide comprises or is composed of an anti-CD19 scFv, a CD8a hinge, a CD8a transmembrane domain, an OX40 domain, and a CD3zeta domain. In several embodiments, the chimeric antigen receptor further comprises mbIL15 (see FIG. 3A, NK19-1b). In such embodiments, the polynucleotide comprises or is composed of an anti-CD19 scFv, a CD8a hinge, a CD8a transmembrane domain, an OX40 domain, a CD3zeta domain, a 2A cleavage site, and an mbIL-15 domain as described herein. In several embodiments, this receptor complex is encoded by a nucleic acid molecule having the sequence of SEQ ID NO: 59. In several embodiments, a nucleic acid sequence encoding an NK19 chimeric antigen receptor comprises a sequence that shares at least about 90%, at least about 94%, at least about 95%, at least about 96%, at least about 97%, at least about 98%, or at least about 99%, sequence identity, homology and/or functional equivalence with SEQ ID NO: 59. In several embodiments, the chimeric receptor comprises the amino acid sequence of SEQ ID NO: 60. In several embodiments, a NK19 chimeric antigen receptor comprises an amino acid sequence that shares at least about 90%, at least about 94%, at least about 95%, at least about 96%, at least about 97%, at least about 98%, or at least about 99%, sequence identity, homology and/or functional equivalence with SEQ ID NO: 60. In several embodiments, the CD19 scFv does not comprise a Flag tag.

In several embodiments, there is provided a polynucleotide encoding an anti-CD19moiety/CD8hinge/CD28TM/CD28/CD3zeta chimeric antigen receptor complex (see FIG. 3A, NK19-2a). The polynucleotide comprises or is composed of an anti-CD19 scFv, a CD8a hinge, a CD28 transmembrane domain, CD28 signaling domain, and a CD3zeta domain. In several embodiments, the chimeric antigen receptor further comprises mbIL15 (see FIG. 3A, NK19-2b). In such embodiments, the polynucleotide comprises or is composed of an anti-CD19 scFv, a CD8a hinge, a CD28 transmembrane domain, CD28 signaling domain, a CD3zeta domain a 2A cleavage site, and an mbIL-15 domain as described herein. In several embodiments, this receptor complex is encoded by a nucleic acid molecule having the sequence of SEQ ID NO: 61. In several embodiments, a nucleic acid sequence encoding an NK19 chimeric antigen receptor comprises a sequence that shares at least about 90%, at least about 94%, at least about 95%, at least about 96%, at least about 97%, at least about 98%, or at least about 99%, sequence identity, homology and/or functional equivalence with SEQ ID NO: 61. In several embodiments, the chimeric receptor comprises the amino acid sequence of SEQ ID NO: 62. In several embodiments, a NK19 chimeric antigen receptor comprises an amino acid sequence that shares at least about 90%, at least about 94%, at least about 95%, at least about 96%, at least about 97%, at least about 98%, or at least about 99%, sequence identity, homology and/or functional equivalence with SEQ ID NO: 62. In several embodiments, the CD19 scFv does not comprise a Flag tag.

In several embodiments, there is provided a polynucleotide encoding an anti-CD19moiety/CD8hinge/CD8aTM/ICOS/CD3zeta chimeric antigen receptor complex (see FIG. 3A, NK19-3a). The polynucleotide comprises or is composed of an anti-CD19 scFv, a CD8a hinge, a CD8a transmembrane domain, inducible costimulator (ICOS) signaling domain, and a CD3zeta domain. In several embodiments, the chimeric antigen receptor further comprises mbIL15 (see FIG. 3A, NK19-3b). In such embodiments, the polynucleotide comprises or is composed of an anti-CD19 scFv, a CD8a hinge, a CD8a transmembrane domain, inducible costimulator (ICOS) signaling domain, a CD3zeta domain, a 2A cleavage site, and an mbIL-15 domain as described herein. In several embodiments, this receptor complex is encoded by a nucleic acid molecule having the sequence of SEQ ID NO: 63. In several embodiments, a nucleic acid sequence encoding an NK19 chimeric antigen receptor comprises a sequence that shares at least about 90%, at least about 94%, at least about 95%, at least about 96%, at least about 97%, at least about 98%, or at least about 99%, sequence identity, homology and/or functional equivalence with SEQ ID NO: 63. In several embodiments, the chimeric receptor comprises the amino acid sequence of SEQ ID NO: 64. In several embodiments, a NK19 chimeric antigen receptor comprises an amino acid sequence that shares at least about 90%, at least about 94%, at least about 95%, at least about 96%, at least about 97%, at least about 98%, or at least about 99%, sequence identity, homology and/or functional equivalence with SEQ ID NO: 64. In several embodiments, the CD19 scFv does not comprise a Flag tag.

In several embodiments, there is provided a polynucleotide encoding an anti-CD19moiety/CD8hinge/CD8aTM/CD28/4-1BB/CD3zeta chimeric antigen receptor complex (see FIG. 3A, NK19-4a).

The polynucleotide comprises or is composed of an anti-CD19 scFv, a CD8a hinge, a CD8a transmembrane domain, a CD28 signaling domain, a 4-1 BB signaling domain, and a CD3zeta domain. In several embodiments, the chimeric antigen receptor further comprises mbIL15 (see FIG. 3A, NK19-4b). In such embodiments, the polynucleotide comprises or is composed of an anti-CD19 scFv, a CD8a hinge, a CD8a transmembrane domain, a CD28 signaling domain, a 4-1 BB signaling domain, a CD3zeta domain, a 2A cleavage site, and an mbIL-15 domain as described herein. In several embodiments, this receptor complex is encoded by a nucleic acid molecule having the sequence of SEQ ID NO: 65. In several embodiments, a nucleic acid sequence encoding an NK19 chimeric antigen receptor comprises a sequence that shares at least about 90%, at least about 94%, at least about 95%, at least about 96%, at least about 97%, at least about 98%, or at least about 99%, sequence identity, homology and/or functional equivalence with SEQ ID NO: 65. In several embodiments, the chimeric receptor comprises the amino acid sequence of SEQ ID NO: 66. In several embodiments, a NK19 chimeric antigen receptor comprises an amino acid sequence that shares at least about 90%, at least about 94%, at least about 95%, at least about 96%, at least about 97%, at least about 98%, or at least about 99%, sequence identity, homology and/or functional equivalence with SEQ ID NO: 66. In several embodiments, the CD19 scFv does not comprise a Flag tag.

Figure 3B:
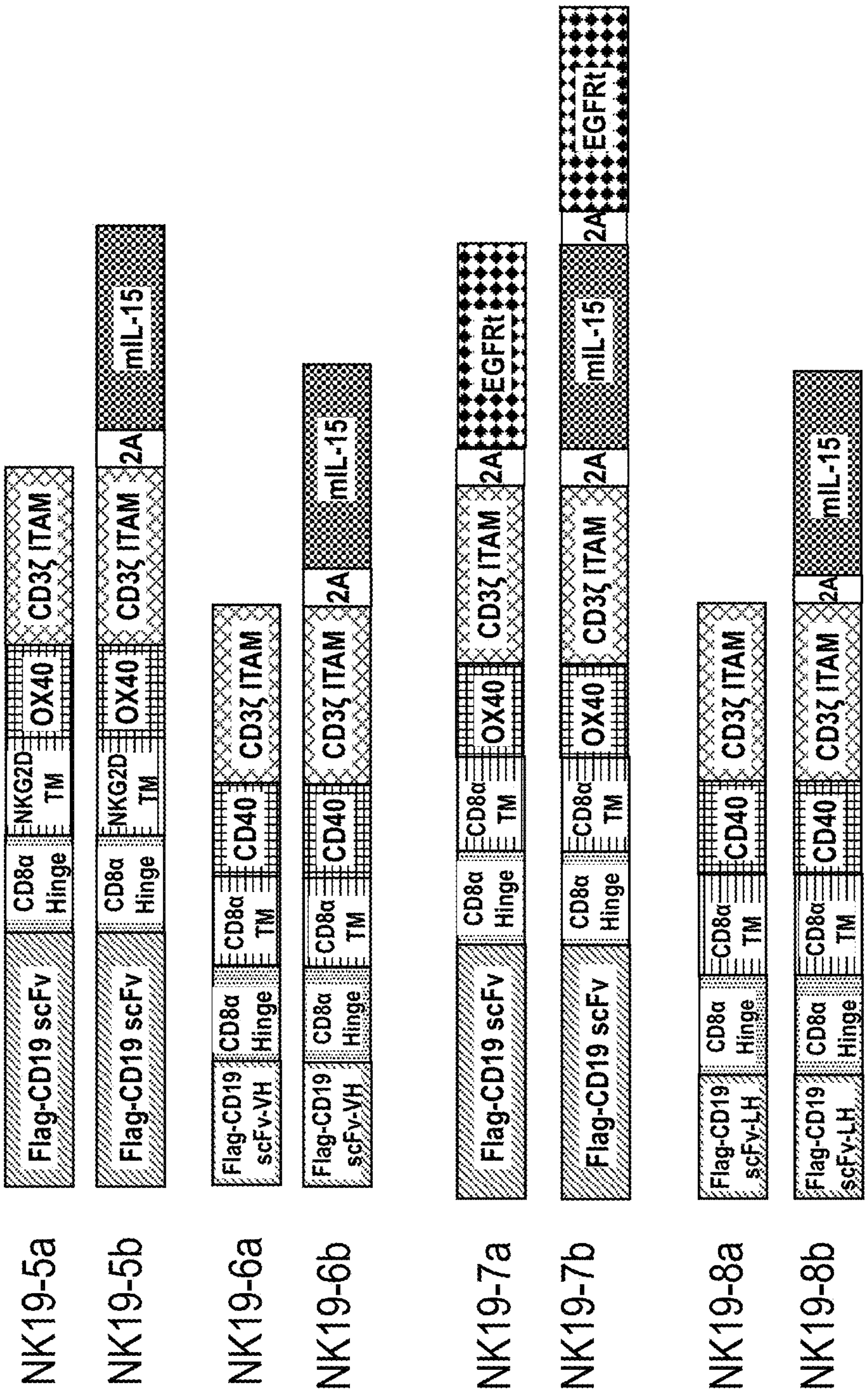
FIG. 3B also includes depictions of non-limiting examples of CD19-directed chimeric receptors.

In several embodiments, there is provided a polynucleotide encoding an anti-CD19moiety/CD8hinge/NKG2DTM/OX40/CD3zeta chimeric antigen receptor complex (see FIG. 3B, NK19-5a). The polynucleotide comprises or is composed of an anti-CD19 scFv, a CD8a hinge, a NKG2D transmembrane domain, an OX40 signaling domain, and a CD3zeta domain. In several embodiments, the chimeric antigen receptor further comprises mbIL15 (see FIG. 3B, NK19-5b). In such embodiments, the polynucleotide comprises or is composed of an anti-CD19 scFv, a CD8a hinge, a NKG2D transmembrane domain, an OX40 signaling domain, a CD3zeta domain, a 2A cleavage site, and an mbIL-15 domain as described herein. In several embodiments, this receptor complex is encoded by a nucleic acid molecule having the sequence of SEQ ID NO: 67. In several embodiments, a nucleic acid sequence encoding an NK19 chimeric antigen receptor comprises a sequence that shares at least about 90%, at least about 94%, at least about 95%, at least about 96%, at least about 97%, at least about 98%, or at least about 99%, sequence identity, homology and/or functional equivalence with SEQ ID NO: 67. In several embodiments, the chimeric receptor comprises the amino acid sequence of SEQ ID NO: 68. In several embodiments, a NK19 chimeric antigen receptor comprises an amino acid sequence that shares at least about 90%, at least about 94%, at least about 95%, at least about 96%, at least about 97%, at least about 98%, or at least about 99%, sequence identity, homology and/or functional equivalence with SEQ ID NO: 68. In several embodiments, the CD19 scFv does not comprise a Flag tag.

In several embodiments, there is provided a polynucleotide encoding an anti-CD19moiety/CD8hinge/CD8aTM/CD40/CD3zeta chimeric antigen receptor complex (see FIG. 3B, NK19-6a). The polynucleotide comprises or is composed of an anti-CD19 scFv variable heavy chain, a CD8a hinge, a CD8a transmembrane domain, a CD40 signaling domain, and a CD3zeta domain. In several embodiments, the chimeric antigen receptor further comprises mbIL15 (see FIG. 3B, NK19-6b). In such embodiments, the polynucleotide comprises or is composed of an anti-CD19 scFv variable heavy chain, a CD8a hinge, a CD8a transmembrane domain, a CD40 signaling domain, a CD3zeta domain, a 2A cleavage site, and an mbIL-15 domain as described herein. In several embodiments, this receptor complex is encoded by a nucleic acid molecule having the sequence of SEQ ID NO: 69. In several embodiments, a nucleic acid sequence encoding an NK19 chimeric antigen receptor comprises a sequence that shares at least about 90%, at least about 94%, at least about 95%, at least about 96%, at least about 97%, at least about 98%, or at least about 99%, sequence identity, homology and/or functional equivalence with SEQ ID NO: 69. In several embodiments, the chimeric receptor comprises the amino acid sequence of SEQ ID NO: 70. In several embodiments, a NK19 chimeric antigen receptor comprises an amino acid sequence that shares at least about 90%, at least about 94%, at least about 95%, at least about 96%, at least about 97%, at least about 98%, or at least about 99%, sequence identity, homology and/or functional equivalence with SEQ ID NO: 70. In several embodiments, the CD19 scFv does not comprise a Flag tag.

In several embodiments, there is provided a polynucleotide encoding an anti-CD19moiety/CD8hinge/CD8aTM/OX40/CD3zeta/2A/EGFRt chimeric antigen receptor complex (see FIG. 3B, NK19-7a). The polynucleotide comprises or is composed of an anti-CD19 scFv, a CD8a hinge, a CD8a transmembrane domain, an OX40 signaling domain, a CD3zeta domain, a 2A cleavage side, and a truncated version of the epidermal growth factor receptor (EGFRt). In several embodiments, the chimeric antigen receptor further comprises mbIL15 (see FIG. 3B, NK19-7b). In such embodiments, the polynucleotide comprises or is composed of an anti-CD19 scFv, a CD8a hinge, a CD8a transmembrane domain, an OX40 signaling domain, a CD3zeta domain, a 2A cleavage side, a truncated version of the epidermal growth factor receptor (EGFRt), an additional 2A cleavage site, and an mbIL-15 domain as described herein. In several embodiments, this receptor complex is encoded by a nucleic acid molecule having the sequence of SEQ ID NO: 71. In several embodiments, a nucleic acid sequence encoding an NK19 chimeric antigen receptor comprises a sequence that shares at least about 90%, at least about 94%, at least about 95%, at least about 96%, at least about 97%, at least about 98%, or at least about 99%, sequence identity, homology and/or functional equivalence with SEQ ID NO: 71. In several embodiments, the chimeric receptor comprises the amino acid sequence of SEQ ID NO: 72. In several embodiments, a NK19 chimeric antigen receptor comprises an amino acid sequence that shares at least about 90%, at least about 94%, at least about 95%, at least about 96%, at least about 97%, at least about 98%, or at least about 99%, sequence identity, homology and/or functional equivalence with SEQ ID NO: 72. In several embodiments, the CD19 scFv does not comprise a Flag tag.

In several embodiments, there is provided a polynucleotide encoding an anti-CD19moiety/CD8hinge/CD8aTM/CD40/CD3zeta chimeric antigen receptor complex (see FIG. 3B, NK19-8a). The polynucleotide comprises or is composed of an anti-CD19 scFv variable light chain, a CD8a hinge, a CD8a transmembrane domain, a CD40 signaling domain, and a CD3zeta domain. In several embodiments, the chimeric antigen receptor further comprises mbIL15 (see FIG. 3B, NK19-7b). In such embodiments, the polynucleotide comprises or is composed of an anti-CD19 scFv variable light chain, a CD8a hinge, a CD8a transmembrane domain, a CD40 signaling domain, a CD3zeta domain, a 2A cleavage site, and an mbIL-15 domain as described herein. In several embodiments, this receptor complex is encoded by a nucleic acid molecule having the sequence of SEQ ID NO: 73. In several embodiments, a nucleic acid sequence encoding an NK19 chimeric antigen receptor comprises a sequence that shares at least about 90%, at least about 94%, at least about 95%, at least about 96%, at least about 97%, at least about 98%, or at least about 99%, sequence identity, homology and/or functional equivalence with SEQ ID NO: 73. In several embodiments, the chimeric receptor comprises the amino acid sequence of SEQ ID NO: 74. In several embodiments, a NK19 chimeric antigen receptor comprises an amino acid sequence that shares at least about 90%, at least about 94%, at least about 95%, at least about 96%, at least about 97%, at least about 98%, or at least about 99%, sequence identity, homology and/or functional equivalence with SEQ ID NO: 74. In several embodiments, the CD19 scFv does not comprise a Flag tag.

In several embodiments, there is provided a polynucleotide encoding an anti-CD19moiety/CD8hinge/CD8aTM/CD40/CD3zeta chimeric antigen receptor complex (see FIG. 3B, NK19-8a). The polynucleotide comprises or is composed of an anti-CD19 scFv variable light chain, a CD8a hinge, a CD8a transmembrane domain, a CD40 signaling domain, and a CD3zeta domain. In several embodiments, the chimeric antigen receptor further comprises mbIL15 (see FIG. 3B, NK19-7b). In such embodiments, the polynucleotide comprises or is composed of an anti-CD19 scFv variable light chain, a CD8a hinge, a CD8a transmembrane domain, a CD40 signaling domain, a CD3zeta domain, a 2A cleavage site, and an mbIL-15 domain as described herein. In several embodiments, this receptor complex is encoded by a nucleic acid molecule having the sequence of SEQ ID NO: 73. In several embodiments, a nucleic acid sequence encoding an NK19 chimeric antigen receptor comprises a sequence that shares at least about 90%, at least about 94%, at least about 95%, at least about 96%, at least about 97%, at least about 98%, or at least about 99%, sequence identity, homology and/or functional equivalence with SEQ ID NO: 73. In several embodiments, the chimeric receptor comprises the amino acid sequence of SEQ ID NO: 74. In several embodiments, a NK19 chimeric antigen receptor comprises an amino acid sequence that shares at least about 90%, at least about 94%, at least about 95%, at least about 96%, at least about 97%, at least about 98%, or at least about 99%, sequence identity, homology and/or functional equivalence with SEQ ID NO: 74. In several embodiments, the CD19 scFv does not comprise a Flag tag.

Figure 3C:
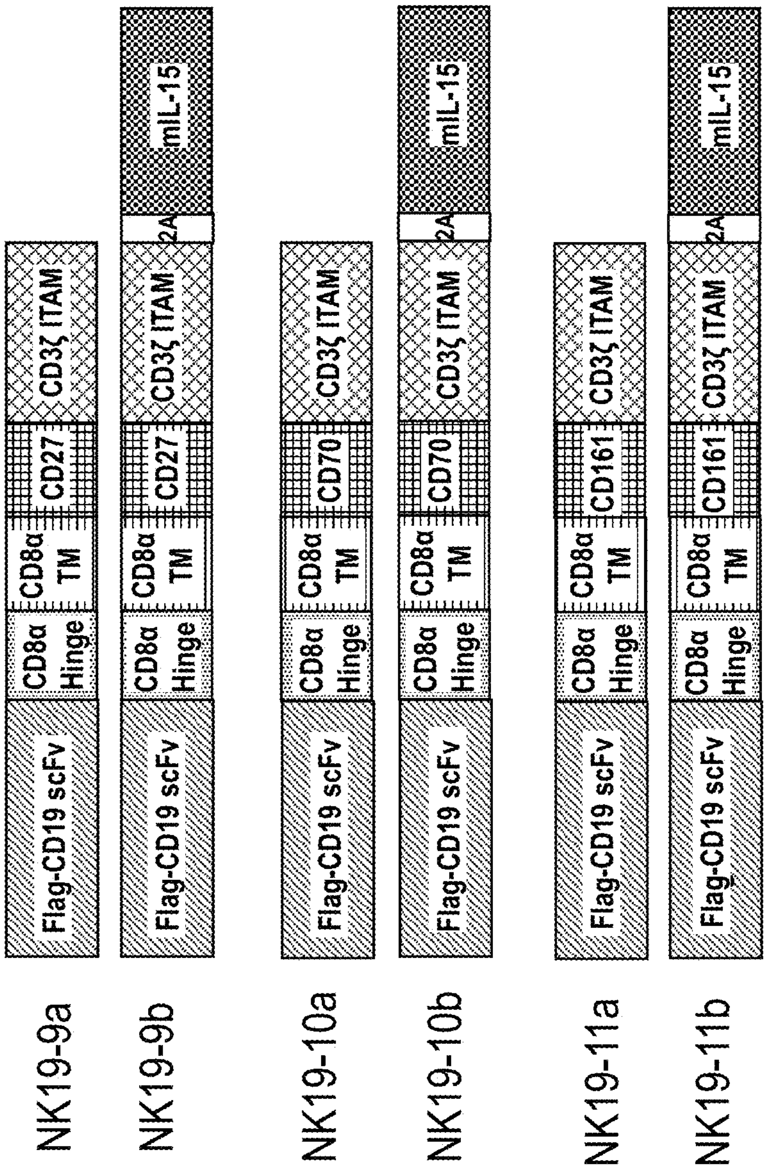
FIG. 3C also includes depictions of non-limiting examples of CD19-directed chimeric receptors.
Figure 3C:
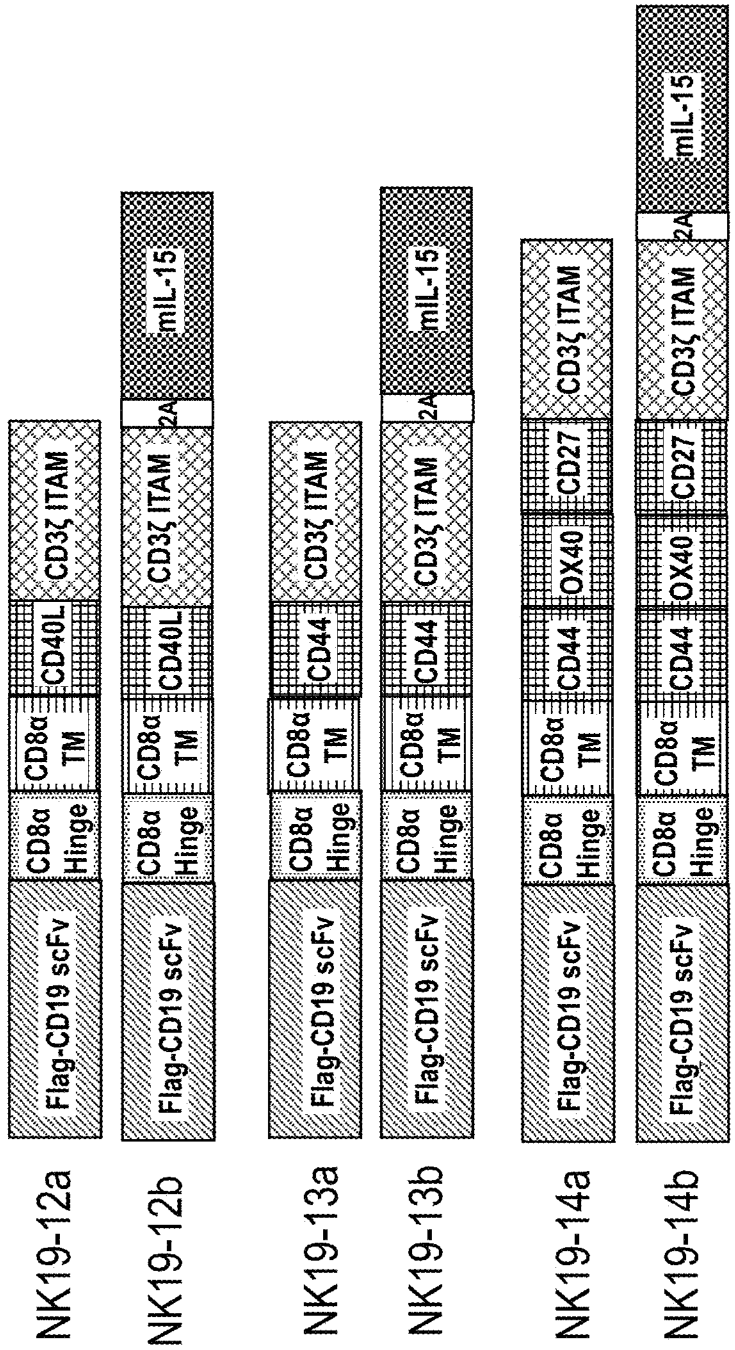

In several embodiments, there is provided a polynucleotide encoding an anti-CD19moiety/CD8hinge/CD8aTM/CD27/CD3zeta chimeric antigen receptor complex (see FIG. 3C, NK19-9a). The polynucleotide comprises or is composed of an anti-CD19 scFv, a CD8a hinge, a CD8a transmembrane domain, a CD27 signaling domain, and a CD3zeta domain. In several embodiments, the chimeric antigen receptor further comprises mbIL15 (see FIG. 3C, NK19-9b). In such embodiments, the polynucleotide comprises or is composed of an anti-CD19 scFv, a CD8a hinge, a CD8a transmembrane domain, a CD27 signaling domain, a CD3zeta domain, a 2A cleavage site, and an mbIL-15 domain as described herein. In several embodiments, this receptor complex is encoded by a nucleic acid molecule having the sequence of SEQ ID NO: 75. In several embodiments, a nucleic acid sequence encoding an NK19 chimeric antigen receptor comprises a sequence that shares at least about 90%, at least about 94%, at least about 95%, at least about 96%, at least about 97%, at least about 98%, or at least about 99%, sequence identity, homology and/or functional equivalence with SEQ ID NO: 75. In several embodiments, the chimeric receptor comprises the amino acid sequence of SEQ ID NO: 76. In several embodiments, a NK19 chimeric antigen receptor comprises an amino acid sequence that shares at least about 90%, at least about 94%, at least about 95%, at least about 96%, at least about 97%, at least about 98%, or at least about 99%, sequence identity, homology and/or functional equivalence with SEQ ID NO: 76. In several embodiments, the CD19 scFv does not comprise a Flag tag.

In several embodiments, there is provided a polynucleotide encoding an anti-CD19moiety/CD8hinge/CD8aTM/CD70/CD3zeta chimeric antigen receptor complex (see FIG. 3C, NK19-10a). The polynucleotide comprises or is composed of an anti-CD19 scFv, a CD8a hinge, a CD8a transmembrane domain, a CD70 signaling domain, and a CD3zeta domain. In several embodiments, the chimeric antigen receptor further comprises mbIL15 (see FIG. 3C, NK19-10b). In such embodiments, the polynucleotide comprises or is composed of an anti-CD19 scFv, a CD8a hinge, a CD8a transmembrane domain, a CD70 signaling domain, a CD3zeta domain, a 2A cleavage site, and an mbIL-15 domain as described herein. In several embodiments, this receptor complex is encoded by a nucleic acid molecule having the sequence of SEQ ID NO: 77. In several embodiments, a nucleic acid sequence encoding an NK19 chimeric antigen receptor comprises a sequence that shares at least about 90%, at least about 94%, at least about 95%, at least about 96%, at least about 97%, at least about 98%, or at least about 99%, sequence identity, homology and/or functional equivalence with SEQ ID NO: 77. In several embodiments, the chimeric receptor comprises the amino acid sequence of SEQ ID NO: 78. In several embodiments, a NK19 chimeric antigen receptor comprises an amino acid sequence that shares at least about 90%, at least about 94%, at least about 95%, at least about 96%, at least about 97%, at least about 98%, or at least about 99%, sequence identity, homology and/or functional equivalence with SEQ ID NO: 78. In several embodiments, the CD19 scFv does not comprise a Flag tag.

In several embodiments, there is provided a polynucleotide encoding an anti-CD19moiety/CD8hinge/CD8aTM/CD161/CD3zeta chimeric antigen receptor complex (see FIG. 3C, NK19-11a). The polynucleotide comprises or is composed of an anti-CD19 scFv, a CD8a hinge, a CD8a transmembrane domain, a CD161 signaling domain, and a CD3zeta domain. In several embodiments, the chimeric antigen receptor further comprises mbIL15 (see FIG. 3C, NK19-11b). In such embodiments, the polynucleotide comprises or is composed of an anti-CD19 scFv, a CD8a hinge, a CD8a transmembrane domain, a CD161 signaling domain, a CD3zeta domain, a 2A cleavage site, and an mbIL-15 domain as described herein. In several embodiments, this receptor complex is encoded by a nucleic acid molecule having the sequence of SEQ ID NO: 79. In several embodiments, a nucleic acid sequence encoding an NK19 chimeric antigen receptor comprises a sequence that shares at least about 90%, at least about 94%, at least about 95%, at least about 96%, at least about 97%, at least about 98%, or at least about 99%, sequence identity, homology and/or functional equivalence with SEQ ID NO: 79. In several embodiments, the chimeric receptor comprises the amino acid sequence of SEQ ID NO: 80. In several embodiments, a NK19 chimeric antigen receptor comprises an amino acid sequence that shares at least about 90%, at least about 94%, at least about 95%, at least about 96%, at least about 97%, at least about 98%, or at least about 99%, sequence identity, homology and/or functional equivalence with SEQ ID NO: 80. In several embodiments, the CD19 scFv does not comprise a Flag tag.

In several embodiments, there is provided a polynucleotide encoding an anti-CD19moiety/CD8hinge/CD8aTM/

CD40L/CD3zeta chimeric antigen receptor complex (see FIG. 3C, NK19-12a). The polynucleotide comprises or is composed of an anti-CD19 scFv, a CD8a hinge, a CD8a transmembrane domain, a CD40L signaling domain, and a CD3zeta domain. In several embodiments, the chimeric antigen receptor further comprises mbIL15 (see FIG. 3C, NK19-12b). In such embodiments, the polynucleotide comprises or is composed of an anti-CD19 scFv, a CD8a hinge, a CD8a transmembrane domain, a CD40L signaling domain, a CD3zeta domain, a 2A cleavage site, and an mbIL-15 domain as described herein. In several embodiments, this receptor complex is encoded by a nucleic acid molecule having the sequence of SEQ ID NO: 81. In several embodiments, a nucleic acid sequence encoding an NK19 chimeric antigen receptor comprises a sequence that shares at least about 90%, at least about 94%, at least about 95%, at least about 96%, at least about 97%, at least about 98%, or at least about 99%, sequence identity, homology and/or functional equivalence with SEQ ID NO: 81. In several embodiments, the chimeric receptor comprises the amino acid sequence of SEQ ID NO: 82. In several embodiments, a NK19 chimeric antigen receptor comprises an amino acid sequence that shares at least about 90%, at least about 94%, at least about 95%, at least about 96%, at least about 97%, at least about 98%, or at least about 99%, sequence identity, homology and/or functional equivalence with SEQ ID NO: 82. In several embodiments, the CD19 scFv does not comprise a Flag tag.

In several embodiments, there is provided a polynucleotide encoding an anti-CD19moiety/CD8hinge/CD8aTM/CD44/CD3zeta chimeric antigen receptor complex (see FIG. 3C, NK19-13). The polynucleotide comprises or is composed of an anti-CD19 scFv, a CD8a hinge, a CD8a transmembrane domain, a CD44 signaling domain, and a CD3zeta domain. In several embodiments, the chimeric antigen receptor further comprises mbIL15 (see FIG. 3C, NK19-13b). In such embodiments, the polynucleotide comprises or is composed of an anti-CD19 scFv, a CD8a hinge, a CD8a transmembrane domain, a CD44 signaling domain, a CD3zeta domain, a 2A cleavage site, and an mbIL-15 domain as described herein. In several embodiments, this receptor complex is encoded by a nucleic acid molecule having the sequence of SEQ ID NO: 83. In several embodiments, a nucleic acid sequence encoding an NK19 chimeric antigen receptor comprises a sequence that shares at least about 90%, at least about 94%, at least about 95%, at least about 96%, at least about 97%, at least about 98%, or at least about 99%, sequence identity, homology and/or functional equivalence with SEQ ID NO: 83. In several embodiments, the chimeric receptor comprises the amino acid sequence of SEQ ID NO: 84. In several embodiments, a NK19 chimeric antigen receptor comprises an amino acid sequence that shares at least about 90%, at least about 94%, at least about 95%, at least about 96%, at least about 97%, at least about 98%, or at least about 99%, sequence identity, homology and/or functional equivalence with SEQ ID NO: 84. In several embodiments, the CD19 scFv does not comprise a Flag tag.

In several embodiments, there is provided a polynucleotide encoding a Flag-tag humanized anti-CD19moiety/CD8hinge/CD8TM/OX40/CD3zeta chimeric antigen receptor complex (see FIG. 3D, NK19H-1a). The polynucleotide comprises or is composed of an anti-CD19 scFv that has been humanized and comprises a first humanized light chain and a first humanized heavy chain (L1/H1), and comprises a Flag tag, a CD8a hinge, a CD8a transmembrane domain, an OX40 signaling domain, and a CD3zeta domain. In several embodiments, the chimeric antigen receptor further comprises mbIL15 (see FIG. 3D, NK19H-1b). In such embodiments, the polynucleotide comprises or is composed of an anti-CD19 scFv that has been humanized and comprises a first humanized light chain and a first humanized heavy chain (L1/H1), and comprises a Flag tag, a CD8a hinge, a CD8a transmembrane domain, an OX40 signaling domain, and a CD3zeta domain, a 2A cleavage site, and an mbIL-15 domain as described herein. In several embodiments, this receptor complex is encoded by a nucleic acid molecule having the sequence of SEQ ID NO: 160. In several embodiments, a nucleic acid sequence encoding an NK19 chimeric antigen receptor comprises a sequence that shares at least about 90%, at least about 94%, at least about 95%, at least about 96%, at least about 97%, at least about 98%, or at least about 99%, sequence identity, homology and/or functional equivalence with SEQ ID NO: 160. In several embodiments, the chimeric receptor comprises the amino acid sequence of SEQ ID NO: 161. In several embodiments, a NK19 chimeric antigen receptor comprises an amino acid sequence that shares at least about 90%, at least about 94%, at least about 95%, at least about 96%, at least about 97%, at least about 98%, or at least about 99%, sequence identity, homology and/or functional equivalence with SEQ ID NO: 161.

In several embodiments, there is provided a polynucleotide encoding a Flag-tag humanized anti-CD19moiety/CD8hinge/CD8TM/OX40/CD3zeta chimeric antigen receptor complex (see FIG. 3D, NK19H-2a). The polynucleotide comprises or is composed of an anti-CD19 scFv that has been humanized, and comprises a second humanized light chain and a first humanized heavy chain (L2/H1), and comprises a Flag tag, a CD8a hinge, a CD8a transmembrane domain, an OX40 signaling domain, and a CD3zeta domain. In several embodiments, the chimeric antigen receptor further comprises mbIL15 (see FIG. 3D, NK19H-2b). In such embodiments, the polynucleotide comprises or is composed of an anti-CD19 scFv that has been humanized comprises a second humanized light chain and a first humanized heavy chain (L2/H1), and comprises a Flag tag, a CD8a hinge, a CD8a transmembrane domain, an OX40 signaling domain, a CD3zeta domain, a 2A cleavage site, and an mbIL-15 domain as described herein. In several embodiments, this receptor complex is encoded by a nucleic acid molecule having the sequence of SEQ ID NO: 162. In several embodiments, a nucleic acid sequence encoding an NK19 chimeric antigen receptor comprises a sequence that shares at least about 90%, at least about 94%, at least about 95%, at least about 96%, at least about 97%, at least about 98%, or at least about 99%, sequence identity, homology and/or functional equivalence with SEQ ID NO: 162. In several embodiments, the chimeric receptor comprises the amino acid sequence of SEQ ID NO: 163. In several embodiments, a NK19 chimeric antigen receptor comprises an amino acid sequence that shares at least about 90%, at least about 94%, at least about 95%, at least about 96%, at least about 97%, at least about 98%, or at least about 99%, sequence identity, homology and/or functional equivalence with SEQ ID NO: 162.

In several embodiments, there is provided a polynucleotide encoding a Flag-tag humanized anti-CD19moiety/CD8hinge/CD8TM/OX40/CD3zeta chimeric antigen receptor complex (see FIG. 3D, NK19H-3a). The polynucleotide comprises or is composed of an anti-CD19 scFv that has been humanized and comprises a third humanized light chain and a first humanized heavy chain (L3/H1), and comprises a Flag tag, a CD8a hinge, a CD8a transmembrane domain, an OX40 signaling domain, and a CD3zeta domain.

In several embodiments, the chimeric antigen receptor further comprises mbIL15 (see FIG. 3D, NK19H-3b). In such embodiments, the polynucleotide comprises or is composed of an anti-CD19 scFv that has been humanized and comprises a third humanized light chain and a first humanized heavy chain (L3/H1), and comprises a Flag tag, a CD8a hinge, a CD8a transmembrane domain, an OX40 signaling domain, and a CD3zeta domain, a 2A cleavage site, and an mbIL-15 domain as described herein. In several embodiments, this receptor complex is encoded by a nucleic acid molecule having the sequence of SEQ ID NO: 164. In several embodiments, a nucleic acid sequence encoding an NK19 chimeric antigen receptor comprises a sequence that shares at least about 90%, at least about 94%, at least about 95%, at least about 96%, at least about 97%, at least about 98%, or at least about 99%, sequence identity, homology and/or functional equivalence with SEQ ID NO: 164. In several embodiments, the chimeric receptor comprises the amino acid sequence of SEQ ID NO: 165. In several embodiments, a NK19 chimeric antigen receptor comprises an amino acid sequence that shares at least about 90%, at least about 94%, at least about 95%, at least about 96%, at least about 97%, at least about 98%, or at least about 99%, sequence identity, homology and/or functional equivalence with SEQ ID NO: 165.

In several embodiments, there is provided a polynucleotide encoding a Flag-tag humanized anti-CD19moiety/CD8hinge/CD8TM/OX40/CD3zeta chimeric antigen receptor complex (see FIG. 3D, NK19H-4a). The polynucleotide comprises or is composed of an anti-CD19 scFv that has been humanized and comprises a first humanized light chain and a second humanized heavy chain (L1/H2), and comprises a Flag tag, a CD8a hinge, a CD8a transmembrane domain, an OX40 signaling domain, and a CD3zeta domain. In several embodiments, the chimeric antigen receptor further comprises mbIL15 (see FIG. 3D, NK19H-4b). In such embodiments, the polynucleotide comprises or is composed of an anti-CD19 scFv that has been humanized and comprises a first humanized light chain and a second humanized heavy chain (L1/H2), and comprises a Flag tag, a CD8a hinge, a CD8a transmembrane domain, an OX40 signaling domain, and a CD3zeta domain, a 2A cleavage site, and an mbIL-15 domain as described herein. In several embodiments, this receptor complex is encoded by a nucleic acid molecule having the sequence of SEQ ID NO: 166. In several embodiments, a nucleic acid sequence encoding an NK19 chimeric antigen receptor comprises a sequence that shares at least about 90%, at least about 94%, at least about 95%, at least about 96%, at least about 97%, at least about 98%, or at least about 99%, sequence identity, homology and/or functional equivalence with SEQ ID NO: 166. In several embodiments, the chimeric receptor comprises the amino acid sequence of SEQ ID NO: 167. In several embodiments, a NK19 chimeric antigen receptor comprises an amino acid sequence that shares at least about 90%, at least about 94%, at least about 95%, at least about 96%, at least about 97%, at least about 98%, or at least about 99%, sequence identity, homology and/or functional equivalence with SEQ ID NO: 167.

Figure 3E:
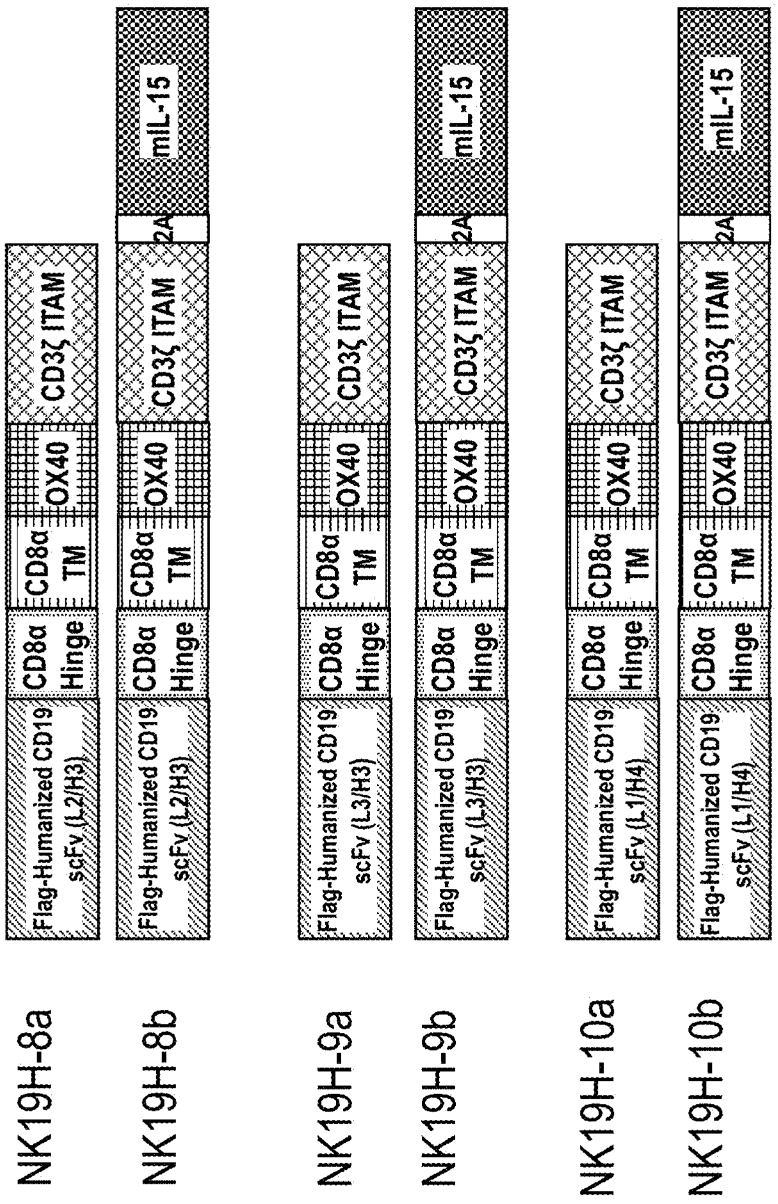
FIG. 3E also includes depictions of non-limiting examples of CD19-directed chimeric receptors comprising humanized CD19 binding domains.

In several embodiments, there is provided a polynucleotide encoding a Flag-tag humanized anti-CD19moiety/CD8hinge/CD8TM/OX40/CD3zeta chimeric antigen receptor complex (see FIG. 3E, NK19H-5a). The polynucleotide comprises or is composed of an anti-CD19 scFv that has been humanized and comprises a second humanized light chain and a second humanized heavy chain (L2/H2), and comprises a Flag tag, a CD8a hinge, a CD8a transmembrane domain, an OX40 signaling domain, and a CD3zeta domain. In several embodiments, the chimeric antigen receptor further comprises mbIL15 (see FIG. 3E, NK19H-5b). In such embodiments, the polynucleotide comprises or is composed of an anti-CD19 scFv that has been humanized and comprises a second humanized light chain and a second humanized heavy chain (L2/H2), and comprises a Flag tag, a CD8a hinge, a CD8a transmembrane domain, an OX40 signaling domain, and a CD3zeta domain, a 2A cleavage site, and an mbIL-15 domain as described herein. In several embodiments, this receptor complex is encoded by a nucleic acid molecule having the sequence of SEQ ID NO: 168. In several embodiments, a nucleic acid sequence encoding an NK19 chimeric antigen receptor comprises a sequence that shares at least about 90%, at least about 94%, at least about 95%, at least about 96%, at least about 97%, at least about 98%, or at least about 99%, sequence identity, homology and/or functional equivalence with SEQ ID NO: 168. In several embodiments, the chimeric receptor comprises the amino acid sequence of SEQ ID NO: 169. In several embodiments, a NK19 chimeric antigen receptor comprises an amino acid sequence that shares at least about 90%, at least about 94%, at least about 95%, at least about 96%, at least about 97%, at least about 98%, or at least about 99%, sequence identity, homology and/or functional equivalence with SEQ ID NO: 169.

In several embodiments, there is provided a polynucleotide encoding a Flag-tag humanized anti-CD19moiety/CD8hinge/CD8TM/OX40/CD3zeta chimeric antigen receptor complex (see FIG. 3E, NK19H-6a). The polynucleotide comprises or is composed of an anti-CD19 scFv that has been humanized and comprises a third humanized light chain and a second humanized heavy chain (L3/H2), and comprises a Flag tag, a CD8a hinge, a CD8a transmembrane domain, an OX40 signaling domain, and a CD3zeta domain. In several embodiments, the chimeric antigen receptor further comprises mbIL15 (see FIG. 3E, NK19H-6b). In such embodiments, the polynucleotide comprises or is composed of an anti-CD19 scFv that has been humanized and comprises a third humanized light chain and a second humanized heavy chain (L3/H2) and comprises a Flag tag, a CD8a hinge, a CD8a transmembrane domain, an OX40 signaling domain, and a CD3zeta domain, a 2A cleavage site, and an mbIL-15 domain as described herein. In several embodiments, this receptor complex is encoded by a nucleic acid molecule having the sequence of SEQ ID NO: 170. In several embodiments, a nucleic acid sequence encoding an NK19 chimeric antigen receptor comprises a sequence that shares at least about 90%, at least about 94%, at least about 95%, at least about 96%, at least about 97%, at least about 98%, or at least about 99%, sequence identity, homology and/or functional equivalence with SEQ ID NO: 170. In several embodiments, the chimeric receptor comprises the amino acid sequence of SEQ ID NO: 171. In several embodiments, a NK19 chimeric antigen receptor comprises an amino acid sequence that shares at least about 90%, at least about 94%, at least about 95%, at least about 96%, at least about 97%, at least about 98%, or at least about 99%, sequence identity, homology and/or functional equivalence with SEQ ID NO: 171.

In several embodiments, there is provided a polynucleotide encoding an Flag-tag humanized anti-CD19moiety/CD8hinge/CD8TM/OX40/CD3zeta chimeric antigen receptor complex (see FIG. 3E, NK19H-7a). The polynucleotide comprises or is composed of an anti-CD19 scFv that has been humanized and comprises a first humanized light chain and a third humanized heavy chain (L1/H3), and comprises a Flag tag, a CD8a hinge, a CD8a transmembrane domain, an OX40 signaling domain, and a CD3zeta domain. In several embodiments, the chimeric antigen receptor further comprises mbIL15 (see FIG. 3E, NK19H-7b). In such embodiments, the polynucleotide comprises or is composed of an anti-CD19 scFv that has been humanized and comprises a first humanized light chain and a third humanized heavy chain (L1/H3), and comprises a Flag tag, a CD8a hinge, a CD8a transmembrane domain, an OX40 signaling domain, and a CD3zeta domain, a 2A cleavage side, a truncated version of the epidermal growth factor receptor (EGFRt), an additional 2A cleavage site, and an mbIL-15 domain as described herein. In several embodiments, this receptor complex is encoded by a nucleic acid molecule having the sequence of SEQ ID NO: 172. In several embodiments, a nucleic acid sequence encoding an NK19 chimeric antigen receptor comprises a sequence that shares at least about 90%, at least about 94%, at least about 95%, at least about 96%, at least about 97%, at least about 98%, or at least about 99%, sequence identity, homology and/or functional equivalence with SEQ ID NO: 172. In several embodiments, the chimeric receptor comprises the amino acid sequence of SEQ ID NO: 173. In several embodiments, a NK19 chimeric antigen receptor comprises an amino acid sequence that shares at least about 90%, at least about 94%, at least about 95%, at least about 96%, at least about 97%, at least about 98%, or at least about 99%, sequence identity, homology and/or functional equivalence with SEQ ID NO: 174.

In several embodiments, there is provided a polynucleotide encoding a Flag-tag humanized anti-CD19moiety/CD8hinge/CD8TM/OX40/CD3zeta chimeric antigen receptor complex (see FIG. 3E, NK19H-8a). The polynucleotide comprises or is composed of an anti-CD19 scFv that has been humanized and comprises a second humanized light chain and a third humanized heavy chain (L2/H3), and comprises a Flag tag, a CD8a hinge, a CD8a transmembrane domain, an OX40 signaling domain, and a CD3zeta domain. In several embodiments, the chimeric antigen receptor further comprises mbIL15 (see FIG. 3E, NKH19-8b). In such embodiments, the polynucleotide comprises or is composed of an anti-CD19 scFv that has been humanized and comprises a second humanized light chain and a third humanized heavy chain (L2/H3), and comprises a Flag tag, a CD8a hinge, a CD8a transmembrane domain, an OX40 signaling domain, and a CD3zeta domain, a 2A cleavage site, and an mbIL-15 domain as described herein. In several embodiments, this receptor complex is encoded by a nucleic acid molecule having the sequence of SEQ ID NO: 174. In several embodiments, a nucleic acid sequence encoding an NK19 chimeric antigen receptor comprises a sequence that shares at least about 90%, at least about 94%, at least about 95%, at least about 96%, at least about 97%, at least about 98%, or at least about 99%, sequence identity, homology and/or functional equivalence with SEQ ID NO: 174. In several embodiments, the chimeric receptor comprises the amino acid sequence of SEQ ID NO: 175. In several embodiments, a NK19 chimeric antigen receptor comprises an amino acid sequence that shares at least about 90%, at least about 94%, at least about 95%, at least about 96%, at least about 97%, at least about 98%, or at least about 99%, sequence identity, homology and/or functional equivalence with SEQ ID NO: 175.

In several embodiments, there is provided a polynucleotide encoding a Flag-tag humanized anti-CD19moiety/CD8hinge/CD8TM/OX40/CD3zeta chimeric antigen receptor complex (see FIG. 3E, NK19H-9a). The polynucleotide comprises or is composed of an anti-CD19 scFv that has been humanized and comprises a third humanized light chain and a third humanized heavy chain (L3/H3), and comprises a Flag tag, a CD8a hinge, a CD8a transmembrane domain, an OX40 signaling domain, and a CD3zeta domain. In several embodiments, the chimeric antigen receptor further comprises mbIL15 (see FIG. 3E, NKH19-9b). In such embodiments, the polynucleotide comprises or is composed of an anti-CD19 scFv that has been humanized and comprises a third humanized light chain and a third humanized heavy chain (L3/H3), and comprises a Flag tag, a CD8a hinge, a CD8a transmembrane domain, an OX40 signaling domain, and a CD3zeta domain, a 2A cleavage site, and an mbIL-15 domain as described herein. In several embodiments, this receptor complex is encoded by a nucleic acid molecule having the sequence of SEQ ID NO: 176. In several embodiments, a nucleic acid sequence encoding an NK19 chimeric antigen receptor comprises a sequence that shares at least about 90%, at least about 94%, at least about 95%, at least about 96%, at least about 97%, at least about 98%, or at least about 99%, sequence identity, homology and/or functional equivalence with SEQ ID NO: 176. In several embodiments, the chimeric receptor comprises the amino acid sequence of SEQ ID NO: 177. In several embodiments, a NK19 chimeric antigen receptor comprises an amino acid sequence that shares at least about 90%, at least about 94%, at least about 95%, at least about 96%, at least about 97%, at least about 98%, or at least about 99%, sequence identity, homology and/or functional equivalence with SEQ ID NO: 177.

In several embodiments, there is provided a polynucleotide encoding a Flag-tag humanized anti-CD19moiety/CD8hinge/CD8TM/OX40/CD3zeta chimeric antigen receptor complex (see FIG. 3E, NKH19-10a). The polynucleotide comprises or is composed of an anti-CD19 scFv that has been humanized and comprises a first humanized light chain and a fourth humanized heavy chain (L1/H4), and comprises a Flag tag, a CD8a hinge, a CD8a transmembrane domain, an OX40 signaling domain, and a CD3zeta domain. In several embodiments, the chimeric antigen receptor further comprises mbIL15 (see FIG. 3E, NK19H-10b). In such embodiments, the polynucleotide comprises or is composed of an anti-CD19 scFv that has been humanized and comprises a first humanized light chain and a fourth humanized heavy chain (L1/H4), and comprises a Flag tag, a CD8a hinge, a CD8a transmembrane domain, an OX40 signaling domain, and a CD3zeta domain, a 2A cleavage site, and an mbIL-15 domain as described herein. In several embodiments, this receptor complex is encoded by a nucleic acid molecule having the sequence of SEQ ID NO: 178. In several embodiments, a nucleic acid sequence encoding an NK19 chimeric antigen receptor comprises a sequence that shares at least about 90%, at least about 94%, at least about 95%, at least about 96%, at least about 97%, at least about 98%, or at least about 99%, sequence identity, homology and/or functional equivalence with SEQ ID NO: 178. In several embodiments, the chimeric receptor comprises the amino acid sequence of SEQ ID NO: 179. In several embodiments, a NK19 chimeric antigen receptor comprises an amino acid sequence that shares at least about 90%, at least about 94%, at least about 95%, at least about 96%, at least about 97%, at least about 98%, or at least about 99%, sequence identity, homology and/or functional equivalence with SEQ ID NO: 179.

In several embodiments, there is provided a polynucleotide encoding a Flag-tag humanized anti-CD19moiety/CD8hinge/CD8TM/OX40/CD3zeta chimeric antigen receptor complex (see FIG. 3F, NK19H-11a). The polynucleotide comprises or is composed of an anti-CD19 scFv that has been humanized and comprises a second humanized light chain and a fourth humanized heavy chain (L2/H4), and comprises a Flag tag, a CD8a hinge, a CD8a transmembrane domain, an OX40 signaling domain, and a CD3zeta domain. In several embodiments, the chimeric antigen receptor further comprises mbIL15 (see FIG. 3F, NK19H-11b). In such embodiments, the polynucleotide comprises or is composed of an anti-CD19 scFv that has been humanized and comprises a second humanized light chain and a fourth humanized heavy chain (L2/H4), and comprises a Flag tag, a CD8a hinge, a CD8a transmembrane domain, an OX40 signaling domain, and a CD3zeta domain, a 2A cleavage site, and an mbIL-15 domain as described herein. In several embodiments, this receptor complex is encoded by a nucleic acid molecule having the sequence of SEQ ID NO: 180. In several embodiments, a nucleic acid sequence encoding an NK19 chimeric antigen receptor comprises a sequence that shares at least about 90%, at least about 94%, at least about 95%, at least about 96%, at least about 97%, at least about 98%, or at least about 99%, sequence identity, homology and/or functional equivalence with SEQ ID NO: 180. In several embodiments, the chimeric receptor comprises the amino acid sequence of SEQ ID NO: 181. In several embodiments, a NK19 chimeric antigen receptor comprises an amino acid sequence that shares at least about 90%, at least about 94%, at least about 95%, at least about 96%, at least about 97%, at least about 98%, or at least about 99%, sequence identity, homology and/or functional equivalence with SEQ ID NO: 181.

In several embodiments, there is provided a polynucleotide encoding a Flag-tag, humanized anti-CD19moiety/CD8hinge/CD8TM/OX40/CD3zeta chimeric antigen receptor complex (see FIG. 3F NK19H-12a). The polynucleotide comprises or is composed of an anti-CD19 scFv that has been humanized and comprises a third humanized light chain and a fourth humanized heavy chain (L3/H4), and comprises a Flag tag, a CD8a hinge, a CD8a transmembrane domain, an OX40 signaling domain, and a CD3zeta domain. In several embodiments, the chimeric antigen receptor further comprises mbIL15 (see FIG. 3F, NK19H-12b). In such embodiments, the polynucleotide comprises or is composed of an anti-CD19 scFv that has been humanized and comprises a third humanized light chain and a fourth humanized heavy chain (L3/H4), and comprises a Flag tag, a CD8a hinge, a CD8a transmembrane domain, an OX40 signaling domain, and a CD3zeta domain, a 2A cleavage site, and an mbIL-15 domain as described herein. In several embodiments, this receptor complex is encoded by a nucleic acid molecule having the sequence of SEQ ID NO: 182. In several embodiments, a nucleic acid sequence encoding an NK19 chimeric antigen receptor comprises a sequence that shares at least about 90%, at least about 94%, at least about 95%, at least about 96%, at least about 97%, at least about 98%, or at least about 99%, sequence identity, homology and/or functional equivalence with SEQ ID NO: 182. In several embodiments, the chimeric receptor comprises the amino acid sequence of SEQ ID NO: 183. In several embodiments, a NK19 chimeric antigen receptor comprises an amino acid sequence that shares at least about 90%, at least about 94%, at least about 95%, at least about 96%, at least about 97%, at least about 98%, or at least about 99%, sequence identity, homology and/or functional equivalence with SEQ ID NO: 183.

In several embodiments, there is provided a polynucleotide encoding chimeric antigen receptor that comprises a Flag-tag, humanized anti-CD19moiety and multiple co-stimulatory domains. For example, a schematic architecture is anti-CD19 moiety/transmembrane domain/co-stimulatory domain 1/co-stimulatory domain 2/co-stimulatory domain 3/signaling domain. The co-stimulatory domains vary in order, depending on the embodiment. For example, in several embodiments the co-stimulatory domains ("CSD") may be positioned as: CSD1/CSD2, CSD2/CSD1, CSD1/CSD2/CSD3, CSD1/CSD2/CSD3, CSD3/CSD2/CSD1, etc. In several embodiments, there is provided a polynucleotide encoding a Flag-tag, humanized anti-CD19moiety/CD8hinge/CD8aTM/CD44/OX40/CD27/CD3zeta chimeric antigen receptor complex (see FIG. 3F, NK19H-13a). The polynucleotide comprises or is composed of an anti-CD19 scFv that has been humanized and comprises a Flag tag, a CD8a hinge, a CD8a transmembrane domain, a CD44 co-stimulatory domain, an OX40 co-stimulatory domain, a CD27 co-stimulatory domain, and a CD3zeta domain. In several embodiments, the chimeric antigen receptor further comprises mbIL15 (see FIG. 3F, NK19H-13b). In such embodiments, the polynucleotide comprises or is composed of an anti-CD19 scFv that has been humanized and comprises a Flag tag, a CD8a hinge, a CD8a transmembrane domain, a CD44 co-stimulatory domain, an OX40 co-stimulatory domain, a CD27 co-stimulatory domain, a CD3zeta domain, a 2A cleavage site, and an mbIL-15 domain as described herein.

In several embodiments, there is provided a polynucleotide encoding a humanized anti-CD19moiety/CD8hinge/CD8TM/OX40/CD3zeta chimeric antigen receptor complex (see FIG. 3G, NK19H-NF-1a). The polynucleotide comprises or is composed of an anti-CD19 scFv that has been humanized and comprises a first humanized light chain and a first humanized heavy chain (L1/H1), a CD8a hinge, a CD8a transmembrane domain, an OX40 signaling domain, and a CD3zeta domain. In several embodiments, the chimeric antigen receptor further comprises mbIL15 (see FIG. 3G, NK19H-NF-1b). In such embodiments, the polynucleotide comprises or is composed of an anti-CD19 scFv that has been humanized and comprises a first humanized light chain and a first humanized heavy chain (L1/H1), a CD8a hinge, a CD8a transmembrane domain, an OX40 signaling domain, and a CD3zeta domain, a 2A cleavage site, and an mbIL-15 domain as described herein. In several embodiments, this receptor complex is encoded by a nucleic acid molecule having the sequence of SEQ ID NO: 184. In several embodiments, a nucleic acid sequence encoding an NK19 chimeric antigen receptor comprises a sequence that shares at least about 90%, at least about 94%, at least about 95%, at least about 96%, at least about 97%, at least about 98%, or at least about 99%, sequence identity, homology and/or functional equivalence with SEQ ID NO: 184. In several embodiments, the chimeric receptor comprises the amino acid sequence of SEQ ID NO: 185. In several embodiments, a NK19 chimeric antigen receptor comprises an amino acid sequence that shares at least about 90%, at least about 94%, at least about 95%, at least about 96%, at least about 97%, at least about 98%, or at least about 99%, sequence identity, homology and/or functional equivalence with SEQ ID NO: 185.

In several embodiments, there is provided a polynucleotide encoding a humanized anti-anti-CD19moiety/CD8hinge/CD8TM/OX40/CD3zeta chimeric antigen receptor complex (see FIG. 3G, NK19H-NF-2a). The polynucleotide comprises or is composed of an anti-CD19 scFv that has been humanized and comprises a second humanized light chain and a first humanized heavy chain (L2/H1), a CD8a hinge, a CD8a transmembrane domain, an OX40 signaling domain, and a CD3zeta domain. In several embodiments, the chimeric antigen receptor further comprises mbIL15 (see FIG. 3G, NK19H-NF-2b). In such embodiments, the polynucleotide comprises or is composed of an anti-CD19 scFv that has been humanized and comprises a second humanized light chain and a first humanized heavy chain (L2/H1), a CD8a hinge, a CD8a transmembrane domain, an OX40 signaling domain, and a CD3zeta domain, a 2A cleavage site, and an mbIL-15 domain as described herein. In several embodiments, this receptor complex is encoded by a nucleic acid molecule having the sequence of SEQ ID NO: 186. In several embodiments, a nucleic acid sequence encoding an NK19 chimeric antigen receptor comprises a sequence that shares at least about 90%, at least about 94%, at least about 95%, at least about 96%, at least about 97%, at least about 98%, or at least about 99%, sequence identity, homology and/or functional equivalence with SEQ ID NO: 186. In several embodiments, the chimeric receptor comprises the amino acid sequence of SEQ ID NO: 187. In several embodiments, a NK19 chimeric antigen receptor comprises an amino acid sequence that shares at least about 90%, at least about 94%, at least about 95%, at least about 96%, at least about 97%, at least about 98%, or at least about 99%, sequence identity, homology and/or functional equivalence with SEQ ID NO: 187.

In several embodiments, there is provided a polynucleotide encoding a humanized anti-anti-CD19moiety/CD8hinge/CD8TM/OX40/CD3zeta chimeric antigen receptor complex (see FIG. 3G, NK19H-NF-3a). The polynucleotide comprises or is composed of an anti-CD19 scFv that has been humanized and comprises a third humanized light chain and a first humanized heavy chain (L3/H1), a CD8a hinge, a CD8a transmembrane domain, an OX40 signaling domain, and a CD3zeta domain. In several embodiments, the chimeric antigen receptor further comprises mbIL15 (see FIG. 3G, NK19H-NF-3b). In such embodiments, the polynucleotide comprises or is composed of an anti-CD19 scFv that has been humanized and comprises a third humanized light chain and a first humanized heavy chain (L3/H1), a CD8a hinge, a CD8a transmembrane domain, an OX40 signaling domain, and a CD3zeta domain, a 2A cleavage site, and an mbIL-15 domain as described herein. In several embodiments, this receptor complex is encoded by a nucleic acid molecule having the sequence of SEQ ID NO: 188. In several embodiments, a nucleic acid sequence encoding an NK19 chimeric antigen receptor comprises a sequence that shares at least about 90%, at least about 94%, at least about 95%, at least about 96%, at least about 97%, at least about 98%, or at least about 99%, sequence identity, homology and/or functional equivalence with SEQ ID NO: 188. In several embodiments, the chimeric receptor comprises the amino acid sequence of SEQ ID NO: 189. In several embodiments, a NK19 chimeric antigen receptor comprises an amino acid sequence that shares at least about 90%, at least about 94%, at least about 95%, at least about 96%, at least about 97%, at least about 98%, or at least about 99%, sequence identity, homology and/or functional equivalence with SEQ ID NO: 189.

In several embodiments, there is provided a polynucleotide encoding a humanized anti-anti-CD19moiety/CD8hinge/CD8TM/OX40/CD3zeta chimeric antigen receptor complex (see FIG. 3G, NK19H-NF-4a). The polynucleotide comprises or is composed of an anti-CD19 scFv that has been humanized and comprises a first humanized light chain and a second humanized heavy chain (L1/H2), a CD8a hinge, a CD8a transmembrane domain, an OX40 signaling domain, and a CD3zeta domain. In several embodiments, the chimeric antigen receptor further comprises mbIL15 (see FIG. 3G, NK19H-NF-4b). In such embodiments, the polynucleotide comprises or is composed of an anti-CD19 scFv that has been humanized and comprises a first humanized light chain and a second humanized heavy chain (L1/H2), a CD8a hinge, a CD8a transmembrane domain, an OX40 signaling domain, and a CD3zeta domain, a 2A cleavage site, and an mbIL-15 domain as described herein. In several embodiments, this receptor complex is encoded by a nucleic acid molecule having the sequence of SEQ ID NO: 190. In several embodiments, a nucleic acid sequence encoding an NK19 chimeric antigen receptor comprises a sequence that shares at least about 90%, at least about 94%, at least about 95%, at least about 96%, at least about 97%, at least about 98%, or at least about 99%, sequence identity, homology and/or functional equivalence with SEQ ID NO: 190. In several embodiments, the chimeric receptor comprises the amino acid sequence of SEQ ID NO: 191. In several embodiments, a NK19 chimeric antigen receptor comprises an amino acid sequence that shares at least about 90%, at least about 94%, at least about 95%, at least about 96%, at least about 97%, at least about 98%, or at least about 99%, sequence identity, homology and/or functional equivalence with SEQ ID NO: 191.

Figure 3H:
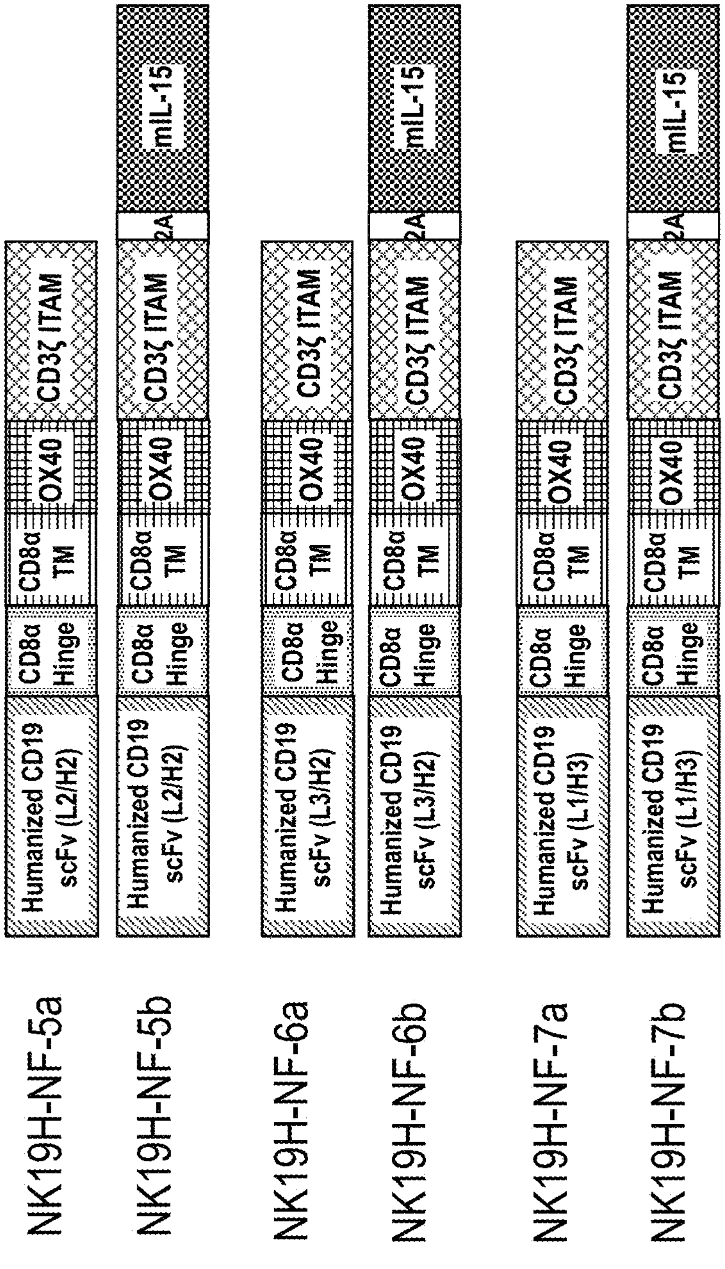
FIG. 3H also includes depictions of non-limiting examples of CD19-directed chimeric receptors comprising humanized CD19 binding domains without a tag sequence.
Figure 3H:
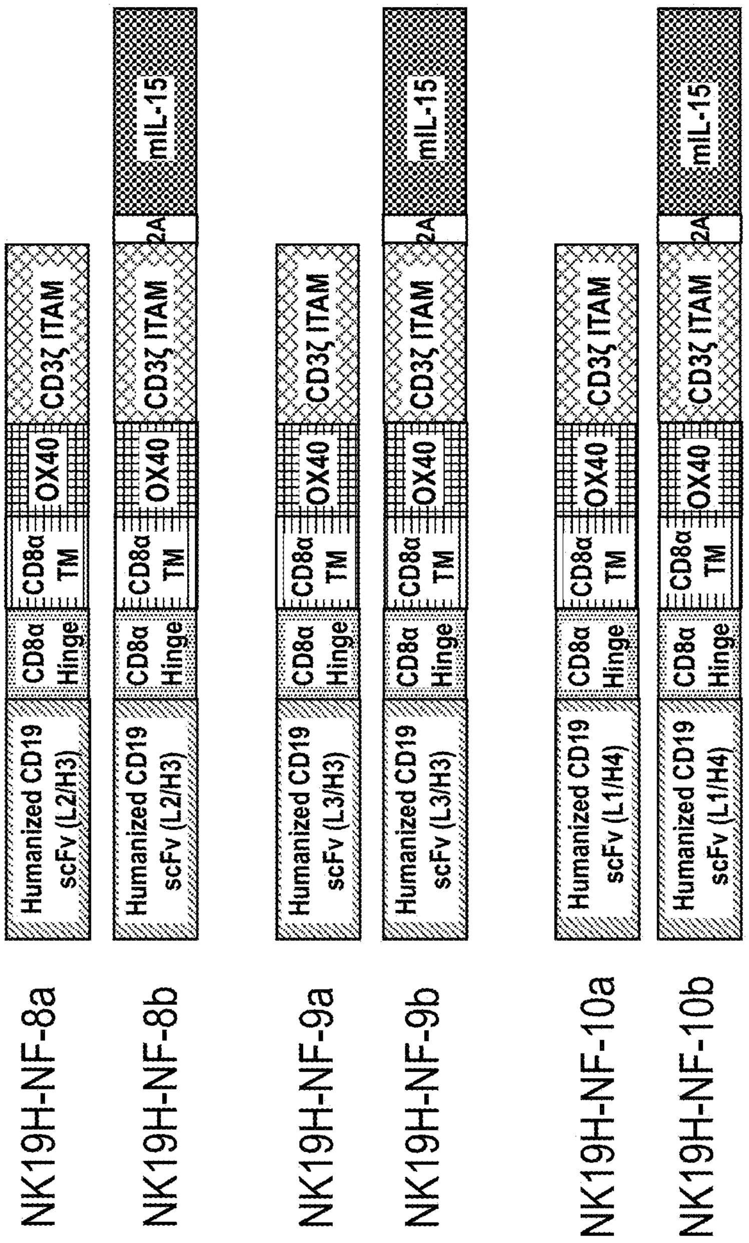

In several embodiments, there is provided a polynucleotide encoding a humanized anti-CD19moiety/CD8hinge/CD8TM/OX40/CD3zeta chimeric antigen receptor complex (see FIG. 3H, NK19H-NF-5a). The polynucleotide comprises or is composed of an anti-CD19 scFv that has been humanized and comprises a second humanized light chain and a second humanized heavy chain (L2/H2), a CD8a hinge, a CD8a transmembrane domain, an OX40 signaling domain, and a CD3zeta domain. In several embodiments, the chimeric antigen receptor further comprises mbIL15 (see FIG. 3H, NK19H-NF-5b). In such embodiments, the polynucleotide comprises or is composed of an anti-CD19 scFv that has been humanized and comprises a second humanized light chain and a second humanized heavy chain (L2/H2), a CD8a hinge, a CD8a transmembrane domain, an OX40 signaling domain, and a CD3zeta domain, a 2A cleavage site, and an mbIL-15 domain as described herein. In several embodiments, this receptor complex is encoded by a nucleic acid molecule having the sequence of SEQ ID NO: 192. In several embodiments, a nucleic acid sequence encoding an NK19 chimeric antigen receptor comprises a sequence that shares at least about 90%, at least about 94%, at least about 95%, at least about 96%, at least about 97%, at least about 98%, or at least about 99%, sequence identity, homology and/or functional equivalence with SEQ ID NO: 192. In several embodiments, the chimeric receptor comprises the amino acid sequence of SEQ ID NO: 193. In several embodiments, a NK19 chimeric antigen receptor comprises an amino acid sequence that shares at least about 90%, at least about 94%, at least about 95%, at least about 96%, at least about 97%, at least about 98%, or at least about 99%, sequence identity, homology and/or functional equivalence with SEQ ID NO: 193.

In several embodiments, there is provided a polynucleotide encoding a humanized anti-CD19moiety/CD8hinge/CD8TM/OX40/CD3zeta chimeric antigen receptor complex (see FIG. 3H, NK19H-NF-6a). The polynucleotide comprises or is composed of an anti-CD19 scFv that has been humanized and comprises a third humanized light chain and a second humanized heavy chain (L3/H2), a CD8a hinge, a CD8a transmembrane domain, an OX40 signaling domain, and a CD3zeta domain. In several embodiments, the chimeric antigen receptor further comprises mbIL15 (see FIG. 3H, NK19H-NF-6b). In such embodiments, the polynucleotide comprises or is composed of an anti-CD19 scFv that has been humanized and comprises a third humanized light chain and a second humanized heavy chain (L3/H2), a CD8a hinge, a CD8a transmembrane domain, an OX40 signaling domain, and a CD3zeta domain, a 2A cleavage site, and an mbIL-15 domain as described herein. In several embodiments, this receptor complex is encoded by a nucleic acid molecule having the sequence of SEQ ID NO: 194. In several embodiments, a nucleic acid sequence encoding an NK19 chimeric antigen receptor comprises a sequence that shares at least about 90%, at least about 94%, at least about 95%, at least about 96%, at least about 97%, at least about 98%, or at least about 99%, sequence identity, homology and/or functional equivalence with SEQ ID NO: 194. In several embodiments, the chimeric receptor comprises the amino acid sequence of SEQ ID NO: 195. In several embodiments, a NK19 chimeric antigen receptor comprises an amino acid sequence that shares at least about 90%, at least about 94%, at least about 95%, at least about 96%, at least about 97%, at least about 98%, or at least about 99%, sequence identity, homology and/or functional equivalence with SEQ ID NO: 195.

In several embodiments, there is provided a polynucleotide encoding a humanized anti-CD19moiety/CD8hinge/CD8TM/OX40/CD3zeta chimeric antigen receptor complex (see FIG. 3G, NK19H-NF-7a). The polynucleotide comprises or is composed of an anti-CD19 scFv that has been humanized and comprises a first humanized light chain and a third humanized heavy chain (L1/H3), a CD8a hinge, a CD8a transmembrane domain, an OX40 signaling domain, and a CD3zeta domain. In several embodiments, the chimeric antigen receptor further comprises mbIL15 (see FIG. 3H, NK19H-NF-7b). In such embodiments, the polynucleotide comprises or is composed of an anti-CD19 scFv that has been humanized and comprises a first humanized light chain and a third humanized heavy chain (L1/H3), a CD8a hinge, a CD8a transmembrane domain, an OX40 signaling domain, a CD3zeta domain, a 2A cleavage site, and an mbIL-15 domain as described herein. In several embodiments, this receptor complex is encoded by a nucleic acid molecule having the sequence of SEQ ID NO: 196. In several embodiments, a nucleic acid sequence encoding an NK19 chimeric antigen receptor comprises a sequence that shares at least about 90%, at least about 94%, at least about 95%, at least about 96%, at least about 97%, at least about 98%, or at least about 99%, sequence identity, homology and/or functional equivalence with SEQ ID NO: 196. In several embodiments, the chimeric receptor comprises the amino acid sequence of SEQ ID NO: 197. In several embodiments, a NK19 chimeric antigen receptor comprises an amino acid sequence that shares at least about 90%, at least about 94%, at least about 95%, at least about 96%, at least about 97%, at least about 98%, or at least about 99%, sequence identity, homology and/or functional equivalence with SEQ ID NO: 197.

In several embodiments, there is provided a polynucleotide encoding a humanized anti-CD19moiety/CD8hinge/CD8TM/OX40/CD3zeta chimeric antigen receptor complex (see FIG. 3H, NK19H-NF-8a). The polynucleotide comprises or is composed of an anti-CD19 scFv that has been humanized and comprises a second humanized light chain and a third humanized heavy chain (L2/H3), a CD8a hinge, a CD8a transmembrane domain, an OX40 signaling domain, and a CD3zeta domain. In several embodiments, the chimeric antigen receptor further comprises mbIL15 (see FIG. 3H, NKH19-NF-8b). In such embodiments, the polynucleotide comprises or is composed of an anti-CD19 scFv variable light chain that has been humanized and comprises a second humanized light chain and a third humanized heavy chain (L2/H3), a CD8a hinge, a CD8a transmembrane domain, an OX40 signaling domain, and a CD3zeta domain, a 2A cleavage site, and an mbIL-15 domain as described herein. In several embodiments, this receptor complex is encoded by a nucleic acid molecule having the sequence of SEQ ID NO: 198. In several embodiments, a nucleic acid sequence encoding an NK19 chimeric antigen receptor comprises a sequence that shares at least about 90%, at least about 94%, at least about 95%, at least about 96%, at least about 97%, at least about 98%, or at least about 99%, sequence identity, homology and/or functional equivalence with SEQ ID NO: 198. In several embodiments, the chimeric receptor comprises the amino acid sequence of SEQ ID NO: 199. In several embodiments, a NK19 chimeric antigen receptor comprises an amino acid sequence that shares at least about 90%, at least about 94%, at least about 95%, at least about 96%, at least about 97%, at least about 98%, or at least about 99%, sequence identity, homology and/or functional equivalence with SEQ ID NO: 199.

In several embodiments, there is provided a polynucleotide encoding a humanized anti-anti-CD19moiety/CD8hinge/CD8TM/OX40/CD3zeta chimeric antigen receptor complex (see FIG. 3H, NK19H-NF-9a). The polynucleotide comprises or is composed of an anti-CD19 scFv that has been humanized and comprises a third humanized light chain and a third humanized heavy chain (L3/H3), a CD8a hinge, a CD8a transmembrane domain, an OX40 signaling domain, and a CD3zeta domain. In several embodiments, the chimeric antigen receptor further comprises mbIL15 (see FIG. 3H, NKH19-NF-9b). In such embodiments, the polynucleotide comprises or is composed of an anti-CD19 scFv that has been humanized and comprises a third humanized light chain and a third humanized heavy chain (L3/H3), a CD8a hinge, a CD8a transmembrane domain, an OX40 signaling domain, and a CD3zeta domain, a 2A cleavage site, and an mbIL-15 domain as described herein. In several embodiments, this receptor complex is encoded by a nucleic acid molecule having the sequence of SEQ ID NO: 200. In several embodiments, a nucleic acid sequence encoding an NK19 chimeric antigen receptor comprises a sequence that shares at least about 90%, at least about 94%, at least about 95%, at least about 96%, at least about 97%, at least about 98%, or at least about 99%, sequence identity, homology and/or functional equivalence with SEQ ID NO: 200. In several embodiments, the chimeric receptor comprises the amino acid sequence of SEQ ID NO: 201. In several embodiments, a NK19 chimeric antigen receptor comprises an amino acid sequence that shares at least about 90%, at least about 94%, at least about 95%, at least about 96%, at least about 97%, at least about 98%, or at least about 99%, sequence identity, homology and/or functional equivalence with SEQ ID NO: 201.

In several embodiments, there is provided a polynucleotide encoding a humanized anti-CD19moiety/CD8hinge/CD8TM/OX40/CD3zeta chimeric antigen receptor complex (see FIG. 3H, NKH19-NF-10a). The polynucleotide comprises or is composed of an anti-CD19 scFv that has been humanized and comprises a first humanized light chain and a fourth humanized heavy chain (L1/H4), a CD8a hinge, a CD8a transmembrane domain, an OX40 signaling domain, and a CD3zeta domain. In several embodiments, the chimeric antigen receptor further comprises mbIL15 (see FIG. 3H, NK19H-NF-10b). In such embodiments, the polynucleotide comprises or is composed of an anti-CD19 scFv that has been humanized and comprises a first humanized light chain and a fourth humanized heavy chain (L1/H4), a CD8a hinge, a CD8a transmembrane domain, an OX40 signaling domain, and a CD3zeta domain, a 2A cleavage site, and an mbIL-15 domain as described herein. In several embodiments, this receptor complex is encoded by a nucleic acid molecule having the sequence of SEQ ID NO: 202. In several embodiments, a nucleic acid sequence encoding an NK19 chimeric antigen receptor comprises a sequence that shares at least about 90%, at least about 94%, at least about 95%, at least about 96%, at least about 97%, at least about 98%, or at least about 99%, sequence identity, homology and/or functional equivalence with SEQ ID NO: 202. In several embodiments, the chimeric receptor comprises the amino acid sequence of SEQ ID NO: 203. In several embodiments, a NK19 chimeric antigen receptor comprises an amino acid sequence that shares at least about 90%, at least about 94%, at least about 95%, at least about 96%, at least about 97%, at least about 98%, or at least about 99%, sequence identity, homology and/or functional equivalence with SEQ ID NO: 203.

Figure 3I:
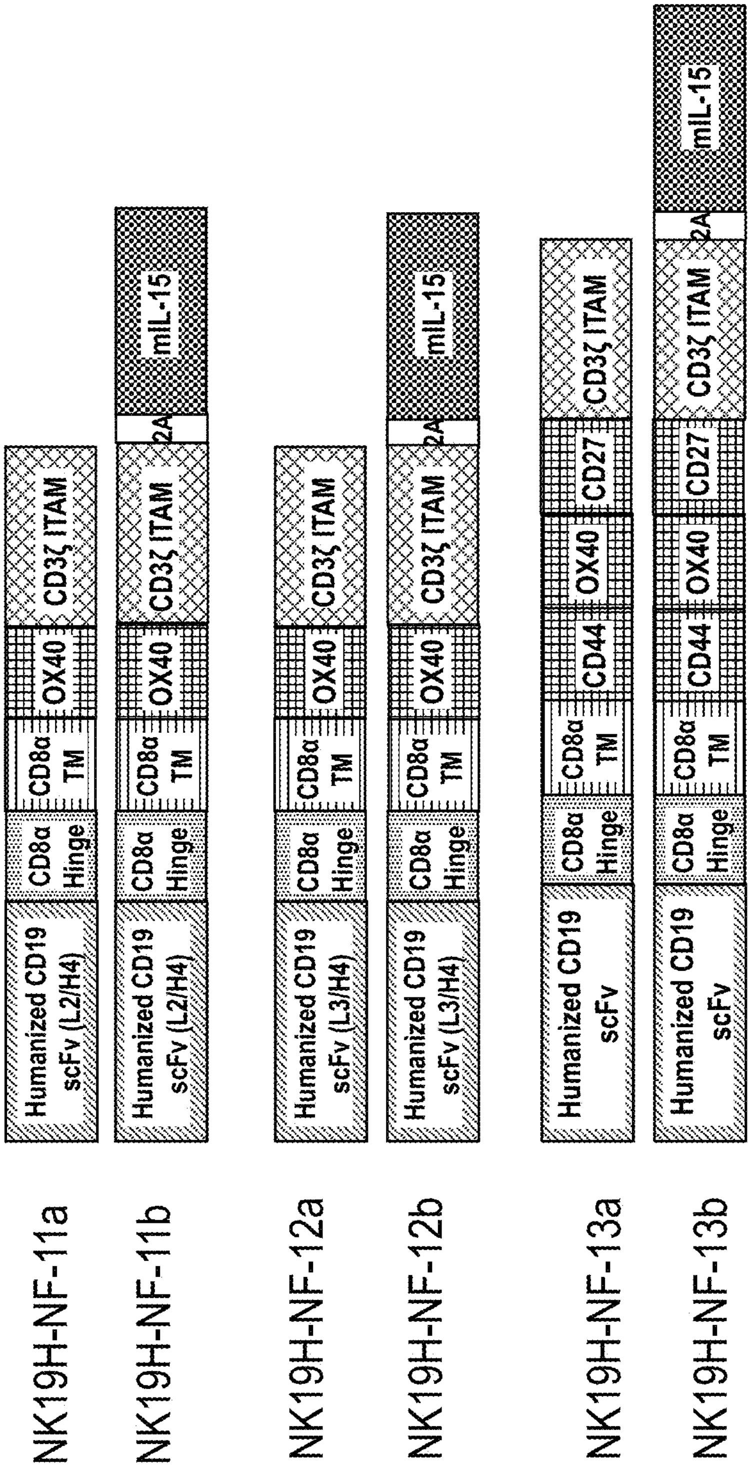
FIG. 3I also includes depictions of non-limiting examples of CD19-directed chimeric receptors comprising humanized CD19 binding domains without a tag sequence.
Figure 4:
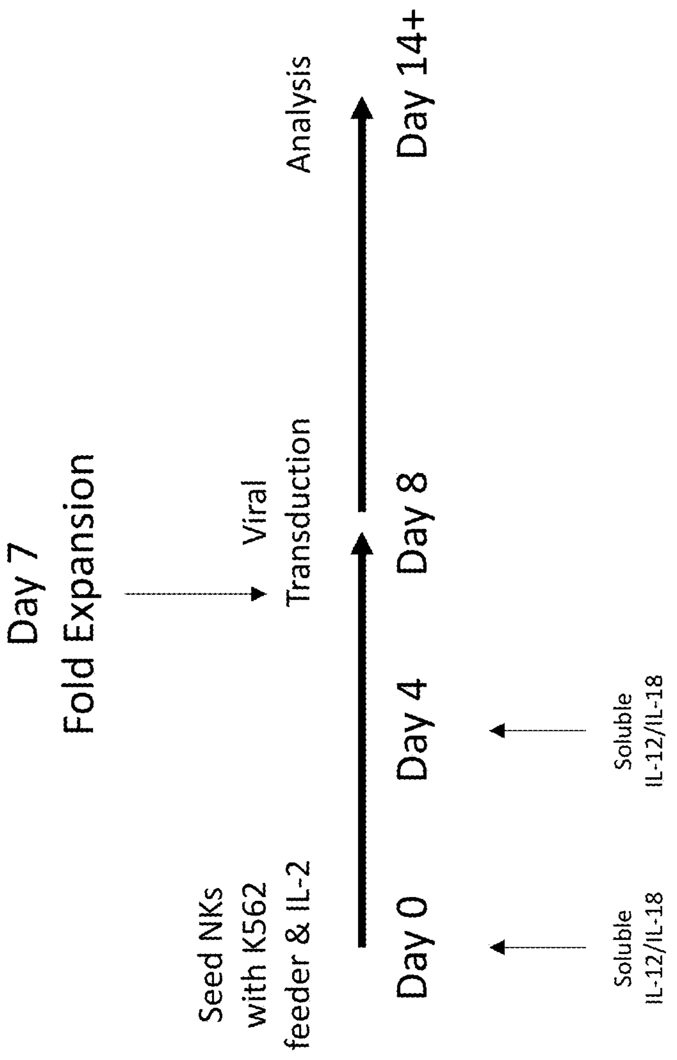
FIG. 4 depicts a schematic of a non-limiting NK cell expansion protocol.

In several embodiments, there is provided a polynucleotide encoding a humanized anti-CD19moiety/CD8hinge/CD8TM/OX40/CD3zeta chimeric antigen receptor complex (see FIG. 3I, NK19H-NF-11a). The polynucleotide comprises or is composed of an anti-CD19 scFv that has been humanized and comprises a second humanized light chain and a fourth humanized heavy chain (L2/H4), a CD8a hinge, a CD8a transmembrane domain, an OX40 signaling domain, and a CD3zeta domain. In several embodiments, the chimeric antigen receptor further comprises mbIL15 (see FIG. 3I, NK19H-NF-11b). In such embodiments, the polynucleotide comprises or is composed of an anti-CD19 scFv that has been humanized, and comprises a second humanized light chain and a fourth humanized heavy chain (L2/H4), a CD8a hinge, a CD8a transmembrane domain, an OX40 signaling domain, and a CD3zeta domain, a 2A cleavage site, and an mbIL-15 domain as described herein. In several embodiments, this receptor complex is encoded by a nucleic acid molecule having the sequence of SEQ ID NO: 204. In several embodiments, a nucleic acid sequence encoding an NK19 chimeric antigen receptor comprises a sequence that shares at least about 90%, at least about 94%, at least about 95%, at least about 96%, at least about 97%, at least about 98%, or at least about 99%, sequence identity, homology and/or functional equivalence with SEQ ID NO: 204. In several embodiments, the chimeric receptor comprises the amino acid sequence of SEQ ID NO: 205. In several embodiments, a NK19 chimeric antigen receptor comprises an amino acid sequence that shares at least about 90%, at least about 94%, at least about 95%, at least about 96%, at least about 97%, at least about 98%, or at least about 99%, sequence identity, homology and/or functional equivalence with SEQ ID NO: 205.

In several embodiments, there is provided a polynucleotide encoding a humanized anti-CD19moiety/CD8hinge/CD8TM/OX40/CD3zeta chimeric antigen receptor complex (see FIG. 3I NK19H-12a). The polynucleotide comprises or is composed of an anti-CD19 scFv that has been humanized and comprises a third humanized light chain and a fourth humanized heavy chain (L3/H4), a CD8a hinge, a CD8a transmembrane domain, an OX40 signaling domain, and a CD3zeta domain. In several embodiments, the chimeric antigen receptor further comprises mbIL15 (see FIG. 3I, NK19H-NF-12b). In such embodiments, the polynucleotide comprises or is composed of an anti-CD19 scFv that has been humanized and comprises a third humanized light chain and a fourth humanized heavy chain (L3/H4), a CD8a hinge, a CD8a transmembrane domain, an OX40 signaling domain, and a CD3zeta domain, a 2A cleavage site, and an mbIL-15 domain as described herein. In several embodiments, this receptor complex is encoded by a nucleic acid molecule having the sequence of SEQ ID NO: 206. In several embodiments, a nucleic acid sequence encoding an NK19 chimeric antigen receptor comprises a sequence that shares at least about 90%, at least about 94%, at least about 95%, at least about 96%, at least about 97%, at least about 98%, or at least about 99%, sequence identity, homology and/or functional equivalence with SEQ ID NO: 206. In several embodiments, the chimeric receptor comprises the amino acid sequence of SEQ ID NO: 207. In several embodiments, a NK19 chimeric antigen receptor comprises an amino acid sequence that shares at least about 90%, at least about 94%, at least about 95%, at least about 96%, at least about 97%, at least about 98%, or at least about 99%, sequence identity, homology and/or functional equivalence with SEQ ID NO: 207.

In several embodiments, there is provided a polynucleotide encoding chimeric antigen receptor that comprises a Flag-tag, humanized anti-CD19moiety and multiple co-stimulatory domains. For example, a schematic architecture is anti-CD19 moiety/transmembrane domain/co-stimulatory domain 1/co-stimulatory domain 2/co-stimulatory domain 3/signaling domain. The co-stimulatory domains vary in order, depending on the embodiment. For example, in several embodiments the co-stimulatory domains ("CSD") may be positioned as: CSD1/CSD2, CSD2/CSD1, CSD1/CSD2/CSD3, CSD1/CSD2/CSD3, CSD3/CSD2/CSD1, etc. In several embodiments, there is provided a polynucleotide encoding a Flag-tag, humanized anti-CD19moiety/CD8hinge/CD8aTM/CD44/OX40/CD27/CD3zeta chimeric antigen receptor complex (see FIG. 3I, NK19H-NF-13a). The polynucleotide comprises or is composed of an anti-CD19 scFv that has been humanized and comprises a Flag tag, a CD8a hinge, a CD8a transmembrane domain, a CD44 co-stimulatory domain, an OX40 co-stimulatory domain, a CD27 co-stimulatory domain, and a CD3zeta domain. In several embodiments, the chimeric antigen receptor further comprises mbIL15 (see FIG. 3I, NK19H-NF-13b). In such embodiments, the polynucleotide comprises or is composed of an anti-CD19 scFv that has been humanized and comprises a Flag tag, a CD8a hinge, a CD8a transmembrane domain, a CD44 co-stimulatory domain, an OX40 co-stimulatory domain, a CD27 co-stimulatory domain, a CD3zeta domain, a 2A cleavage site, and an mbIL-15 domain as described herein.

In several embodiments, there is provided a polynucleotide encoding chimeric antigen receptor that comprises a Flag-tag, humanized anti-CD19moiety and multiple co-stimulatory domains. For example, a schematic architecture is anti-CD19 moiety/transmembrane domain/co-stimulatory domain 1/co-stimulatory domain 2/co-stimulatory domain 3/signaling domain. The co-stimulatory domains vary in order, depending on the embodiment. For example, in several embodiments the co-stimulatory domains ("CSD") may be positioned as: CSD1/CSD2, CSD2/CSD1, CSD1/CSD2/CSD3, CSD1/CSD2/CSD3, CSD3/CSD2/CSD1, etc. In several embodiments, there is provided a polynucleotide encoding a Flag-tag, humanized anti-CD19moiety/CD8hinge/CD8aTM/CD44/OX40/CD27/CD3zeta chimeric antigen receptor complex (see FIG. 3F, NK19H-13a). The polynucleotide comprises or is composed of an anti-CD19 scFv that has been humanized and comprises a Flag tag, a CD8a hinge, a CD8a transmembrane domain, a CD44 co-stimulatory domain, an OX40 co-stimulatory domain, a CD27 co-stimulatory domain, and a CD3zeta domain. In several embodiments, the chimeric antigen receptor further comprises mbIL15 (see FIG. 3F, NK19H-13b). In such embodiments, the polynucleotide comprises or is composed of an anti-CD19 scFv that has been humanized and comprises a Flag tag, a CD8a hinge, a CD8a transmembrane domain, a CD44 co-stimulatory domain, an OX40 co-stimulatory domain, a CD27 co-stimulatory domain, a CD3zeta domain, a 2A cleavage site, and an mbIL-15 domain as described herein.

It shall be appreciated that, for any receptor construct described herein, certain sequence variability, extensions, and/or truncations of the disclosed sequences may result when combining sequences, as a result of, for example, ease or efficiency in cloning (e.g., for creation of a restriction site).

Methods of Treatment

Some embodiments relate to a method of treating, ameliorating, inhibiting, or preventing cancer with a cell or immune cell comprising a chimeric receptor such as a CD19-directed chimeric receptor. In some embodiments, the method includes treating or preventing cancer. In some embodiments, the method includes administering a therapeutically effective amount of immune cells expressing a CD19-directed chimeric receptor as described herein. Examples of types of cancer that may be treated as such are described herein.

In certain embodiments, treatment of a subject with a genetically engineered cell(s) described herein achieves one, two, three, four, or more of the following effects, including, for example: (i) reduction or amelioration the severity of disease or symptom associated therewith; (ii) reduction in the duration of a symptom associated with a disease; (iii) protection against the progression of a disease or symptom associated therewith; (iv) regression of a disease or symptom associated therewith; (v) protection against the development or onset of a symptom associated with a disease; (vi) protection against the recurrence of a symptom associated with a disease; (vii) reduction in the hospitalization of a subject; (viii) reduction in the hospitalization length; (ix) an increase in the survival of a subject with a disease; (x) a reduction in the number of symptoms associated with a disease; (xi) an enhancement, improvement, supplementation, complementation, or augmentation of the prophylactic or therapeutic effect(s) of another therapy. Administration can be by a variety of routes, including, without limitation, intravenous, intra-arterial, subcutaneous, intramuscular, intrahepatic, intraperitoneal and/or local delivery to an affected tissue.

Administration and Dosing

Further provided herein are methods of treating a subject having cancer, comprising administering to the subject a composition comprising immune cells (such as NK and/or T cells) engineered to express a cytotoxic receptor complex as disclosed herein. For example, some embodiments of the compositions and methods described herein relate to use of a CD19-directed chimeric receptor, or use of cells expressing the CD19-directed chimeric receptor, for treating a cancer patient. Uses of such engineered immune cells for treating cancer are also provided.

In certain embodiments, treatment of a subject with a genetically engineered cell(s) described herein achieves one, two, three, four, or more of the following effects, including, for example: (i) reduction or amelioration the severity of disease or symptom associated therewith; (ii) reduction in the duration of a symptom associated with a disease; (iii) protection against the progression of a disease or symptom associated therewith; (iv) regression of a disease or symptom associated therewith; (v) protection against the development or onset of a symptom associated with a disease; (vi) protection against the recurrence of a symptom associated with a disease; (vii) reduction in the hospitalization of a subject; (viii) reduction in the hospitalization length; (ix) an increase in the survival of a subject with a disease; (x) a reduction in the number of symptoms associated with a disease; (xi) an enhancement, improvement, supplementation, complementation, or augmentation of the prophylactic or therapeutic effect(s) of another therapy. Each of these comparisons are versus, for example, a different therapy for a disease, which includes a cell-based immunotherapy for a disease using cells that do not express the constructs disclosed herein.

Administration can be by a variety of routes, including, without limitation, intravenous, intra-arterial, subcutaneous, intramuscular, intrahepatic, intraperitoneal and/or local delivery to an affected tissue. Doses of immune cells such as NK and/or T cells can be readily determined for a given subject based on their body mass, disease type and state, and desired aggressiveness of treatment, but range, depending on the embodiments, from about $10^5$ cells per kg to about $10^{12}$ cells per kg (e.g., $10^5$-$10^7$, $10^7$-$10^{10}$, $10^{10}$-$10^{12}$ and overlapping ranges therein). In one embodiment, a dose escalation regimen is used. In several embodiments, a range of immune cells such as NK and/or T cells is administered, for example between about $1\times10^6$ cells/kg to about $1\times10^8$ cells/kg. In several embodiments, the dosage ranges from about $2\times10^5$ cells/kg to about $2\times10^8$ cells/kg, including about $2\times10^6$ and $2\times10^7$ cells/kg. In several embodiments, a dose is determined by the maximum number of viable engineered cells at the time of dosing. For example, in some embodiments, a single dose comprises a maximum of between about $2\times10^5$ and about $2\times10^9$ viable engineered cells, including about $2\times10^6$, about $2\times10^7$, or about $2\times10^8$ viable engineered cells. Depending on the embodiment, various types of cancer can be treated. In several embodiments, hepatocellular carcinoma is treated. Additional embodiments provided for herein include treatment or prevention of the following non-limiting examples of cancers including, but not limited to, acute lymphoblastic leukemia (ALL), acute myeloid leukemia (AML), adrenocortical carcinoma, Kaposi sarcoma, lymphoma, gastrointestinal cancer, appendix cancer, central nervous system cancer, basal cell carcinoma, bile duct cancer, bladder cancer, bone cancer, brain tumors (including but not limited to astrocytomas, spinal cord tumors, brain stem glioma, glioblastoma, craniopharyngioma, ependymoblastoma, ependymoma, medulloblastoma, medulloepithelioma), breast cancer, bronchial tumors, Burkitt lymphoma, cervical cancer, colon cancer, chronic lymphocytic leukemia (CLL), chronic myelogenous leukemia (CML), chronic myeloproliferative disorders, ductal carcinoma, endometrial cancer, esophageal cancer, gastric cancer, Hodgkin lymphoma, non-Hodgkin lymphoma, hairy cell leukemia, renal cell cancer, leukemia, oral cancer, nasopharyngeal cancer, liver cancer, lung cancer (including but not limited to, non-small cell lung cancer, (NSCLC) and small cell lung cancer), pancreatic cancer, bowel cancer, lymphoma, melanoma, ocular cancer, ovarian cancer, pancreatic cancer, prostate cancer, pituitary cancer, uterine cancer, and vaginal cancer.

In some embodiments, also provided herein are nucleic acid and amino acid sequences that have sequence identity or homology of at least 80%, 85%, 90%, 95%, 96%, 97%, 98%, 99% (and ranges therein) as compared with the respective nucleic acid or amino acid sequences of SEQ ID NOS. 1-207 (or combinations of two or more of SEQ ID NOS: 1-207) and that also exhibit one or more of the functions as compared with the respective SEQ ID NOS. 1-207 (or combinations of two or more of SEQ ID NOS: 1-207) including but not limited to, (i) enhanced proliferation, (ii) enhanced activation, (iii) enhanced cytotoxic activity against cells presenting ligands to which NK cells harboring receptors encoded by the nucleic acid and amino acid sequences bind, (iv) enhanced homing to tumor or infected sites, (v) reduced off target cytotoxic effects, (vi) enhanced secretion of immunostimulatory cytokines and chemokines (including, but not limited to IFNg, TNFa, IL-22, CCL3, CCL4, and CCL5), (vii) enhanced ability to stimulate further innate and adaptive immune responses, and (viii) combinations thereof.

Additionally, in several embodiments, there are provided amino acid sequences that correspond to any of the nucleic acids disclosed herein, while accounting for degeneracy of the nucleic acid code. Furthermore, those sequences (whether nucleic acid or amino acid) that vary from those expressly disclosed herein, but have functional similarity or equivalency are also contemplated within the scope of the present disclosure. The foregoing includes mutants, truncations, substitutions, or other types of modifications.

In several embodiments, polynucleotides encoding the disclosed cytotoxic receptor complexes or CD19-directed chimeric receptors are mRNA. In some embodiments, the polynucleotide is DNA. In some embodiments, the polynucleotide is operably linked to at least one regulatory element for the expression of the cytotoxic receptor complex.

Additionally provided, according to several embodiments, is a vector comprising the polynucleotide encoding any of the polynucleotides provided for herein, wherein the polynucleotides are optionally operatively linked to at least one regulatory element for expression of a cytotoxic receptor complex. In several embodiments, the vector is a retrovirus.

Further provided herein are engineered immune cells (such as NK and/or T cells) comprising the polynucleotide, vector, or cytotoxic receptor complexes as disclosed herein. Further provided herein are compositions comprising a mixture of engineered immune cells (such as NK cells and/or engineered T cells), each population comprising the polynucleotide, vector, or cytotoxic receptor complexes as disclosed herein.

Doses of immune cells such as NK cells or T cells can be readily determined for a given subject based on their body mass, disease type and state, and desired aggressiveness of treatment, but range, depending on the embodiments, from about $10^5$ cells per kg to about $10^{12}$ cells per kg (e.g., $10^5$-$10^7$, $10^7$-$10^{10}$, $10^{10}$-$10^{12}$ and overlapping ranges therein). In one embodiment, a dose escalation regimen is used. In several embodiments, a range of NK cells is administered, for example between about $1\times10^6$ cells/kg to about $1\times10^8$ cells/kg. Depending on the embodiment, various types of cancer or infection disease can be treated.

Cancer Types

Some embodiments of the compositions and methods described herein relate to administering immune cells comprising a chimeric receptor, such as a CD19-directed chimeric receptor, to a subject with cancer. Various embodiments provided for herein include treatment or prevention of the following non-limiting examples of cancers. Examples of cancer include, but are not limited to, acute lymphoblastic leukemia (ALL), acute myeloid leukemia (AML), adrenocortical carcinoma, Kaposi sarcoma, lymphoma, gastrointestinal cancer, appendix cancer, central nervous system cancer, basal cell carcinoma, bile duct cancer, bladder cancer, bone cancer, brain tumors (including but not limited to astrocytomas, spinal cord tumors, brain stem glioma, craniopharyngioma, ependymoblastoma, ependymoma, medulloblastoma, medulloepithelioma), breast cancer, bronchial tumors, Burkitt lymphoma, cervical cancer, colon cancer, chronic lymphocytic leukemia (CLL), chronic myelogenous leukemia (CML), chronic myeloproliferative disorders, ductal carcinoma, endometrial cancer, esophageal cancer, gastric cancer, Hodgkin lymphoma, non-Hodgkin lymphoma, hairy cell leukemia, renal cell cancer, leukemia, oral cancer, nasopharyngeal cancer, liver cancer, lung cancer (including but not limited to, non-small cell lung cancer, (NSCLC) and small cell lung cancer), pancreatic cancer, bowel cancer, lymphoma, melanoma, ocular cancer, ovarian cancer, pancreatic cancer, prostate cancer, pituitary cancer, uterine cancer, and vaginal cancer.

Cancer Targets

Some embodiments of the compositions and methods described herein relate to immune cells comprising a chimeric receptor that targets a cancer antigen. Non-limiting examples of target antigens include: CD5, CD19; CD123; CD22; CD30; CD171; CS1 (also referred to as CD2 subset 1, CRACC, SLAMF7, CD319, and 19A24); C-type lectin-like molecule-1 (CLL-1 or CLECL1); CD33; epidermal growth factor receptor variant III (EGFRviii); ganglioside G2 (GD2); ganglioside GD3 (aNeu5Ac(2-8)aNeu5Ac(2-3)bDGalp(I-4)bDGIcp(I-I)Cer); TNF receptor family member B cell maturation (BCMA); Tn antigen ((Tn Ag) or (GaIN-Aca-Ser/Thr)); prostate-specific membrane antigen (PSMA); Receptor tyrosine kinase-like orphan receptor 1 (ROR1); Fms Like Tyrosine Kinase 3 (FLT3); Tumor-associated glycoprotein 72 (TAG72); CD38; CD44v6; a glycosylated CD43 epitope expressed on acute leukemia or lymphoma but not on hematopoietic progenitors, a glycosylated CD43 epitope expressed on non-hematopoietic cancers, Carcinoembryonic antigen (CEA); Epithelial cell adhesion molecule (EPCAM); B7H3 (CD276); KIT (CD117); Interleukin-13 receptor subunit alpha-2 (IL-13Ra2 or CD213A2); Mesothelin; Interleukin 11 receptor alpha (IL-IIRa); prostate stem cell antigen (PSCA); Protease Serine 21 (Testisin or PRSS21); vascular endothelial growth factor receptor 2 (VEGFR2); Lewis(Y) antigen; CD24; Platelet-derived growth factor receptor beta (PDGFR-beta); Stage-specific embryonic antigen-4 (SSEA-4); CD20; Folate receptor alpha (FRa or FR1); Folate receptor beta (FRb); Receptor tyrosine-protein kinase ERBB2 (Her2/neu); Mucin 1, cell surface associated (MUC1); epidermal growth factor receptor (EGFR); neural cell adhesion molecule (NCAM); Prostase; prostatic acid phosphatase (PAP); elongation factor 2 mutated (ELF2M); Ephrin B2; fibroblast activation protein alpha (FAP); insulin-like growth factor 1 receptor (IGF-I receptor), carbonic anhydrase IX (CAIX); Proteasome (Prosome, Macropain) Subunit, Beta Type, 9 (LMP2); glycoprotein 100 (gp100); oncogene fusion protein consisting of breakpoint cluster region (BCR) and Abelson murine leukemia viral oncogene homolog 1 (Abl) (bcr-abl); tyrosinase; ephrin type-A receptor 2 (EphA2); sialyl Lewis adhesion molecule (sLe); ganglioside GM3 (aNeu5Ac(2-3)bDClalp(I-4)bDGIcp(I-I)Cer); transglutaminase 5 (TGS5); high molecular weight-melanoma associated antigen (HMWMAA); o-acetyl-GD2 ganglioside (OAcGD2); tumor endothelial marker 1 (TEM1/CD248); tumor endothelial marker 7-related (TEM7R); claudin 6 (CLDN6); thyroid stimulating hormone receptor (TSHR); G protein coupled receptor class C group 5, member D (GPRC5D); chromosome X open reading frame 61 (CXORF61); CD97; CD179a; anaplastic lymphoma kinase (ALK); Polysialic acid; placenta-specific 1 (PLAC1); hexasaccharide portion of globoH glycoceramide (GloboH); mammary gland differentiation antigen (NY-BR-1); uroplakin 2 (UPK2); Hepatitis A virus cellular receptor 1 (HAVCR1); adrenoceptor beta 3 (ADRB3); pannexin 3 (PANX3); G protein-coupled receptor 20 (GPR20); lymphocyte antigen 6 complex, locus K 9 (LY6K); Olfactory receptor 51E2 (OR51E2); TCR Gamma Alternate Reading Frame Protein (TARP); Wilms tumor protein (WT1); Cancer/testis antigen 1 (NY-ES0-1); Cancer/testis antigen 2 (LAGE-la); Melanoma-associated antigen 1 (MAGE-A1); ETS translocation-variant gene 6, located on chromosome 12p (ETV6-AML); sperm protein 17 (SPA17); X Antigen Family, Member 1A (XAGE1); angiopoietin-binding cell surface receptor 2 (Tie 2); melanoma cancer testis antigen-1 (MAD-CT-1); melanoma cancer testis antigen-2 (MAD-CT-2); Fos-related antigen 1; tumor protein p53 (p53); p53 mutant; prostein; survivin; telomerase; prostate carcinoma tumor antigen-1 (PCT A-I or Galectin 8), melanoma antigen recognized by T cells 1 (MelanA or MARTI); Rat sarcoma (Ras) mutant; human Telomerase; reverse transcriptase (hTERT); sarcoma translocation breakpoints; melanoma inhibitor of apoptosis (ML-IAP); ERG (transmembrane protease, serine 2 (TMPRSS2) ETS fusion gene); N-Acetyl glucosaminyl-transferase V (NA17); paired box protein Pax-3 (PAX3); Androgen receptor; Cyclin BI; v-myc avian myelocytomatosis viral oncogene neuroblastoma derived homolog (MYCN); Ras Homolog Family Member C (RhoC); Tyrosinase-related protein 2 (TRP-2); Cytochrome P450 IB 1 (CYPIB 1); CCCTC-Binding Factor (Zinc Finger Protein)-Like (BORIS or Brother of the Regulator of Imprinted Sites), Squamous Cell Carcinoma Antigen Recognized By T Cells 3 (SART3); Paired box protein Pax-5 (PAX5); proacrosin binding protein sp32 (OY-TES1); lymphocyte-specific protein tyrosine kinase (LCK); A kinase anchor protein 4 (AKAP-4); synovial sarcoma, X breakpoint 2 (SSX2); Receptor for Advanced Gly cation Endproducts (RAGE-1); renal ubiquitous 1 (RU1); renal ubiquitous 2 (RU2); legumain; human papilloma virus E6 (HPV E6); human papilloma virus E7 (HPV E7); intestinal carboxyl esterase; heat shock protein 70-2 mutated (mut hsp70-2); CD79a; CD79b; CD72; Leukocyte-associated immunoglobulin-like receptor 1 (LAIR1); Fc fragment of IgA receptor (FCAR or CD89); Leukocyte immunoglobulin-like receptor subfamily A member 2 (LILRA2); CD300 molecule-like family member f (CD300LF); C-type lectin domain family 12 member A (CLEC12A); bone marrow stromal cell antigen 2 (BST2); EGF-like module-containing mucin-like hormone receptor-like 2 (EMR2); lymphocyte antigen 75 (LY75); Glypican-3 (GPC3); Fc receptor-like 5 (FCRLS); and immunoglobulin lambda-like polypeptide 1 (IGLLI), MPL, Biotin, c-MYC epitope Tag, CD34, LAMP1 TROP2, GFRalpha4, CDH17, CDH6, NYBR1, CDH19, CD200R, Slea (CA19.9; Sialyl Lewis Antigen); Fucosyl-GMI, PTK7, gpNMB, CDH1-CD324, DLL3, CD276/B7H3, ILI IRa, IL13Ra2, CD179b-IGLII, TCRgamma-delta, NKG2D, CD32 (FCGR2A), Tn ag, Timl-/HVCR1, CSF2RA (GM-CSFR-alpha), TGF-betaR2, Lews Ag, TCR-betal chain, TCR-beta2 chain, TCR-gamma chain, TCR-delta chain, FITC, Luteinizing hormone receptor (LHR), Follicle stimulating hormone receptor (FSHR), Gonadotropin Hormone receptor (CGHR or GR), CCR4, GD3, SLAMF6, SLAMF4, HIV1 envelope glycoprotein, HTLVI-Tax, CMV pp65, EBV-EBNA3c, KSHV K8.1, KSHV-gH, influenza A hemagglutinin (HA), GAD, PDL1, Guanylyl cyclase C (GCC), auto antibody to desmoglein 3 (Dsg3), auto antibody to desmoglein 1 (Dsgl), HLA, HLA-A, HLA-A2, HLA-B, HLA-C, HLA-DP, HLA-DM, HLA-DOA, HLA-DOB, HLA-DQ, HLA-DR, HLA-G, IgE, CD99, Ras G12V, Tissue Factor 1 (TF1), AFP, GPRC5D, Claudin 18.2 (CLD18A2 or CLDN18A.2)), P-glycoprotein, STEAP1, Livl, Nectin-4, Cripto, gpA33, BST1/CD157, low conductance chloride channel, and the antigen recognized by TNT antibody.

Additionally, in several embodiments there is provided an immune cell that expresses a CD19-directed chimeric antigen receptor, the chimeric antigen receptor comprising an extracellular anti-CD19 binding moiety, wherein the anti-CD19 binding moiety comprises a heavy chain variable (VH) domain and a and a light chain variable (VL) domain, the VH domain comprising a VH domain having at least 95% identity to the VH domain amino acid sequence set forth in SEQ ID NO: 33, the VL domain having at least 95% identity to the VL domain amino acid sequence set forth in SEQ ID NO: 32, a hinge and/or transmembrane domain, an intracellular signaling domain, wherein the intracellular signaling domain comprises an OX40 subdomain, and wherein the cell also expresses membrane-bound interleukin-15 (mbIL15). In several embodiments, the intracellular signaling domain further comprises a CD3zeta subdomain. In several embodiments, the OX40 subdomain comprises the amino acid sequence of SEQ ID NO: 6 and the CD3zeta subdomain comprises the amino acid sequence of SEQ ID NO: 7. In several embodiments, the hinge domain comprises a CD8a hinge domain. In several embodiments, the CD8a hinge domain, comprises the amino acid sequence of SEQ ID NO: 2. In several embodiments, the mbIL15 comprises the amino acid sequence of SEQ ID NO: 12. In several embodiments, the chimeric receptor further comprises an extracellular domain of an NKG2D receptor. In several embodiments, the extracellular domain of the NKG2D receptor comprises a functional fragment of NKG2D comprising the amino acid sequence of SEQ ID NO: 26. In several embodiments, the immune cell is a natural killer (NK) cell. In several embodiments, the immune cell is a T cell. In several embodiments, the such immune cells are administered to a subject in a method of treating cancer, or are otherwise used to the treatment of cancer, such as in the preparation of a medicament for the treatment of cancer. In several embodiments, the cancer is acute lymphocytic leukemia.

In several embodiments there is provided a polynucleotide encoding a CD19-directed chimeric antigen receptor, the chimeric antigen receptor comprising an extracellular anti-CD19 binding moiety, wherein the anti-CD19 binding moiety comprises a heavy chain variable (VH) domain and a and a light chain variable (VL) domain, the VH domain having at least 95% identity to the VH domain amino acid sequence set forth in SEQ ID NO: 33, the VL domain having at least 95% identity to the VL domain amino acid sequence set forth in SEQ ID NO: 32, a hinge and/or transmembrane domain, an intracellular signaling domain, wherein the intracellular signaling domain comprises an OX40 subdomain, and wherein the polynucleotide also encodes membrane-bound interleukin-15 (mbIL15). In several embodiments, the intracellular signaling domain further comprises a CD3zeta subdomain. In several embodiments, the encoded OX40 subdomain comprises the amino acid sequence of SEQ ID NO: 16 and the encoded CD3zeta subdomain comprises the amino acid sequence of SEQ ID NO: 8. In several embodiments, the hinge domain comprises a CD8a hinge domain and comprises the amino acid sequence of SEQ ID NO: 2. In several embodiments, the encoded mbIL15 comprises the amino acid sequence of SEQ ID NO: 12. In several embodiments, the chimeric receptor further comprises an extracellular domain of an NKG2D receptor.

In several embodiments, the encoded extracellular domain of the NKG2D receptor comprises a functional fragment of NKG2D comprising the amino acid sequence of SEQ ID NO: 26.

Also provided herein is an immune cell that expresses a CD19-directed chimeric receptor comprising an extracellular anti-CD19 moiety, a hinge and/or transmembrane domain, and an intracellular signaling domain. In several embodiments, the immune cell is an NK cell. In several embodiments, the immune cell is a T cell. In several embodiments, the hinge domain comprises a CD8a hinge domain or an Ig4 SH domain. In several embodiments, the transmembrane domain comprises a CD8a transmembrane domain, a CD28 transmembrane domain and/or a CD3 transmembrane domain. In several embodiments, the signaling domain comprises an OX40 signaling domain, a 4-1 BB signaling domain, a CD28 signaling domain, an NKp80 signaling domain, a CD16 IC signaling domain, a CD3zeta or CD3ζ ITAM signaling domain, and/or a mIL-15 signaling domain. In several embodiments, the signaling domain comprises a 2A cleavage domain. In several embodiments, the mIL-15 signaling domain is separated from the rest or another portion of the CD19-directed chimeric receptor by a 2A cleavage domain. In several embodiments, such immune cells are administered to a subject having cancer in order to treat, inhibit or prevent progression of the cancer.

Provided herein is also an engineered NK or T cell that expresses a CD19-directed chimeric antigen receptor, the chimeric antigen receptor comprising an extracellular anti-CD19 binding moiety, wherein the anti-CD19 binding moiety comprises a heavy chain variable (VH) domain and a and a light chain variable (VL) domain, the VH domain comprising a VH domain resulting from humanization of the VH domain amino acid sequence set forth in SEQ ID NO: 33, the VL domain comprising a VL domain resulting from humanization the VL domain amino acid sequence set forth in SEQ ID NO: 32, a hinge and/or transmembrane domain, an intracellular signaling domain, wherein the intracellular signaling domain comprises an OX40 subdomain, and wherein the cell also expresses membrane-bound interleukin-15 (mbIL15).

Provided herein is a polynucleotide encoding a CD19-directed chimeric antigen receptor, the chimeric antigen receptor comprising an extracellular anti-CD19 binding moiety, wherein the anti-CD19 binding moiety comprises a heavy chain variable (VH) domain and a and a light chain variable (VL) domain, the VH domain comprising a VH domain resulting from humanization of the VH domain amino acid sequence set forth in SEQ ID NO: 33, the VL domain comprising a VL domain resulting from humanization the VL domain amino acid sequence set forth in SEQ ID NO: 32; a hinge and/or transmembrane domain, an intracellular signaling domain, wherein the intracellular signaling domain comprises an OX40 subdomain, and wherein the polynucleotide also encodes membrane-bound interleukin-15 (mbIL15).

Provided here is a polynucleotide encoding a CD19-directed chimeric antigen receptor, the chimeric antigen receptor comprising an extracellular anti-CD19 binding moiety, wherein the anti-CD19 binding moiety comprises a scFv; a hinge, wherein the hinge is a CD8 alpha hinge; a transmembrane domain; and an intracellular signaling domain, wherein the intracellular signaling domain comprises a CD3 zeta ITAM. In several embodiments, the transmembrane domain comprises a CD8 alpha transmembrane domain, an NKG2D transmembrane domain, and/or a CD28 transmembrane domain. In several embodiments, the intracellular signaling domain comprises a CD28 signaling domain, a 4-1 BB signaling domain, and/or an OX40 domain. In several embodiments, the intracellular signaling domain may also comprise a domain selected from ICOS, CD70, CD161, CD40L, CD44, and combinations thereof.

Provided herein is a polynucleotide encoding a CD19-directed chimeric antigen receptor, the chimeric antigen receptor comprising an extracellular anti-CD19 binding moiety, wherein the anti-CD19 binding moiety comprises a variable heavy chain of a scFv or a variable light chain of a scFv; a hinge, wherein the hinge is a CD8 alpha hinge; a transmembrane domain, wherein the transmembrane domain comprises a CD8 alpha transmembrane domain; and an intracellular signaling domain, wherein the intracellular signaling domain comprises a CD3 zeta ITAM. In several embodiments, the polynucleotide also encodes a truncated epidermal growth factor receptor (EGFRt). In several embodiments, the polynucleotide also encodes membrane-bound interleukin-15 (mbIL15). Provided herein is an engineered NK or T cell that expresses such a CD19-directed chimeric antigen, as well as methods of treating cancer by administering such an NK cell or T cell. Also provided for is the use of such polynucleotides in the treatment of cancer, for example, in the manufacture of a medicament for the treatment of cancer.

Provided herein is a polynucleotide encoding a humanized CD19-directed chimeric antigen receptor, the chimeric antigen receptor comprising an extracellular anti-CD19 binding moiety, wherein the anti-CD19 binding moiety comprises a heavy chain variable (VH) domain and a and a light chain variable (VL) domain, the VH domain comprising a VH domain selected from SEQ ID NO: 120, SEQ ID NO: 121, SEQ ID NO: 122, and SEQ ID NO: 123, the VL domain comprising a VL domain selected from SEQ ID NO: 117, SEQ ID NO: 118, and SEQ ID NO: 119; a hinge and/or transmembrane domain, an intracellular signaling domain, and wherein the polynucleotide also encodes membrane-bound interleukin-15 (mbIL15). In several embodiments, the intracellular signaling domain comprises an OX40 subdomain, a CD28 subdomain, an iCOS subdomain, a CD28-41 BB subdomain, a CD27 subdomain, a CD44 subdomain, or combinations thereof. In several embodiments, the chimeric antigen receptor comprises a hinge and a transmembrane domain, wherein the hinge is a CD8 alpha hinge, wherein the transmembrane domain is either a CD8 alpha or an NKG2D transmembrane domain. In several embodiments, the intracellular signaling domain comprises a CD3zeta domain.

Provided for herein is a polynucleotide encoding a humanized chimeric antigen receptor (CAR), wherein the CAR comprises a single chain antibody or single chain antibody fragment which comprises a humanized anti-CD19 binding domain, a transmembrane domain, a primary intracellular signaling domain comprising a native intracellular signaling domain of CD3-zeta, or a functional fragment thereof, and a costimulatory domain comprising a native intracellular signaling domain of a protein selected from the group consisting of OX40, CD27, CD28, ICOS, and 4-1BB, or a functional fragment thereof, wherein said anti-CD19 binding domain comprises a light chain complementary determining region 1 (LC CDR1) of SEQ ID NO: 124, 127, or 130, a light chain complementary determining region 2 (LC CDR2) of SEQ ID NO: 125, 128, or 131, and a light chain complementary determining region 3 (LC CDR3) of SEQ ID NO: 126, 129, or 132, and a heavy chain complementary determining region 1 (HC CDR1) of SEQ ID NO: 133, 136, 139, or 142, a heavy chain complementary determining region 2 (HC CDR2) of SEQ ID NO: 134, 137, 140, or 143, and a heavy chain complementary determining region 3 (HC CDR3) of SEQ ID NO: 135, 138, 141, or 144. In several embodiments, the polynucleotide further comprises a region encoding membrane-bound interleukin 15 (mbIL15).

Provided for herein is a polynucleotide encoding a humanized CD19-directed chimeric antigen receptor, the chimeric antigen receptor comprising an extracellular anti-CD19 binding moiety, wherein the anti-CD19 binding moiety comprises a humanized scFv sequence comprising a variable light (VL) domain of SEQ ID NO: 117, a hinge and/or transmembrane domain, an intracellular signaling domain, and wherein the polynucleotide also encodes membrane-bound interleukin-15 (mbIL15). In several embodiments, the polynucleotide encodes the humanized chimeric antigen receptor of SEQ ID NO: 161, SEQ ID NO: 167, SEQ ID NO: 173, SEQ ID NO: 179, SEQ ID NO: 185, SEQ ID NO: 191, SEQ ID NO: 197, or SEQ ID NO: 203.

Provided for is a polynucleotide encoding a humanized CD19-directed chimeric antigen receptor, the chimeric antigen receptor comprising an extracellular anti-CD19 binding moiety, wherein the anti-CD19 binding moiety comprises a humanized scFv sequence comprising a variable light (VL) domain of SEQ ID NO: 118, a hinge and/or transmembrane domain, an intracellular signaling domain, and wherein the polynucleotide also encodes membrane-bound interleukin-15 (mbIL15). In several embodiments, the polynucleotide encodes the humanized chimeric antigen receptor of SEQ ID NO: 163, SEQ ID NO: 169, SEQ ID NO: 175, SEQ ID NO: 181, SEQ ID NO: 187, SEQ ID NO: 193, SEQ ID NO: 199, or SEQ ID NO: 205.

Provided for is a polynucleotide encoding a humanized CD19-directed chimeric antigen receptor, the chimeric antigen receptor comprising an extracellular anti-CD19 binding moiety, wherein the anti-CD19 binding moiety comprises a humanized scFv sequence comprising a variable light (VL) domain of SEQ ID NO: 119, a hinge and/or transmembrane domain, an intracellular signaling domain, and wherein the polynucleotide also encodes membrane-bound interleukin-15 (mbIL15). In several embodiments, the polynucleotide encodes the humanized chimeric antigen receptor of SEQ ID NO: 165, SEQ ID NO: 171, SEQ ID NO: 177, SEQ ID NO: 183, SEQ ID NO: 189, SEQ ID NO: 195, SEQ ID NO: 201, or SEQ ID NO: 207.

Provided for is a polynucleotide encoding a humanized CD19-directed chimeric antigen receptor, the chimeric antigen receptor comprising an extracellular anti-CD19 binding moiety, wherein the anti-CD19 binding moiety comprises a humanized scFv sequence comprising a variable heavy (VH) domain of SEQ ID NO: 120, a hinge and/or transmembrane domain, an intracellular signaling domain, and wherein the polynucleotide also encodes membrane-bound interleukin-15 (mbIL15). In several embodiments, the polynucleotide encodes the humanized chimeric antigen receptor of SEQ ID NO: 161, SEQ ID NO: 163, SEQ ID NO: 165, SEQ ID NO: 185, SEQ ID NO: 187, or SEQ ID NO: 189.

Provided for is a polynucleotide encoding a humanized CD19-directed chimeric antigen receptor, the chimeric antigen receptor comprising an extracellular anti-CD19 binding moiety, wherein the anti-CD19 binding moiety comprises a humanized scFv sequence comprising a variable heavy (VH) domain of SEQ ID NO: 121, a hinge and/or transmembrane domain, an intracellular signaling domain, and wherein the polynucleotide also encodes membrane-bound interleukin-15 (mbIL15). In several embodiments, the polynucleotide encodes the humanized chimeric antigen receptor of SEQ ID NO: 167, SEQ ID NO: 169, SEQ ID NO: 171, SEQ ID NO: 191, SEQ ID NO: 193, or SEQ ID NO: 195.

Provided for is a polynucleotide encoding a humanized CD19-directed chimeric antigen receptor, the chimeric antigen receptor comprising an extracellular anti-CD19 binding moiety, wherein the anti-CD19 binding moiety comprises a humanized scFv sequence comprising a variable heavy (VH) domain of SEQ ID NO: 122, a hinge and/or transmembrane domain, an intracellular signaling domain, and wherein the polynucleotide also encodes membrane-bound interleukin-15 (mbIL15). In several embodiments, the polynucleotide encodes the humanized chimeric antigen receptor of SEQ ID NO: 173, SEQ ID NO: 175, SEQ ID NO: 177, SEQ ID NO: 197, SEQ ID NO: 199, or SEQ ID NO: 201.

Provided for is a polynucleotide encoding a humanized CD19-directed chimeric antigen receptor, the chimeric antigen receptor comprising an extracellular anti-CD19 binding moiety, wherein the anti-CD19 binding moiety comprises a humanized scFv sequence comprising a variable heavy (VH) domain of SEQ ID NO: 123, a hinge and/or transmembrane domain, an intracellular signaling domain, and wherein the polynucleotide also encodes membrane-bound interleukin-15 (mbIL15). In several embodiments, the polynucleotide encodes the humanized chimeric antigen receptor of SEQ ID NO: 179, SEQ ID NO: 181, SEQ ID NO: 183, SEQ ID NO: 203, SEQ ID NO: 205, or SEQ ID NO: 207.

In several embodiments, the provided for polynucleotides do not encode SEQ ID NO: 112, 113, 114, or 116.

Provided for is a polynucleotide encoding a humanized CD19-directed chimeric antigen receptor, the chimeric antigen receptor comprising an extracellular anti-CD19 binding moiety; a hinge and/or transmembrane domain; an intracellular signaling domain, and wherein the polynucleotide also encodes membrane-bound interleukin-15 (mbIL15), and wherein the polynucleotide is selected from the group consisting of polynucleotides having at least 95% identity to SEQ ID NO: 184, SEQ ID NO: 186, SEQ ID NO: 192, or SEQ ID NO: 200. In several embodiments, the polynucleotide has the sequence of SEQ ID NO: 184, SEQ ID NO: 186, SEQ ID NO: 192, or SEQ ID NO: 200. In several embodiments, there are provided engineered NK or T cells that express such a humanized CD19-directed chimeric antigen receptor. Also provided for is a method of treating cancer in a subject comprising administering to a subject having cancer such engineered NK or T cells. Also provided is the use of such polynucleotides in the treatment of cancer, such as in the manufacture of a medicament for the treatment of cancer.

EXAMPLES

The materials and methods disclosed herein are non-limiting examples that are employed according to certain embodiments disclosed herein.

According to several embodiments, NK cells are isolated from peripheral blood mononuclear cells and expanded through the use of a feeder cell line. As discussed in more detail below, in several embodiments, the feeder cells are engineered to express certain stimulatory molecules (e.g. interleukins, CD3, 4-1BBL, etc.) to promote immune cell expansion and activation. Engineered feeder cells are disclosed in, for example, International Patent Application PCT/SG2018/050138, which is incorporated in its entirety by reference herein. In several embodiments, the stimulatory molecules, such as interleukin 12, 18, and/or 21 are separately added to the co-culture media, for example at defined times and in particular amounts, to effect an enhanced expansion of a desired sub-population(s) of immune cells.

NK cells isolated from PBMC were cocultured with K562 cells expressing membrane-bound IL15 and 4-1BBL, with the media being supplemented with IL2. For one group of engineered NK cells, they were expanded in media was supplemented (at Day 0) with a combination of soluble IL12 and soluble IL18. The media was refreshed with additional soluble IL12 and soluble IL18 at Day 4. Additional details on embodiments of such culture methodology is disclosed in U.S. Provisional Patent Application No. 62/881,311, filed Jul. 31, 2019 and incorporated in its entirety by reference here. Viral transduction, with a CD19-directed chimeric receptor construct, was performed at Day 7. The resultant engineered NK cells were evaluated at 14, or more, days of total culture time.

Example 1

Figure 5:
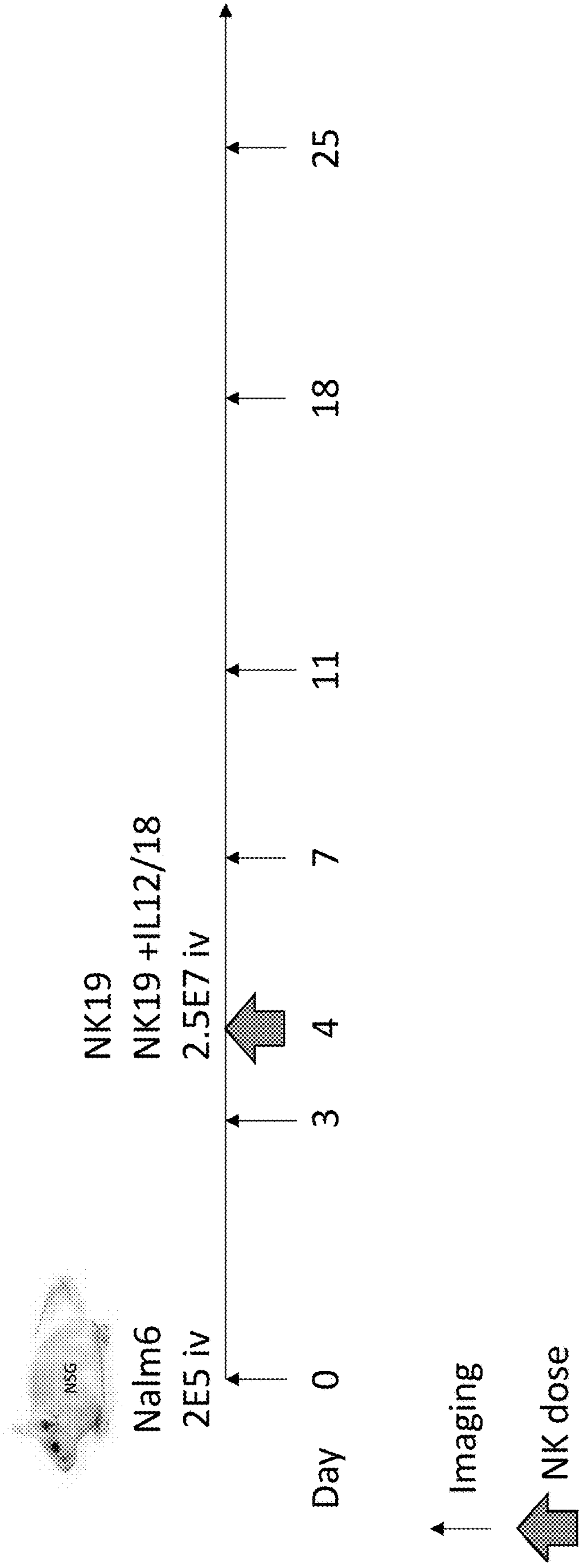
FIG. 5 shows a schematic of an experimental protocol assessing the effectiveness of a CD19-directed chimeric antigen receptor in accordance with several embodiments disclosed herein.
Figure 6A:
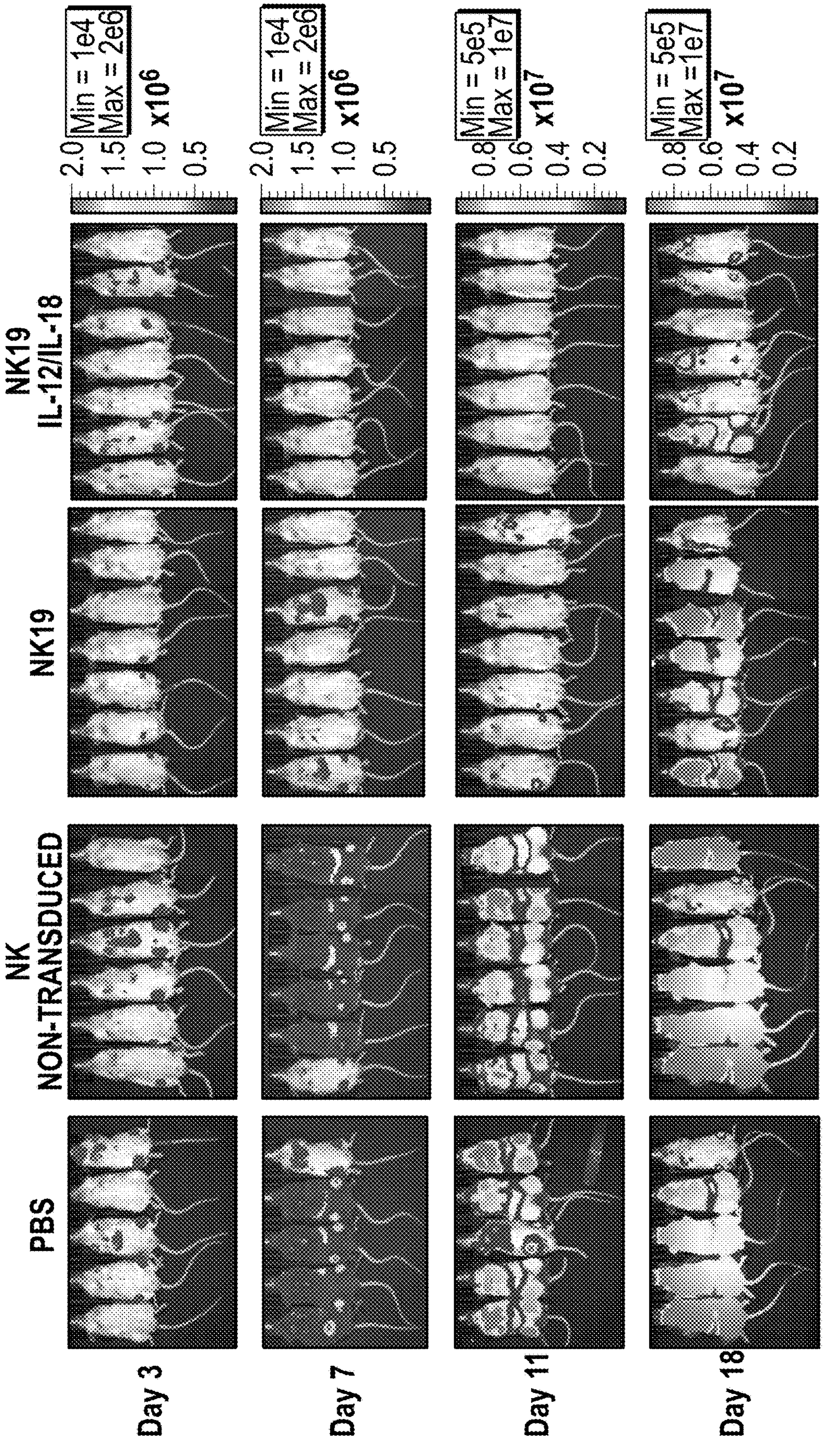
FIG. 6A depicts in vivo data related to the anti-tumor effect of various non-limiting CD19-directed chimeric receptors.
Figure 6B:
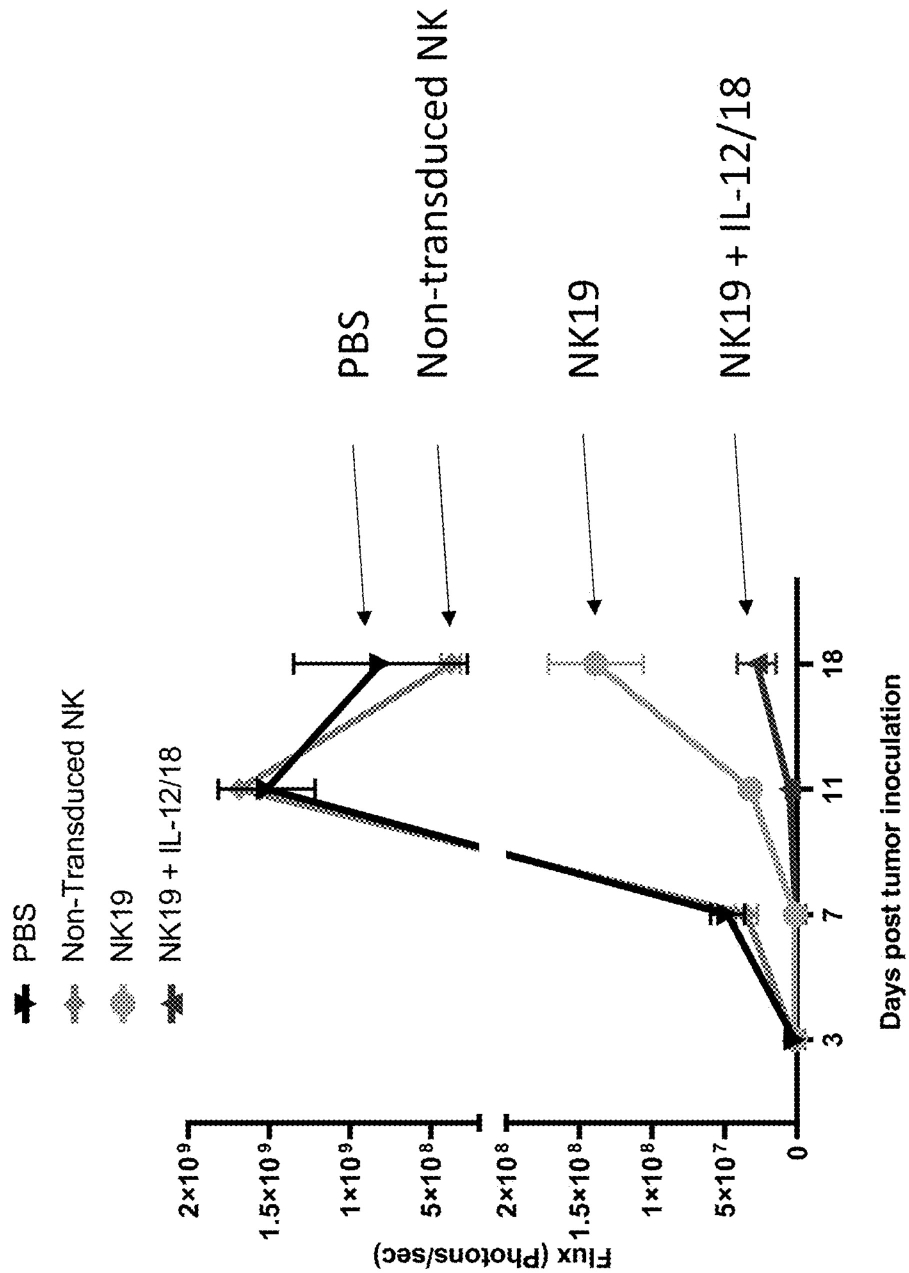
FIG. 6B depicts summary data related to the anti-tumor effect of various non-limiting CD19-directed chimeric receptors.

FIG. 5 depicts a schematic experimental model for evaluating the anti-tumor efficacy of engineered NK cells generated according to methods disclosed herein. NOD-scid IL2Rgamma$^{null}$ mice were administered $2\times10^5$ Nalm6 cells (B cell precursor leukemia cell line) intravenously at Day 0. At Day 4, one group of mice received $2.7\times10^7$ NK cells expressing an NK19 CAR (see FIG. 3A, though it shall be appreciated that other CD19-directed chimeric receptors could be used) while another group received NK cells that had been expanded using soluble IL12/IL18 (identified as NK19-IL12/18 cells). Leukemic tumor burden was assessed by fluorescent imaging performed at Days 3, 7, 11, 18, and 25. FIG. 6A shows the imaging results from Days 3, 7, 11, and 18. As can be seen, mice receiving either NK19 or NK19 IL12/18 had significantly less tumor burden than mice receiving either non-transduced NK cells or PBS as a control. FIG. 6B shows a summary of the imaging data in a line graph (greater values of Flux (photons/second) indicates more fluorescent signal detection and greater tumor burden). Both NK19 and NK19 IL12/18 groups have less tumor burden as early as Day 7 post-injection of the Nalm6 leukemia cells. This difference is even more pronounced at Day 11, when the PBS and NT NK cell groups are exhibiting large amounts of tumor growth. Even as far out as Day 18, when tumor burden in the PBS and NT NK groups is extensive, the NK19 and NK19 IL12/18 groups show much less tumor burden. Unexpectedly, the NK19 IL12/18 groups show less tumor burden than this receiving the NK19 construct. This is surprising not only because NK19 cells are quite efficacious at preventing leukemia cell growth, so the further enhancement of this effect is unexpected, but also because an upstream methodology of expanding the cells has not only impacted the cell number itself, but also the activity level of those expanded cells.

Example 2

Experiments were undertaken to determine if a given stimulatory domain (also referred to as co-stimulatory domains, given that many construct employ multiple "signaling" domains in tandem, triplet or other multiplex fashion) utilized in a CAR impacted expression (as well as activity). NK cells were generated by transduction with viruses encoding various CARs depicted in FIGS. 3A-3C (though other constructs are used, in several embodiments). By way of non-limiting example, NK cells were cells were generated by transduction with a bicistronic virus encoding an anti-CD19 scFv, an intracellular OX40 costimulatory domain, CD3 signaling domain, and membrane-bound IL-15 (see NK19, FIG. 3A) which supports prolonged cell survival and proliferation. The other CAR constructs tested, NK19-1, 2, 3, 4, 5, 8, 9, 10, 11, 12, and NK19-13, were transduced into NK cells in similar fashion. It shall be appreciated that, for those constructs that employ a Flag domain to determine expression, analogous constructs not including the Flag (or other tag domain) are provided for, in several embodiments.

Figure 7:
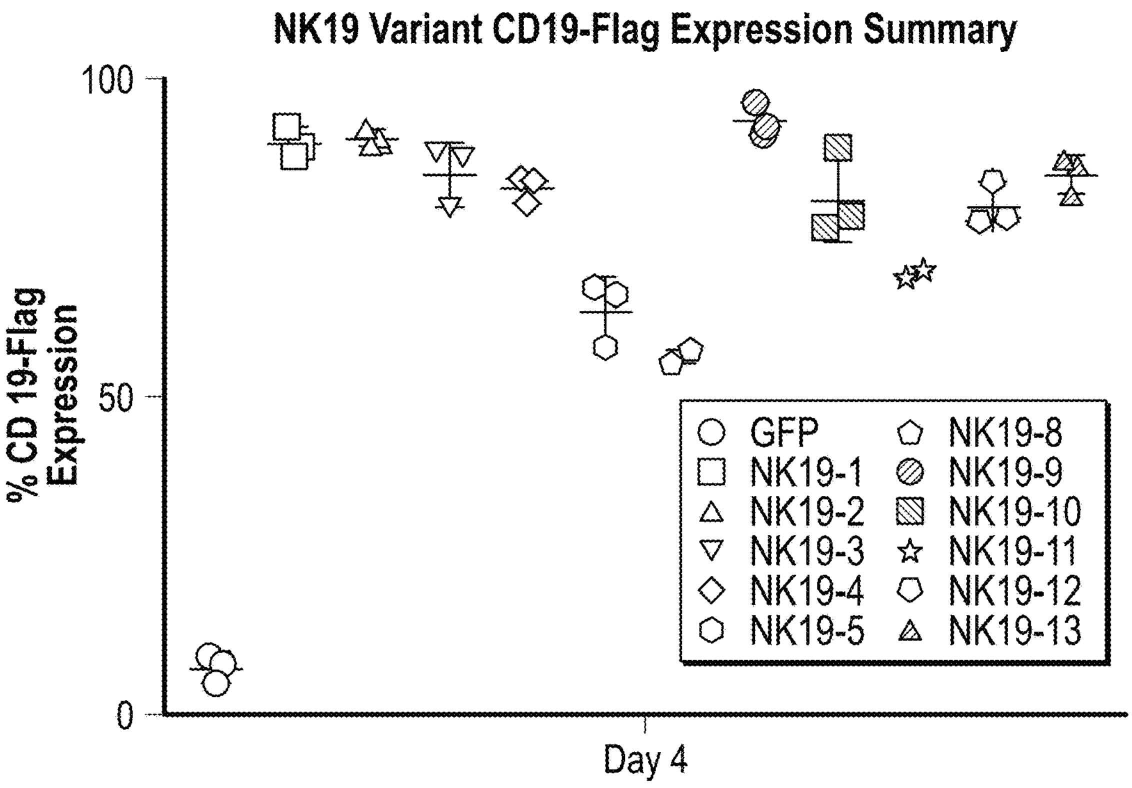
FIG. 7 depicts data related to the expression of various CD19-directed chimeric receptor constructs by NK cells.

FIG. 7 summarizes the expression data of NK 19-1 to NK5 and NK8 to NK19-13 as evidenced by detection of CD19Flag. Data are presented as percentage of NK cells expressing CD19-Flag relative to the total number of NK cells presented. The data were collected at 4 days after transduction with the relevant virus encoding the NK19-"X" CAR. As evidenced by the expression data, all constructs were expressed by at least 55% of the NK cells. In fact, for eight of the eleven constructs for which data was generated expression was detected in approximately 75% or more of the total number of NK cells, with several constructs expressed at over 80% efficiency. This expression data indicates that, according to several embodiments, selection of specific stimulatory domains can enable a more efficient expression of the CAR by the NK cell. This is advantageous, in several embodiments, because a greater portion of a given NK cell preparation is useful clinically (e.g., fewer input NK cells needed to generate a clinically relevant engineered NK cell dose).

Figure 8A:
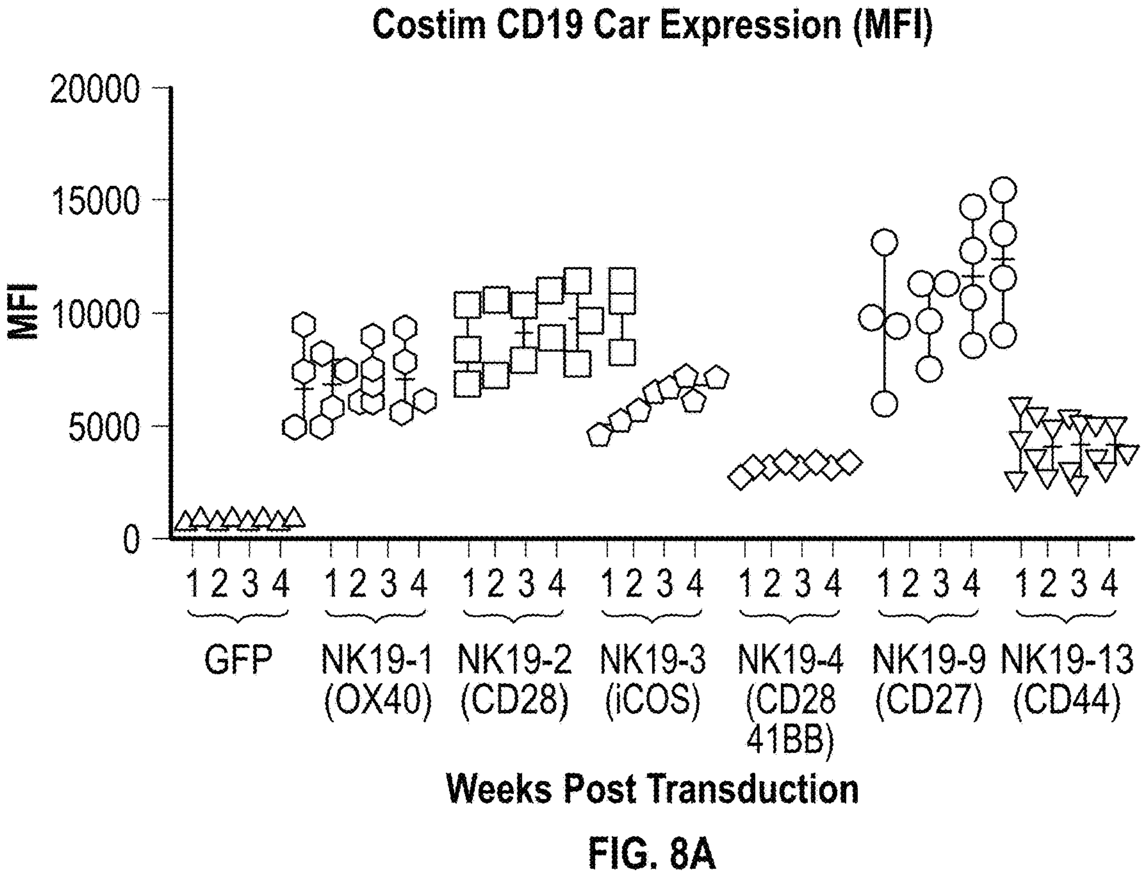
FIG. 8A depicts raw fluorescence data (mean fluorescence intensity, MFI) related to the expression of selected CD19-directed chimeric receptors.
Figure 8B:
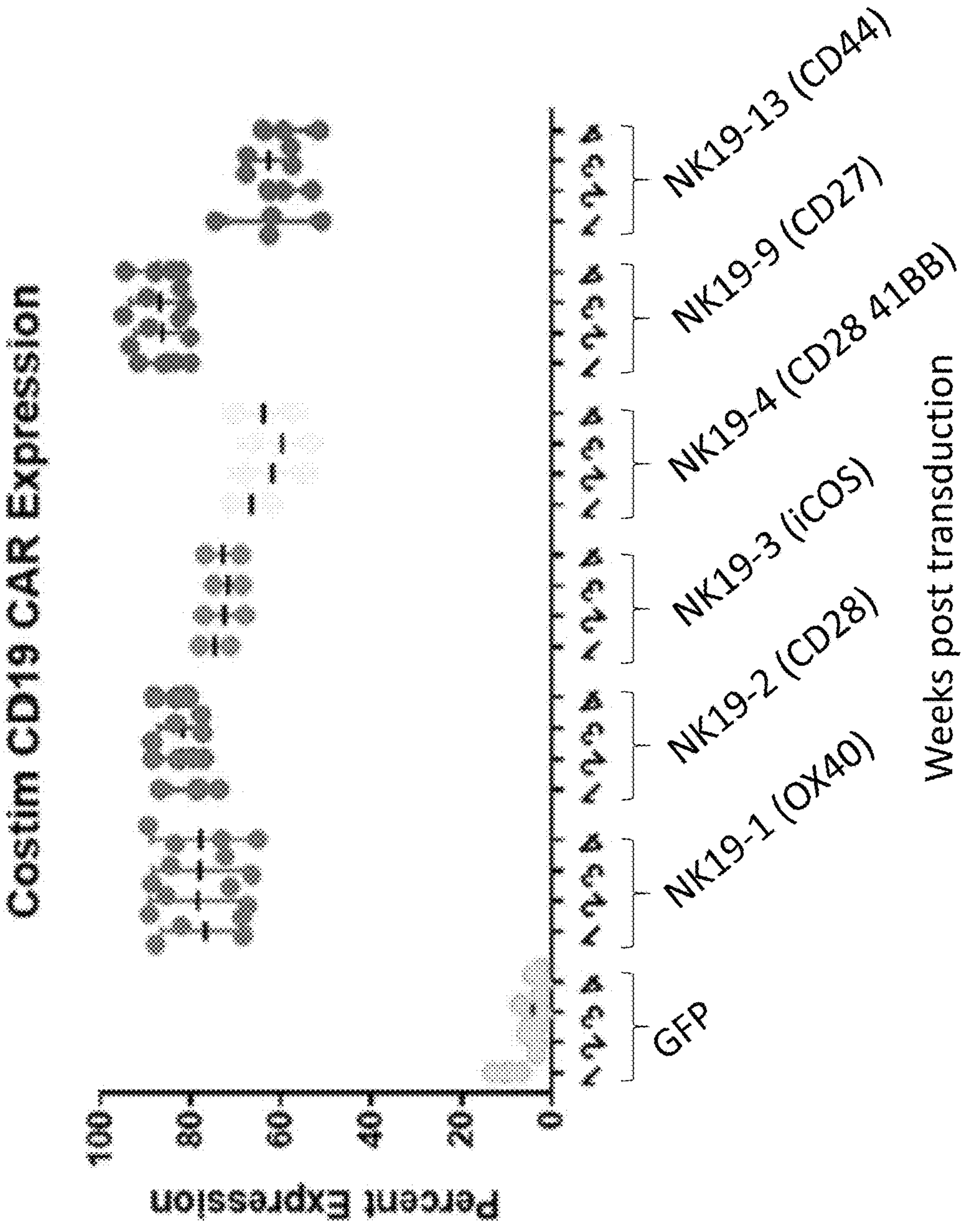
FIG. 8B depicts data related to the expression of selected CD19-directed chimeric receptors, displayed as percent of NK cells expressing the indicated receptor.

As discussed herein, various co-stimulatory domains can be employed in chimeric antigen receptors that Target CD19 (or other tumor markers). FIG. 8A depicts data related to the expression of CARs targeting CD19 using various co-stimulatory domains. By way of non-limiting example, co-stimulatory domains can include, but are not limited to, OX40, CD28, iCOS, CD28/41 BB, CS27, and CD44). FIG. 8A shows mean fluorescence intensity data representing expression of the indicated CAR constructs by NK cells. As evidenced by the low MFI detected for the GFP control, these data indicate that these construct (a) are expressed by NK cells, and (b) are expressed relatively stably by NK cells over a 4 week period post-transduction. FIG. 8B shows the efficiency of expression of the CARs with the indicated co-stimulatory domains. While there is some variability in efficiency of expression, ranging from about 60% to about 80% efficiency, each of the CARs with the indicated co-stimulatory domains expressed well, and also expressed relatively consistently over at least 4 weeks.

Figure 9A:
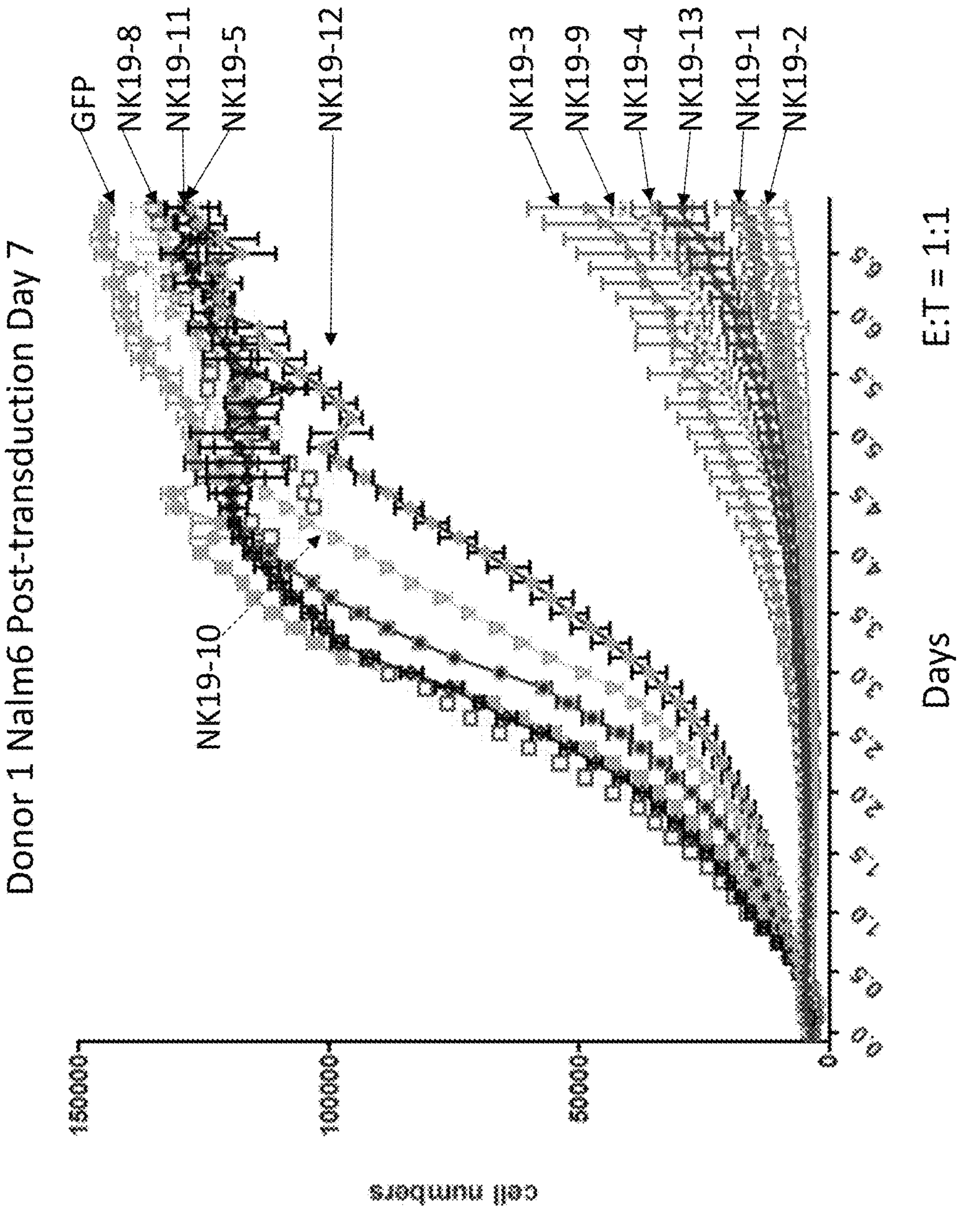
FIGS. 9A-9D depicts data related to the cytotoxicity (against Nalm6 or Raji cells) for the indicated CD19-directed chimeric receptors.

With respect to the cytotoxic efficacy of the NK cells expressing the CD19-directed CARs utilizing the various co-stimulatory domains, that data is shown in FIG. 9A-9F. Cultured Nalm6 or Raji cells were exposed to engineered NK cells expressing the indicated NK19 constructs and co-cultured for the indicated number of days (X axis represents days) of exposure to NK19-X-expressing NK cells. FIG. 9A shows the cytotoxic effects of the indicated constructs against Nalm6 cells 7 days after NK cells from a first donor were transduced with the indicated construct. The effector cell to target cell ratio for this experiment was 1:1. As shown in the traces, each of NK19-10, NK19-8, NK-1911, NK19-5, and NK19-12 allowed increases in the number of Nalm6 cells detected, on par with that of NK cells expressing only GFP as a control. However, each of NK19-3, NK19-9, NK19-4, NK19-13, NK19-1 and NK19-2 showed significantly less increase in Nalm6 cell number (e.g., greater cytotoxicity). In several embodiments, such constructs are therefore expressed in NK cells and used in treating B cell leukemia (or other tumor types). In several embodiments, one or more of the stimulatory domains from one of the constructs is engineered into another construct with a different stimulatory domain, which advantageously results in synergistic signaling and further enhanced cytotoxicity. By way of non-limiting example, an NK19-1 construct with an OX40 stimulatory domain is, in several embodiments, further engineered to also express a CD44 stimulatory domain in addition to OX40. By way of further non-limiting example, an NK19-1 construct with an OX40 stimulatory domain is, in several embodiments, further engineered to also express a CD44 stimulatory domain and a CD17 stimulatory domain in addition to OX40.

Figure 9B:
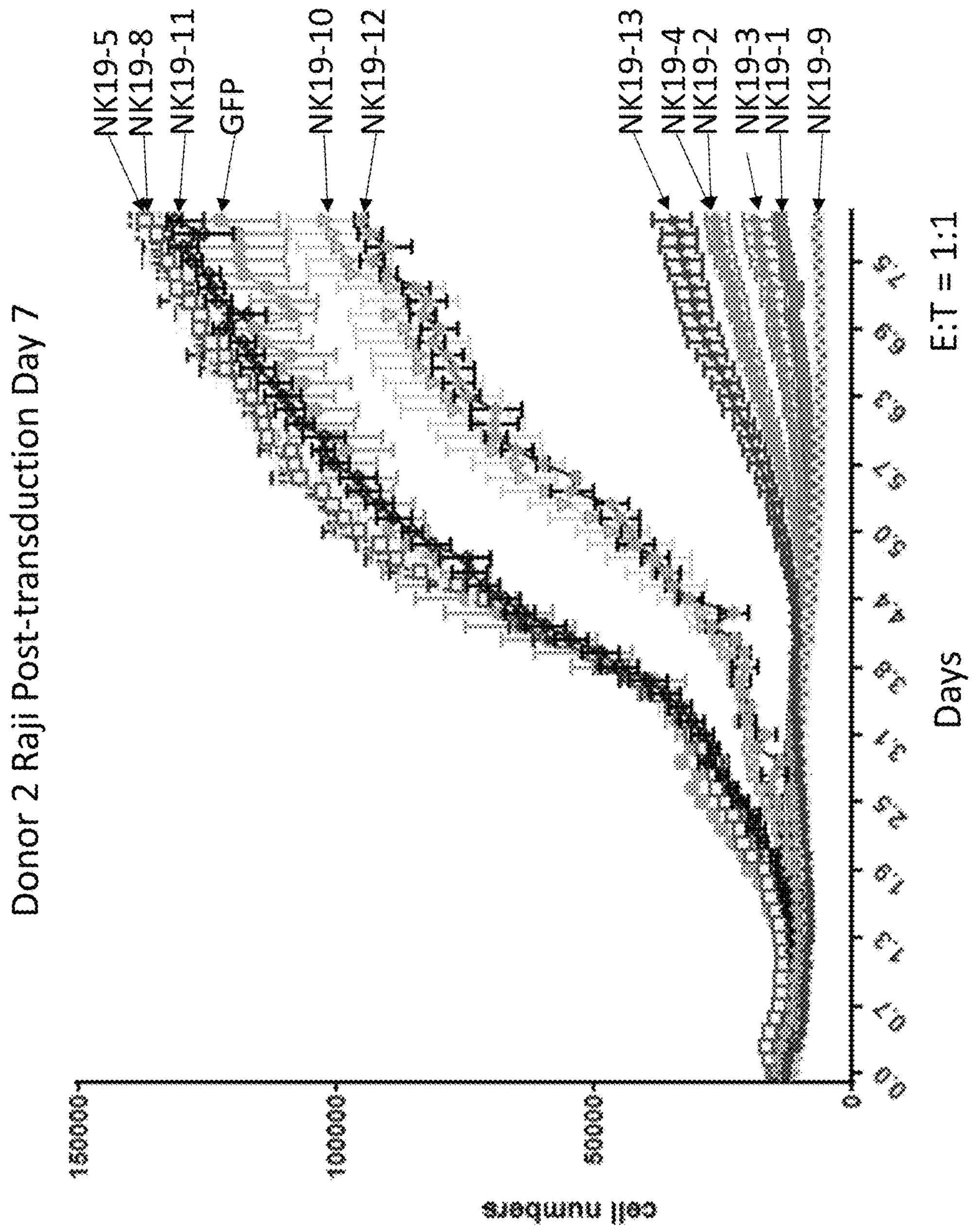

FIG. 9B shows corresponding cytotoxicity data for engineered NK cells from a second donor against Raji B-cell leukemia cells, 7 days post-transduction. The effector cell to target cell ratio here was also 1:1. As shown, similar to the engineered constructs activity against Nalm6 cells, several constructs allowed for increased Raji cell count. However, each of NK19-13, NK 19-4, NK19-2, NK19-3, NK19-1, and NK19-9 prevented Raji cell growth to a substantial degree, with several of the constructs resulting in nearly no Raji cell growth. In several embodiments, such constructs are therefore expressed in NK cells and used in treating B cell leukemia (or other tumor types).

Figure 9C:
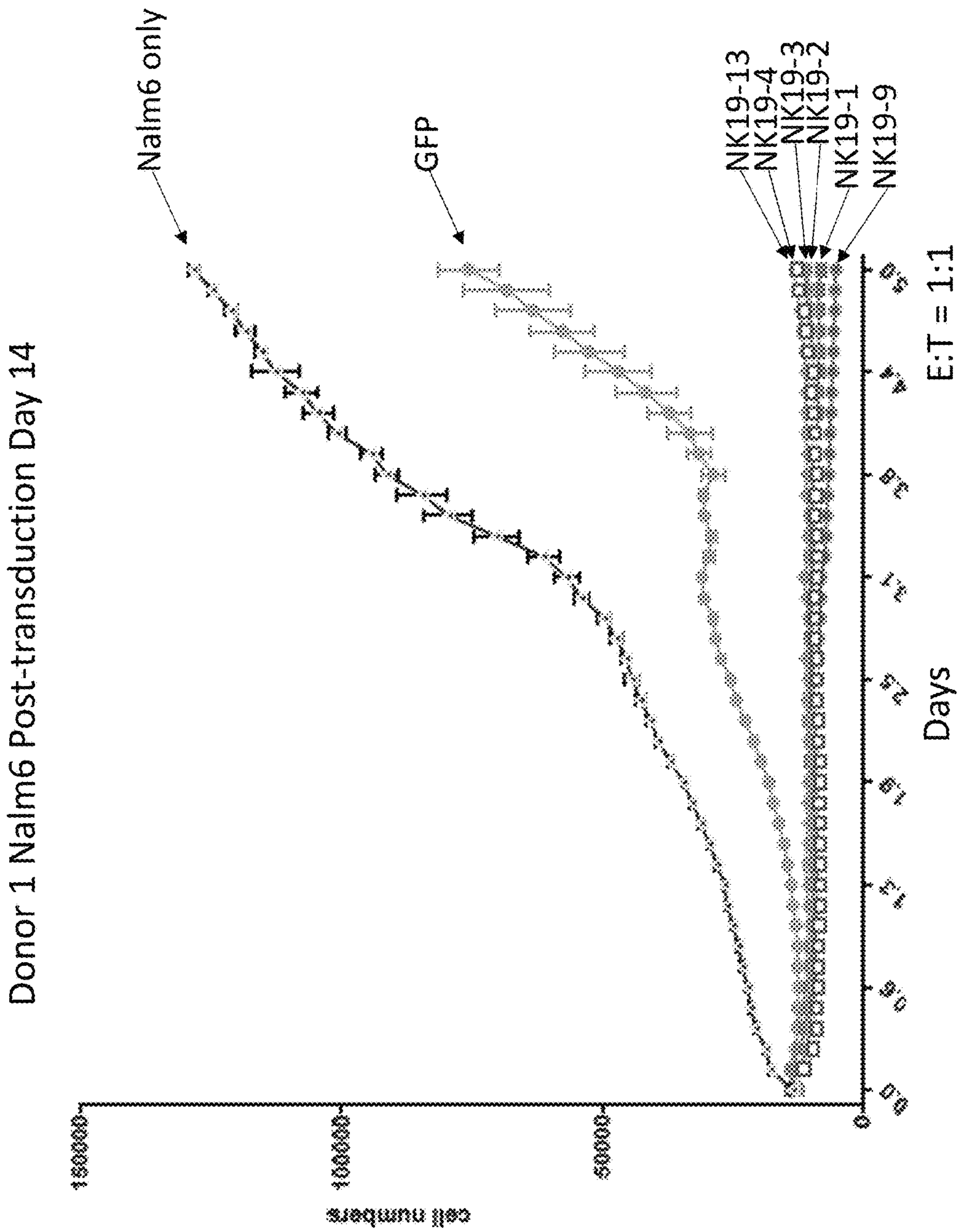

FIG. 9C shows data for NK cells from Donor 1 against Nalm6 cells 14 days post-transduction. The effector to target cell ratio is 1:1. As shown, even at two weeks post-transduction, the NK19-13, NK19-4, NK19-3, NK19-2, NK19-1, and NK19-9 expressing NK cells prevented virtually all Nalm6 cell growth, indicative of their highly cytotoxic effect against tumor cells. In several embodiments, such constructs are therefore expressed in NK cells and used in treating B cell leukemia (or other tumor types). As discussed above, in several embodiments, a construct is generated that employs a combination two, three, or more of the stimulatory domains, resulting in a synergistic NK cell stimulation and enhanced cytotoxicity.

Figure 9D:
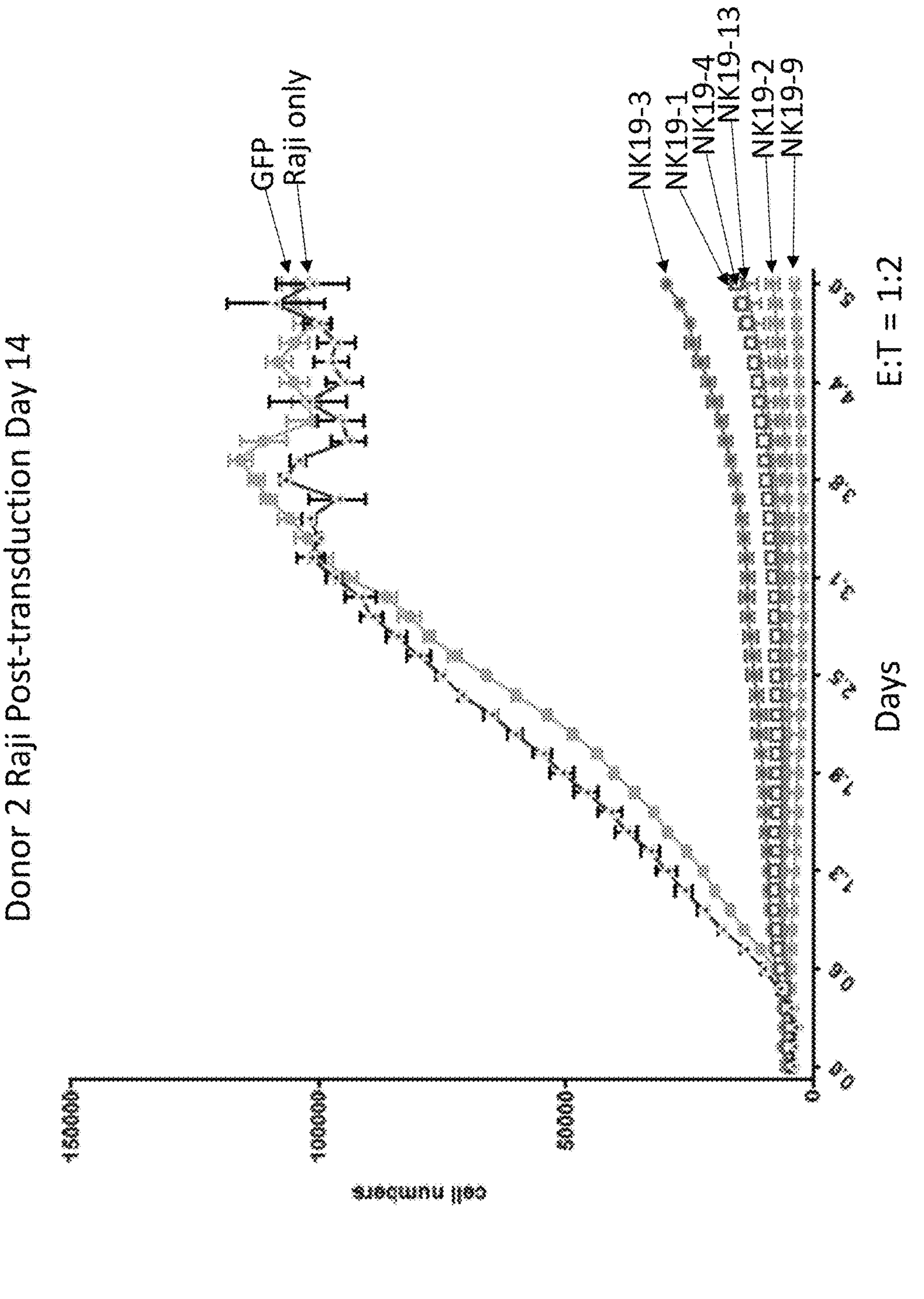

FIG. 9D shows data for NK cells from Donor 2 against Raji cells at 14 days post-transduction. The effector cell to target cell ratio was 1:2. As shown, NK cells expressing GFP only allowed growth of Raji cells essentially the same as untreated Raji cells. In contrast, each of NK19-3, NK19-1, NK19-4, NK19-13, NK19-2, and NK19-9 expressing NK cells significantly retarded the growth of Raji cells, with several of the constructs allowing little to no Raji cell growth. In several embodiments, such constructs are therefore expressed in NK cells and used in treating B cell leukemia (or other tumor types). As discussed above, in several embodiments, a construct is generated that employs a combination two, three, or more of the stimulatory domains, resulting in a synergistic NK cell stimulation and enhanced cytotoxicity.

Figure 9E:
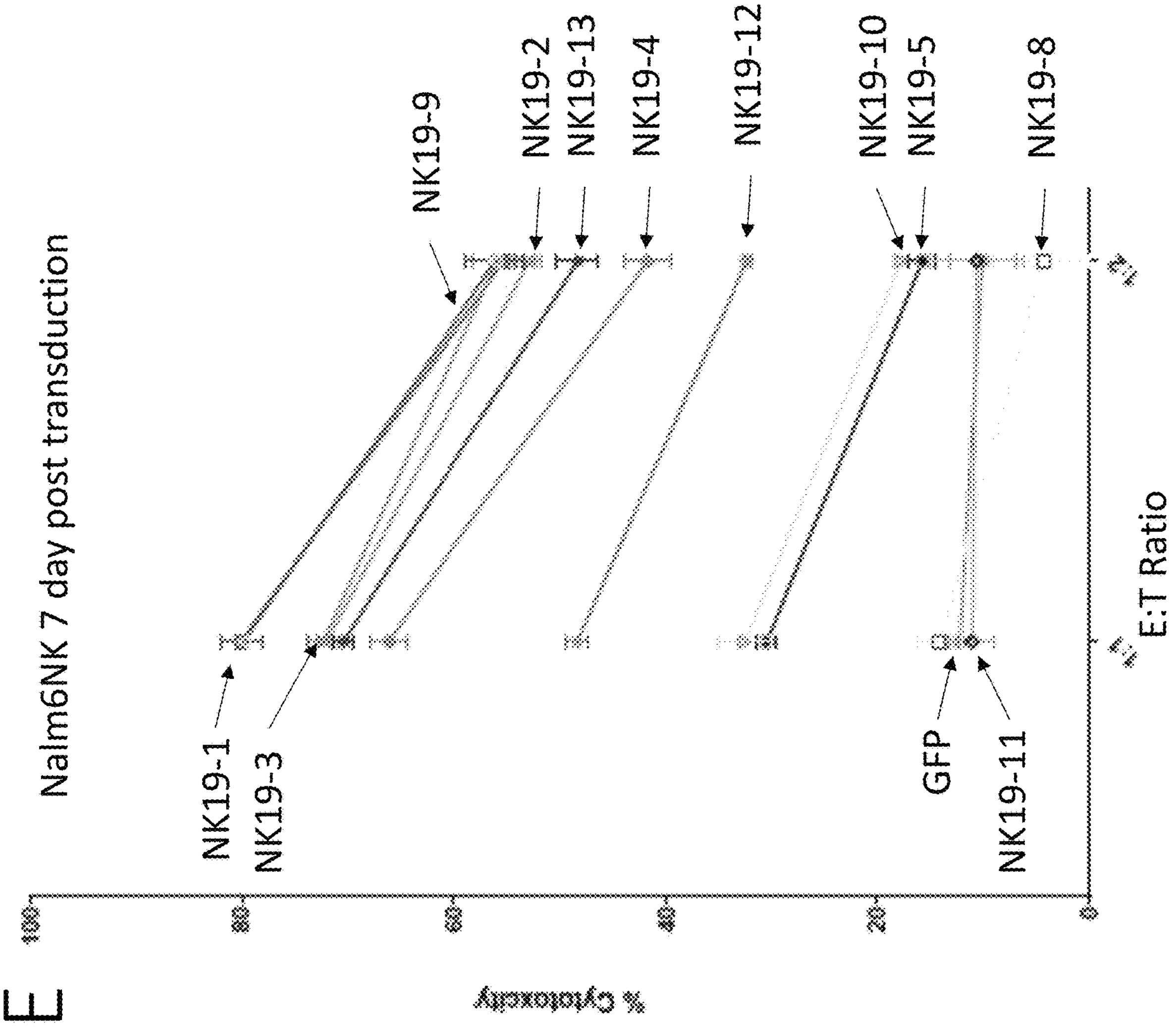
FIG. 9E depicts summary data related to the cytotoxicity (against Nalm6 cells) for the indicated CD19-directed chimeric receptors at various effector:target ratios.
Figure 9F:
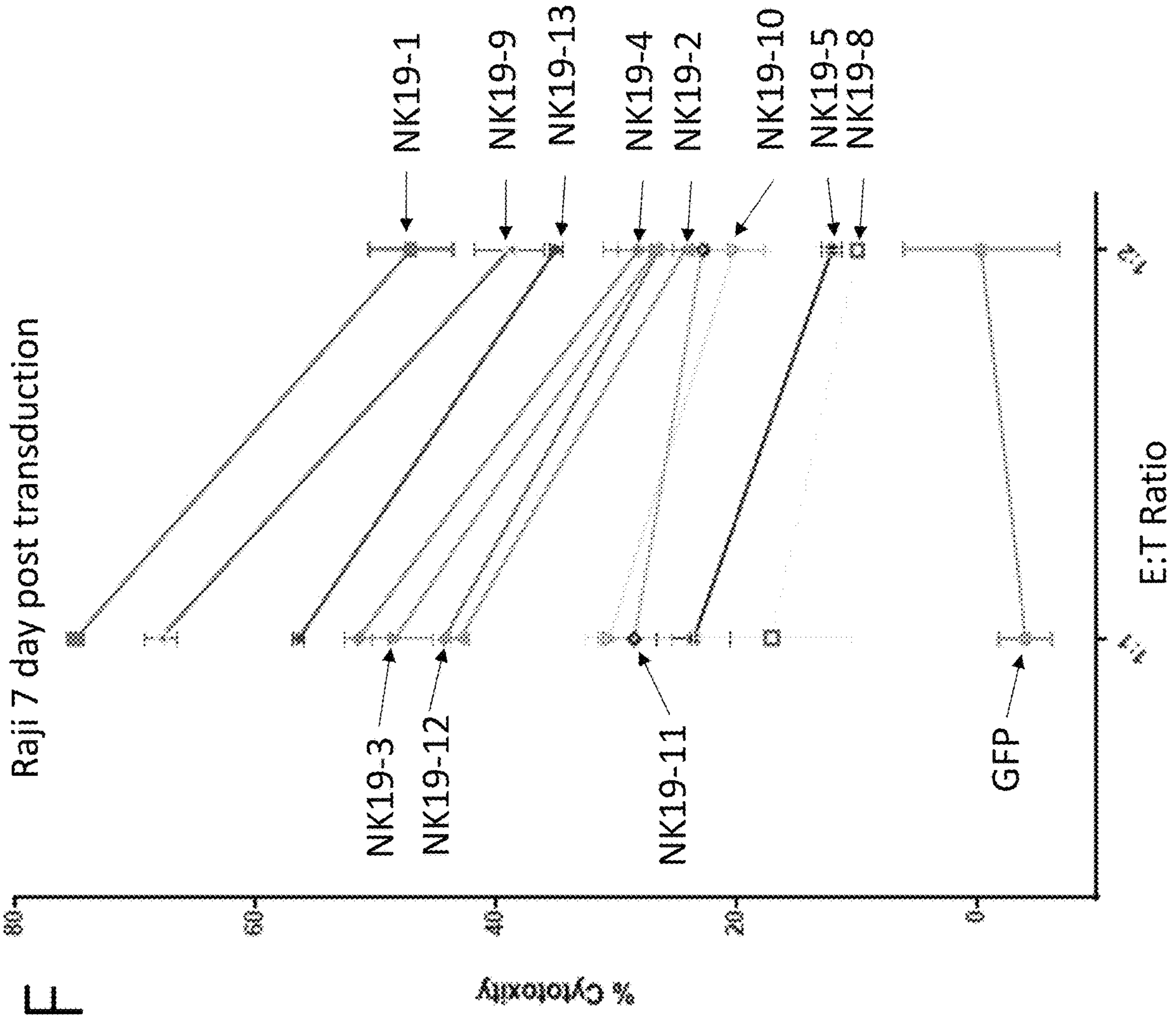
FIG. 9F depicts summary data related to the cytotoxicity (against Raji cells) for the indicated CD19-directed chimeric receptors at various effector:target ratios.

FIG. 9E shows summary data for cytotoxicity against Nalm6 cells at an E:T ratio of 1:1 and 1:2 at 7 days post-transduction. At an E:T ratio of 1:2, all but one of the NK19 constructs was equivalent to, or more, cytotoxic than NK cells expressing GFP alone. In fact, even while at a 1:2 ratio, six of the constructs achieved ~50% or greater cytotoxicity. When tested at an E:T of 1:1, seven of the constructs achieved ~50% or greater cytotoxicity, however, five of the constructs (NK19-13, NK19-2, NK19-9, NK19-3, and NK19-1) yielded cytotoxicity exceeding 70%. FIG. 9F shows the corresponding data for Raji cells. All constructs tested showed enhanced cytotoxicity over GFP-expressing NK cells at both 1:2 and 1:1 E:T ratios. At an E:T of 1:2, four of the constructs exceeded 40% cytotoxicity, while at 1:1, seven constructs exceeded that kill rate. Furthermore, at a 1:1 E:T, three constructs yielded cytotoxicity of 60% or more, with the most efficacious construct achieving nearly 90% cytotoxicity. Taken together, these data demonstrated that various CD19-directed CAR constructs can not only be expressed, but are stably expressed, and are also effective an inducing cytotoxicity in multiple cancer cell types, in some cases exceeding an 80% kill rate. According to additional embodiments, CD19-targeting constructs are generated that employ combinations of two, three or more stimulatory domains, which result in further enhancements in the cytotoxicity of the NK cells expressing them. In several embodiments, CD19-directed constructs can synergistically interact with NK cells expressing receptors directed against other tumor markers, such as ligands of NKG2D (such chimeric receptor bearing NK cells are described in PCT/US2018/024650, which is incorporated by reference herein in its entirety). For example, a chimeric receptor comprising an binding domain that binds ligands of NKG2D, an OX40 stimulatory domain, and a CD3zeta signaling domain could be used in conjunction with any of the CD19-targeting constructs disclosed herein. In several embodiments, such a chimeric receptor is at least 90% identical in sequence to the nucleic acid sequence of SEQ ID NO: 145. In several embodiments, such a chimeric receptor is at least 90% identical in sequence to the amino acid sequence of SEQ ID NO: 146.

Figure 10A:
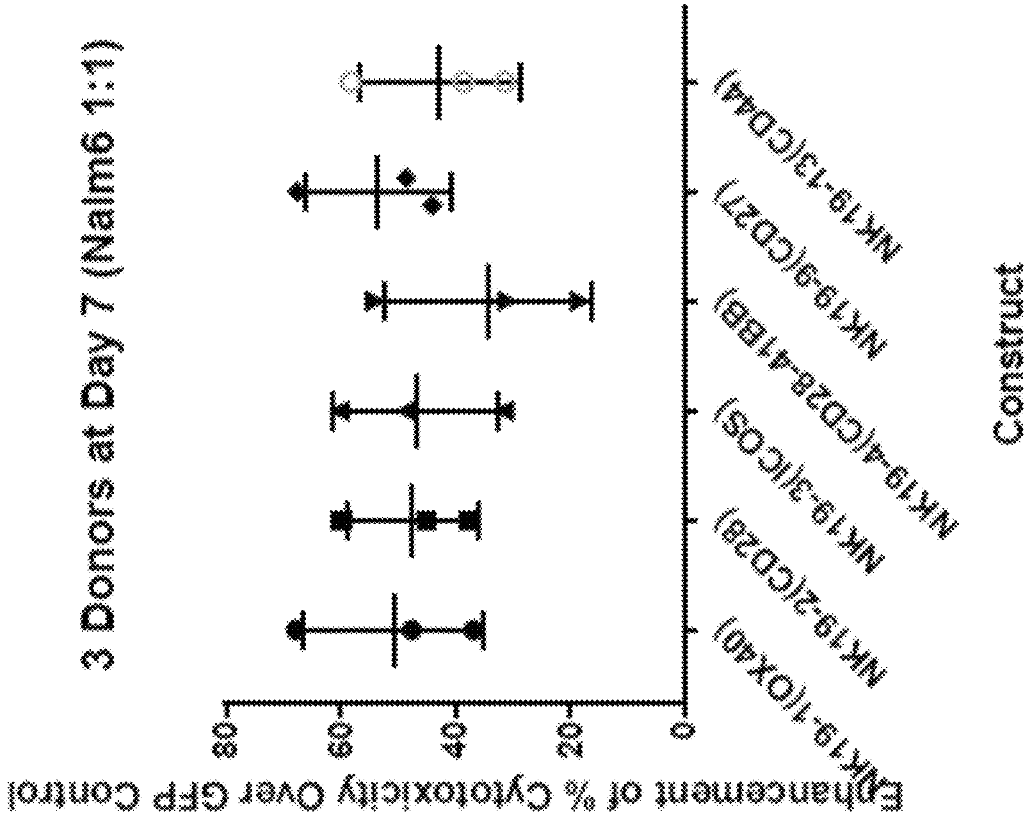
FIG. 10A depicts data related to the degree of enhanced cytotoxicity (against Nalm6 cells) for the indicated CD19-directed chimeric receptors at 7 days post transduction.
Figure 10B:
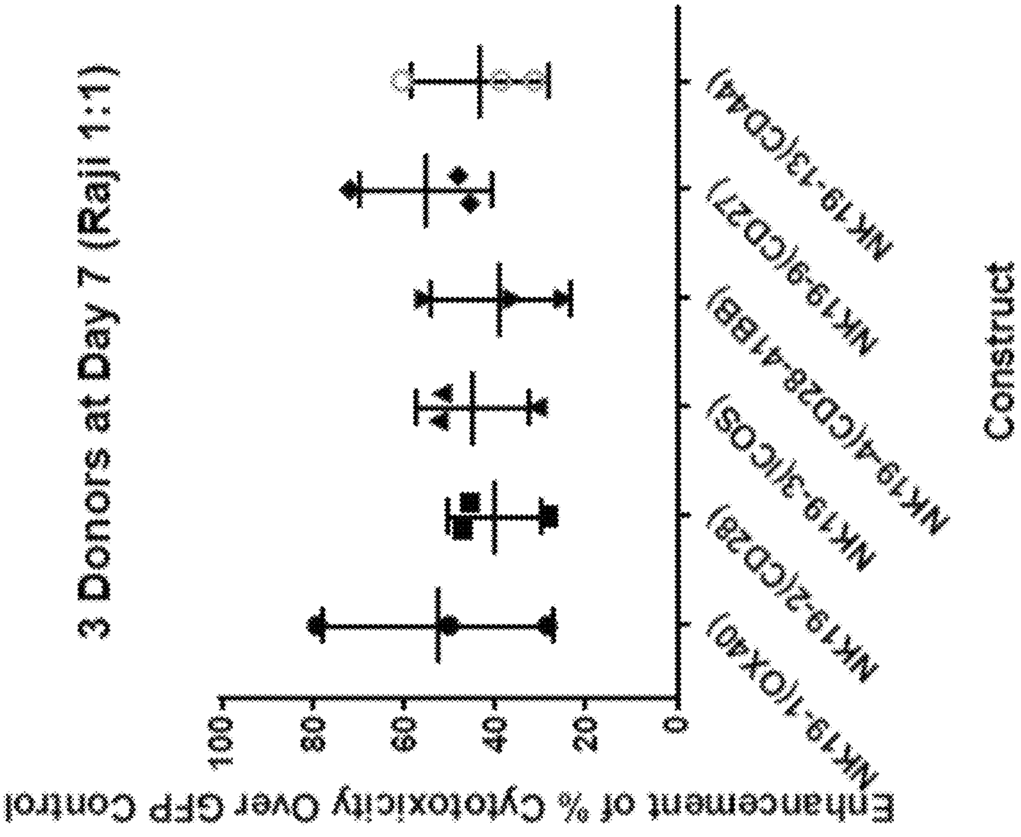
FIG. 10B depicts data related to the degree of enhanced cytotoxicity (against Raji cells) for the indicated CD19-directed chimeric receptors at 7 days post transduction.
Figure 10C:
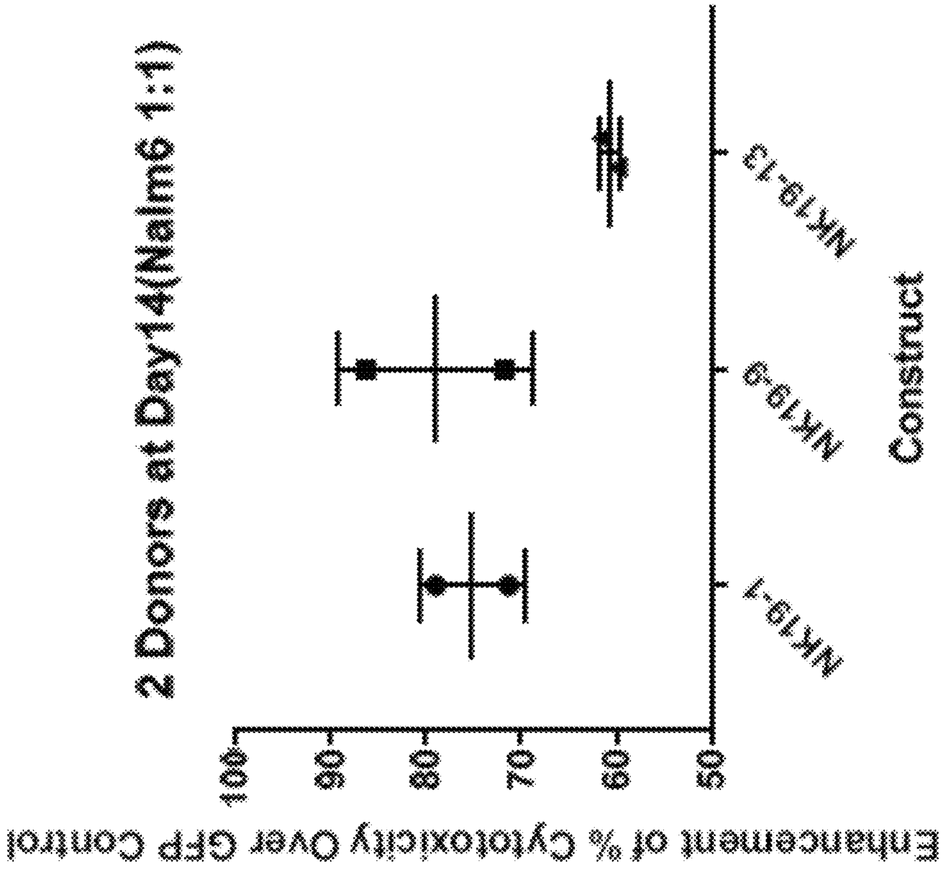
FIG. 10C depicts data related to the degree of enhanced cytotoxicity (against Nalm6 cells) for the indicated CD19-directed chimeric receptors at 14 days post transduction.
Figure 10D:
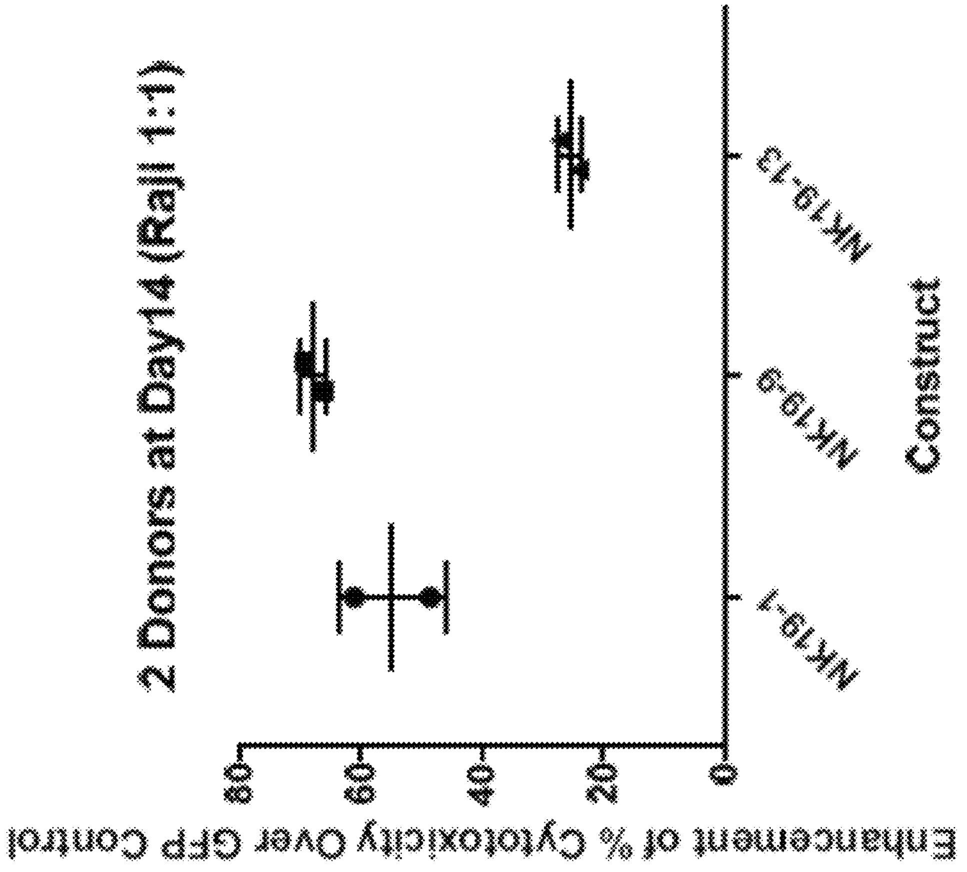
FIG. 10D depicts data related to the degree of enhanced cytotoxicity (against Raji cells) for the indicated CD19-directed chimeric receptors at 14 days post transduction.

Further experiments were performed to evaluate the cytotoxicity of selected CD19-directed CAR constructs. NK cells isolated from three different donors (two donors for 14 day experiment) were transduced with vectors encoding the indicated constructs, NK19-1 (OX40 co-stimulatory domain); NK19-2 (CD28 co-stimulatory domain); NK19-3 (ICOS co-stimulatory domain); NK19-4 (CD28-41BB co-stimulatory domain); NK19-9 (CD27 co-stimulatory domain); and NK19-13 (CD44 co-stimulatory domain). Seven (n=3) or 14 (n=2) days after transduction, those engineered NK cells were co-cultured with Nalm6 or Raji cells at an E:T ratio of 1:1. Results are shown in FIG. 10A (expressed as percent enhanced cytotoxicity over NK cells expressing GFP). Consistent with the data from FIG. 9, each of the constructs tested yielded enhanced cytotoxic effects against Nalm6 cells, ranging from a mean 40% increase with NK19-4 to an overall average of about 50% increase with the other 5 constructs. FIG. 10B shows the corresponding data against Raji cells. Again, each construct outperformed NK cells expressing only GFP, with mean increases in cytotoxicity over GFP NK cells ranging from about 40% increase to about 50% increase. Using cells from two donors at 14 days post-transduction, NK19-1, NK19-9 and NK19-13 were tested on Nalm6 and Raji cells. FIG. 10C shows the calculated enhanced cytotoxicity of these constructs over GFP-expressing NK cells, where average increases of nearly 80% were seen with NK19-9 expressing NK cells, about 75% with NK19-1 expressing cells and over 60% with NK19-13 expressing cells. Similar results were obtained against Raji cells—NK19-13 expressing cells showed over a 20% improvement in cytotoxicity, NK19-1 expressing cells exhibiting nearly 60% enhanced activity and NK19-9 expressing cells showing almost 70% more cytotoxic activity against Raji cells. These results further support the embodiments disclosed herein wherein engineered NK cells expressing CD19-directed CARs are provided, as are methods for their use in treating cancer immunotherapy results in enhanced cytotoxicity against target tumor cells.

Figure 11E:
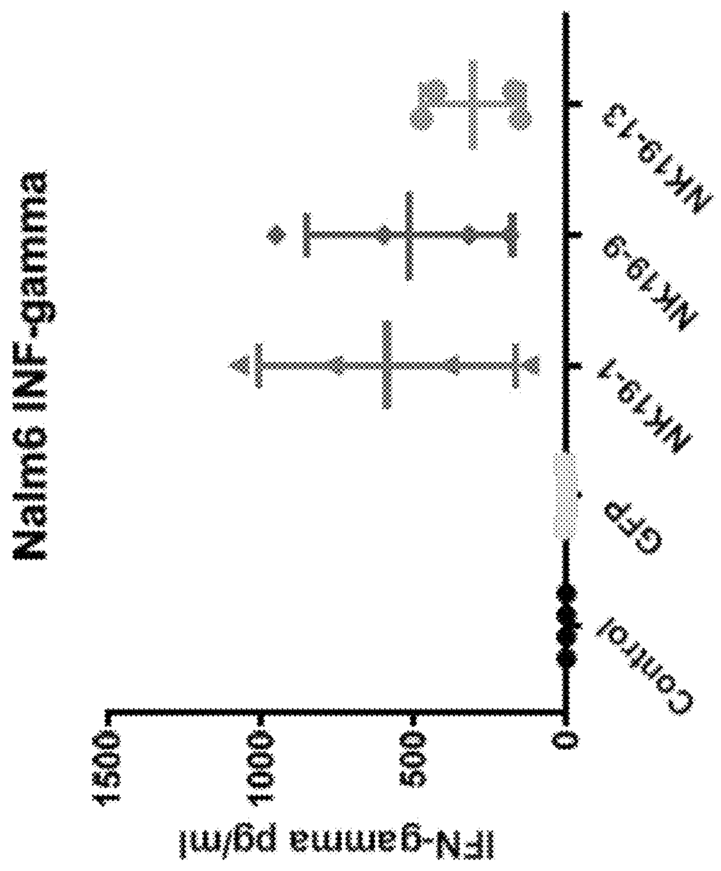
Figure 12E:
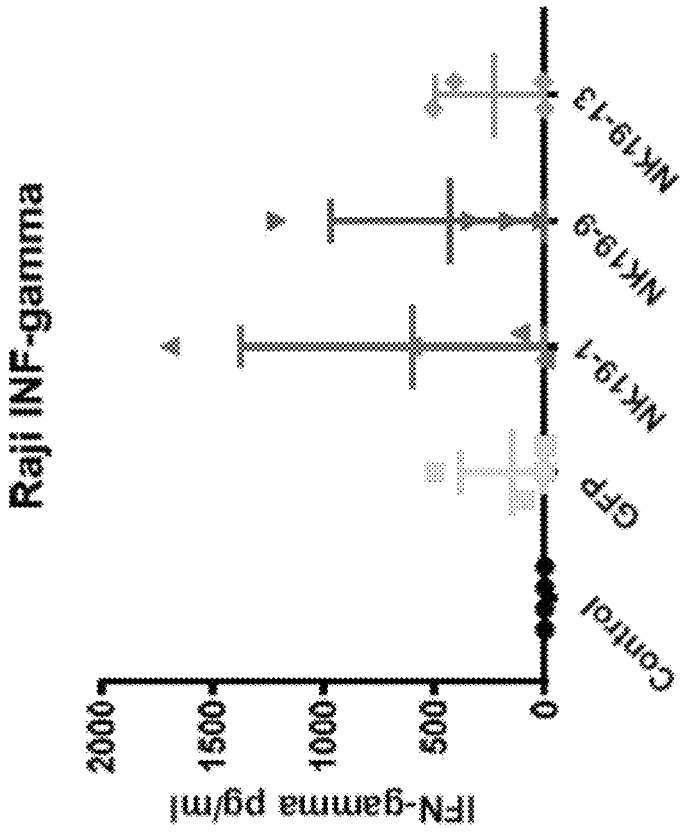

FIGS. 11A-11E depict data related to the cytokine release profiles from NK cells when cultured the Nalm6 cells, which ties into the mechanism by which NK cells control tumor and virus-infected cells—through releasing cytotoxic granules and proinflammatory cytokines. FIG. 11A shows that as compared to control, or even GFP-expressing NK cells, NK cells expressing NK19-1, NK19-9, or NK19-13 all express greater concentrations of the serine protease, Granzyme B, that is present in the granules released by NK cells. NK cells expressing these CD19-directed CARs released approximately 4 times more Granzyme B than control GFP-expressing NK cells. FIG. 11B shows data related to increased release of perforin by the engineered NK cells. Interestingly, perforin levels were not substantially elevated over the concentrations resulting from GFP-expressing NK cells (though perforin concentration was elevated over control. Perforins work in concert with Granzyme B (and other granzymes), with perforins functioning to generate pores through a cell membrane to allow granzymes to cross the membrane, then exert their protease effects on intracellular protein targets. The data raise the possibility that the perforin release while approximately the same, or reduced in connection with certain constructs, are actually more efficient at pore-formation, thus allowing the same degree of pore formation. Alternatively, if the perforins released from NK19 expressing NK cells are no more efficient at pore formation, this is offset by the elevated increase of granzyme B (and/or other granzymes). Thus, enhanced cytotoxicity is still achieved.

FIG. 11C shows that as compared to control, or even GFP-expressing NK cells, NK cells expressing NK19-1, NK19-9, or NK19-13 all release greater concentrations of the inflammatory cytokine TNF alpha. FIG. 11D shows similar data for GM-CSF release by NK19-expressing NK cells and FIG. 11E shows similar data for interferon gamma release. Likewise, when tested on Raji cells, similar patterns of release result, as shown in FIGS. 12A-12E. These data indicate that the NK19-epressing cells exert their cytotoxic effects, at least in part, through the increased release of inflammatory cytokines and/or cytotoxic granules. As mentioned above, in several embodiments, the engineered CARs are designed to have combinations of two, three or more co-stimulatory domains, with synergistically increased cytokine/granule release and cytotoxicity against target cancers.

Figure 13:
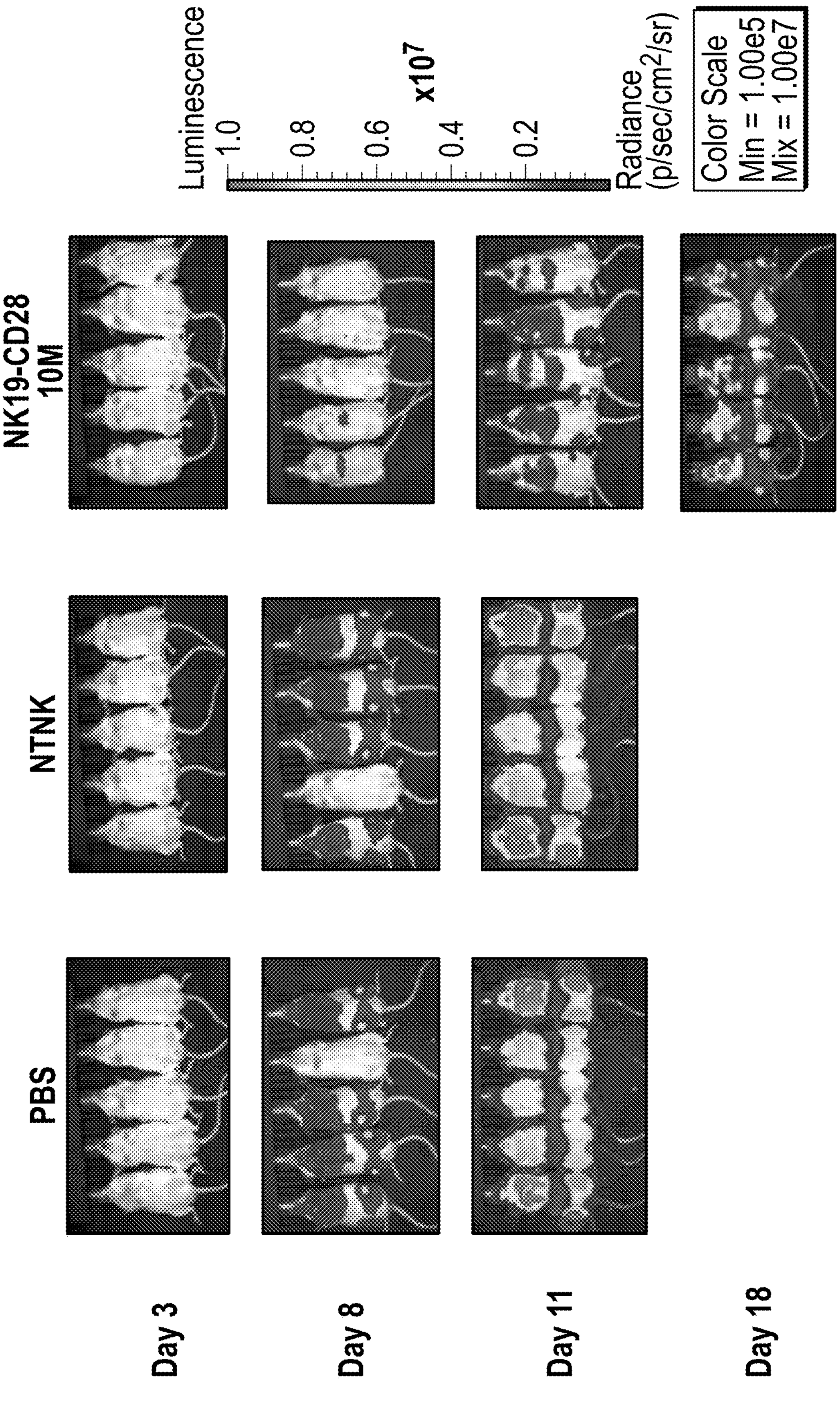
FIG. 13 depicts in vivo imaging data related to tumor burden over time in mice treated with PBS, non-transduced NK cells, or NK cells expressing the indicated CD19-directed chimeric receptors, with the indicated number of engineered NK cells administered (M=million cells).
Figure 13:
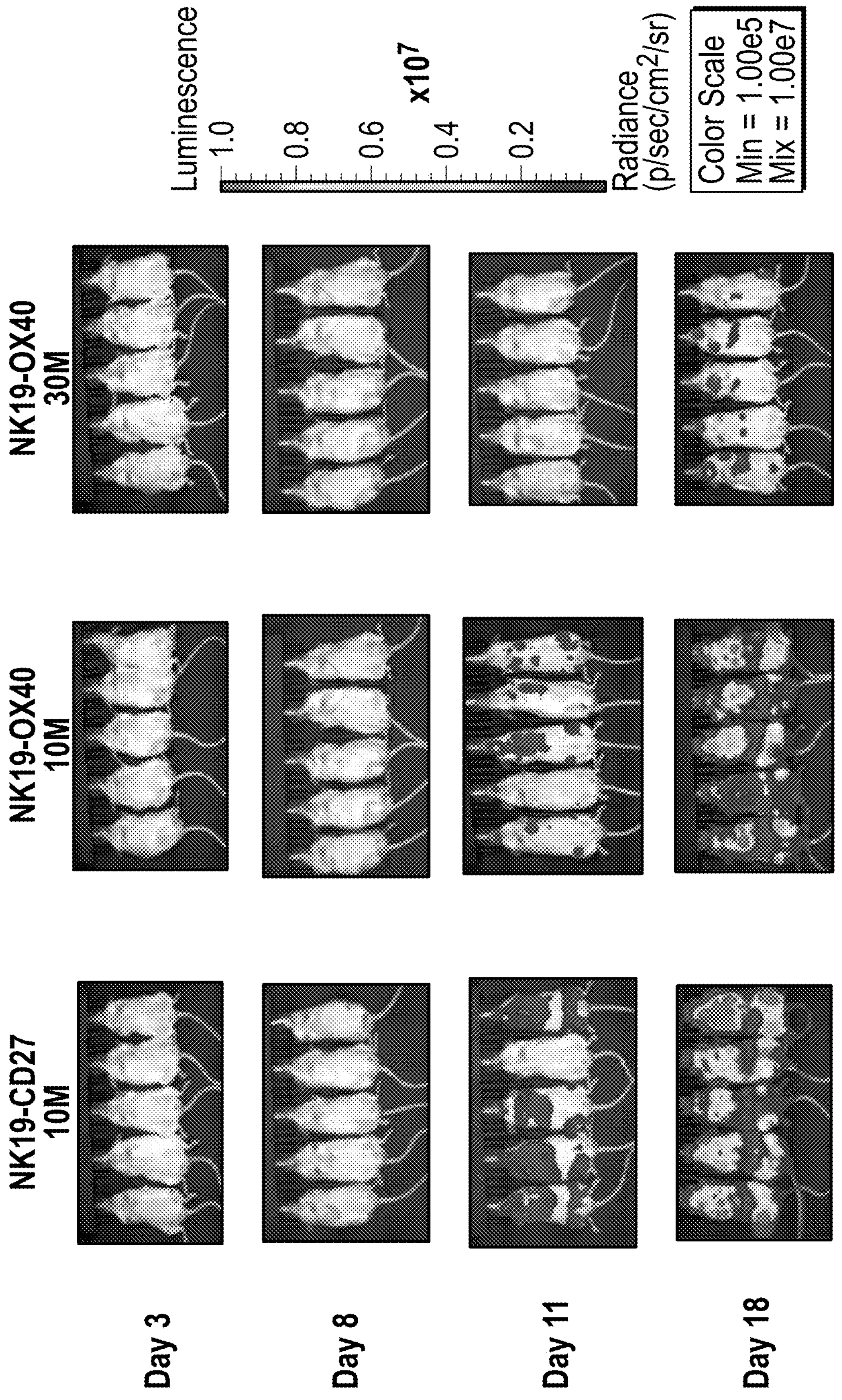

Further evidencing the enhanced effects of NK19 constructs on tumor progression, NSG mice were injected on Day 0 with $1\times10^5$ Nalm6 cells (expressing a fluorescent reporter) intravenously. At Day 3, mice received either a PBS control injection, non-transduced NK cells ("NTNK", 10M), NK19-2 expressing NK cells (10 million cells), NK19-9 expressing cells (10 million), NK19-1 expressing cells (10 million, or NK19-1 expressing cells (30 million). Fluorescent imaging to detect the Nalm6 cells was performed on Days 3, 8, 11, 18, and 25 (imaging data not shown). The data is shown in FIG. 13. As shown, the injection of NK cells expressing any NK19 variant resulted in a reduced progression of Nalm6 growth. NK19-2 expressing NK cells showed minor Nalm6 growth on Day 8, with more Nalm6 growth by Day 11, and substantial growth by Day 18 (though less than with NTNK cells). Neither NK19-9 or NK19-1 (at either dose) expressing NK cells showed detectable tumor burden on Day 8 by imaging. Mice receiving NK19-9 expressing NK cells did show some increase in Nalm6 cell growth by Day 11, with further progression by Day 18. At Day 11, mice receiving either dose of NK19-1 expressing cells did not exhibit Nalm6 cell growth. By day 18, mice receiving 10 million NK19-9 cells showed some tumor growth. However, with a 30 million cell dose, those mice receiving NK19-9 expressing NK cells showed only minor amounts of Nalm6 cell growth.

Figure 14A:
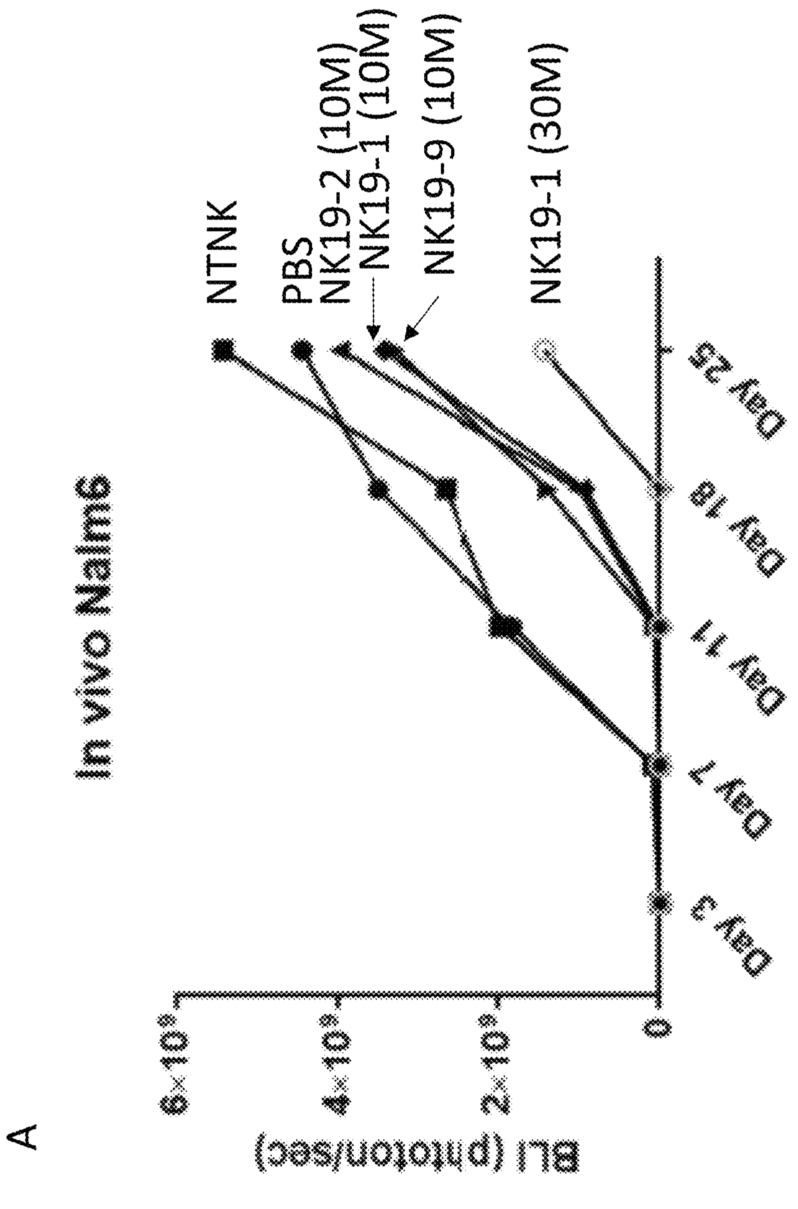
FIG. 14A shows raw data related to the detected fluorescent signal from the in vivo data shown in FIG. 13, with data being tracked for 25 days post-administration of Nalm6 cells.
Figure 14B:
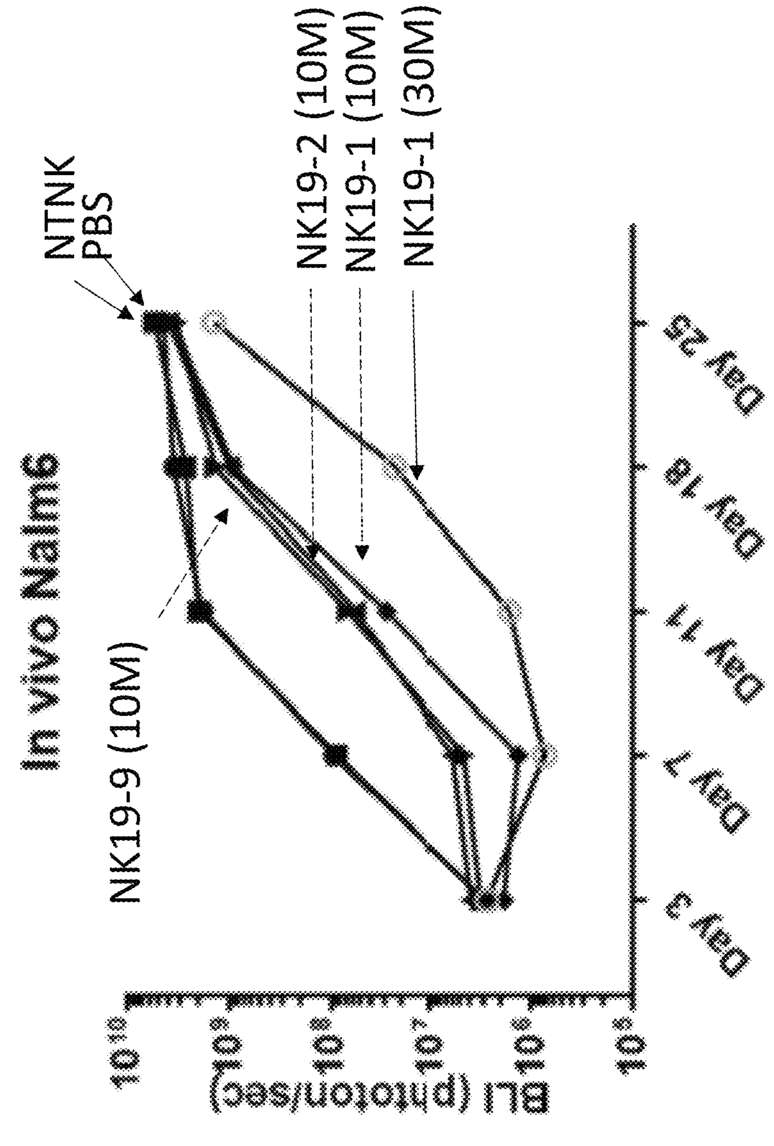
FIG. 14B shows the data from FIG. 14A on a logarithmic scale.
Figure 14C:
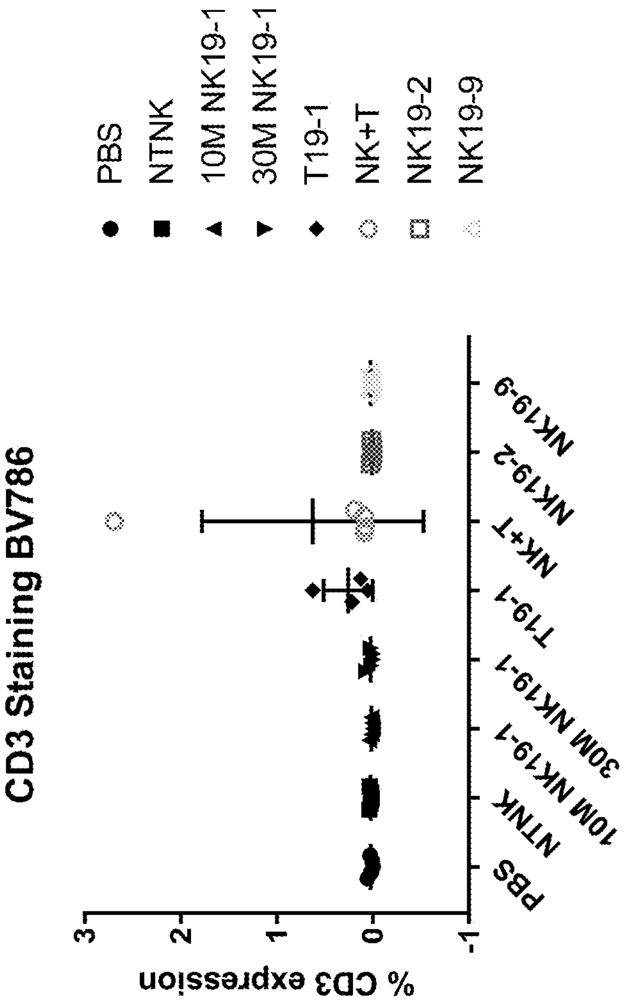
FIG. 14C shows data related to CD3 expression by the indicated cells expressing the indicated constructs.
Figure 14D:
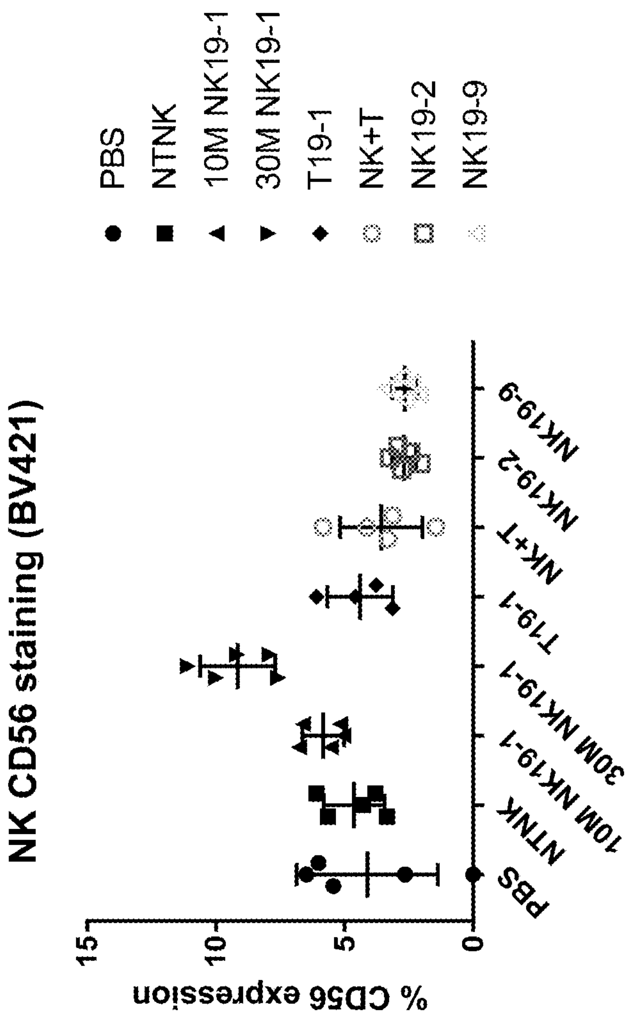
FIG. 14D shows data related to CD56 expression by the indicated cells expressing the indicated constructs.
Figure 14E:
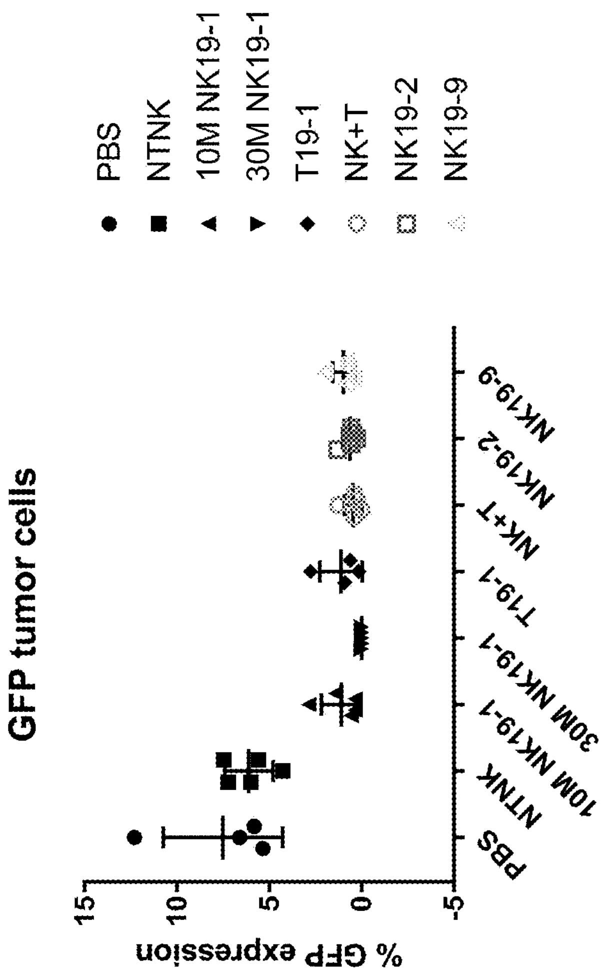
FIG. 14E shows data related to GFP-expressing tumor cells when contacted with the indicated cells expressing the indicated constructs.
Figure 14F:
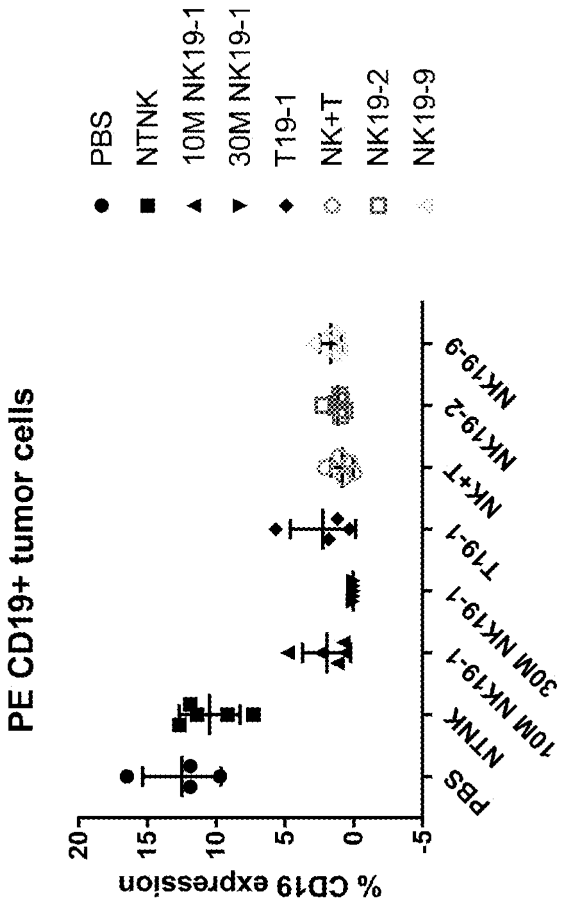
FIG. 14F shows the data related to CD19-expressing tumor cells when contacts with the indicated cells expressing the indicated constructs.

FIG. 14A depicts a line graph of the bioluminescence intensity shown detected in the mice (e.g., the fluorescent signal shown in FIG. 13, note that FIG. 13 does not show imaging data for Day 25). Consistent with the images of FIG. 13, the line graph of FIG. 14A shows increased Nalm6 cell count (as represented by increased BLI) for all groups at Day 25, with significant cell numbers detected in PBS and NTNK groups, and somewhat less for NK19-2, NK19-1 (10M) and NK19-9 groups. NK19-1 (30M) showed the smallest increase, representing that construct's ability to reduce the rate of Nalm6 progression due to cytotoxic effects on the Nalm6 cells. While each construct eventually allows some Nalm6 growth, even if modest, the tested NK19 constructs delayed the onset of that growth, as evidenced by the flat line through Day 11 for the NK19 curves. To better show that aspect, the data are replotted on a log scale Y-axis in FIG. 14B, which allows for curve separation. As displayed, the NTNK and PBS curves show an upward trend after Day 3, indicating nearly immediate Nalm6 growth. In contrast, the NK19-9, NK19-2 and both NK19-1 curves either drop, or only slightly trend upward through Day 7. At Day 11, consistent with the images in FIG. 13, Nalm6 cell growth is detected in the NK19-9, NK19-2 and NK19-1 (10M) groups. In contrast, the NK19-1 (30M) group is still approximately at baseline, reflecting the lack on any significant Nalm6 cell growth. Cell growth trends upward in the NK19-9 (30M group) on Day 18. While increases in tumor cell number occur, even with the NK19 constructs being administered, the delay of the growth onset could be advantageous in several embodiments. For example, this presents an opportunity to re-dose a patient with another dose of engineered NK cells expressing a CD19-directed construct. In several embodiments, a subsequent dose (as could the initial dose) may optionally comprise NK cells that have been edited to reduce allogenicty, for example by gene editing. Thus, in several embodiments, two, three, four or more doses of CD19-directed CAR expressing NK cells are administered. This delay in tumor cell growth presents an opportunity to dose, either serially (or concurrently) with an NK cell expressing a chimeric construct directed to a different tumor marker and/or some other variety of anti-cancer therapy (e.g., checkpoint inhibitor, antibody therapy, chemotherapy, etc.). FIG. 14C depicts data related to CD3 expression of cells transduced with the various constructs within blood samples taken from mice treated as indicated in the X axis. CD3 is a T cell marker. As indicated, but for T cells engineered to express the NK19-1 construct and a mixed population of NK cells and T cells, CD3 expression was essentially negligible. FIG. 14D depicts data related to CD56 expression, which is a marker for human NK cells. While there is some small amount of background staining, the blood samples from mice treated with NK cells expressing the indicated constructs is relatively low (as would be expected given that (i) the blood is a murine blood sample and murine cells would make the majority of the total, and (ii) CD56 is detecting only human NK cells (e.g., those administered). The data are consisting in that regard, with the 30M NK19-1 treatment group shoring markedly more CD56 expression than the other groups, and T cells/NK+ T cells groups expressing CD56 at background levels. FIG. 14E shows data related to the GFP expression by tumor cells. The blood samples were collected at ~3 weeks into the in vivo experiment. As shown (consistent with the images/BLI data), the control PBS and NTNK groups exhibit higher percentages of GFP expression (e.g., a greater percentage of the total of live blood cells in the sample is tumor cells). Each of the engineered constructs shows significantly less GFP expression, based on the engineered constructs controlling/reducing tumor cell growth. FIG. 14F shows similar data to FIG. 14D, but measures CD19 expression across all the live cells in a given murine blood sample. As with GFP, the PBS and NKNT groups show CD19 expression at approximately 10-12%, meaning 10-12% of the live cells in the blood sample are tumor cells, the remainder being murine blood cells. As shown in the other experimental group, CD19 expression is much lower, reflective of the engineered CAR constructs limiting the growth of the tumor cells. These data are in accordance with embodiments disclosed herein, wherein engineered NK cells expressing CD19-directed CARs are highly cytotoxic and allow for the treatment of cancerous tumors.

Further Evaluation of Humanized Constructs

As discussed in detail above, in several embodiments, several embodiments of the CARs disclosed herein involve the use of humanized sequences, such as in the extracellular binding moiety. In several embodiments, one or more aspects of that region is subjected to a humanization campaign. In several embodiments, one or more of the heavy and/or light chain of an antibody is humanized, which (as discussed above) can provide advantages including, but not limited to, reduced immunogenicity, increased stability, longer efficacy, increased potency, and the like.

Example 3

FIG. 15 shows a schematic of a series of humanized constructs according to several embodiments disclosed herein. Such constructs are designated by "H" in their identifier. By way of explanation, NK19H-1 is a humanized anti-CD19 CAR employing an scFv made up of a first light chain and a first heavy chain CU H1'), while NK19H-3 employs an scFv made up of a third light chain and the first heavy chain ('L3H1'). FIG. 15 also shows data related to the stability and aggregation of the various combinations of heavy and light chains following transient expression and secretion from 293T cells. Data are shown related to the mean fluorescence intensity detected by flow cytometry when each antibody was heated to 70° C. and then cooled back to room temperature ('Heating') vs. the same variant held on ice ('Unheating'). After heat treatment, the ScFv variants are used in a flow cytometry protocol at various concentrations (0.4, 0.25, and 0.125 ug/mL). Loss of fluorescence intensity indicates that the ScFv either lost structural integrity or aggregated through the heating process. ScFv's with the best thermal stability as indicated by comparable MFI under both conditions are favored for further development, according to some embodiments.

Figure 16:
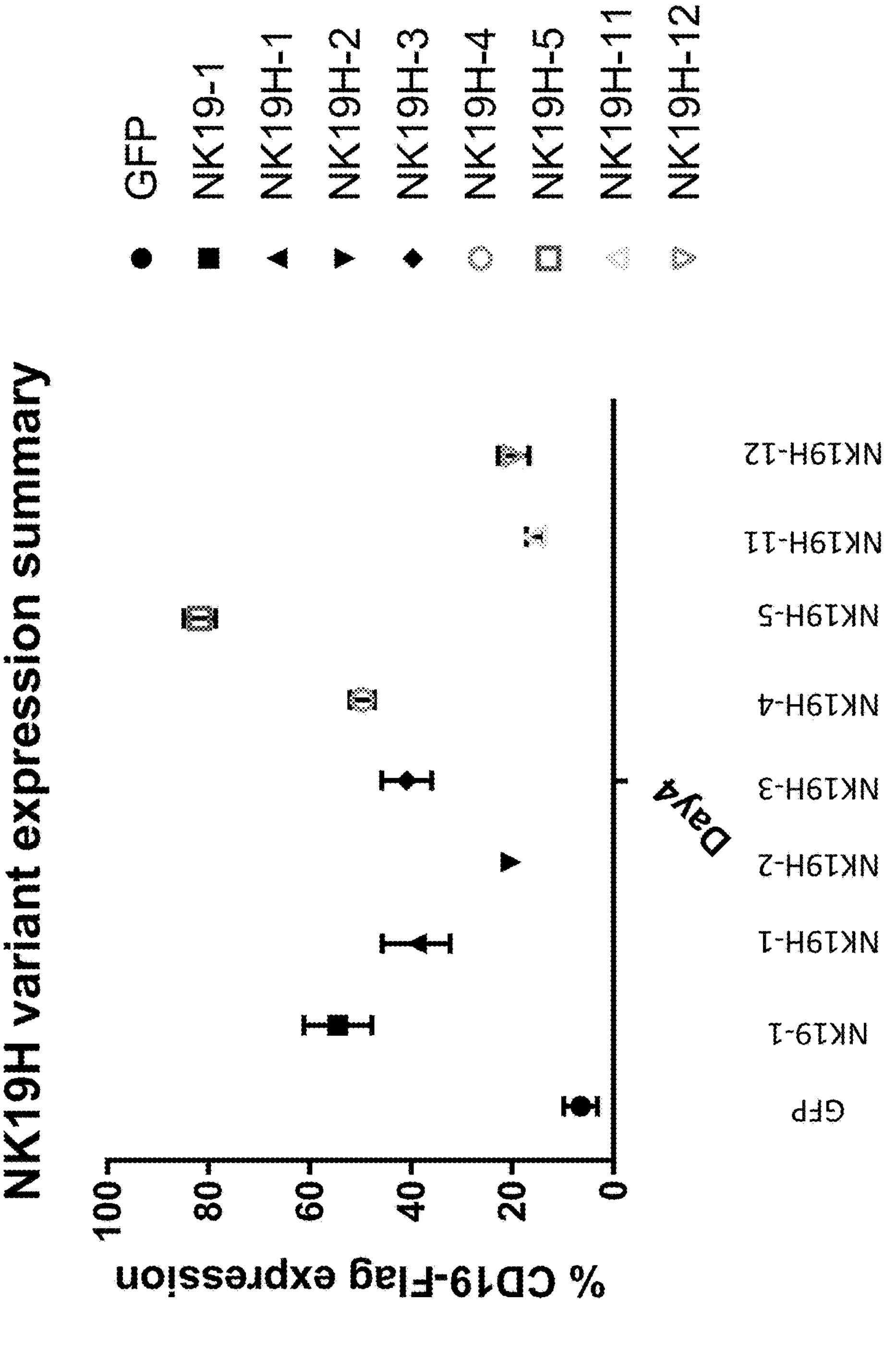
FIG. 16 depicts data related to the expression of various humanized anti-CD19 CAR constructs disclosed in embodiments herein.

After having assessed the stability of the constructs, selected anti-CD19 CAR constructs were further evaluated. FIG. 16 shows summary data of expression of the indicated constructs by the NK cells of 3 donors (#140, #9, and #20). As depicted in the Figure, expression is evaluated by detection of CD19Flag. Data are presented as percentage of NK cells expressing CD19-Flag relative to the total number of NK cells presented. The data were collected at 4 days after transduction with the relevant virus encoding the NK19H-"X" CAR. As evidenced by the expression data, each of the selected constructs were expressed by NK cells, to varying degrees. Expression levels ranged from expression by about 20% of the total NK cells with NK19H-2, NK19H-11 and NK19H-12. Most of the other constructs were successfully expression by ~40%-60% of the NK cells, which is on par with expression of the non-humanized NK19-1 construct. The NK19H-5 construct was expressed by over 80% of the NK cells. While certain constructs may be more efficiently expressed, those with lower expression levels were still evaluated because, as with several embodiments such constructs still exhibit significant cytotoxicity against target cells. According to several embodiments, however, those with higher expression efficiency can be advantageous, for example because a greater portion of a given NK cell preparation is useful clinically (e.g., fewer input NK cells needed to generate a clinically relevant engineered NK cell dose).

Figure 17A:
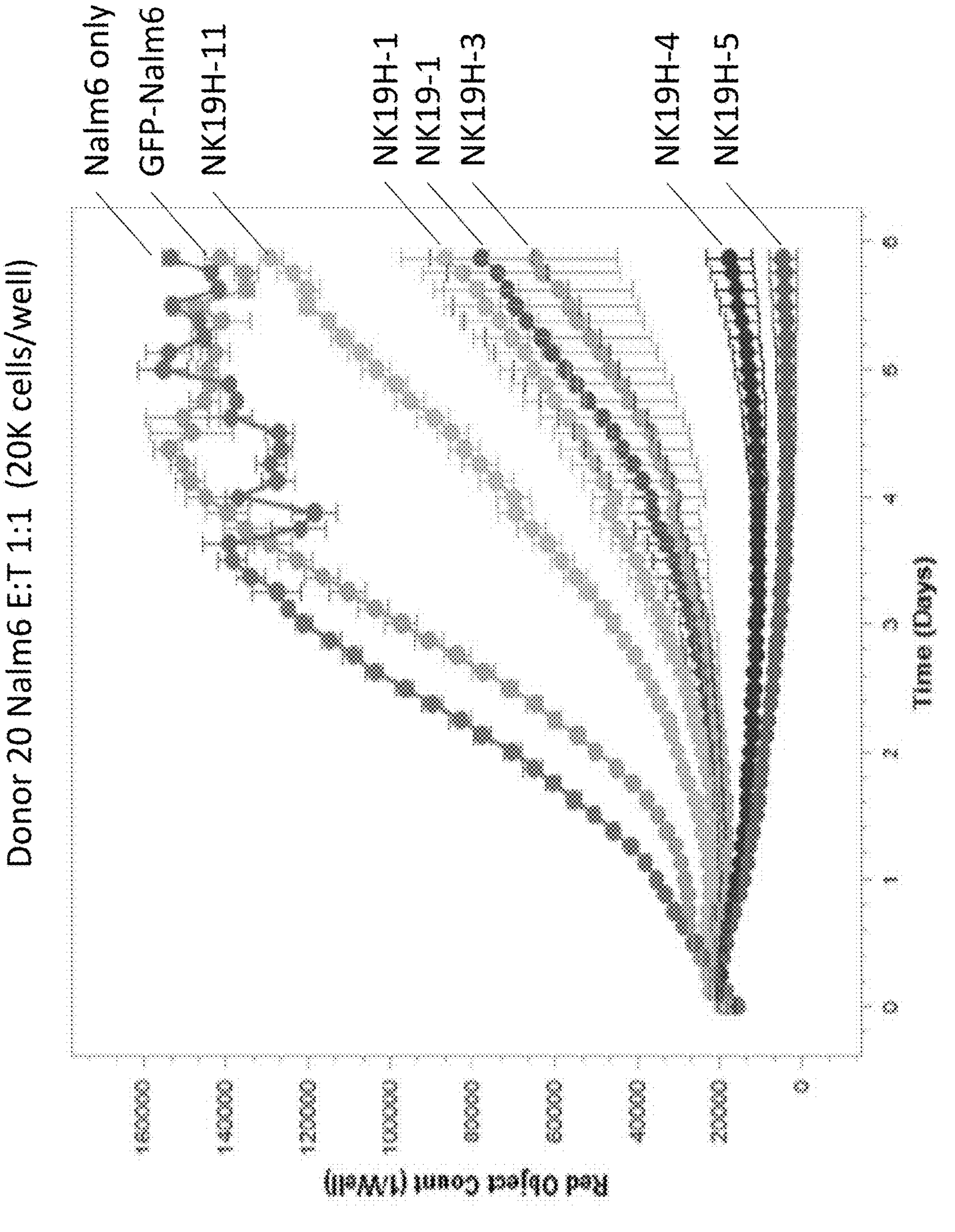
FIGS. 17A-17E show cytotoxicity data. 17A shows data related to the cytotoxicity of NK cells from a first donor engineered to express selected humanized CD19 CAR constructs disclosed herein against Nalm6 cells. 17A shows data related to the cytotoxicity of NK cells from a first donor engineered to express selected humanized CD19 CAR constructs disclosed herein against Raji cells. 17C shows data related to the cytotoxicity of NK cells from a second donor engineered to express selected humanized CD19 CAR constructs disclosed herein against Nalm6 cells. 17D shows data related to the cytotoxicity of NK cells from a third donor engineered to express selected humanized CD19 CAR constructs disclosed herein against Raji cells. 17E shows data related to the cytotoxicity of NK cells from a third donor engineered to express selected humanized CD19 CAR constructs disclosed herein against Nalm6 cells.

FIGS. 17A-17E depict such cytotoxicity data. FIG. 17A shows cytotoxicity of NK cells from Donor 20 and transduced with the indicated constructs against the CD19-positive Nalm6 leukemia cell line (at an E:T of 1:1; 20K cells per well). The data shows that, despite the varied expression levels, most of the NK19H constructs were able to exert cytotoxic effects against the Nalm6 target cells. NK19H-11 showed the least efficacy, allowing Nalm6 cell growth at levels just below the controls. In contrast, NK19H-1 and NK19H-3 showed cytotoxicity on par with the non-humanized NK19-1 construct, allowing for some cell growth at the later time points of co-culture. Notably NK19H-4 and NK19H-5 showed significant cytotoxicity, allowing only very limited Nalm6 growth throughout the experiment.

Figure 17B:
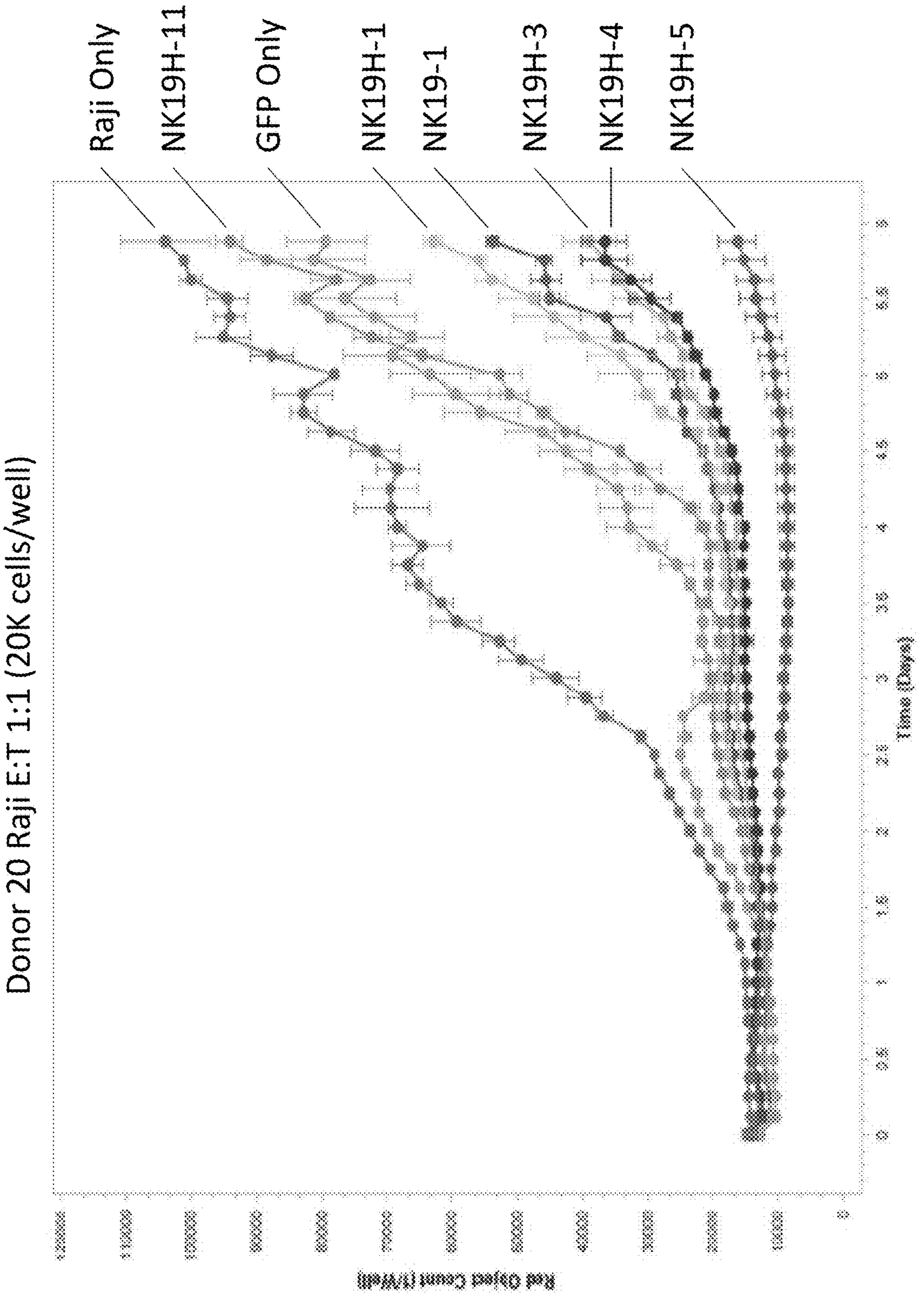
Figure 17C:
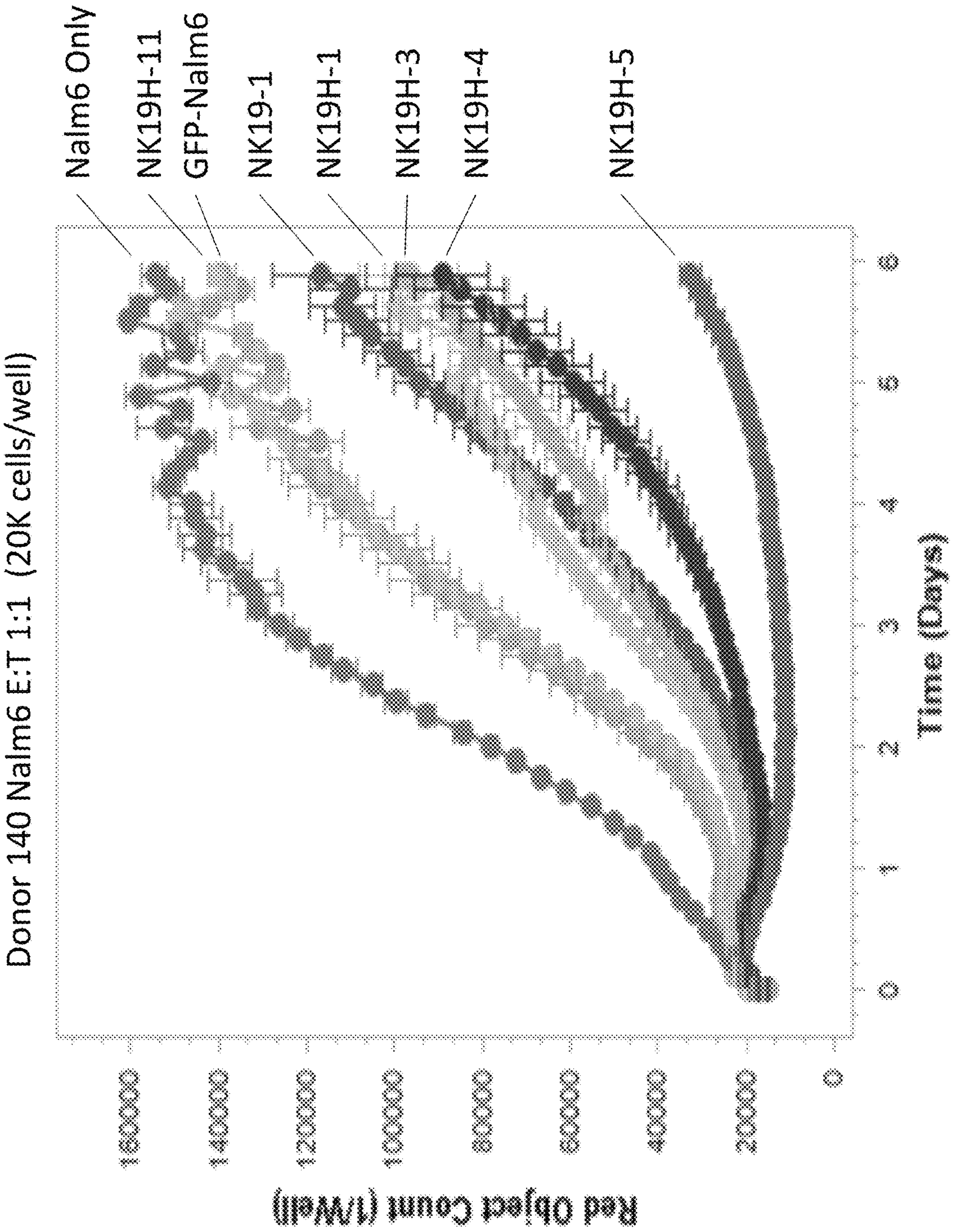
Figure 17D:
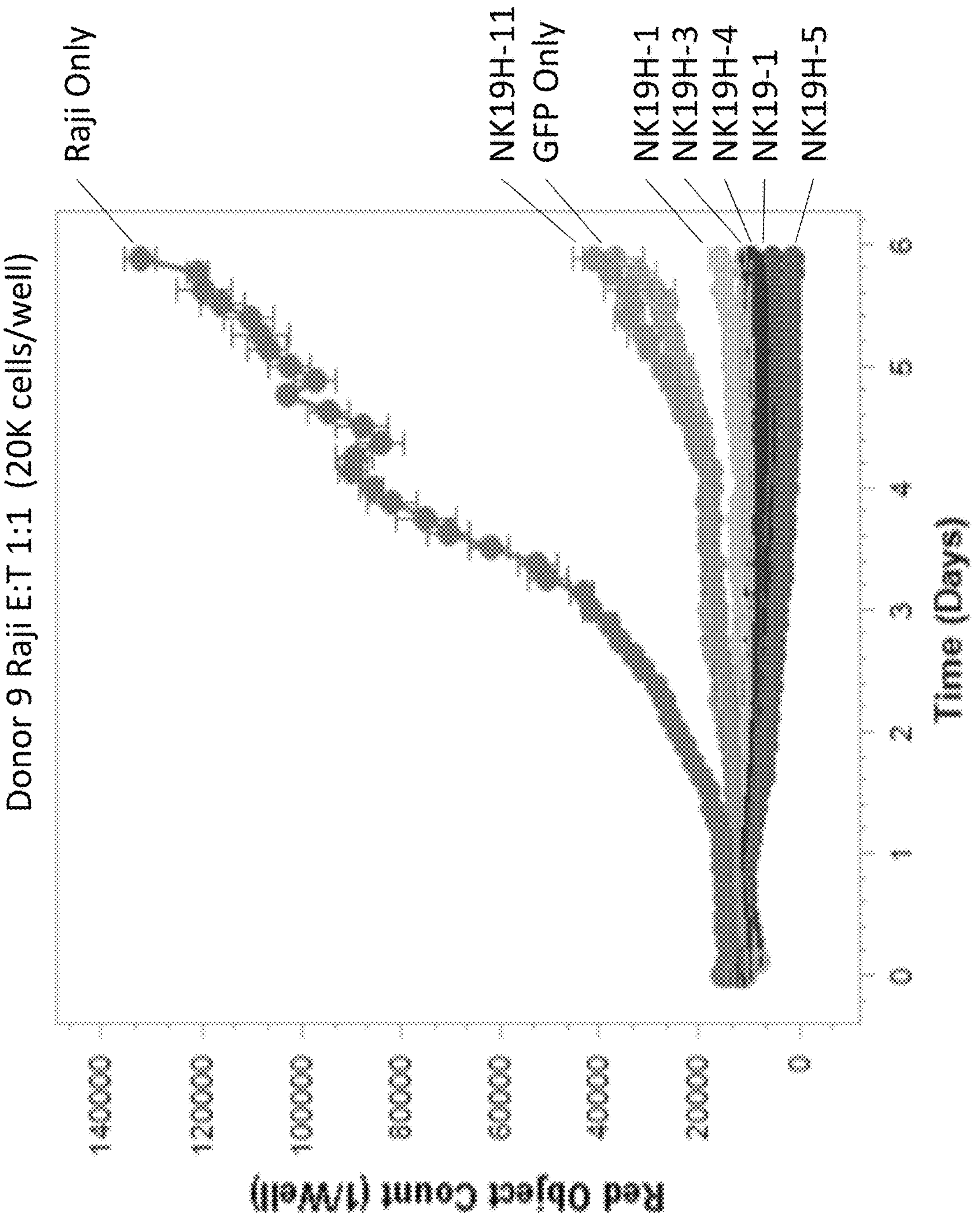
Figure 17E:
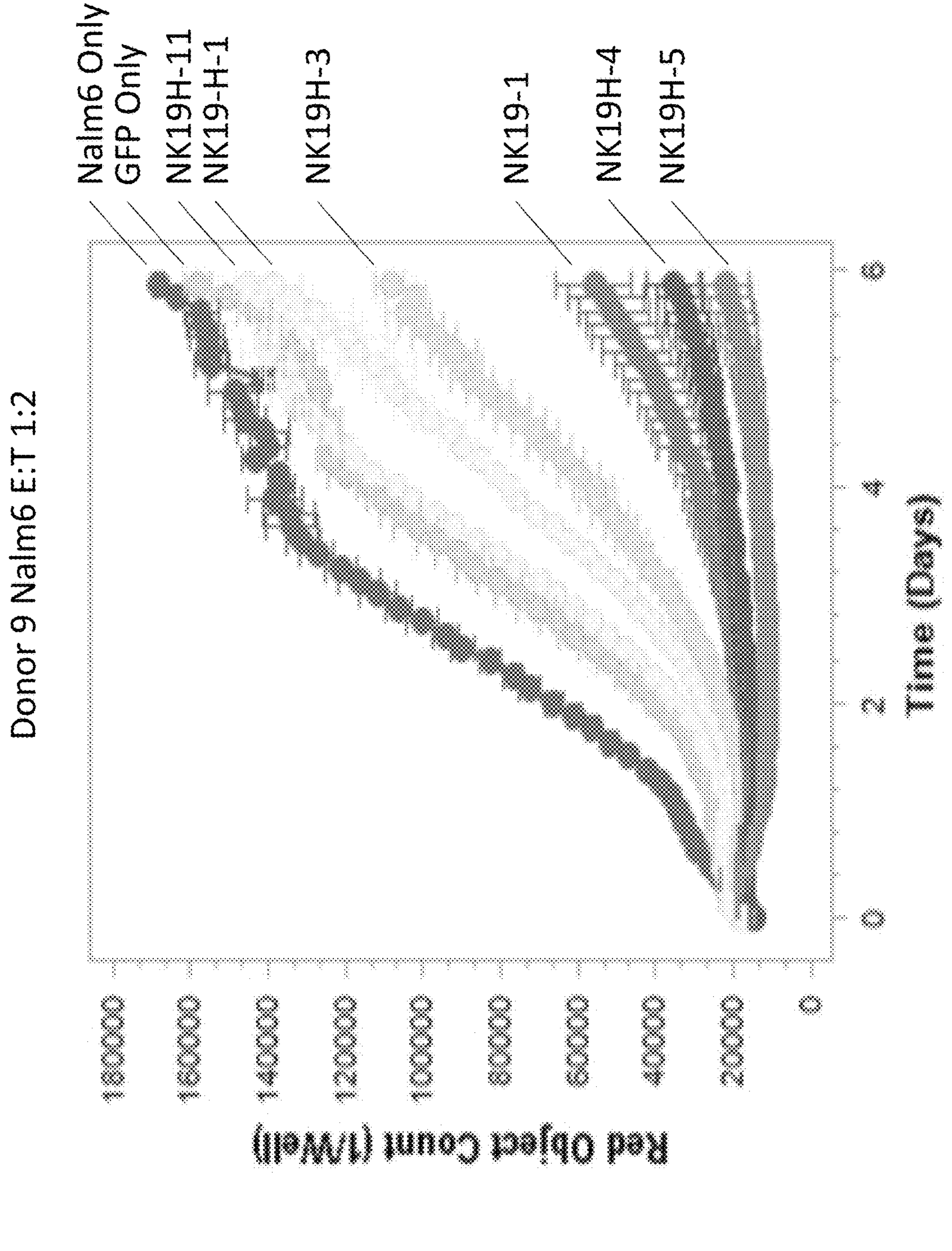

FIG. 17B shows NK cells from Donor 20 tested against the CD19-positive Burkitt's lymphoma cell line Raji. As with Nalm6 cells, the various humanized anti-CD19 constructs showed variable cytotoxicity against the target cells. Similar to the data of FIG. 17A, the NK19H-11 construct showed limited cytotoxicity, but all other constructs showed promising cytotoxicity against the target cells, with NK19H-1 performing on par with the non-humanized NK19-1 construct, and each of NK19H-3, 19H-4, and 19H-5 constructs inducing greater levels of cytotoxicity, limiting Raji growth until the later stages of the co-culture (with NK19H-5 allowing only very limited Raji cell growth). FIG. 17C shows corresponding Nalm6 data from Donor 140. Here, a similar pattern of efficacy was detected, with NK19H-11 allowing Nalm6 growth approximating negative controls. However, each of NK19H-1, 19H-3 and 19H-4 induced at least as much cytotoxicity as non-humanized NK19-1. Again, NK19H-5 showed significant cytotoxicity, limiting Nalm6 growth throughout the experiment. FIG. 17D shows data from Donor 9 against Raji cells. Only NK19H-11 allowed any substantial Raji cell growth. In contrast, NK cells from this donor expressed the non-humanized NK19-1 or any of the humanized NK19H-1, 19H-3, 19H-4, or 19H-5 constructs suppressed any Raji cell growth through the induced cytotoxic effects. FIG. 17E shows data for NK cells from Donor 9 against Nalm6 cells. In this experiment, the cytotoxicity of three of the humanized constructs (NK19H-11, 19H-1, and 19H-3) was limited. There is some donor to donor variability, as certain of these constructs induced cytotoxicity when expressed by NK cells of other donors. The NK19H-4 and 19H-5 constructs exhibited significant cytotoxic effects, nearly limiting Nalm6 growth to zero over the course of the experiment. Taken together, these data complement the expression data and show that, in accordance with several embodiments, humanized CAR constructs targeting CD19 are effective at killing tumor cells, even if they have variable expression efficiencies. Additionally, according to some embodiments, the expression efficiency is not correlated with cytotoxicity and even constructs with limited expression efficiency can demonstrate significant cytotoxicity.

Example 4

Figure 18:
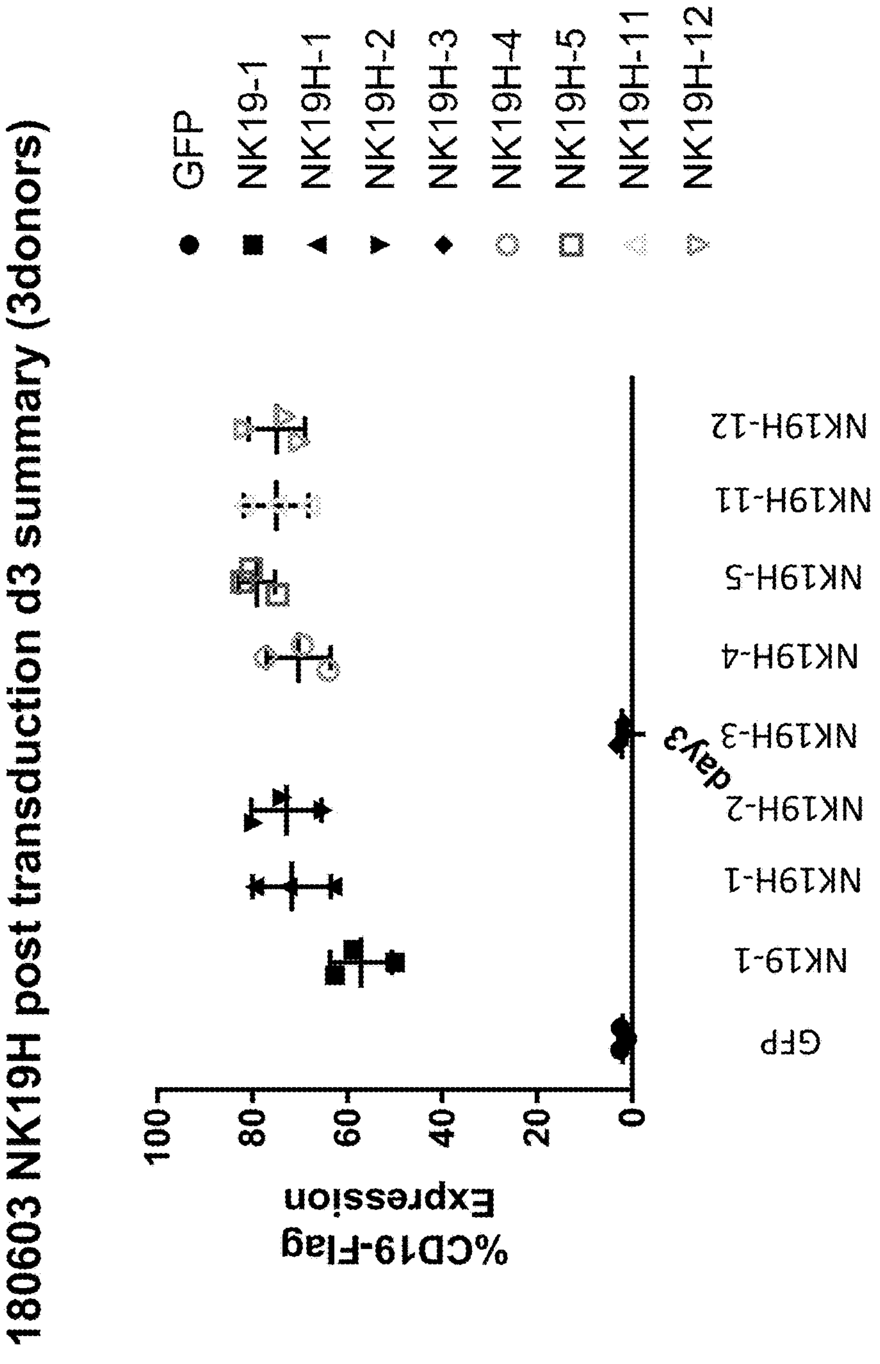
FIG. 18 shows summary (from 3 donors) expression data for NK cells expressing the indicated non-limiting anti-CD19 CAR constructs at 3 days post-transduction.
Figure 19A:
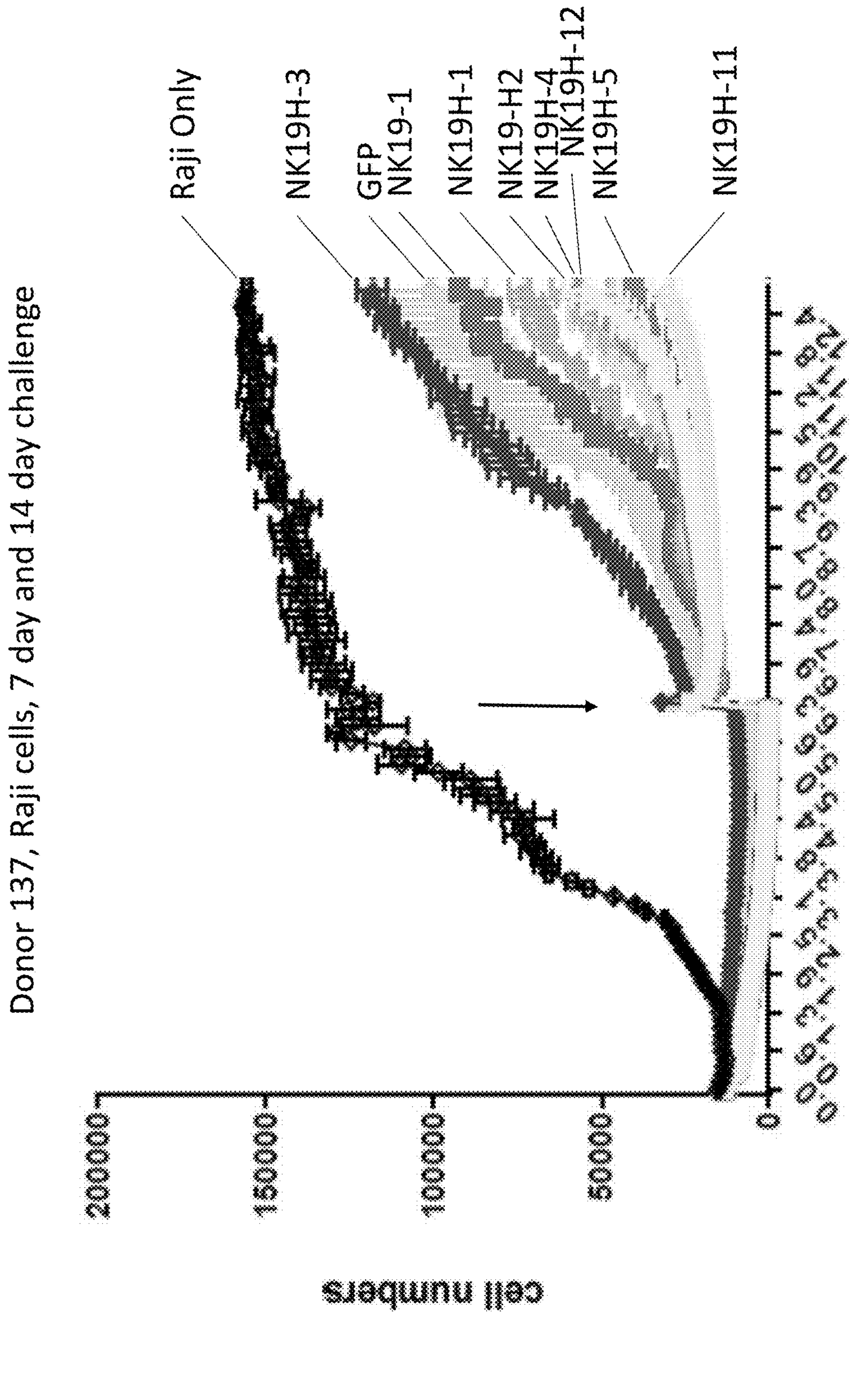
FIGS. 19A-19D show cytotoxicity rechallenge data.
Figure 19B:
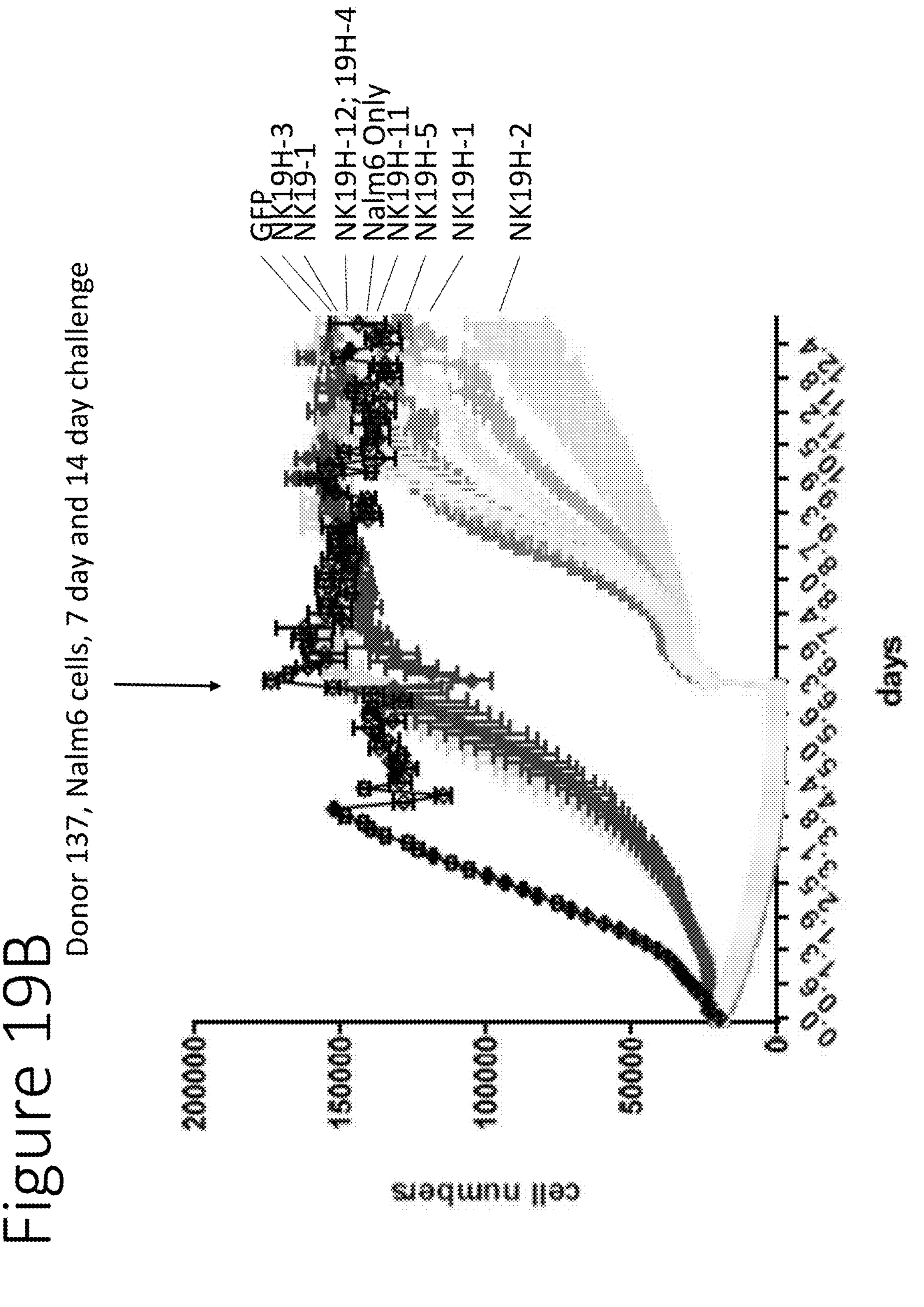
Figure 19C:
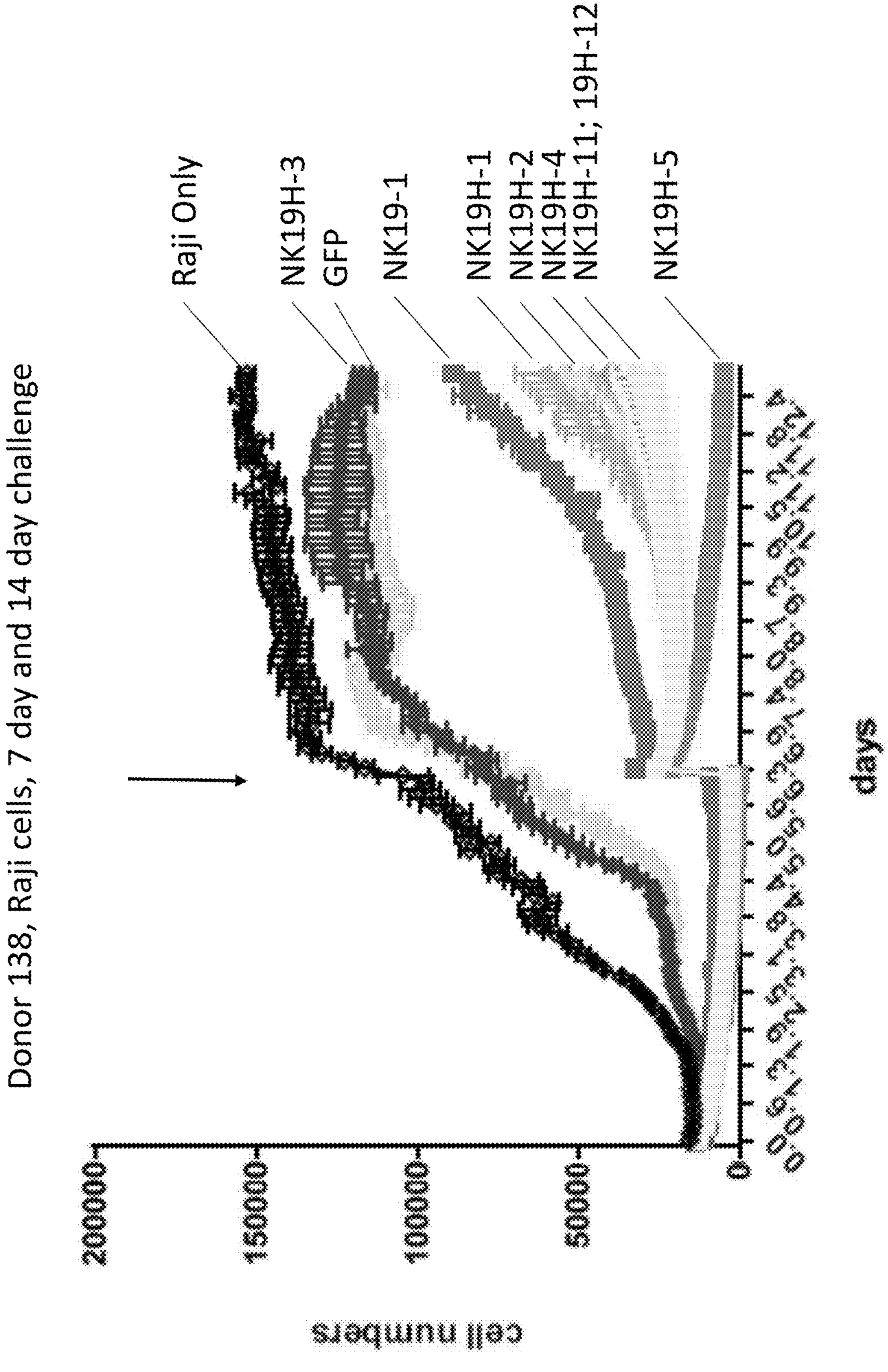
Figure 19D:
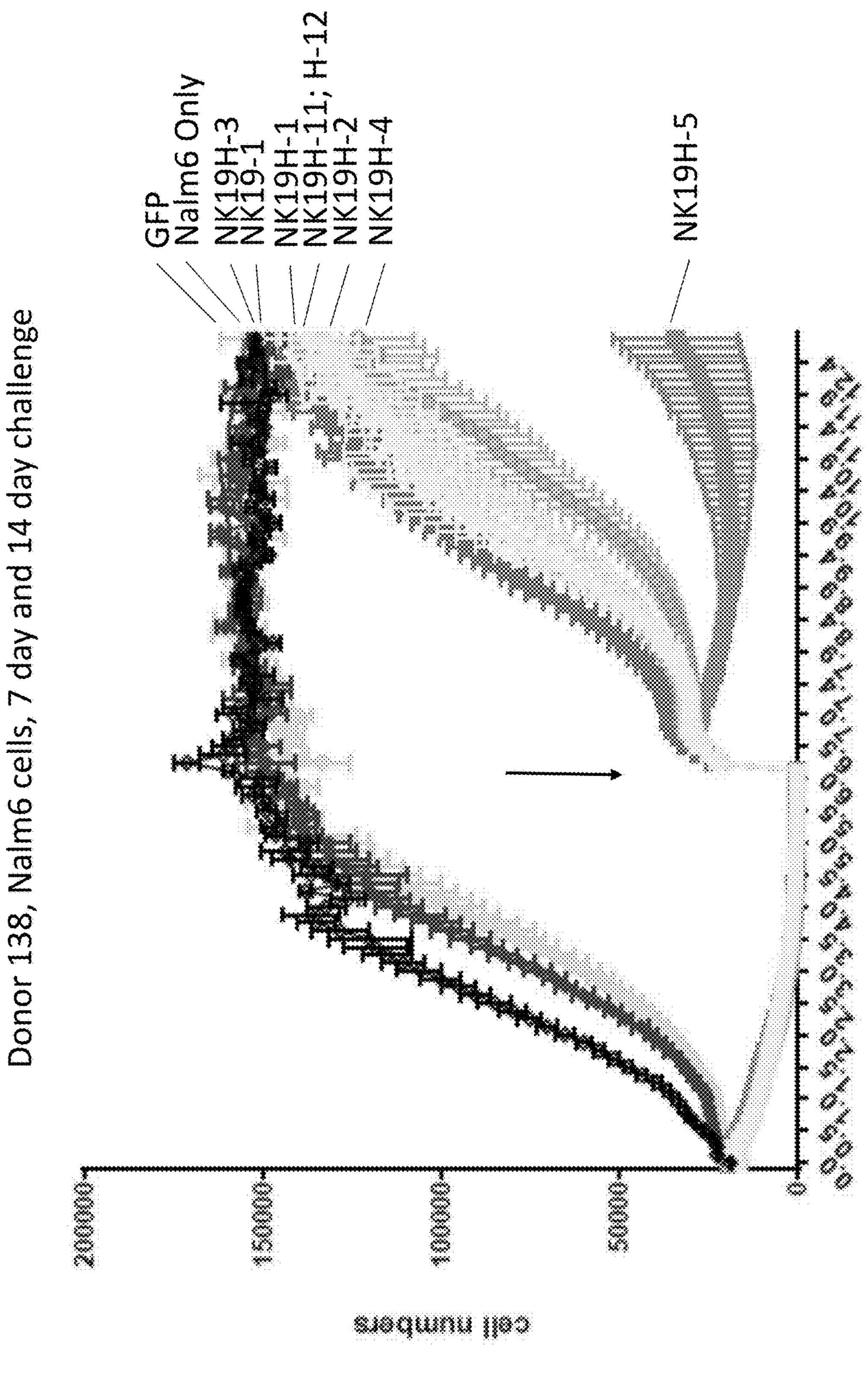

Further experiments paralleling those discussed above were performed using NK cells from additional donors. FIG. 18 shows construct expression efficiency for three donors (#945, 137 and 138) for the indicated constructs. As with the prior experiment the data presented represent the number of CD19-Flag positive cells out of the total number of NK cells evaluated. The data for these donors shows a higher overall efficiency of expression for all but one of the humanized constructs. Only NK19H-3 was expressed less than the non-humanized NK19-1 construct. With these donor NK cells, expression of the humanized constructs was detected on about 70% to 80% of the NK cells. As above, further to evaluation of expression, cytotoxicity against CD19 expression target cells was evaluated. FIG. 19A shows data related to NK cells from a donor (#137) expressing the indicated constructs and co-cultured with Raji cells. In this experiment, the engineered NK cells expressing the indicated constructs were exposed to the tumor cells at two time points, 7-days and an additional bolus of tumor cells was added at 14-days post-transduction. The arrow shows the second administration of tumor cells. As shown, untreated Raji cells expanded throughout the experiment. NK cells expressing GFP or non-humanized NK19-1 induced some cytotoxicity as shown by the reduced Raji cell growth as compared to control. NK cells expressing NKH19-3 (the humanized construct with the lowest expression efficiency) were also able to reduce Raji growth. Each of the other humanized NK constructs were able to reduce Raji cell growth compared to controls, even at 14 days post-transduction, which is indicative of the enhanced persistence of engineered NK cells disclosed herein. FIG. 19B shows corresponding data for Donor 137 NK cells against Nalm6 cells with engineered NK cells again being added at day 7 (day 0 of experiment) and day 14 post-transduction (~day 7 of experiment). Cytotoxicity of the indicated constructs was more variable in this particular experiment. However, several humanized anti-CD19 constructs were able to produce marked cytotoxicity and reduce Nalm6 cell growth as compared to controls. These data suggest that, according to several embodiments, a more frequent dosing schedule (e.g., every 2 days, every 3 days, every 4 days, every 5 days, etc.) would be beneficial for certain subjects. Advantageously, in several embodiments, engineered NK cells as disclosed herein are allogeneic and can be readily used in more frequent dosing regimens. FIG. 19C shows corresponding data for Donor 138 against Raji cells. Here, many of the humanized constructs still had significant cytotoxic effects on the Raji cells, even with the second dose of Raji cells at 14 days post-transduction. Six of the 7 humanized constructs showed this behavior, and outperformed the non-humanized NK19-1 construct. FIG. 19D shows the corresponding data for Donor 138 against Nalm6 cells. While the additional bolus of Nalm6 led to increased Nalm6 growth in the latter stages the experiment, nearly all of the humanized constructs performed better than controls. In fact, NK19H-5-bearing NK cells were able to limit Nalm6 growth until the final few days of the experiment (after the second dose). As above, these data show that humanized anti-CD19 CAR constructs can not only be expressed by NK cells, but can also exert cytotoxic activity against target cells, with an enhanced persistence. In several embodiments, this allows multiple dosing to be separated by longer periods of time, which could be advantageous for treating cancers, while limiting potential immunogenicity (at least in part due to the humanization and/or because of the reduced frequency of administration).

Example 5

Figures 20A, 20B:
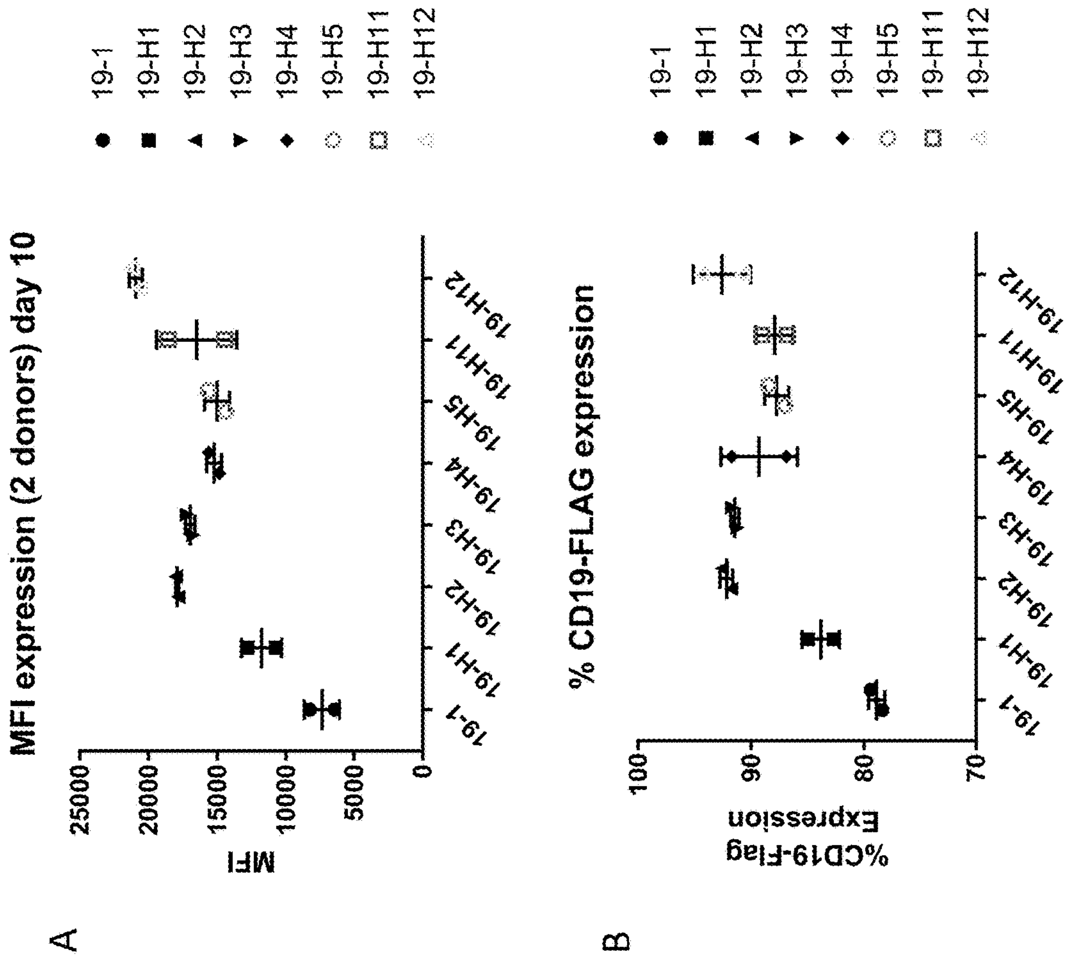
FIGS. 20A-20B show expression data.
Figure 21A:
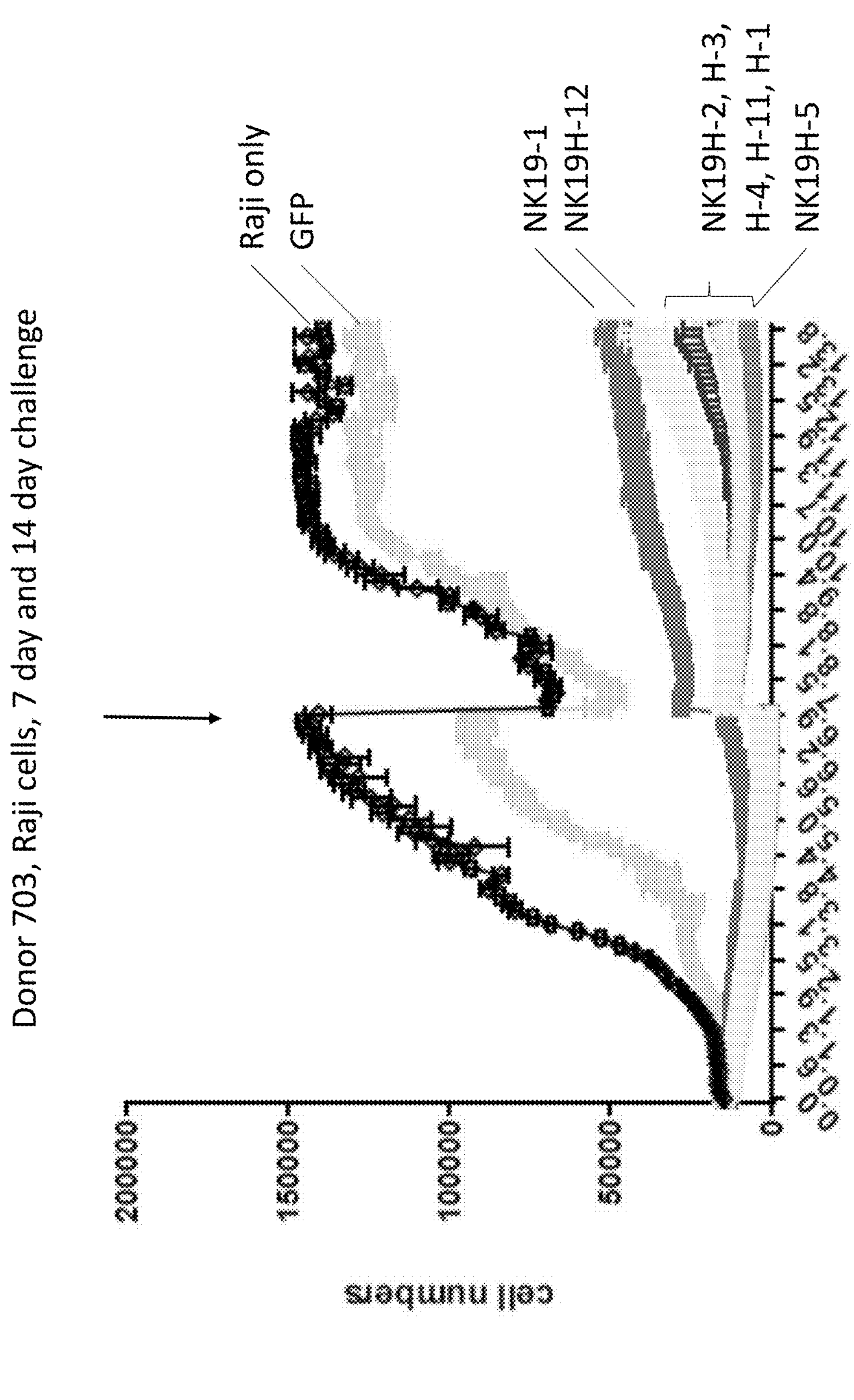
FIGS. 21A-21B show cytotoxicity data.
Figure 21B:
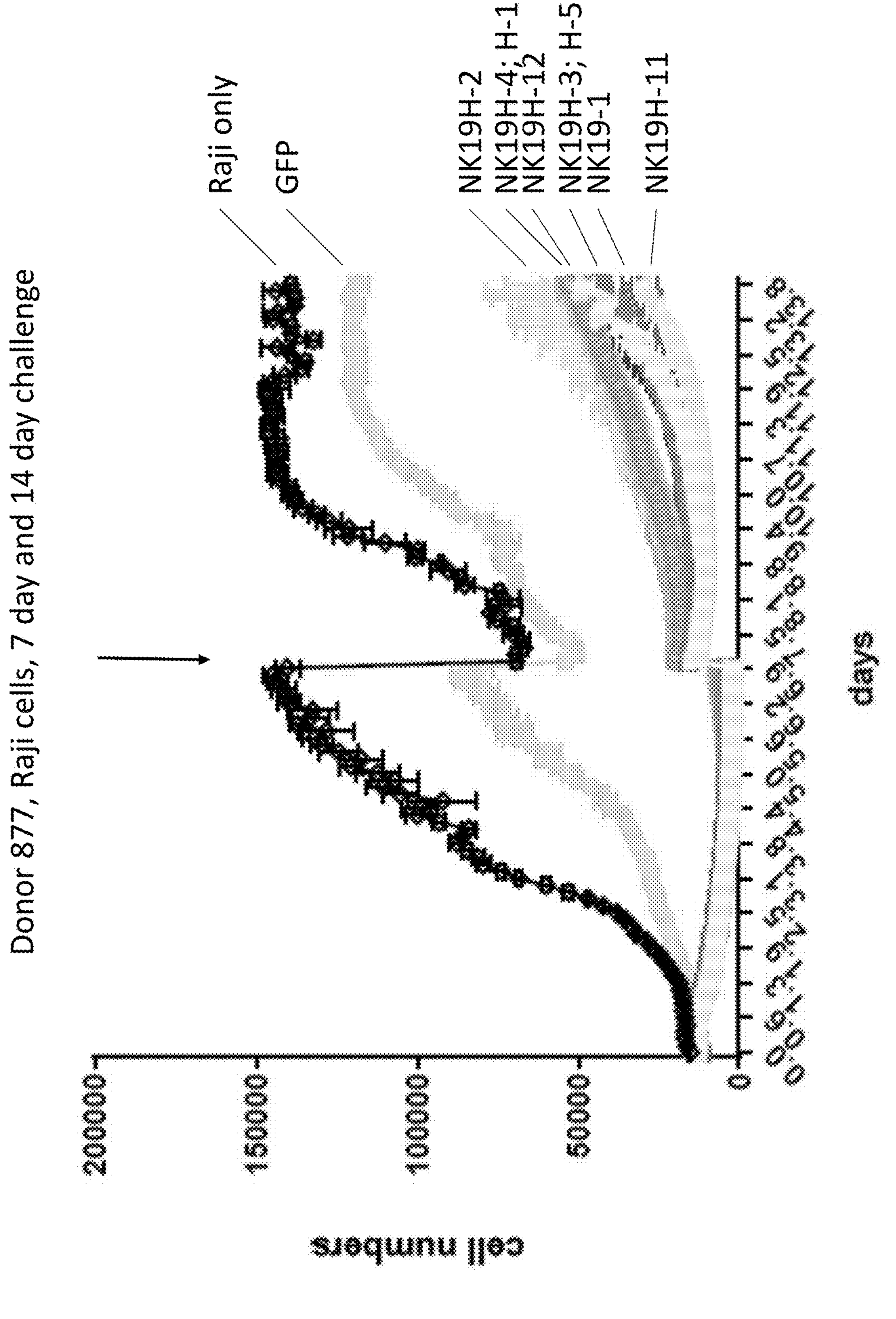

Further data for various humanized constructs in additional donors was collected. FIGS. 20A-20B show expression data for various anti-CD19 CAR constructs in NK cells from two additional donors. FIG. 20A shows the mean fluorescence intensity for NK cells at 10 days post-transduction. As indicated, as in accordance with several embodiments disclosed herein, each of the humanized anti-CD19 CAR constructs showed enhanced overall expression as compared to a non-humanized anti-CD19 CAR. FIG. 20B shows the expression data of CD19-Flag positive NK cells as a percentage of the total number of NK cells analyzed. As shown, each of the humanized anti-CD19 constructs were more efficiently expressed than the non-humanized construct (which was already expressed by almost 80% of the NK cells). The humanized CARs were expressed by approximately 85% to 95% of the NK cells, depending on the construct. FIG. 21A shows cytotoxicity data for engineered NK cells from Donor 703 (one of the two donors from FIG. 20) against Raji cells co-cultured with the NK cells at day 7 post-transduction and again at day 14 post-transduction. As shown in the Figure, Raji cells and NK cells expressing GFP alone grew robustly through day 7 and again through day 14. The non-humanized anti-CD19 CAR NK19-1 was able to suppress Raji cell growth through 7 days, and allowed relatively limited growth through 14 days. Each of the humanized anti-CD19 CAR constructs further suppressed Raji cell growth with several of the constructs nearly completely suppressing Raji cell growth. FIG. 21B shows corresponding data for cytotoxicity against Raji cells for NK cells isolated from Donor 877. These data show a similar trend to that from the prior donor. The two control groups allowed significant Raji cell growth, while each of the humanized anti-CD19 CAR constructs yielded significant cytotoxic effects.

Figures 22A, 22B:
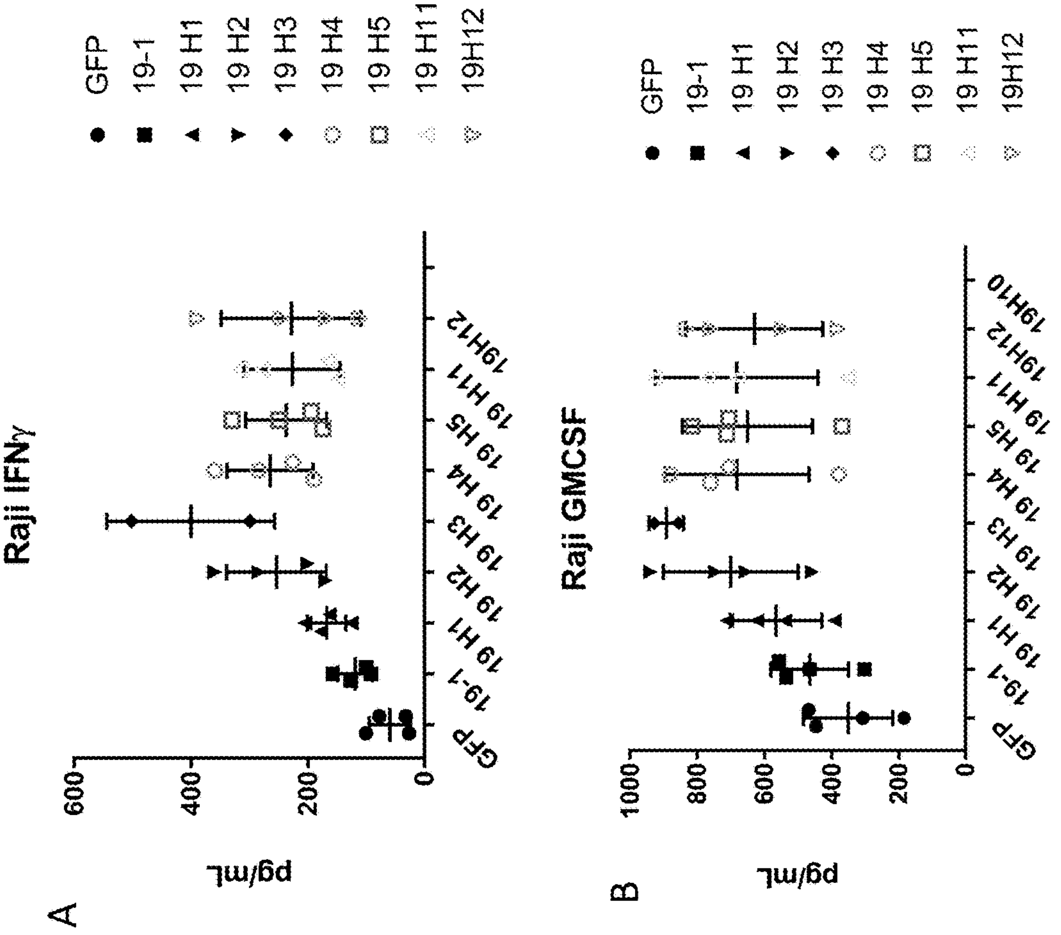
FIGS. 22A-22E show data related to cytokine release by NK cells expressing various CD19-directed chimeric receptors when co-cultured with Raji cells.
Figures 22C, 22D:
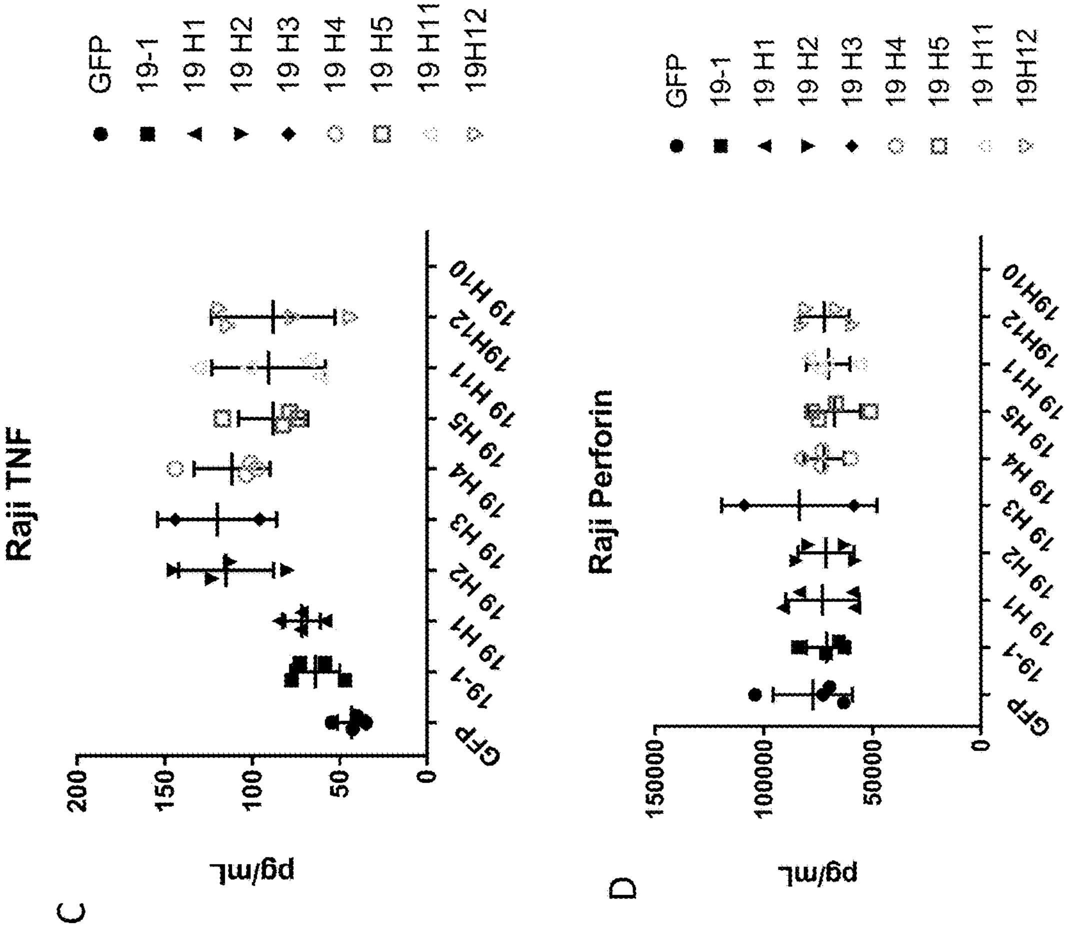
Figure 22E:
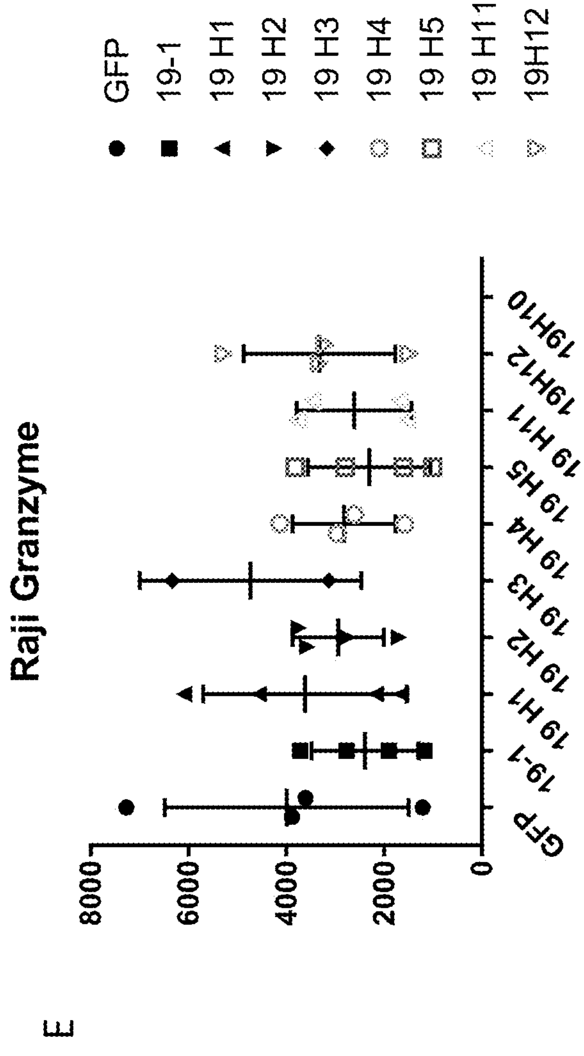

FIGS. 22A-22E show cytokine release profiles from Raji cells co-cultured with NK cells expressing the indicated constructs. FIG. 22A shows IFNg release by NK cells co-cultured with Raji cells. Each of the indicated humanized constructs resulted in increased IFNg release as compared to the non-humanized NK19-1 construct. Similarly, as shown in FIG. 22B, the humanized anti-CD19 constructs enabled the NK cells to release greater amounts of GM-CSF as compared to control NK cells. FIG. 22C show that humanized anti-CD19 CAR constructs induce elevated TNF release from the NK cells. Perforin levels were not significantly different across the constructs tested, as shown in FIG. 22D. Likewise Granzyme levels were relatively constant across the constructs. These data, taken together, indicate that according some embodiments, humanized anti-CD19 CAR constructs expressed on NK cells cause those NK cells to release greater amounts of one or more cytokines that lead to cytotoxic effects on target cells.

Example 6

Figure 23A:
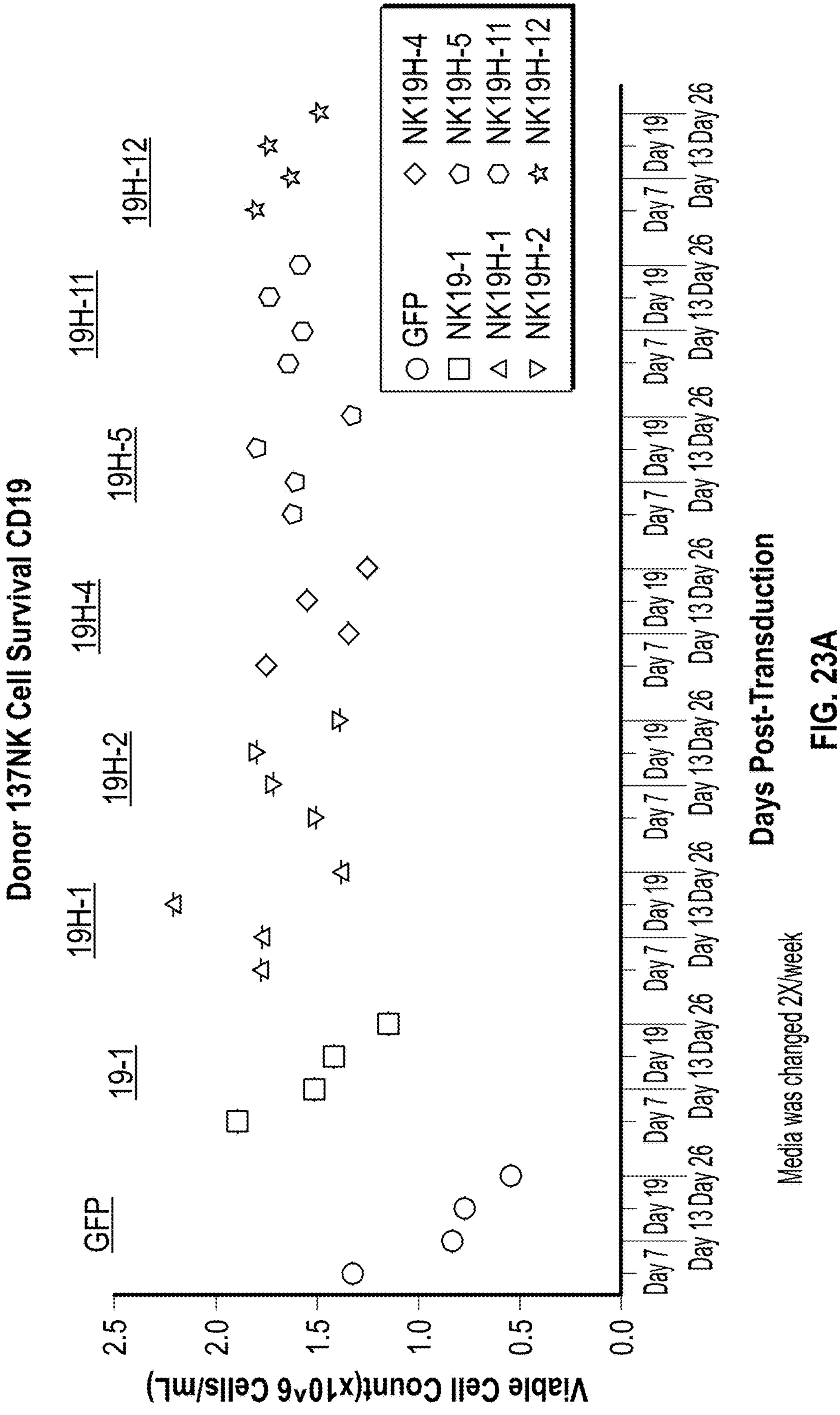
FIGS. 23A-23D show data related to NK cell survival.
Figure 23B:
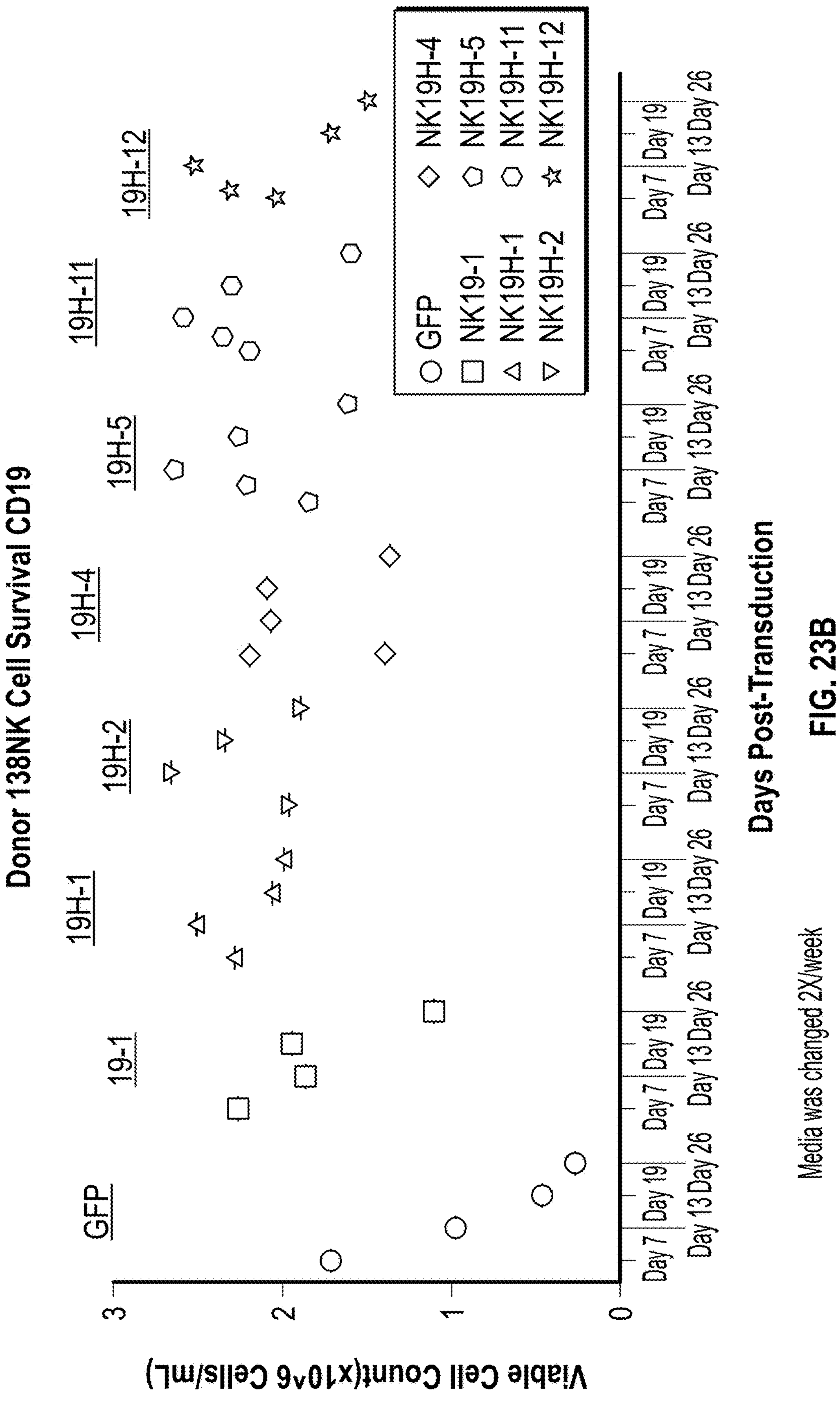
Figure 23C:
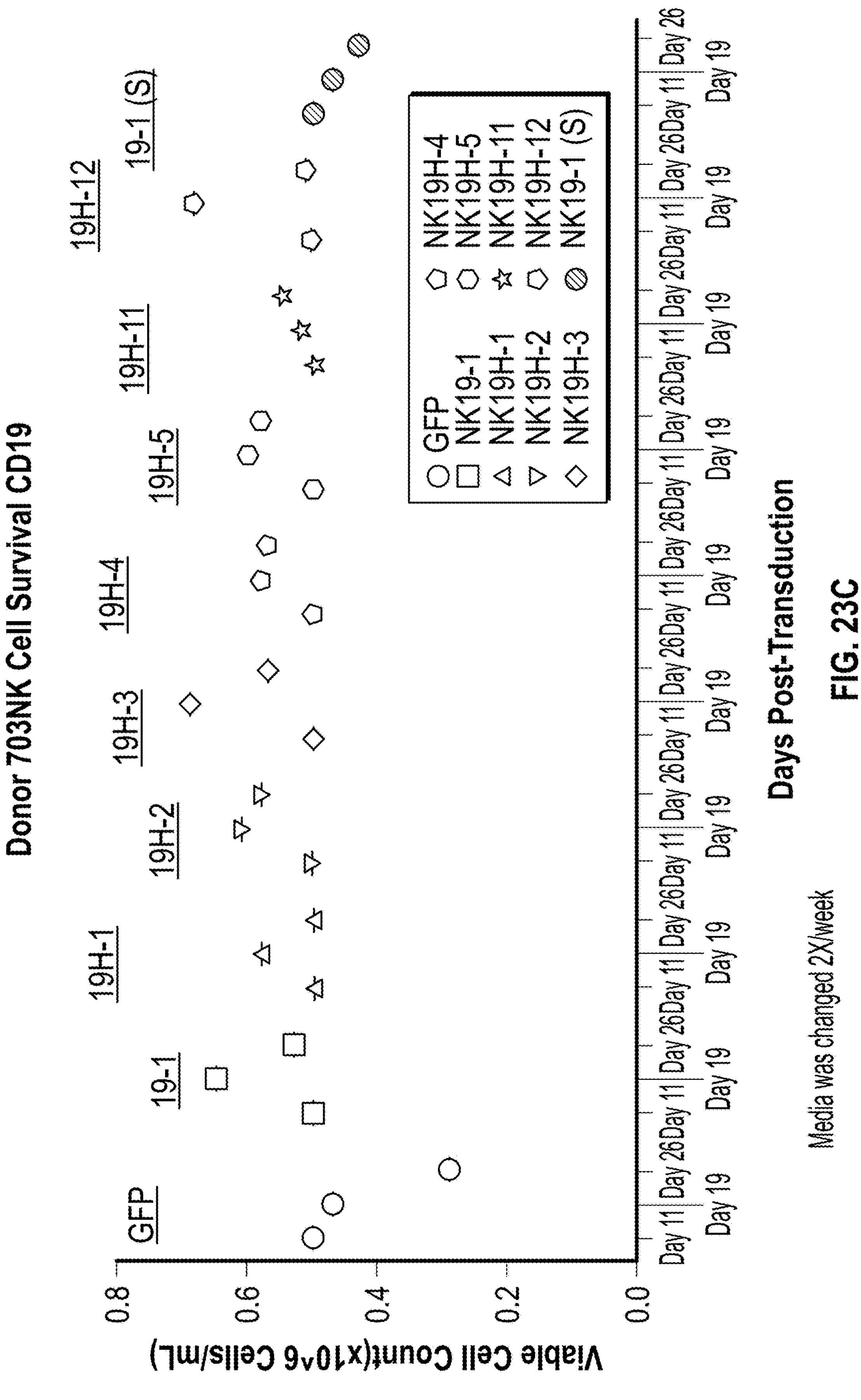
Figure 23D:
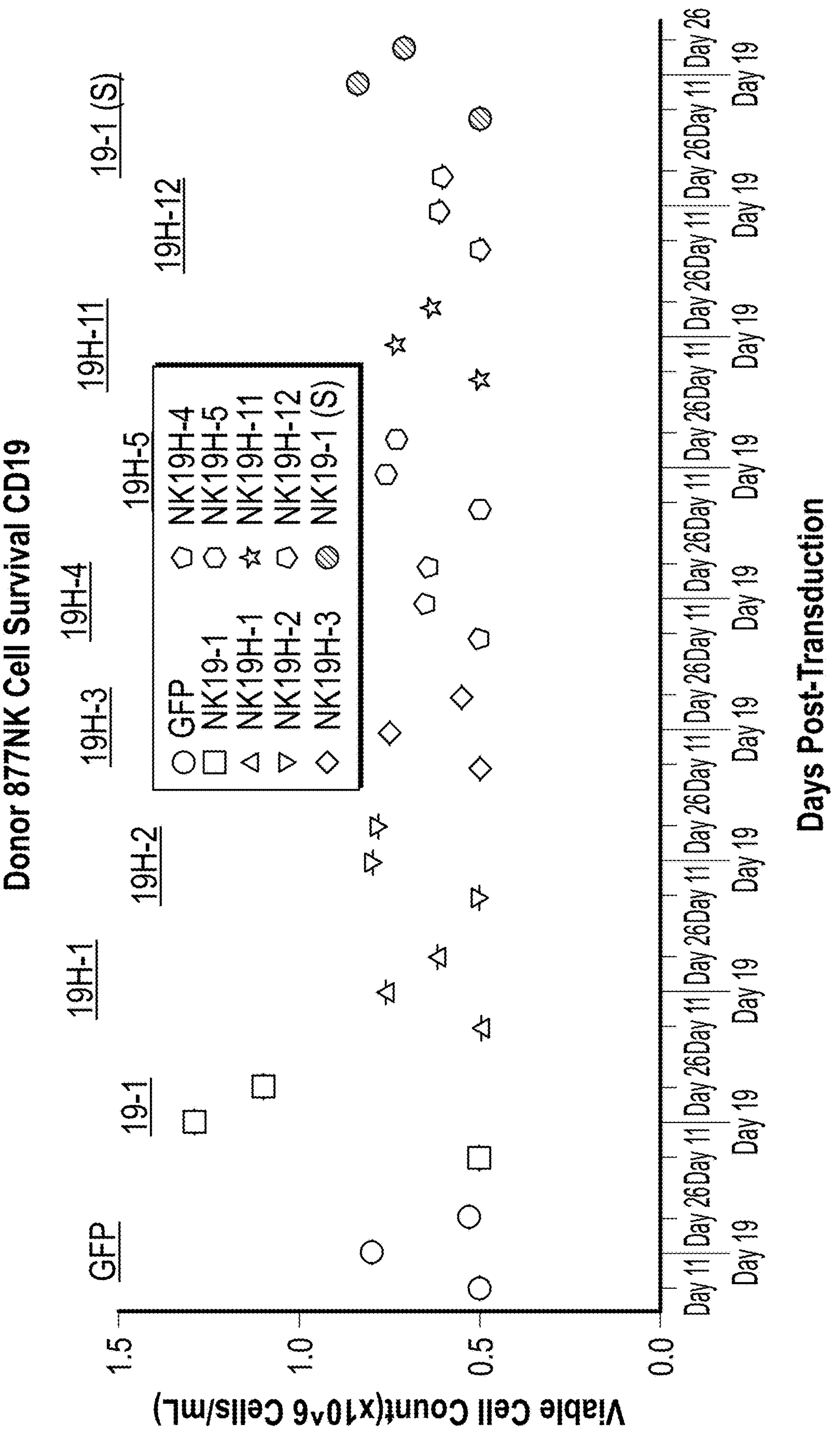

While the data presented above show that humanized anti-CD19 CARs can be expressed by NK cells and have cytotoxic effects on target tumor cells, additional experiments were performed to determine the longevity of the engineered NK cells. NK cells expressing the indicated anti-CD19 CAR constructs were cultured and the cell count was measured at various time points, out to 26 days post-transduction. FIG. 23A shows the survival data for NK cells from Donor 137. The data for the GFP-expressing NK cells show that the cell count at day 7 is higher than the cell count at any other time-point, suggesting that GFP has provided no additional longevity-inducing effects to the NK cells. Likewise, NK cells expressing non-humanized NK19-1 shows a fall off of cell number over time. While each of the humanized constructs shows some variability in terms of cell count, the trend of the data shows that expression of the humanized anti-CD19 constructs results in less NK cell death over time. A similar trend is shown in the data of FIG. 23B, which shows cell viability for NK cells from Donor 138. While the timing of analysis is modified, FIG. 23C shows data yielding a similar trend (for Donor 703), in that the expression of the humanized constructs results in longer NK cell survival over time in culture. FIG. 23D shows data for NK cells from Donor 877, where the expression of humanized anti-CD19 CAR constructs allows for reduced NK cell death over time in culture.

Figure 24:
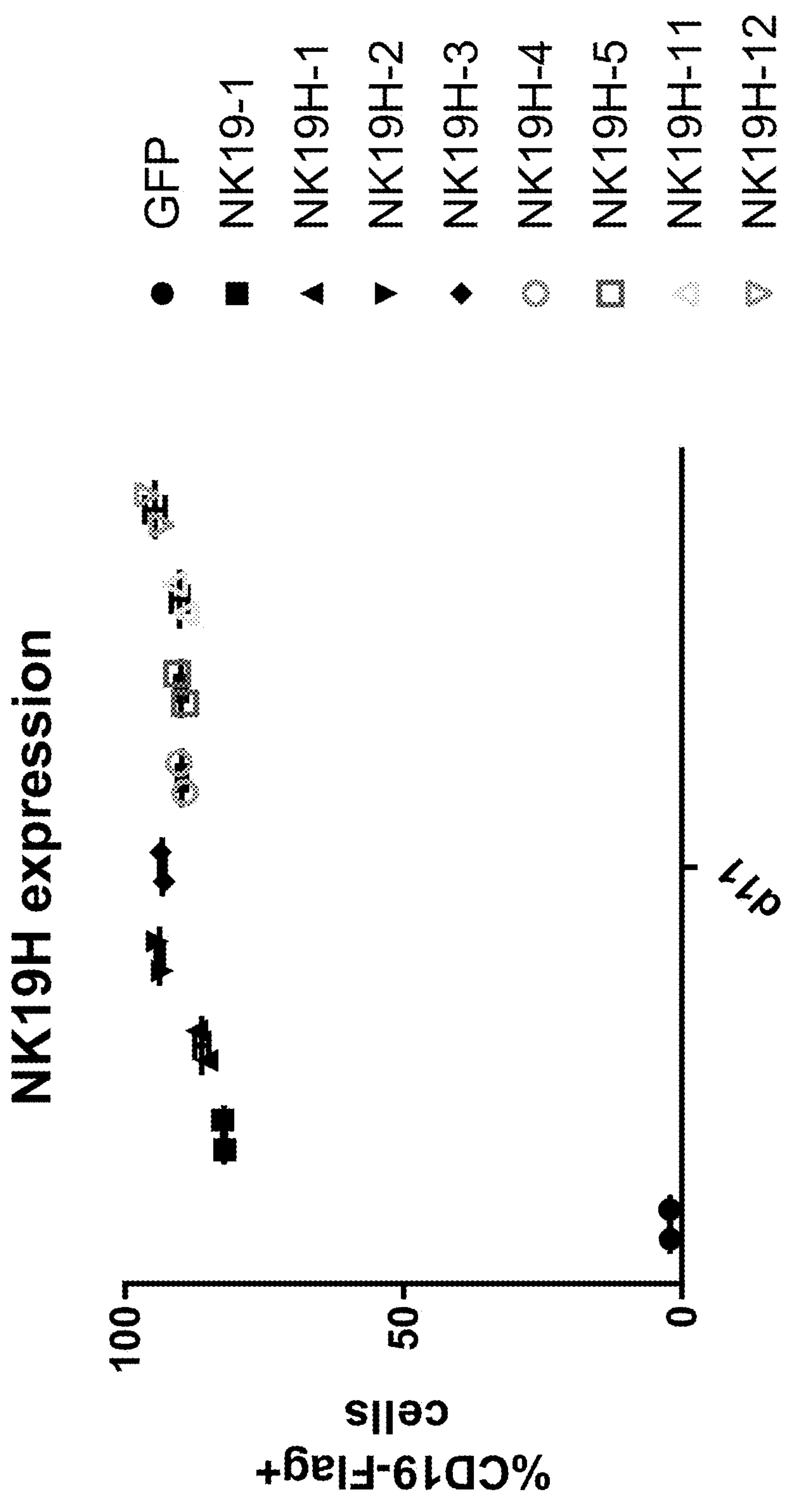
FIG. 24 shows data related to the percent of NK cells expressing the indicated non-limiting embodiments of anti-CD19 CAR constructs at 11 days post-transduction.

Summary data for the expression of the various anti-CD19 CAR constructs is shows in FIG. 24, which displays the expression efficiency of the indicated constructs at day 11 post-transduction. As anticipated, the GFP-transduced NK cells exhibit no CD19-Flag expression, serving as a negative control. Likewise, the non-humanized NK19-1 construct serves as a positive control. Each of the humanized constructs assessed showed enhanced expression efficiency as compared to NK19-1, with efficiencies ranging from about 85% to about 95% (e.g., 85%-95% of all the NK cells tested expressed the Flag-tagged CAR construct).

Figure 25A:
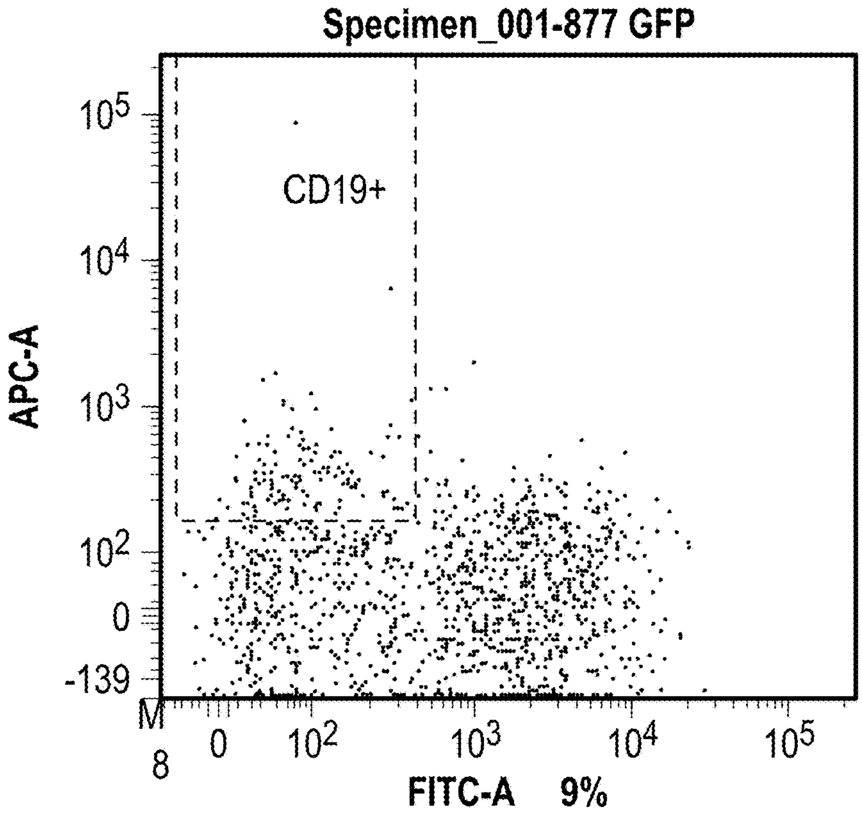
FIGS. 25A-25I show data related to the expression of CD19 by NK cells transduced with various non-limiting embodiments of anti-CD19 CAR constructs disclosed herein.
Figure 25B:
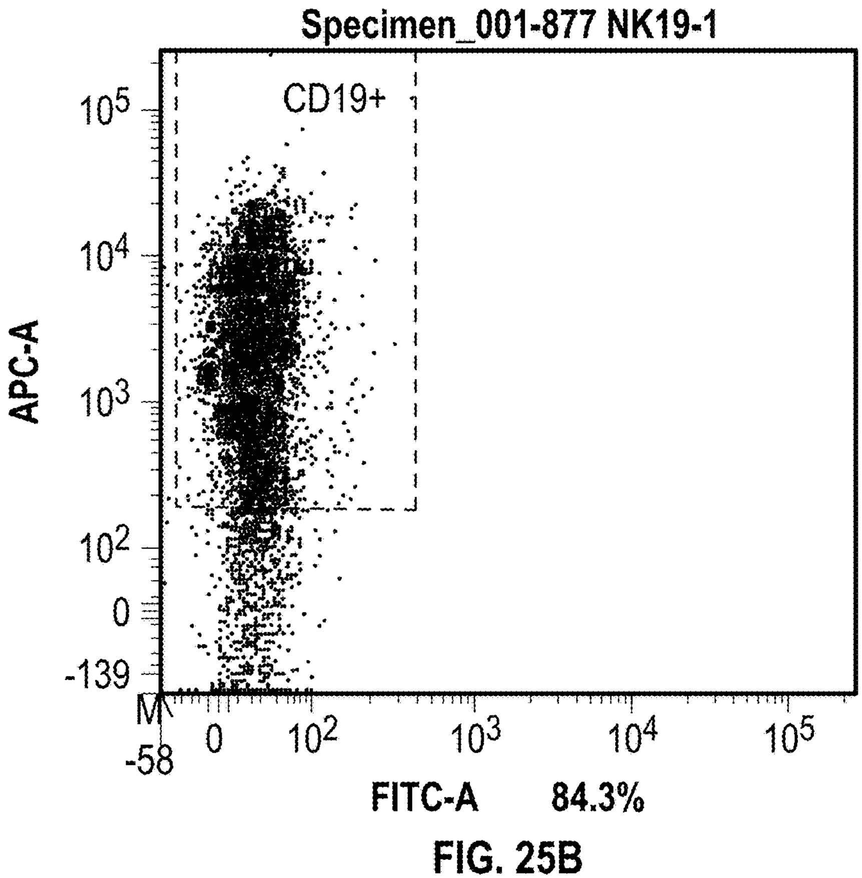
Figure 25C:
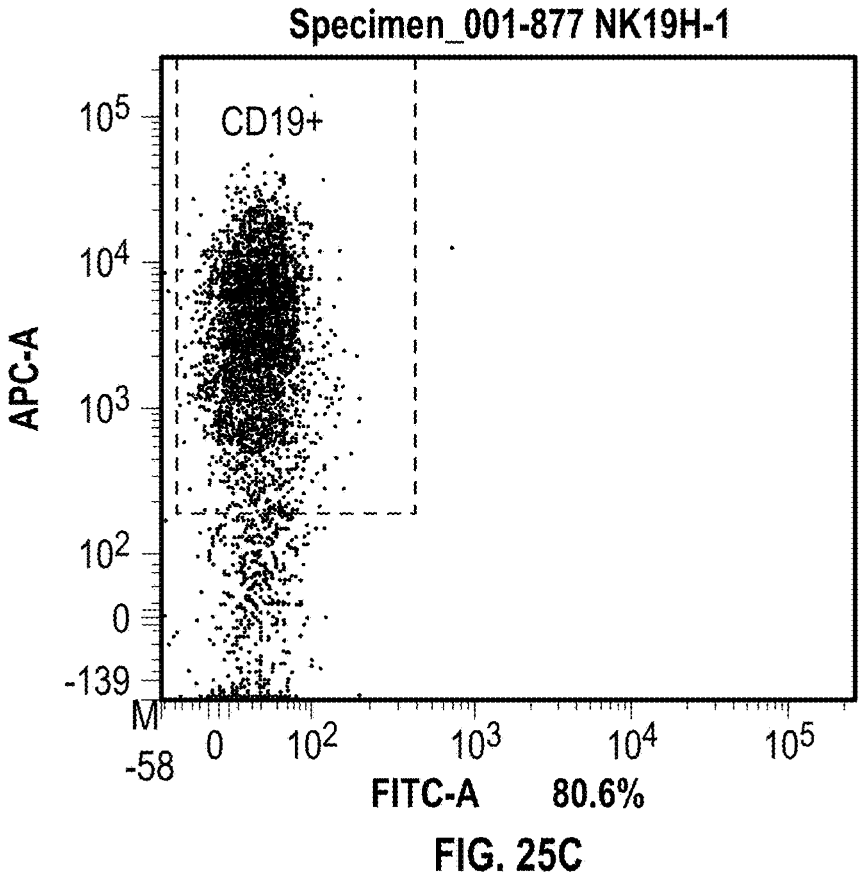
Figure 25D:
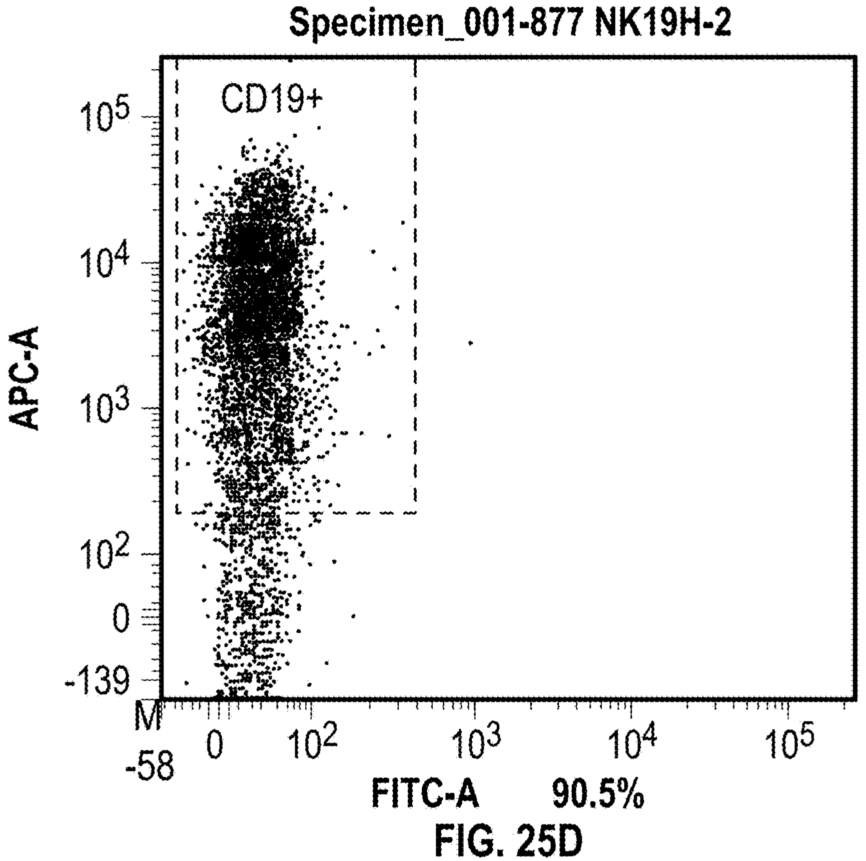
Figure 25E:
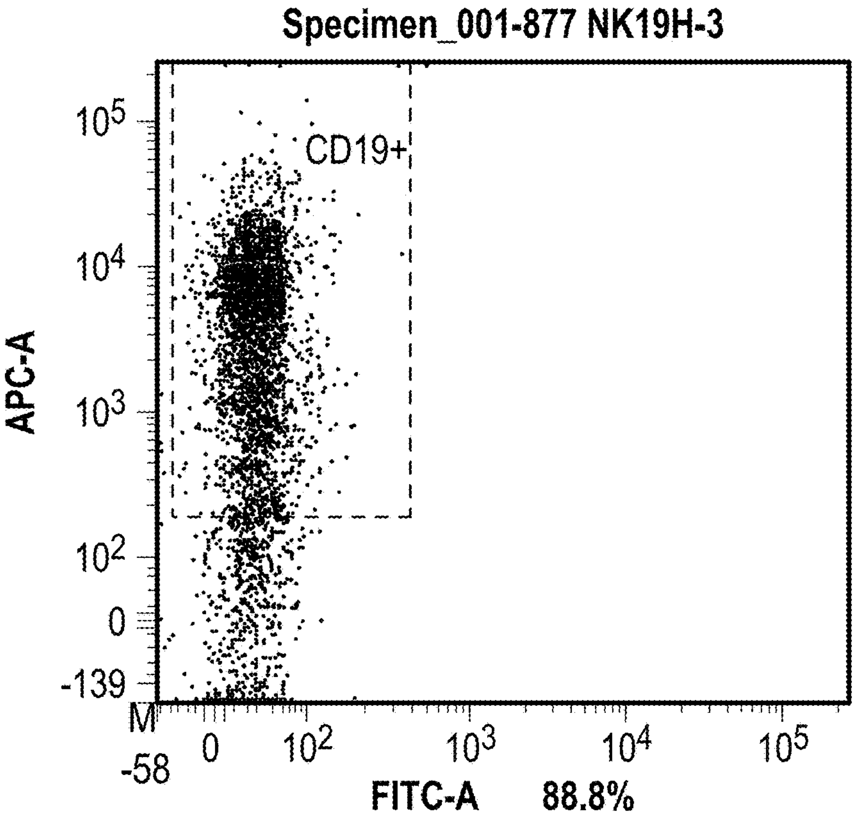
Figure 25F:
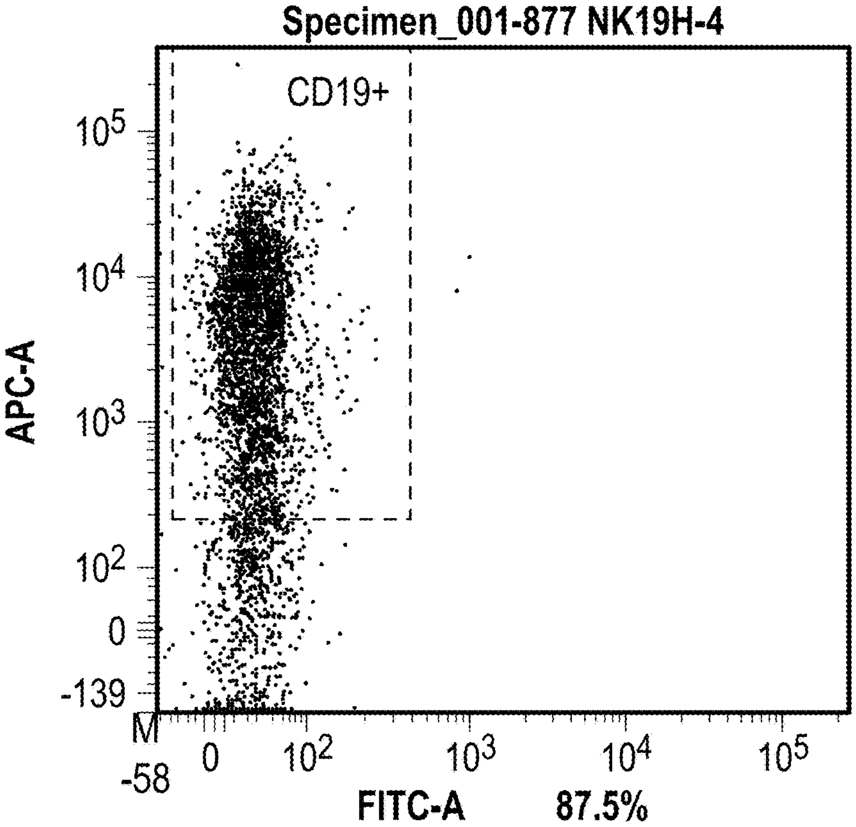
Figure 25G:
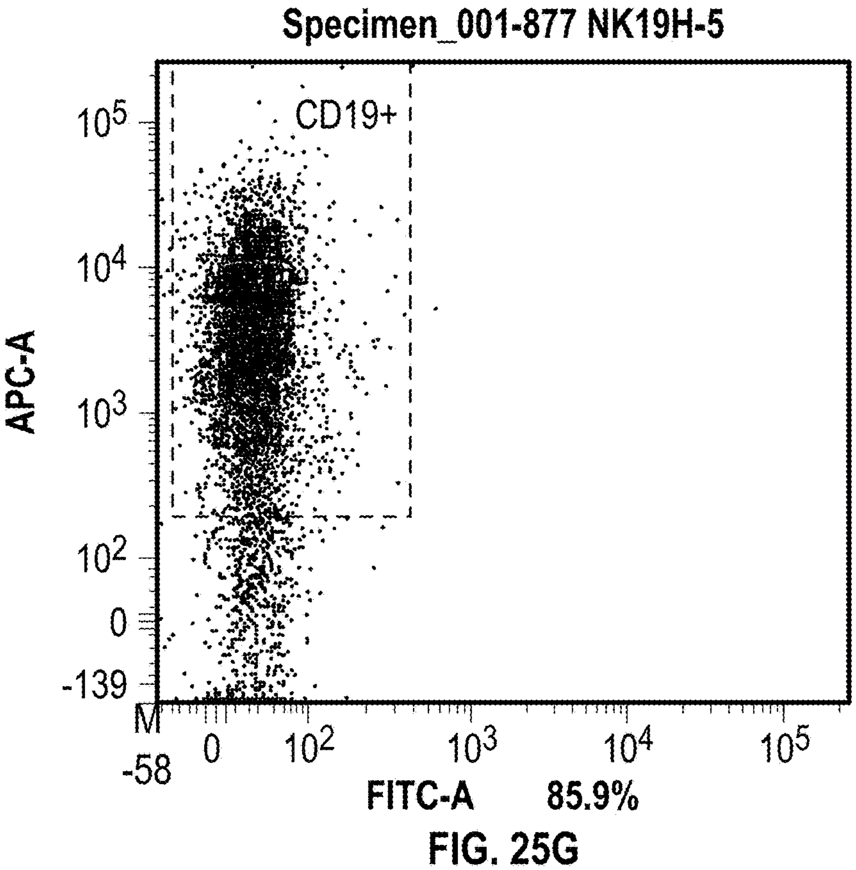
Figure 25H:
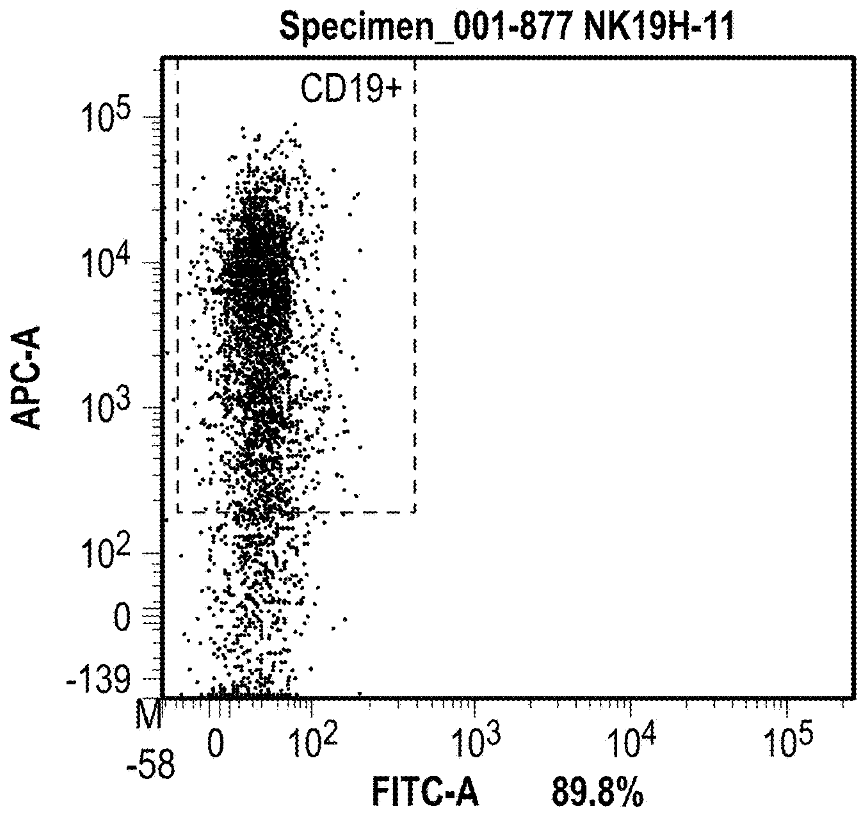
Figure 25I:
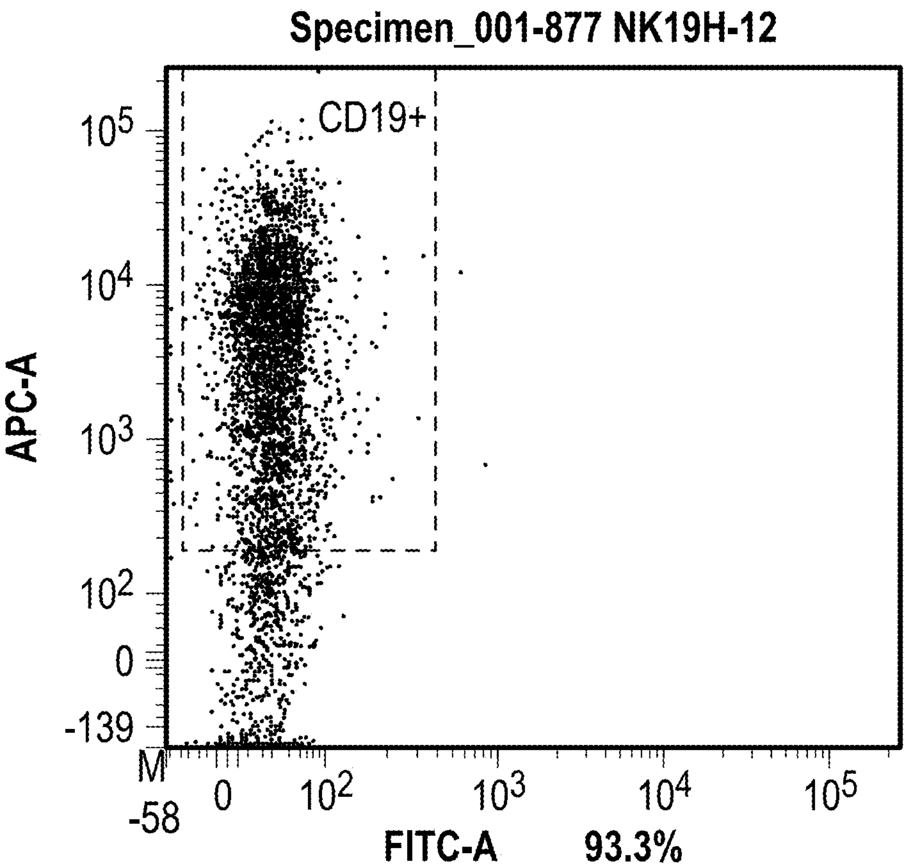

FIGS. 25A-25I show raw flow cytometry data for one donor wherein expression of CD19-Flag (indicative of CAR expression) is measured. FIG. 25A shows the GFP-control, with little to no Flag expression. FIG. 25B shows Flag detection with the NK19-1 positive control. FIGS. 25C-25I show the results of Flag detection for the indicated humanized anti-CD19 CAR constructs, with the percentage of cells expressing the constructs ranging from about 80% to about 95%. As with the experiments above, these data confirm that the humanized anti-CD19 CAR constructs can be robustly expressed by transduced NK cells.

Example 7

Figure 26A:
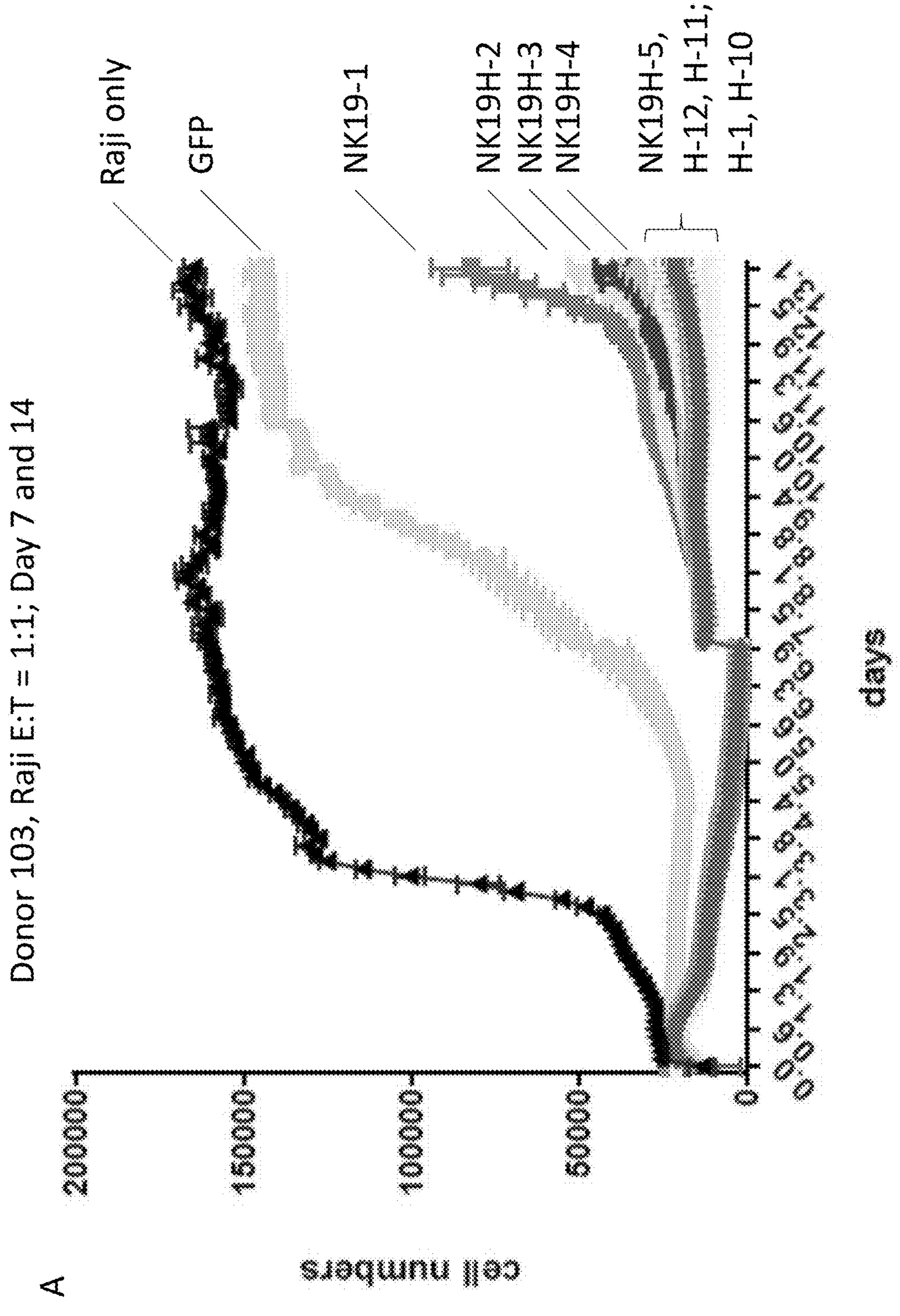
FIGS. 26A-26D show cytotoxicity data.
Figure 26B:
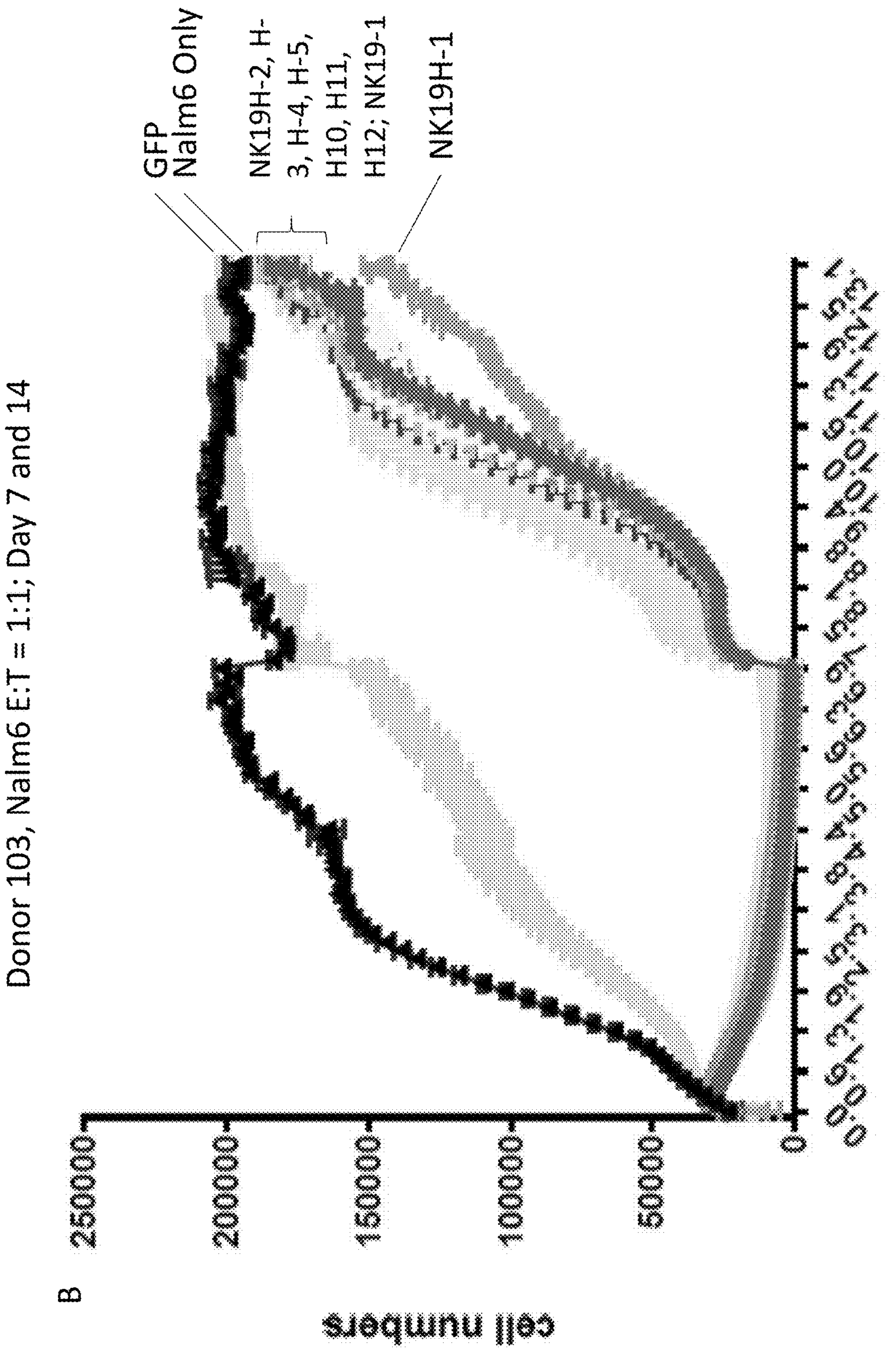

Similar to the experiments discussed above, Raji cells were exposed to NK cells from donor 103 which were transduced with the various constructs indicated (see FIG. 26A). Raji cells were co-cultured on day 7 post-transduction of the NK cells, and the NK cells were re-challenged again on day 14. As expected Raji cells alone exhibited continued growth, while GFP-transduced NK cells reduced that cell growth a small amount. In contrast, the positive control non-humanized NK19-1 construct reduced Raji cell growth until the very late stages of the experiment. Each of the humanized anti-CD19 CAR constructs yielded enhanced cytotoxicity against the Raji cells. Three of the constructs (NK19H-2, H-3, and H-4) allowed for minor Raji cell growth at the late stage of the experiment, while the other humanized constructs effectively eliminated Raji cell growth, even with the re-challenge at day 14. FIG. 26B shows corresponding data regarding the cytotoxicity of donor 103 NK cells against Nalm6 cells. As indicated in the Figure, all of the anti-CD19 CAR constructs (whether humanized or not) appeared exhibit significant cytotoxicity against the Nalm6 cells through 7 days of co-culture. However, Nalm6 growth increased for all groups with the day 14 re-challenge. While the growth curves initially were somewhat flat, Nlam6 growth later increased in rate. These data suggest that, according to some embodiments, a more frequent dosing strategy is employed to keep target cells from reaching a threshold growth rate. In several embodiments, a larger dose is given and/or a dose is given more frequently, to prevent target cell growth under a physiological equivalent context to a "re-challenge."

Figure 26C:
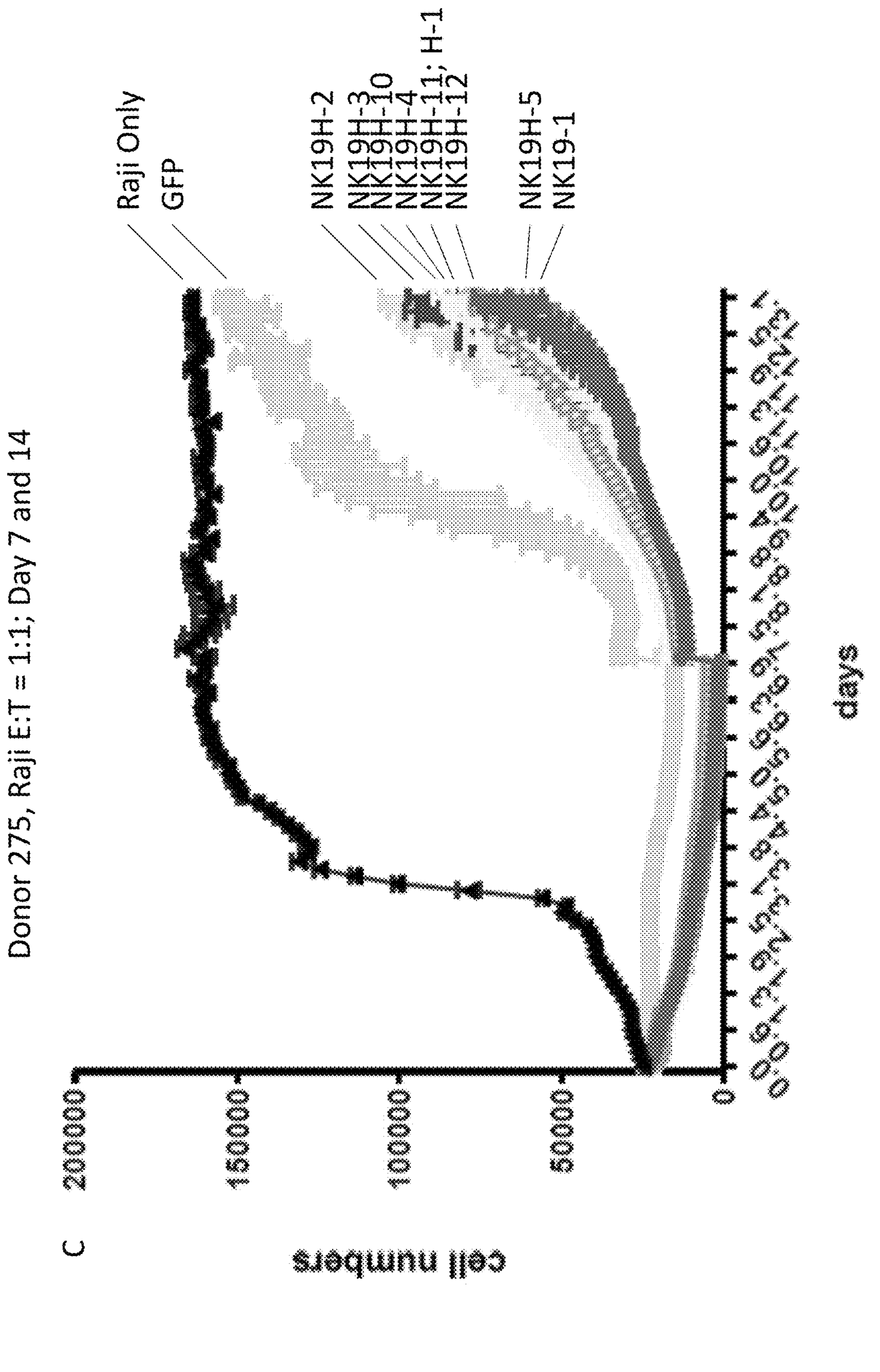
Figure 26D:
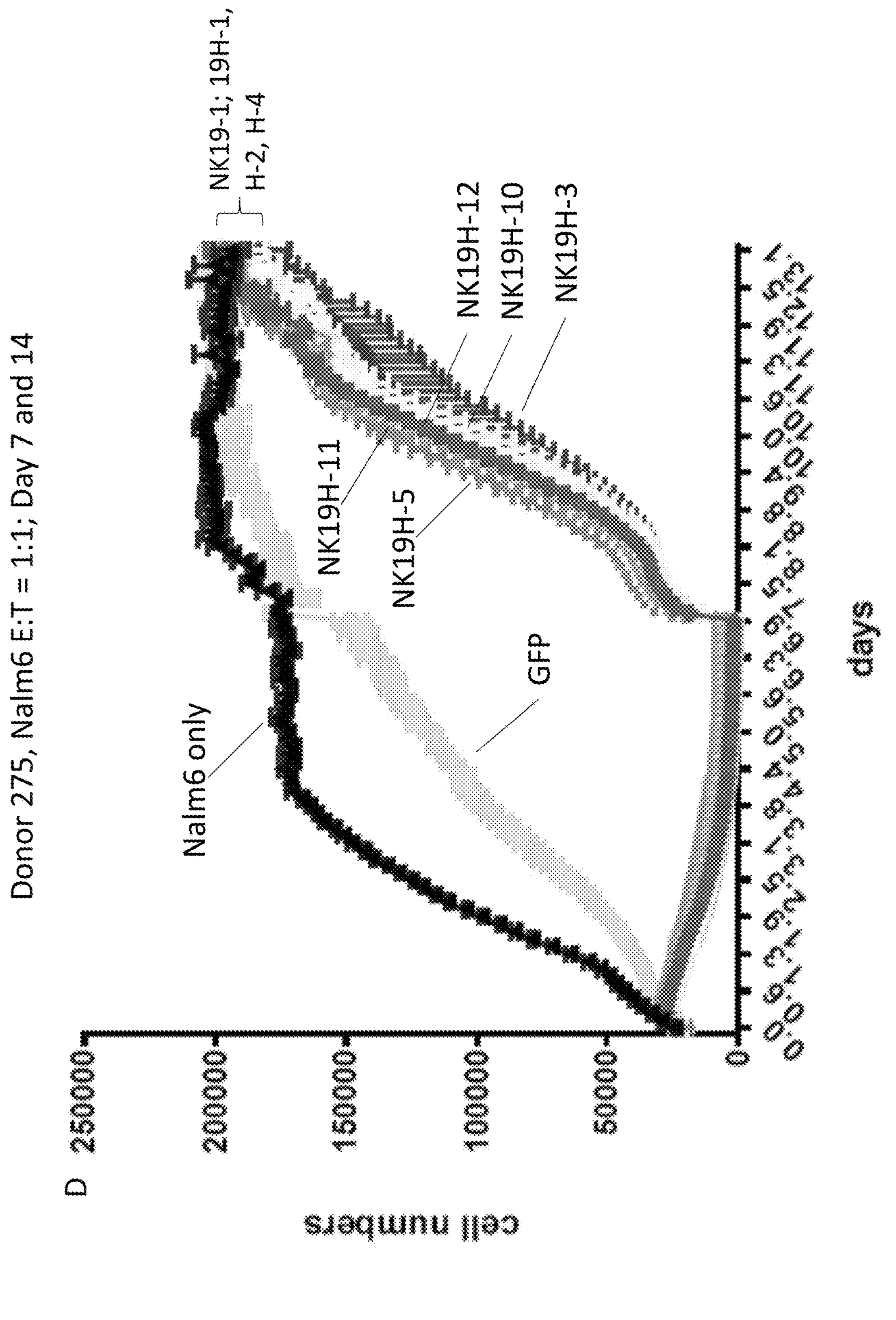

FIG. 26C shows data for Raji cells (as with FIG. 26A) with NK cells from donor 275. Similar to those of FIG. 26A, each of the anti-CD19 CAR constructs showed significant cytotoxicity against Raji cells, and allowing limited growth of the target cells, even with a re-challenge. FIG. 26D shows data for Nalm6 cells (as with FIG. 26B) with NK cells from donor 275. Results for this experiment were also similar to those for donor 103, with effective control of Nalm6 cells through 7 days, but reduced cytotoxicity after re-challenge. These data indicated that dosing strategies, depending on the embodiment, are developed for a specific donor and/or for a specific target tumor type. For example, while Nalm6 cells are CD19 positive, they may express less CD19 than, for example, Raji cells, thereby accounting for the reduced cytotoxicity of NK cells from donor 103 and 275 against the Nalm6 cell line. The efficacy of the transduced NK cells against the Raji cells indicates that the NK cells are capable of cytotoxicity, even showing persistence out to nearly two weeks post-transduction. Thus, according to several embodiments, an NK cell dose and/or dosing frequency can be tailored to a given patient's tumor type, native NK cell activity, and/or the aggressiveness/stage of a cancer to allow robust and ongoing cytotoxicity against the target cells and achieving control of tumor burden.

Figure 27A:
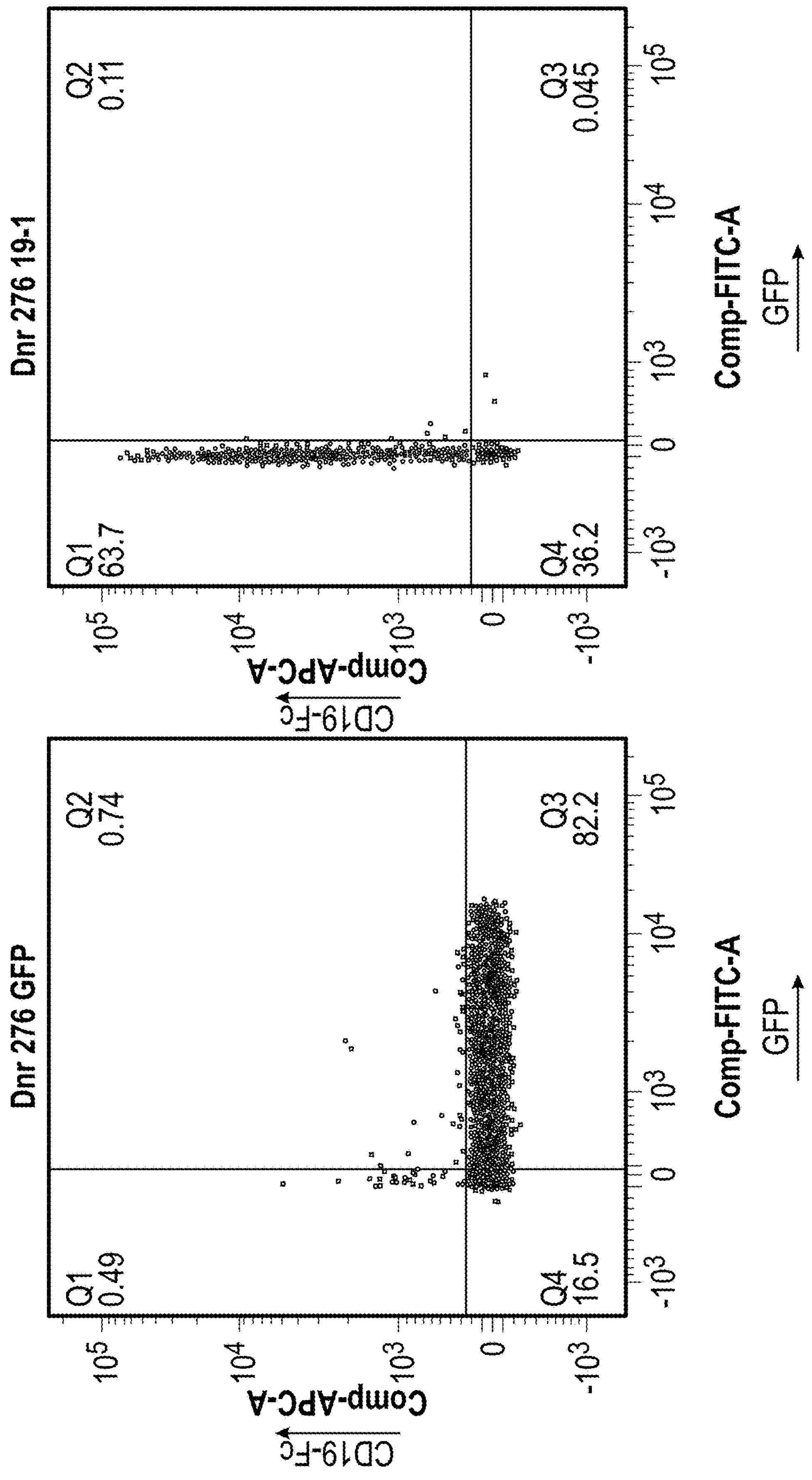
FIGS. 27A-27B show data related to CD19 expression by engineered NK cells.
Figure 27A:
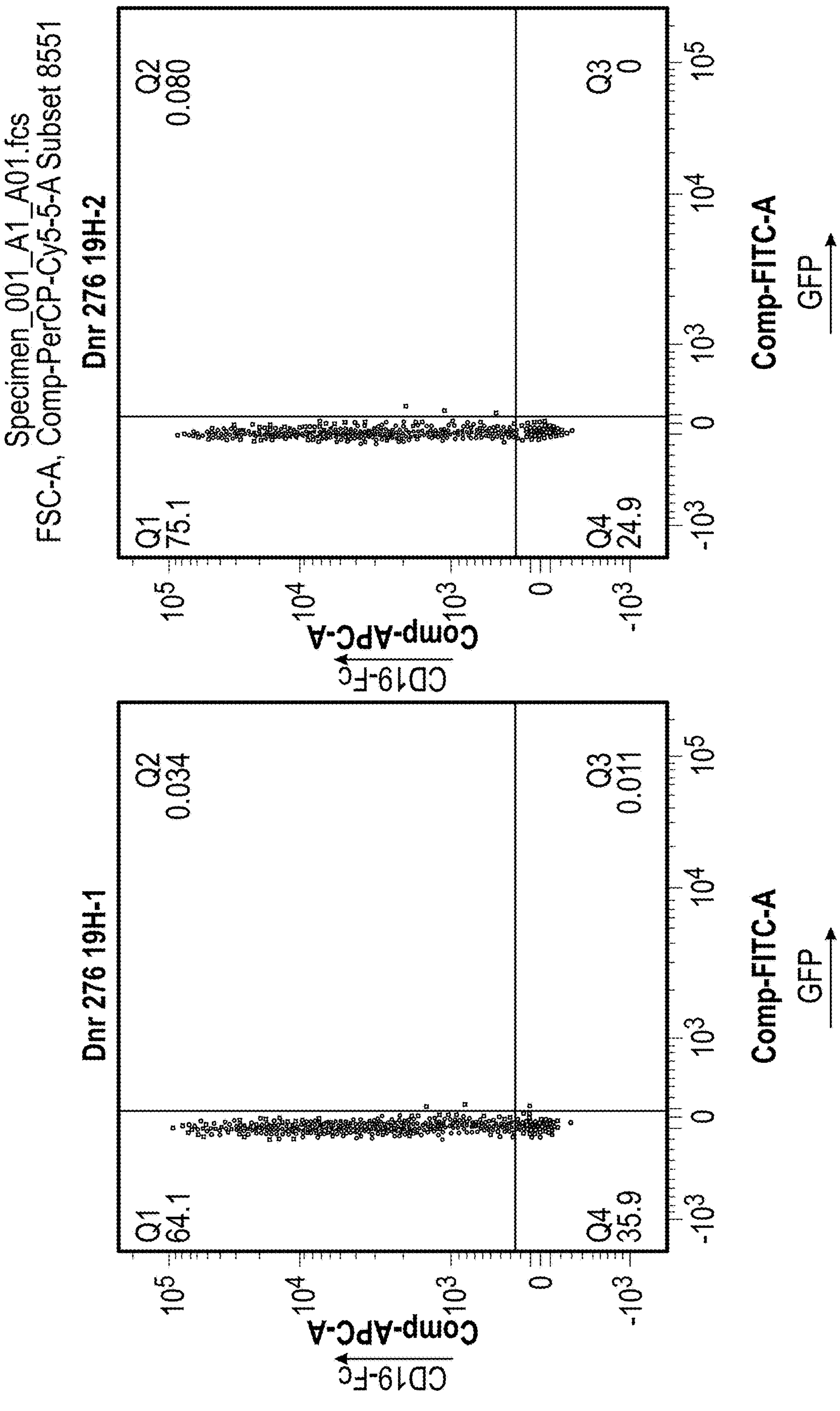
Figure 27A:
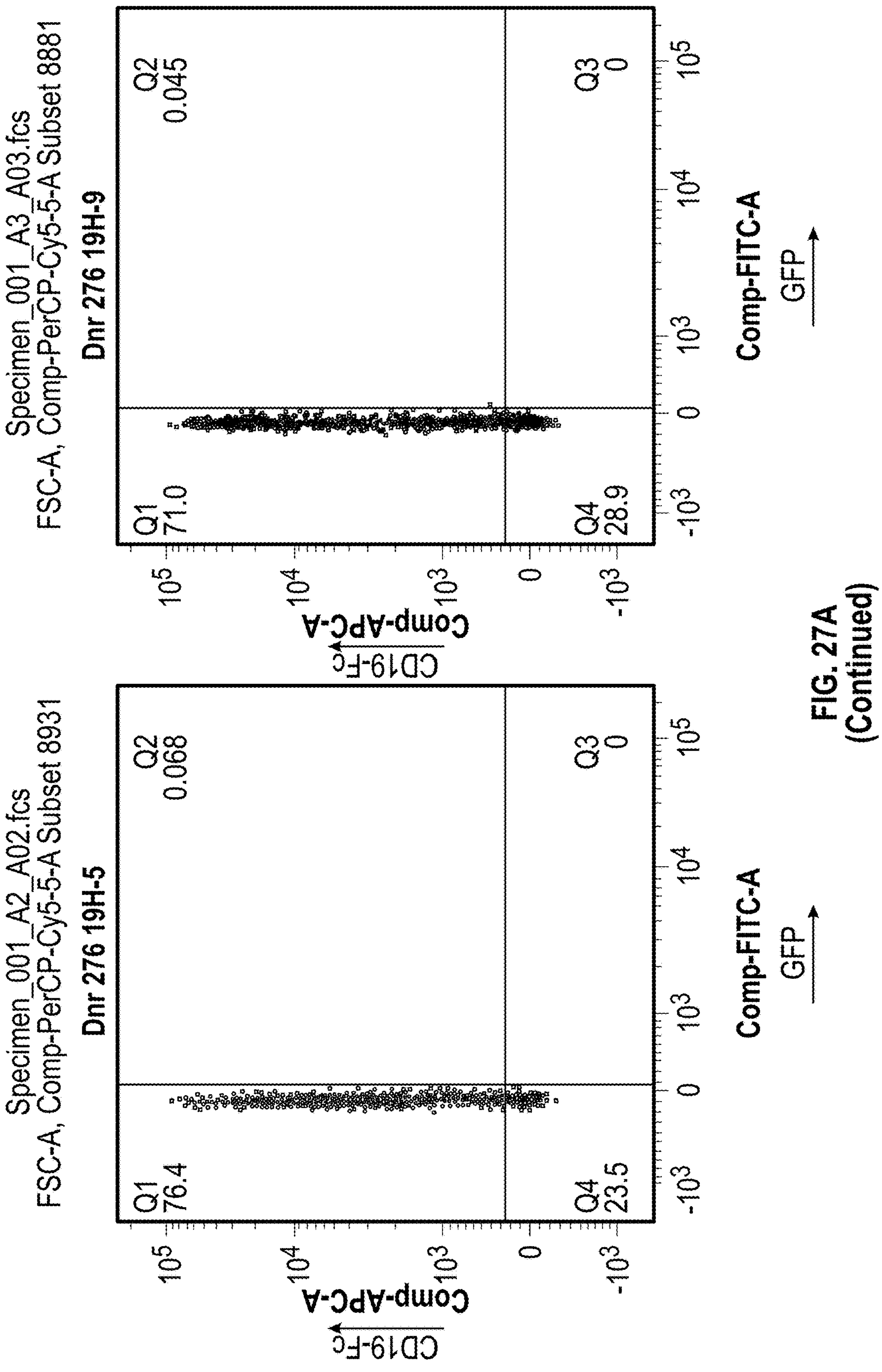
Figure 27B:
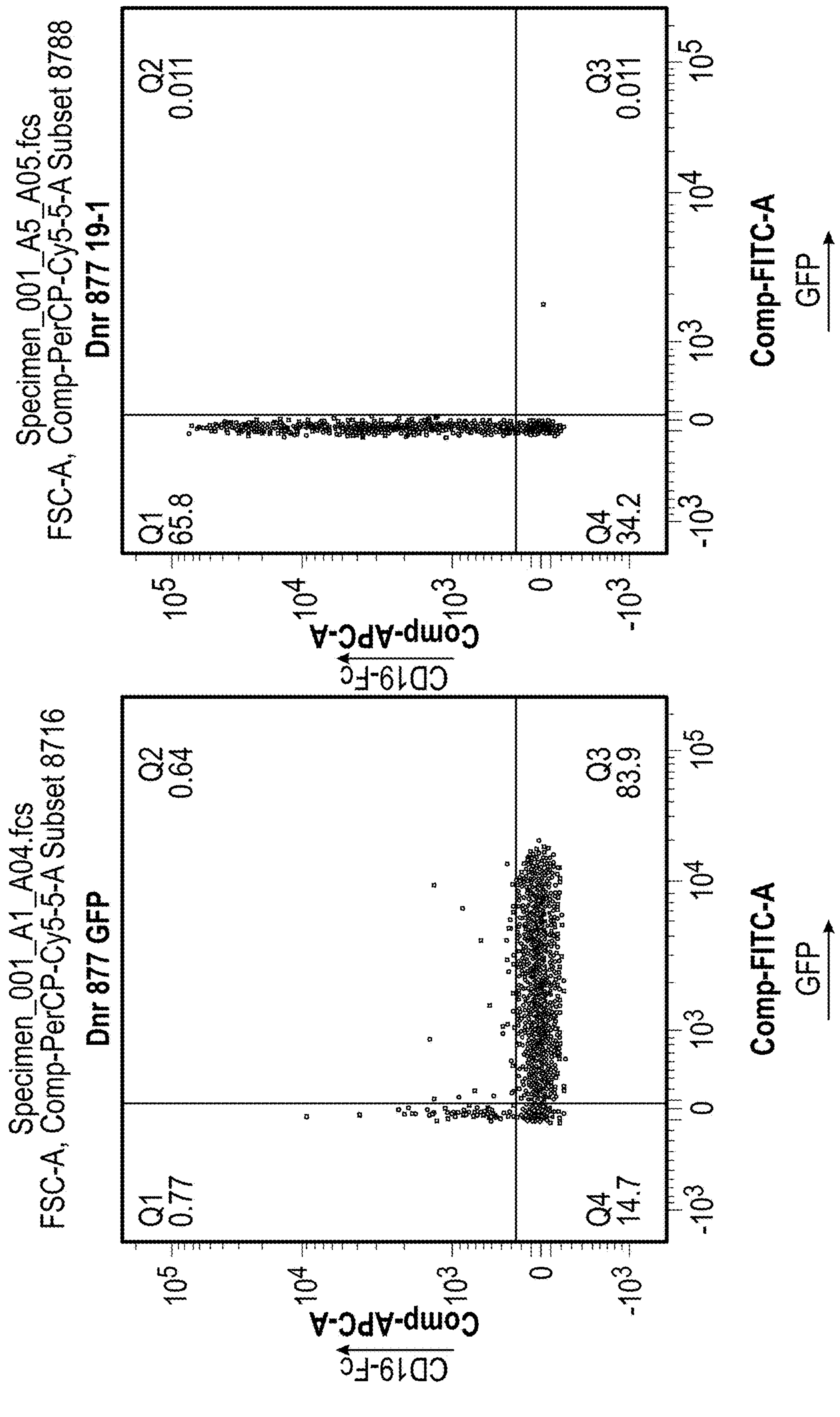
Figure 27B:
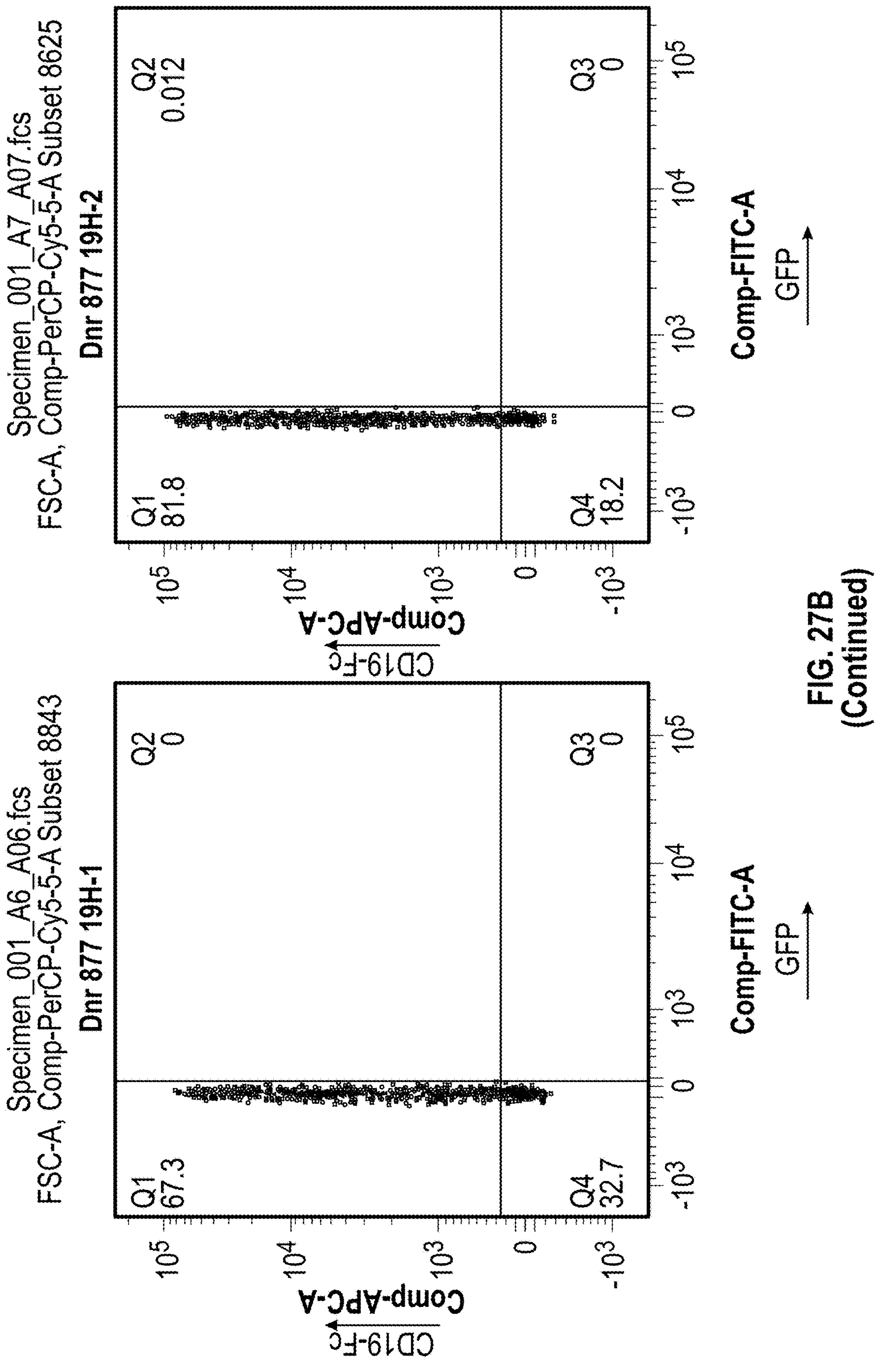
Figure 27B:
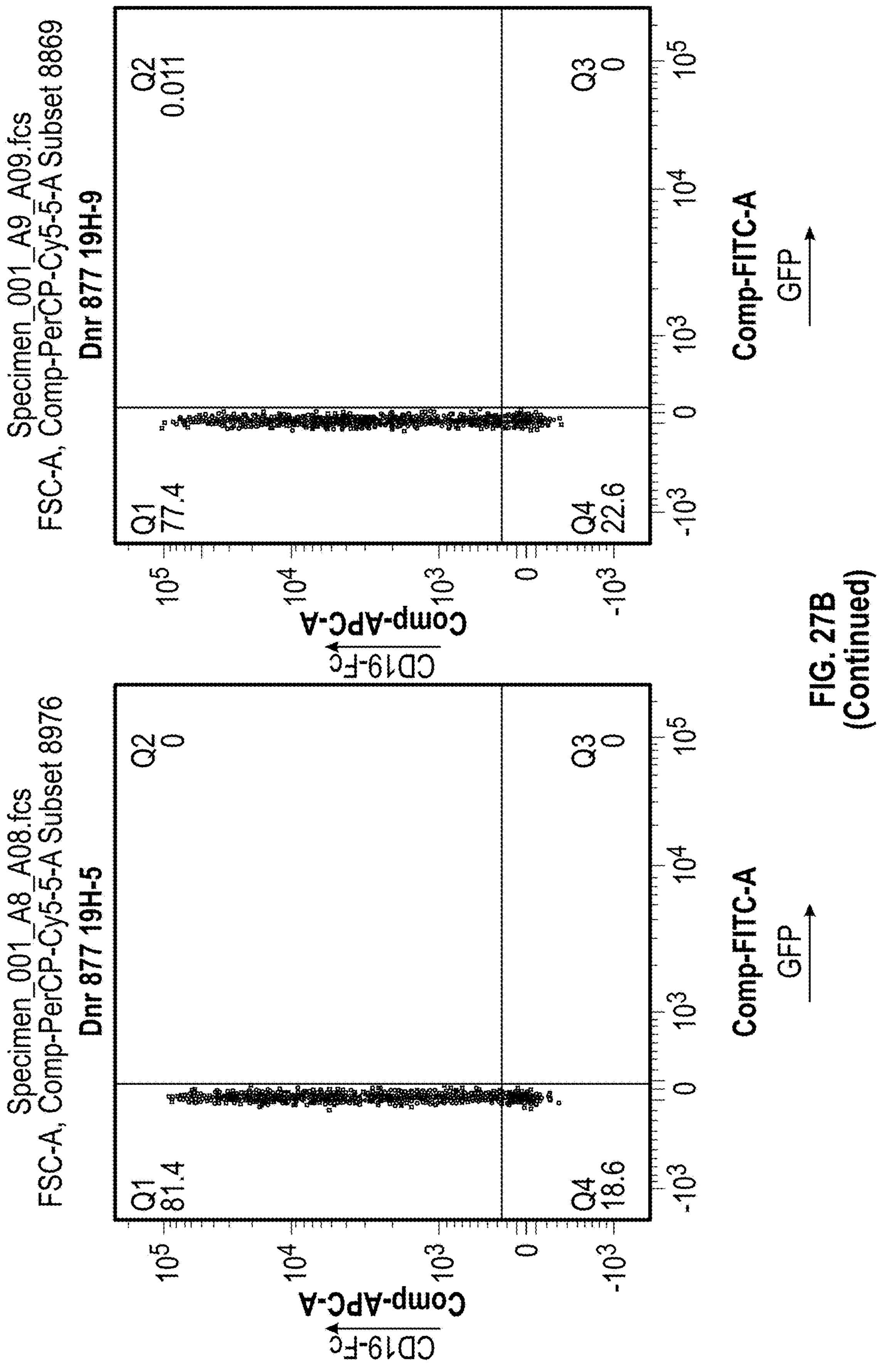

FIGS. 27A-27B show flow cytometry data that characterizes NK cells from two donors (276 in FIG. 17A and 877 in 27B) transduced with non-limiting examples of anti-CD19 CAR constructs as disclosed herein. FIGS. 27A and 27B both show that NK cells transduced with GFP express little to no CD19-Flag. Each of the other panels demonstrates that the NK cells from these donors can express not only the positive control non-humanized NK19-1 construct, but also efficiently express the selected humanized anti-CD19 CAR constructs. This is indicative of the limited impact that humanization of the anti-CD19 binder has on expression characteristics.

Figure 28A:
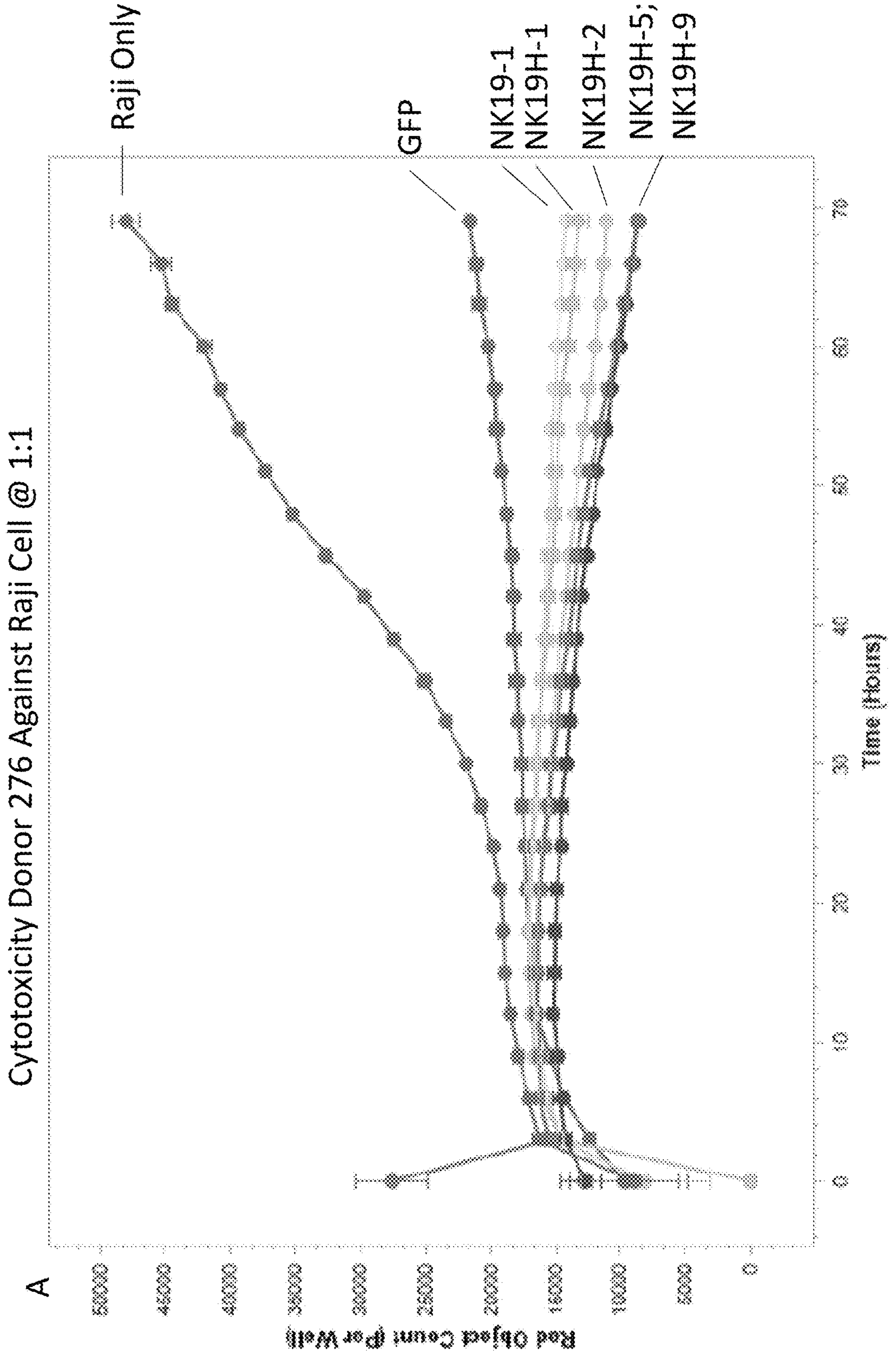
FIGS. 28A-28B show cytotoxicity data.
Figure 28B:
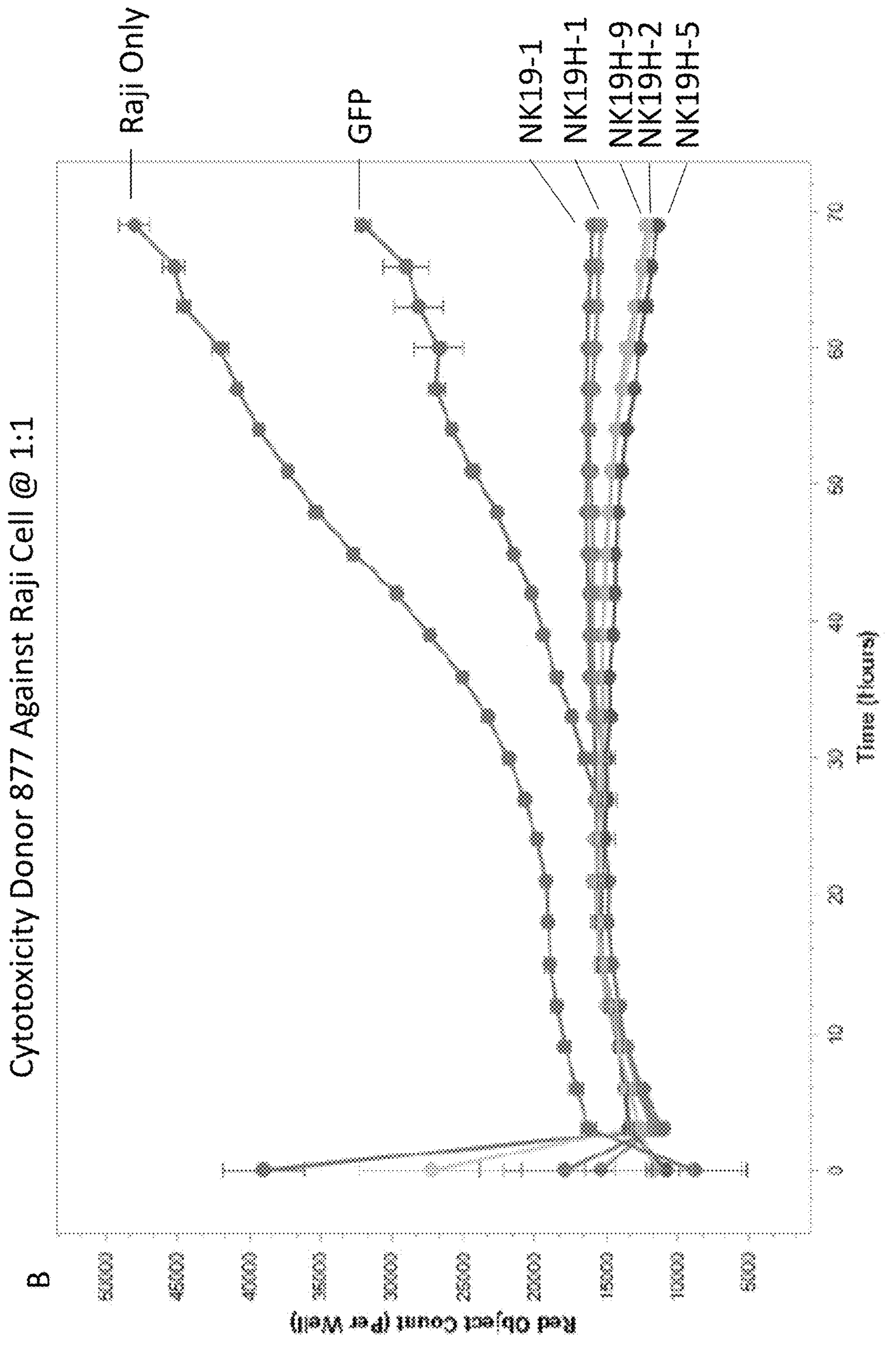

FIGS. 28A-28B show initial data for NK cell cytotoxicity of those two donors from FIG. 27 against Raji cells at an E:T ratio of 1:1. Consistent with results discussed above, each of the selected humanized anti-CD19 CAR constructs endowed transduced NK cells with significant cytotoxic potential against the target Raji cells. Each of the indicated non-limiting examples of anti-CD19 CAR constructs effectively controlled Raji cell growth (equivalent to, or enhanced as compared to, the non-humanized NK19-1 construct) with the trend of decreasing Raji cell numbers even as long as 70 hours after inception of the experiment. Similarly, FIG. 28B shows that transduced NK cells from donor 877 also effectively control Raji cell growth, equivalent to, or enhanced as compared to, the non-humanized NK19-1 construct. These data are in line with those presented for NK cells from other donors, discussed above, and indicate that, in accordance with several embodiments disclosed herein, transduction of NK cells with humanized anti-CD19 CARs enable the engineered NK cells to exert significant cytotoxic effects against target tumor cells and can effectively control growth of tumor cells. According to several embodiments, such engineered anti-CD19 NK cells (whether allogeneic or autologous) allow for robust and effective cellular immunotherapy to treat cancers.

Example 8

Figure 29A:
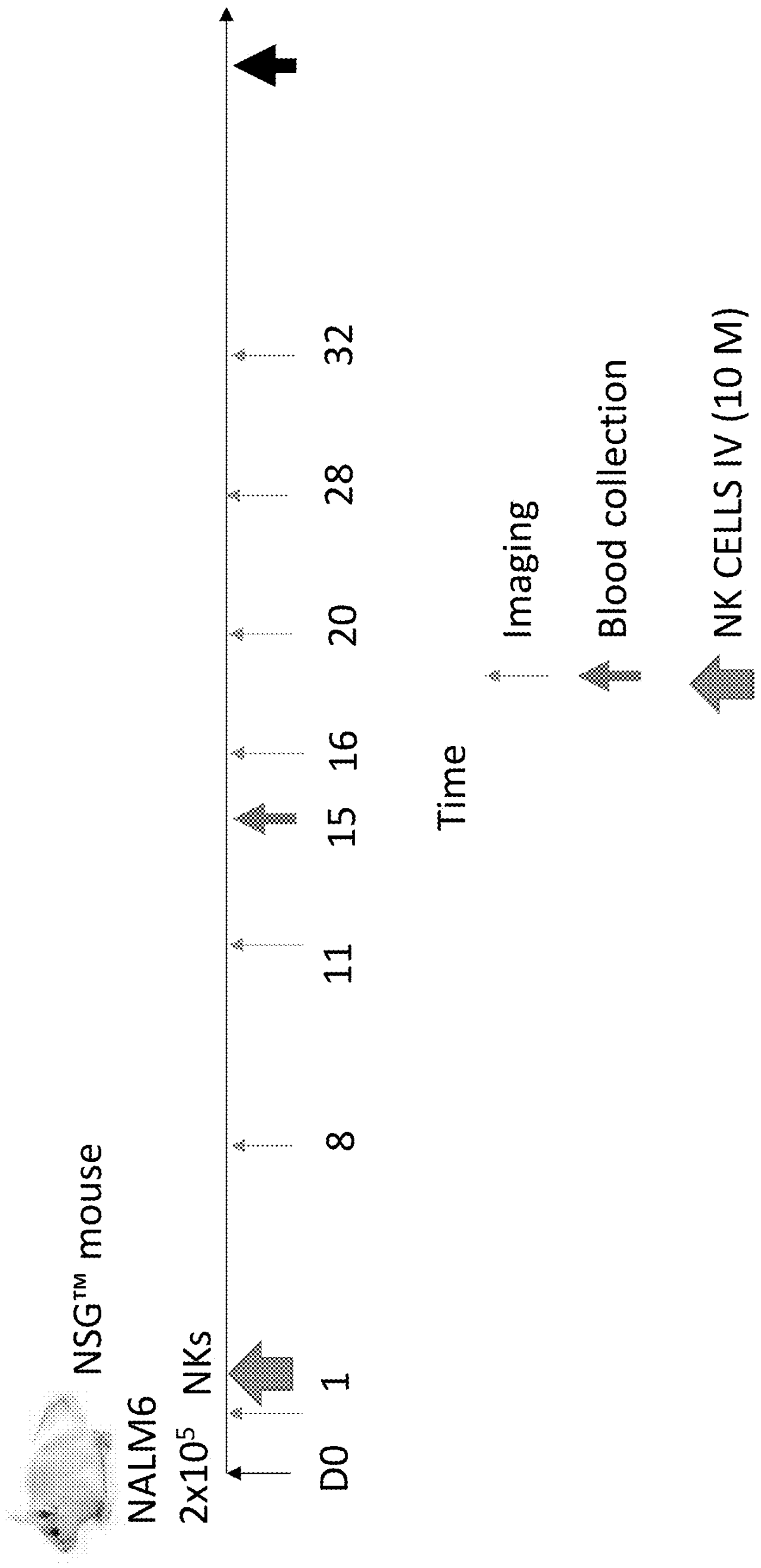
FIGS. 29A-29E show data related to various humanized CD19-directed CAR constructs and their efficacy in an in vivo model.
Figure 29B:
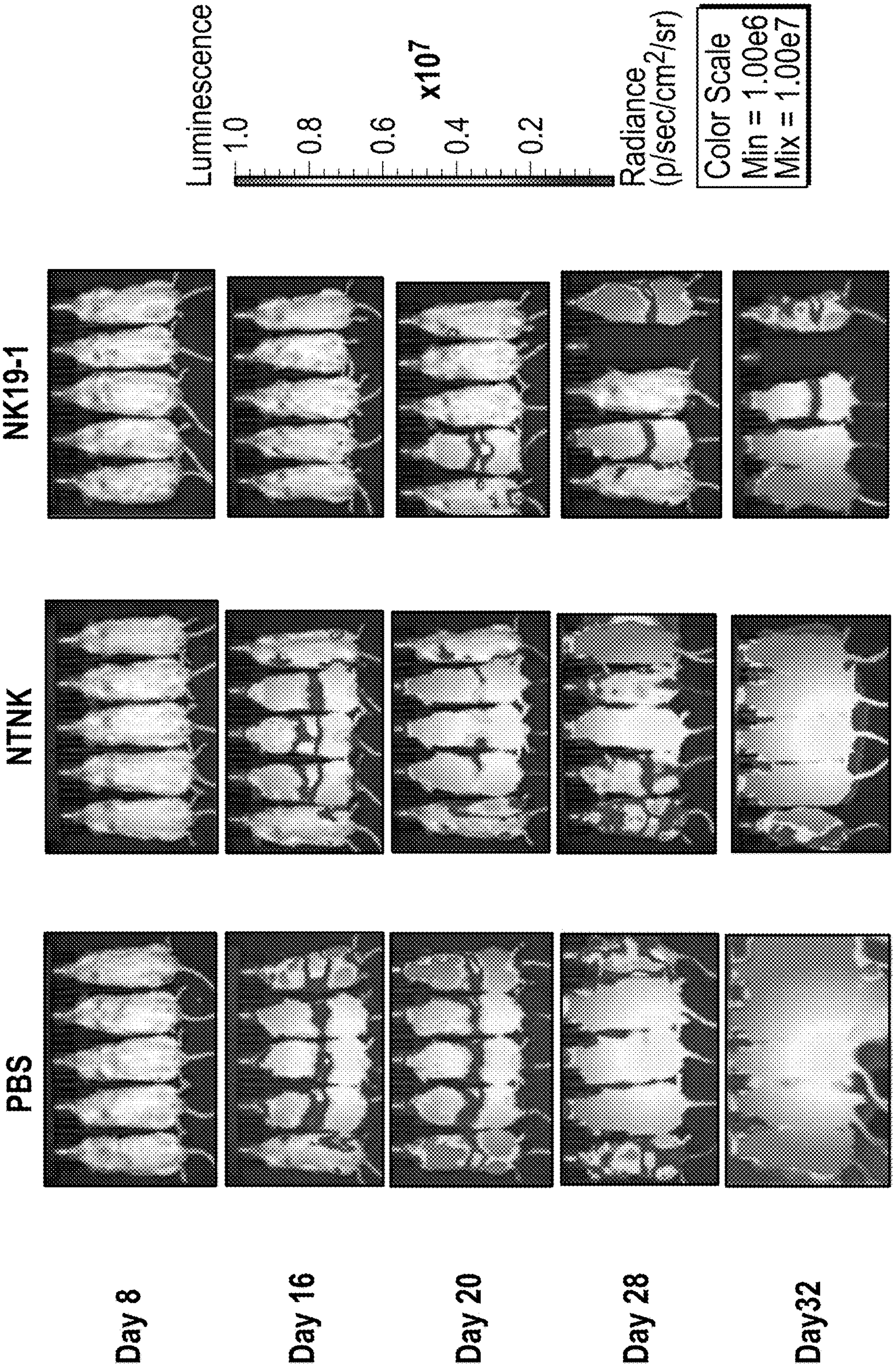
Figure 29B:
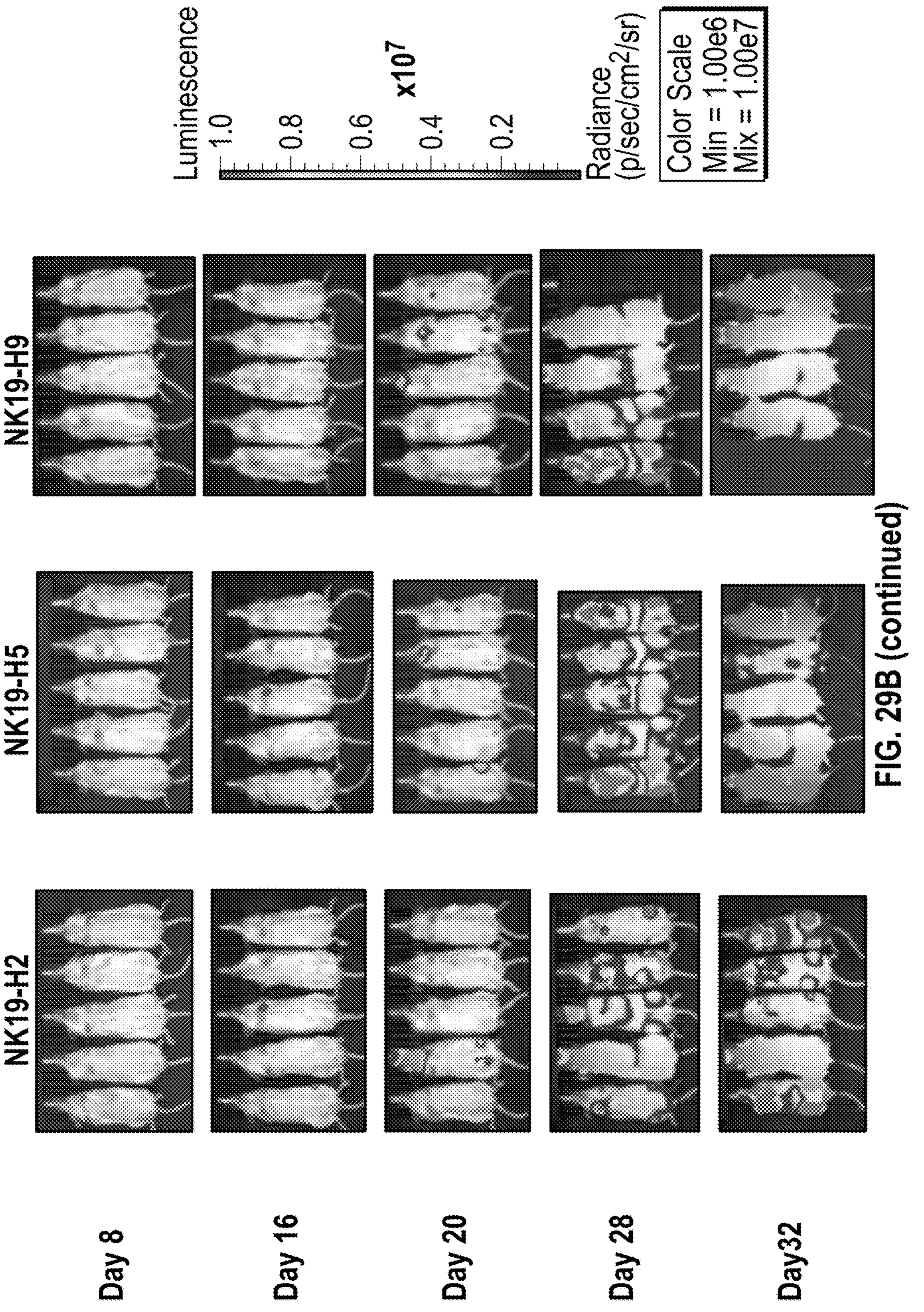
Figure 29C:
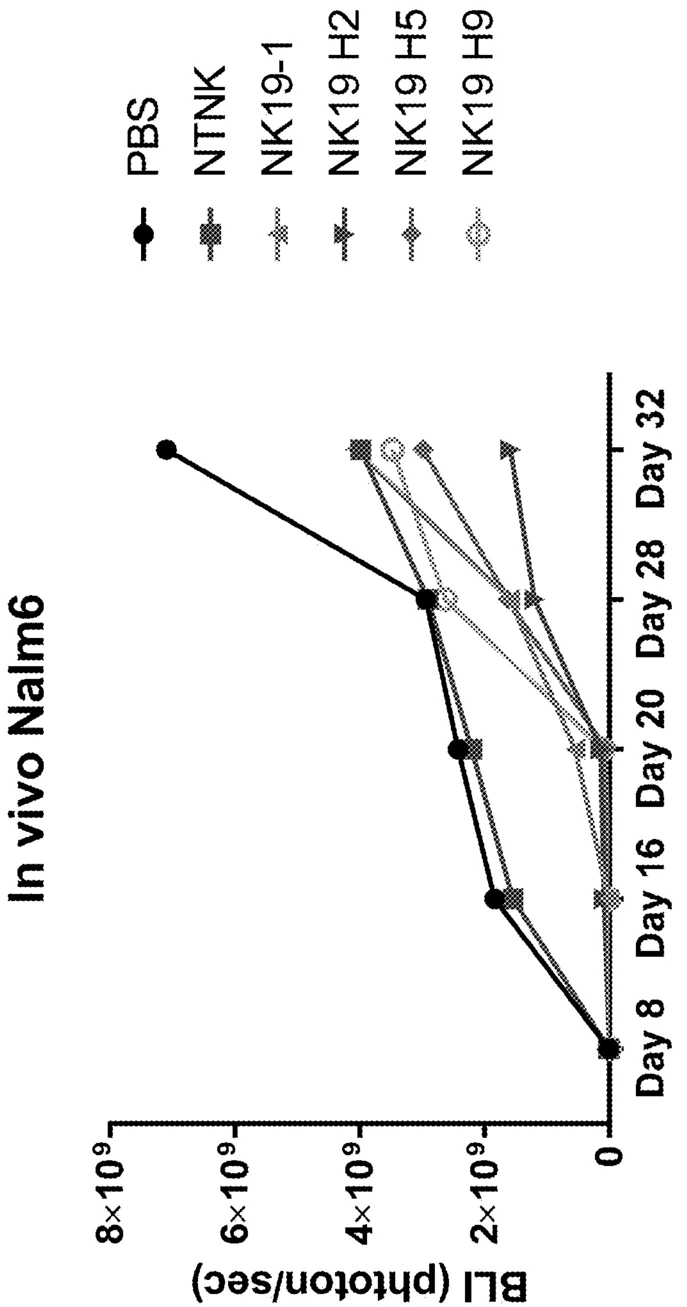
Figure 29D:
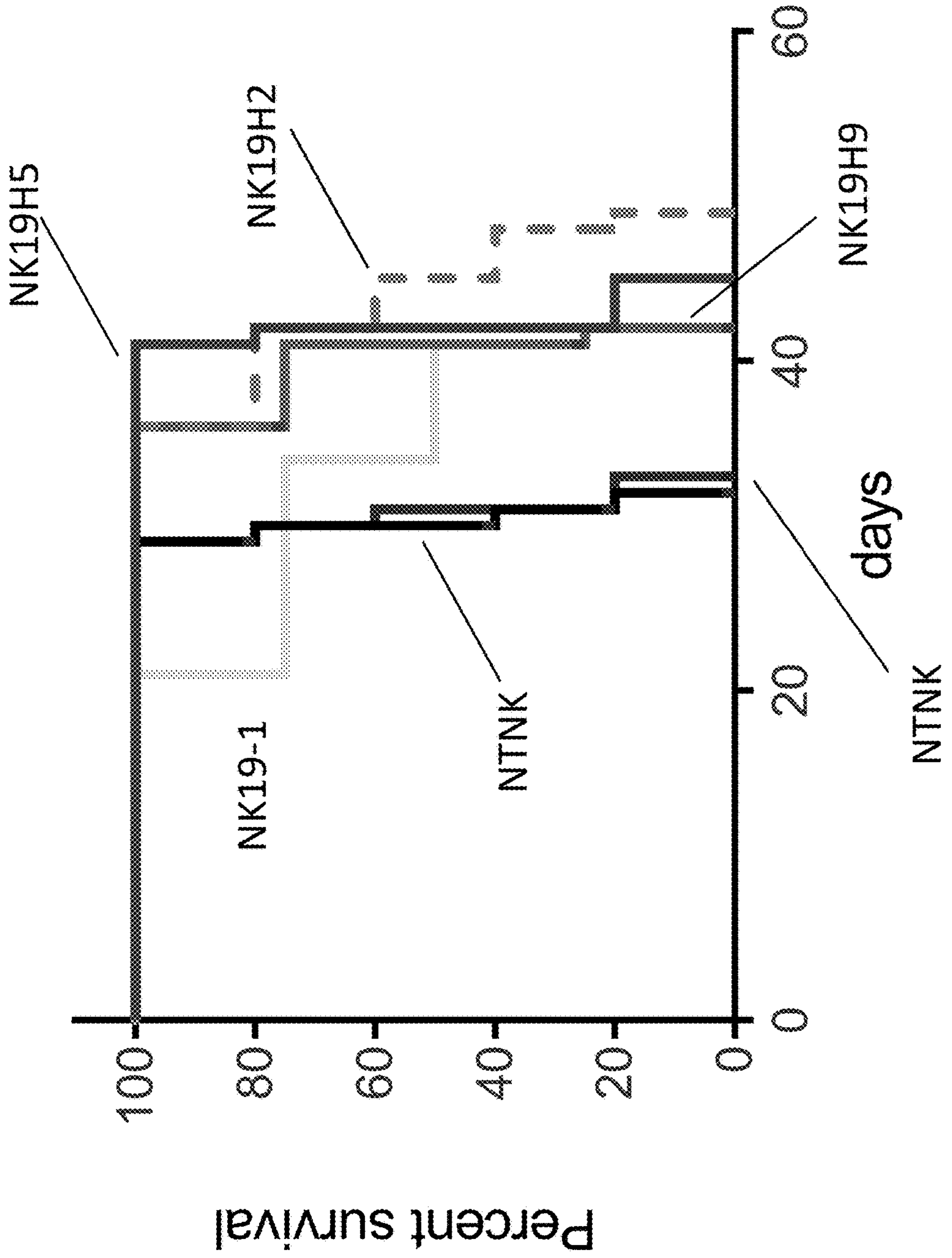
Figure 29E:
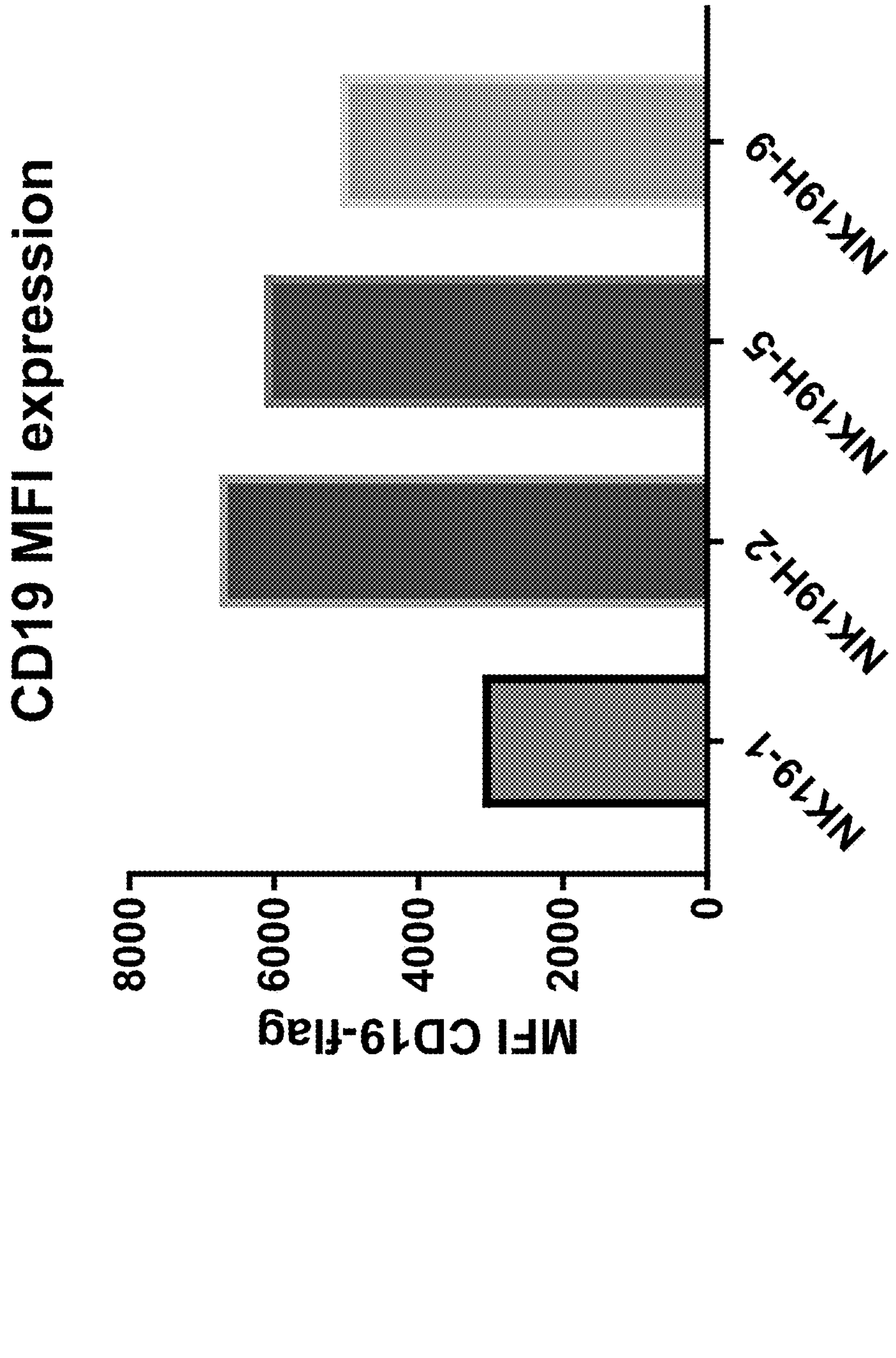

Further experiments were conducted to evaluate humanized CD19 CAR constructs as disclosed herein. FIG. 29A shows a schematic of the experimental protocol. Briefly, NSG mice were injected on Day 0 with $1\times10^5$ Nalm6 cells (expressing a fluorescent reporter) intravenously. At Day 1, mice received either a PBS control injection, non-transduced K cells ("NTNK", 10M), 10 million NK cells expressing the non-humanized NK19-1 CAR, or 10 million NK cells expressing one of various humanized CD19 CAR constructs. Blood collection and fluorescent imaging were performed as indicated. Bioluminescence data is shown in FIG. 29B. As shown, the injection of NK cells expressing any CD19 CAR construct resulted in a reduced progression of Nalm6 growth. The humanized constructs tested (NK19-H2, NK19-H5, and NK19H-9) each showed significant delay in Nalm6 growth compared to controls. FIG. 29C is a line graph depicting the measured bioluminescence over 31 days. As shown, each of the humanized constructs tested in this experiment showed reduced tumor progression as compared to controls, and slightly reduced as compared to non-humanized NK19-1. FIG. 29D shows a survival curve that reflects the reduction in tumor progression, with the mice treated with NK19-1 or any of the selected humanized constructs surviving longer than the control groups. FIG. 29E shows data related to an evaluation of the expression of each of the humanized constructs on the NK cells. As shown, each of the humanized constructs expressed more robustly than the non-humanized NK19-1 construct. In accordance with several embodiments disclosed herein, the use of a humanized construct results in a more efficacious therapeutic, at least in part due to the enhanced expression (and/or activity) of the CAR by the NK cells.

Figures 30A, 30B:
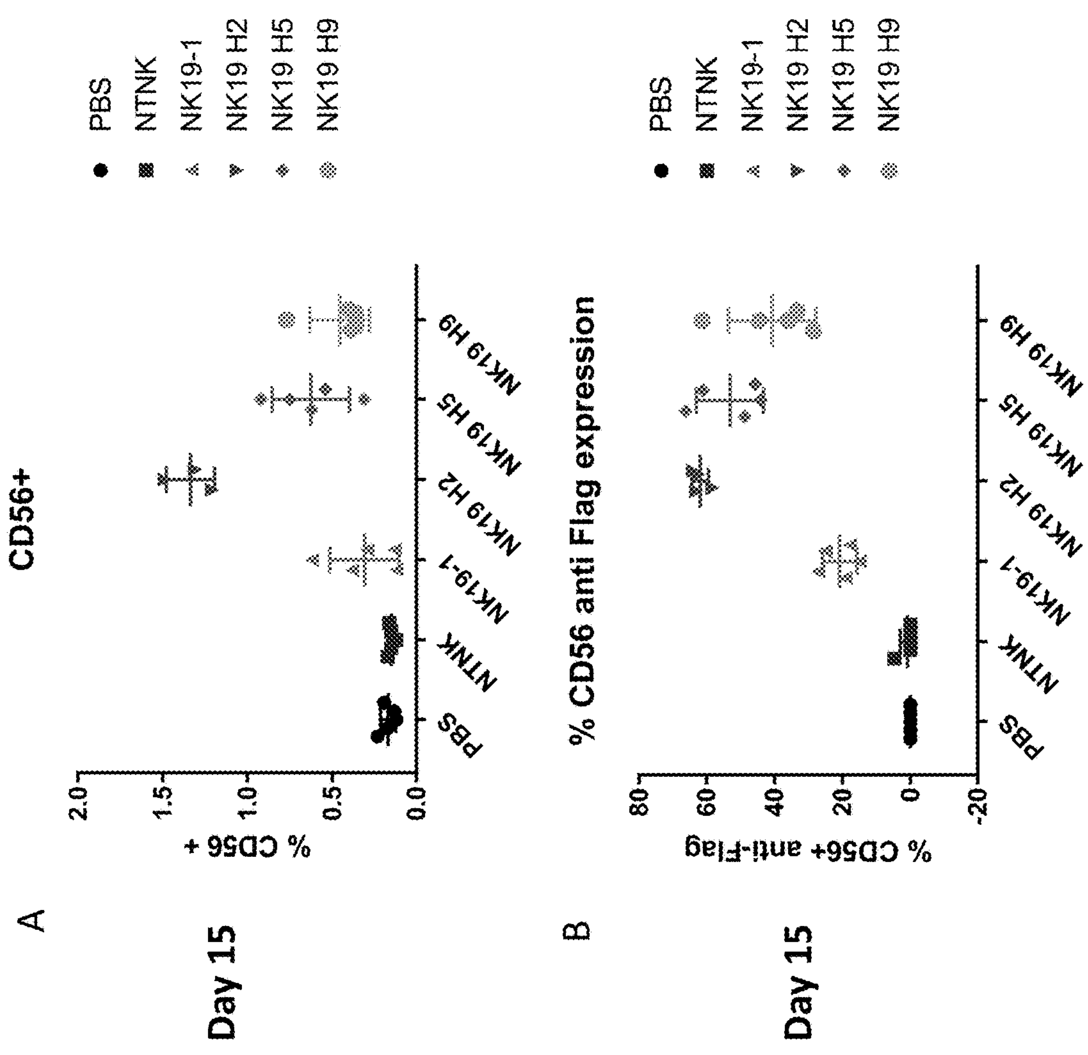
FIGS. 30A-30F relate to expression of the indicated CD19-directed CAR constructs.
Figures 30C, 30D:
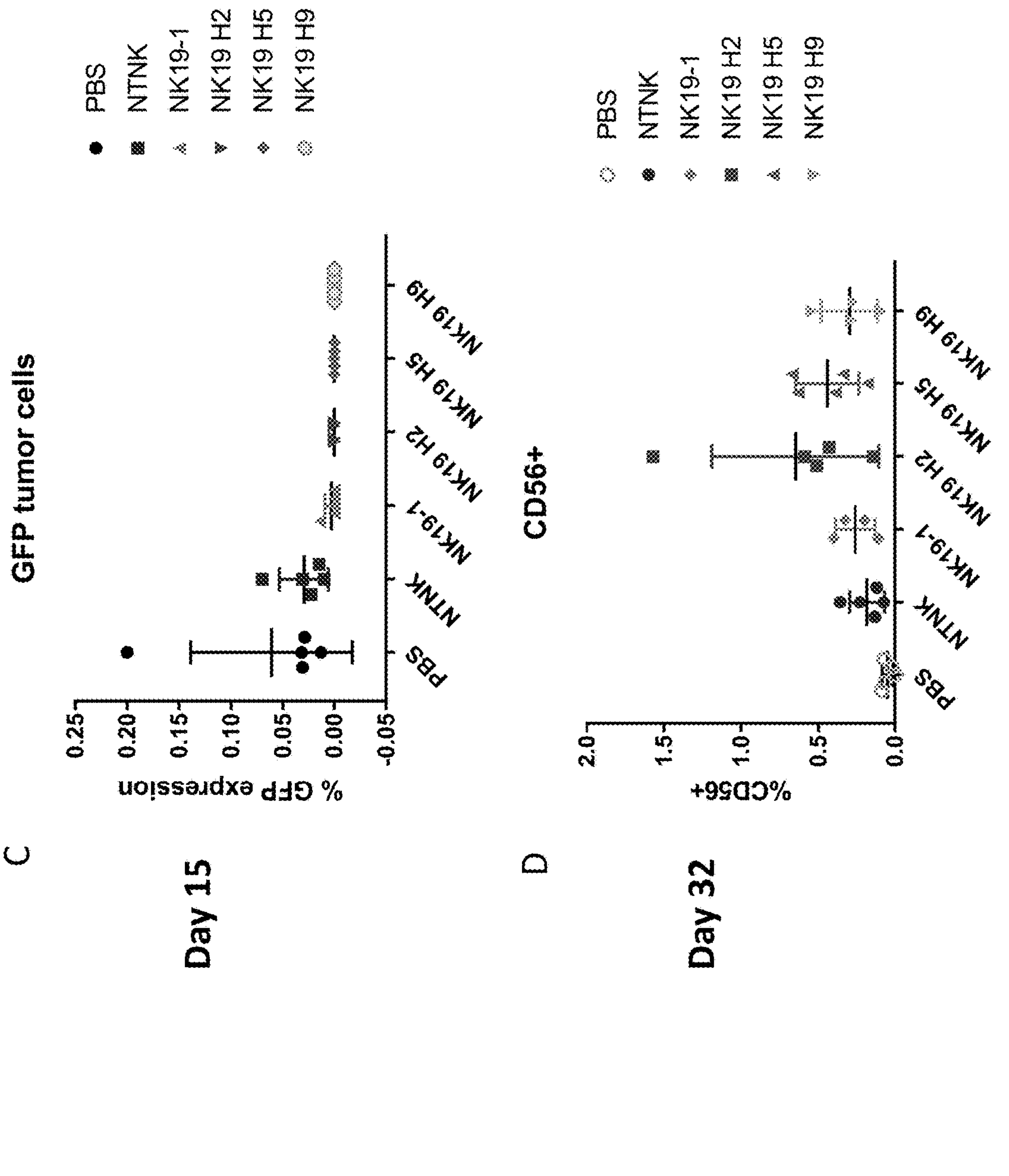
Figures 30E, 30F:
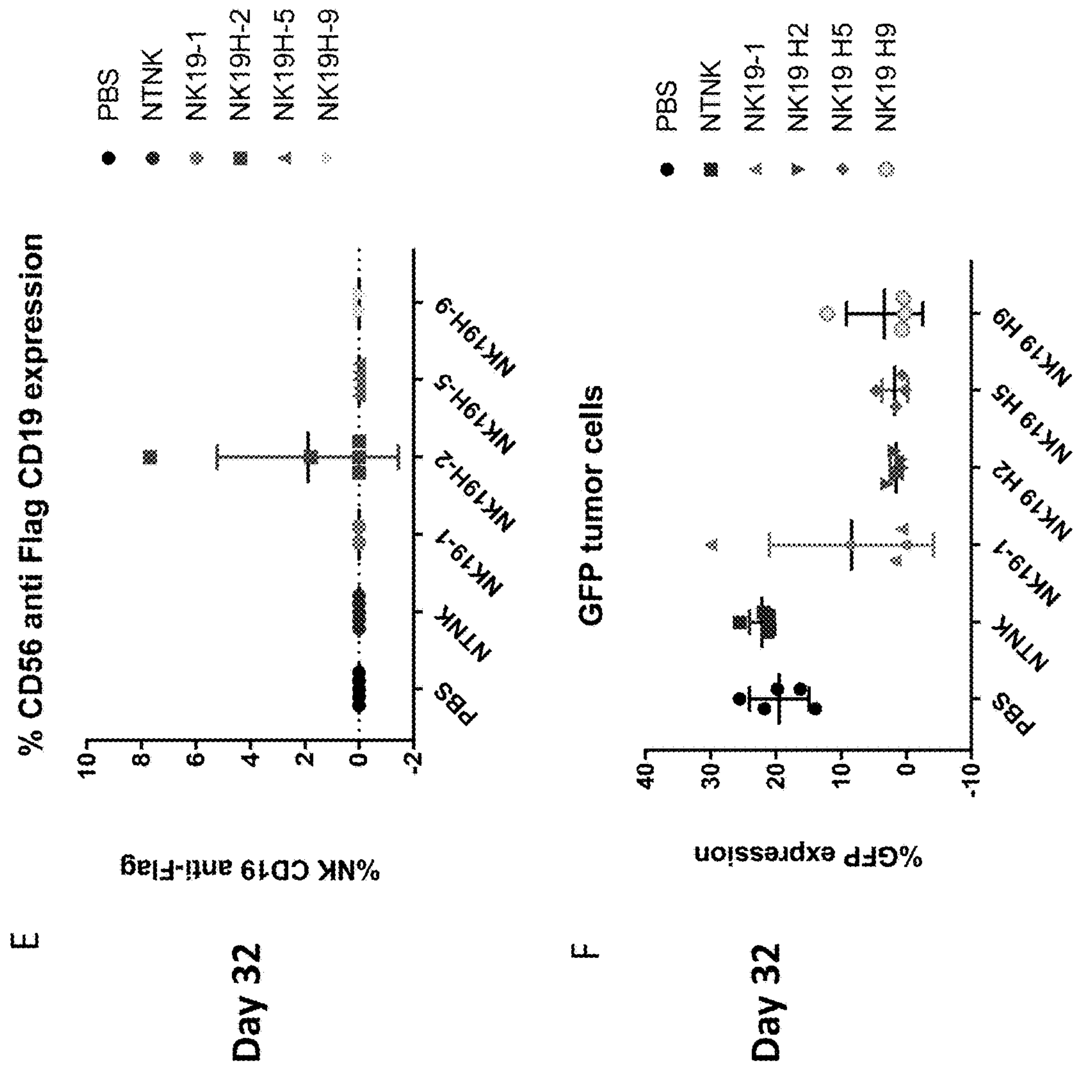

FIGS. 30A-30F relate to characteristics of cells in the blood of the mice treated with the indicated constructs at various time points during the experiment. FIG. 30A shows the percentage of human CD56+ cells in the peripheral blood of the mice, which represents the survival of the administered NK cells through the first fifteen days of the experiment. Each of the experimental groups exhibit a higher percentage of cells, with the NK19-H2 construct exhibiting the most persistence of those tested. FIG. 30B shows similar data, based on the detection of the flag expression tag used in these constructs (though, in several embodiments, no tag is used). These data show that the humanized constructs are expressed at greater levels than the non-humanized constructs. FIG. 30C shows the detection of GFP positive tumor cells after 15 days. The CAR-expressing NK cells show nearly zero GFP expression, reflective of their inhibition of Nalm6 growth at Day 15. FIGS. 30D-30F show similar data at Day 32. These data show that the NK cells expressing humanized CD19 CAR constructs make up a greater percentage of the cells present in the peripheral blood of the mice tested, which is consistent with the increased efficacy of these constructs at controlling tumor growth at later time points. FIG. 30F shows that there is little difference in expression among the humanized CD19 CAR constructs at day 32. FIG. 32F reflects the enhanced ability of NK cells expressing the humanized CD19 CAR constructs at controlling tumor growth, with the detected GFP-positive cells being lower in the humanized treatment groups, even as compared to the animals receiving NK19-1.

In several embodiments, the enhanced efficacy is due, at least in part, to the enhanced expression of the humanized CD19 CAR constructs.

Example 9

Figures 31A, 31B:
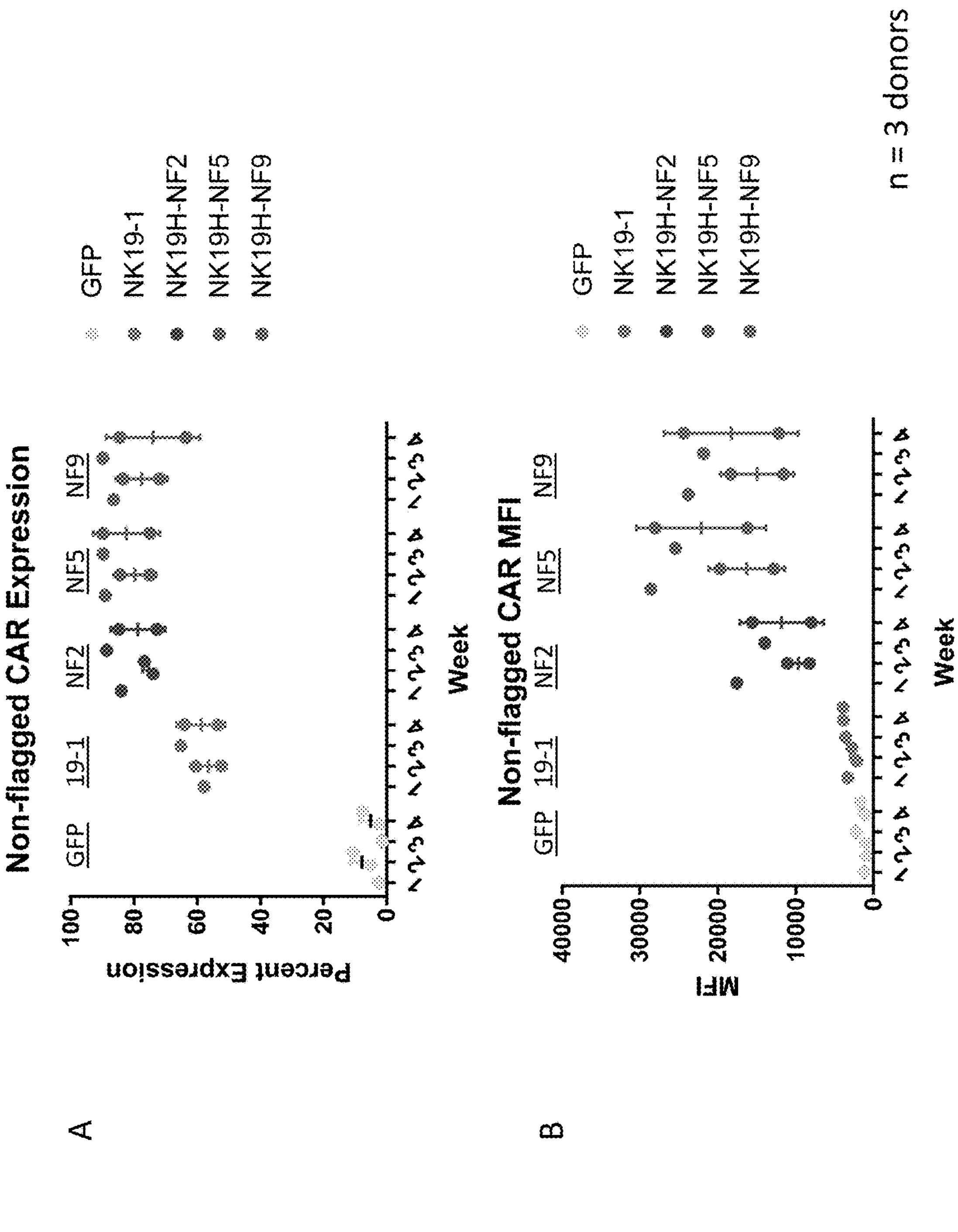
FIGS. 31A-31B show data related to the expression of non-tagged CD19 CAR constructs. As discussed herein, in several embodiments the CD19 CAR constructs comprise a Flag, or other tag, for detection purposes. However, all constructs disclosed herein with a tag are also included herein without a tag.

As discussed above, in some embodiments, CAR constructs comprise a detection tag. However, in several embodiments, no tag is used. Experiments were performed in order to evaluate the expression of non-flagged humanized CARS. This experiment employed NK19H-NK-2, -5 and -9 as non-limiting examples of non-flagged humanized CARs. FIGS. 31A-31B show expression data (percent expression in 31A, mean fluorescence in 31B) of the indicated construct by NK cells from three different donors, measured each week for 4 weeks. These data demonstrate that non-flagged versions of the CD19 CAR constructs as provided for herein express relatively similarly to one another, but more robustly than non-humanized constructs. Each of the non-flagged humanized constructs were expressed on at least about 70-80% of the NK cells.

Example 10

Figures 32A, 32B:
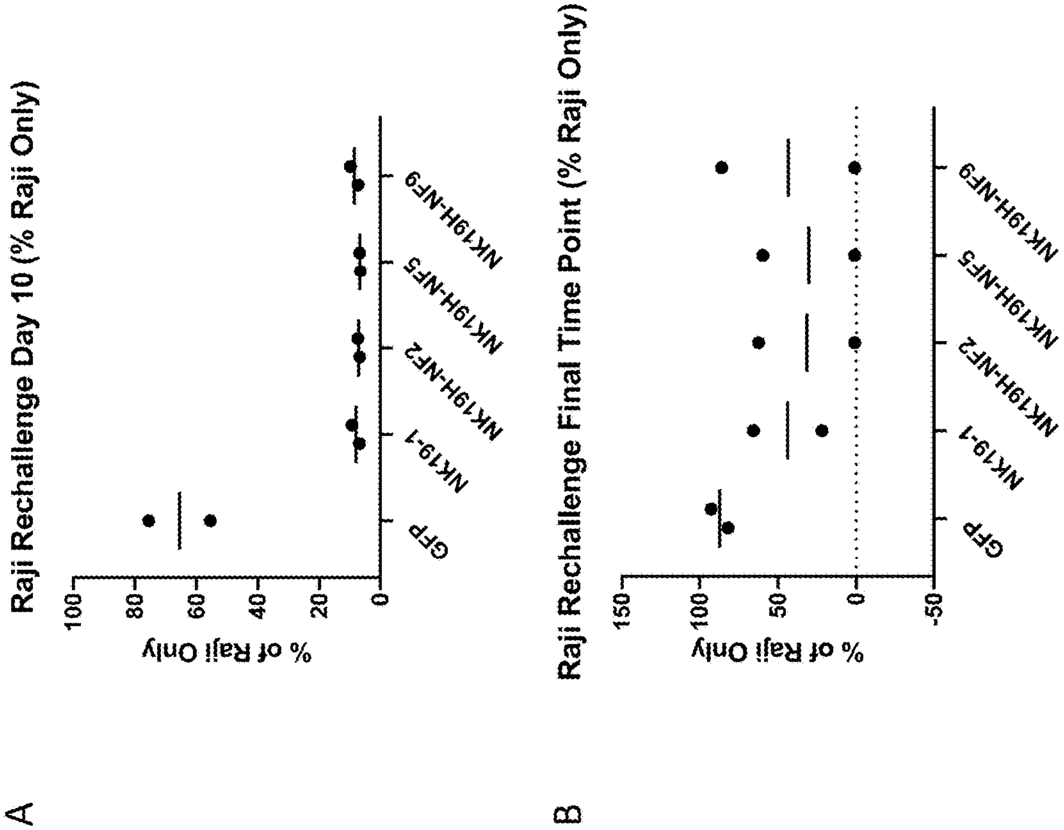
FIGS. 32A-32D show data related to an in vitro re-challenge experiment in which a first population of tumor cells were co-cultured with NK cells expressing the indicated constructs and the NK cells were "rechallenged" with an additional bolus of tumor cells.
Figures 32C, 32D:
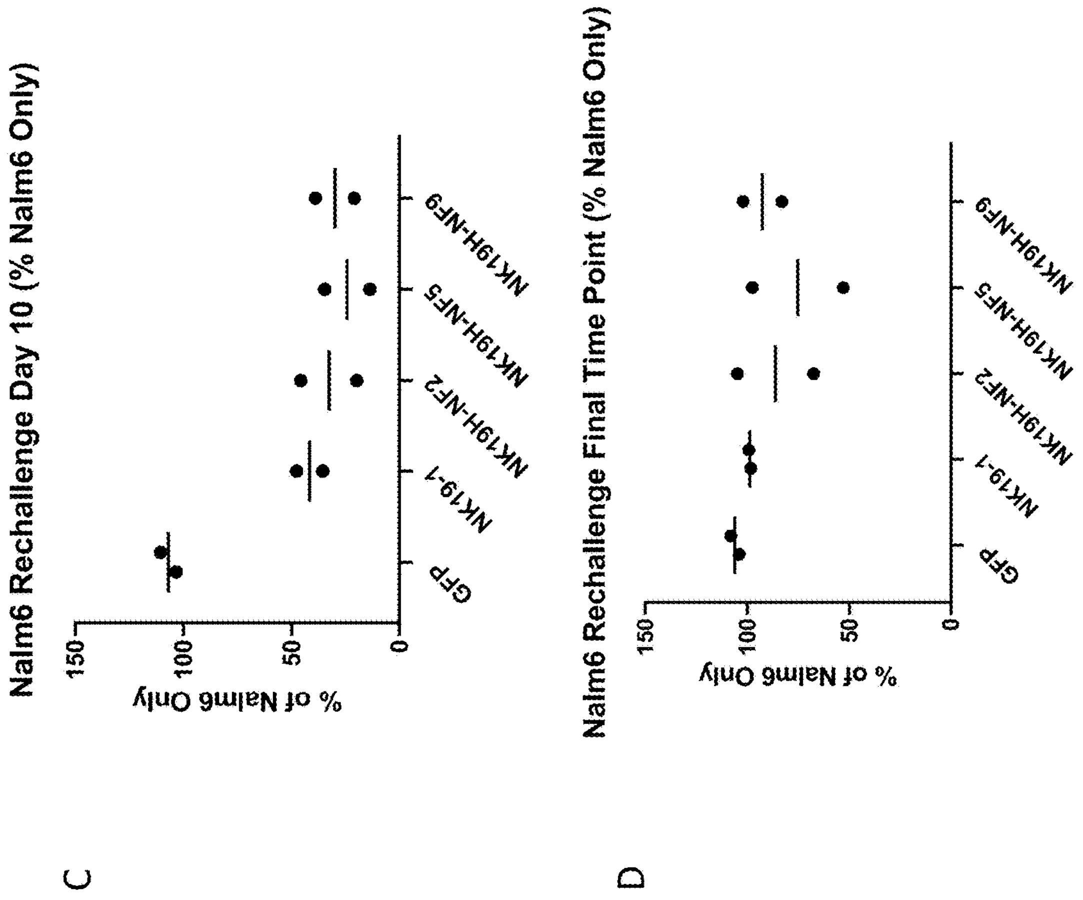
Figures 33A, 33B:
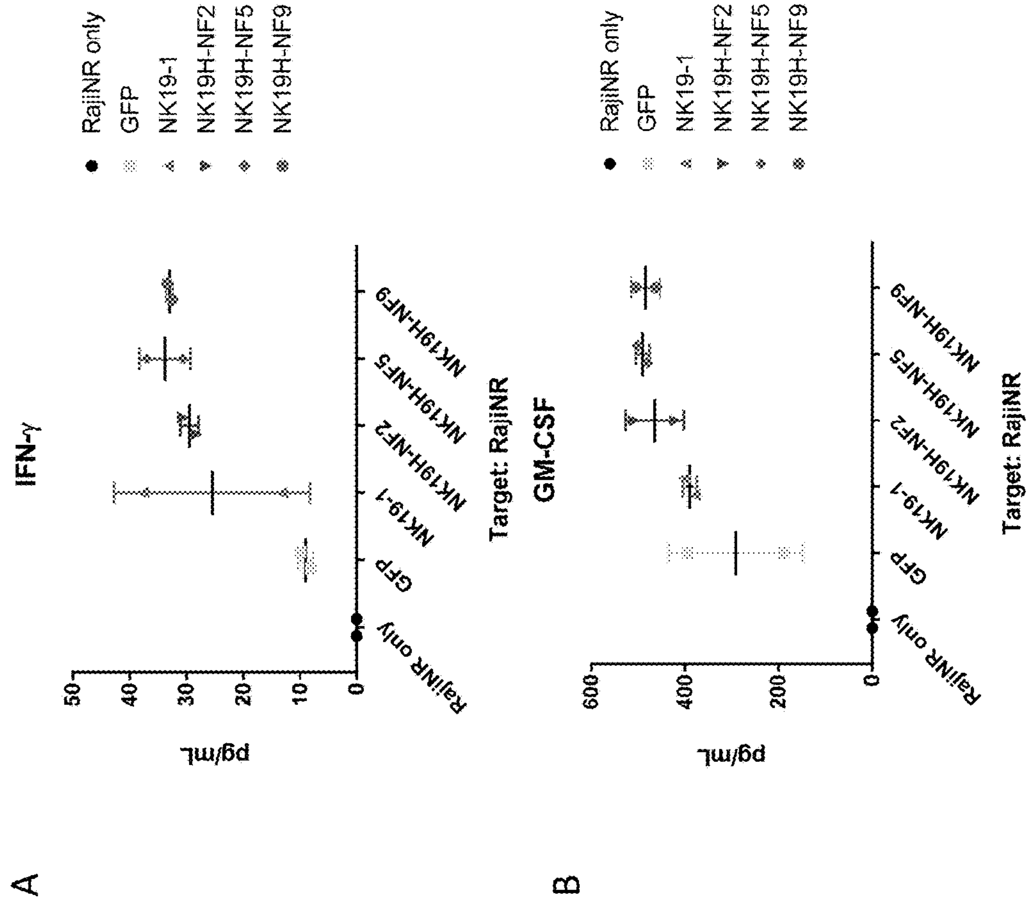
FIGS. 33A-33J relate to evaluation of cytokine production by NK cells expressing the indicated constructs.
Figures 33C, 33D:
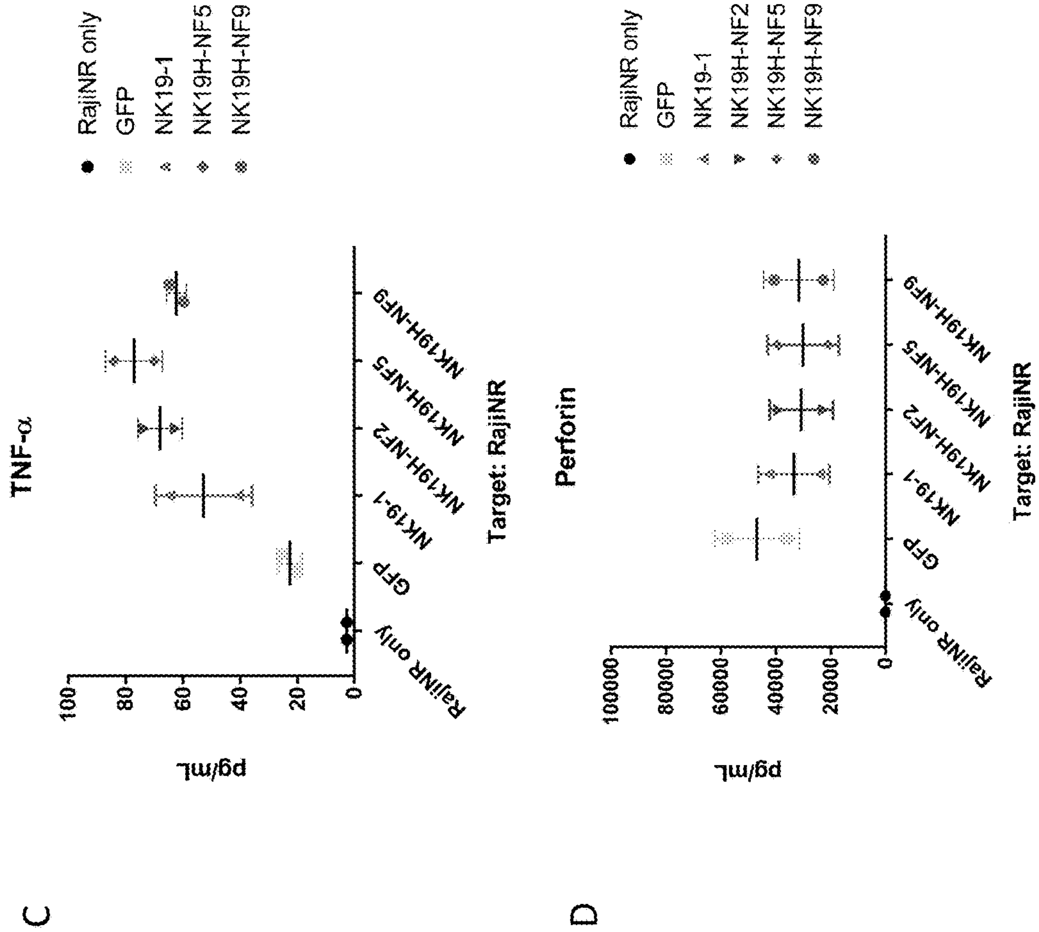
Figures 33E, 33F:
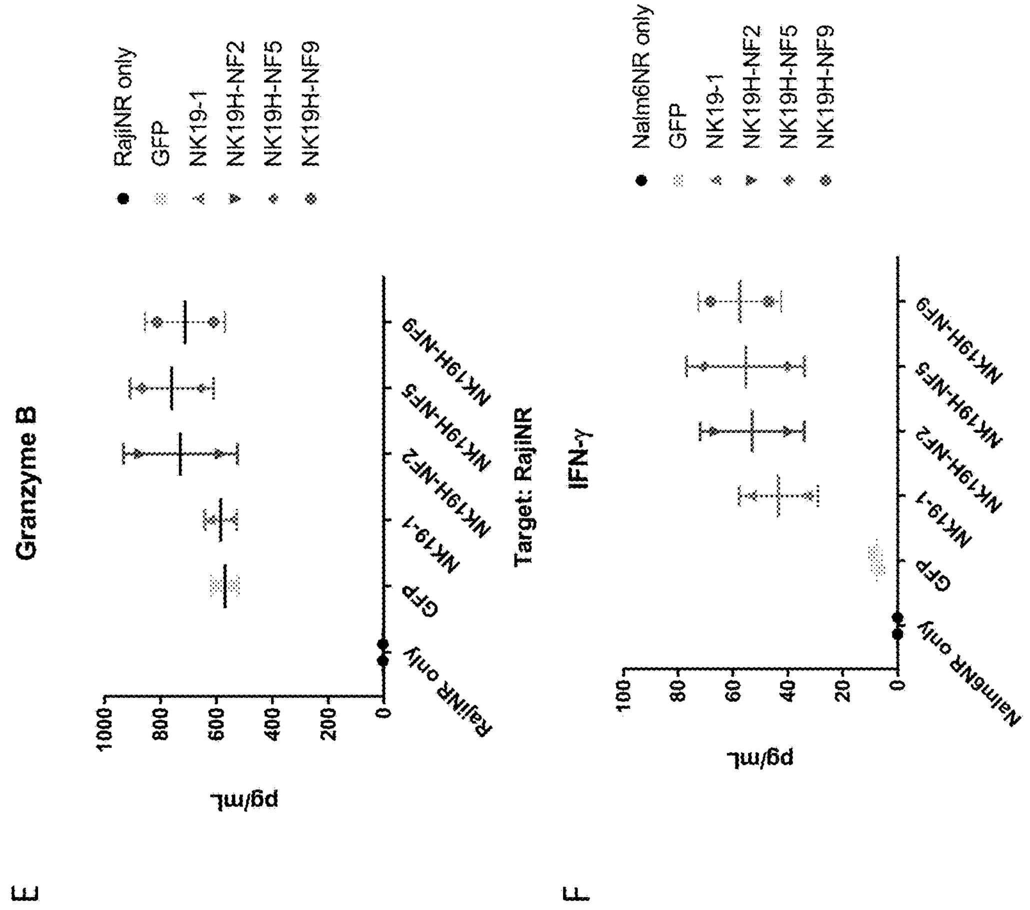
Figures 33G, 33H:
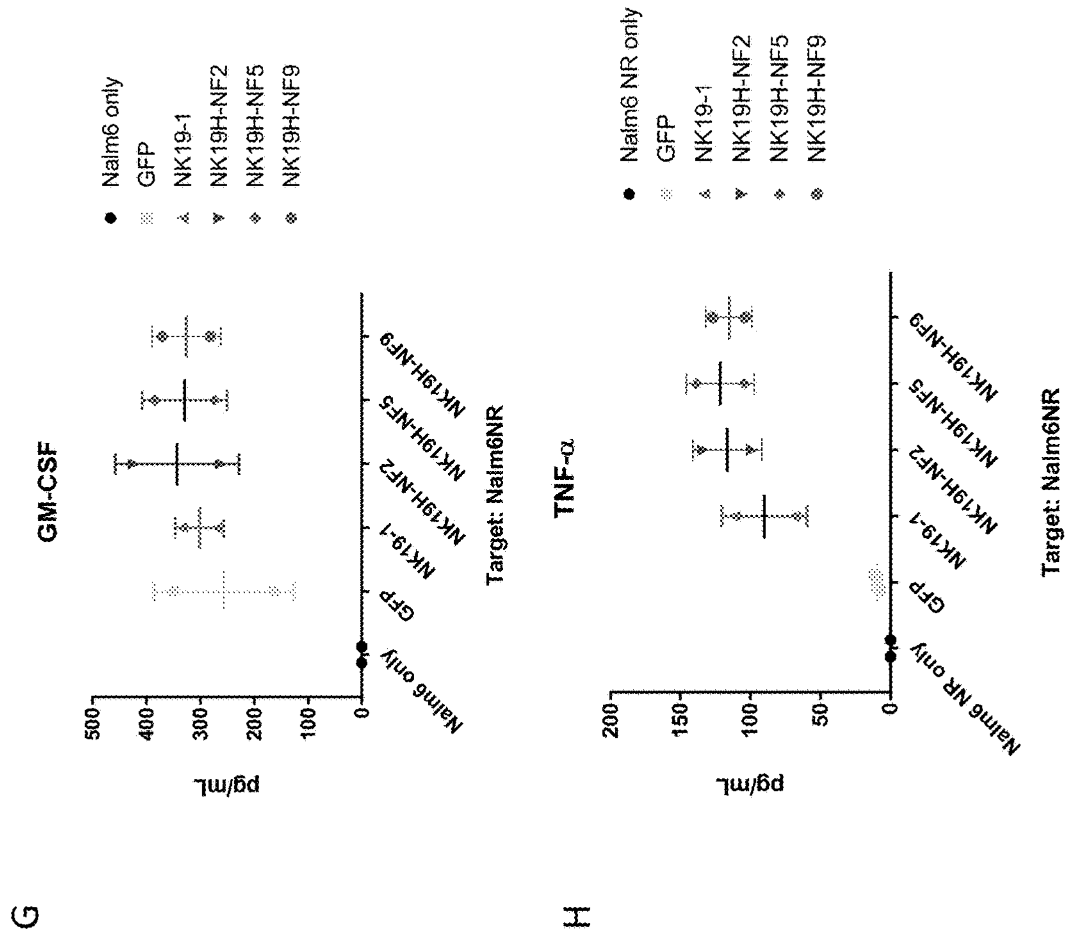
Figures 33I, 33J:
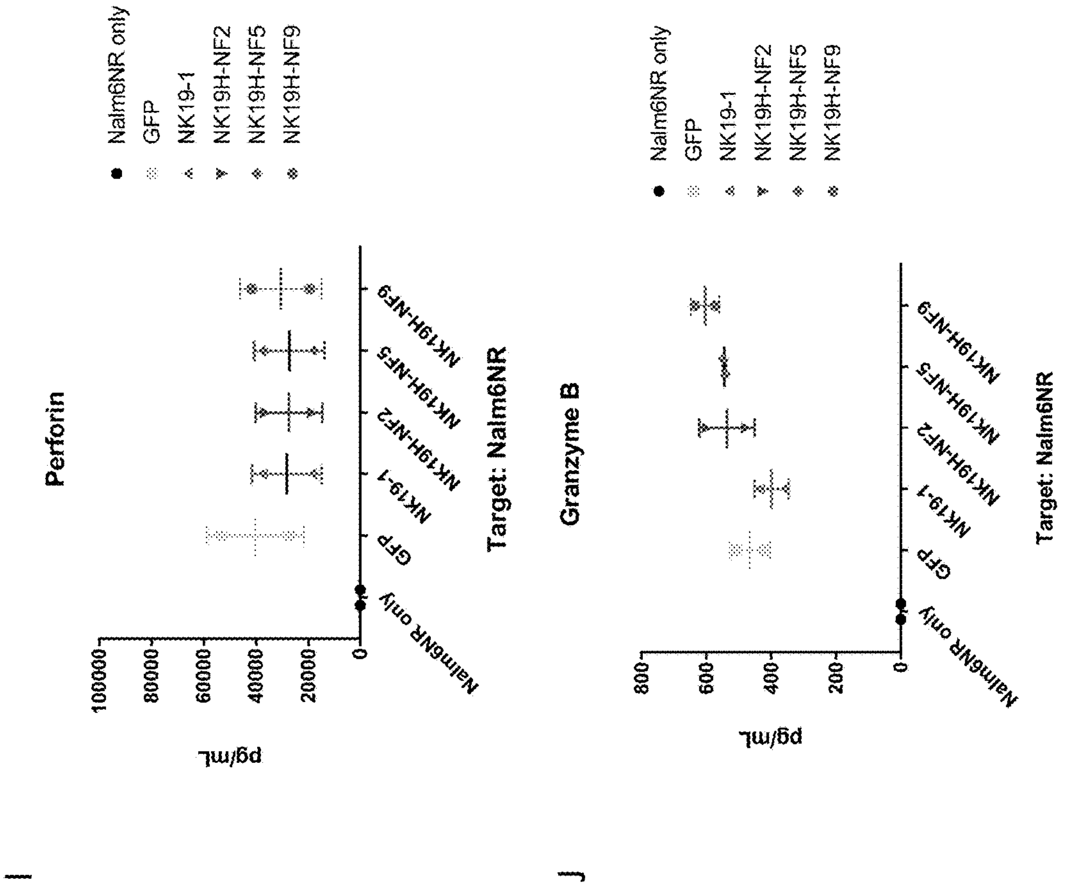

Experiments to evaluate the cytotoxicity of NK cells expressing humanized, non-flagged CD19 CAR constructs were performed. An in vitro re-challenge assay was performed as described above, using Raji cells (FIG. 32A-32B) or Nalm6 cells (FIGS. 32C-32D) as the target cell. FIG. 32A shows the percent of Raji cells co-cultured with the indicated treatment, measured as a percent of the number of cells measured in a Raji-only control group at day 10 of the experiment. As shown, each of the CD19 CAR constructs, whether humanized or not, and whether tagged or not, substantially eliminated Raji cell growth through Day 10. FIG. 32B shows the final time point, and there remains limited Raji cell growth in each of the experimental groups with CD19 CARs, though the data show a small trend to greater prevention of Raji growth in with the NK19H-NF-2 and NK19H-NF-5 groups. FIGS. 32C and 32D show the corresponding data using Nalm6 cells. FIG. 32C shows that, similar to Raji cells, each of the CD19 CAR constructs, whether humanized or not, and whether tagged or not, substantially eliminated Nalm6 cell growth through 10 days. At the final time point, there was Nalm6 cell growth across all groups, though the data trends to the humanized constructs being more effective at preventing growth.

Figure 34:
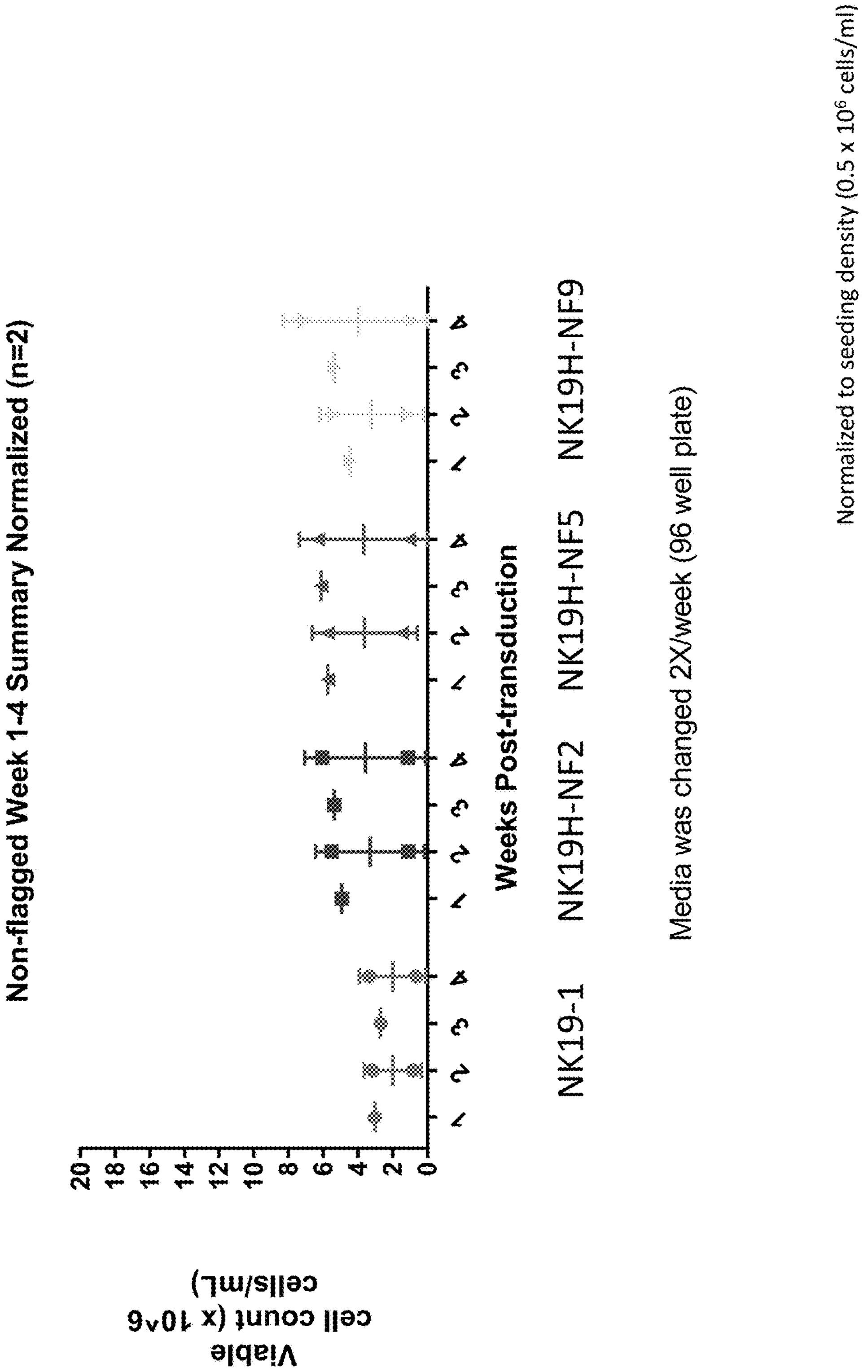
FIG. 34 shows data related to the viability of NK cells expressing humanized non-tagged CD19 CAR constructs over four weeks post-transduction.

FIGS. 33A-33J relate to the detected cytokine profile for NK cells expressing the indicated constructs. As discussed above, the culture media from each treatment group was assayed for interferon gamma (33A/33F), GM-CSF (33B/33G), TNF-alpha (33C/33H), Perforin (33D/33I), and Granzyme B (33E/33J). FIGS. 33A-33E show data from the Raji cell rechallenge, while 33F-33J show data from the Nalm6 rechallenge. As shown, the non-flagged, humanized CD19 CAR expressing NK cells release similar levels of similar amount of IFN-gamma into the media, with those levels being slightly greater than the amount released by NK cells expressing the non-humanized NK19-1 CAR. Similarly, GM-CSF release was fairly consistent among the humanized, non-flagged CAR bearing NK cells, and at a level slightly about the NK19-1 expressing cells. TNF-alpha release showed a similar pattern, while perforin release was consistent among all the CD19 CAR expressing NK cells, and at a level below control. Lastly in the Raji cells, granzyme B showed a similar degree of release for the non-flagged, humanized CD19 CARs, at a level slightly above the NK19-1 expressing cells. For the most part, the data collected from the Nalm6 experiment showed similar patterns. According to several embodiments, the greater degree of release of cytotoxicity-mediating cytokines leads to a more effective therapeutic. In some embodiments, the greater degree of cytokine release is due, at least in part, to the enhanced expression of the non-flagged, humanized CD19 CAR constructs by the NK cells and/or due, at least in part, to the enhanced persistence of the NK cells expressing the non-flagged, humanized CD19 CAR constructs. Further supporting these concepts, FIG. 34 shows data related to the persistence of NK cells expressing the indicated non-flagged, humanized constructs over four weeks in culture, as compared to NK cells expressing NK19-1. While the overall cell counts appear similar among the NK cells expressing the humanized constructs, the cell counts show the same basic pattern as the cytokines, that is, slightly greater than NK cells expressing non-humanized NK19-1.

Example 11

Figure 35A:
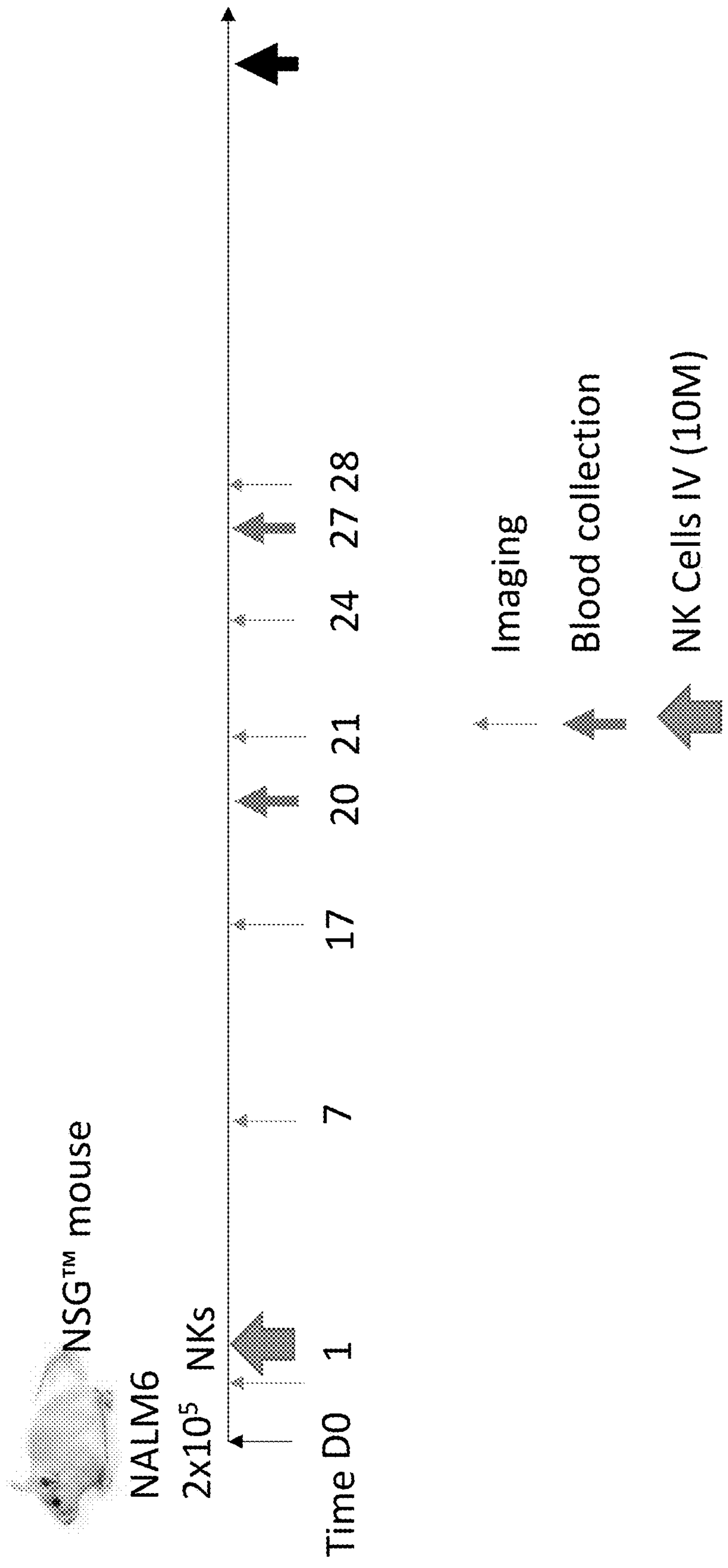
FIGS. 35A-35D show data related to various humanized, non-tagged, CD19-directed CAR constructs and their efficacy in an in vivo model.
Figure 35B:
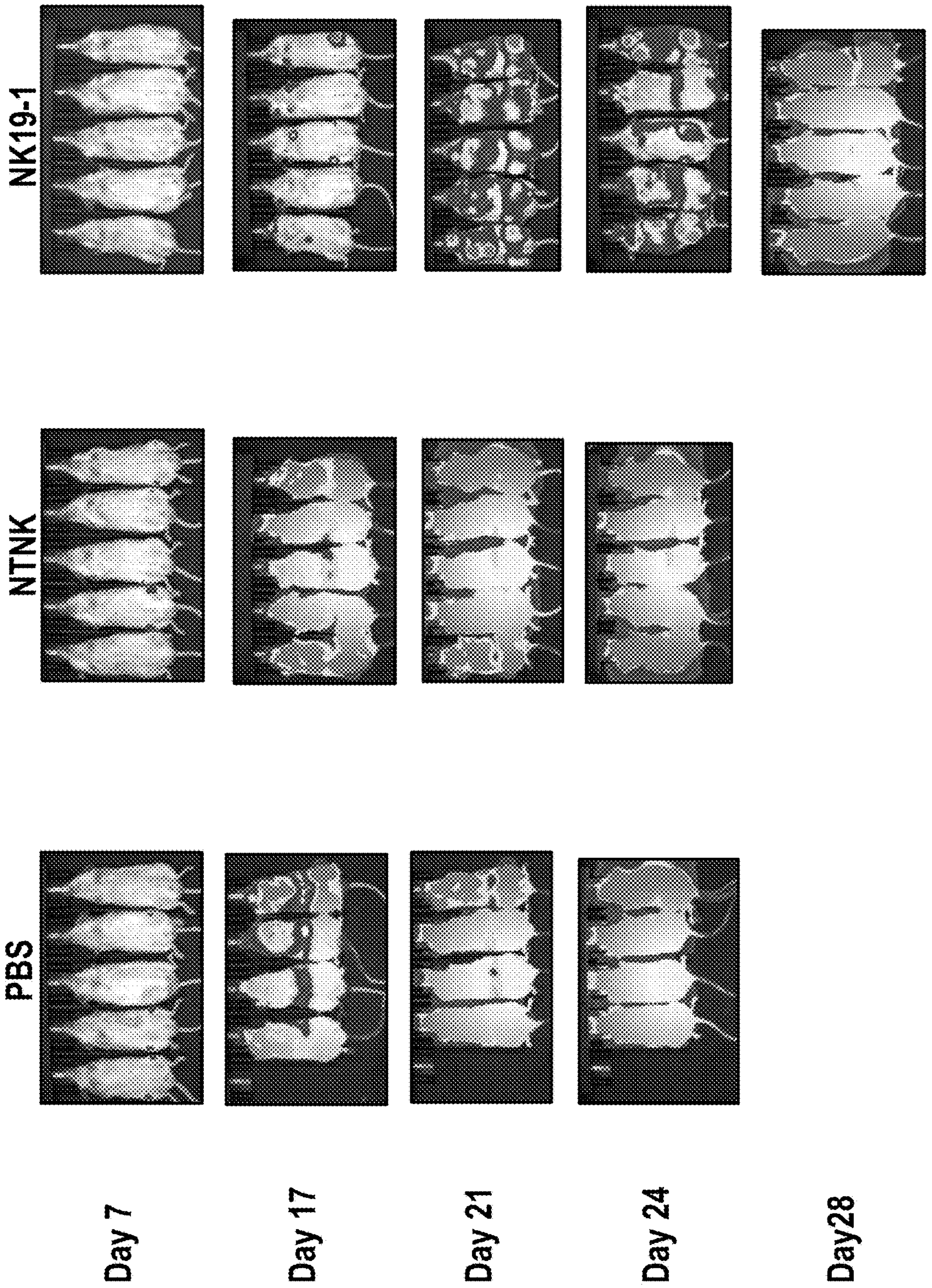
Figure 35B:
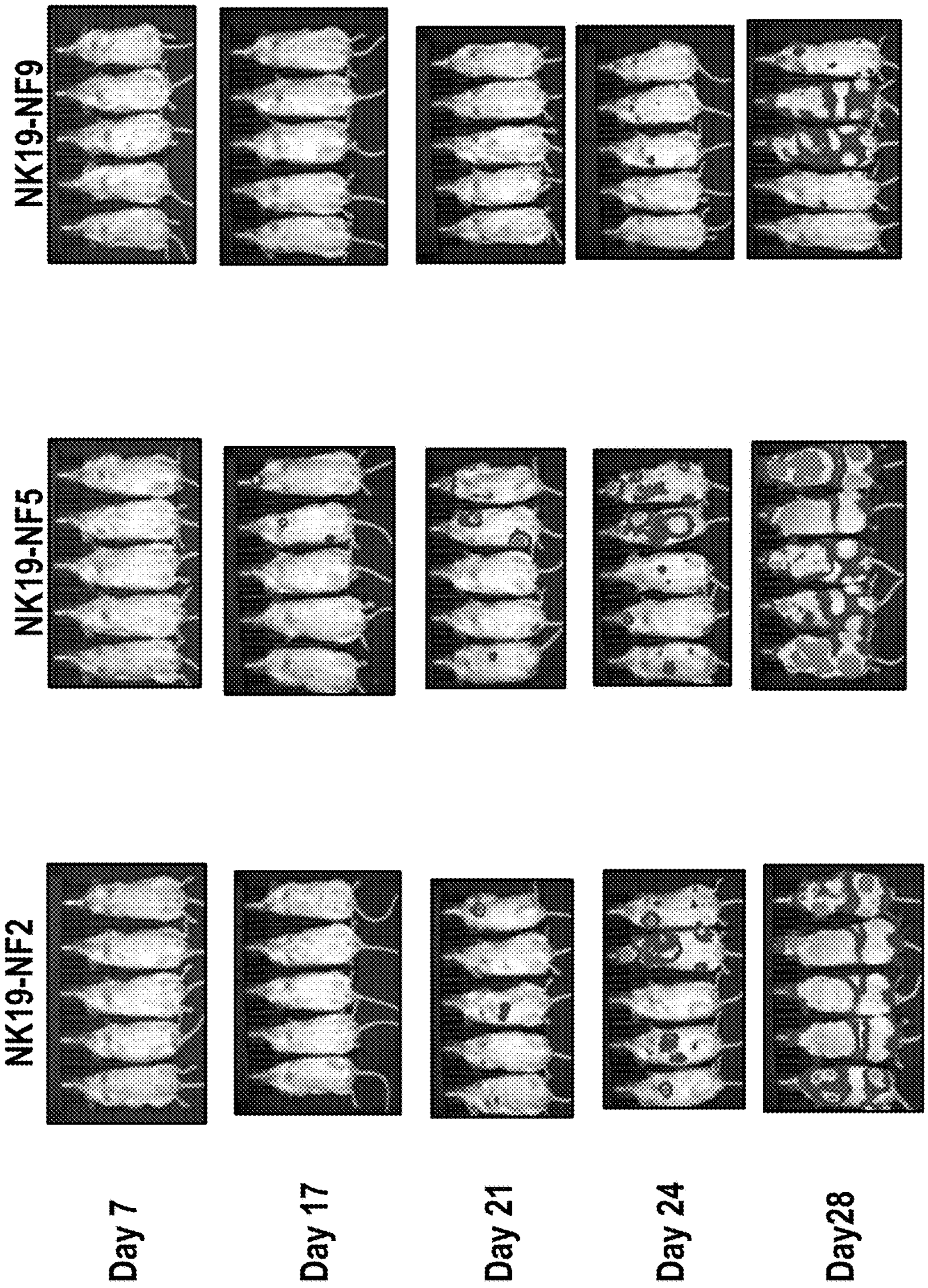
Figures 35C, 35D:
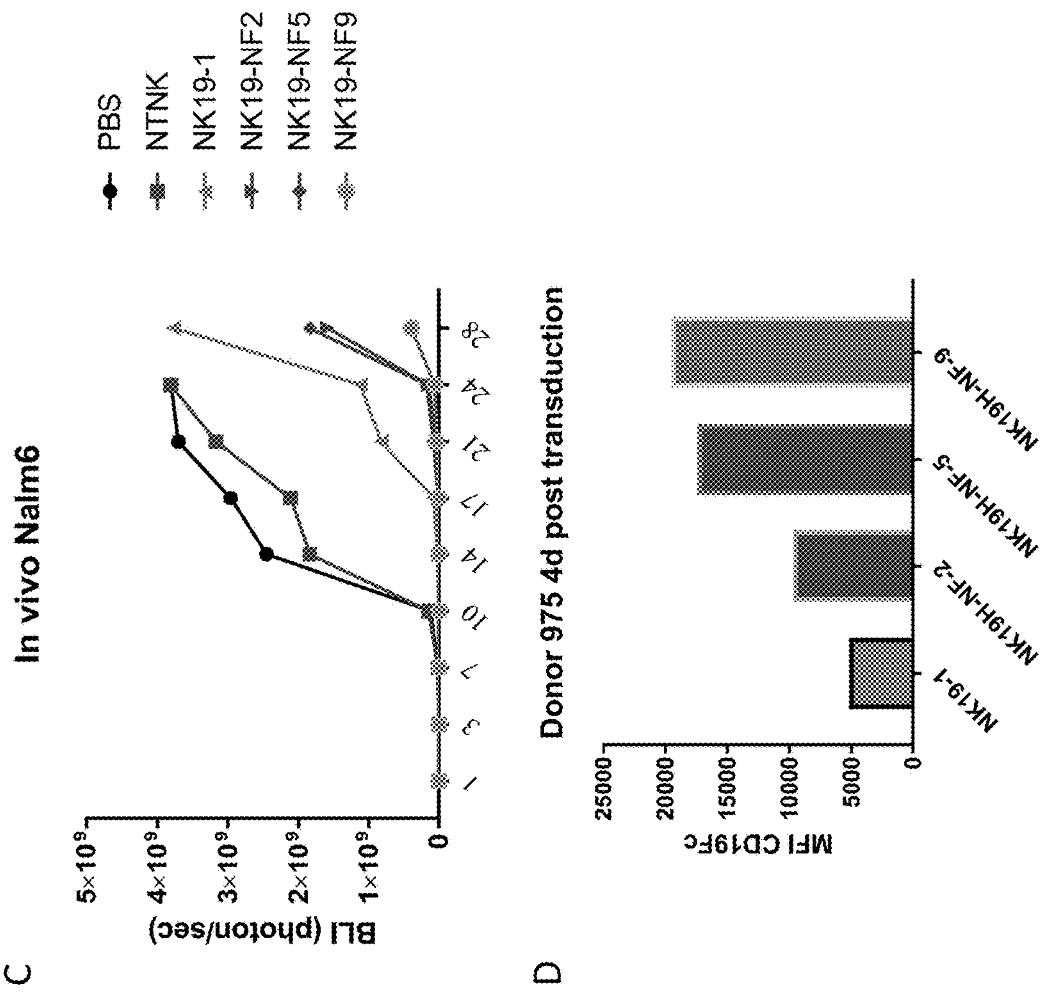
Figures 36A, 36B:
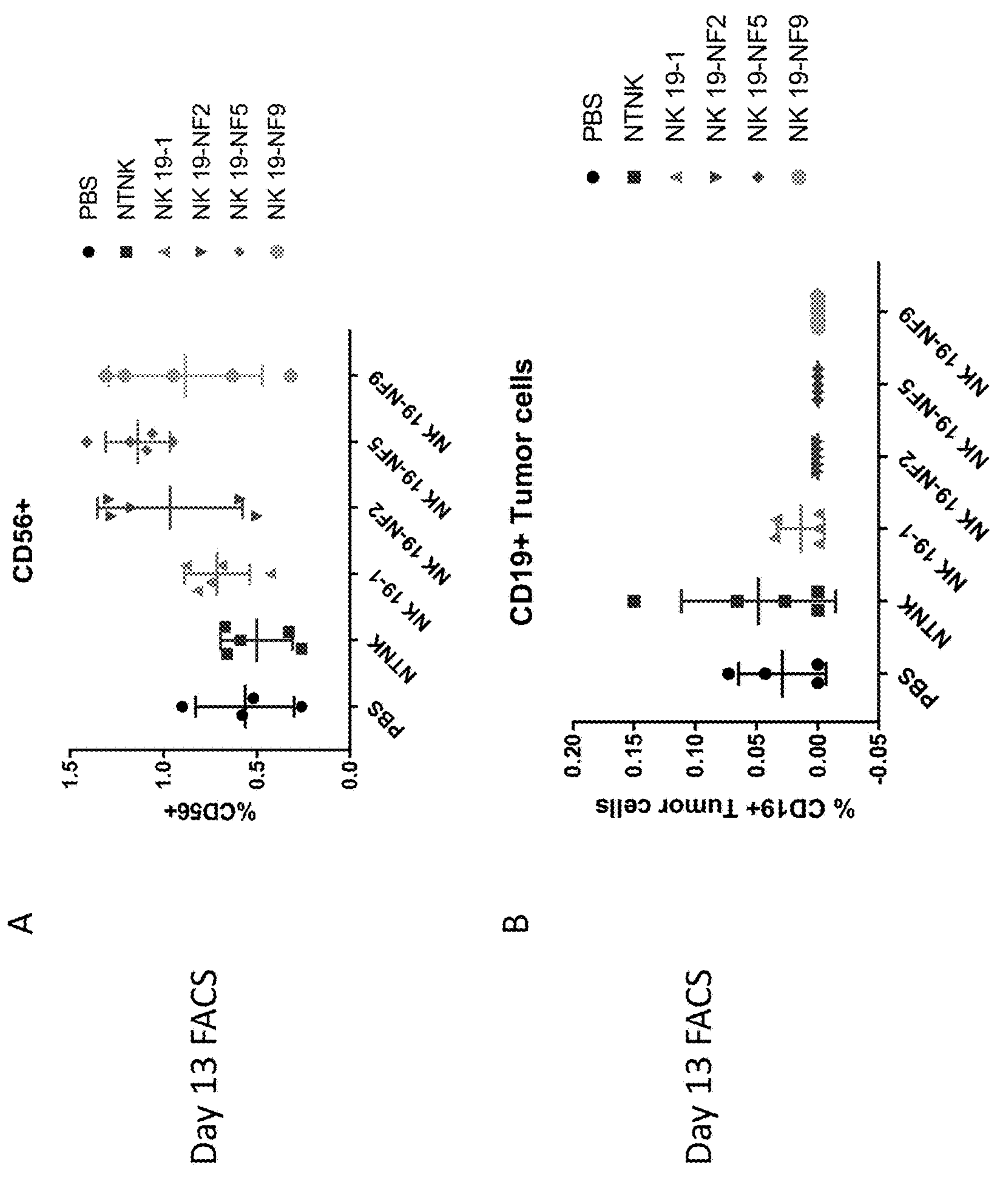
FIGS. 36A-36F relate to expression of the indicated CD19-directed CAR constructs.
Figures 36C, 36D:
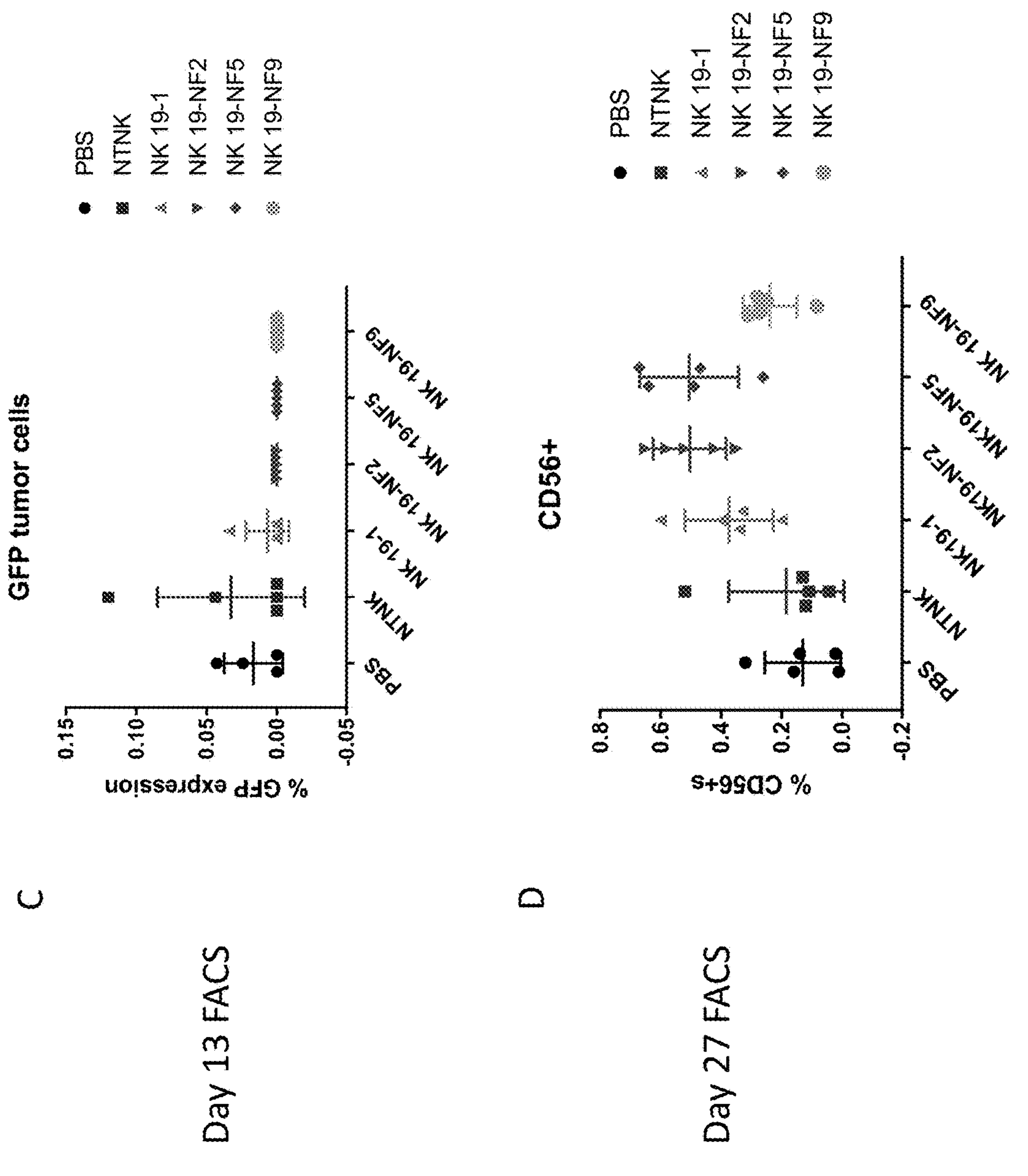
Figures 36E, 36F:
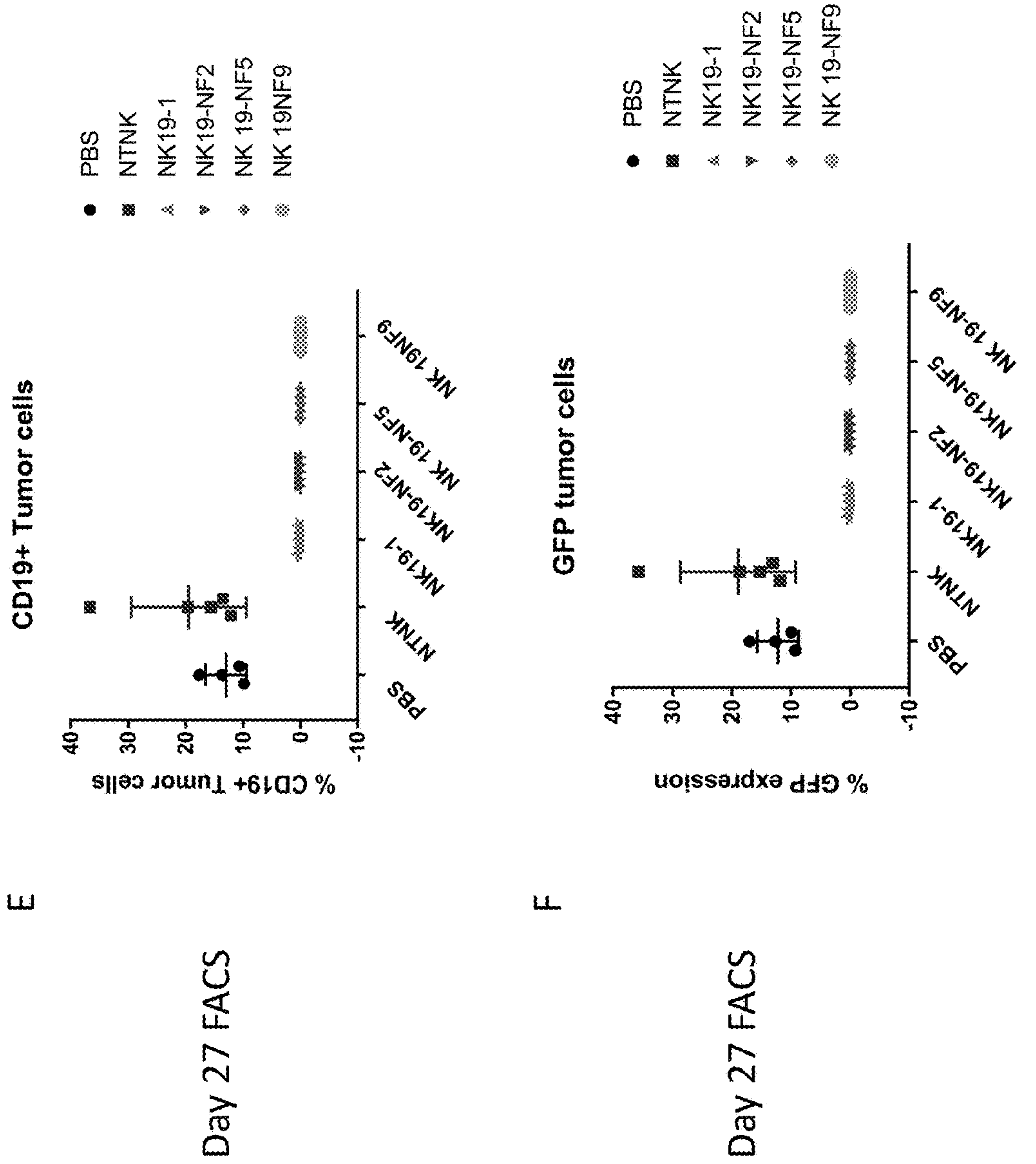

Similar to the experiments above, an in vivo assessment of the efficacy of non-flagged, humanized constructs was performed. FIG. 35A shows a schematic of the protocol used. FIG. 35B shows the in vivo bioluminescence measurements, which show that humanized, non-flagged constructs appear to slow tumor progression to a greater extent than NK cells expressing the NK19-1 construct. FIG. 35C, recapitulates the imaging data in a line graph, where the enhanced inhibition of tumor cell growth can clearly be seen when the mice received NK cells expressing any of the non-flagged, humanized CD19 CAR constructs. FIG. 35D reflects the enhanced expression of the non-flagged, humanized constructs by NK cells. FIGS. 36A-36F relate to the persistence of NK cells expressing the indicated constructs over the timeline of the experiment. FIG. 36A indicates that NK cells expressing the non-flagged, humanized CD19 CAR constructs are more persistent in vivo, making up a larger percentage of the overall CD56+ cells in the peripheral blood at Day 13. FIG. 36B demonstrates that, at Day 13, NK cells expressing any CD19 CAR inhibit tumor growth better than control, with the that NK cells expressing the non-flagged, humanized CD19 CAR constructs showing a slight advantage over the NK19-1 expressing NK cells in terms of limiting CD19+ tumor cell growth. FIG. 36C shows similar data to 36B, using GFP positive tumor cell count as the benchmark. FIG. 36D shows persistence data at day 27, wherein the NK19-NF-2 and -9 expressing NK cells have elevated population numbers compared to the other groups, indicating enhanced persistence over a longer period of time. Similar to the earlier time-point, FIGS. 36E and 36F show that the CD19-targeting CAR constructs are all effective at limiting tumor cell growth, compared to controls. According to several embodiments provided for herein, expression of a non-flagged, humanized CD19 targeting CAR by NK cells engenders those NK cells with enhanced in vivo persistence and cytotoxicity.

Example 11

Figure 37A:
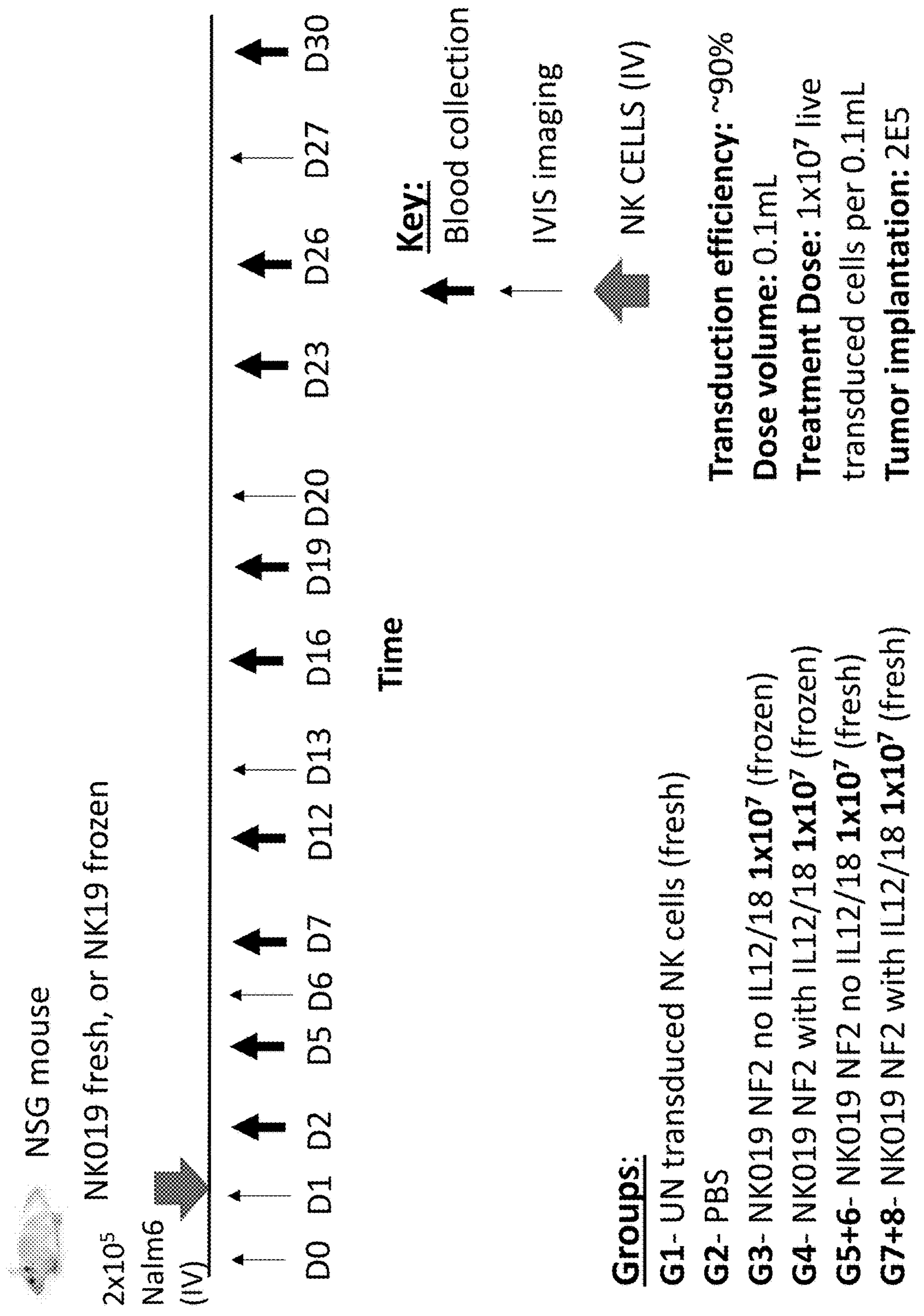
FIGS. 37A-37C relate to the in vivo efficacy of various CD19-directed CAR according to embodiments disclosed herein.
Figure 37B:
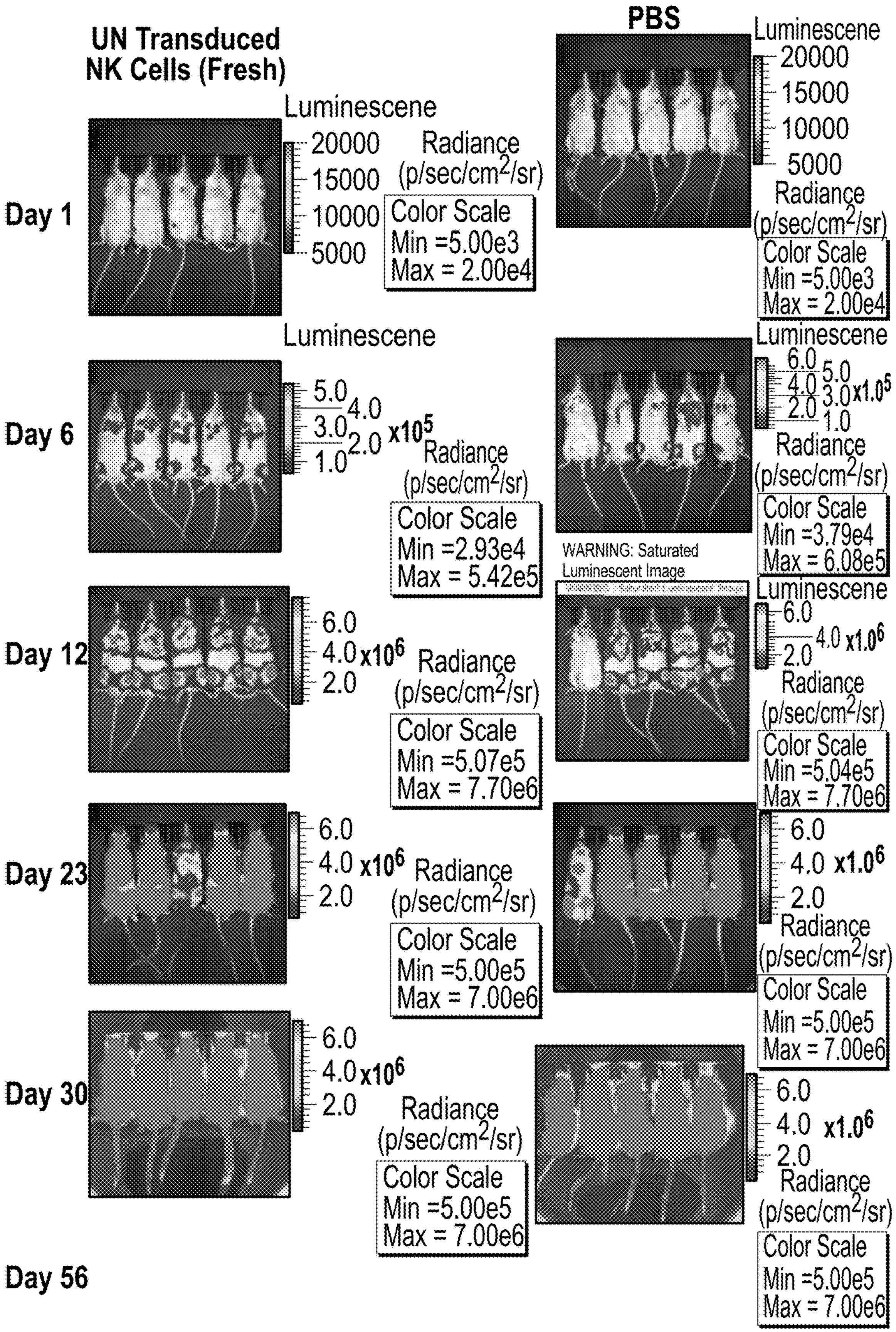
Figure 37B:
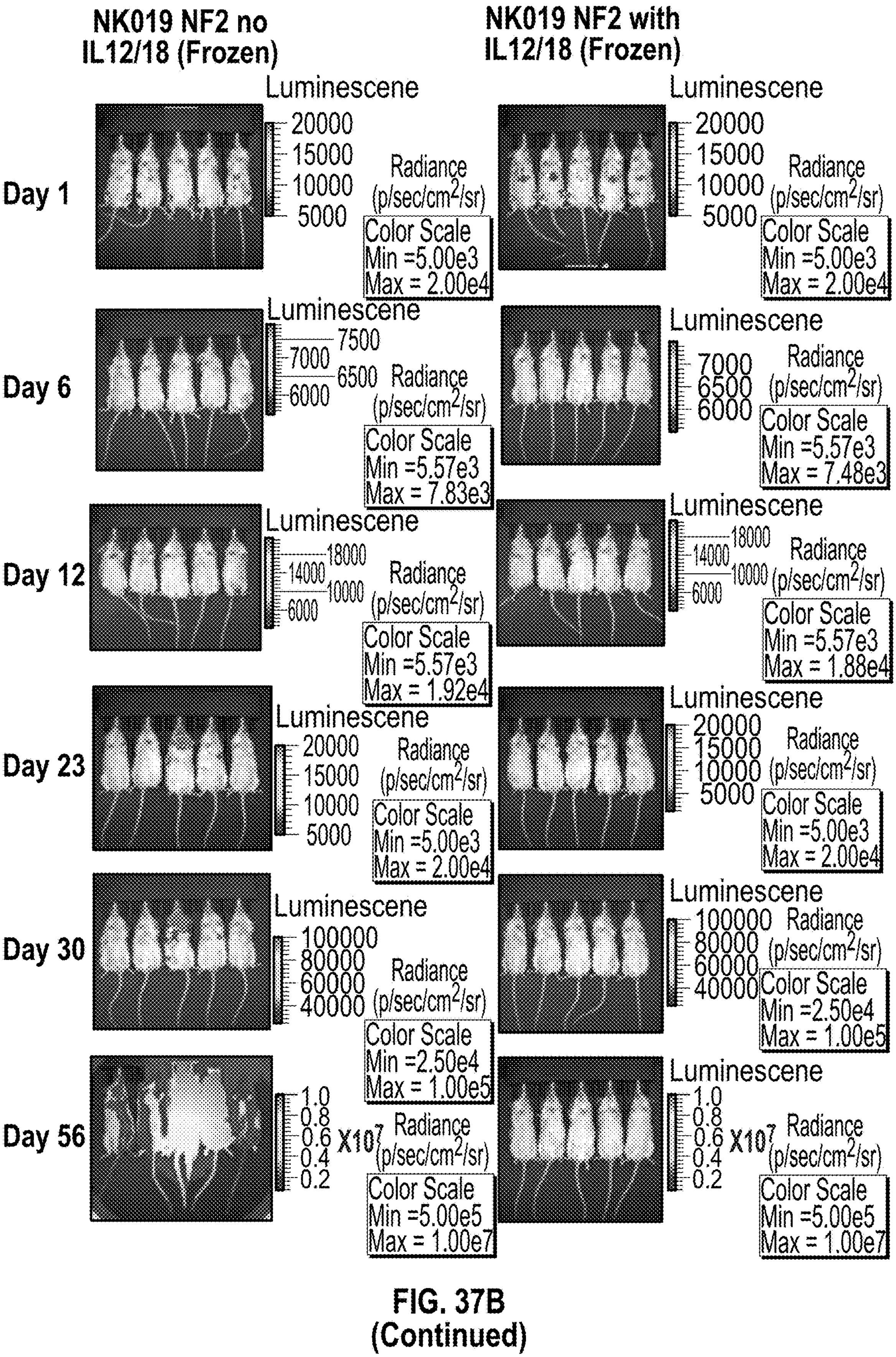
Figure 37B:
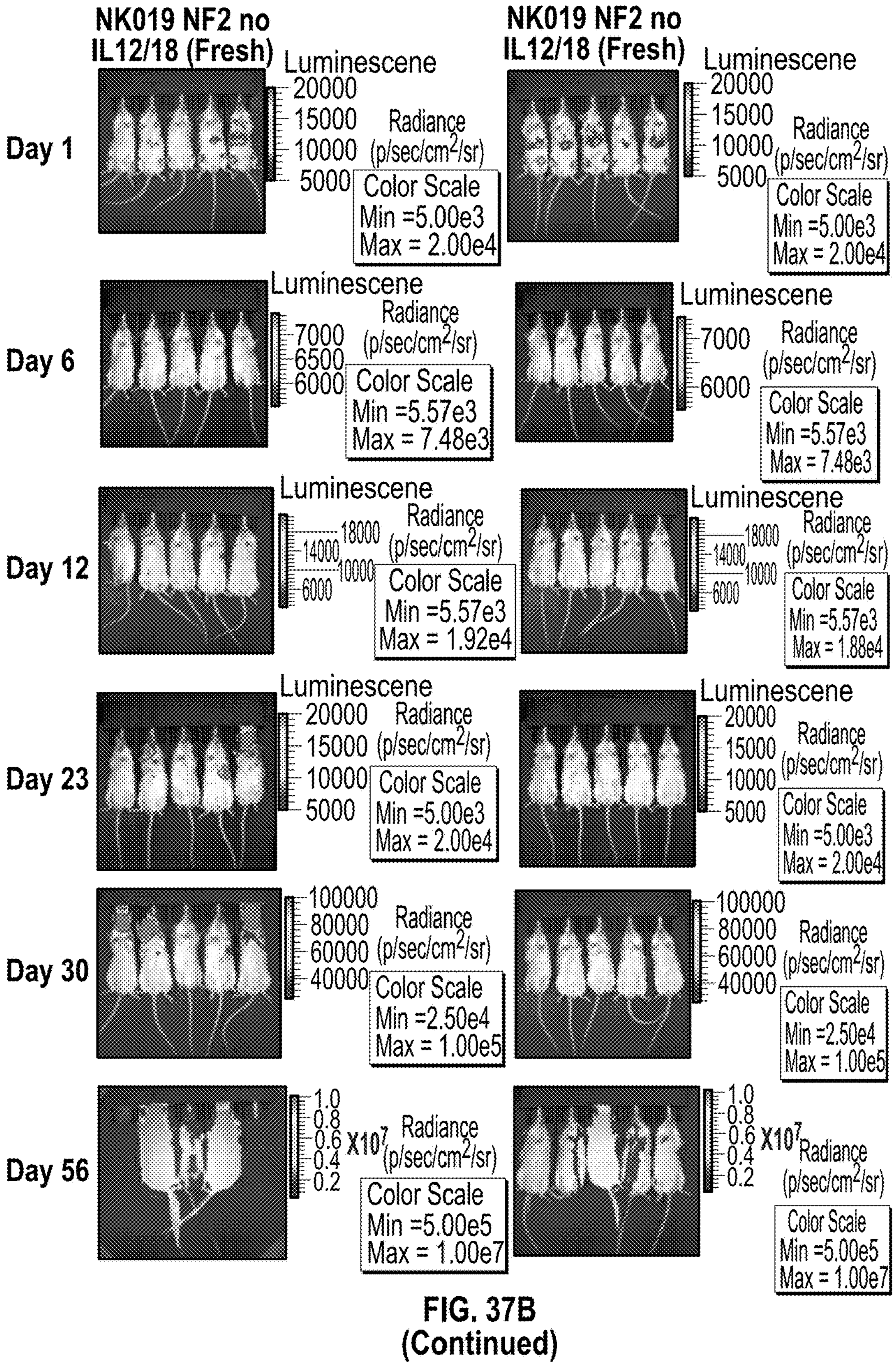
Figure 37B:
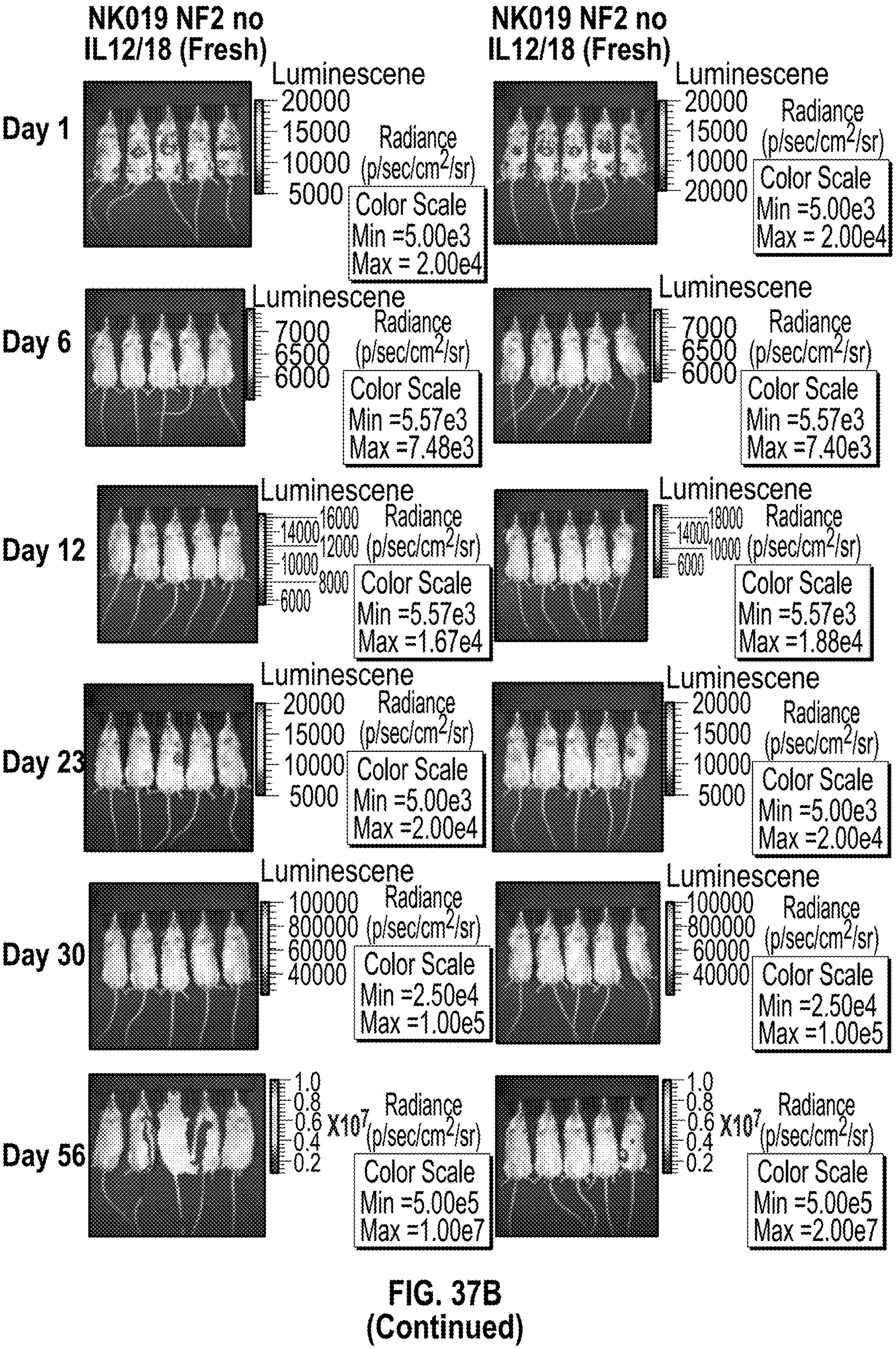
Figure 37C:
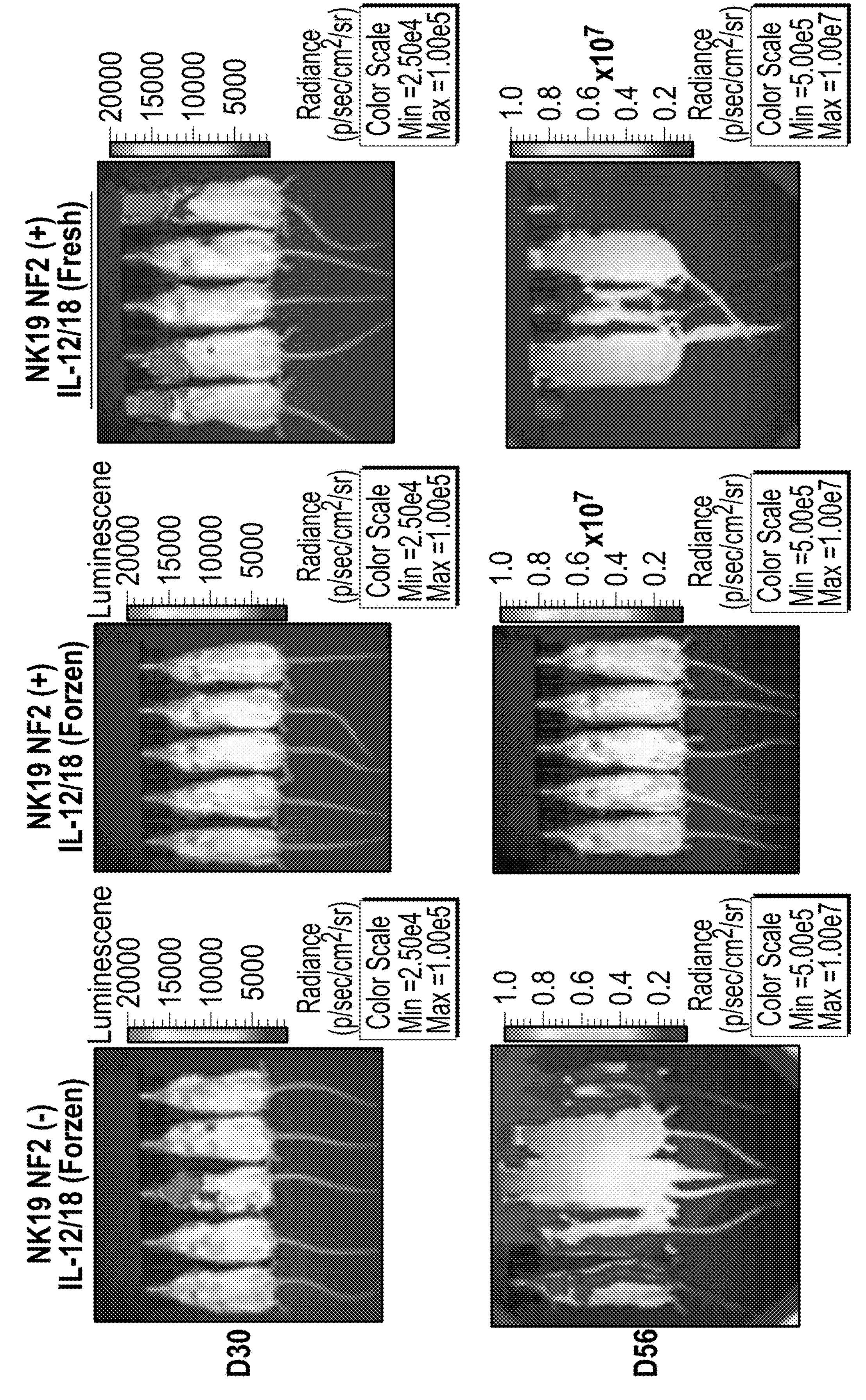
Figure 37C:
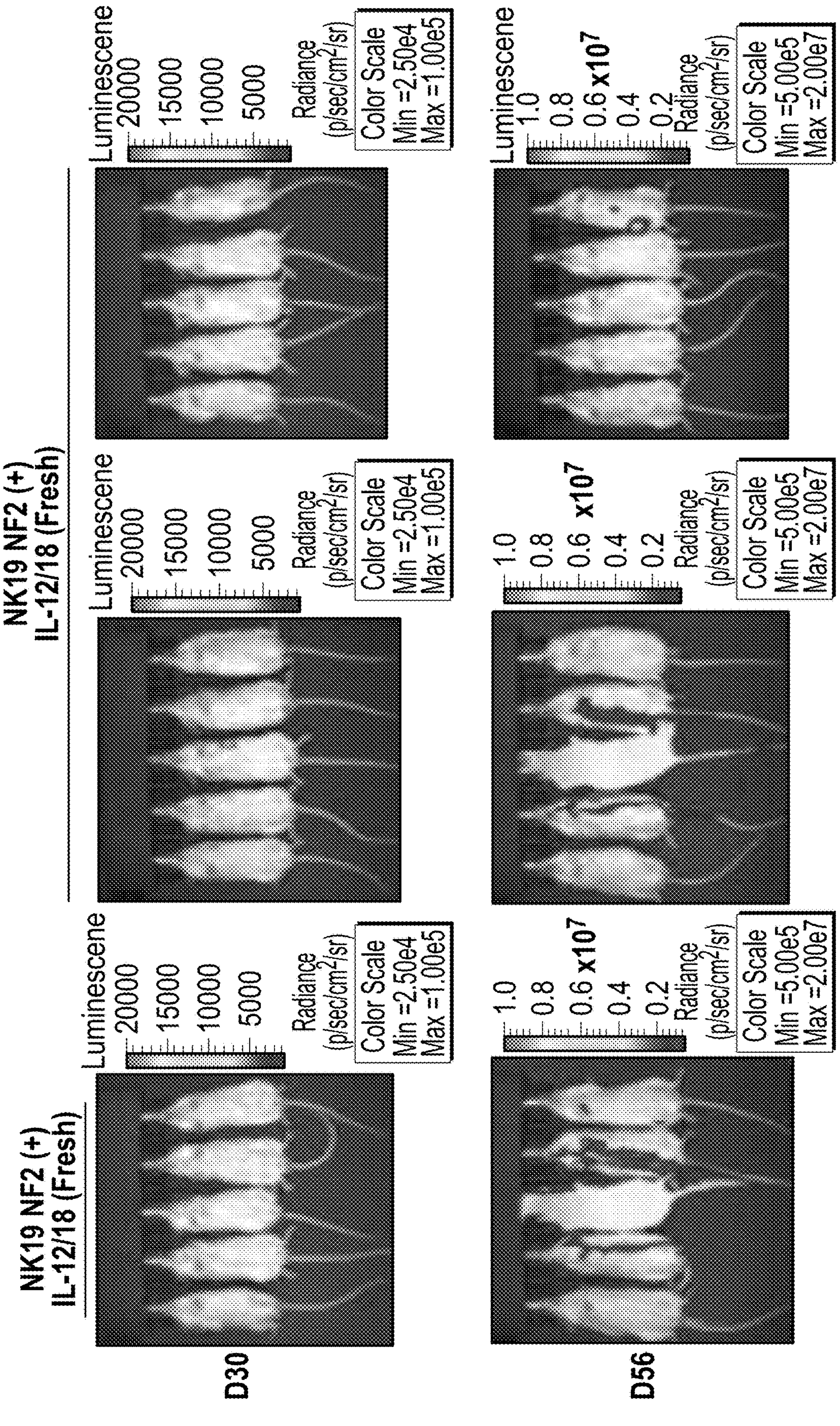
Figure 38A:
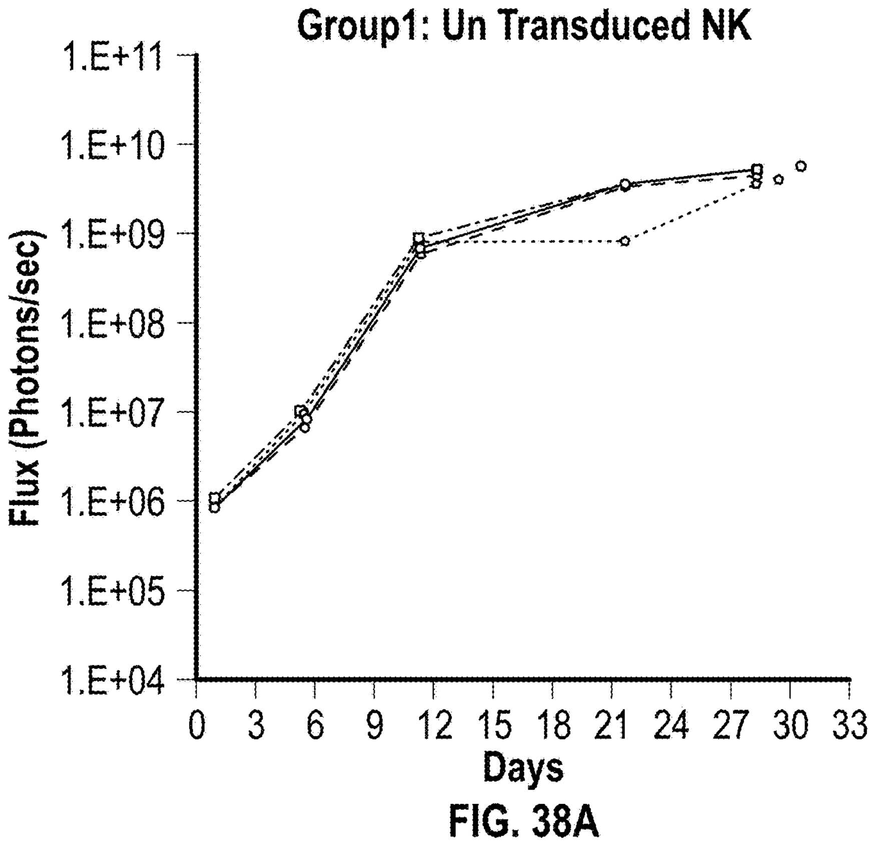
FIGS. 38A-38J show graphical depictions of the bioluminescence data from FIG. 37B.
Figure 38B:
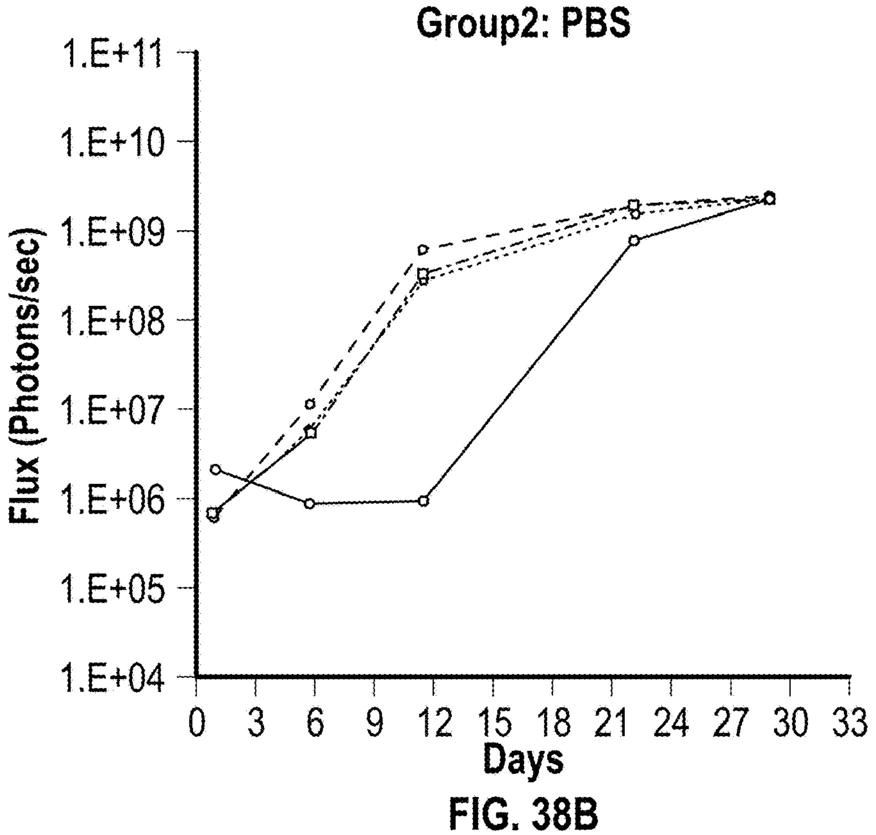
Figure 38C:
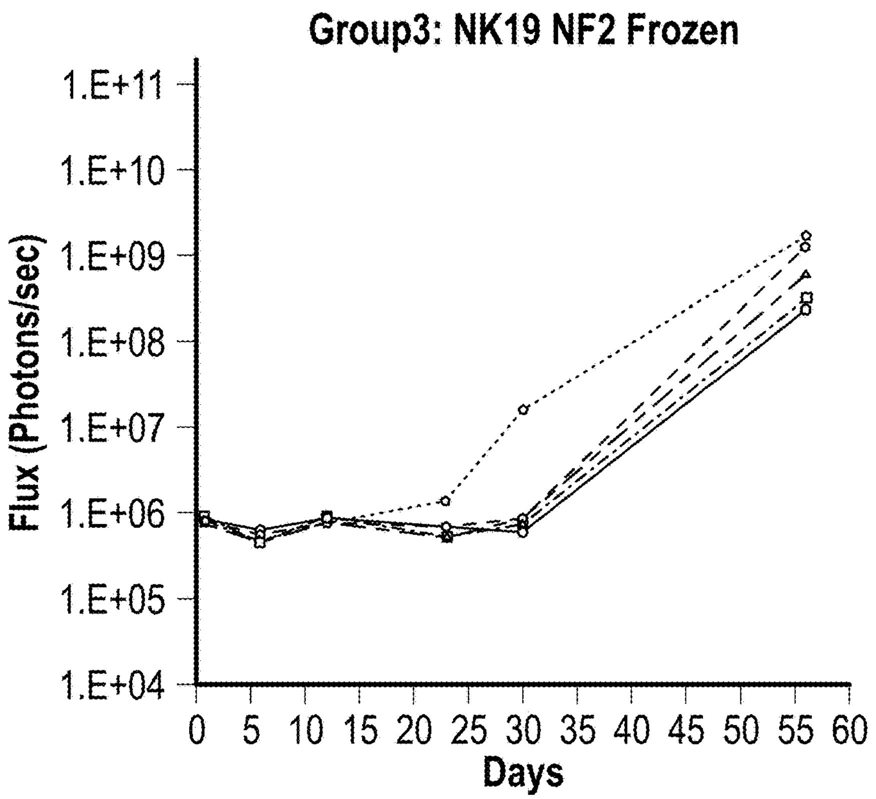
Figure 38D:
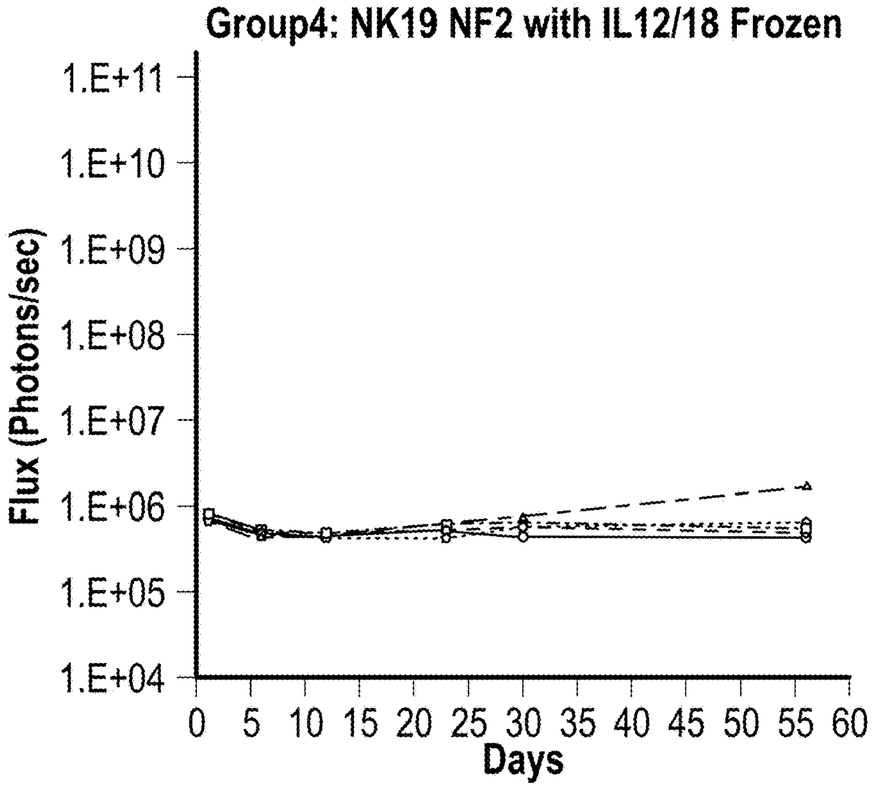
Figure 38E:
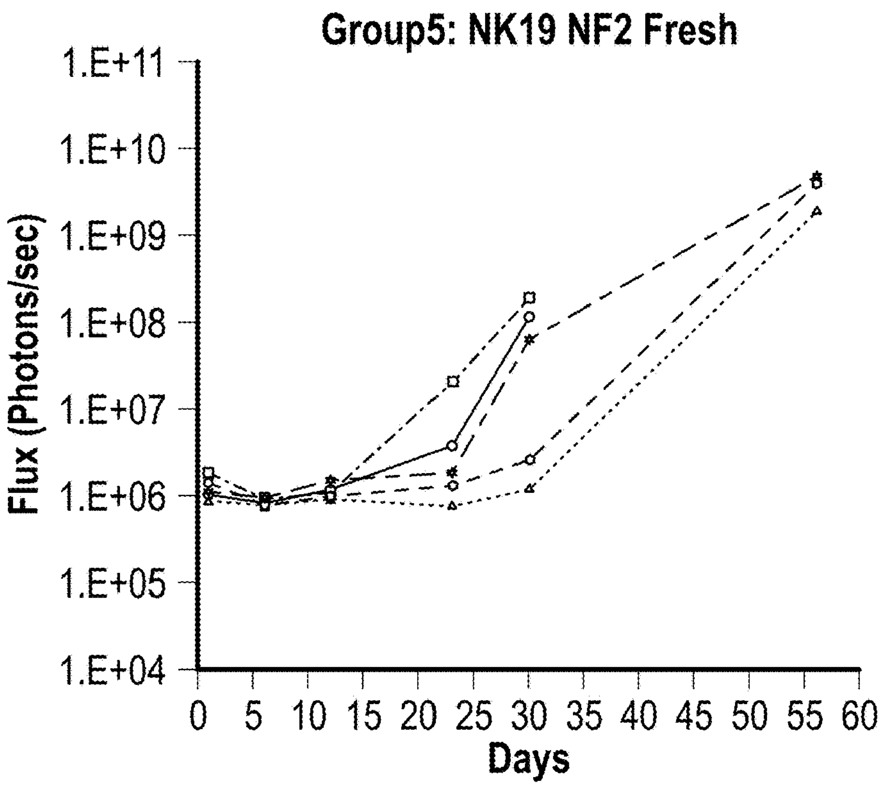
Figure 38F:
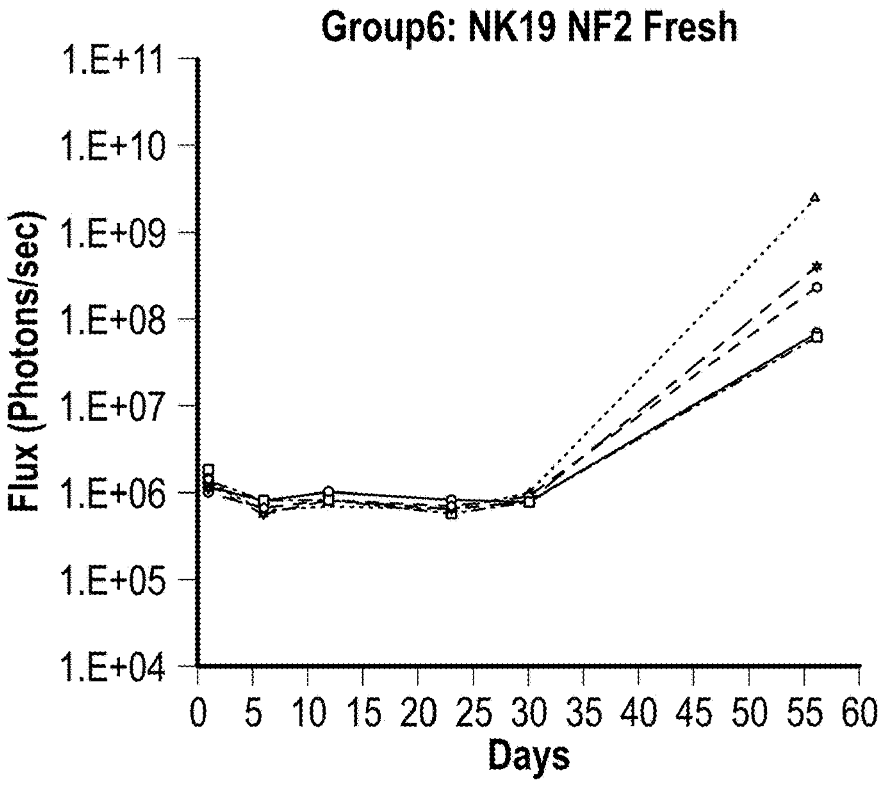
Figure 38G:
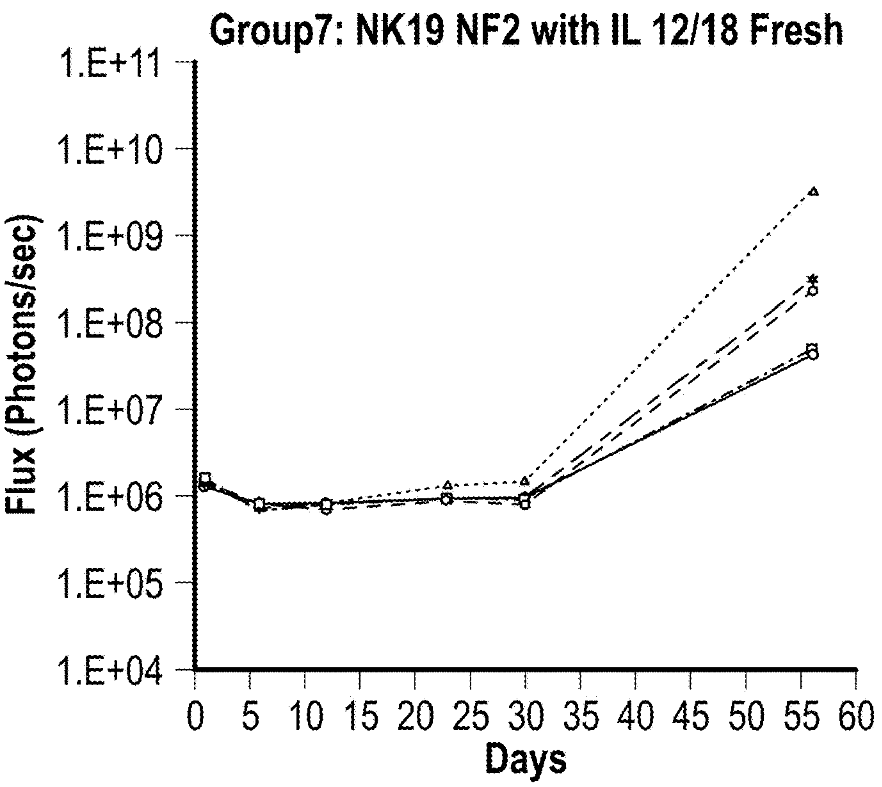
Figure 38H:
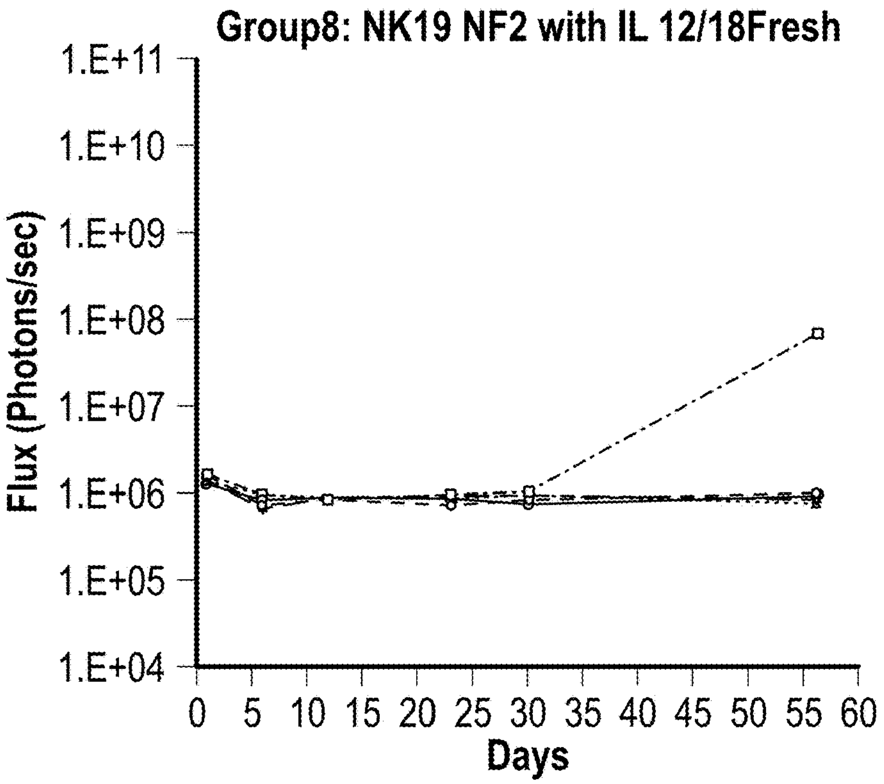
Figure 38I:
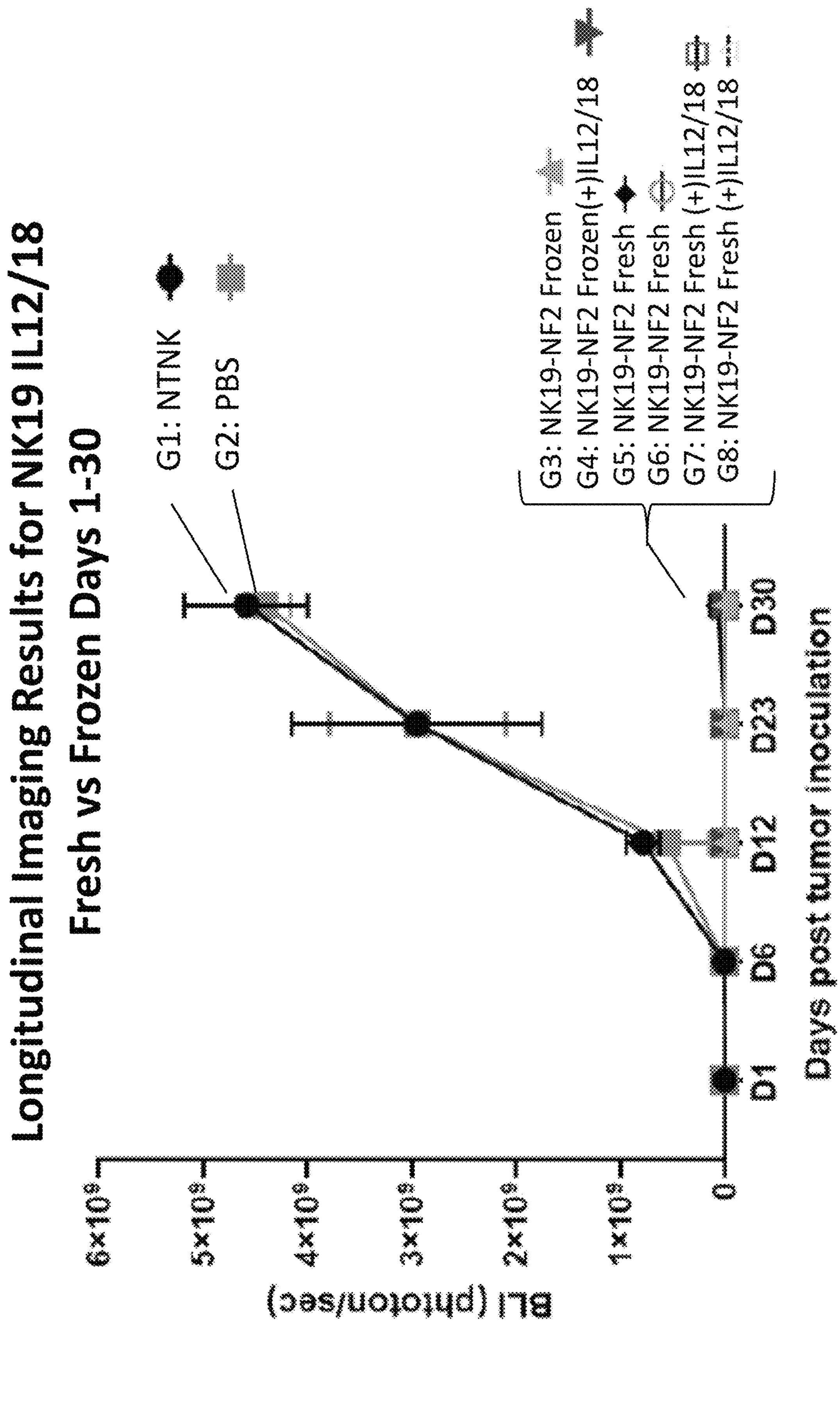
Figure 38J:
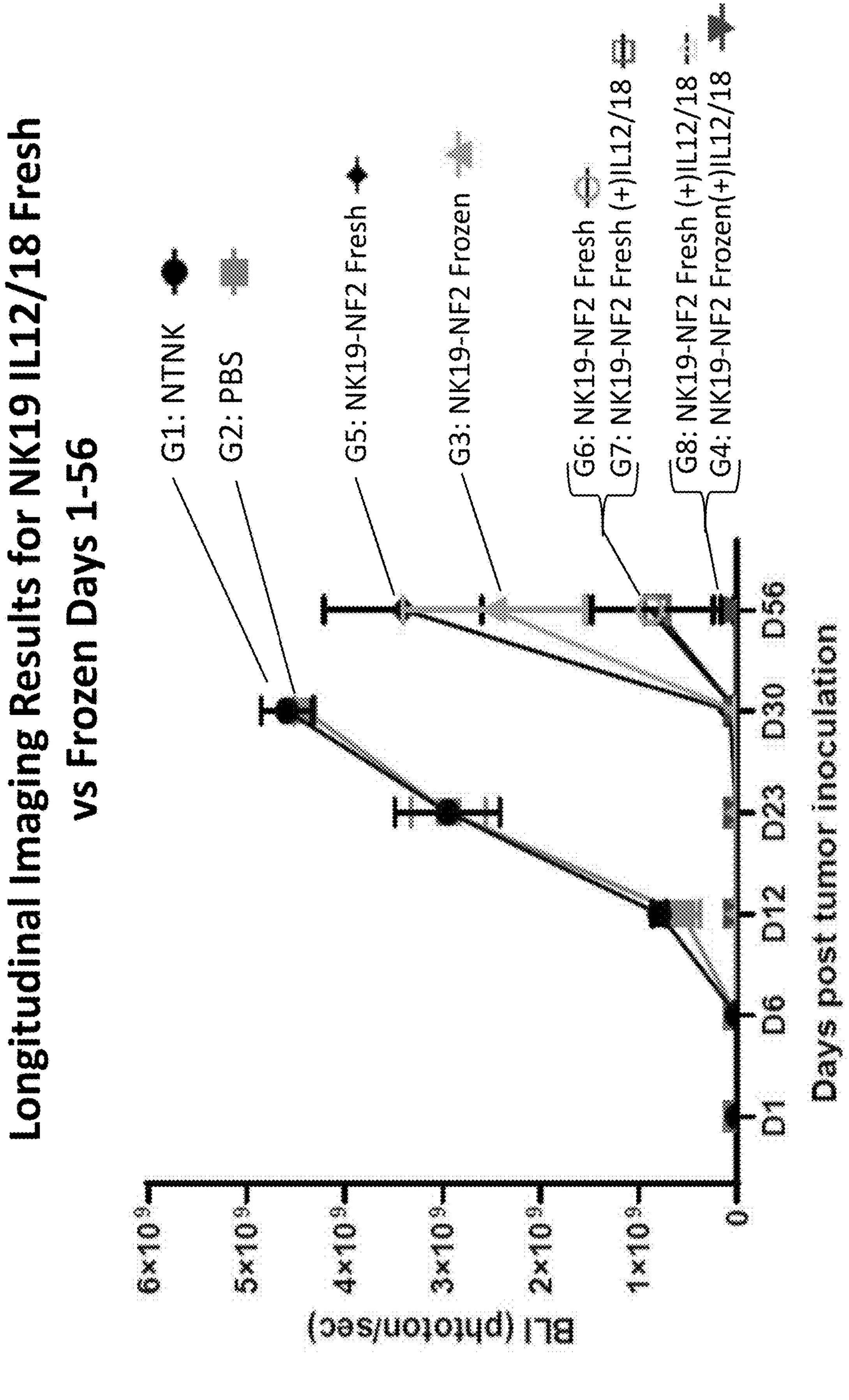

As discussed herein, in several embodiments engineered NK cells are prepared for allogeneic cell therapy. As such, in several embodiments, the engineered NK cells to be administered are prepared and then frozen for later use in a subject. Experiments were performed to determine whether the process of cryopreservation followed by thawing would adversely impact the engineered NK cells, such as by reducing their viability, persistence or cytotoxicity. FIG. 37A shows the schematic experimental protocol employed, as well as the experimental groups and other conditions used. For cells with an "IL12/IL18" designation, the cells were expanded in the presence of soluble IL12 and/or IL18, as described in in U.S. Provisional Patent Application No. 62/881,311, filed Jul. 31, 2019 and Application No. 62/932,342, filed Nov. 7, 2019, each of which is incorporated in its entirety by reference herein. FIGS. 37B and 37C shows the in vivo bioluminescence imaging from the indicated experimental groups. FIG. 38A-38H show line graphs that reflect the bioluminescence intensity over time. These data are recapitulated in FIG. 38I, which shows the first 30 days, and FIG. 38J which shows data through 56 days. While FIG. 38I shows a clear distinction between the NK cells expressing CD19 CARs and the controls, there is nominal separation among the experimental groups. However, FIG. 38J shows data through 56 days, and there is a greater distinction of the ability of NK cells expressing the various CAR constructs and processed under the indicated conditions at inhibiting tumor cell growth. Of note is that the "pairs" of groups (same CAR construct, fresh vs. frozen) show fairly similar anti-tumor activity. This indicates, that, according to several embodiments, engineered NK cells expressing anti-CD19 CARs are effective not only when prepared and administered fresh. Additionally, according to several embodiments, engineered NK cells expressing anti-CD19 CARs are effective not only when prepared, frozen, then thawed and administered (e.g., as in an allogeneic context).

Figure 39:
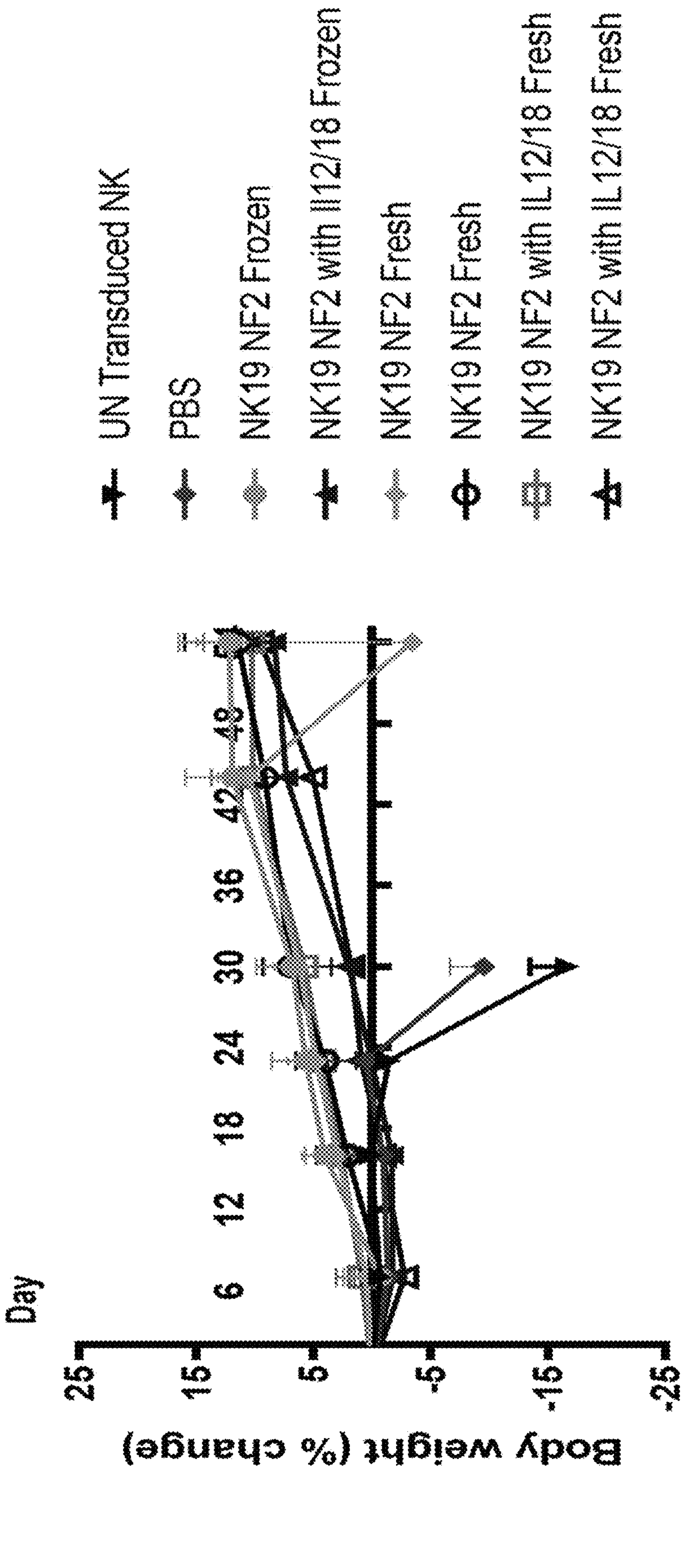
FIG. 39 shows data related to the body mass of mice over time when receiving the indicated therapy.

FIG. 39 shows a line graph of body mass of the mice treated with the indicated constructs over 56 days of the experiment. A reduction in body weight is correlated with increased tumor growth, e.g., progression of the tumor results in a decreased health of the mice, and corresponding loss of body weight (e.g., wasting). As shown, the control groups show substantial loss of body mass by 30 days, while experimental groups are increasing in body mass for the majority of the experiment. As with the bioluminescence data discussed above, there is a notable trend that many of the fresh versus frozen preparations exhibit substantially similar effects on body weight. According to several embodiments, engineered NK cells expressing anti-CD19 CARs are effective not only when prepared and administered fresh. Additionally, according to several embodiments, engineered NK cells expressing anti-CD19 CARs are effective not only when prepared, frozen, then thawed and administered (e.g., as in an allogeneic context).

It is contemplated that various combinations or subcombinations of the specific features and aspects of the embodiments disclosed above may be made and still fall within one or more of the inventions. Further, the disclosure herein of any particular feature, aspect, method, property, characteristic, quality, attribute, element, or the like in connection with an embodiment can be used in all other embodiments set forth herein. Accordingly, it should be understood that various features and aspects of the disclosed embodiments can be combined with or substituted for one another in order to form varying modes of the disclosed inventions. Thus, it is intended that the scope of the present inventions herein disclosed should not be limited by the particular disclosed embodiments described above. Moreover, while the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents, and alternatives falling within the spirit and scope of the various embodiments described and the appended claims. Any methods disclosed herein need not be performed in the order recited. The methods disclosed herein include certain actions taken by a practitioner; however, they can also include any third-party instruction of those actions, either expressly or by implication. In addition, where features or aspects of the disclosure are described in terms of Markush groups, those skilled in the art will recognize that the disclosure is also thereby described in terms of any individual member or subgroup of members of the Markush group.

The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers. For example, "about 90%" includes "90%." In some embodiments, at least 95% sequence identity or homology includes 96%, 97%, 98%, 99%, and 100% sequence identity or homology to the reference sequence. In addition, when a sequence is disclosed as "comprising" a nucleotide or amino acid sequence, such a reference shall also include, unless otherwise indicated, that the sequence "comprises", "consists of" or "consists essentially of" the recited sequence.

In several embodiments, there are provided amino acid sequences that correspond to any of the nucleic acids disclosed herein, while accounting for degeneracy of the nucleic acid code. Furthermore, those sequences (whether nucleic acid or amino acid) that vary from those expressly disclosed herein, but have functional similarity or equivalency are also contemplated within the scope of the present disclosure. The foregoing includes mutants, truncations, substitutions, or other types of modifications.

Any titles or subheadings used herein are for organization purposes and should not be used to limit the scope of embodiments disclosed herein.

What is claimed is:

1. A polypeptide comprising a CD19-directed chimeric antigen receptor (CAR), the CAR comprising:

- an extracellular anti-CD19 binding moiety comprising a single-chain variable fragment (scFv), wherein the scFv comprises a variable heavy (VH) domain and a variable light (VL) domain,
  - wherein the VH domain comprises the CDR-H1, CDR-H2, and CDR-H3 of the VH domain set forth in SEQ ID NO: 120, and
  - wherein the VL domain comprises the CDR-L1, CDR-L2, and CDR-L3 of the VL domain set forth in SEQ ID NO: 118;
- a CD8 alpha hinge domain;
- a CD8 alpha transmembrane domain; and
- an intracellular signaling domain comprising an OX40 subdomain and a CD3zeta subdomain.

2. The polypeptide of claim 1, wherein the OX40 subdomain comprises the amino acid sequence set forth in SEQ ID NO:6.

3. The polypeptide of claim 1, wherein the CD3zeta subdomain comprises the amino acid sequence set forth in SEQ ID NO:8.

4. The polypeptide of claim 1, wherein the polypeptide is encoded by a polynucleotide that also encodes a membrane-bound interleukin-15 (mbIL15).

5. The polypeptide of claim 4, wherein the mbIL15 comprises the amino acid sequence set forth in SEQ ID NO: 12.

6. An immune cell that expresses the polypeptide of claim 1.

7. The immune cell of claim 6, wherein the immune cell also expresses a membrane-bound interleukin-15 (mbIL15).

8. The immune cell of claim 6, wherein the immune cell is a natural killer (NK) or a T cell.

9. A method of obtaining an immune cell that expresses a CD19-directed chimeric antigen receptor, the method comprising:

- transfecting an immune cell with a polynucleotide encoding a CD19-directed chimeric antigen receptor (CAR), the CAR comprising:
  - an extracellular anti-CD19 binding moiety comprising a variable heavy (VH) domain, and a variable light (VL) domain, wherein the VH domain comprises the CDR-H1, CDR-H2, and CDR-H3 of the VH domain set forth in SEQ ID NO: 120 and the VL domain comprises the CDR-L1, CDR-L2, and CDR-L3 of the VL domain set forth in SEQ ID NO: 118;
  - a hinge domain;
  - a CD8 alpha transmembrane domain; and
  - an intracellular signaling domain comprising an OX40 subdomain and a CD3 zeta subdomain.

10. The method of claim 9, wherein the immune cell is a natural killer (NK) cell or a T cell.

11. The polypeptide of claim 1, wherein the VH domain comprises the amino acid sequence set forth in SEQ ID NO: 120.

12. The polypeptide of claim 1, wherein the VL domain comprises the amino acid sequence set forth in SEQ ID NO: 118.

13. The polypeptide of claim 1, wherein the VH domain comprises the amino acid sequence set forth in SEQ ID NO: 120, and the VL domain comprises the amino acid sequence set forth in SEQ ID NO: 118.

14. The immune cell of claim 6, wherein the immune cell is a natural killer (NK) cell.

15. The immune cell of claim 14, wherein the immune cell also expresses a membrane-bound interleukin-15 (mbIL15).

16. The immune cell of claim 6, wherein the immune cell is a T cell.

17. The immune cell of claim 16, wherein the immune cell also expresses a membrane-bound interleukin-15 (mbIL15).

18. A polypeptide comprising a CD19-directed chimeric antigen receptor (CAR), the CAR comprising:

- an extracellular anti-CD19 binding moiety comprising a single-chain variable fragment (scFv), wherein the scFv comprises a variable heavy (VH) domain and a variable light (VL) domain,
  - wherein the VH domain comprises the amino acid sequence set forth in SEQ ID NO: 120, and
  - wherein the VL domain comprises the amino acid sequence set forth in SEQ ID NO: 118;
- a CD8alpha transmembrane domain; and
- an intracellular signaling domain comprising an OX40 subdomain and a CD3zeta subdomain.

19. The polypeptide of claim 18, wherein the OX40 subdomain comprises the amino acid sequence set forth in SEQ ID NO: 6.

20. An immune cell expressing the polypeptide of claim 18.

21. The immune cell of claim 20, wherein the immune cell is a natural killer (NK) cell.

22. The immune cell of claim 20, wherein the immune cell also expresses a membrane-bound interleukin-15 (IL-15).

23. An immune cell expressing:

(a) a CD19-directed chimeric antigen receptor (CAR), the CAR comprising:

an extracellular anti-CD19 binding moiety comprising a single-chain variable fragment (scFv), wherein the scFv comprises a variable heavy (VH) domain and a variable light (VL) domain, wherein the VH domain comprises the CDR-H1, CDR-H2, and CDR-H3 of the VH domain set forth in SEQ ID NO: 120, and wherein the VL domain comprises the CDR-L1, CDR-L2, and CDR-L3 of the VL domain set forth in SEQ ID NO: 118;

a transmembrane domain; and an intracellular signaling domain comprising an OX40 subdomain and a CD3zeta subdomain; and (b) a membrane-bound interleukin-15 (mbIL15).

24. The immune cell of claim 23, wherein the VH domain comprises the amino acid sequence set forth in SEQ ID NO: 120, and the VL domain comprises the amino acid sequence set forth in SEQ ID NO: 118.

* * * * *